US012753423B2

(12) United States Patent
Ellsworth et al.

(10) Patent No.: US 12,753,423 B2
(45) Date of Patent: Oct. 6, 2026

(54) BIOSYNTHESIS OF CHEMICALLY DIVERSIFIED NON-NATURAL TERPENE PRODUCTS

(71) Applicant: Board of Trustees of Michigan State University, East Lansing, MI (US)

(72) Inventors: Edmund Ellsworth, Vicksburg, MI (US); Matthew Giletto, Lansing, MI (US); Björn Hamberger, Okemos, MI (US); Garret Miller, Lansing, MI (US); Richard Neubig, East Lansing, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 929 days.

(21) Appl. No.: 17/774,571

(22) PCT Filed: Nov. 5, 2020

(86) PCT No.: PCT/US2020/059144
§ 371 (c)(1),
(2) Date: May 5, 2022

(87) PCT Pub. No.: WO2021/092200
PCT Pub. Date: May 14, 2021

(65) Prior Publication Data

US 2023/0159961 A1 May 25, 2023

Related U.S. Application Data

(60) Provisional application No. 62/930,898, filed on Nov. 5, 2019.

(51) Int. Cl.
*C07F 9/12* (2006.01)
*C12P 5/00* (2006.01)

(52) U.S. Cl.
CPC ................ *C12P 5/007* (2013.01); *C07F 9/12* (2013.01); *C12Y 402/03* (2013.01); *C12Y 402/03008* (2013.01)

(58) Field of Classification Search
CPC .......... C12P 5/007; C07F 9/12; C12Y 402/03; C12Y 402/03008
USPC .......................................................... 558/70
See application file for complete search history.

(56) References Cited

U.S. PATENT DOCUMENTS

2018/0037912 A1 2/2018 Hamberger et al.

FOREIGN PATENT DOCUMENTS

IN 202217031683 A 11/2022
WO WO-2021092200 A1 5/2021

OTHER PUBLICATIONS

Johnson et al., Promiscuous terpene synthases from Prunella vulgaris highlight the importance of substrate and compartment switching in terpene synthase evolution, 2019, New Phytologist, 223, 323-335 (Year: 2019).*

"European Application Serial No. 20884610.5, Extended European Search Report mailed Feb. 19, 2024", 12 pgs.

"European Application Serial No. 20884610.5, Partial Supplementary European Search Report mailed Nov. 27, 2023", 14 pgs.

"European Application Serial No. 20884610.5, Response to Communication pursuant to Rules 161(2) and 162 EPC filed Dec. 21, 2022", 19 pgs.

"International Application Serial No. PCT/US2020/059144, International Preliminary Report on Patentability mailed May 19, 2022", 8 pgs.

Cane, David E, et al., "Aristolochene Synthase. Mechanism-Based Inhibition Terpenoid Cyclase", Journal of the American Chemical Society, vol. 116, No. 26, (Dec. 1, 1994), 12063-12064.

Huynh, et al., "Sesquiterpene Synthase-Catalyzed Formation of a New Medium-Sized Cyclic Terpenoid Ether from Farnesyl Diphosphate Analogues", ChemBioChem vol. 19, (2018), 1834-1838.

Nakano, Chiaki, et al., "Characterization of the Rv3377c Gene Product, a Type-B Diterpene Cyclase, from the Mycobacterium tuberculosis H37 Genome", Chembiochem, John Wiley & Sons, Inc, Hoboken, USA, vol. 10, No. 12, (Jul. 17, 2009), 2060-2071.

Touchet, Sabrina, et al., "Novel olfactory ligands via terpene synthases", Chemical Communications, vol. 51, No. 35, (Jan. 1, 2015), 7550-7553.

"International Application Serial No. PCT/US2020/059144, International Search Report mailed Mar. 25, 2021", 6 pgs.

"International Application Serial No. PCT/US2020/059144, Invitation to Pay Additional Fees and Partial Search Report mailed Jan. 25, 2021", 3 pgs.

"International Application Serial No. PCT/US2020/059144, Written Opinion mailed Mar. 25, 2021", 6 pgs.

"Pubchem, SID 228198746", Available Date: Feb. 12, 2015 [retrieved on Jan. 14, 2021] Retrieved from the Internet: <URL:https://pubchem.ncbi.nlm.nih.gov/substance/228198746>.

"Pubchem. SID 226496109", Available Date: Feb. 12, 2015 [retrieved on Mar. 8, 2021], Retrieved from the Internet: <URL:https://pubchem.ncbi.nlm.nih.gov/substance/226496109>.

(Continued)

*Primary Examiner* — Kristin A Vajda
(74) *Attorney, Agent, or Firm* — McKee, Voorhees & Sease, PLC

(57) ABSTRACT

The disclosure relates to compounds of the formulae (I)-(IV) and their use as substrates for making terpenoids. New substrates for terpene biosynthesis and methods for making new types of terpenes are described herein. Diterpenes occupy a unique molecular space with critical pharmaceutical applications over a diverse spectrum including antimicrobial, anti-cancer, immunomodulatory and psychoactive properties.

13 Claims, 12 Drawing Sheets

Specification includes a Sequence Listing.

(56) References Cited

OTHER PUBLICATIONS

Oberhauser, "Exploiting the Synthetic Potential of Sesquiterpene Cyclases for Generating Unnatural Terpenoids", Angew. Chem., Int. Ed .. Vol. 57, Iss. 36, (Jun. 28, 2018), 11802-11806.

* cited by examiner

| MSU # / Notebook # | Structure / MW (g/mol) |
| --- | --- |
| MSU-42465 / MBG-2-132 |  |
| MSU-42466 / MBG-2-131 |  |
| MSU-42705 / MBG-3-23 |  |
| MSU-42587 / MBG-2-156 |  |
| MSU-42586 / MBG-2-172 |  |
| MSU-42585 / MBG-3-1 |  |
| MSU-42588 / MBG-3-4 |  |
| MSU-42709 / MBG-3-91 |  |
| MSU-42707 / MBG-3-101 |  |
| MSU-42745 / MBG-3-141 |  |
| MSU-42708 / MBG-3-95 |  |
| MSU-42805 / MBG-3-162 |  |

SEQUENCE LISTING

<160> NUMBER OF SEQ ID NOS: 71

<210> SEQ ID NO 1
<211> LENGTH: 588
<212> TYPE: PRT
<213> ORGANISM: Ajuga reptans

<400> SEQUENCE: 1

Met Ser Leu Ser Phe Thr Ile Lys Val Thr Pro Phe Ser Gly Gln Arg
1 5 10 15

Val His Ser Ser Thr Glu Ser Phe Pro Ile Gln Gln Phe Pro Thr Ile
20 25 30

Thr Thr Lys Ser Ala Met Ala Val Lys Cys Ser Ser Leu Ser Thr Ala
35 40 45

Thr Val Ser Phe Gln Asp Phe Val Gly Lys Ile Arg Asp Thr Ile Asn
50 55 60

Gly Lys Val Asp Asn Ser Pro Ala Ala Thr Thr Ile His Pro Ala Asp
65 70 75 80

Ile Pro Ser Asn Leu Cys Val Val Asp Thr Leu Gln Arg Leu Gly Val
85 90 95

Asp Arg Tyr Phe Gln Ser Glu Ile Asp Ser Val Leu Asn Asp Thr Tyr
100 105 110

-continued

```
Arg Phe Trp Gln Gln Lys Gly Glu Asp Ile Phe Thr Asp Val Ala Cys
        115                 120                 125

Arg Ala Met Ala Phe Arg Leu Leu Arg Val Lys Gly Tyr Glu Val Ser
    130                 135                 140

Ser Asp Glu Leu Ala Ser Tyr Ala Glu Gln Glu His Val Asn Leu Gln
145                 150                 155                 160

Pro Ser Asp Ile Thr Thr Val Ile Glu Leu Tyr Arg Ala Ser Gln Thr
                165                 170                 175

Arg Leu Tyr Glu Asp Glu Gly Asn Leu Glu Lys Leu His Thr Trp Thr
            180                 185                 190

Ser Asn Phe Leu Lys Gln Gln Leu Gln Ser Glu Thr Ile Ser Asp Glu
        195                 200                 205

Lys Leu His Lys Gln Val Glu Tyr Tyr Leu Lys Asn Tyr His Gly Ile
    210                 215                 220

Leu Asp Arg Ala Gly Val Arg Gln Ser Leu Asp Leu Tyr Asp Ile Asn
225                 230                 235                 240

Gln Tyr Gln Asn Leu Lys Ser Thr Asp Arg Phe Pro Thr Leu Ser Asn
                245                 250                 255

Glu Asp Leu Leu Glu Phe Ala Lys Gln Asp Phe Asn Phe Cys Gln Ala
            260                 265                 270

Gln His Gln Lys Glu Leu Gln Gln Leu Gln Arg Trp Tyr Ala Asp Cys
        275                 280                 285

Lys Leu Asp Thr Leu Thr Tyr Gly Arg Asp Val Val Arg Val Ala Ser
    290                 295                 300

Phe Leu Thr Ala Ala Ile Phe Gly Glu Pro Glu Phe Ser Asp Ala Arg
305                 310                 315                 320

Leu Ala Phe Ala Lys His Ile Ile Leu Val Thr Arg Ile Asp Asp Phe
                325                 330                 335

Phe Asp His Gly Gly Ser Ile Glu Glu Ser Tyr Lys Ile Leu Asp Leu
            340                 345                 350

Val Lys Glu Trp Glu Asp Lys Pro Ala Glu Glu Tyr Pro Ser Lys Glu
        355                 360                 365

Val Glu Ile Leu Phe Thr Ala Val Tyr Asn Thr Val Asn Asp Leu Ala
    370                 375                 380

Glu Met Ala Tyr Ile Glu Gln Gly Arg Ser Ile Lys Pro Leu Leu Ile
385                 390                 395                 400

Lys Leu Trp Val Glu Ile Leu Thr Ser Phe Lys Lys Glu Leu Asp Ser
                405                 410                 415

Trp Thr Glu Asp Thr Glu Leu Thr Leu Glu Glu Tyr Leu Ala Ser Ser
            420                 425                 430

Trp Val Ser Ile Gly Cys Arg Ile Cys Ser Leu Asn Ser Leu Gln Phe
        435                 440                 445

Leu Gly Ile Thr Leu Ser Glu Glu Met Leu Ser Ser Glu Glu Cys Met
    450                 455                 460

Glu Leu Cys Arg His Val Ser Ser Val Asp Arg Leu Leu Asn Asp Val
465                 470                 475                 480

Gln Thr Phe Glu Lys Glu Arg Leu Glu Asn Thr Ile Asn Ser Val Ser
                485                 490                 495

Leu Gln Leu Ala Glu Ala Gln Arg Glu Gly Arg Thr Ile Thr Glu Glu
            500                 505                 510

Glu Ala Met Ser Lys Ile Lys Asp Leu Ala Asp Tyr His Arg Arg Gln
        515                 520                 525
```

-continued

```
Leu Met Gln Met Val Tyr Lys Asp Gly Thr Ile Phe Pro Arg Gln Cys
    530                 535                 540

Lys Asp Val Phe Leu Arg Val Cys Arg Ile Gly Tyr Tyr Leu Tyr Ala
545                 550                 555                 560

Ser Gly Asp Glu Phe Thr Thr Pro Gln Gln Met Met Gly Asp Met Lys
                565                 570                 575

Ser Leu Val Tyr Glu Pro Leu Asn Thr Ser Ser Ser
            580                 585


<210> SEQ ID NO 2
<211> LENGTH: 1767
<212> TYPE: DNA
<213> ORGANISM: Ajuga reptans

<400> SEQUENCE: 2

atgtcactct cgttcaccat caaagtcacc cccttttcgg gccagagagt tcacagcagc      60

acagaaagct ttccaatcca acaatttcca acgatcacca ccaaatccgc catggctgtc     120

aaatgcagca gcctcagtac cgcaacagta agcttccagg atttcgtcgg aaaaatcaga     180

gatacgatca acgggaaagt tgacaattct ccagcagcga ccactattca tcctgcagat     240

ataccctcca atctctgcgt ggtggatacc ctccaaagat tgggagttga ccgttacttc     300

caatctgaaa tcgacagcgt tcttaacgac acatacaggt tctggcagca gaaaggagaa     360

gatatcttca ctgatgttgc ttgtcgtgca atggcatttc gacttttgcg agttaaagga     420

tatgaagttt catcagatga actggcttcg tatgctgaac aagagcatgt taacctgcaa     480

ccaagtgaca taactacggt tatcgagctt tacagagcat cacagacaag attatatgaa     540

gacgagggca atcttgagaa gttacatact tggactagca attttctgaa gcaacaattg     600

cagagtgaaa ctatttctga cgagaaattg cacaaacagg tggagtatta cttgaagaac     660

taccacggca tactagaccg tgctggagtt agacaaagtc tcgatttata tgacataaac     720

caataccaga atctaaaatc tacagataga ttccctactt taagtaacga agatttactt     780

gaattcgcga agcaagattt taacttttgc caagctcaac accagaaaga gcttcagcaa     840

ctgcaaaggt ggtatgcgga ttgtaaattg gatacattga cttacggaag agatgtggta     900

cgtgttgcaa gtttcctgac agctgcaatt tttggtgagc ctgaattctc tgatgctcgt     960

ctagccttcg ccaaacacat catcctcgtg acacgtattg atgatttctt cgatcatggt    1020

gggtctatag aagagtcata caagatcctg gatttagtaa aagaatggga agataagcca    1080

gctgaggaat atccttccaa ggaagttgaa atcctcttta cagcagtata taatacagta    1140

aatgacttgg cagaaatggc ttatattgag caaggccgtt ccattaaacc tcttctaatt    1200

aaactgtggg ttgaaatact gacaagtttc aagaaagaac tggattcatg gacagaagac    1260

acagaactaa ccttggagga gtacttggct tcctcctggg tgtcgatcgg ttgcagaatc    1320

tgcagtctca attcgctgca gttccttggt ataacattat ccgaagaaat gctttcaagc    1380

gaagagtgca tggagttgtg taggcatgtt tcttcagtcg acaggctact caatgacgtg    1440

caaactttcg agaaggaacg cctagaaaat acgataaaca gtgtgagcct acagctagca    1500

gaagctcaga gagaaggaag aaccattaca gaagaggagg ctatgtcaaa gattaaagac    1560

ctggctgatt atcacaggag acaactgatg cagatggttt ataaggatgg gaccatattt    1620

ccgagacaat gcaaagatgt ctttttgagg gtatgcagga ttggctacta cttatacgcg    1680

agcggcgatg aattcactac tccacaacaa atgatggggg atatgaaatc attggtttat    1740

gaacccctaa acacttcatc ctcttga                                        1767
```

<210> SEQ ID NO 3
<211> LENGTH: 567
<212> TYPE: PRT
<213> ORGANISM: Leonotis leonurus

<400> SEQUENCE: 3

```
Met Ser Val Ala Phe Asn Leu Ile Val Val Arg Phe Pro Gly His Gly
1               5                   10                  15

Ile Gln Ser Ser Arg Glu Thr Phe Pro Ala Lys Ile Ile Thr Arg Thr
            20                  25                  30

Lys Ser Ser Met Arg Phe Gln Ser Ser Leu Asn Thr Ser Thr Asp Phe
        35                  40                  45

Val Gly Lys Ile Arg Glu Met Ile Arg Gly Lys Thr Asp Asn Ser Ile
    50                  55                  60

Asn Pro Leu Asp Ile Pro Ser Thr Leu Cys Val Ile Asp Thr Leu His
65                  70                  75                  80

Ser Phe Gly Ile Asp Arg Tyr Phe Gln Ser Glu Ile Asn Ser Val Leu
                85                  90                  95

His His Thr Tyr Arg Leu Trp Asn Asp Arg Asn Asn Ile Ile Phe Lys
            100                 105                 110

Asp Val Ile Cys Cys Ala Ile Ala Phe Arg Leu Leu Arg Val Lys Gly
        115                 120                 125

Tyr Gln Val Ser Ser Asp Glu Leu Ala Pro Phe Ala Gln Gln Gln Val
    130                 135                 140

Thr Gly Leu Gln Thr Ser Asp Ile Ala Thr Ile Leu Glu Leu Tyr Arg
145                 150                 155                 160

Ala Ser Gln Glu Arg Leu His Glu Asp Asp Asp Thr Leu Asp Lys Leu
                165                 170                 175

His Asp Trp Ser Ser Asn Leu Leu Lys Leu His Leu Leu Asn Glu Asn
            180                 185                 190

Ile Pro Asp His Lys Leu His Lys Arg Val Gly Tyr Phe Leu Lys Asn
        195                 200                 205

Tyr His Gly Met Leu Asp Arg Val Ala Val Arg Arg Asn Ile Asp Leu
    210                 215                 220

His Asn Ile Asn His Tyr Gln Ile Pro Glu Val Ala Asp Arg Phe Pro
225                 230                 235                 240

Thr Glu Ala Phe Leu Glu Phe Ser Arg Gln Asp Phe Asn Ile Cys Gln
                245                 250                 255

Ala Gln His Gln Lys Glu Leu Gln Gln Leu His Arg Trp Tyr Ala Asp
            260                 265                 270

Cys Arg Leu Asp Thr Leu Asn His Gly Thr Asp Val Val His Phe Ala
        275                 280                 285

Asn Phe Leu Thr Ser Ala Ile Phe Gly Glu Pro Glu Phe Ser Glu Ala
    290                 295                 300

Arg Leu Ala Phe Ala Lys Gln Val Ile Leu Ile Thr Arg Met Asp Asp
305                 310                 315                 320

Phe Phe Asp His Asp Gly Ser Arg Glu Glu Ser His Lys Ile Leu His
                325                 330                 335

Leu Val Gln Gln Trp Lys Glu Lys Pro Ala Glu Glu Tyr Gly Ser Lys
            340                 345                 350

Glu Val Glu Ile Leu Phe Thr Ala Val Tyr Thr Thr Val Asn Ser Leu
        355                 360                 365

Ala Glu Lys Ala Cys Met Glu Gln Gly Arg Ser Val Lys Gln Leu Leu
```

```
    370                 375                 380

Ile Lys Leu Trp Val Glu Leu Leu Thr Ser Phe Lys Lys Glu Leu Asp
385                 390                 395                 400

Ser Trp Thr Glu Lys Met Ala Leu Thr Leu Asp Glu Tyr Leu Ser Phe
                405                 410                 415

Ser Trp Val Ser Ile Gly Cys Arg Leu Cys Ile Leu Asn Ser Leu Gln
            420                 425                 430

Phe Leu Gly Ile Lys Leu Ser Glu Glu Met Leu Trp Ser Gln Glu Cys
        435                 440                 445

Leu Asp Leu Cys Arg His Val Ser Ser Val Val Arg Leu Leu Asn Asp
    450                 455                 460

Leu Gln Thr Phe Lys Lys Glu Arg Ile Glu Asn Thr Ile Asn Gly Val
465                 470                 475                 480

Asp Val Gln Leu Ala Ala Arg Lys Gly Glu Arg Ala Ile Thr Glu Glu
                485                 490                 495

Glu Ala Met Ser Lys Ile Lys Glu Met Ala Asp His His Arg Arg Lys
            500                 505                 510

Leu Met Gln Ile Val Tyr Lys Glu Gly Thr Ile Phe Pro Arg Glu Cys
        515                 520                 525

Lys Asp Val Phe Leu Arg Val Cys Arg Ile Gly Tyr Tyr Leu Tyr Ser
    530                 535                 540

Gly Asp Glu Leu Thr Ser Pro Gln Gln Met Lys Glu Asp Met Lys Ala
545                 550                 555                 560

Leu Val His Glu Ser Ser Ser
                565
```

<210> SEQ ID NO 4
<211> LENGTH: 1704
<212> TYPE: DNA
<213> ORGANISM: Leonotis leonurus

<400> SEQUENCE: 4

```
atgtcggtgg cgttcaacct catagtcgtc cgttttccgg gccatggaat tcagagcagt      60

agagaaactt ttccagccaa aattattacc agaactaaat caagcatgag attccaaagc     120

agcctcaaca cttcaacaga tttcgtggga aaaataagag agatgatcag agggaaaact     180

gataattcta ttaatcccct ggatattccc tccactctat gcgtaatcga caccctacac     240

agcttcggaa ttgatcgcta ctttcaatcc gaaatcaact ctgttcttca ccacacatac     300

agattatgga acgacagaaa taatatcatc ttcaaagatg tcatttgctg cgcaattgcc     360

tttagacttt tgcgagtgaa aggatatcaa gtctcatcag atgaactggc gccatttgcc     420

caacaacagg tgactggact acaaacaagc gacattgcca cgattctaga gctctacaga     480

gcatcacagg agagattaca cgaagacgac gacactcttg acaaactaca tgattggagc     540

agcaaccttc tgaagctgca tctgctgaat gagaacattc ctgatcataa actgcacaaa     600

cgggtggggt atttcttgaa gaactaccat ggcatgctag atcgcgttgc ggttagacga     660

aacatcgacc ttcacaacat aaaccattac caaatcccag aagttgcaga taggttccct     720

actgaagctt ttcttgaatt ttcaaggcaa gattttaata tttgccaagc tcaacaccag     780

aaagaacttc agcaactgca taggtggtat gcagattgta gattggacac actgaatcac     840

ggaacagacg tagtacattt tgctaatttt ctaacttcag caattttcgg agagcctgaa     900

ttctccgagg ctcgtctagc ctttgctaaa caggttatcc taataacacg tatggatgat     960

ttcttcgatc acgatgggtc tagagaagaa tcacacaaga tcctccatct agttcaacaa    1020
```

-continued

```
tggaaagaga agcccgccga agaatatggt tcaaaggaag ttgagatcct ctttacagca   1080

gtgtacacta cagtaaatag cttggcagaa aaggcttgta tggagcaagg ccgtagtgtc   1140

aaacaacttc taattaagct gtgggtcgag ctgctaacaa gtttcaagaa agaattggat   1200

tcatggacgg agaagatggc gctaaccttg gatgagtact tgtctttctc ctgggtgtca   1260

attggctgca gactctgcat tctcaattcc ctgcaatttc ttgggataaa attatctgaa   1320

gaaatgctgt ggagtcaaga gtgtctggat ttatgccggc atgtttcatc agtggttcgc   1380

ctgctcaacg atttacaaac tttcaagaag gagcgcatag aaaatacgat aaacggtgtg   1440

gacgttcagc tagctgctcg taaaggcgaa agagccatta cagaagagga ggccatgtcc   1500

aagattaagg aaatggctga ccatcacagg agaaaactga tgcaaattgt gtataaagaa   1560

ggaaccattt ttccaagaga atgcaaagat gtgtttttga gagtgtgcag gattggctac   1620

tatctctact cgggcgatga gttaacttct ccacaacaaa tgaaggagga tatgaaagcg   1680

ttggtacatg aatcatcctc ttga                                          1704
```

```
<210> SEQ ID NO 5
<211> LENGTH: 751
<212> TYPE: PRT
<213> ORGANISM: Mentha spicata
<220> FEATURE:
<221> NAME/KEY: VARIANT
<222> LOCATION: (1)...(751)
<223> OTHER INFORMATION: Xaa = Any Amino Acid

<400> SEQUENCE: 5

Met Ser Ser Ile Arg Asn Leu Ser Leu His Ile Asp Leu Pro Lys Ala
1               5                   10                  15

Glu Lys Lys Leu Val Glu Lys Ile Arg Glu Arg Ile Arg Asn Gly Arg
            20                  25                  30

Val Glu Met Ser Pro Ser Ala Tyr Asp Thr Ala Trp Val Ala Met Val
        35                  40                  45

Pro Ser Arg Gly Tyr Ser Gly Arg Pro Gly Phe Pro Glu Cys Val Asp
    50                  55                  60

Trp Ile Ile Glu Asn Gln Asn Pro Asp Gly Ser Trp Gly Leu Asp Ser
65                  70                  75                  80

Asp Gln Pro Leu Leu Val Lys Asp Ser Leu Ser Ser Thr Leu Ala Cys
                85                  90                  95

Leu Leu Ala Leu Arg Lys Trp Lys Thr His Asn Gln Leu Val Gln Arg
            100                 105                 110

Gly Met Glu Phe Ile Asp Ser Arg Gly Trp Ala Ala Thr Asp Asp Asp
        115                 120                 125

Asn Gln Ile Ser Pro Ile Gly Phe Asn Ile Ala Phe Pro Ala Met Ile
    130                 135                 140

Asn Tyr Ala Lys Glu Leu Asn Leu Thr Leu Pro Leu His Pro Pro Ser
145                 150                 155                 160

Ile His Ser Leu Leu His Ile Arg Asp Ser Glu Ile Arg Lys Arg Asn
                165                 170                 175

Trp Glu Tyr Val Ala Glu Gly Val Val Asp Asp Thr Ser Asn Trp Lys
            180                 185                 190

Gln Ile Ile Gly Thr His Gln Arg Asn Asn Gly Ser Leu Phe Asn Ser
        195                 200                 205

Pro Ala Thr Thr Ala Ala Ala Val Ile His Ser His Asp Asp Lys Cys
    210                 215                 220
```

-continued

```
Phe Arg Tyr Leu Ile Ser Thr Leu Glu Asn Ser Asn Gly Gly Trp Val
225                 230                 235                 240

Pro Thr Ile Tyr Pro Tyr Asp Ile Tyr Ala Pro Leu Cys Met Ile Asp
                245                 250                 255

Thr Leu Glu Arg Leu Gly Ile His Thr Tyr Phe Glu Val Glu Leu Ser
            260                 265                 270

Gly Ile Phe Asp Asp Ile Tyr Arg Asn Trp Gln Glu Arg Glu Glu Glu
        275                 280                 285

Ile Phe Cys Asn Val Met Cys Arg Ala Leu Ala Phe Arg Leu Leu Arg
    290                 295                 300

Met Arg Gly Tyr His Val Ser Ser Asp Glu Leu Ala Glu Phe Val Asp
305                 310                 315                 320

Lys Glu Glu Phe Phe Asn Ser Val Ser Met Gln Glu Ser Gly Glu Gly
                325                 330                 335

Thr Val Leu Glu Leu Tyr Arg Ala Ser Leu Thr Lys Ile Asn Glu Glu
            340                 345                 350

Glu Arg Ile Leu Asp Lys Ile His Ala Trp Thr Lys Pro Phe Leu Lys
        355                 360                 365

His Gln Leu Leu Asn Arg Ser Ile Arg Asp Lys Arg Leu Glu Lys Gln
    370                 375                 380

Val Glu Tyr Asp Leu Lys Asn Phe Tyr Gly Ala Leu Val Arg Phe Gln
385                 390                 395                 400

Asn Arg Arg Thr Ile Asp Ser Tyr Asp Ala Lys Ser Ile Gln Ile Ser
                405                 410                 415

Lys Thr Ala Tyr Arg Cys Ser Thr Val Tyr Asn Glu Asp Phe Ile His
            420                 425                 430

Leu Ser Val Glu Asp Phe Lys Ile Ser Arg Ala Gln Tyr Leu Lys Glu
        435                 440                 445

Leu Glu Glu Met Asn Lys Trp Tyr Ser Asp Cys Arg Leu Asp Leu Leu
    450                 455                 460

Thr Lys Gly Arg Asn Ala Cys Arg Glu Ser Tyr Ile Leu Thr Ala Ala
465                 470                 475                 480

Ile Ile Val Asp Pro His Glu Ser Met Ala Arg Ile Ser Tyr Ala Gln
                485                 490                 495

Ser Ile Leu Leu Ile Thr Val Phe Asp Asp Phe Phe Asp His Tyr Gly
            500                 505                 510

Ser Lys Glu Glu Ala Leu Asn Ile Ile Asp Leu Val Lys Glu Trp Lys
        515                 520                 525

Pro Ala Gly Ser Tyr Cys Ser Lys Glu Val Glu Ile Leu Phe Thr Ala
    530                 535                 540

Leu His Asp Thr Ile Asn Glu Ile Ala Ala Lys Ala Asp Ala Glu Gln
545                 550                 555                 560

Gly Phe Ser Ser Lys Gln Gln Leu Ile Asn Met Trp Val Glu Leu Leu
                565                 570                 575

Glu Ser Ala Val Arg Glu Lys Asp Ser Leu Ser Xaa Asn Lys Val Ser
            580                 585                 590

Thr Leu Glu Glu Tyr Leu Ser Phe Ala Pro Ile Thr Ile Gly Cys Lys
        595                 600                 605

Leu Cys Val Leu Thr Ser Val His Phe Leu Gly Ile Lys Leu Ser Glu
    610                 615                 620

Glu Ile Trp Thr Ser Glu Glu Leu Ser Ser Leu Cys Arg His Gly Asn
625                 630                 635                 640

Val Val Cys Arg Leu Leu Asn Asp Leu Lys Thr Tyr Glu Arg Glu Arg
```

```
                645                 650                 655

Glu Glu Asn Thr Leu Asn Ser Val Ser Val Gln Thr Val Gly Gly Gly
            660                 665                 670

Val Ser Glu Glu Glu Ala Val Thr Lys Val Glu Glu Val Leu Glu Phe
        675                 680                 685

His Arg Arg Lys Val Met Gln Leu Ala Cys Arg Arg Gly Gly Ser Ser
    690                 695                 700

Val Pro Arg Glu Cys Lys Glu Leu Val Trp Lys Thr Cys Thr Ile Gly
705                 710                 715                 720

Tyr Cys Leu Tyr Gly His Asp Gly Gly Asp Glu Leu Ser Ser Pro Lys
                725                 730                 735

Asp Ile Leu Lys Asp Ile Asn Ala Met Met Phe Glu Pro Leu Lys
            740                 745                 750


<210> SEQ ID NO 6
<211> LENGTH: 2256
<212> TYPE: DNA
<213> ORGANISM: Mentha spicata
<220> FEATURE:
<221> NAME/KEY: misc_feature
<222> LOCATION: (1)...(2256)
<223> OTHER INFORMATION: n = A,T,C or G

<400> SEQUENCE: 6

atgagttcca ttcgaaattt aagtttgcat attgatctgc caaaggccga gaagaagttg     60

gttgagaaaa tcagagagag gataagaaat gggagggtgg agatgtcgcc gtcggcttac    120

gacaccgcgt gggtggccat ggtgccgtct cgaggatatt ccggcaggcc gggtttcccg    180

gagtgcgtgg attggataat cgagaaccag aatccggacg ggtcgtgggg tttggattcg    240

gatcaaccac ttctggtcaa agactccctc tcgtccacct tggcatgcct acttgccctg    300

cgtaaatgga aaacacacaa ccaactagtg caaaggggca tggagttcat cgactcccgt    360

ggttgggctg caactgatga tgacaatcag atttctccta ttggattcaa tattgccttt    420

cctgcaatga ttaattacgc caaagagctt aatttaactc tgcctctaca tccaccttcg    480

attcattcat tgttacacat tagagattca gaaataagaa agcgaaactg ggaatacgta    540

gctgaaggag tagtcgacga tacaagcaat tggaagcaaa taatcggcac gcatcaaaga    600

aataatggat ccttgttcaa ctcacctgct accactgcag ctgctgttat tcactctcac    660

gacgataaat gtttccgata tttgatctcc actcttgaga attctaacgg tggatgggta    720

ccaactatct atccatacga tatatacgct cctctctgca tgatcgatac gctagaaaga    780

ttaggaatac acacatattt tgaagttgaa ctcagcggca tttttgatga catatacagg    840

aattggcaag agagagaaga agagatcttt tgtaatgtta tgtgtcgagc tctggcattt    900

cggcttctac gaatgagggg atatcatgtt tcatctgatg aactagcaga atttgtggac    960

aaggaggagt tttttaatag cgtgagcatg caagagagcg gcgaaggcac agtgcttgag   1020

ctttacagag cttcactcac aaaaatcaac gaagaagaaa ggattctcga caaaattcat   1080

gcatggacca aaccatttct caagcaccag cttctcaacc gcagcattcg cgacaaacga   1140

ttagagaagc aggtggaata cgacttgaag aacttctacg gcgcactagt ccgattccag   1200

aacagaagaa ccatcgactc atacgatgct aaatcaatcc aaatttcgaa aacagcatat   1260

aggtgctcta cagtttacaa tgaagacttc atccatttat ccgttgagga cttcaaaatc   1320

tcccgagcac aatacctaaa agaacttgaa gaaatgaaca agtggtactc tgattgtagg   1380

ttggacctct taactaaagg aagaaatgca tgtcgagaat cttacatttt aacagctgca   1440
```

-continued

```
atcattgtcg atcctcacga atccatggct cgaatctctt acgctcaatc tattcttctt   1500

ataactgttt tcgacgactt tttcgatcat tatgggtcta aagaagaggc tctcaatatt   1560

attgatctag tcaaggaatg gaagccagct ggcagttact gctccaaaga agtggagatt   1620

ttgtttactg cattacacga cacgataaat gagattgcag ccaaggctga tgcagagcaa   1680

ggcttttctt ccaaacaaca gcttatcaac atgtgggtgg agctacttga gagcgccgtg   1740

agagaaaagg actcgctgag tggnaacaaa gtgtcgactc tagaagagta cttatctttc   1800

gcaccaatca ccatcggctg caaactttgc gtcctgacgt ctgtccattt cctcggaatc   1860

aaactgtccg aggaaatctg gacttccgag gagttgagca gtctgtgcag gcacggcaat   1920

gttgtctgca gactgctcaa cgacctcaag acttacgaga gagagcgcga agagaacacg   1980

ctcaacagcg tgagcgtgca gacagtggga ggaggcgttt cggaggaaga ggcggtgacg   2040

aaggtggagg aggtgttgga atttcataga agaaaagtga tgcagctcgc gtgtcgaaga   2100

ggaggaagca gtgttccgag agaatgtaag gagctggtgt ggaagacgtg cacgataggt   2160

tactgcttgt acggtcacga cggaggcgat gagttatcgt ctccgaagga tattctaaag   2220

gacattaatg caatgatgtt tgagcctctc aagtga                              2256
```

<210> SEQ ID NO 7
<211> LENGTH: 800
<212> TYPE: PRT
<213> ORGANISM: Nepeta mussinii

<400> SEQUENCE: 7

```
Met Ser Leu Pro Leu Ser Ser Cys Val Leu Phe Pro Pro Asn Asp Ser
1               5                   10                  15

Arg Phe Pro Val Ser Arg Phe Ser Arg Ala Ser Ala Ser Leu Glu Val
            20                  25                  30

Gly Leu Gln Gly Ala Thr Ser Ala Lys Val Ser Ser Gln Ser Ser Cys
        35                  40                  45

Phe Glu Glu Thr Lys Arg Arg Ile Thr Lys Leu Phe His Lys Asp Glu
    50                  55                  60

Leu Ser Val Ser Thr Tyr Asp Thr Ala Trp Val Ala Met Val Pro Ser
65                  70                  75                  80

Pro Thr Ser Ser Glu Glu Pro Cys Phe Pro Gly Cys Leu Thr Trp Leu
                85                  90                  95

Leu Glu Asn Gln Cys Arg Asp Gly Ser Trp Ala Arg Pro His His His
            100                 105                 110

Ser Leu Leu Lys Lys Asp Val Leu Ser Ser Thr Leu Ala Cys Ile Leu
        115                 120                 125

Ala Leu Lys Lys Trp Gly Val Gly Glu Glu Gln Ile Asn Lys Gly Leu
    130                 135                 140

His Phe Ile Glu Leu Asn Cys Ala Ser Ala Thr Glu Lys Cys Gln Ile
145                 150                 155                 160

Thr Pro Val Gly Phe Asp Ile Ile Phe Pro Ala Met Leu Asp Tyr Ala
                165                 170                 175

Arg Asp Phe Ser Leu Asn Leu Arg Leu Glu Pro Thr Thr Phe Asn Asp
            180                 185                 190

Leu Met Asp Lys Arg Asp Leu Glu Leu Lys Arg Cys Tyr Gln Asn Tyr
        195                 200                 205

Thr Pro Glu Arg Glu Ala Tyr Leu Ala Tyr Ile Val Glu Gly Met Gly
    210                 215                 220
```

-continued

Arg Leu Gln Asp Trp Glu Leu Val Met Lys Tyr Gln Arg Lys Asn Gly
225 230 235 240

Ser Leu Phe Asn Cys Pro Ser Thr Thr Ala Ala Ala Phe Ile Ala Leu
245 250 255

Arg Asp Ser Ala Cys Leu Asn Tyr Leu Asn Leu Ser Leu Lys Lys Phe
260 265 270

Gly Asn Ala Val Pro Ala Val Tyr Pro Leu Asp Ile Tyr Ser Gln Leu
275 280 285

Cys Thr Val Asp Asn Leu Glu Arg Leu Gly Ile Asn Gln Tyr Phe Ile
290 295 300

Ala Glu Ile Gln Ser Val Leu Asp Glu Thr Tyr Arg Cys Trp Ile Gln
305 310 315 320

Gly Asn Glu Asp Ile Phe Leu Asp Thr Ser Thr Cys Ala Leu Ala Phe
325 330 335

Arg Ile Leu Arg Met Asn Gly Tyr Asp Val Thr Ser Asp Ser Leu Thr
340 345 350

Lys Ile Leu Glu Glu Cys Phe Ser Ser Ser Phe Arg Gly Asn Met Thr
355 360 365

Asp Ile Asn Thr Thr Leu Asp Leu Tyr Arg Ala Ser Glu Leu Met Leu
370 375 380

Tyr Pro Asp Glu Lys Asp Leu Glu Lys His Asn Leu Arg Leu Lys Leu
385 390 395 400

Leu Leu Lys Gln Lys Leu Ser Thr Val Leu Ile Gln Ser Phe Gln Leu
405 410 415

Gly Arg Asn Ile Asn Glu Glu Val Lys Gln Thr Leu Glu His Pro Phe
420 425 430

Tyr Ala Ser Leu Asp Arg Ile Ala Lys Arg Lys Asn Ile Glu His Tyr
435 440 445

Asn Phe Asp Asn Thr Arg Ile Leu Lys Thr Ser Tyr Cys Ser Pro Asn
450 455 460

Phe Gly Asn Lys Asp Phe Phe Phe Leu Ser Ile Glu Asp Phe Asn Trp
465 470 475 480

Cys Gln Val Ile His Arg Gln Glu Leu Ala Glu Leu Glu Arg Trp Leu
485 490 495

Ile Glu Asn Arg Leu Asp Glu Leu Lys Phe Ala Arg Ser Lys Ser Ala
500 505 510

Tyr Cys Tyr Phe Ser Ala Ala Ala Thr Phe Phe Ala Pro Glu Leu Ser
515 520 525

Asp Ala Arg Met Ser Trp Ala Lys Ser Gly Val Leu Thr Thr Val Val
530 535 540

Asp Asp Phe Phe Asp Val Gly Gly Ser Met Glu Glu Leu Lys Asn Leu
545 550 555 560

Ile Gln Leu Val Glu Leu Trp Asp Val Asp Ala Ser Thr Lys Cys Ser
565 570 575

Ser His Asn Val His Ile Ile Phe Ser Ala Leu Arg Arg Thr Ile Tyr
580 585 590

Glu Ile Gly Asn Lys Gly Phe Lys Leu Gln Gly Arg Asn Ile Thr Asn
595 600 605

His Ile Ile Asp Ile Trp Leu Asp Leu Leu Asn Ser Met Met Lys Glu
610 615 620

Thr Glu Trp Ala Arg Asp Asn Phe Val Pro Thr Ile Asp Glu Tyr Met
625 630 635 640

Ser Asn Ala Tyr Thr Ser Phe Ala Leu Gly Pro Ile Val Leu Pro Thr

-continued

```
                645                 650                 655

Leu Tyr Leu Val Gly Pro Lys Leu Ser Glu Glu Met Ile Asn His Ser
            660                 665                 670

Glu Tyr His Asn Leu Phe Lys Leu Met Ser Thr Cys Gly Arg Leu Leu
        675                 680                 685

Asn Asp Ile Arg Gly Tyr Glu Arg Glu Leu Lys Asp Gly Lys Leu Asn
    690                 695                 700

Ala Leu Ser Leu Tyr Ile Ile Asn Asn Gly Gly Lys Val Ser Lys Glu
705                 710                 715                 720

Ala Gly Ile Ser Glu Met Lys Ser Trp Ile Glu Ala Gln Arg Arg Glu
                725                 730                 735

Leu Leu Arg Leu Val Leu Glu Ser Asn Lys Ser Val Leu Pro Lys Ser
            740                 745                 750

Cys Lys Glu Leu Phe Trp His Met Cys Ser Val Val His Leu Phe Tyr
        755                 760                 765

Cys Lys Asp Asp Gly Phe Thr Ser Gln Asp Leu Ile Gln Val Val Asn
    770                 775                 780

Ala Val Ile His Glu Pro Ile Ala Leu Lys Asp Phe Lys Val His Glu
785                 790                 795                 800


<210> SEQ ID NO 8
<211> LENGTH: 2403
<212> TYPE: DNA
<213> ORGANISM: Nepeta mussinii

<400> SEQUENCE: 8

atgtctcttc cgctctcctc ttgtgtctta tttcccccca atgactcacg ttttccggtc     60

tcccgctttt ctcgcgcttc agcttctttg gaagtcgggc ttcaaggagc tacttcagca    120

aaagtctcct cacaatcatc gtgttttgag gagacaaaga gaaggataac aaagttgttt    180

cataaggacg aactttcggt ttcgacatat gacacagcat gggttgctat ggtcccttct    240

ccaacttctt cagaggaacc ttgcttccca ggttgtttga cttggttgct tgaaaaccag    300

tgtcgagatg gttcatgggc tcgtccccac catcactctt tgttaaaaaa agatgtcctt    360

tcttctacct tggcatgcat tctcgcactt aaaaaatggg gggttggtga agaacaaatc    420

aacaagggtt tgcattttat agagctaaat tgtgcttcag ctaccgagaa gtgtcaaatt    480

actcccgtgg ggtttgacat tatatttcct gccatgcttg attatgcaag agacttctct    540

ttgaacttgc gtttagagcc aactacgttt aatgatttga tggataaaag ggatttagag    600

ctcaaaaggt gttaccaaaa ttacacaccg gagagggaag catacttggc atatatagtt    660

gaaggaatgg gaagattgca agattgggaa ttggtgatga aatatcaaag aaagaatgga    720

tctcttttca attgtccatc tacaactgca gcagctttta ttgcccttcg ggattctgcg    780

tgcctcaact atctgaattt gtctttgaaa aagttcggga atgcagttcc tgcagtttat    840

cctctagata tatattctca actttgcacg gttgataatc ttgaaaggct ggggatcaac    900

caatatttta tagcagaaat tcagagtgtg ttggatgaaa cgtacagatg ttggatacag    960

ggaaacgaag acatattttt ggacacctca acttgtgctt tagcattccg aatattgaga   1020

atgaatggct atgatgtgac ttcagattca cttacaaaaa tcctagaaga gtgcttttca   1080

agttcctttc gtggaaatat gacagacatt aacacaactc ttgacttata tagggcatca   1140

gaacttatgt tatatccaga tgaaaaggat ctggagaaac ataatttaag gcttaaactc   1200

ttacttaagc aaaaactatc cactgtttta atccaatcat ttcaacttgg aagaaatatc   1260
```

```
aatgaagagg tgaaacagac tctcgagcat cccttttatg caagtttgga taggattgca   1320
aagcggaaaa atatagagca ttacaacttt gataacacaa gaattcttaa aacttcatat   1380
tgttcgccaa attttggcaa caaggatttc ttttttcttt ccatagaaga cttcaattgg   1440
tgtcaagtca tacatcgaca agaactcgca gaacttgaaa gatggttaat tgaaaataga   1500
ttggatgagc tgaagtttgc aaggagtaag tctgcatact gttatttttc tgcggcagca   1560
acttttttttg ctccagaatt gtcggatgcc cgcatgtcat gggctaaaag tggtgttcta   1620
accacagtgg tagatgactt ttttgatgtt ggaggttcta tggaggaatt gaagaactta   1680
attcaattgg ttgaactatg ggatgtggat gctagcacaa aatgctcttc tcataatgtc   1740
catataatat tttcagcact taggcgcacc atctatgaga tagggaacaa aggatttaag   1800
ctacaaggac gtaacattac caatcatata attgacattt ggctagattt actaaactct   1860
atgatgaaag aaaccgaatg ggccagagac aactttgtcc caacaattga tgaatacatg   1920
agcaatgcat atacatcgtt tgctctgggg ccaattgtcc ttccaactct ctatcttgtc   1980
gggcccaagc tctcagaaga gatgattaac cactccgaat accataacct attcaaattg   2040
atgagtacgt gcggacgtct tctaaatgac atccgtggtt atgagagaga actgaaagat   2100
ggtaaattga acgcgttatc attgtacata attaataatg gtggtaaagt aagtaaagaa   2160
gctggcatct cggagatgaa aagttggatc gaggcacaac gaagagagtt actgagatta   2220
gttttggaga gcaacaaaag cgtccttccg aagtcgtgca aggaattgtt ttggcatatg   2280
tgctcagtgg tgcatctatt ctactgcaaa gatgatggat tcacctcgca ggatttgatt   2340
caagttgtaa atgcagttat tcatgaacct attgctctca aggattttaa ggtgcatgaa   2400
taa                                                                 2403
```

<210> SEQ ID NO 9
<211> LENGTH: 579
<212> TYPE: PRT
<213> ORGANISM: Origanum majorana

<400> SEQUENCE: 9

```
Met Ala Ser Leu Ala Phe Thr Pro Gly Ala Ala Thr Phe Ser Gly Asn
1               5                   10                  15

Val Val Arg Arg Arg Lys Asp Asn Phe Pro Val His Gly Phe Pro Thr
            20                  25                  30

Thr Ile Arg Ser Ser Val Ser Val Thr Val Lys Cys Tyr Val Ser Thr
        35                  40                  45

Thr Asn Leu Met Val Lys Ile Lys Glu Lys Phe Lys Gly Lys Asn Val
    50                  55                  60

Asn Ser Leu Thr Val Glu Ala Ala Asp Asp Asp Met Pro Ser Asn Leu
65                  70                  75                  80

Cys Ile Ile Asp Thr Leu Gln Arg Leu Gly Ile Asp Arg Tyr Phe Gln
                85                  90                  95

Pro Gln Val Asp Ser Val Leu Asp His Ala Tyr Lys Leu Trp Gln Gly
            100                 105                 110

Lys Glu Lys Asp Thr Val Tyr Ser Asp Ile Ser Ile His Ala Met Ala
        115                 120                 125

Phe Arg Leu Leu Arg Val Lys Gly Tyr Gln Val Ser Ser Glu Glu Leu
    130                 135                 140

Asp Pro Tyr Ile Asp Val Glu Arg Met Lys Lys Leu Lys Thr Val Asp
145                 150                 155                 160

Val Pro Thr Val Ile Glu Leu Tyr Arg Ala Ala Gln Glu Arg Met Tyr
```

-continued

```
                165                 170                 175

Glu Glu Glu Gly Ser Leu Glu Arg Leu His Val Trp Ser Thr Asn Phe
            180                 185                 190

Leu Met His Gln Leu Gln Ala Asn Ser Ile Pro Asp Glu Lys Leu His
        195                 200                 205

Lys Leu Val Glu Tyr Tyr Leu Lys Asn Tyr His Gly Ile Leu Asp Arg
    210                 215                 220

Val Gly Val Arg Arg Asn Leu Asp Leu Phe Asp Ile Ser His Tyr Pro
225                 230                 235                 240

Thr Leu Arg Ala Arg Val Pro Asn Leu Cys Thr Glu Asp Phe Leu Ser
                245                 250                 255

Phe Ala Lys Glu Asp Phe Asn Thr Cys Gln Ala Gln His Gln Lys Glu
            260                 265                 270

His Glu Gln Leu Gln Arg Trp Phe Glu Asp Cys Arg Phe Asp Thr Leu
        275                 280                 285

Lys Phe Gly Arg Glu Thr Ala Val Gly Ala Ala His Phe Leu Ser Ser
    290                 295                 300

Ala Ile Leu Gly Glu Ser Glu Leu Cys Asn Val Arg Leu Ala Leu Ala
305                 310                 315                 320

Lys His Met Val Leu Val Val Phe Ile Asp Asp Phe Phe Asp His Tyr
                325                 330                 335

Gly Ser Arg Glu Asp Ser Phe Lys Ile Leu His Leu Leu Lys Glu Trp
            340                 345                 350

Lys Glu Lys Pro Ala Gly Glu Tyr Gly Ser Glu Glu Val Glu Ile Leu
        355                 360                 365

Phe Thr Ala Val Tyr Asn Thr Val Asn Glu Leu Ala Glu Met Ala His
    370                 375                 380

Val Glu Gln Gly Arg Asn Ile Lys Gly Phe Leu Ile Glu Leu Trp Val
385                 390                 395                 400

Glu Ile Val Ser Ile Phe Lys Ile Glu Leu Asp Thr Trp Ser Asn Asp
                405                 410                 415

Thr Thr Leu Thr Leu Asp Glu Tyr Leu Ser Ser Ser Trp Val Ser Val
            420                 425                 430

Gly Cys Arg Ile Cys Ile Leu Val Ser Met Gln Leu Leu Gly Val Gln
        435                 440                 445

Leu Thr Asp Glu Met Leu Leu Ser Asp Glu Cys Ile Asn Leu Cys Lys
    450                 455                 460

His Val Ser Met Val Asp Arg Leu Leu Asn Asp Val Gly Thr Phe Glu
465                 470                 475                 480

Lys Glu Arg Lys Glu Asn Thr Gly Asn Ser Val Ser Leu Leu Leu Ala
                485                 490                 495

Ala Ala Val Lys Glu Gly Arg Pro Ile Thr Glu Glu Glu Ala Ile Ile
            500                 505                 510

Lys Ile Lys Lys Met Ala Glu Asn Glu Arg Arg Lys Leu Met Gln Ile
        515                 520                 525

Val Tyr Lys Arg Glu Ser Val Phe Pro Arg Lys Cys Lys Asp Met Phe
    530                 535                 540

Leu Lys Val Cys Arg Ile Gly Cys Tyr Leu Tyr Ala Ser Gly Asp Glu
545                 550                 555                 560

Phe Thr Ser Pro Gln Lys Met Lys Glu Asp Val Lys Ser Leu Ile Tyr
                565                 570                 575

Glu Ser Leu
```

<210> SEQ ID NO 10
<211> LENGTH: 1740
<212> TYPE: DNA
<213> ORGANISM: Origanum majorana

<400> SEQUENCE: 10
atggcgtcgc tcgcgttcac acccggagcc gccactttct ccggcaacgt agttcggagg 60
aggaaagata actttccggt ccacggattt ccgacgacga tcaggtcatc ggtctccgtc 120
accgtcaaat gctacgtcag tacaacgaat ttgatggtga aaatcaaaga gaagttcaag 180
ggtaaaaacg tcaattcgct gacagttgaa gctgctgatg acgatatgcc ctctaatctg 240
tgcataattg acaccctcca acgattggga atcgaccgtt acttccaacc ccaagtcgac 300
tctgttctcg accacgccta caaactatgg caagggaaag agaaagatac ggtgtattcg 360
gacattagta ttcatgcgat ggcatttaga cttttacgag tcaaaggcta tcaagtctct 420
tcggaggaac tggatccata catcgatgtg gagcgaatga agaaactgaa aacagttgat 480
gttccgacgg ttatcgaact gtacagagcg gcacaggaga gaatgtatga agaagaaggt 540
agccttgaga gactccatgt ttggagcacc aacttcctca tgcaccagct gcaggctaac 600
tcaattcctg atgaaaagct acacaaactg gtggaatact acttgaagaa ctaccatggc 660
atactggata gagttggagt tcgacgaaac ctcgacctat tcgacataag ccattatcca 720
acactcagag ctagggttcc gaacctatgt accgaagatt ttctatcgtt cgcgaaggaa 780
gatttcaata cttgccaagc ccaacaccag aaagaacatg agcaactaca aaggtggttc 840
gaagattgta ggttcgatac gttgaagttc ggaagggaga cagccgtagg cgctgctcat 900
tttctatctt cagcaatact tggtgaatct gaactatgta atgttcgtct tgcccttgct 960
aagcatatgg tgcttgtggt attcatcgat gacttcttcg accattatgg ctctagagaa 1020
gactccttca agatcctcca cctcttaaaa gaatggaaag agaagccggc cggagaatac 1080
ggttccgagg aagtcgaaat cctcttcaca gccgtataca atacagtaaa cgagttggcg 1140
gagatggctc atgtcgaaca aggacgtaat atcaaaggat ttctaattga attgtgggtt 1200
gaaatagtgt caattttcaa gatagaactg gatacatgga gcaatgacac aacactaacc 1260
ttggatgagt acttgtcctc ctcatgggtg tcggtcggtt gcagaatctg catcctcgtc 1320
tcaatgcagc tcctcggtgt acaactaacc gacgaaatgc ttctgagcga cgagtgcata 1380
aacctgtgta agcatgtctc gatggtcgat cgcctcctca acgacgtcgg aacattcgag 1440
aaggaacgga aggagaatac aggaaacagt gtgagccttc tgctagcagc agctgtgaaa 1500
gaaggaaggc ctattaccga agaggaagct attattaaaa ttaaaaaaat ggcggaaaac 1560
gagaggagga aactaatgca gattgtgtat aaaagagaga gtgttttccc cagaaaatgc 1620
aaggatatgt tcttgaaggt gtgtagaatt gggtgctatc tatacgcgag cggcgacgaa 1680
tttacgtctc ctcagaaaat gaaggaagat gtgaaatcct taatttatga atccttgtag 1740

<210> SEQ ID NO 11
<211> LENGTH: 563
<212> TYPE: PRT
<213> ORGANISM: Origanum majorana

<400> SEQUENCE: 11

Met Ser Leu Ala Phe Ser His Val Ser Thr Phe Phe Ser Gly Gln Arg
1 5 10 15

Val Val Gly Ser Arg Arg Glu Ile Ile Pro Val Asn Gly Val Pro Thr
20 25 30

-continued

```
Thr Ala Asn Lys Pro Ser Phe Ala Val Lys Cys Asn Leu Thr Thr Lys
        35                  40                  45

Asp Leu Met Val Lys Met Lys Glu Lys Leu Lys Gly Gln Asp Gly Asn
    50                  55                  60

Leu Thr Val Gly Val Ala Asp Met Pro Ser Ser Leu Cys Val Ile Asp
65                  70                  75                  80

Thr Leu Glu Arg Leu Gly Val Asp Arg Tyr Phe Arg Ser Glu Ile His
                85                  90                  95

Val Ile Leu His Asp Thr Tyr Arg Leu Trp Gln Gln Lys Asp Lys Asp
            100                 105                 110

Ile Cys Ser Asn Val Thr Thr His Ala Met Ala Phe Arg Leu Leu Arg
        115                 120                 125

Val Asn Gly Tyr Glu Val Ser Ser Glu Glu Leu Ala Pro Tyr Ala Asn
    130                 135                 140

Leu Glu His Phe Ser Gln Gln Lys Val Asp Thr Ala Met Ala Ile Glu
145                 150                 155                 160

Leu Tyr Arg Ala Ala Gln Glu Arg Ile His Glu Asp Glu Ser Gly Leu
                165                 170                 175

Asp Lys Ile Leu Ala Trp Thr Thr Thr Phe Leu Glu Gln Gln Leu Leu
            180                 185                 190

Thr Asn Ser Ile Leu Asp Asn Lys Leu His Lys Leu Val Glu Tyr Tyr
        195                 200                 205

Leu Asn Asn Tyr His Gly Gln Thr Asn Arg Val Gly Ala Arg Arg His
    210                 215                 220

Leu Asp Leu Tyr Glu Met Ser His Tyr Gln Asn Leu Lys Pro Ser His
225                 230                 235                 240

Ser Leu Cys Asn Glu Asp Leu Leu Ala Phe Ala Lys Gln Gly Phe Arg
                245                 250                 255

Asp Phe Gln Ile Gln Gln Gln Lys Glu Phe Glu Gln Leu Gln Arg Trp
            260                 265                 270

Tyr Glu Asp Cys Arg Leu Asp Lys Leu Ser Tyr Gly Arg Asp Val Val
        275                 280                 285

Lys Ile Ser Ser Phe Met Ala Ser Ile Leu Met Asp Asp Pro Glu Leu
    290                 295                 300

Ala Asp Val Arg Leu Ser Ile Ala Lys Gln Met Val Leu Val Thr Arg
305                 310                 315                 320

Ile Asp Asp Phe Phe Asp His Gly Gly Ser Arg Glu Asp Ser Tyr Lys
                325                 330                 335

Ile Ile Glu Leu Val Lys Glu Trp Lys Glu Lys Ala Glu Tyr Asp Ser
            340                 345                 350

Glu Glu Val Lys Ile Leu Phe Thr Ala Val Tyr Thr Thr Val Asn Glu
        355                 360                 365

Leu Ala Glu Ala Cys Val Gln Gln Gly Arg Asn Ser Thr Thr Val Lys
    370                 375                 380

Glu Phe Leu Val Gln Leu Trp Ile Glu Ile Leu Ser Ala Phe Lys Val
385                 390                 395                 400

Glu Leu Asp Thr Trp Ser Asp Gly Thr Glu Val Ser Leu Asp Glu Tyr
                405                 410                 415

Leu Ser Trp Ser Trp Ile Ser Asn Gly Cys Arg Val Ser Ile Val Thr
            420                 425                 430

Thr Met His Leu Leu Pro Thr Lys Leu Cys Ser Asp Glu Met Leu Arg
        435                 440                 445
```

-continued

```
Ser Glu Glu Cys Lys Asp Leu Cys Arg His Val Ser Met Val Gly Arg
    450                 455                 460

Leu Leu Asn Asp Ile His Ser Phe Glu Lys Glu His Glu Glu Asn Thr
465                 470                 475                 480

Gly Asn Ser Val Ser Ile Leu Val Ala Gly Glu Asp Thr Glu Glu Glu
                485                 490                 495

Ala Ile Gly Lys Ile Lys Glu Ile Val Glu Tyr Glu Arg Arg Lys Leu
            500                 505                 510

Met Gln Ile Val Tyr Lys Arg Gly Thr Ile Leu Pro Arg Glu Cys Lys
        515                 520                 525

Asp Ile Phe Leu Lys Ala Cys Arg Ala Thr Phe Tyr Val Tyr Ser Ser
    530                 535                 540

Thr Asp Glu Phe Thr Ser Pro Arg Gln Val Met Glu Asp Met Lys Thr
545                 550                 555                 560

Leu Ser Ser
```

<210> SEQ ID NO 12
<211> LENGTH: 1692
<212> TYPE: DNA
<213> ORGANISM: Origanum majorana

<400> SEQUENCE: 12

```
atgtcactcg ccttcagcca tgttagtacc tttttctccg gccaaagagt cgtcggaagc      60

aggagagaga ttattccagt taacggagtt ccgacgacgg ccaataagcc gtcgttcgcc     120

gttaagtgca accttactac aaaggatttg atggtgaaaa tgaaggagaa gttgaagggg     180

caagacggta atttgactgt cggagtagcc gatatgccct ctagcctgtg cgtgatcgac     240

actcttgaaa ggttgggagt tgaccgatac ttccgatctg aaatccacgt tattctacac     300

gacacttacc ggttatggca acaaaaggac aaagatatat gttccaacgt tactactcat     360

gcaatggcgt ttagacttct gagagtgaat ggatacgagg tttcatcaga ggaactggct     420

ccatatgcta acctagagca ctttagccag caaaaagttg atactgcaat ggctatagag     480

ctctacagag cagcacagga gagaatacac gaagacgaga gcggtctcga caaaatactt     540

gcttggacca ccacttttct cgagcaacag ctgctcacta actccattct tgacaataaa     600

ttgcataaac tggtggagta ctacttgaac aactaccacg gccaaacgaa tagggtcgga     660

gctagacgac acctcgacct atatgagatg agccattacc aaaatctaaa accttcacat     720

agtctatgca atgaagacct tctagcattt gcaaagcaag gttttcgaga ttttcaaatc     780

cagcagcaga aagaattcga gcaactgcaa aggtggtatg aagattgcag gttggacaag     840

ttgagttatg ggagagatgt agtaaaaatt tctagtttca tggcttcaat attgatggat     900

gatccagaat tagccgatgt tcgtctctcc atcgccaaac agatggtgct cgtgacacgt     960

atcgatgatt tcttcgacca cggtggctct agagaagact cctacaagat cattgaacta    1020

gtaaaagaat ggaaggagaa ggcagaatac gattccgagg aagtaaaaat cctttttaca    1080

gcagtataca ccacagtaaa tgagctagca gaggcttgtg ttcaacaagg aaggaatagt    1140

actactgtca aagaattcct agttcagttg tggattgaaa tactatcagc tttcaaggtc    1200

gagctagata cgtggagcga tggcacggaa gtaagcctgg acgagtactt gtcgtggtcg    1260

tggatttcga atggctgcag agtgtctata gtaacgacga tgcatttgct ccctacgaaa    1320

ttatgcagtg atgaaatgct taggagtgaa gagtgcaagg atttgtgtag gcatgtttct    1380

atggttggcc gcttgctcaa cgacatccac tcttttgaga aggagcatga ggagaatacg    1440
```

-continued

```
ggaaacagtg tgagcattct agtagcaggt gaggataccg aagaggaagc tattggaaag   1500

atcaaagaga tagttgagta tgagaggaga aaattgatgc aaattgtgta caagagagga   1560

accattctcc caagagaatg caaagacata ttcttgaagg cgtgtagggc tacattttac   1620

gtgtactcga gcacggatga gtttacgtct cctcgacaag tgatggaaga tatgaaaacc   1680

ctaagctcct ag                                                       1692
```

<210> SEQ ID NO 13
<211> LENGTH: 580
<212> TYPE: PRT
<213> ORGANISM: Origanum majorana

<400> SEQUENCE: 13

```
Met Val Ser Ala Cys Leu Lys Leu Lys Asn Asn Pro Phe Leu Asp His
1               5                   10                  15

Arg Phe Arg Lys Ser Ser Asn Gly Phe Ser Val Asn Phe Pro Ala Thr
            20                  25                  30

Met Leu Thr Thr Val Lys Cys Ser Arg Asp Asn Ser Glu Asp Leu Ile
        35                  40                  45

Ala Lys Ile Lys Glu Arg Met Asn Glu Lys Phe Val Thr Val Pro Ala
    50                  55                  60

Arg Glu Tyr Ser Val Ile Glu His Arg Asn Pro Lys Pro Ala Trp Cys
65                  70                  75                  80

Gly Gly Leu Gln Ser Lys Thr Val Ile Glu Glu Glu Val Cys Ser Arg
                85                  90                  95

Leu Phe Leu Val Glu His Leu Gln Asp Leu Gly Val Asp Arg Phe Phe
            100                 105                 110

Gln Ser Glu Ile Gln His Ile Leu His His Thr Phe Arg Leu Trp Gln
        115                 120                 125

Gln Lys Asp Glu Gln Val Phe Lys Asp Val Thr Cys Arg Ala Met Ala
    130                 135                 140

Phe Arg Leu Leu Arg Leu Glu Gly Tyr His Val Ser Ser Gly Glu Leu
145                 150                 155                 160

Gly Glu Tyr Val Asp Glu Glu Lys Phe Phe Arg Thr Val Arg Leu Glu
                165                 170                 175

Trp Arg Ser Thr Asp Thr Ile Leu Glu Leu Tyr Lys Ala Ser Gln Val
            180                 185                 190

Arg Leu Pro Glu Asp Asp Asn Asp Asn Ser Asn Ile Leu Lys Asn Leu
        195                 200                 205

His Glu Trp Thr Phe Ile Phe Leu Lys Glu Gln Leu Arg Arg Lys Thr
    210                 215                 220

Ile Leu Asp Lys Gly Leu Glu Arg Lys Val Glu Phe Tyr Leu Lys Asn
225                 230                 235                 240

Tyr His Gly Ile Leu Asp Ala Val Lys His Arg Arg Ser Leu Asp His
                245                 250                 255

Thr Arg Phe Trp Lys Thr Thr Ala Tyr Asn Pro Ala Val Tyr Asp Glu
            260                 265                 270

Asp Leu Phe Arg Leu Ser Ala Gln Asp Phe Met Ala Arg Gln Ala Gln
        275                 280                 285

Ser Gln Lys Glu Leu Glu Met Leu Leu Lys Trp Tyr Asp Glu Cys Arg
    290                 295                 300

Leu Asp Lys Met Glu Tyr Gly Arg Asn Val Ile His Val Ser His Phe
305                 310                 315                 320

Leu Asn Ala Asn Asn Phe Pro Asp Pro Arg Leu Ser Glu Thr Arg Leu
```

-continued

```
                325                 330                 335

Ser Phe Ala Lys Thr Met Thr Leu Val Thr Arg Leu Asp Asp Phe Phe
            340                 345                 350

Asp His His Gly Ser Arg Glu Asp Ser Val Leu Ile Ile Glu Leu Ile
        355                 360                 365

Arg Gln Trp Asn Glu Pro Ser Thr Ile Thr Thr Ile Phe Pro Ser Glu
    370                 375                 380

Glu Val Glu Ile Leu Tyr Ser Ala Leu His Ser Thr Val Thr Asp Ile
385                 390                 395                 400

Ala Glu Lys Ala Tyr Pro Ile Gln Gly Arg Cys Ile Lys Ser Leu Ile
                405                 410                 415

Ile His Leu Trp Val Glu Ile Leu Ser Ser Phe Met Ser Glu Met Asp
            420                 425                 430

Ser Cys Thr Ala Glu Thr Gln Pro Asp Phe His Glu Tyr Leu Gly Phe
        435                 440                 445

Ala Trp Ile Ser Ile Gly Cys Arg Ile Cys Ile Leu Ile Ala Ile His
    450                 455                 460

Phe Leu Gly Glu Lys Val Ser Gln Gln Met Val Met Gly Ala Glu Cys
465                 470                 475                 480

Thr Glu Leu Cys Arg His Val Ser Thr Ile Ala Arg Leu Leu Asn Asp
                485                 490                 495

Leu Gln Thr Phe Lys Lys Glu Arg Glu Glu Arg Lys Val Asn Ser Val
            500                 505                 510

Ile Ile Gln Leu Lys Gly Asp Lys Ile Ser Glu Glu Val Ala Val Ser
        515                 520                 525

Asn Ile Glu Arg Met Val Glu Tyr His Arg Lys Glu Leu Leu Lys Met
    530                 535                 540

Val Val Arg Arg Glu Gly Ser Leu Val Pro Lys Arg Cys Lys Asp Val
545                 550                 555                 560

Phe Trp Lys Ser Cys Asn Ile Ala Tyr Tyr Leu Tyr Ala Phe Thr Asp
                565                 570                 575

Glu Phe Thr Ser
            580
```

<210> SEQ ID NO 14
<211> LENGTH: 1815
<212> TYPE: DNA
<213> ORGANISM: Origanum majorana

<400> SEQUENCE: 14

```
atggtatctg catgtctaaa actcaaaaat aatcctttct tggaccatcg attcaggaaa     60

agcagcaatg gattttcagt taattttccg gcgaccatgc tcaccactgt caagtgcagc    120

cgcgataatt cagaagactt gatagcaaag ataaaagaaa ggatgaatga aaaatttgtt    180

acggtgccgg cgagggaata ttccgtcatt gagcatcgga atccgaagcc ggcgtggtgc    240

ggtggtttgc aatccaaaac agtaatagaa gaagaagtgt gcagccgtct gtttctggtc    300

gaacaccttc aagatttagg agtagaccgc ttctttcaat cagaaatcca acatattcta    360

catcacacat tcagattatg gcagcaaaaa gatgaacaag tttttaaaga cgtgacatgt    420

cgcgccatgg cattcagact cctgcgtctc gaaggttatc atgtctcgtc aggagaattg    480

ggggagtatg ttgatgagga aaaattcttt agaacggtaa ggttagaatg gagaagtacg    540

gatacaattc ttgagctgta caaagcatca caggtaagac tacctgaaga cgacaacgac    600

aattccaata tcctcaaaaa cttgcacgaa tggaccttca tatttttgaa ggagcagttg    660
```

```
cggcgtaaaa ctattcttga taaaggttta gagagaaagg tagaatttta cttgaagaat    720

taccacggca tattagacgc ggttaagcat agacgaagcc tcgatcacac acgattctgg    780

aaaactactg cgtataaccc tgcagtgtat gatgaggatc ttttccgatt gtcggcccaa    840

gatttcatgg ctcgccaagc tcagagccag aaggaacttg agatgttgct caagtggtac    900

gatgaatgta gactggacaa gatggagtat gggcgaaacg tgatacacgt ttcccatttc    960

ttaaacgcaa acaacttccc cgatcctcgc ctgtccgaaa ctcgtctatc ctttgcgaaa   1020

accatgactc tcgtcacgcg tttggatgat ttcttcgatc accatggctc tagagaagat   1080

tcggtcctca tcatcgaatt aataaggcag tggaatgagc cttcaactat tacaacaata   1140

ttcccctccg aagaagtgga gattctctac tctgcactcc actccaccgt aacagatata   1200

gcagagaagg cttatcccat ccagggtcgc tgcatcaaat cgctcataat tcatctgtgg   1260

gtcgagatac tgtcgagctt catgagcgaa atggactcgt gcaccgcgga aactcagccg   1320

gactttcacg agtacttagg gtttgcatgg atctcgatcg gctgcagaat ctgcattctc   1380

atagctatac atttcttggg ggagaaggta tctcaacaaa tggttatggg tgctgagtgc   1440

accgagttat gtaggcacgt ttctacgatc gcacgccttc tcaacgatct ccaaaccttt   1500

aagaaggaga gagaagagag gaaggtaaac agcgtgataa tccagctcaa aggggataag   1560

atatcggagg aggtggccgt gtcgaatata gagagaatgg ttgaatatca caggaaagag   1620

ctgctgaaga tggtggttcg gagagaagga agcttggttc ctaagaggtg taaggacgtg   1680

ttctggaaat cctgcaacat tgcttactat ctgtacgctt ttacagatga attcacttcg   1740

cctcaacaaa tgaaggaaga tatgaaacta ctctttcgtg atccaatcaa ctgcgttcct   1800

tcaattcctt catga                                                    1815

<210> SEQ ID NO 15
<211> LENGTH: 584
<212> TYPE: PRT
<213> ORGANISM: Perovskia atriplicifolia

<400> SEQUENCE: 15

Met Leu Leu Ala Phe Asn Ile Ser Asp Val Pro Leu Ser Gln His Arg
1               5                   10                  15

Val Ile Leu Ser Arg Arg Glu His Phe Pro Arg His Ala Phe Gln Glu
            20                  25                  30

Phe Pro Met Ile Ala Ala Thr Lys Ser Ser Val Asn Ala Ile Cys Ser
        35                  40                  45

Leu Ala Thr Pro Thr Asp Leu Met Gly Lys Ile Lys Glu Lys Phe Lys
    50                  55                  60

Ala Lys Asp Gly Asp Pro Leu Ala Ala Ala Ala Ile Gln Leu Ala Ala
65                  70                  75                  80

Asp Ile Pro Ser Ser Leu Cys Ile Ile Asp Thr Leu Gln Arg Leu Gly
                85                  90                  95

Val Asp Arg Tyr Phe Gln Ser Glu Ile Asp Ser Ile Leu Glu Glu Thr
            100                 105                 110

His Lys Leu Trp Lys Val Lys Asp Arg Asp Ile Tyr Ser Glu Val Thr
        115                 120                 125

Thr His Ala Met Ala Phe Arg Leu Leu Arg Val Lys Gly Tyr Glu Val
    130                 135                 140

Ser Ser Glu Glu Leu Ala Pro Tyr Ala Glu Gln Glu Arg Phe Asp Leu
145                 150                 155                 160
```

-continued

```
Gln Thr Ile Asp Leu Ala Thr Val Ile Glu Leu Tyr Arg Ala Ala Gln
                165                 170                 175

Glu Arg Thr Cys Glu Glu Asn Asp Asn Ser Leu Glu Lys Leu Leu Ala
            180                 185                 190

Trp Thr Thr Thr Phe Leu Lys His Gln Leu Leu Thr Asn Ser Ile Pro
        195                 200                 205

Asp Thr Lys Leu His Lys Gln Val Glu Tyr Tyr Leu Lys Asn Tyr His
    210                 215                 220

Gly Ile Leu Asp Arg Met Gly Val Arg Arg Ser Leu Asp Leu Tyr Asp
225                 230                 235                 240

Ile Ser His Tyr Arg Pro Leu Arg Ala Arg Phe Pro Asn Leu Cys Asn
                245                 250                 255

Glu Asp Phe Leu Ser Phe Ala Arg Gln Asp Phe Ser Met Cys Gln Ala
            260                 265                 270

Gln His Gln Lys Glu Leu Glu Gln Leu Gln Arg Trp Tyr Ser Asp Cys
        275                 280                 285

Arg Leu Asp Ala Leu Leu Lys Phe Gly Arg Asn Val Val Arg Val Ser
    290                 295                 300

Ser Phe Leu Thr Ser Ala Ile Ile Gly Glu Pro Glu Leu Ser Glu Val
305                 310                 315                 320

Arg Leu Val Phe Ala Lys His Ile Ile Leu Val Thr Leu Ile Asp Asp
                325                 330                 335

Leu Phe Asp His Gly Gly Thr Arg Glu Glu Ser Tyr Lys Ile Leu Glu
            340                 345                 350

Leu Val Thr Glu Trp Lys Glu Lys Thr Ala Ala Glu Tyr Gly Ser Glu
        355                 360                 365

Glu Val Glu Ile Leu Phe Thr Ala Val Tyr Asn Thr Val Asn Glu Leu
    370                 375                 380

Val Glu Arg Ala His Val Glu Gln Gly Arg Ser Val Lys Glu Phe Leu
385                 390                 395                 400

Ile Lys Leu Trp Val Gln Ile Leu Ser Ile Phe Lys Ile Glu Leu Asp
                405                 410                 415

Thr Trp Ser Asp Glu Thr Ala Leu Thr Leu Asp Glu Tyr Leu Ser Ser
            420                 425                 430

Ser Trp Val Ser Ile Gly Cys Arg Ile Cys Ile Leu Met Ser Met Gln
        435                 440                 445

Phe Ile Gly Ile Lys Leu Thr Asp Glu Met Leu Leu Ser Glu Glu Cys
    450                 455                 460

Thr Asp Leu Cys Arg His Val Ser Met Val Asp Arg Leu Leu Asn Asp
465                 470                 475                 480

Val Gln Thr Phe Glu Lys Glu Arg Lys Glu Asn Thr Gly Asn Ser Val
                485                 490                 495

Ser Leu Leu Leu Ala Ala Asn Lys Asp Val Thr Glu Glu Glu Ala Ile
            500                 505                 510

Arg Arg Ala Lys Glu Met Ala Glu Cys Asn Arg Arg Gln Leu Met Gln
        515                 520                 525

Ile Val Tyr Lys Thr Gly Thr Ile Phe Pro Arg Lys Cys Lys Asp Met
    530                 535                 540

Phe Leu Lys Val Cys Arg Ile Gly Cys Tyr Leu Tyr Ala Ser Gly Asp
545                 550                 555                 560

Glu Phe Thr Ser Pro Gln Gln Met Met Glu Asp Met Lys Ser Leu Val
                565                 570                 575

Tyr Glu Pro Leu Tyr Leu Pro Asn
```

580

<210> SEQ ID NO 16
<211> LENGTH: 1755
<212> TYPE: DNA
<213> ORGANISM: Perovskia atriplicifolia

<400> SEQUENCE: 16
atgttacttg cgttcaacat aagcgatgtc cctctctcgc agcatagagt aattctgagc 60
aggagggaac attttccacg tcatgcattc caggaatttc cgatgatcgc cgctactaag 120
tcatctgtta atgccatttg cagcctcgct actccaactg atttgatggg aaaaataaaa 180
gagaagttca aggccaagga cggcgatcct cttgccgccg cggctattca actcgcggcg 240
gatataccct cgagtctgtg tataatcgac accctccaga ggttgggagt cgaccgatac 300
ttccaatccg aaatcgactc tattctagag gaaacacaca agttatggaa agtgaaagat 360
agagatatat actctgaggt tactactcat gcaatggcgt ttagacttct gcgagtgaag 420
ggatatgaag tttcatcaga ggaactagct ccgtatgctg agcaagagcg ctttgacctg 480
caaacgattg atctggcgac ggttatcgag ctttacagag cagcacagga gagaacatgc 540
gaagaaaacg acaacagtct tgagaaacta cttgcttgga ccaccacctt tctcaagcac 600
caattgctca ccaactccat acctgacacc aaattgcaca aacaggtgga atactacttg 660
aagaactacc acgggatatt agatagaatg ggagttagac gaagcctcga cctatacgac 720
ataagccatt atcgacctct gagagcaaga ttccctaatc tgtgtaatga agatttccta 780
tcatttgcga ggcaagattt cagtatgtgc caagcccaac accagaagga acttgagcaa 840
ctgcaaaggt ggtattctga ttgtaggttg gacgcgttgt tgaagtttgg aagaaatgta 900
gtgcgcgttt ctagctttct gacttcagca attattggtg aacccgaatt gtctgaagtt 960
cgactagtct ttgccaaaca tattattctc gttacactta ttgatgattt attcgatcat 1020
ggtggaacta gagaagagtc atacaagatc cttgaattag taacagaatg gaaagagaag 1080
accgcagcag aatatggttc cgaggaagtt gaaatccttt ttacagcggt ctacaacaca 1140
gtaaatgagt tggtagagag ggctcatgtc gaacaagggc gcagtgtcaa agaatttctt 1200
attaaactgt gggttcaaat actatcaatt ttcaagatag aattagatac atggagcgat 1260
gagactgcgc taaccttgga tgaatacttg tcttcgtcgt gggtgtcaat tggttgcaga 1320
atctgcattc tcatgtcgat gcaattcatc ggtataaaat taactgatga aatgcttctg 1380
agtgaagagt gcactgattt gtgtaggcat gtttcgatgg ttgaccggct gctcaacgat 1440
gtgcaaacct tcgagaagga acgcaaagaa aatacaggaa acagtgtaag ccttctgcta 1500
gcagctaaca aagatgttac tgaagaggaa gcaattagaa gagcaaaaga aatggcggaa 1560
tgcaacagga gacaactgat gcagattgtg tataaaacag gaaccatttt cccaagaaaa 1620
tgcaaagata tgtttctcaa ggtatgcagg attggctgtt atttgtatgc aagcggcgac 1680
gaattcacat ctccacaaca aatgatggaa gatatgaaat ccttggttta tgaacccctc 1740
tacctaccta attaa 1755

<210> SEQ ID NO 17
<211> LENGTH: 593
<212> TYPE: PRT
<213> ORGANISM: Perovskia atriplicifolia

<400> SEQUENCE: 17

Met Ser Leu Thr Phe Asn Ala Gly Val Val Arg Phe Ser Ser His Arg

-continued

```
1               5                   10                  15

Val Arg Ser Thr Lys Asp Cys Phe Thr Val Tyr Gly Phe Pro Met Ile
            20                  25                  30

Ala Asn Lys Ala Ala Phe Ala Val Lys Cys Ser Leu Thr Pro Thr Asp
        35                  40                  45

Leu Met Gly Arg Val Glu Glu Lys Phe Lys Gly Lys Asn Gly Asn Ser
    50                  55                  60

Leu Ala Ala Ser Thr Thr Val Glu Ser Ala Asp Ile Pro Ser Asn Leu
65                  70                  75                  80

Cys Ile Ile Asp Thr Leu Gln Arg Leu Gly Val Asp Arg Tyr Phe Gln
                85                  90                  95

Thr Glu Ile Asn Ala Ile Leu Glu Asp Thr Tyr Arg Leu Trp Glu Arg
            100                 105                 110

Lys Asp Lys Asp Ile Tyr Ser Asp Ala Thr Thr His Ala Met Ala Phe
        115                 120                 125

Arg Leu Leu Arg Val Lys Gly Tyr Glu Val Ser Ser Glu Glu Leu Ala
    130                 135                 140

Pro Tyr Ala Asp Gln Glu Cys Val Asn Val Gln Thr Ala Asp Val Ala
145                 150                 155                 160

Thr Val Ile Glu Leu Tyr Arg Ala Ala Gln Val Arg Ile Ser Glu Glu
                165                 170                 175

Glu Ser Ser Leu Lys Lys Leu His Ala Trp Thr Thr Thr Phe Leu Lys
            180                 185                 190

Tyr Gln Leu Gln Ser Asn Ser Ile Pro Glu Lys Lys Leu His Lys Leu
        195                 200                 205

Val Glu Tyr Tyr Leu Lys Asn Tyr His Gly Ile Leu Asp Arg Met Gly
    210                 215                 220

Val Arg Met Asp Leu Asp Leu Phe Asp Ile Ser His Tyr Arg Thr Leu
225                 230                 235                 240

Gln Ala Ser Asp Arg Phe Ser Ser Leu Arg Asn Glu Asp Phe Leu Glu
                245                 250                 255

Phe Ala Arg Gln Asp Phe Asn Ile Cys Gln Ala Lys His Gln Lys Glu
            260                 265                 270

Leu Gln Gln Leu Gln Arg Trp Tyr Ala Asp Cys Arg Leu Asp Thr Leu
        275                 280                 285

Lys Phe Gly Arg Asp Val Val Arg Val Ala Asn Phe Leu Thr Ser Ala
    290                 295                 300

Ile Phe Gly Glu Pro Glu Leu Ser Asp Ala Arg Leu Ile Phe Ala Lys
305                 310                 315                 320

His Ile Val Leu Val Thr Cys Ile Asp Glu Phe Phe Asp His Gly Gly
                325                 330                 335

Ser Lys Glu Glu Ser Tyr Lys Ile Leu Glu Leu Val Glu Glu Trp Lys
            340                 345                 350

Glu Lys Pro Thr Gly Glu Tyr Gly Cys Glu Glu Val Glu Ile Leu Phe
        355                 360                 365

Thr Ala Val Tyr Ser Thr Val Asn Glu Leu Ala Glu Met Ala His Val
    370                 375                 380

Glu Gln Gly Arg Ser Val Lys Glu Phe Leu Val Lys Leu Trp Val Gln
385                 390                 395                 400

Ile Leu Ser Ile Phe Lys Ile Glu Leu Asp Thr Trp Ser Asp Asp Thr
                405                 410                 415

Glu Leu Thr Leu Asp Ser Tyr Leu Asn Asn Ser Trp Val Ser Ile Gly
            420                 425                 430
```

```
Cys Arg Ile Cys Ile Leu Met Ser Met Gln Phe Ala Gly Val Lys Leu
        435                 440                 445

Ser Asp Glu Met Leu Leu Ser Glu Glu Cys Val Asp Leu Cys Arg His
    450                 455                 460

Val Ser Met Val Asp Arg Leu Leu Asn Asp Val Gln Thr Phe Glu Lys
465                 470                 475                 480

Glu Arg Lys Glu Asn Thr Gly Asn Ser Val Ser Leu Leu Gln Ala Ala
                485                 490                 495

Ala Glu Arg Glu Gly Arg Ala Ile Thr Glu Glu Glu Ala Ile Thr Gln
            500                 505                 510

Ile Lys Glu Leu Ala Glu Tyr His Arg Arg Lys Leu Met Gln Ile Val
        515                 520                 525

Tyr Lys Thr Asp Thr Ile Phe Pro Arg Lys Cys Lys Asp Met Phe Leu
    530                 535                 540

Lys Val Cys Arg Ile Gly Cys Tyr Leu Tyr Ala Ser Gly Asp Glu Phe
545                 550                 555                 560

Thr Thr Pro Gln Gln Met Met Glu Asp Met Lys Ser Leu Val Tyr Gln
                565                 570                 575

Pro Leu Thr Val Asp Asp Met Ser Ala Lys Glu Leu Thr Ser Val Arg
            580                 585                 590

Asn
```

<210> SEQ ID NO 18
<211> LENGTH: 1782
<212> TYPE: DNA
<213> ORGANISM: Perovskia atriplicifolia

<400> SEQUENCE: 18

```
atgtcactca ctttcaacgc tggagtcgtc cgtttctcca gccaccgcgt tcggagcacg     60

aaagattgct ttacagttta cggatttccg atgattgcaa ataaggcagc tttcgcagtt    120

aaatgcagcc ttactccaac cgatttgatg gggagagtag aggagaagtt caagggcaaa    180

aatggtaatt cactagcagc ctcgacgacg gttgaatccg cggatatacc ctcgaacctg    240

tgtataatcg acaccctcca aagattggga gtcgaccgat actttcaaac tgaaatcaat    300

gccattctag aggacactta cagattatgg gaacgaaaag acaaagacat atattccgat    360

gccacaactc acgcgatggc gtttaggtta ctacgagtga aaggatacga agtttcatca    420

gaggaactgg ctccttacgc tgatcaagag tgcgtgaacg tgcaaacggc tgatgtggca    480

acagttatcg agctttacag agcagcgcag gtgagaataa gcgaagaaga gagcagtctt    540

aagaagcttc atgcttggac caccaccttt ctcaaatatc agttgcagag taactccata    600

cctgaaaaga aactgcacaa actggtggaa tattacttga agaactacca tggcatattg    660

gatagaatgg gagttcgaat ggacctcgac ttattcgaca tcagccatta tcgaactcta    720

caagcttccg ataggttctc tagtctgcgt aacgaagatt ttctagagtt tgcaaggcaa    780

gatttcaata tctgccaagc caagcaccag aaagaactcc aacaactgca aaggtggtat    840

gcagattgca ggctcgacac cttgaagttc gggagagacg tcgtacgcgt tgctaatttt    900

ctgacttcag caatctttgg cgaacccgag ctatccgatg ctcgtctgat ctttgccaag    960

catatcgtgc tcgtaacatg tatcgatgaa ttcttcgatc atggtgggtc taaagaagag   1020

tcctacaaga tccttgaatt agtagaagaa tggaaagaga agccaactgg agaatatggg   1080

tgtgaggagg ttgagatcct tttcacagca gtgtacagta cagtgaatga gttggcagag   1140
```

-continued

```
atggctcatg tcgaacaagg acgtagtgtg aaagagtttc tagttaaact gtgggtgcag   1200

atactgtcga ttttcaagat agaactggat acatggagtg atgacacgga actgacgttg   1260

gacagctact tgaacaactc gtgggtgtcg atcggatgca gaatctgcat tctcatgtcg   1320

atgcagttcg ccggtgtaaa actgtccgac gaaatgcttc tgagtgaaga gtgtgttgac   1380

ttgtgcaggc acgtctccat ggtcgatcgc ctcctgaacg atgtgcaaac tttcgagaag   1440

gaacgcaagg aaaatacagg aaacagtgtg agccttctgc aagcagcagc tgagagagaa   1500

ggaagagcca ttacagaaga ggaagctatt acacagatca aagaattggc tgaataccac   1560

aggagaaaac tgatgcagat tgtgtacaaa acagacacca ttttcccaag aaaatgcaaa   1620

gatatgttct tgaaggtgtg caggattggg tgctatctgt acgcaagtgg agacgaattc   1680

acaactccac aacaaatgat ggaagacatg aaatcattgg tttatcaacc cctaacagtt   1740

gatgacatga gtgccaaaga attgacttct gtgagaaact ag                      1782
```

```
<210> SEQ ID NO 19
<211> LENGTH: 590
<212> TYPE: PRT
<213> ORGANISM: Salvia officinalis

<400> SEQUENCE: 19

Met Ser Leu Ala Phe Asn Ala Ala Val Ala Thr Phe Ser Gly His Arg
1               5                   10                  15

Ile Arg Ser Arg Arg Glu Ile Leu Pro Gly Gln Gly Phe Pro Met Ile
            20                  25                  30

Thr Asn Lys Ser Ser Phe Ala Val Lys Cys Asn Leu Thr Thr Thr Asp
        35                  40                  45

Leu Met Gly Lys Ile Thr Glu Lys Phe Lys Gly Arg Asp Ser Asn Phe
    50                  55                  60

Ser Ala Ala Thr Ala Val Gln Pro Ala Ala Asp Ile Pro Ser Asn Leu
65                  70                  75                  80

Cys Ile Ile Asp Thr Leu Gln Arg Leu Gly Val Asp Arg Tyr Phe Gln
                85                  90                  95

Ser Glu Ile Asp Thr Ile Leu Glu Asp Thr Tyr Arg Leu Trp Gln Arg
            100                 105                 110

Lys Glu Arg Glu Ile Phe Ser Asp Ile Thr Ile His Ala Met Ala Phe
        115                 120                 125

Arg Leu Leu Arg Val Lys Gly Tyr Val Val Ser Ser Glu Glu Leu Ala
    130                 135                 140

Pro Tyr Ala Asp Gln Glu Arg Ile Asn Leu Gln Arg Ile Asp Val Ala
145                 150                 155                 160

Thr Val Ile Glu Leu Tyr Arg Ala Ala Gln Glu Arg Ile Ser Glu Asp
                165                 170                 175

Glu Ser Ser Leu Glu Lys Leu His Ala Trp Thr Ala Thr Tyr Leu Lys
            180                 185                 190

Gln Gln Leu Leu Thr Asn Ser Ile Pro Asp Lys Lys Leu Asn Lys Leu
        195                 200                 205

Val Glu Cys Tyr Leu Lys Asn Tyr His Gly Ile Leu Asp Arg Met Gly
    210                 215                 220

Val Arg Gln Asn Leu Asp Leu Tyr Asp Ile Ser His Tyr Gln Thr Leu
225                 230                 235                 240

Lys Ala Ala Asp Arg Phe Ser Asn Leu Arg Asn Glu Asp Phe Leu Ala
                245                 250                 255

Phe Ala Arg Gln Asp Phe Asn Ile Cys Gln Glu Gln His Gln Lys Glu
```

-continued

```
            260                 265                 270

Leu Gln Gln Leu Gln Arg Trp Tyr Ala Asp Cys Arg Leu Asp Thr Leu
        275                 280                 285

Lys Tyr Gly Arg Asp Val Val Arg Val Ala Asn Phe Leu Thr Ser Ala
    290                 295                 300

Ile Ile Gly Asp Pro Glu Leu Ser Glu Val Arg Leu Val Phe Ala Lys
305                 310                 315                 320

His Ile Val Leu Val Thr Arg Ile Asp Asp Phe Phe Asp His Gly Gly
                325                 330                 335

Ser Arg Glu Glu Ser Tyr Lys Ile Leu Glu Leu Leu Lys Glu Trp Lys
            340                 345                 350

Glu Lys Pro Ala Ala Glu Tyr Gly Ser Lys Glu Val Glu Ile Leu Phe
        355                 360                 365

Thr Ala Val Tyr Asn Thr Val Asn Glu Leu Ala Glu Met Ala His Ile
    370                 375                 380

Glu Gln Gly Arg Ser Val Lys Glu Phe Leu Ile Lys Leu Trp Val Gln
385                 390                 395                 400

Ile Ile Ser Ile Phe Lys Ile Glu Leu Asp Thr Trp Ser Asp Glu Thr
                405                 410                 415

Ala Leu Thr Leu Asp Glu Tyr Leu Ser Ser Ser Trp Val Ser Ile Gly
            420                 425                 430

Cys Arg Ile Cys Ile Leu Met Ser Met Gln Phe Ile Gly Ile Lys Leu
        435                 440                 445

Ser Asp Glu Met Leu Leu Ser Glu Glu Cys Ile Asp Leu Cys Arg His
    450                 455                 460

Val Ser Met Val Asp Arg Leu Leu Asn Asp Val Gln Thr Phe Glu Lys
465                 470                 475                 480

Glu Arg Lys Glu Asn Thr Gly Asn Ser Val Ser Leu Leu Leu Ala Ala
                485                 490                 495

Asn Lys Asp Asp Ser Ala Phe Thr Glu Glu Glu Ala Ile Thr Lys Ala
            500                 505                 510

Lys Glu Met Ala Glu Cys Asn Arg Arg Gln Leu Met Lys Ile Val Tyr
        515                 520                 525

Lys Thr Gly Thr Ile Phe Pro Arg Lys Cys Lys Asp Met Phe Leu Lys
    530                 535                 540

Val Cys Arg Ile Gly Cys Tyr Leu Tyr Ala Ser Gly Asp Glu Phe Thr
545                 550                 555                 560

Ser Pro Gln Gln Met Met Glu Asp Met Lys Ser Leu Val Tyr Glu Pro
                565                 570                 575

Leu Thr Val Asp Pro Leu Glu Ala Lys Asn Val Ser Gly Lys
            580                 585                 590
```

<210> SEQ ID NO 20
<211> LENGTH: 1773
<212> TYPE: DNA
<213> ORGANISM: Salvia officinalis

<400> SEQUENCE: 20

```
atgtccctcg ccttcaacgc agcagttgcc actttctccg gccacagaat tcggagcagg     60

agagaaattc ttccggggca aggatttccg atgatcacca acaagtcgtc tttcgccgtg    120

aaatgtaacc ttactacaac agatttgatg ggcaagataa cagagaaatt caagggaaga    180

gacagtaatt tttcagcagc aacggctgtt caacctgcgg cggatatacc ctctaacctg    240

tgcataatcg acaccctcca aaggttggga gtcgaccgat acttccaatc tgaaatcgac    300
```

```
actattctag aggacacata caggttatgg caaaggaaag agagagagat attttcggat    360

ataactattc atgcaatggc atttagactt ttgcgagtta aaggatatgt agtttcatca    420

gaggaactgg ctccgtatgc tgaccaagag cgcattaacc tgcaaaggat tgatgtagcg    480

acagttatcg agctttacag agcagcacag gagagaataa gtgaagacga gagcagtctt    540

gagaaactac atgcttggac cgccacctat ctcaagcagc agctgctcac taactccatt    600

cctgacaaga aattgaacaa actggtggaa tgctacttga agaactatca cgggatatta    660

gatagaatgg gagttagaca aaacctcgac ctctacgaca taagccacta tcaaactcta    720

aaagctgcag ataggttctc taatctacgt aatgaagatt ttctagcatt tgcgaggcaa    780

gattttaata tttgccaaga acaacaccaa aaagaacttc agcaactgca aaggtggtat    840

gcagattgta ggttggacac attgaagtat ggaagagatg tcgtgcgggt tgctaatttt    900

ctaacatcag caattattgg tgatcctgaa ttgtctgaag tccgtctagt cttcgccaaa    960

catattgtgc ttgtaacacg tattgatgat tttttcgatc atggtggatc tagagaagag   1020

tcctacaaga tccttgaatt actaaaagaa tggaaagaga agccagctgc agaatatggt   1080

tccaaagaag ttgaaattct tttcacagca gtatacaata cagtaaacga gttggcagag   1140

atggctcaca tcgaacaagg acgtagtgtt aaagaatttc taataaagct gtgggttcaa   1200

atcatatcga ttttcaagat agaattagat acatggagcg atgagacagc gctgaccttg   1260

gatgagtact tgtcttcgtc gtgggtgtca attgggtgca gaatctgcat tctcatgtcg   1320

atgcaattca ttggtataaa attatctgat gaaatgcttc tgagtgaaga gtgtattgat   1380

ttgtgtcggc atgtctccat ggttgaccgg ctgctcaacg acgtgcagac tttcgagaag   1440

gaacgcaagg aaaatacagg aaatagcgtg agccttctgc tagcagctaa caaagacgac   1500

agcgccttta ctgaagagga agctattaca aaagcaaaag aaatggcgga atgtaacagg   1560

agacaactga tgaagattgt gtataaaaca ggaaccattt tcccaagaaa atgcaaagat   1620

atgtttctga aggtatgcag gattggctgt tacttgtatg caagcggcga tgaattcaca   1680

tctccacaac aaatgatgga agatatgaaa tccttggtct atgaacccct aacagttgat   1740

cctctcgagg ccaaaaatgt gagtggcaaa tga                                1773
```

<210> SEQ ID NO 21
<211> LENGTH: 798
<212> TYPE: PRT
<213> ORGANISM: Ajuga reptans

<400> SEQUENCE: 21

```
Met Ala Ser Leu Ser Thr Phe His Leu Tyr Ser Ser Ser Leu Leu His
1               5                   10                  15

Arg Lys Thr Leu Gln Ser Ser Pro Lys Leu Asn Leu Ser Ser Glu Cys
            20                  25                  30

Phe Ser Thr Arg Thr Trp Met Asn Ser Ser Lys Asn Leu Ser Leu Asn
        35                  40                  45

Tyr Gln Val Asn Gln Lys Ile Gly Lys Leu Thr Gly Thr Arg Val Ala
    50                  55                  60

Thr Val Asp Ala Pro Gln Gln Leu Glu His Asp Asp Ser Thr Ala Lys
65                  70                  75                  80

Gly His Asp Ile Val Asp Ile Glu Thr Gln Asp Pro Ile Glu Tyr Ile
                85                  90                  95

Arg Met Leu Leu Asn Thr Thr Gly Asp Gly Arg Ile Ser Val Ser Pro
            100                 105                 110
```

-continued

```
Tyr Asp Thr Ala Trp Ile Ala Leu Ile Lys Asp Val Glu Gly Arg Asp
        115                 120                 125

Phe Pro Gln Phe Pro Ser Ser Leu Glu Trp Ile Ala Asn His Gln Leu
    130                 135                 140

Ala Asp Gly Ser Trp Gly Asp Glu Gly Phe Phe Cys Val Tyr Asp Arg
145                 150                 155                 160

Leu Val Asn Thr Ile Ala Cys Val Val Ala Leu Arg Ser Trp Asn Val
                165                 170                 175

His His Asp Lys Ser Gln Arg Gly Ile Gln Tyr Ile Lys Glu Asn Val
            180                 185                 190

His Gln Leu Lys Asp Gly Asn Ala Glu His Met Met Cys Gly Phe Glu
        195                 200                 205

Val Val Phe Pro Ala Leu Leu Gln Lys Ala Lys Asn Met Gly Ile Asp
    210                 215                 220

Asp Leu Pro Tyr Glu Ala Pro Val Ile Gln Asp Ile Tyr His Thr Arg
225                 230                 235                 240

Glu Gln Lys Leu Lys Arg Ile Pro Leu Glu Met Met His Lys Val Pro
                245                 250                 255

Thr Ser Leu Leu Phe Ser Leu Glu Gly Leu Glu Asn Leu Asp Trp Asp
            260                 265                 270

Lys Leu Leu Lys Leu Gln Ser Ala Asp Gly Ser Phe Leu Thr Ser Pro
        275                 280                 285

Ser Ser Thr Ala Phe Ala Phe Met Gln Thr Lys Asp Glu Lys Cys Phe
    290                 295                 300

Gln Phe Ile Lys Asn Thr Val Glu Thr Phe Asn Gly Gly Ala Pro His
305                 310                 315                 320

Thr Tyr Pro Val Asp Val Phe Gly Arg Leu Trp Ala Val Asp Arg Leu
                325                 330                 335

Gln Arg Leu Gly Ile Ser Arg Phe Phe Glu Ala Glu Ile Ala Asp Cys
            340                 345                 350

Leu Ser His Ile His Arg Tyr Trp Asn Asp Lys Gly Leu Phe Ser Gly
        355                 360                 365

Arg Glu Ser Asp Phe Val Asp Ile Asp Asp Thr Ser Met Gly Phe Arg
    370                 375                 380

Leu Leu Arg Met Gln Gly Tyr Asp Val Ser Pro Asn Val Leu Arg Asn
385                 390                 395                 400

Phe Lys Asn Gly Asp Lys Phe Ser Cys Tyr Gly Gly Gln Thr Ile Glu
                405                 410                 415

Ser Ser Thr Pro Ile Tyr Asn Leu Tyr Arg Ala Ser Gln Phe Arg Phe
            420                 425                 430

Pro Gly Glu Glu Ile Leu Glu Glu Ala Asp Lys Phe Ala His Glu Phe
        435                 440                 445

Leu Ser Glu Gln Leu Gly Asn Asn Gln Leu Leu Asp Lys Trp Val Ile
    450                 455                 460

Ser Asp Arg Leu Gln Glu Glu Ile Ser Ile Gly Leu Gly Met Pro Phe
465                 470                 475                 480

Tyr Ala Thr Leu Pro Arg Val Glu Ala Ser Tyr Tyr Ile Gln His Tyr
                485                 490                 495

Ala Gly Ala Asp Asp Val Trp Ile Gly Lys Thr Leu Tyr Arg Met Pro
            500                 505                 510

Glu Ile Ser Asn Asp Thr Tyr Leu Glu Leu Ala Arg Asn Asp Phe Lys
        515                 520                 525
```

```
Arg Cys Gln Ala Gln His Gln Phe Glu Trp Ile Tyr Met Gln Glu Trp
    530                 535                 540

Tyr Glu Ser Cys Asn Ile Glu Glu Phe Gly Ile Ser Arg Lys Glu Leu
545                 550                 555                 560

Leu Arg Val Tyr Phe Leu Ala Cys Ser Ser Ile Phe Glu Val Glu Arg
                565                 570                 575

Thr Lys Glu Arg Met Ala Trp Ala Lys Ser Gln Ile Ile Ser Arg Met
            580                 585                 590

Ile Thr Ser Phe Phe Asn Lys Gln Thr Thr Ser Ser Glu Glu Lys Glu
        595                 600                 605

Thr Leu Leu Thr Glu Phe Arg Asn Ile Asn Gly Leu His Lys Ser Asn
    610                 615                 620

Asn Thr Arg Asp Gly Asp Met Asn Ile Val Leu Ala Thr Leu His Gln
625                 630                 635                 640

Phe Phe Ala Gly Phe Asp Arg Tyr Thr Ser His Gln Leu Lys Asn Ala
                645                 650                 655

Trp Gly Val Trp Leu Ser Lys Leu Gln Arg Gly Ala Val Asp Gly Gly
            660                 665                 670

Ala Asp Ala Glu Leu Ile Thr Thr Thr Ile Asn Val Cys Ala Gly His
        675                 680                 685

Ile Ala Leu Lys Glu Asp Ile Leu Ser His Asp Glu Tyr Lys Thr Leu
    690                 695                 700

Thr Asp Leu Thr Ser Lys Ile Cys Gln Gln Leu Ser His Ile Gln Asn
705                 710                 715                 720

Glu Lys Val Val Glu Ile Asp Gly Gly Ile Thr Ala Lys Ser Arg Leu
                725                 730                 735

Lys Asn Glu Glu Leu Gln Arg Asp Met Gln Ser Leu Val Lys Leu Val
            740                 745                 750

Leu Glu Lys Ser Val Gly Leu Asn Arg Asn Ile Lys Gln Thr Phe Leu
        755                 760                 765

Thr Val Ala Lys Thr Tyr Tyr Tyr Arg Ala Tyr Asn Ala Glu Glu Thr
    770                 775                 780

Met Asp Ala His Ile Phe Lys Val Leu Phe Glu Pro Val Ala
785                 790                 795
```

<210> SEQ ID NO 22
<211> LENGTH: 2397
<212> TYPE: DNA
<213> ORGANISM: Ajuga reptans

<400> SEQUENCE: 22

```
atggcctctt tgtccacttt ccacctctac tcttcctcac tccttcaccg caaaacactg     60

caatcttcac caaagcttaa cctgtcttca gaatgcttct ccaccagaac ttggatgaac    120

agcagcaaaa acttgtcgtt aaattaccaa gttaatcaga aaataggaaa gctgacaggg    180

actcgagttg ccactgtgga tgcgccacaa caacttgaac acgatgattc aactgctaaa    240

ggccatgata tagtcgatat tgaaactcag gatccaattg aatatattag aatgctgttg    300

aacacaacag gcgatggcag aatcagcgtt tcgccttacg acacagcatg gattgctctt    360

attaaggacg tggaaggacg tgattttcct caatttccat ccagccttga gtggatcgcg    420

aaccatcaac tcgctgatgg ttcatgggga gacgaaggat ttttctgtgt gtatgatcgg    480

ctcgtaaata ctatagcatg tgtcgtagca ttgagatcat ggaatgtcca tcacgacaag    540

agccaaagag gaatacaata tatcaaggaa aatgtgcatc aacttaagga tggaaatgct    600
```

```
gagcacatga tgtgtggttt cgaagtagtg tttcctgcac ttcttcaaaa agccaaaaat    660

atgggcattg atgatcttcc atatgaggct cctgtcatcc aggatattta ccatacaagg    720

gagcagaaat tgaaaaggat accattggag atgatgcaca aagtgcctac ttctctgctg    780

tttagtttgg aaggactgga gaatttagat tgggataaac tccttaagtt gcagtcagct    840

gatggctctt tcctcacttc tccctcctct actgctttcg cattcatgca aacaaaagac    900

gaaaaatgct tccagttcat caagaacact gttgaaacct ttaatggagg agcaccacat    960

acttatccgg tcgatgtttt tggaagactt tgggcggttg ataggctgca gcgcctcgga   1020

atttctcgat tctttgaggc tgagattgct gattgcttaa gtcacattca tagatattgg   1080

aatgataagg ggcttttcag tggacgtgaa tcggactttg tcgatattga cgacacatcc   1140

atgggtttca gacttctaag aatgcaaggc tatgatgtta gtccaaatgt actgaggaat   1200

ttcaagaatg gtgacaagtt ttcatgttac ggaggtcaaa cgatcgagtc atcaactcca   1260

atatacaatc tgtacagagc ttctcaattc cggtttccag gagaagaaat tcttgaagaa   1320

gccgacaagt tcgcccatga gttcttgtcc gaacagcttg gcaacaacca attgcttgat   1380

aaatgggtta tatccgaccg cttgcaggaa gagataagta ttggattggg gatgccattt   1440

tatgccaccc ttcccagagt tgaagcaagc tactatatac aacattacgc tggtgccgac   1500

gacgtgtgga tcggcaagac actctacagg atgccggaaa taagtaatga tacatacctg   1560

gagctagcaa gaaatgattt caagagatgc caagcacaac atcagttcga gtggatctac   1620

atgcaagaat ggtatgagag ttgcaacatt gaagaattcg ggataagccg aaaggagctc   1680

cttcgcgttt actttttggc ttgctctagc atctttgagg tcgagaggac taaagagaga   1740

atggcatggg caaaatctca aattatttct agaatgatca cttctttctt taataaacaa   1800

actacttcat ctgaggaaaa agaaacactt ttaaccgaat tcagaaacat caacggtctg   1860

cacaaatcaa acaatacaag agatggagat atgaacattg tgcttgcaac cctccatcaa   1920

ttcttcgctg gatttgacag atatactagc catcaactga aaaatgcttg gggagtatgg   1980

ttgagcaagc tgcaacgagg agcagtagac ggtggagcag acgcagagct gataacaacc   2040

accataaacg tatgcgccgg tcatatagct cttaaggaag acatattgtc ccacgatgag   2100

tacaagactc tcaccgacct caccagcaag atttgtcagc agctttctca tattcaaaac   2160

gaaaaggttg tggaaattga cggtgggatt acagcaaaat ctaggttgaa gaatgaggaa   2220

ctgcaacgtg acatgcaatc attggtgaaa ttagtacttg agaaatcagt tgggctcaac   2280

cggaatataa agcaaacatt tctaacggtt gcaaaaacat actactacag agcctacaat   2340

gctgaggaaa ctatggatgc ccatatattc aaagttcttt tcgaaccagt tgcgtga      2397
```

```
<210> SEQ ID NO 23
<211> LENGTH: 798
<212> TYPE: PRT
<213> ORGANISM: Ajuga reptans

<400> SEQUENCE: 23

Met Ser Phe Ala Ser Gln Ala Thr Ser Leu Leu Ser Ser Pro Asn Arg
1               5                   10                  15

Leu Gly His Val Pro Thr Pro Ser Ser Pro Ala Arg Phe Ala Ala Gly
            20                  25                  30

Gly Ala Pro Phe Trp Lys Ile Leu Phe Thr Ala Arg Ser Asn Gly Gln
        35                  40                  45

Tyr Lys Ala Ile Ser Arg Ala Arg Asn Gln Gly Asn Val Glu Tyr Ile
    50                  55                  60
```

```
Asp Glu Ile Gln Lys Gly Pro Gln Val Val Leu Glu Ala Glu Asn Ser
65                  70                  75                  80

Leu Glu Asp Asp Thr Gln Lys Asp Thr Asp Gln Ile Arg Glu Leu Val
                85                  90                  95

Glu Asn Val Arg Val Lys Leu Gln Asn Ile Gly Gly Gly Gly Ile Ser
            100                 105                 110

Ile Ser Ala Tyr Asp Thr Ala Trp Val Ala Leu Val Glu Asp Ile Asn
        115                 120                 125

Gly Ser Gly Gln Pro Gln Phe Pro Thr Ser Leu Asp Trp Ile Ser Asn
    130                 135                 140

His Gln Phe Pro Asp Gly Ser Trp Gly Ser Ser Lys Phe Leu Tyr Tyr
145                 150                 155                 160

Asp Arg Ile Leu Cys Thr Leu Ala Cys Ile Val Ala Leu Lys Thr Trp
                165                 170                 175

Asn Val His Pro Asp Lys Tyr His Lys Gly Leu Asp Phe Ile Arg Glu
            180                 185                 190

Asn Ile His Lys Leu Ala Asp Glu Glu Glu Val His Met Pro Ile Gly
        195                 200                 205

Phe Glu Val Ala Phe Pro Ser Ile Ile Glu Thr Ala Lys Lys Val Gly
    210                 215                 220

Ile Glu Ile Pro Glu Asp Phe Pro Gly Lys Lys Glu Ile Tyr Ala Lys
225                 230                 235                 240

Arg Asp Leu Lys Leu Lys Lys Ile Pro Met Asp Ile Leu His Lys Met
                245                 250                 255

Pro Thr Pro Leu Leu Phe Ser Ile Glu Gly Met Glu Gly Leu Asp Trp
            260                 265                 270

Gln Lys Leu Phe Lys Phe Arg Asp Asp Gly Ser Phe Leu Thr Ser Pro
        275                 280                 285

Ser Ser Thr Ala Tyr Ala Leu Gln Gln Thr Lys Asp Glu Leu Cys Leu
    290                 295                 300

Lys Tyr Leu Thr Asp Leu Val Lys Lys Asp Asn Gly Gly Val Pro Asn
305                 310                 315                 320

Ala Phe Pro Val Asp Leu Phe Asp Arg Asn Tyr Thr Val Asp Arg Leu
                325                 330                 335

Arg Arg Leu Gly Ile Ser Arg Tyr Phe Gln Pro Glu Ile Glu Glu Cys
            340                 345                 350

Met Lys Tyr Val Tyr Arg Phe Trp Asp Lys Arg Gly Ile Ser Trp Ala
        355                 360                 365

Arg Asn Thr Asn Val Gln Asp Leu Asp Asp Thr Ala Gln Gly Phe Arg
    370                 375                 380

Asn Leu Arg Met His Gly Tyr Glu Val Thr Leu Asp Val Phe Lys Gln
385                 390                 395                 400

Phe Glu Lys Cys Gly Glu Phe Phe Ser Phe His Gly Gln Ser Ser Asp
                405                 410                 415

Ala Val Leu Gly Met Phe Asn Leu Tyr Arg Ala Ser Gln Val Leu Phe
            420                 425                 430

Pro Gly Glu His Met Leu Ala Asp Ala Arg Lys Tyr Ala Ala Asn Tyr
        435                 440                 445

Leu His Lys Arg Arg Leu Asn Asn Arg Val Val Asp Lys Trp Ile Ile
    450                 455                 460

Asn Lys Asp Leu Glu Gly Glu Val Ala Tyr Gly Leu Asp Val Pro Phe
465                 470                 475                 480
```

-continued

```
Tyr Ala Ser Leu Pro Arg Leu Glu Ala Arg Phe Tyr Ile Glu Gln Tyr
                485                 490                 495

Gly Gly Ser Asp Asp Val Trp Ile Gly Lys Ala Leu Tyr Arg Met Val
            500                 505                 510

Asn Val Ser Cys Asp Thr Tyr Leu Glu Leu Ala Lys Leu Asp Tyr Asn
        515                 520                 525

Lys Cys Gln Ser Val His Gln Asn Glu Trp Lys Ser Phe Gln Lys Trp
    530                 535                 540

Tyr Lys Ser Cys Ser Leu Gly Glu Phe Gly Phe Ser Glu Gly Ser Leu
545                 550                 555                 560

Leu Gln Ala Tyr Tyr Ile Ala Ala Ser Thr Ile Phe Glu Pro Glu Lys
                565                 570                 575

Ser Gly Glu Arg Leu Ala Trp Ala Lys Thr Ala Ala Leu Met Glu Thr
            580                 585                 590

Ile Gln Gln Leu Ser Ser Gln Gln Lys Arg Glu Phe Val Asp Glu Phe
        595                 600                 605

Lys His Lys Asn Ile Leu Lys Asn Glu Asn Gly Glu Arg Tyr Arg Ser
    610                 615                 620

Ser Thr Ser Leu Val Glu Thr Leu Ile Ser Thr Val Asn Gln Leu Ser
625                 630                 635                 640

Ser Asp Ile Leu Leu Glu Gln Gly Arg Asp Val His Gln Glu Leu Cys
                645                 650                 655

His Val Trp Leu Lys Trp Leu Ser Thr Trp Glu Glu Arg Gly Asn Leu
            660                 665                 670

Val Glu Ala Glu Ala Glu Leu Leu Leu Arg Thr Leu His Leu Asn Ser
        675                 680                 685

Gly Leu Asp Glu Ser Ser Phe Ser His Pro Lys Tyr Gln Gln Leu Leu
    690                 695                 700

Glu Val Ser Thr Lys Val Cys His Leu Leu Arg Leu Phe Gln Lys Arg
705                 710                 715                 720

Lys Val Tyr Asp Pro Glu Gly Cys Thr Thr Asp Ile Ala Thr Gly Thr
                725                 730                 735

Thr Phe Gln Ile Glu Ala Cys Met Gln Glu Leu Val Lys Leu Val Phe
            740                 745                 750

Ser Arg Ser Ser Glu Asp Leu Asp Ser Leu Thr Lys Leu Arg Phe Leu
        755                 760                 765

Asp Val Ala Arg Ser Phe Tyr Tyr Thr Ala His Cys Asp Pro Gln Val
    770                 775                 780

Val Glu Ser His Ile Asp Lys Val Leu Phe Glu Lys Val Val
785                 790                 795
```

<210> SEQ ID NO 24
<211> LENGTH: 2397
<212> TYPE: DNA
<213> ORGANISM: Ajuga reptans

<400> SEQUENCE: 24

```
atgtcatttg cttcccaagc cacctccctc ctatcatccc ccaaccgtct cggccatgtt      60

ccgacgccaa gctcgccggc tcgtttcgct gccggtggtg ccccattttg gaagatatta     120

tttacagcta ggtctaatgg gcagtataaa gctatttcaa gagctcgtaa ccaaggaaat     180

gtagagtaca ttgatgagat tcagaaaggc ccgcaagtcg tattggaggc agaaaacagc     240

ttggaagatg acacacaaaa agatactgat cagataaggg aactagtgga aaatgtccga     300

gtaaagctgc agaatatcgg tggtggaggg ataagcatat cggcgtacga caccgcatgg     360
```

```
gtggcgctgg tggaggacat caacggcagt ggccagccac agtttccgac gagcctcgat    420
tggatatcga accatcagtt ccctgatggg tcatggggca gcagcaagtt tttgtattat    480
gatcggattc tatgcacatt agcatgtata gttgcattga aaacctggaa tgtgcatcct    540
gataagtacc acaaagggtt ggatttcatc agagagaaca ttcacaagct tgcggacgaa    600
gaagaagtgc acatgccaat tgggttcgaa gtggcattcc catcaattat tgaaacagct    660
aaaaaagtag gaatcgaaat ccctgaggat tttcctggca agaaagaaat ttatgcaaaa    720
agagatttaa agctaaaaaa aataccaatg gatatactgc ataaaatgcc cacaccattg    780
ctcttcagca tagaaggaat ggaaggcctt gactggcaaa agctattcaa attccgcgat    840
gatggctcgt ttcttacgtc tccgtcctca acagcctatg cactccagca aacaaaggat    900
gagctatgcc tcaagtatct aacagatctt gtcaagaaag acaacggagg agttccgaat    960
gcatttccag tagacctgtt tgatcgtaac tatacagtag accgcttgcg aaggctagga   1020
atttcacggt actttcaacc tgaaattgaa gaatgcatga aatatgttta cagattttgg   1080
gataaaagag gaattagctg ggcaagaaat accaatgttc aggaccttga tgacactgca   1140
cagggattca ggaatttaag gatgcatggt tatgaagtca ctctagatgt tttcaaacaa   1200
tttgagaaat gtggagagtt tttcagtttt catgggcaat ccagcgatgc tgttttagga   1260
atgttcaact tgtaccgggc ttctcaggtt ttatttccgg gagaacacat gcttgcagat   1320
gcgaggaagt atgcagccaa ctatttgcat aaacgaagac ttaataatag ggtggtcgac   1380
aaatggatta tcaacaaaga ccttgaaggc gaggtggcat atgggctaga tgttccgttc   1440
tacgccagcc tacctcgact cgaagcaagg ttctacatag aacaatatgg gggtagtgat   1500
gatgtgtgga ttggaaaagc tttatacaga atggtaaatg taagctgcga cacttacctt   1560
gagctagcaa aattagacta caacaaatgc caatccgtgc atcagaatga gtggaaaagc   1620
tttcaaaaat ggtacaaaag ttgcagtctt ggggagtttg ggttcagtga aggaagccta   1680
ctccaagctt actacatagc agcctcaact atattcgagc cagagaaatc aggagaacgc   1740
ctagcttggg ctaaaacagc agctctaatg gagacaattc aacaactttc cagccagcaa   1800
aaacgtgaat ttgttgatga attcaaacat aaaaacatac tgaagaatga aaatggagaa   1860
aggtatagat caagtaccag tttggtagag actctgataa gcactgtaaa tcagctctca   1920
tcagacatac tattggagca aggcagagac gttcatcaag aattatgtca cgtgtggcta   1980
aaatggctga gtacatggga ggaaagagga aacctggtgg aagcggaagc cgagcttctt   2040
ctgcgaacct tacatctcaa cagcggattg gatgaatcat cattttccca ccctaaatat   2100
caacagctct tggaggtgtc taccaaagtt tgccacctcc ttcgcctatt tcagaaacga   2160
aaggtgtatg atcccgaagg gtgtacaacc gacatagcaa caggaacaac gttccagata   2220
gaagcatgca tgcaagaact agtgaaatta gtgttcagca gatcctcaga agatttagat   2280
tctcttacta agttgagatt tttggatgtt gctagaagtt tctattacac tgcccattgt   2340
gatccacagg tggtcgagtc ccacatcgat aaagtattgt ttgagaaggt agtctag      2397
```

<210> SEQ ID NO 25
<211> LENGTH: 801
<212> TYPE: PRT
<213> ORGANISM: Plectranthus barbatus
<220> FEATURE:
<221> NAME/KEY: VARIANT
<222> LOCATION: (1)...(801)
<223> OTHER INFORMATION: Xaa = Any Amino Acid

<400> SEQUENCE: 25

Met Gln Ala Ser Met Ser Ser Leu Asn Leu Asn Asn Ala Pro Ala Val
1 5 10 15

Cys Ser Ser Arg Ser Gln Leu Ser Ala Lys Leu His Pro Pro Glu Tyr
20 25 30

Ser Thr Val Gly Ala Trp Leu Asn Arg Gly Asn Lys Asn Gln Arg Leu
35 40 45

Gly Tyr Arg Ile Arg Pro Lys Gln Leu Ser Lys Leu Thr Glu Cys Arg
50 55 60

Val Ala Ser Ala Asp Val Ser Gln Glu Ile Gly Lys Val Gly Gln Ser
65 70 75 80

Val Arg Thr Pro Glu Glu Val Asn Lys Lys Ile Glu Glu Ser Ile Lys
85 90 95

Tyr Val Lys Glu Leu Leu Met Thr Ser Gly Asp Gly Arg Ile Ser Val
100 105 110

Ala Pro Tyr Asp Thr Ala Ile Val Ala Leu Ile Lys Asp Leu Glu Gly
115 120 125

Arg Asp Ala Pro Glu Phe Pro Ser Cys Leu Glu Trp Ile Ala Asn Asn
130 135 140

Gln Lys Asp Asp Gly Ser Trp Gly Asp Asp Phe Phe Cys Ile Tyr Asp
145 150 155 160

Arg Ile Val Asn Thr Ile Ala Ser Val Val Ala Leu Lys Ser Trp Asn
165 170 175

Val His Pro Asp Lys Ile Glu Arg Gly Val Ser Tyr Ile Lys Glu Asn
180 185 190

Ala His Lys Leu Lys Gly Gly Asn Leu Glu His Met Thr Ser Gly Phe
195 200 205

Glu Phe Val Val Pro Gly Cys Phe Asp Arg Ala Lys Ala Leu Gly Ile
210 215 220

Glu Gly Leu Pro Tyr Asp Asp Pro Ile Ile Lys Glu Ile Tyr Ala Thr
225 230 235 240

Lys Glu Arg Arg Leu Ser Lys Val Pro Lys Asp Met Ile Tyr Lys Val
245 250 255

Pro Thr Thr Leu Leu Phe Ser Leu Glu Gly Leu Gly Met Glu Asp Leu
260 265 270

Asp Trp Gln Lys Ile Leu Lys Leu Gln Ser Gly Asp Gly Ser Phe Leu
275 280 285

Thr Ser Pro Ser Ser Thr Ala Tyr Ala Phe Met Gln Thr Gly Asp Glu
290 295 300

Lys Cys Tyr Lys Phe Leu Gln Asn Ala Val Arg Asn Cys Asn Gly Gly
305 310 315 320

Ala Pro His Thr Tyr Pro Val Asp Val Phe Ala Arg Leu Trp Ala Val
325 330 335

Asp Arg Leu Gln Arg Leu Gly Ile Ser Arg Phe Phe Gln Pro Glu Ile
340 345 350

Lys Phe Cys Leu Asp His Ile Lys Asn Val Trp Thr Lys Asn Gly Val
355 360 365

Phe Ser Gly Arg Asp Ser Glu Phe Val Asp Ile Asp Asp Thr Ser Met
370 375 380

Gly Ile Arg Leu Leu Lys Met His Gly Tyr Asp Val Asp Pro Asn Ala
385 390 395 400

Leu Lys His Phe Lys Gln Glu Asp Gly Arg Phe Ser Cys Tyr Gly Gly
405 410 415

```
Gln Met Ile Glu Ser Ala Ser Pro Ile Tyr Asn Leu Tyr Arg Ala Ala
            420                 425                 430

Gln Leu Arg Phe Pro Gly Glu Glu Ile Leu Glu Glu Ala Thr Lys Phe
        435                 440                 445

Ala Tyr Asn Phe Leu Gln Gln Lys Leu Ala Asn Asn Gln Ile Gln Glu
    450                 455                 460

Lys Trp Val Ile Ser Glu His Leu Ile Asp Glu Ile Lys Met Gly Leu
465                 470                 475                 480

Lys Met Pro Trp Tyr Ala Thr Leu Pro Arg Val Glu Ala Ser Tyr Tyr
                485                 490                 495

Leu Gln Tyr Tyr Ala Ala Ser Gly Asp Val Trp Ile Gly Lys Thr Phe
            500                 505                 510

Tyr Arg Met Pro Glu Ile Ser Asn Asp Thr Tyr Lys Glu Leu Ala Leu
        515                 520                 525

Leu Asp Phe Asn Arg Cys Gln Ala Gln His Gln Phe Glu Trp Ile Tyr
    530                 535                 540

Met Gln Glu Trp Tyr Gln Ser Asn Asn Ile Lys Glu Phe Gly Ile Ser
545                 550                 555                 560

Lys Lys Glu Leu Leu Leu Ala Tyr Phe Leu Ala Ala Ala Thr Ile Phe
                565                 570                 575

Glu Pro Glu Arg Ser Gln Glu Arg Ile Val Trp Ala Lys Thr Gln Val
            580                 585                 590

Val Ser Lys Met Ile Thr Ser Phe Leu Ser Gln Glu Asn Ala Leu Ser
        595                 600                 605

Ser Xaa Gln Lys Thr Ala Leu Phe Ile Asp Phe Gly His Ser Ile Asn
    610                 615                 620

Gly Leu Asn Gln Ile Thr Ser Val Glu Lys Glu Asn Gly Leu Ala Gln
625                 630                 635                 640

Thr Val Leu Ala Thr Phe Gly Gln Leu Leu Glu Glu Phe Asp Arg Tyr
                645                 650                 655

Thr Arg His Gln Leu Lys Asn Ala Trp Ser Gln Trp Phe Met Lys Leu
            660                 665                 670

Gln Gln Gly Asp Asp Asn Gly Gly Ala Asp Ala Glu Leu Leu Ala Asn
        675                 680                 685

Thr Leu Asn Ile Cys Ala Gly His Ile Ala Phe Asn Glu Asp Ile Leu
    690                 695                 700

Ser His Asn Glu Tyr Thr Ser Leu Ser Ser Leu Thr Asn Lys Ile Cys
705                 710                 715                 720

Gln Arg Leu Ser Gln Ile Arg Asp Asn Lys Ile Leu Glu Ile Glu Asp
                725                 730                 735

Gly Ser Ile Lys Asp Lys Glu Leu Glu Gln Glu Met Gln Ala Leu Val
            740                 745                 750

Lys Leu Val Leu Glu Glu Thr Gly Gly Ile Asp Arg Asn Ile Lys Gln
        755                 760                 765

Thr Phe Leu Ser Val Phe Lys Met Phe Tyr Tyr Arg Ala Tyr His Asp
    770                 775                 780

Ala Glu Ala Ile Asp Xaa His Ile Phe Lys Val Met Phe Glu Pro Val
785                 790                 795                 800

Val
```

<210> SEQ ID NO 26
<211> LENGTH: 2406
<212> TYPE: DNA

<213> ORGANISM: Plectranthus barbatus
<220> FEATURE:
<221> NAME/KEY: misc_feature
<222> LOCATION: (1)...(2406)
<223> OTHER INFORMATION: n = A,T,C or G

<400> SEQUENCE: 26
atgcaggctt ctatgtcatc tctgaacttg aacaatgcac cggccgtctg cagcagcagg 60
tcacagctat ccgctaaact tcacccgccg gaatattcca ccgtgggtgc atggctgaat 120
cgtggcaaca aaaaccagcg gttgggctac cggattcgtc caaagcaact atcaaaacta 180
actgagtgtc gagtagcaag tgcagatgtg tcacaagaga ttggaaaagt cggccaatct 240
gttcggactc ctgaagaggt aaataaaaag atagaggaat ccatcaagta cgtgaaggag 300
ctgctgatga cgtcgggcga cgggcgaatc agtgtggcgc cctacgacac ggccatagtt 360
gcccttatca aggacttgga agggcgcgat gccccggagt ttccatcttg cttggagtgg 420
attgcaaaca atcaaaaaga cgatggttct tggggggatg acttcttctg catctatgat 480
cggatcgtta ataccatagc atccgtcgtc gccttaaaat catggaatgt gcacccagac 540
aagattgaga gaggagtatc ctacatcaag gaaaacgcgc ataaactaaa aggtgggaat 600
ctcgaacaca tgacatcagg gttcgagttc gtggttcccg gctgttttga cagagccaaa 660
gccttgggga tcgaaggcct tccctatgat gatcccatca tcaaggagat ttatgctaca 720
aaagaaagga gattgagcaa ggtaccgaag gacatgatct acaaagttcc gacaactcta 780
ttgtttagtt tagagggact gggcatggag gatttggact ggcaaaagat actgaaactg 840
cagtcgggcg acggctcatt cctcacctct ccgtcgtcca ccgcctacgc attcatgcag 900
accggagacg aaaaatgcta caaattcctc cagaacgccg tcagaaattg caacggcgga 960
gcgccgcaca cttatccagt cgacgtcttt gcacggctct gggcggtcga ccgacttcag 1020
cgactcggaa tttctcgctt ctttcagccc gagatcaagt tttgcctaga ccacatcaaa 1080
aatgtgtgga ctaagaacgg agttttcagt ggacgggatt cagagtttgt ggatatcgac 1140
gacacatcca tgggcatcag gcttctgaaa atgcacggat acgatgtcga cccaaatgca 1200
ctgaaacatt tcaagcagga ggatgggagg ttttcatgct acggtggtca aatgatcgag 1260
tctgcatctc cgatttacaa tctctacagg gctgctcagc ttcgttttcc aggagaagaa 1320
attcttgaag aagccactaa atttgcctac aacttcctgc aacagaagct ggccaacaat 1380
caaattcaag aaaagtgggt catatccgag cacctaattg atgagataaa aatgggattg 1440
aagatgccat ggtacgccac cctacctaga gttgaggctt catactatct ccaatattat 1500
gcagcttctg gcgacgtatg gattggcaag actttttaca ggatgccaga aataagtaat 1560
gacacgtaca aagagcttgc actattggat ttcaaccgat gccaagcaca acatcagttc 1620
gaatggattt acatgcaaga gtggtatcaa agcaacaaca ttaaagaatt tgggataagc 1680
aagaaagagc ttcttcttgc ttacttcttg gctgctgcaa ccatttttga acccgaacga 1740
tcgcaagagc ggatcgtgtg ggctaaaacc caagttgttt ctaagatgat cacatcgttt 1800
ctgtctcaag aaaacgcttt gtcatcggan caaaagactg cacttttcat cgattttggg 1860
catagtatca atggcctcaa tcaaataact agtgttgaga aagagaatgg gcttgctcag 1920
actgtgctgg caaccttcgg acaactactc gaggaattcg acagatacac aaggcatcaa 1980
ctgaaaaatg cttggagcca atggttcatg aaactgcagc aaggagatga caatggcggg 2040
gcagacgcag agctcctagc aaacacattg aacatctgcg ctggtcatat tgcttttaac 2100
gaagacatat tatctcacaa cgaatacacc tctctctcct ccctcacaaa caaaatctgt 2160

-continued

```
cagcggctaa gtcaaattcg agataataag atactggaaa ttgaggatgg gagcataaaa   2220

gataaggaac tagaacagga aatgcaggcg ctggtgaagt tagtcctgga agaaaccggt   2280

ggcatcgaca ggaacatcaa gcaaacattt ttgtcagttt tcaaaatgtt ttactacaga   2340

gcctaccacg atgctgaggc tatcgatgnc catattttca aagtaatgtt tgaaccagtc   2400

gtatga                                                              2406


<210> SEQ ID NO 27
<211> LENGTH: 776
<212> TYPE: PRT
<213> ORGANISM: Hyptis suaveolens

<400> SEQUENCE: 27

Met Ala Tyr Met Ile Ser Ile Ser Asn Leu Asn Cys Ser Ser Leu Leu
1               5                   10                  15

Asn Thr Asn Leu Ser Ala Lys Ile Gln Leu His Gln Gly Leu Lys Gly
            20                  25                  30

Thr Trp Leu Lys Thr Ser Lys Arg Met Cys Met Asp Gln Gln Val His
        35                  40                  45

Gly Lys Gln Ile Ala Lys Val Ile Glu Ser Arg Val Thr Asp Lys Asp
    50                  55                  60

Val Ser Thr Ala Gln Asp Phe Glu Val Leu Lys Val Asn Arg Val Glu
65                  70                  75                  80

Asp Leu Ile Ser Ser Ile Lys Ser Ser Leu Lys Thr Met Glu Asp Gly
                85                  90                  95

Arg Ile Ser Val Ser Pro Tyr Ser Thr Ser Trp Ile Ala Leu Ile Pro
            100                 105                 110

Ser Ile Asp Gly Arg Gln Thr Pro Gln Phe Pro Ser Ser Leu Glu Trp
        115                 120                 125

Ile Val Lys His Gln Leu Ser Asp Gly Ser Trp Gly Asp Ala Leu Phe
    130                 135                 140

Phe Cys Val Tyr Asp Arg Leu Val Asn Thr Ile Ala Cys Ile Ile Ala
145                 150                 155                 160

Leu His Thr Trp Lys Val His Ala Asp Lys Val Lys Lys Gly Val Ser
                165                 170                 175

Phe Val Lys Glu Asn Ile Trp Lys Leu Glu Asp Ala Asn Glu Val His
            180                 185                 190

Met Thr Ser Gly Phe Glu Val Ile Phe Pro Ile Leu Leu Arg Arg Ala
        195                 200                 205

Arg Asp Met Gly Ile Asp Gly Leu Pro Ser Asp Asp Thr Pro Val Val
    210                 215                 220

Arg Met Ile Ser Ala Ala Arg Asp His Lys Leu Lys Lys Ile Pro Arg
225                 230                 235                 240

Glu Val Met His Gln Val Thr Thr Thr Leu Leu Tyr Ser Leu Glu Gly
                245                 250                 255

Leu Glu Asp Leu Asp Trp Ser Arg Leu Phe Lys Leu Gln Ser Ala Asp
            260                 265                 270

Gly Ser Phe Leu Thr Ser Pro Ser Ser Thr Ala Phe Ala Phe Met Gln
        275                 280                 285

Thr Asn Asn His Asn Cys Leu Arg Phe Ile Thr Ser Val Val Gln Thr
    290                 295                 300

Phe Asn Gly Gly Ala Pro Asp Asn Tyr Pro Ile Asp Ile Phe Ala Arg
305                 310                 315                 320
```

-continued

```
Leu Trp Ala Val Asp Arg Leu Gln Arg Leu Gly Ile Ser Arg Phe Phe
                325                 330                 335

Glu Gln Glu Ile Asn Asp Cys Leu Ser Tyr Val Tyr Arg Phe Trp Asn
            340                 345                 350

Ala Asn Gly Val Phe Ser Ala Gly Ala Thr Asn Phe Cys Asp Leu Asp
        355                 360                 365

Asp Thr Ser Met Ala Phe Arg Leu Leu Arg Leu His Gly Tyr Asp Val
    370                 375                 380

Asp Pro Asn Val Leu Arg Lys Phe Lys Glu Gly Asp Arg Phe Cys Cys
385                 390                 395                 400

His Ser Gly Glu Val Ala Met Ser Thr Ser Pro Thr Tyr Ala Leu Tyr
                405                 410                 415

Arg Ala Ser Gln Ile Gln Phe Pro Gly Glu Glu Ile Leu Asp Glu Ala
            420                 425                 430

Phe Ser Phe Thr Arg Asp Tyr Leu Gln Asp Trp Leu Ala Arg Asp Gln
        435                 440                 445

Val Leu Asp Lys Trp Ile Val Ser Lys Asp Leu Pro Asp Glu Ile Lys
    450                 455                 460

Val Gly Leu Glu Val Pro Trp Tyr Ala Ser Leu Pro Arg Val Glu Ala
465                 470                 475                 480

Ala Tyr Tyr Met Gln Arg His Tyr Gly Gly Ser Thr Asp Ala Trp Val
                485                 490                 495

Ala Lys Thr Cys Tyr Arg Met Pro Asp Val Ser Asn Asp Asp Tyr Leu
            500                 505                 510

Glu Leu Ala Arg Leu Asp Phe Lys Arg Cys Gln Ala Gln His Gln Ser
        515                 520                 525

Glu Leu Ser Tyr Met Gln Arg Trp Tyr Asp Ser Cys Asn Val Glu Glu
    530                 535                 540

Phe Gly Ile Ser Arg Lys Glu Leu Leu Val Ala Tyr Phe Val Ala Ala
545                 550                 555                 560

Ala Thr Ile Phe Glu Pro Glu Arg Ala Thr Glu Arg Ile Val Trp Ala
                565                 570                 575

Lys Thr Glu Ile Val Ser Lys Met Ile Lys Ala Phe Phe Gly Glu Asp
            580                 585                 590

Ser Leu Asp Gln Lys Thr Met Leu Leu Lys Glu Phe Arg Asn Ser Ile
        595                 600                 605

Asn Asn Gly Ser His Arg Phe Met Lys Ser Glu His Arg Ile Val Asn
    610                 615                 620

Ile Leu Leu Gln Ala Leu Gln Glu Leu Leu His Gly Ser Asp Asp Cys
625                 630                 635                 640

Arg Ile Gly Gln Leu Lys Asn Ala Trp Tyr Glu Trp Leu Met Lys Phe
                645                 650                 655

Glu Gly Gly Asp Glu Ala Ser Leu Trp Gly Glu Gly Glu Leu Leu Val
            660                 665                 670

Thr Thr Leu Asn Ile Cys Thr Ala His Phe Leu Gln His His Asp Leu
        675                 680                 685

Leu Leu Asn His Asp Tyr Ile Thr Leu Ser Glu Leu Thr Asn Lys Ile
    690                 695                 700

Cys Leu Lys Leu Ser Gln Ile Gln Val Gly Glu Met Asn Glu Met Arg
705                 710                 715                 720

Glu Asp Met Gln Ala Leu Thr Lys Leu Val Ile Gly Glu Ser Cys Ile
                725                 730                 735

Val Asn Lys Asn Ile Lys Gln Thr Phe Leu Ala Val Ala Lys Thr Phe
```

-continued

```
            740                 745                 750

Tyr Tyr Arg Ala Tyr Phe Asp Ala Asp Thr Val Asp Leu His Ile Phe
        755                 760                 765

Lys Val Leu Phe Glu Pro Ile Val
    770                 775


<210> SEQ ID NO 28
<211> LENGTH: 2331
<212> TYPE: DNA
<213> ORGANISM: Hyptis suaveolens

<400> SEQUENCE: 28

atggcgtata tgatatctat ttcaaatctc aactgttcct cgctactaaa caccaatctt     60

tcagcaaaga ttcagctgca ccaaggtctc aaaggaacat ggctaaaaac cagcaaacgc    120

atgtgcatgg atcaacaggt tcatggcaag cagatagcaa aagtgatcga gagccgagtt    180

actgataagg atgtttccac tgctcaggac tttgaagtgt taaaggtcaa tagagtggag    240

gatctgatat caagcattaa gagttcattg aagacaatgg aagatggaag aataagcgtg    300

tcgccctaca gcacatcatg gatcgcactc attccaagta ttgatgggcg ccagacgccc    360

cagtttccat cttcactgga gtggatcgtg aagcatcagc tatcagatgg ttcatggggt    420

gatgcccttt ttttctgcgt ttatgatcgt ctcgtaaata cgattgcatg catcattgcc    480

ctgcacacct ggaaggttca tgcagacaag gttaaaaaag gagtaagttt tgtgaaggaa    540

aatatatgga aacttgaaga cgccaacgag gtccacatga ctagtggttt cgaagttata    600

tttcccatcc ttcttcgaag agcacgagac atgggaattg atggtcttcc ttctgatgat    660

actccagttg ttaggatgat ttctgctgct agggatcaca aattgaaaaa gattccgagg    720

gaggtgatgc accaagtgac aacaactcta ttatatagtt tggaagggtt ggaagattta    780

gactggtcaa ggcttttcaa acttcagtca gctgatggtt cattcttaac ttctccatct    840

tcaactgcct tcgcattcat gcaaactaat aaccacaatt gcttgagatt catcactagc    900

gttgtccaaa cattcaatgg aggagctcca gataactatc caatcgacat ctttgcgaga    960

ctgtgggcag ttgacaggtt acagcggtta gggatttctc gtttcttcga gcaggagata   1020

aatgattgcc taagctatgt atatagattt tggaatgcaa atggagtttt cagtgcagga   1080

gccactaatt tttgtgatct tgacgacaca tccatggctt tccggctact acgtttgcat   1140

ggatatgatg tcgacccaaa tgttctgagg aaattcaaag agggagacag attctgttgc   1200

cacagtggtg aagtggcgat gtcgacatcg ccaacgtacg ctctctacag agcttcccaa   1260

attcagtttc caggagaaga aattctggat gaagccttca gcttcactcg cgactatcta   1320

caggactggt tagcaagaga tcaagttctt gataagtgga ttgtatccaa ggaccttcca   1380

gatgagatta aggtaggact agaggtgcca tggtatgcca gcctgccacg ggtagaggct   1440

gcttattaca tgcaacgaca ttacggcggg tctactgatg cgtgggtggc caagacttgt   1500

tacaggatgc ctgatgtgag caacgatgat tacctggagc ttgcaagatt ggatttcaag   1560

agatgtcaag cccaacatca gagtgaattg agttacatgc aacgatggta tgacagttgc   1620

aatgtcgaag aattcggaat aagcagaaaa gagttgcttg tagcttattt tgtggctgct   1680

gcaactattt ttgaacctga gagagcaact gagagaattg tgtgggcaaa aactgaaata   1740

gtttctaaga tgatcaaagc attttttggt gaagactcat tagaccaaaa aactatgttg   1800

ttaaaagaat tcagaaacag catcaataat ggctcccaca gattcatgaa gagtgagcat   1860

agaatcgtca acattctact acaagccttg caggagctat tacatggatc tgatgattgt   1920
```

```
cgtattggtc aactcaaaaa tgcttggtat gagtggctga tgaaattcga gggaggagat   1980

gaagcaagtt tgtggggaga aggagagctt cttgtcacca ccttaaacat ttgcacagct   2040

catttccttc aacaccatga tttactgttg aatcatgact acataactct ttctgagctc   2100

acaaacaaga tctgcctcaa gctttctcag attcaggtag gagaaatgaa tgaaatgaga   2160

gaagatatgc aggcgttgac gaaattagtg attggggaat catgcatcgt caacaaaaac   2220

attaagcaaa catttcttgc agttgcaaag actttctatt acagagccta cttcgatgcc   2280

gacaccgttg atctccatat atttaaagtt ctatttgagc ccattgtctg a            2331


<210> SEQ ID NO 29
<211> LENGTH: 787
<212> TYPE: PRT
<213> ORGANISM: Leonotis leonurus

<400> SEQUENCE: 29

Met Ala Ser Thr Ala Ser Thr Leu Asn Leu Thr Ile Asn Ser Thr Pro
1               5                   10                  15

Phe Val Ser Thr Lys Thr Gln Ala Lys Val Ser Leu Pro Ala Cys Leu
            20                  25                  30

Trp Met Gln Asp Arg Ser Ser Ser Arg His Val Ser Leu Lys His Lys
        35                  40                  45

Phe Cys Arg Asn Gln Gln Leu Lys Cys Arg Ala Ser Leu Asp Val Gln
    50                  55                  60

Gln Val Arg Asp Glu Val Phe Ser Thr Ala Gln Ser Pro Glu Ser Val
65                  70                  75                  80

Asp Lys Lys Ile Glu Glu Arg Lys Lys Trp Val Lys Asn Leu Leu Ser
                85                  90                  95

Thr Met Asp Asp Gly Arg Ile Asn Trp Ser Ala Tyr Asp Thr Ala Trp
            100                 105                 110

Ile Ser Leu Ile Lys Glu Phe Glu Gly Arg Asp Ala Pro Gln Phe Pro
        115                 120                 125

Ser Thr Leu Met Arg Ile Ala Glu Asn Gln Leu Ala Asp Gly Ser Trp
    130                 135                 140

Gly Asp Pro Asp Tyr Asp Cys Ser Tyr Asp Arg Ile Ile Asn Thr Leu
145                 150                 155                 160

Ala Cys Val Val Ala Leu Thr Thr Trp Asn Ala His Pro Glu His Asn
                165                 170                 175

Lys Lys Gly Ile Lys Tyr Ile Lys Glu Asn Met Tyr Lys Leu Glu Glu
            180                 185                 190

Thr Pro Val Val Leu Met Thr Ser Ala Phe Glu Val Val Phe Pro Ala
        195                 200                 205

Leu Leu Asn Arg Ala Lys Asn Leu Gly Ile Gln Asp Leu Pro Tyr Asp
    210                 215                 220

Met Pro Ile Val Lys Glu Ile Cys Lys Ile Gly Asp Glu Lys Leu Ala
225                 230                 235                 240

Arg Ile Pro Lys Lys Met Met Glu Lys Glu Pro Thr Ser Leu Met Tyr
                245                 250                 255

Ala Ala Glu Gly Val Glu Asn Leu Asp Trp Glu Lys Leu Leu Lys Gln
            260                 265                 270

Arg Thr Pro Glu Asn Gly Ser Phe Leu Ser Ser Pro Ala Ala Thr Ala
        275                 280                 285

Val Ala Phe Met His Thr Lys Asp Glu Asn Cys Leu Arg Tyr Ile Met
    290                 295                 300
```

-continued

Tyr Leu Leu Asp Lys Phe Asn Gly Gly Ala Pro Asn Val Tyr Pro Ile
305 310 315 320

Asp Leu Trp Ser Arg Leu Trp Ala Thr Asp Arg Ile Gln Arg Leu Gly
325 330 335

Ile Ser Arg Phe Phe Lys Glu Glu Ile Lys Glu Ile Leu Ser Tyr Val
340 345 350

Tyr Ser Tyr Trp Thr Asp Ile Gly Val Tyr Cys Thr Arg Asp Ser Lys
355 360 365

Tyr Ala Asp Ile Asp Asp Thr Ser Met Gly Phe Arg Leu Leu Arg Met
370 375 380

His Gly Phe Lys Met Asp Pro Asn Val Phe Lys Tyr Phe Gln Lys Asp
385 390 395 400

Asp Arg Phe Val Cys Leu Gly Gly Gln Met Asn Asp Ser Pro Thr Ala
405 410 415

Thr Tyr Asn Leu Tyr Arg Ala Ala Gln Tyr Gln Phe Pro Gly Glu Lys
420 425 430

Ile Leu Glu Asp Ala Arg Lys Phe Ser Gln Glu Phe Leu Gln His Cys
435 440 445

Ile Asp Thr Asn Asn Leu Leu Asp Lys Trp Val Ile Ser Pro Arg Phe
450 455 460

Pro Glu Glu Leu Lys Phe Gly Met Glu Met Thr Trp Tyr Ser Cys Leu
465 470 475 480

Pro Arg Ile Glu Ala Arg Tyr Tyr Val Gln His Tyr Gly Ala Thr Glu
485 490 495

Asp Val Trp Leu Gly Lys Thr Phe Phe Arg Met Glu Glu Ile Ser Asn
500 505 510

Glu Asn Tyr Lys Glu Leu Ala Lys Leu Asp Phe Ser Lys Cys Gln Ala
515 520 525

Gln His Gln Thr Glu Trp Ile His Met Gln Glu Trp Tyr Glu Ser Ser
530 535 540

Asn Ala Lys Glu Phe Gly Ile Ser Arg Lys Asp Leu Leu Phe Ala Tyr
545 550 555 560

Phe Leu Ala Ala Ala Ser Ile Phe Glu Thr Glu Arg Ala Lys Glu Arg
565 570 575

Ile Leu Trp Ala Lys Ser Gln Ile Ile Cys Lys Met Val Lys Ser Tyr
580 585 590

Leu Glu Asn Gln Thr Ala Ser Leu Glu His Lys Ile Ala Phe Leu Thr
595 600 605

Gly Phe Gly Asp Asn Asn Asn Gly Leu His Thr Ile Asn Lys Gly Ser
610 615 620

Gly Pro Val Asn Asn Val Met Arg Thr Leu Gln Gln Leu Leu Gly Glu
625 630 635 640

Phe Asp Gly Tyr Ile Ser Ser Gln Leu Glu Asn Ala Trp Ala Ala Trp
645 650 655

Leu Thr Lys Leu Glu Gln Gly Glu Ala Asn Asp Gly Glu Leu Leu Ala
660 665 670

Thr Thr Leu Asn Ile Cys Ser Gly Arg Ile Val Tyr Asn Glu Asp Thr
675 680 685

Leu Ser Asn Lys Glu Tyr Lys Ala Phe Ala Asp Leu Thr Asn Lys Ile
690 695 700

Cys Gln Asn Leu Ala Gln Ile Gln Asn Lys Lys Gly Asp Glu Ile Lys
705 710 715 720

-continued

```
Asp Pro Asn Glu Gly Glu Lys Asp Lys Glu Val Glu Gln Gly Met Gln
                725                 730                 735

Ala Leu Ala Lys Leu Val Phe Glu Glu Ser Gly Leu Glu Arg Ser Ile
            740                 745                 750

Lys Glu Thr Phe Leu Ala Val Val Arg Thr Tyr His Tyr Gly Ala Tyr
        755                 760                 765

Val Ala Asp Glu Lys Ile Asp Val His Met Phe Lys Val Leu Phe Glu
    770                 775                 780

Pro Val Glu
785
```

<210> SEQ ID NO 30
<211> LENGTH: 2364
<212> TYPE: DNA
<213> ORGANISM: Leonotis leonurus

<400> SEQUENCE: 30

```
atggcctcca ctgcatccac tctaaatttg accatcaata gtacaccatt tgtaagcacc     60
aaaacgcaag caaaggtttc cttgcccgca tgtttatgga tgcaggatag aagcagcagt    120
agacacgtgt cgttaaaaca caaattctgt cgaaatcaac aacttaagtg tcgagcaagt    180
ctggatgttc agcaagtacg tgatgaagtt ttttccactg ctcaatcccc tgaatcggtg    240
gataaaaaaa tagaggaacg taaaaaatgg gtgaagaatt tgttgagtac aatggacgat    300
ggacgaataa attggtcagc ctatgacacg gcatggattt cacttattaa agaatttgaa    360
ggacgagatg ctccccagtt tccgtcgact ctcatgcgca tcgcggagaa ccaattggcc    420
gacgggtcat ggggcgatcc agattacgac tgctcctatg atcggataat aaacacacta    480
gcgtgtgttg tagccttgac aacatggaat gctcatcctg aacacaataa aaaaggaata    540
aaatacatca aggaaaatat gtataaacta gaagagacgc ctgttgtact catgactagt    600
gcatttgaag ttgtgtttcc ggcgcttctt aacagagcta aaaacttggg cattcaagat    660
cttccctatg atatgcccat cgtgaaggag atttgtaaaa taggggatga gaagttggca    720
aggataccaa agaaaatgat ggagaaagag ccaacatcgc tgatgtatgc cgcggaagga    780
gtcgaaaact tggactggga aaagcttctg aaacagcgga cacccgagaa tggctcgttc    840
ctctcttccc cggccgcaac tgccgttgca tttatgcaca caaaagatga aaattgctta    900
agatacatca tgtacctttt ggacaaattt aatggaggag caccaaatgt ttatccgatc    960
gacctctggt caagactttg ggcaacggac aggatacaac gtctgggaat ttcccgcttc   1020
tttaaggaag agattaagga aatcttaagt tatgtctata gctattggac agacattgga   1080
gtctattgta cacgagattc caaatatgct gacattgacg acacatccat gggattcagg   1140
cttctgagga tgcacggatt taaaatggac ccaaatgtat ttaaatactt ccagaaagac   1200
gacagatttg tttgtctagg tggtcaaatg aatgattctc caactgcaac atacaatctt   1260
tacagggctg ctcaatacca atttccaggt gaaaaaattc tagaagatgc tagaaagttc   1320
tctcaagagt ttctacaaca ttgtatagac accaataacc ttctagataa atgggtgata   1380
tccccgcgct ttccggaaga gttgaaattt ggaatggaga tgacatggta ttcctgccta   1440
ccacgaattg aggctagata ctacgtacaa cattatggtg ctacagagga cgtctggctt   1500
ggaaagactt ttttcaggat ggaagaaatc agtaatgaga actataagga gcttgcaaaa   1560
cttgatttca gtaaatgcca agcacaacat cagacagagt ggattcatat gcaagagtgg   1620
tatgaaagta gcaatgctaa ggaatttggg ataagcagaa aagacctact tttgcttac    1680
```

```
tttttggctg cagcttccat atttgaaacc gaaagggcaa aagagagaat tctgtgggca   1740

aaatctcaaa ttatttgcaa gatggttaag tcatatctgg aaaaccaaac ggcgtcgttg   1800

gagcacaaaa tcgccttttt aactggattc ggagataaca acaatggcct gcacacaatt   1860

aataaggggt ctggacctgt taacaatgtc atgagaaccc tccaacagct ccttggagaa   1920

ttcgacggat atattagtag tcaattggaa aatgcttggg cagcatggtt gacgaaactc   1980

gagcaaggcg aggccaacga tggcgagctc ctcgcaacca cactaaacat ttgttctggg   2040

cgtattgtgt ataacgagga tacattatcg aacaaggagt acaaggcttt cgcagacctc   2100

acaaataaaa tttgtcaaaa tcttgctcaa atccaaaata aaaagggtga cgaaattaag   2160

gatccgaatg aaggcgaaaa ggacaaggaa gtcgagcaag gcatgcaggc attggctaag   2220

ttagtttttg aggaatctgg gcttgagagg agtatcaaag aaacattctt agcagtggtg   2280

agaacttatc actatggggc ctatgttgct gatgagaaga ttgatgtcca catgttcaag   2340

gttttgttcg aaccagttga atga                                          2364
```

<210> SEQ ID NO 31
<211> LENGTH: 799
<212> TYPE: PRT
<213> ORGANISM: Nepeta mussinii

<400> SEQUENCE: 31

```
Met Thr Ser Ile Ser Ser Leu Asn Leu Ser Asn Ala Ala Ala Ala Arg
1               5                   10                  15

Arg Arg Leu Gln Leu Pro Ala Asn Val His Leu Pro Glu Phe His Ser
            20                  25                  30

Val Cys Ala Trp Leu Asn Ser Ser Ser Lys His Asp Pro Phe Ser Cys
        35                  40                  45

Arg Ile His Arg Lys Gln Lys Ser Lys Val Thr Glu Cys Arg Val Ala
    50                  55                  60

Ser Val Asp Ala Ser Pro Val Ser Asp His Lys Met Ser Ser Pro Val
65                  70                  75                  80

Gln Thr Gln Glu Glu Ala Asn Lys Asn Met Glu Glu Ser Ile Glu Tyr
                85                  90                  95

Ile Lys Asn Leu Leu Met Thr Ser Gly Asp Gly Arg Ile Ser Val Ser
            100                 105                 110

Ala Tyr Asp Thr Ser Ile Val Ala Leu Ile Lys Asp Ile Glu Gly Arg
        115                 120                 125

Asp Ala Pro Gln Phe Pro Ser Cys Leu Glu Trp Ile Gly Gln Asn Gln
    130                 135                 140

Lys Ala Asp Gly Ser Trp Gly Asp Asp Phe Phe Cys Ile Tyr Asp Arg
145                 150                 155                 160

Phe Val Asn Thr Leu Ala Cys Ile Val Ala Leu Lys Ser Trp Asn Leu
                165                 170                 175

His Pro His Lys Ile Gln Lys Gly Val Thr Tyr Ile Lys Lys Asn Val
            180                 185                 190

His Lys Leu Lys Asp Gly Arg Pro Glu Leu Met Thr Ser Gly Phe Glu
        195                 200                 205

Ile Cys Val Pro Ala Ile Leu Gln Arg Ala Lys Asp Leu Gly Ile Gln
    210                 215                 220

Asp Leu Pro Tyr Asp Asp Pro Met Ile Lys Gln Ile Thr Asp Thr Lys
225                 230                 235                 240

Glu Arg Arg Leu Lys Lys Ile Pro Lys Asp Phe Ile Tyr Gln Leu Pro
                245                 250                 255
```

-continued

```
Thr Thr Leu Leu Phe Ser Leu Glu Gly Gln Glu Asn Leu Asp Trp Glu
            260                 265                 270

Lys Ile Leu Lys Leu Gln Ser Ala Asp Gly Ser Phe Leu Thr Ser Pro
        275                 280                 285

Ser Ser Thr Ala Ala Val Phe Met His Thr Lys Asp Glu Lys Cys Leu
    290                 295                 300

Lys Phe Ile Glu Asn Ala Val Lys Asn Cys Asp Gly Gly Val Pro His
305                 310                 315                 320

Thr Tyr Pro Val Asp Val Phe Ala Arg Leu Trp Ala Val Asp Arg Leu
                325                 330                 335

Gln Arg Leu Gly Ile Ser Arg Phe Phe Gln Pro Glu Ile Lys Tyr Phe
            340                 345                 350

Leu Asp His Ile Gln Ser Val Trp Thr Glu Asn Gly Val Phe Ser Gly
        355                 360                 365

Arg Asp Ser Gln Phe Cys Asp Ile Asp Asp Thr Ser Met Gly Ile Arg
    370                 375                 380

Leu Leu Lys Met His Gly Tyr Lys Ile Asp Pro Asn Ala Leu Glu His
385                 390                 395                 400

Phe Lys Gln Glu Asp Gly Lys Phe Ser Cys Tyr Gly Gly Gln Met Ile
                405                 410                 415

Glu Ser Ala Ser Pro Ile Tyr Asn Leu Tyr Arg Ala Ala Gln Leu Arg
            420                 425                 430

Phe Pro Gly Glu Glu Ile Leu Glu Glu Ala Ile Lys Phe Ser Tyr Asn
        435                 440                 445

Phe Leu Gln Glu Lys Leu Ala Lys Asp Glu Ile Gln Glu Lys Trp Val
    450                 455                 460

Ile Ser Glu His Leu Ile Asp Glu Ile Lys Ile Gly Leu Lys Met Pro
465                 470                 475                 480

Trp Tyr Ala Thr Leu Pro Arg Val Glu Ala Ala Tyr Tyr Leu Asp Tyr
                485                 490                 495

Tyr Ala Gly Ser Gly Asp Val Trp Ile Gly Lys Thr Phe Tyr Arg Met
            500                 505                 510

Pro Glu Ile Ser Asn Asp Thr Tyr Lys Glu Met Ala Ile Leu Asp Phe
        515                 520                 525

Asn Arg Cys Gln Ala Gln His Gln Phe Glu Trp Ile Tyr Met Gln Glu
    530                 535                 540

Trp Tyr Glu Ser Ser Asn Val Lys Glu Phe Gly Ile Ser Lys Lys Glu
545                 550                 555                 560

Leu Leu Val Ala Tyr Phe Leu Ala Ala Ser Thr Ile Phe Glu Pro Glu
                565                 570                 575

Arg Ala Gln Glu Arg Ile Met Trp Ala Lys Thr Lys Ile Val Ser Lys
            580                 585                 590

Met Ile Ala Ser Ser Leu Asn Lys Gln Thr Thr Leu Ser Leu Asp Gln
        595                 600                 605

Lys Thr Ala Leu Phe Thr Gln Leu Glu His Ser Leu Asn Gly Leu Asp
    610                 615                 620

Ser Asp Glu Lys Asp Asn Gly Val Ala Glu Thr Lys Asn Leu Val Ala
625                 630                 635                 640

Thr Phe Gln Gln Leu Leu Asp Gly Phe Asp Lys Tyr Thr Arg His Gln
                645                 650                 655

Leu Lys Asn Ala Trp Ser Gln Trp Leu Lys Gln Val Gln Gln Gly Glu
            660                 665                 670
```

```
Ala Thr Gly Gly Ala Asp Ala Glu Leu Glu Ala Asn Thr Leu Asn Ile
        675                 680                 685

Cys Ala Gly His Ile Ala Phe Asn Glu Gln Val Leu Ser His Asn Glu
    690                 695                 700

Tyr Thr Thr Leu Ser Thr Leu Thr Asn Lys Ile Cys His Arg Leu Thr
705                 710                 715                 720

Gln Ile Gln Asp Lys Lys Thr Leu Glu Ile Ile Asp Gly Gly Ile Arg
                725                 730                 735

Tyr Lys Glu Leu Glu Gln Glu Met Gln Ala Leu Val Lys Leu Val Val
            740                 745                 750

Glu Glu Asn Asp Gly Gly Gly Ile Asp Arg Asn Ile Lys Gln Thr Phe
        755                 760                 765

Leu Ser Val Phe Lys Asn Tyr Tyr Tyr Ser Ala Tyr His Asp Ala His
    770                 775                 780

Thr Thr Asp Val His Ile Phe Lys Val Leu Phe Gly Pro Val Val
785                 790                 795


<210> SEQ ID NO 32
<211> LENGTH: 2400
<212> TYPE: DNA
<213> ORGANISM: Nepeta mussinii

<400> SEQUENCE: 32

atgacttcaa tatcctctct aaatttgagc aatgcagcag ctgctcgccg caggttacaa     60

ctaccagcaa acgttcacct gccggaattt cactccgtct gtgcatggct gaatagcagc    120

agcaaacacg atccctttag ttgccgaatt catcgaaagc aaaaatcgaa agtaaccgag    180

tgtcgagtag caagcgtgga tgcatcacca gtgagtgatc ataaaatgag ttctcctgtt    240

caaactcaag aagaggcaaa taaaaatatg gaggagtcaa tcgagtacat aaagaatttg    300

ttgatgacat ctggagacgg gcgaataagc gtgtcggcat acgacacgtc aatagtcgcc    360

ctaattaagg acatagaagg acgggacgcc ccgcaatttc catcatgcct ggagtggatc    420

gggcaaaacc aaaaggccga tggctcgtgg ggggacgact tcttctgtat ttacgaccgc    480

ttcgtaaata cactagcatg tatcgtggcc ttgaaatcat ggaaccttca ccctcacaag    540

attcaaaaag gagtgacata catcaagaaa aacgtgcata agcttaaaga tgggaggcct    600

gagctgatga cgtcagggtt cgaaatttgt gttcccgcca ttcttcaaag agccaaagac    660

ttgggcatcc aagatcttcc ctatgatgat cccatgatta aacagatcac tgatacgaaa    720

gagcgacgac tcaaaaagat accgaaggat tttatatacc aattgccgac gactttactc    780

ttcagtttgg aagggcagga gaatttggac tgggaaaaga tactcaaact gcagtcagct    840

gacggctcct tccttacttc gccgtcctcc accgccgccg tcttcatgca taccaaagat    900

gaaaaatgct tgaagttcat agagaacgcc gtcaaaaatt gcgacggcgg agtgccccat    960

acctacccag tagacgtgtt tgcaagactt tgggcagttg acagactaca acgcctaggg   1020

atttctcgct tttttcagcc tgagattaaa tatttcttag atcacataca aagcgtttgg   1080

actgagaacg gagttttcag tggacgagat tcacaatttt gcgacattga tgatacgtcc   1140

atggggataa ggcttctgaa aatgcatgga tacaaaatcg acccaaatgc acttgagcat   1200

ttcaagcagg aggatggtaa attttcgtgc tacggtggtc aaatgatcga gtctgcatca   1260

ccgatataca atctgtaccg agctgctcaa ctccgatttc caggagaaga aattcttgaa   1320

gaggccatta aattttccta taactttttg caagaaaagc tagccaagga tgaaattcaa   1380

gaaaaatggg tcatatcgga gcacttaatt gatgagatta agatcgggct aaagatgcca   1440
```

```
tggtacgcca ctctaccccg agttgaagct gcatattacc tggactatta tgcaggatcc   1500

ggcgatgtgt ggattggcaa gactttctac aggatgccag aaatcagtaa tgatacatac   1560

aaagaaatgg ccattttgga tttcaaccga tgccaagcac aacatcagtt tgaatggatt   1620

tacatgcaag agtggtatga aagtagcaac gtaaaggaat ttgggataag caaaaaagag   1680

ctacttgttg cttatttctt ggctgcatca accatatttg aaccggaaag agcacaagag   1740

aggattatgt gggcaaaaac aaaaattgtt tccaaaatga tcgcatcatc tcttaacaaa   1800

caaaccactc tatcgttaga ccaaaagact gcacttttta cccaactcga acatagtctc   1860

aatggcctcg acagtgatga gaaagataat ggagtagctg agacgaaaaa tctagtggca   1920

accttccagc agctgctaga tggattcgac aaatacactc gccatcaatt gaaaaatgct   1980

tggagccagt ggttgaagca agtgcagcaa ggagaggcga ccgggggcgc agacgcggag   2040

ctggaagcaa acacgttgaa catctgtgcc ggtcatatcg cattcaacga acaagtatta   2100

tcgcacaacg aatacacaac tctctccaca ctcacaaaca agatctgcca ccggcttacc   2160

caaattcaag acaaaaagac gcttgagata atcgacggcg gcataagata taaggagctg   2220

gagcaggaga tgcaggcgtt ggtgaaatta gttgttgaag aaaacgacgg cggcggcata   2280

gacaggaata ttaaacaaac atttttatca gttttcaaga attattacta cagtgcctac   2340

cacgatgctc acacaaccga tgttcatatt ttcaaagtat tatttggacc ggtcgtctga   2400
```

```
<210> SEQ ID NO 33
<211> LENGTH: 796
<212> TYPE: PRT
<213> ORGANISM: Origanum majorana

<400> SEQUENCE: 33

Met Thr Asp Val Ser Ser Leu Arg Leu Ser Asn Ala Pro Ala Ala Gly
1               5                   10                  15

Gly Arg Leu Pro Leu Pro Gly Lys Val His Leu Pro Glu Phe Arg Thr
            20                  25                  30

Val Cys Ala Trp Leu Asn Asn Gly Cys Lys Tyr Glu Pro Leu Thr Cys
        35                  40                  45

Arg Ile Ser Arg Arg Lys Ile Ser Glu Cys Arg Val Ala Ser Leu Asn
    50                  55                  60

Ser Ser Gln Leu Ile Glu Lys Val Gly Ser Pro Ala Gln Ser Leu Glu
65                  70                  75                  80

Glu Ala Asn Lys Lys Ile Glu Asp Ser Ile Glu Tyr Ile Lys Asn Leu
                85                  90                  95

Leu Met Thr Ser Gly Asp Gly Arg Ile Ser Val Ser Ala Tyr Asp Thr
            100                 105                 110

Ser Leu Val Ala Leu Ile Lys Asp Val Lys Gly Arg Asp Ala Pro Gln
        115                 120                 125

Phe Pro Ser Cys Leu Glu Trp Ile Ala Gln Asn Gln Met Ala Asp Gly
    130                 135                 140

Ser Trp Gly Asp Glu Phe Phe Cys Ile Tyr Asp Arg Ile Val Asn Thr
145                 150                 155                 160

Leu Ala Cys Leu Val Ala Leu Lys Ser Trp Asn Leu His Pro Asp Lys
                165                 170                 175

Ile Glu Lys Gly Val Thr Tyr Ile Asn Glu Asn Val His Lys Leu Lys
            180                 185                 190

Asp Gly Ser Thr Glu His Met Thr Ser Gly Phe Glu Ile Val Val Pro
        195                 200                 205
```

```
Ala Thr Leu Glu Arg Ala Lys Val Leu Gly Ile Gln Gly Leu Pro Tyr
    210                 215                 220

Asp His Pro Phe Ile Lys Glu Ile Ile Asn Thr Lys Glu Arg Arg Leu
225                 230                 235                 240

Ser Lys Ile Pro Lys Asp Leu Ile Tyr Lys Leu Pro Thr Thr Leu Leu
                245                 250                 255

Phe Ser Leu Glu Gly Gln Gly Glu Leu Asp Trp Glu Lys Ile Leu Lys
            260                 265                 270

Leu Gln Ser Ser Asp Gly Ser Phe Leu Thr Ser Pro Ser Ser Thr Ala
        275                 280                 285

Ser Val Phe Met Arg Thr Lys Asp Glu Lys Cys Leu Lys Phe Ile Glu
    290                 295                 300

Asn Ala Val Lys Asn Cys Gly Gly Gly Ala Pro His Thr Tyr Pro Val
305                 310                 315                 320

Asp Val Phe Ala Arg Leu Trp Ala Val Asp Arg Leu Gln Arg Leu Gly
                325                 330                 335

Ile Ser Arg Phe Phe Gln His Glu Ile Lys Tyr Phe Leu Asp His Ile
            340                 345                 350

Asn Ser Val Trp Thr Glu Asn Gly Val Phe Ser Gly Arg Asp Ser Gln
        355                 360                 365

Phe Cys Asp Ile Asp Asp Thr Ser Met Gly Val Arg Leu Leu Lys Met
    370                 375                 380

His Gly Tyr Asn Val Asp Pro Asn Ala Leu Lys His Phe Lys Gln Glu
385                 390                 395                 400

Asp Gly Lys Phe Ser Cys Tyr Pro Gly Gln Met Ile Glu Ser Ala Ser
                405                 410                 415

Pro Ile Tyr Asn Leu Tyr Arg Ala Ala Gln Leu Arg Phe Pro Gly Glu
            420                 425                 430

Glu Ile Leu Glu Glu Ala Ser Arg Phe Ala Phe Asn Phe Leu Gln Glu
        435                 440                 445

Lys Ile Ala Asn His Glu Ile Gln Glu Lys Trp Val Ile Ser Glu His
    450                 455                 460

Leu Ile Asp Glu Ile Lys Leu Gly Leu Lys Met Pro Trp Tyr Ala Thr
465                 470                 475                 480

Leu Pro Arg Val Glu Ala Ala Tyr Tyr Leu Glu Tyr Tyr Ala Gly Ser
                485                 490                 495

Gly Asp Val Trp Ile Gly Lys Thr Phe Tyr Arg Met Pro Glu Ile Ser
            500                 505                 510

Asn Asp Thr Tyr Lys Glu Val Ala Ile Leu Asp Phe Asn Thr Cys Gln
        515                 520                 525

Ala Gln His Gln Phe Glu Trp Ile Tyr Met Gln Glu Trp Tyr Glu Ser
    530                 535                 540

Ser Lys Val Lys Asp Phe Gly Ile Ser Lys Lys Asp Leu Leu Val Ala
545                 550                 555                 560

Tyr Phe Leu Ala Ala Ser Thr Ile Phe Glu Pro Glu Arg Thr Gln Glu
                565                 570                 575

Arg Ile Ile Trp Ala Lys Thr Leu Ile Leu Ser Arg Met Ile Thr Ser
            580                 585                 590

Phe Leu Asn Lys Gln Ala Thr Leu Ser Ser Gln Gln Lys Asn Ala Ile
        595                 600                 605

Leu Thr Gln Leu Gly Glu Ser Val Asp Gly Leu Asp Lys Ile Tyr Ser
    610                 615                 620
```

-continued

```
Gly Glu Lys Asp Ser Gly Leu Ala Glu Thr Leu Leu Ala Thr Phe Gln
625                 630                 635                 640

Gln Leu Leu Asp Gly Phe Asp Arg Tyr Thr Arg His Gln Leu Arg Asn
                645                 650                 655

Ala Trp Gly Gln Trp Leu Met Lys Val Gln Gln Gly Glu Ala Asn Gly
            660                 665                 670

Gly Ala Asp Ala Glu Leu Ile Ala Asn Thr Leu Asn Ile Cys Ala Gly
        675                 680                 685

Leu Ile Ala Phe Asn Glu Asp Val Leu Leu His Ser Glu Tyr Thr Thr
    690                 695                 700

Leu Ser Ser Leu Thr Asn Lys Ile Cys Gln Arg Leu Ser Gln Ile Glu
705                 710                 715                 720

Asp Glu Lys Thr Leu Glu Val Ile Glu Gly Gly Ile Lys Asp Lys Glu
                725                 730                 735

Leu Glu Glu Asp Ile Gln Ala Leu Val Lys Leu Ala Leu Glu Glu Asn
            740                 745                 750

Gly Gly Cys Gly Val Asp Arg Arg Ile Lys Gln Ser Phe Leu Ser Val
        755                 760                 765

Phe Lys Thr Phe Tyr Tyr Arg Ala Tyr His Asp Ala Glu Thr Thr Asp
    770                 775                 780

Leu His Ile Phe Lys Val Leu Phe Gly Pro Val Met
785                 790                 795
```

<210> SEQ ID NO 34
<211> LENGTH: 2391
<212> TYPE: DNA
<213> ORGANISM: Origanum majorana

<400> SEQUENCE: 34

```
atgaccgatg tatcctctct tcgtttgagc aatgcaccag ctgccggcgg caggttgccg      60

ctgccgggaa aggttcacct gcctgaattt cgcaccgttt gtgcatggtt gaacaatggc     120

tgcaaatacg agcccttgac ttgtcgaatt agtcgacgga agatatctga atgtcgagta     180

gcaagtctga attcgtcgca actaattgaa aaggtcggtt ctcctgctca atctctagaa     240

gaggcaaaca aaaagatcga ggactccatc gagtacatta agaatctatt gatgacatct     300

ggcgacgggc ggataagtgt gtcggcttac gacacgtcgc tagtcgccct aataaaggac     360

gtgaaaggac gagatgcccc tcagttcccg tcgtgcctgg agtggatagc gcaaaaccaa     420

atggccgacg ggtcgtgggg ggatgagttc ttctgtattt acgaccggat cgtgaataca     480

ttagcatgcc tcgttgcctt gaaatcatgg aaccttcacc ccgacaagat cgaaaaagga     540

gtgacgtaca tcaacgaaaa tgtgcacaaa ctgaaagacg ggagcaccga gcacatgacg     600

tcagggttcg aaatcgtggt ccccgccact ctagaaagag ccaaagtctt gggcatccaa     660

ggcctccctt atgatcatcc cttcattaag gagattatta atactaagga gcgaagatta     720

agcaaaatac ccaaggattt gatatacaaa ctgccaacga cgctgctgtt cagtttagaa     780

gggcagggag aattagattg ggaaaagata ctgaaactgc agtcaagcga tggctccttc     840

cttacttcgc cctcgtcgac cgcctccgtc ttcatgcgga cgaaagacga gaaatgcctc     900

aagttcattg agaacgccgt taagaattgc ggcgggggag cgccgcatac ttacccagtg     960

gatgtgtttg caagactttg ggcagttgac agactacagc gattagggat ttctcgattc    1020

ttccaacacg agattaaata cttcttagat cacattaaca gtgtatggac cgagaatgga    1080

gttttcagtg gacgagattc acaattttgt gatatcgacg acacttctat gggagttagg    1140
```

-continued

```
cttctaaaaa tgcatggata caatgttgat ccaaatgcgc tcaagcattt caagcaggag   1200

gatggcaaat tctcttgcta ccctggccaa atgatcgagt ctgcatctcc gatatacaat   1260

ctctaccgag ccgctcaact ccggttcccc ggagaagaaa ttctcgaaga agcaagtcga   1320

ttcgccttca actttctgca ggaaaagata gccaaccatg aaattcaaga aaaatgggtc   1380

atatctgagc acttaattga tgagataaag ttgggactga agatgccatg gtacgcgact   1440

ctgccccgag ttgaggccgc ttattatcta gagtattatg ctggctcagg cgacgtatgg   1500

attggaaaga ctttctaccg gatgccggaa atcagtaacg atacgtataa agaggtggcc   1560

attttggatt tcaacacatg ccaagctcaa caccagtttg aatggattta catgcaagag   1620

tggtacgaaa gtagcaaggt taaagatttc gggataagca aaaaggacct acttgttgct   1680

tactttctgg cggcatcgac tatatttgaa cccgaaagaa cacaagagag gattatttgg   1740

gcaaaaaccc taattctttc taggatgatc acatcatttc tcaacaaaca agctacactt   1800

tcatcccaac aaaagaatgc catcttaaca caacttggag agagtgtcga tggcctcgat   1860

aaaatatata gtggtgagaa agattctggg ctggctgaga ctctgctggc taccttccag   1920

caactgctcg acggattcga tagatacact cgccatcaac tgagaaatgc ttgggggcaa   1980

tggttgatga aagtgcagca aggagaggcc aacggtggcg ccgacgctga gctcatagca   2040

aacacactca atatctgcgc cggccttatc gccttcaacg aagacgtatt gttgcacagc   2100

gaatacacga ctctctcctc cctcaccaac aaaatatgcc agcgccttag ccagattgaa   2160

gatgaaaaga cgcttgaagt gattgaaggg ggcataaaag ataaggaact ggaggaggat   2220

attcaggcgt tggtgaagct agccctcgaa gaaaacggcg gctgcggcgt cgacagaaga   2280

atcaagcagt cattcttatc agtattcaag actttttact acagagccta ccatgatgct   2340

gagaccaccg atcttcatat tttcaaagta ctgtttgggc cggttatgtg a            2391
```

<210> SEQ ID NO 35
<211> LENGTH: 798
<212> TYPE: PRT
<213> ORGANISM: Perovskia atriplicifolia

<400> SEQUENCE: 35

```
Met Thr Ser Met Ser Ser Leu Asn Leu Ser Arg Ala Pro Ala Thr Thr
1               5                   10                  15

His Arg Leu Gln Leu Gln Ala Lys Val His Val Pro Glu Phe Tyr Ala
            20                  25                  30

Val Cys Ala Trp Leu Asn Ser Ser Ser Lys Gln Ala Pro Leu Ser Cys
        35                  40                  45

Gln Ile Arg Cys Lys Gln Leu Ser Arg Val Thr Glu Cys Arg Val Ala
    50                  55                  60

Ser Leu Asp Ala Ser Gln Val Ser Glu Lys Asp Thr Ser His Val Gln
65                  70                  75                  80

Thr Pro Asp Glu Val Asn Lys Lys Ile Glu Asp Tyr Ile Glu Tyr Val
                85                  90                  95

Lys Asn Leu Leu Met Thr Ser Gly Asp Gly Arg Ile Ser Val Ser Pro
            100                 105                 110

Tyr Asp Thr Ser Ile Val Ala Leu Ile Lys Asp Ser Lys Gly Arg Asn
        115                 120                 125

Ile Pro Gln Phe Pro Ser Cys Leu Glu Trp Ile Ala Gln His Gln Met
    130                 135                 140

Ala Asp Gly Ser Trp Gly Asp Gln Phe Phe Cys Ile Tyr Asp Arg Ile
145                 150                 155                 160
```

-continued

```
Leu Asn Thr Leu Ala Cys Val Val Ala Leu Lys Ser Trp Asn Val His
                165                 170                 175

Gly Asp Met Ile Glu Lys Gly Val Thr Tyr Val Lys Glu Asn Val His
            180                 185                 190

Lys Leu Lys Asp Gly Asn Ile Glu His Met Thr Ser Gly Phe Glu Ile
        195                 200                 205

Val Val Pro Ala Leu Val Gln Arg Ala Lys Asp Leu Gly Ile Gln Gly
    210                 215                 220

Leu Pro Tyr Asp Asp Pro Leu Ile Lys Glu Ile Ala Asp Thr Lys Glu
225                 230                 235                 240

Arg Arg Leu Lys Lys Ile Pro Lys Asp Met Ile Tyr Gln Thr Pro Thr
                245                 250                 255

Thr Leu Leu Phe Ser Leu Glu Gly Gln Gly Asp Leu Glu Trp Glu Lys
            260                 265                 270

Ile Leu Lys Leu Gln Ser Gly Asp Gly Ser Phe Leu Thr Ser Pro Ser
        275                 280                 285

Ser Thr Ala His Val Phe Val Gln Thr Lys Asp Glu Lys Cys Leu Lys
    290                 295                 300

Phe Ile Glu Asn Ala Val Lys Asn Cys Ser Gly Gly Ala Pro His Thr
305                 310                 315                 320

Tyr Pro Val Asp Val Phe Ala Arg Leu Trp Ala Ile Asp Arg Leu Gln
                325                 330                 335

Arg Leu Gly Ile Ser Arg Phe Phe Gln Pro Glu Ile Lys Tyr Phe Ile
            340                 345                 350

Asp His Ile Asn Ser Val Trp Thr Glu Asn Gly Val Phe Ser Gly Arg
        355                 360                 365

Asp Ser Glu Phe Cys Asp Ile Asp Asp Thr Ser Met Gly Ile Arg Leu
    370                 375                 380

Leu Lys Met His Gly Tyr Lys Val Asp Pro Asn Ala Leu Asn His Phe
385                 390                 395                 400

Lys Gln Gln Asp Gly Lys Phe Ser Cys Tyr Gly Gly Gln Met Ile Glu
                405                 410                 415

Ser Ala Ser Pro Ile Tyr Asn Leu Tyr Arg Ala Ala Gln Leu Arg Phe
            420                 425                 430

Pro Gly Glu Glu Ile Leu Glu Glu Ala Ser Lys Phe Ala Phe Asn Phe
        435                 440                 445

Leu Gln Glu Lys Ile Ala Asn Asp Gln Phe Gln Glu Lys Trp Val Ile
    450                 455                 460

Ser Asp His Leu Ile Asp Glu Val Lys Leu Gly Leu Lys Met Pro Trp
465                 470                 475                 480

Tyr Ala Thr Leu Pro Arg Val Glu Ala Ala Tyr Tyr Leu Gln Tyr Tyr
                485                 490                 495

Ala Gly Ser Gly Asp Val Trp Ile Gly Lys Val Phe Tyr Arg Met Pro
            500                 505                 510

Glu Ile Ser Asn Asp Thr Tyr Lys Glu Leu Ala Ile Leu Asp Phe Asn
        515                 520                 525

Arg Cys Gln Ala Gln His Gln Phe Glu Trp Ile Tyr Met Gln Glu Trp
    530                 535                 540

Tyr His Arg Ser Ser Val Ser Glu Phe Gly Ile Ser Lys Lys Glu Leu
545                 550                 555                 560

Leu Arg Thr Tyr Phe Leu Ala Ala Ala Thr Ile Phe Glu Pro Glu Arg
                565                 570                 575
```

-continued

```
Thr Gln Glu Arg Leu Val Trp Ala Lys Thr Gln Ile Val Ser Arg Met
            580                 585                 590

Ile Thr Ser Phe Val Asn Asn Gly Thr Thr Leu Ser Leu Asp Gln Met
        595                 600                 605

Thr Ala Leu Ala Thr Gln Ile Gly His Asn Phe Asp Gly Leu Asp Gln
    610                 615                 620

Ile Ile Ser Ala Met Lys Asp His Gly Leu Ala Gly Thr Leu Leu Thr
625                 630                 635                 640

Thr Phe Gln Gln Leu Leu Asp Gly Phe Asp Arg Tyr Thr Arg His Gln
                645                 650                 655

Leu Lys Asn Ala Trp Ser Gln Trp Phe Met Lys Leu Gln Gln Gly Glu
            660                 665                 670

Ala Asn Gly Gly Glu Asp Ala Glu Leu Leu Ala Asn Thr Leu Asn Ile
        675                 680                 685

Cys Ala Gly Phe Ile Ala Phe Asn Glu Asp Val Leu Ser His Asp Glu
    690                 695                 700

Tyr Thr Thr Leu Ser Thr Leu Thr Asn Lys Ile Cys Lys Arg Leu Ser
705                 710                 715                 720

Gln Ile Gln Asp Lys Lys Ala Leu Glu Val Val Asp Gly Ser Ile Lys
                725                 730                 735

Asp Lys Glu Leu Glu Gln Asp Met Gln Ala Leu Val Lys Leu Val Leu
            740                 745                 750

Glu Glu Asn Gly Gly Gly Val Asp Arg Asn Ile Lys Gln Thr Phe Leu
        755                 760                 765

Ser Val Phe Lys Thr Phe Tyr Tyr Thr Ala Tyr His Asp Asp Glu Thr
    770                 775                 780

Thr Asp Val His Ile Phe Lys Val Leu Phe Gly Pro Val Val
785                 790                 795
```

<210> SEQ ID NO 36
<211> LENGTH: 2397
<212> TYPE: DNA
<213> ORGANISM: Perovskia atriplicifolia

<400> SEQUENCE: 36

```
atgacctcta tgtcctctct aaatttgagc agagcaccag ctaccaccca ccggttacag      60

ctacaggcaa aggttcacgt gccggaattt tatgccgtgt gtgcatggct gaatagcagc     120

agcaaacagg cacccttgag ttgccaaatt cgctgcaagc aactatcaag agtaactgaa     180

tgtcgggtag caagtctgga tgcgtcgcaa gtgagtgaaa aagacacttc tcatgtccaa     240

actcccgatg aggtgaacaa aaagatcgag gactatatcg agtacgtcaa gaatctgttg     300

atgacgtcgg gcgacgggcg aataagcgtg tcgccctacg acacgtcaat agtcgccctt     360

attaaggact cgaaagggcg caacatcccg cagtttccgt cgtgcctcga gtggatagcg     420

cagcaccaaa tggcggatgg ctcatggggg gatcaattct tctgcattta cgaccggatt     480

ctaaatacat tagcatgtgt cgtagctttg aaatcctgga acgttcacgg tgacatgatc     540

gaaaaaggag tgacgtacgt caaggaaaat gtgcataagc ttaaagatgg gaatattgag     600

cacatgacgt cggggttcga aattgtggtt cccgcccttg ttcaaagagc caaagacttg     660

ggcatccaag gcctgcccta tgatgatccc ctcatcaagg agattgctga tacaaaagaa     720

agaagattga aaaagatacc caaggatatg atttaccaaa cgccaacgac attactattc     780

agtttagaag ggcagggaga tttggagtgg gaaaagatac tgaaactgca gtcaggcgat     840

ggctccttcc tcacttcgcc gtcatccacc gcccacgtgt tcgtgcagac caaagatgaa     900
```

-continued

```
aaatgcttga aattcatcga gaacgccgtc aagaattgca gtggaggagc gccgcatact    960

tatccagtcg atgtcttcgc aagactttgg gcaattgaca gactacaacg cctaggaatt   1020

tctcgtttct tccagccgga aattaagtat ttcatagacc acatcaacag cgtttggaca   1080

gagaacggag ttttcagtgg gcgagattcg gaattttgcg atattgatga cacgtccatg   1140

ggcatcaggc ttctcaaaat gcacggatac aaagtcgacc caaatgcact caatcatttc   1200

aagcagcaag atggtaaatt ttcttgctac ggtggtcaaa tgatcgagtc tgcatctcca   1260

atatacaatc tctacagggc tgctcagcta cgatttccag gagaagaaat tcttgaagaa   1320

gccagtaaat ttgcctttaa ctttttgcaa gaaaaaatag ccaacgatca atttcaagaa   1380

aaatgggtga tatccgacca cttaatcgat gaggtgaagc tcgggctgaa gatgccatgg   1440

tacgccactc taccccgggt tgaggctgca tattatctac aatactatgc tggttctggc   1500

gacgtatgga ttggcaaggt tttctacagg atgccggaaa tcagcaatga tacatacaaa   1560

gagctggcca tattggattt caacagatgc caagcacagc atcagttcga atggatttat   1620

atgcaagagt ggtatcacag aagcagcgtt agtgaattcg ggataagcaa aaaagagctg   1680

cttcgtactt actttctggc tgcagcaacc atattcgaac ccgagagaac acaagagagg   1740

cttgtgtggg caaaaaccca aattgtctct aggatgatca catcatttgt taacaatgga   1800

actacactat ctttggacca aatgactgca cttgcaacac aaatcggcca taatttcgat   1860

ggcctcgatc aaataattag tgctatgaaa gatcatggac tggctgggac tctgctgaca   1920

accttccagc aacttctaga tggattcgac agatacactc gccatcaact caaaaatgct   1980

tggagccaat ggttcatgaa actccagcaa ggggaggcga acggcgggga agacgcggag   2040

ctcctagcaa acacgctcaa catctgcgcg ggtttcattg ctttcaacga agacgtattg   2100

tcgcacgatg aatacacgac tctctccacc cttacaaaca aaatctgcaa gcgccttagc   2160

caaattcaag ataaaaaggc gctggaagtt gtcgacggga gcataaagga taaggagctc   2220

gaacaggata tgcaggcgtt ggtgaagttg gtccttgaag aaaatggcgg cggcgtcgac   2280

aggaacatca aacagacatt tttgtccgtt ttcaagactt tttactacac cgcctaccac   2340

gatgatgaga ccactgatgt tcatattttc aaagtactgt ttggaccggt cgtatga      2397
```

```
<210> SEQ ID NO 37
<211> LENGTH: 783
<212> TYPE: PRT
<213> ORGANISM: Pogostemon cablin

<400> SEQUENCE: 37

Met Ser Phe Ala Ser Gln Ser His Val Ala Phe Val Leu Arg Arg Pro
1               5                   10                  15

Ser Ala Val Ala Pro Pro Pro Pro Thr Arg Ile Pro Thr Thr Ala Ala
            20                  25                  30

Leu Ser Pro Leu Lys Pro Gly Asp Phe Ser His Gly Arg Ser Ser Phe
        35                  40                  45

Met Pro Thr Ser Ile Lys Cys Asn Ala Ile Ser Thr Ser Arg Val Glu
    50                  55                  60

Glu Tyr Lys Tyr Thr Asp Asp His Asn Gln Ser Gly Leu Leu Glu His
65                  70                  75                  80

Asp Gly Leu Ile Ser Asp Lys Ile Asn Glu Leu Val Thr Lys Ile Gln
                85                  90                  95

Leu Met Leu Gln Asn Met Asp Asp Gly Glu Ile Ser Ile Ser Pro Tyr
            100                 105                 110
```

```
Asp Thr Ala Trp Val Ser Leu Val Glu Asp Val Gly Gly Asn Asp Arg
        115                 120                 125

Pro Gln Phe Pro Thr Ser Leu Glu Trp Ile Ser Asn Asn Gln Leu Pro
    130                 135                 140

Asp Gly Ser Trp Gly Asp Pro Asn Ala Phe Leu Val His Asp Arg Ile
145                 150                 155                 160

Leu Asn Thr Leu Ala Cys Val Val Ala Leu Lys Ser Trp Lys Met His
                165                 170                 175

Pro His Lys Cys Asn Arg Gly Val Ser Phe Val Arg Glu Asn Ile Tyr
            180                 185                 190

Arg Met Asp Asp Glu Lys Glu Glu His Met Pro Asn Gly Phe Glu Val
        195                 200                 205

Val Phe Pro Ala Leu Leu Gln Lys Ala Lys Thr Leu Asn Ile Asp Ile
    210                 215                 220

Pro Tyr Glu Phe Pro Gly Ile Gln Lys Phe Tyr Ala Lys Arg Asp Leu
225                 230                 235                 240

Lys Phe Ala Arg Ile Pro Met Asp Ile Leu His Ser Val Pro Thr Thr
                245                 250                 255

Leu Leu Phe Ser Leu Glu Gly Val Arg Cys Gly Leu Asp Leu Asp Trp
            260                 265                 270

Gly Lys Leu Leu Glu Leu Gln Ala Ala Asp Gly Ser Phe Leu Tyr Ser
        275                 280                 285

Pro Ser Ser Thr Ala Phe Ala Leu Glu Gln Thr Lys Asp Gln Asn Cys
    290                 295                 300

Leu Lys Tyr Leu Ser Lys Leu Val Arg Lys Phe Asp Gly Gly Val Pro
305                 310                 315                 320

Asn Val Tyr Pro Val Asp Leu Phe Glu His Asn Trp Ala Val Asp Arg
                325                 330                 335

Leu Gln Arg Leu Gly Ile Ser Arg Tyr Phe Thr Pro Glu Ile Asn Gln
            340                 345                 350

Cys Leu Asp Tyr Ser Tyr Arg Tyr Trp Ser Asn Ser Lys Gly Met Tyr
        355                 360                 365

Ser Ala Ser Asn Ser Gln Ile Gln Asp Val Asp Asp Thr Ala Met Gly
    370                 375                 380

Phe Arg Leu Leu Arg Leu Asn Gly Tyr Asp Val Ser Thr Gln Gly Phe
385                 390                 395                 400

Arg Gln Phe Glu Ala Gly Gly Asp Phe Phe Cys Phe Ala Gly Gln Ser
                405                 410                 415

Ser Gln Ala Val Thr Gly Met Tyr Asn Leu Tyr Arg Ala Ser Gln Val
            420                 425                 430

Met Phe Pro Gly Glu Lys Leu Leu Glu Asp Ala Lys Lys Phe Ser Thr
        435                 440                 445

Asn Phe Leu Gln Gln Lys Arg Ala Asn Asn Gln Leu Thr Asp Lys Trp
    450                 455                 460

Val Ile Ala Lys Asp Val Pro Ala Glu Val Gly Tyr Ala Leu Asp Ile
465                 470                 475                 480

Pro Trp Tyr Ala Ser Leu Pro Arg Leu Glu Ala Arg Phe Phe Ile Gln
                485                 490                 495

Gln Tyr Gly Gly Asp Asp Asp Val Trp Ile Gly Lys Thr Leu Tyr Arg
            500                 505                 510

Met Gly Tyr Val Asn Asn Asn Thr Tyr Leu Glu Leu Ala Lys Leu Asp
        515                 520                 525
```

-continued

```
Tyr Asn Thr Cys Gln Arg Leu His Gln His Glu Trp Ile Thr Ile Gln
    530                 535                 540

Arg Trp Tyr Glu Ile Asn Leu Lys Ile Thr Ser Val Gly Leu Ser Lys
545                 550                 555                 560

Arg Gly Val Leu Leu Ser Tyr Tyr Leu Ala Ala Ala Asn Leu Phe Glu
                565                 570                 575

Pro Gln Asn Ser Thr His Arg Ile Ala Trp Ala Lys Thr Ser Ile Leu
            580                 585                 590

Val Ser Ala Ile Gln Leu Ser Pro Leu Gln Lys Arg Asp Phe Ile Asn
        595                 600                 605

Gln Phe His Arg Ser Thr Ala Asn Asn Gly Tyr Glu Thr Ser Asn Val
    610                 615                 620

Leu Val Lys Ser Val Ile Lys Gly Val His Glu Leu Ser Met Asp Ala
625                 630                 635                 640

Met Leu Thr His Asn Lys Asp Ile His Arg Gln Leu Phe Asn Ala Trp
                645                 650                 655

Arg Lys Trp Met Ser Val Trp Glu Glu Gly Gly Asp Gly Glu Ala Glu
            660                 665                 670

Leu Leu Leu Ser Thr Leu Asn Thr Cys Asp Gly Val Asp Glu Ser Thr
        675                 680                 685

Phe Ser Asp Pro Lys Tyr Glu His Leu Leu Glu Ile Thr Val Arg Val
    690                 695                 700

Thr His Gln Leu His Leu Ile Gln Asn Ala Glu Thr Lys Arg Val Gly
705                 710                 715                 720

Asp Arg Glu Glu Ile Asp Leu Ser Met Gln Gln Leu Val Lys Leu Val
                725                 730                 735

Phe Thr Lys Ser Ser Ser Asp Leu Asp Ser Cys Ile Lys Gln Arg Phe
            740                 745                 750

Phe Ala Ile Ala Arg Ser Phe Tyr Tyr Val Ala His Cys Asp Pro Glu
        755                 760                 765

Met Val Asp Ser His Ile Ala Lys Val Leu Phe Glu Arg Val Met
    770                 775                 780
```

<210> SEQ ID NO 38
<211> LENGTH: 2352
<212> TYPE: DNA
<213> ORGANISM: Pogostemon cablin

<400> SEQUENCE: 38

```
atgtcatttg cttctcaatc acatgtcgcc tttgtactcc gacggccatc tgccgttgct      60

ccgccaccac cgactagaat tccgacaaca gccgctcttt ctcctctcaa accaggtgat     120

ttttcccatg gcagatcatc atttatgccc acttccatta aatgtaatgc aatttccaca     180

tctcgcgtcg aagaatacaa gtacacggat gatcataatc agagtggttt attggagcat     240

gatggtttga tatcagacaa gataaatgaa ttggtgacca agatacaatt gatgctacaa     300

aacatggatg acggagagat aagcatctcc ccatatgaca ccgcatgggt gtcgttggtg     360

gaggatgtgg gcggcaacga ccgcccacag tttcctacga gcctggagtg gatatcgaat     420

aaccagctcc ccgacggctc gtggggcgac ccgaatgcct tttggtgca cgaccgtatc     480

ctcaacacat tggcatgcgt cgttgcactc aaatcctgga aatgcaccc ccacaaatgc     540

aatagaggag ttagtttcgt gagagaaaat atatacagaa tggatgatga aaaagaggaa     600

cacatgccaa atggattcga agtggtattt ccagcactcc ttcaaaaagc gaaaacccta     660

aacattgata tcccgtacga gtttccagga atacaaaaat tttatgccaa aagagattta     720
```

```
aaattcgcca ggattccaat ggatatattg catagcgttc cgacaacatt actgttcagc    780
ttagaaggtg taagatgtgg tcttgatctg gattggggga agcttctaga attgcaagct    840
gctgatggct catttctcta ctctccatcc tctactgcct ttgcactaga acaaaccaag    900
gatcaaaact gcctcaaata tctatctaaa cttgttcgaa aattcgatgg cggagtaccc    960
aacgtgtacc cggtggactt gttcgaacat aattgggcag ttgatcgtct ccaaaggctc   1020
ggaatttctc gttattttac gcctgaaatc aaccaatgtc ttgattattc ttacagatat   1080
tggtcaaata gtaaagggat gtactcggca agcaattccc agattcagga cgttgatgac   1140
accgccatgg gattcaggct tttgagactc aacggctacg atgtctctac acaagggttt   1200
aggcaattcg aggcaggggg ggacttcttc tgcttcgcgg ggcagtcgag ccaagctgta   1260
accggaatgt acaacctcta cagagcttcc caagtgatgt tccctggaga gaagctactg   1320
gaagatgcca agaaattctc caccaacttc ttgcaacaaa aacgagccaa taaccagctc   1380
actgacaagt gggttattgc caaagatgtt ccagctgagg tgggatatgc cttggatatt   1440
ccctggtatg ccagtctgcc ccgactggaa gcaagatttt tcatacaaca atacggtgga   1500
gacgacgacg tttggatcgg caaaaccttg tatagaatgg gatatgtgaa caacaacact   1560
tatctggaac tcgcaaagct agactacaac acctgccaaa ggttgcatca gcatgagtgg   1620
ataaccattc aacgatggta cgaaattaat ttaaaaatta ctagtgttgg gttgagcaaa   1680
agaggggtcc tgttgagtta ttacttagcc gcagccaatc tgtttgagcc tcaaaactca   1740
acacaccgca tcgcttgggc caaaacttcg attttagtaa gcgctattca actttctccc   1800
ctccaaaagc gcgactttat taaccaattc caccgctcca ccgcaaataa tgggtatgaa   1860
acaagtaatg tgttggtgaa gagtgtaatc aagggtgtgc atgagctctc catggacgct   1920
atgttgacgc acaataaaga catacatcgc caacttttta atgcttggcg aaagtggatg   1980
tcagtgtggg aagagggagg tgatggagaa gcggagctgt tattgtcgac gcttaacacg   2040
tgcgacggag tagatgaatc cacattcagc gatcccaaat acgagcacct cttagagatc   2100
accgtcagag tcacccacca gcttcatctc attcagaatg cagagacgaa gcgtgtgggt   2160
gaccgtgagg aaatagattt gagcatgcaa caacttgtta agttggtgtt cactaaatca   2220
tcatcggatc tggattcttg tatcaagcaa agatttttg cgattgccag aagtttctat   2280
tacgtggctc attgtgatcc ggagatggtg gactcccaca tagccaaagt attgtttgag   2340
agggtgatgt ag                                                       2352
```

<210> SEQ ID NO 39
<211> LENGTH: 599
<212> TYPE: PRT
<213> ORGANISM: Prunella vulgaris

<400> SEQUENCE: 39

```
Met Ser Ser Leu Ser Ile Pro Phe Ser Ser Ala Ile Cys Thr Ser Ser
1               5                   10                  15

Ile Pro Lys Ile Ser Thr Gly His His Arg Arg Thr Ala Arg Met Pro
            20                  25                  30

Ala His Asp Thr Ser Arg Leu Val Phe Arg Pro Ser Ala Val Met Val
        35                  40                  45

Glu Gly Ser Pro Met Thr Thr Ser Ser Asn Gly Lys Glu Val Gln Arg
    50                  55                  60

Leu Ile Thr Thr Phe Lys Pro Ser Met Trp Lys Asp Ile Phe Ser Thr
65                  70                  75                  80
```

-continued

```
Phe Ser Phe Asp Asn Gln Val Gln Glu Lys Tyr Leu Lys Glu Ile Glu
                85                  90                  95

Glu Leu Lys Lys Glu Val Arg Ser Thr Leu Met Ser Ala Thr His Arg
            100                 105                 110

Lys Leu Phe Asp Leu Ile Asp Asn Leu Glu Arg Met Gly Ile Ala Tyr
        115                 120                 125

His Phe Glu Thr Glu Ile Glu Asp Lys Leu Lys Gln Ala His Ala Ser
    130                 135                 140

Leu Glu Glu Glu Asp Asp Tyr Asp Leu Phe Thr Thr Ala Leu Arg Phe
145                 150                 155                 160

Arg Leu Leu Arg Gln His Arg Tyr His Val Ser Cys Asp Pro Phe Ala
                165                 170                 175

Lys Phe Val Asp Gln Asp Asn Lys Leu Lys Glu Ser Leu Ser Ser Asp
            180                 185                 190

Val Glu Gly Leu Leu Ser Leu Phe Glu Ala Ser His Leu Arg Ile His
        195                 200                 205

Asn Glu Asp Val Leu Asp Glu Ala Ile Val Phe Thr Thr His His Leu
    210                 215                 220

Asn Arg Met Met Pro Gln Leu Glu Ser Pro Leu Lys Glu Glu Val Lys
225                 230                 235                 240

His Ala Leu Arg Tyr Pro Leu His Lys Cys Leu Gly Ile Leu Ser Leu
                245                 250                 255

Arg Phe His Ile Asp Arg Tyr Glu Asn Asp Lys Ser Arg Asp Glu Val
            260                 265                 270

Val Leu Arg Leu Gly Gln Val Asn Phe Asn Tyr Met Gln Asn Ile Tyr
        275                 280                 285

Met Asn Glu Leu Tyr Glu Ile Thr Thr Trp Trp Asn Lys Leu Gln Met
    290                 295                 300

Thr Ser Lys Val Pro Tyr Phe Arg Asp Arg Leu Val Glu Cys Tyr Met
305                 310                 315                 320

Trp Gly Leu Ala Tyr His Phe Glu Pro Glu Tyr Ala Pro Val Arg Val
                325                 330                 335

Leu Ile Thr Lys Tyr Tyr Met Thr Ala Thr Thr Val Asp Asp Thr Tyr
            340                 345                 350

Asp Asn Tyr Ala Thr Leu Glu Glu Ile Glu Leu Phe Thr Gln Ala Ile
        355                 360                 365

Asp Arg Trp Ser Glu Asp Glu Ile Asp Gln Leu Pro Asp Glu Tyr Leu
    370                 375                 380

Lys Ile Val Tyr Lys Gly Leu Met Asn Phe Thr Glu Glu Phe Arg Arg
385                 390                 395                 400

Asp Ala Glu Glu Arg Gly Lys Gly Tyr Val Ile Pro Tyr Phe Ile Glu
                405                 410                 415

Glu Thr Lys Arg Ala Thr Gln Gly Tyr Ala Asn Glu Gln Arg Trp Ile
            420                 425                 430

Met Lys Arg Glu Met Pro Ser Phe Glu Glu Tyr Met Val Asn Ser Arg
        435                 440                 445

Val Thr Ser Leu Met Tyr Val Thr Tyr Val Ala Val Val Ala Val Ile
    450                 455                 460

Glu Ser Ala Thr Lys Glu Thr Val Asp Trp Ala Leu Ser Asp Ser Asp
465                 470                 475                 480

Ile Phe Val Tyr Thr Asn Asp Ile Gly Arg Leu Ile Asp Asp Leu Ala
                485                 490                 495
```

```
Thr His Arg Arg Glu Arg Lys Asp Gly Thr Met Leu Thr Ser Met Asp
            500                 505                 510

Tyr Tyr Met Lys Glu Tyr Gly Gly Thr Met Glu Glu Gly Glu Ala Ala
        515                 520                 525

Phe Arg Lys Leu Met Glu Glu Lys Trp Lys Leu Leu Asn Ala Ala Trp
    530                 535                 540

Val Asp Thr Ile Asn Gly Lys Glu Ser Lys Glu Ile Val Val Gln Val
545                 550                 555                 560

Leu Asp Leu Ala Arg Ile Cys Gly Thr Leu Tyr Gly Asp Glu Glu Asp
                565                 570                 575

Gly Phe Thr Tyr Pro Glu Lys Asn Phe Ala Pro Leu Val Ala Ala Leu
            580                 585                 590

Leu Met Asn Pro Ile His Ile
        595
```

<210> SEQ ID NO 40
<211> LENGTH: 1800
<212> TYPE: DNA
<213> ORGANISM: Prunella vulgaris

<400> SEQUENCE: 40

```
atgagctctc tctcaattcc cttttcttcc gccatttgca cttcatcaat cccaaagatc     60

agtactgggc atcatcgccg caccgcgagg atgcccgcgc acgacacatc gcgtctcgtc    120

tttcgccctt cagctgtgat ggtggaagga agtccgatga ctacttcaag caacgggaag    180

gaagtccaac gacttataac cactttcaag cctagcatgt ggaaagatat tttttctacc    240

ttctctttcg ataatcaggt gcaagaaaag tatttgaaag aaattgagga attgaagaaa    300

gaagtaagaa gcacactaat gagtgctacg cataggaaat tgtttgactt gatcgacaat    360

ctcgagcgta tgggaatcgc ctatcatttc gagacagaaa tcgaagacaa gctcaaacaa    420

gctcatgctt ctctagagga ggaagatgac tacgacttgt tcactactgc acttcgcttt    480

cgtctgctca gacaacatcg ctatcatgtt tcttgcgatc cctttgcgaa atttgttgac    540

caagacaaca aattgaaaga gagtcttagt agcgacgtcg aggggctatt aagcttgttc    600

gaggcatccc atcttcggat ccacaacgag gatgttctag atgaagctat agtgttcaca    660

acccatcact tgaatcgaat gatgccacaa ttggaatcgc cccttaaaga agaagtgaag    720

catgctcttc gataccccct tcacaagtgt cttggaatcc ttagccttcg ttttcatatc    780

gacagatatg agaatgataa gtcgagggat gaagttgttc tcagactagg ccaagttaat    840

ttcaattaca tgcagaacat ttacatgaac gagctctatg aaatcaccac gtggtggaac    900

aagttgcaga tgacttcaaa agtaccttac tttagagata gattggtaga gtgctatatg    960

tggggtttgg catatcattt cgaaccagaa tacgctcccg ttcgagtcct cattaccaag   1020

tactatatga ccgccacaac tgtcgacgat acctatgata attatgctac actcgaagaa   1080

atcgaactct tcactcaggc cattgacagg tggagcgagg atgagattga tcagctacct   1140

gatgaatacc taaaaatagt gtacaaaggt ctaatgaact tcactgaaga gtttagacgt   1200

gacgcagaag agcgagggaa aggctatgtg attccttact ttattgaaga aacgaagaga   1260

gcaacacagg gttatgcaaa cgagcagagg tggataatga agagagaaat gccgagtttt   1320

gaagagtata tggtgaactc aagggtaaca tcacttatgt atgtgaccta cgttgctgtt   1380

gtggcagtca tagaatcagc taccaaagaa accgtagatt gggcgctaag tgactccgat   1440

atctttgtct acactaacga tatcggccga cttatcgacg accttgccac tcatcgacgc   1500
```

```
gagaggaaag acgggacaat gcttacatcg atggattatt acatgaagga atatggcggt   1560

acgatggaag agggggaagc tgcatttagg aaattgatgg aggagaaatg gaaacttttg   1620

aatgcagcat gggtagatac tattaatgga aaagagtcga aggaaatagt tgtgcaagtt   1680

ctcgacctcg ccaggatatg cggaacgctc tatggggacg aagaagatgg cttcacctac   1740

ccagagaaga attttgcacc actcgttgct gctctattga tgaatcctat acatatttga   1800
```

<210> SEQ ID NO 41
<211> LENGTH: 821
<212> TYPE: PRT
<213> ORGANISM: Chiococca alba

<400> SEQUENCE: 41

```
Met Ser Ser Ser Thr Ser Ala Ala Ala Thr Leu Leu Gly Leu Ser Pro
1               5                   10                  15

Ala Ser Arg Arg Phe Val Ser Phe Pro Pro Ala Asn Gly Pro Ile Glu
            20                  25                  30

Thr Ile Thr Gly Ile Trp Ser Pro Gly Lys Ala Leu His His Phe Asn
        35                  40                  45

Phe Arg Leu Arg Cys Ser Thr Val Ser Ser Pro Arg Thr Gln Glu Leu
    50                  55                  60

Gly Gln Val Ser Gln Asn Gly Met Ser Gly Ile Lys Trp His Asp Ile
65                  70                  75                  80

Val Glu Glu Gly Val Thr Glu Lys Gly Thr Leu Glu Ala Asn Thr Ser
                85                  90                  95

Ser Trp Ile Lys Glu Ser Ile Glu Ala Ile Arg Trp Met Leu Arg Thr
            100                 105                 110

Met Asp Asp Gly Asp Ile Ser Ile Ser Ala Tyr Asp Thr Ala Trp Val
        115                 120                 125

Ala Leu Val Glu Asp Ile Asn Gly Ser Gly Gly Pro Gln Phe Pro Ser
    130                 135                 140

Ser Leu Glu Trp Ile Ala Asn Asn Gln Leu Pro Asp Gly Ser Trp Gly
145                 150                 155                 160

Asp Ser Asp Ile Phe Ser Ala His Asp Arg Ile Leu Asn Thr Leu Gly
                165                 170                 175

Cys Val Val Ala Leu Lys Ser Trp Asn Met His Pro Glu Lys Ser Glu
            180                 185                 190

Lys Gly Leu Leu Tyr Leu Arg Asp Asn Ile His Lys Leu Glu Asp Glu
        195                 200                 205

Asn Val Glu His Met Pro Ile Gly Phe Glu Val Ala Phe Pro Ser Leu
    210                 215                 220

Ile Glu Ile Ala Lys Lys Leu Ser Ile Asp Ile Pro Asp Asp Ser Ala
225                 230                 235                 240

Ile Leu Gln Glu Ile Tyr Ala Arg Arg Asn Leu Lys Leu Thr Arg Ile
                245                 250                 255

Pro Lys Asp Ile Met His Thr Val Pro Thr Thr Leu Leu His Ser Leu
            260                 265                 270

Glu Gly Met Pro Glu Leu Asp Trp Lys Arg Leu Ile Ser Leu Lys Cys
        275                 280                 285

Glu Asp Gly Ser Phe Leu Phe Ser Pro Ser Ser Thr Ala Phe Ala Leu
    290                 295                 300

Thr Gln Thr Lys Asp Ala Asp Cys Leu Arg Tyr Leu Thr Lys Thr Val
305                 310                 315                 320

Gln Lys Phe Asn Gly Gly Val Pro Asn Val Tyr Pro Val Asp Leu Phe
```

-continued

```
                325                 330                 335

Glu His Ile Trp Ala Val Asp Arg Leu Gln Arg Leu Gly Ile Ser Arg
            340                 345                 350

Tyr Phe Gln Ser Glu Ile Arg Glu Cys Ile Asp Tyr Val His Arg Tyr
        355                 360                 365

Trp Thr Asp Lys Gly Ile Cys Trp Ala Arg Asn Thr His Val Tyr Asp
    370                 375                 380

Ile Asp Asp Thr Ala Met Gly Phe Arg Leu Leu Arg Leu His Gly Tyr
385                 390                 395                 400

Asp Val Ser Ala Asp Val Phe Arg Tyr Tyr Glu Lys Asp Gly Glu Phe
                405                 410                 415

Val Cys Phe Ala Gly Gln Ser Asn Gln Ala Val Thr Gly Met Tyr Asn
            420                 425                 430

Leu Tyr Arg Ala Ser Gln Val Met Phe Pro Gly Glu Asn Ile Leu Ser
        435                 440                 445

Asp Ala Arg Lys Phe Ser Ser Glu Phe Leu His Asp Lys Arg Ala Asn
    450                 455                 460

Asn Glu Leu Leu Asp Lys Trp Ile Ile Thr Lys Asp Leu Pro Gly Glu
465                 470                 475                 480

Val Ala Tyr Ala Leu Asp Val Pro Trp Tyr Ala Ser Leu Pro Arg Leu
                485                 490                 495

Glu Thr Arg Leu Tyr Leu Glu Gln Tyr Gly Gly Glu Asp Asp Val Trp
            500                 505                 510

Ile Gly Lys Thr Leu Tyr Arg Met Gln Lys Val Asn Asn Asn Ile Tyr
        515                 520                 525

Leu Glu Leu Gly Lys Leu Asp Tyr Asn Asn Cys Gln Ala Leu His Gln
    530                 535                 540

Leu Glu Trp Arg Ser Ile Gln Lys Trp Tyr Asn Glu Cys Gly Leu Gly
545                 550                 555                 560

Glu Tyr Gly Leu Ser Glu Arg Ser Leu Leu Leu Ser Tyr Tyr Leu Ala
                565                 570                 575

Ala Ala Ser Ile Phe Glu Pro Glu Arg Ser Lys Glu Arg Leu Ala Trp
            580                 585                 590

Ala Lys Thr Thr Met Leu Ile Arg Thr Ile Glu Ser Tyr Leu Ser Ser
        595                 600                 605

Glu Gln Met Val Glu Asp His Asn Gly Ala Phe Val Ser Glu Phe Gln
    610                 615                 620

Tyr Tyr Cys Ser Asn Leu Asp Tyr Val Asn Gly Gly Arg His Lys Pro
625                 630                 635                 640

Thr Gln Arg Leu Val Arg Thr Leu Leu Gly Thr Leu Asn Gln Ile Ser
                645                 650                 655

Leu Asp Ala Val Leu Val His Gly Arg Asp Ile His Gln Tyr Leu Arg
            660                 665                 670

Gln Ala Trp Glu Lys Trp Leu Ile Ala Leu Gln Glu Gly Asp Asp Ser
        675                 680                 685

Asp Met Gly Gln Glu Glu Ala Glu Leu Leu Val Arg Thr Leu Asn Leu
    690                 695                 700

Cys Ala Gly Arg Tyr Ala Ser Glu Glu Leu Leu Leu Ser His Pro Lys
705                 710                 715                 720

Tyr Gln Gln Leu Leu His Ile Thr Thr Arg Val Cys Asn Gln Ile Arg
                725                 730                 735

His Phe Gln His Lys Lys Val Gln Asp Gly Glu Asn Gly Arg Ala Asn
            740                 745                 750
```

```
Met Gly Asp Gly Ile Thr Ser Ile Ser Ser Ile Glu Ser Asp Met Gln
        755                 760                 765

Glu Leu Thr Lys Leu Val Val Gly Asn Thr Gln Asn Asp Leu Asp Ala
    770                 775                 780

Asp Thr Lys Gln Thr Phe Leu Thr Val Ala Lys Ser Phe Tyr Tyr Thr
785                 790                 795                 800

Ala His Cys Asn Pro Gly Thr Ile Asn Cys His Ile Ala Lys Val Leu
                805                 810                 815

Phe Glu Arg Val Leu
            820


<210> SEQ ID NO 42
<211> LENGTH: 2466
<212> TYPE: DNA
<213> ORGANISM: Chiococca alba

<400> SEQUENCE: 42

atgtcttctt ctacctcagc agcagcaacc cttctcggat tatcgccggc aagccgccgg     60

tttgtatcat ttcctccggc aaatggacct atagaaacta ttaccggtat ttggtcgccc    120

ggcaaagctc ttcatcactt taatttccgt ctgcgttgta gcacggtgtc cagtcctcgc    180

acccaagaat tgggccaggt gtcacaaaat ggcatgtctg gtataaagtg gcatgacata    240

gtggaagaag gagtcacaga aaaaggaact cttgaggcga acacatcaag ctggataaaa    300

gaaagcatag aagccattcg ttggatgctg cgtaccatgg atgacgggga tatcagcata    360

tctgcttatg atactgcatg ggttgccctt gtggaagata tcaacggaag tggcggtcct    420

caatttcctt caagcctcga gtggattgcc aacaatcagc ttcctgatgg ttcatggggc    480

gacagcgaca tcttttcagc tcacgatcgg attctcaaca ctttgggatg cgttgttgca    540

ttaaaatctt ggaacatgca ccctgaaaag agtgaaaaag gattattata tttaagggat    600

aacattcaca agcttgagga tgaaaatgtc gagcacatgc ctatcggttt tgaagtggca    660

tttccttcac taattgagat agccaaaaag ttgagcattg atattccgga tgattctgca    720

atcttgcagg agatatatgc cagaagaaat ctaaagctaa caaggatacc gaaggacatt    780

atgcacacag tgcccacaac attgctccac agcttggaag gcatgccaga actagactgg    840

aaaaggctaa tatctctaaa gtgtgaggat ggttcctttc tgttttctcc atcctccact    900

gcttttgccc tcacgcaaac taaagatgct gattgcctca gatatttaac taaaaccgta    960

caaaaattca atggaggagt tcccaatgtt taccccgtgg acttattcga acacatctgg   1020

gctgttgatc gacttcaaag actaggaatt tctcgatact tccagtcaga aatccgcgag   1080

tgcatcgatt atgttcaccg atattggacg gataaaggta tctgttgggc tagaaatacc   1140

cacgtttatg acattgatga tacagctatg ggttttagac ttctaaggtt gcatggctac   1200

gatgtttctg cagatgtttt cagatactat gagaaggatg gcgaattcgt ttgctttgcc   1260

ggacagtcaa accaggcggt gaccggaatg tataacctgt atagagcttc tcaagtgatg   1320

tttccagggg agaatatact ttcggatgct aggaaattct cgtccgaatt cttgcatgat   1380

aagcgagcca acaatgagct cctagataaa tggatcataa ccaaagattt gcctggggag   1440

gtagcatatg ctttagatgt tccatggtat gccagtttac ctcgtttaga aaccagattg   1500

tatttggaac aatatggcgg cgaagatgat gtctggattg gcaagacatt gtacaggatg   1560

caaaaagtta acaacaacat ctatcttgaa cttggcaaat tagattacaa caactgtcag   1620

gcattgcatc agcttgagtg gagaagcatc caaaaatggt acaatgaatg cggtcttgga   1680
```

```
gagtacggat taagcgagag aagcctcctt ctttcgtatt atttggccgc agccagtata   1740

tttgaaccgg agaggtcaaa ggaacggctt gcctgggcca aaactactat gctaatccgc   1800

acaattgaat cttatttgag tagtgaacaa atggttgagg atcacaatgg agcctttgtt   1860

agcgagttcc aatactattg cagtaacctt gactacgtaa atggtggaag gcataagcca   1920

acacaaaggc tagtgaggac tctactcgga actttaaatc agatttcttt ggacgcagtg   1980

ttagtccacg gcagagatat ccatcaatat ttgcgtcaag cctgggaaaa gtggttgata   2040

gctttgcaag agggagatga tagtgacatg ggtcaagagg aagcagaact tttagtgcgc   2100

acactaaacc tatgcgccgg tcgctacgca tcggaggagc tattgttgtc ccatcccaag   2160

tatcaacaac ttttgcacat cactactaga gtctgtaacc aaattcgtca tttccaacac   2220

aaaaaggtgc aagatgggga aaatggaaga gcaaacatgg gtgatggcat cacaagcatc   2280

agctcaatag agtcggacat gcaagaacta acgaaattag ttgtcggcaa tacccaaaac   2340

gatctagatg ctgatacgaa gcaaacattt ctcacggtgg caaaaagctt ctactacacc   2400

gcccactgca atcccggaac aatcaattgc catattgcta aagtattatt tgagagagta   2460

ctttga                                                              2466
```

```
<210> SEQ ID NO 43
<211> LENGTH: 747
<212> TYPE: PRT
<213> ORGANISM: Chiococca alba

<400> SEQUENCE: 43

Met Pro Val Ile Lys Ser His Glu Phe Ile Glu Glu Val Gly Pro Glu
1               5                   10                  15

Lys Gly Thr Leu Lys Leu Ser Arg Ser Ser Arg Ile Asn Glu Leu Val
            20                  25                  30

Glu Ser Ile Gln Thr Met Leu Gln Ser Met Asp Asp Gly Glu Ile Ser
        35                  40                  45

Met Ser Ala Tyr Asp Thr Ala Trp Val Ala Leu Val Glu Asp Ile Asn
    50                  55                  60

Gly Ser Ser Tyr Pro Gln Phe Pro Met Ser Leu Glu Trp Ile Ala Asn
65                  70                  75                  80

Asn Gln Leu Pro Asp Gly Ser Trp Gly Asp Gly Ser Ile Phe Ser Val
                85                  90                  95

His Asp Arg Ile Ile Ser Thr Leu Gly Cys Val Leu Ala Leu Lys Ser
            100                 105                 110

Trp Asn Met His Pro Asp Lys Ser Glu Lys Gly Leu Leu Phe Ile Arg
        115                 120                 125

Asp Asn Ile His Lys Val Gly Asp Glu Ser Ala Glu His Met Pro Ile
    130                 135                 140

Gly Phe Glu Val Val Phe Pro Ser Leu Ile Glu Arg Ala Lys Asn Leu
145                 150                 155                 160

Asp Ile Asp Ile Pro Asp Ile Ser Ala Ile Leu Gln Glu Ile Tyr Ala
                165                 170                 175

Arg Arg Asn Leu Lys Leu Ala Arg Ile Pro Lys Asp Ile Leu Tyr Thr
            180                 185                 190

Val Pro Thr Thr Leu Leu His Ser Leu Glu Gly Met Pro Glu Leu Asp
        195                 200                 205

Trp Gln Lys Leu Leu Pro Leu Lys Cys Glu Asp Gly Ser Phe Leu Phe
    210                 215                 220
```

-continued

```
Ser Pro Ser Cys Thr Ala Phe Ala Leu Met Gln Thr Lys Asp Gly Asp
225                 230                 235                 240

Cys Leu Arg Tyr Leu Thr Asn Thr Ile Glu Lys Phe Asn Gly Gly Val
                245                 250                 255

Pro Gly Val Tyr Pro Val Asp Leu Phe Glu His Ile Trp Ala Val Asp
            260                 265                 270

Arg Leu Gln Arg Leu Gly Ile Ser Arg Tyr Phe Gln Thr Glu Ile Glu
        275                 280                 285

Glu Cys Met Ser Tyr Val Tyr Arg Tyr Trp Thr Asp Lys Gly Ile Cys
    290                 295                 300

Trp Ala Arg Asn Ser Lys Val Glu Asp Ile Asp Asp Thr Ala Met Gly
305                 310                 315                 320

Phe Arg Leu Leu Arg Leu His Gly Tyr Met Val Ser Ala Asp Val Phe
                325                 330                 335

Ala Gln Phe Glu Lys Gly Gly Glu Phe Val Cys Phe Ala Gly Gln Ser
            340                 345                 350

Asn Gln Ala Leu Thr Gly Met Phe Asn Leu Tyr Arg Ala Ser Gln Val
        355                 360                 365

Met Phe Pro Gly Glu Lys Ile Leu Ala Asp Ala Lys Lys Phe Ser Ser
    370                 375                 380

Asn Phe Leu His Glu Lys Arg Ala Asn Asn Glu Leu Leu Asp Lys Trp
385                 390                 395                 400

Ile Ile Thr Lys Asp Leu Pro Gly Glu Val Thr Tyr Ala Leu Asp Val
                405                 410                 415

Pro Trp Tyr Ala Ser Leu Pro Arg Val Glu Thr Arg Leu Tyr Leu Glu
            420                 425                 430

Gln Tyr Gly Gly Glu Asp Asp Val Trp Ile Ala Lys Thr Leu Tyr Arg
        435                 440                 445

Met Arg Lys Val Asn Asn Lys Ile Tyr Leu Glu Leu Gly Ile Leu Asp
    450                 455                 460

Tyr Asn Asn Cys Gln Ala Leu His Gln Leu Glu Trp Arg Ser Ile Gln
465                 470                 475                 480

Lys Trp Tyr Lys Asp Ser Gly Leu Glu Glu Tyr Gly Leu Ser Glu Arg
                485                 490                 495

Asn Leu Leu Leu Ala Tyr Tyr Leu Ala Thr Ala Cys Ile Phe Glu Pro
            500                 505                 510

Glu Arg Leu Val Glu Arg Leu Ser Trp Ala Lys Thr Thr Ala Leu Ile
        515                 520                 525

Tyr Thr Thr Lys Ser Tyr Phe Arg Thr Glu Cys Asn Ser Gly Glu Gln
    530                 535                 540

Arg Lys Ala Phe Leu His Glu Phe Gln Gln Tyr Cys Asn Asp Leu Asp
545                 550                 555                 560

Tyr Val Ser Gly Ala Arg His Lys Pro Thr Ile Arg Leu Ile Glu Ala
                565                 570                 575

Leu Leu Gly Thr Leu Glu Gln Val Ser Leu Asp Ala Ile Leu Asp His
            580                 585                 590

Gly Arg Tyr Ile His Gln Asp Leu Arg Asn Ala Trp Glu Lys Trp Leu
        595                 600                 605

Ile Ala Leu Gln Glu Gly Val Asp Met Asp Gln Glu Glu Ala Glu Leu
    610                 615                 620

Thr Val Leu Thr Leu His Leu Cys Ala Gly Ser Tyr Thr Ser Glu Glu
625                 630                 635                 640

Leu Leu Leu Ser His Pro Lys Tyr Gln Gln Leu Leu Asn Ile Thr Ser
```

```
                645                 650                 655

Arg Val Cys His Gln Ile Arg Gln Phe Gln Arg Glu Lys Ala Gln Asp
            660                 665                 670

Thr Asp Asn Gly Arg Glu Asn Leu Val Ala Ile Thr Ser Ile Lys Ala
        675                 680                 685

Ile Glu Ser Asp Met Gln Glu Leu Ala Lys Leu Val Leu Thr Lys Ser
    690                 695                 700

Thr Gly Asp Leu Ala Ala Lys Ile Lys Gln Thr Phe Leu Ile Val Ala
705                 710                 715                 720

Lys Ser Phe Tyr Tyr Thr Ala His Cys Leu Pro Gly Ile Ile Ser Thr
                725                 730                 735

His Ile Ala Lys Val Leu Phe Glu Lys Val Phe
            740                 745
```

```
<210> SEQ ID NO 44
<211> LENGTH: 2244
<212> TYPE: DNA
<213> ORGANISM: Chiococca alba

<400> SEQUENCE: 44

atgccagtaa taaagtcgca tgagtttatt gaagaggtcg gcccggaaaa aggaactctg     60

aagctgagca gatcaagtag gataaacgaa cttgtagaat caattcaaac gatgcttcaa    120

tcgatggatg atggggaaat aagcatgtct gcttatgaca ccgcgtgggt tgcccttgtg    180

gaagatatta atggaagcag ctaccctcaa ttccctatga gcctcgagtg gattgccaac    240

aatcagcttc ctgatggttc atggggtgac ggcagtatct tttcggttca tgatcggata    300

atcagcacat taggatgtgt tcttgcatta aaatcatgga acatgcaccc ggacaaaagc    360

gaaaaaggac tgttatttat aagggacaat attcacaagg ttggagatga gagcgctgag    420

cacatgccta ttggttttga ggtggtattt ccttcgctta ttgagagagc caaaaacttg    480

gacattgata ttccagatat ttctgctatc ttgcaagaga tttatgcacg aagaaatcta    540

aagctcgcaa ggattccaaa ggatatactg tataccgtgc ccacgacatt acttcatagc    600

ttagaaggaa tgccagaact ggactggcaa aagctactgc cattaaaatg tgaggatggt    660

tcatttctat tttctccatc gtgcactgct tttgccctca tgcagactaa ggatggtgat    720

tgcctcagat atctaactaa taccatagaa aaattcaatg gggagttcc cggtgtatac    780

cctgtggact tgttcgaaca catttgggct gttgatcgct tgcaaagact aggaatttcc    840

cggtattttc agacagaaat tgaagaatgt atgagttatg tttaccgata ttggacggat    900

aaaggtatct gttgggctag aaactccaaa gttgaagaca tcgatgacac agccatgggt    960

tttagacttc taaggttgca tggttacatg gtttctgcag atgtgtttgc acagtttgag   1020

aaagggggtg aattcgtttg ctttgctgga cagtcgaacc aggcgctgac tggaatgttt   1080

aacctgtata gagcttctca agtaatgttt ccaggggaga agatacttgc tgatgccaag   1140

aaattctcat cgaacttctt acatgaaaag cgtgcaaaca acgagcttct agataaatgg   1200

atcataacta aagatttgcc tggagaggtg acgtatgcgc tagatgttcc atggtacgcc   1260

agtttacctc gtgtagaaac gagattatat ctggaacaat atggaggaga ggatgatgtc   1320

tggattgcca agacattgta caggatgaga aaagttaaca acaaaattta ccttgaactt   1380

ggcatattag attacaataa ctgtcaagca ttgcatcagc tggagtggag aagcatccaa   1440

aaatggtata aggattctgg ccttgaagag tacgggttga gcgagaggaa ccttctcctg   1500

gcatattatc tggccacagc ttgtatattt gaacccgaaa ggttggtgga gcgccttttcc  1560
```

```
tgggcgaaaa caaccgcctt aatctacaca acaaaatctt atttcagaac tgaatgcaac   1620

tctggggaac agagaaaagc ttttcttcat gagttccaac agtactgcaa tgacctggac   1680

tacgttagtg gcgcaaggca caagccaaca ataagattga tcgaagctct acttggaacc   1740

ctagagcagg tctctttgga tgcaatatta gatcatggcc gatatatcca tcaagatttg   1800

cgtaatgctt gggagaaatg gttgatagct ttgcaagagg gagttgacat ggaccaagaa   1860

gaagcagaac ttacagtgct cacactacac ctgtgtgccg gcagctacac atcggaggag   1920

ttactgttat ctcatcccaa gtatcaacaa cttttaaata tcactagtag agtctgccac   1980

caaattcgtc aattccagcg cgaaaaggca caggatacgg ataatggaag agaaaacttg   2040

gttgccatca caagcatcaa ggcgatagaa tcagacatgc aagaacttgc gaaattagtt   2100

ctgaccaaat ccactggcga tttagctgct aaaatcaagc aaacatttct tatagtggca   2160

aagagcttct actacaccgc acattgcctt cctggaatta tcagtaccca cattgccaaa   2220

gtactatttg agaaagtttt ctga                                           2244
```

<210> SEQ ID NO 45
<211> LENGTH: 822
<212> TYPE: PRT
<213> ORGANISM: Chiococca alba

<400> SEQUENCE: 45

```
Met Met Met Met Met Val Val Met Asn Thr Ala Pro Ala His Ser Tyr
1               5                   10                  15

His Pro Phe Pro Phe Ala Gly Pro Lys Ser Ser Ala Thr Leu Phe Ser
            20                  25                  30

Asn Tyr Tyr Cys Ser Ser Arg Lys Lys Ser Ser Pro Pro Arg Ile Ser
        35                  40                  45

Ala Ser Val Ser Leu Leu Thr Gly Val Glu Ser Thr Thr Ala Ile Asn
    50                  55                  60

Ser Ser Asp Pro Glu Ile Lys Glu Arg Ile Arg Lys Leu Phe His Asp
65                  70                  75                  80

Val Asp Ile Ser Leu Ser Ser Tyr Asp Thr Ala Trp Val Ala Met Val
                85                  90                  95

Pro Ala Pro His Ser Ser Gln Ser Pro Leu Phe Pro Gln Cys Ile Asn
            100                 105                 110

Trp Leu Leu Asp Asn Gln Leu Pro Asp Gly Ser Trp Ser Leu Pro Pro
        115                 120                 125

Pro His His His Pro Leu Leu Leu Lys Asp Ala Leu Ser Ser Thr Leu
    130                 135                 140

Ala Cys Val Leu Ala Leu Arg Arg Trp Gly Ile Gly Gln Glu Gln Val
145                 150                 155                 160

Asp Lys Gly Ile Arg Phe Val Glu Leu Asn Phe Ala Ser Ala Ser Asp
                165                 170                 175

Gln Asn Gln His Leu Pro Val Gly Phe Asp Ile Ile Phe Pro Gly Met
            180                 185                 190

Leu Glu Tyr Ala Arg Asp Leu Asn Leu Asn Leu Gln Leu Glu Ser Ala
        195                 200                 205

Thr Val Asn Ala Leu Leu Leu Lys Arg Asp Gln Glu Leu Thr Arg Phe
    210                 215                 220

Phe Lys Ser Tyr Ser Asp Glu Ser Lys Ala Tyr Leu Ala Tyr Val Ser
225                 230                 235                 240

Glu Gly Ile Val Lys Leu Gln Asn Trp Asp Thr Val Met Lys Phe Gln
```

```
                245                 250                 255

Arg Lys Asn Gly Ser Leu Phe Asn Ser Pro Ser Ala Thr Ala Ala Ala
            260                 265                 270

Val Met His Val His Asn Pro Gly Cys Leu Asp Tyr Leu His Ser Val
        275                 280                 285

Leu Glu Lys His Gly Asn Ala Val Pro Thr Val Tyr Pro Leu Asp Ile
    290                 295                 300

Tyr Pro Arg Leu Cys Leu Val Asp Asn Leu Glu Arg Leu Gly Ile Cys
305                 310                 315                 320

Gly His Phe Arg Lys Glu Ile Leu Ser Val Leu Asp Asp Thr Tyr Arg
                325                 330                 335

Cys Trp Met Gln Gly Asp Glu Glu Ile Phe Ala Glu Lys Ser Thr Cys
            340                 345                 350

Ala Ile Ala Phe Thr Leu Leu Arg Lys His Gly Tyr Asn Ile Ser Ala
        355                 360                 365

Asp Pro Leu Thr Pro Phe Leu Lys Glu Glu Cys Phe Ser Asn Ser Leu
    370                 375                 380

Gly Gly Cys Leu Lys Asp Thr Ser Ala Val Leu Glu Leu Tyr Arg Ala
385                 390                 395                 400

Leu Glu Met Ile Ile Ser Gln Asn Glu Ser Ala Leu Val Lys Lys Ser
                405                 410                 415

Leu Trp Ser Arg Ser Phe Leu Lys Glu His Ile Ser Gly Gly Cys Asp
            420                 425                 430

Leu Lys Gly Phe Ser Asn Gln Ile Ser Ile Leu Val Asp Asp Ile Leu
        435                 440                 445

Asn Phe Pro Ser His Ala Thr Leu Gln Arg Val Ala Asn Arg Arg Ser
    450                 455                 460

Ile Glu Gln Tyr Asn Leu Asp Ser Thr Lys Ile Leu Lys Thr Ser Tyr
465                 470                 475                 480

Cys Ser Ser Asn Phe Ser Asn Lys Asp Leu Leu Ile Leu Ala Val Lys
                485                 490                 495

Asp Phe Asn His Cys Gln Leu Ile His Arg Glu Glu Leu Lys Glu Leu
            500                 505                 510

Glu Arg Trp Val Thr Asp Asn Arg Leu Asp Lys Leu Lys Phe Ala Arg
        515                 520                 525

Gln Lys Ser Ala Tyr Cys Tyr Phe Ser Ala Ala Ala Thr Ile Phe Ser
    530                 535                 540

Pro Glu Leu Ser Asp Ala Arg Met Ser Trp Ala Lys Asn Gly Val Leu
545                 550                 555                 560

Ala Thr Leu Val Asp Asp Phe Phe Asp Val Gly Gly Ser Leu Glu Glu
                565                 570                 575

Leu Lys Lys Leu Ile Glu Leu Val Glu Lys Trp Asp Ile Asn Val Ser
            580                 585                 590

Asp Gly Cys Cys Ser Glu Pro Val Gln Ile Leu Phe Ser Ala Leu His
        595                 600                 605

Ser Thr Ile Gln Glu Ile Gly Asp Lys Ala Phe Lys Trp Gln Ala Arg
    610                 615                 620

Ser Val Thr Asn His Ile Phe Lys Ile Trp Leu Asp Leu Leu Asn Ser
625                 630                 635                 640

Met Leu Arg Glu Ala Glu Trp Ala Arg Asn Ala Thr Val Pro Thr Val
                645                 650                 655

Glu Glu Tyr Met Thr Asn Gly Tyr Val Ser Phe Ala Leu Gly Pro Ile
            660                 665                 670
```

```
Ile Leu Pro Ala Leu Tyr Leu Val Gly Pro Lys Leu Ser Glu Glu Val
        675                 680                 685

Val Lys Asp Ser Glu Phe His Ser Leu Phe Lys Leu Val Ser Thr Cys
    690                 695                 700

Gly Arg Leu Leu Asn Asp Val His Ser Phe Glu Arg Glu Ser Lys Ser
705                 710                 715                 720

Gly Gln Leu Asn Ala Leu Ser Leu Arg Leu Ile His Gly Gly Val Gly
                725                 730                 735

Ile Thr Glu Ala Ala Ala Val Ala Glu Met Lys Ser Ser Ile Glu Asn
            740                 745                 750

Leu Arg Arg Glu Leu Leu Arg Leu Val Leu Arg Lys Glu Gly Ser Val
        755                 760                 765

Val Pro Arg Ala Cys Lys Asp Leu Phe Trp Asn Met Ser Lys Val Leu
    770                 775                 780

His Gln Phe Tyr Asn Lys Asp Asp Gly Phe Thr Ser Glu Glu Met Ile
785                 790                 795                 800

Gln Leu Val Lys Ser Ile Ile Tyr Glu Pro Ile Ala Val Asn Glu Phe
                805                 810                 815

Leu Asn Ser Cys His Thr
            820


<210> SEQ ID NO 46
<211> LENGTH: 2469
<212> TYPE: DNA
<213> ORGANISM: Chiococca alba

<400> SEQUENCE: 46

atgatgatga tgatggtggt gatgaacaca gctcccgccc actcttacca tcctttcccc      60

tttgccggcc caaaatcctc agccacactt ttttccaatt attattgttc cagtaggaag     120

aaatcatcgc cacctcgcat ctctgcctca gtttctttgc taactggagt tgaaagcaca     180

actgcaatta attcttcaga cccggagatc aaagaaagaa taaggaaact atttcatgat     240

gttgatatct cgctttcttc atatgacact gcatgggtgg caatggtccc tgctccacat     300

tcttcccagt ctccccttttt tccccagtgc attaattggt tattggacaa tcagcttcct     360

gatggctcat ggagtcttcc tcctcctcat catcatcctc tattacttaa agatgcatta     420

tcctctaccc ttgcatgtgt tcttgcgctc aggagatggg gaattggtca agaacaagtt     480

gacaagggta ttcgttttgt tgagttaaat tttgcttcag catctgacca gaaccagcat     540

ttgccagttg gatttgacat tatattccct ggcatgctcg aatatgctag agatttaaat     600

ttaaatcttc aactagaatc tgcaacagta aatgccttac ttcttaaaag agatcaggag     660

cttacaagat tctttaaaag ctactcagac gagagtaaag cataccttgc atatgtatca     720

gaaggtatag taaagttaca gaactgggat acagttatga agttccaaag aaagaacggg     780

tcactattca attcaccttc agctacagca gctgctgtta tgcatgtcca caatcctggt     840

tgcctcgatt accttcactc agtgttggag aagcatggaa atgctgttcc aacagtttac     900

cctttggata tatatccacg cctctgcttg gttgacaacc ttgagagact gggtatttgt     960

ggtcatttta ggaaggaaat tctgagtgta ttggatgata catacagatg ctggatgcag    1020

ggggatgaag agatatttgc agaaaaatca acttgtgcca tagcatttac attattgcga    1080

aagcatgggt acaacatctc tgcagatcca ttgaccccat tcttaaagga agagtgtttt    1140

tccaattctt tgggtggatg tttgaaagat actagtgctg tacttgaatt ataccgggca    1200
```

-continued ttagagatga ttattagcca gaatgaatca gctctggtga aaaaaagctt gtggtccaga 1260
agcttcctga aagagcatat ttctggtggt tgtgatttaa agggattcag caatcaaatt 1320
tccatactgg tggatgatat cctcaacttt ccatcgcatg ctactttgca acgggttgct 1380
aacaggagaa gcatagagca atacaactta gacagtacaa aaattttaaa aacttcatat 1440
tgctcgtcga attttagcaa caaagattta ttgatcctgg cagtcaaaga ttttaatcat 1500
tgccaactca tacaccgtga agaactgaaa gaactagaaa ggtgggtcac agacaataga 1560
ttggacaagt taaagtttgc taggcagaag tctgcatact gttacttttc tgctgcagca 1620
accatattct cacctgaact ttctgatgcc cgcatgtcat gggccaagaa tggtgtactt 1680
gctactttgg ttgatgactt ctttgacgtg ggaggttctc tagaggaatt aaagaaactg 1740
attgagttgg ttgaaaagtg ggatataaat gtcagtgatg gttgttgctc tgaaccagtg 1800
caaatcctct tctcagcact acatagtaca atccaggaga ttggagataa agcattcaaa 1860
tggcaagcac gcagtgtaac aaaccacata tttaagatat ggttagattt gcttaattct 1920
atgttgaggg aagctgagtg ggctagaaat gcaacagtgc ctacagttga agaatatatg 1980
acaaatggtt atgtatcatt tgctttgggg ccaattatcc tccctgctct ttatcttgtt 2040
ggacctaagc tgtcagagga agtagttaag gattctgaat tccactccct ttttaagcta 2100
gtgagtacct gtgggcggct tctgaatgat gtccacagct tcgagaggga atcaaagtcc 2160
ggccaactaa atgctctgtc tctgcgcctg attcatggtg gtgttggcat tactgaagca 2220
gctgctgttg cagagatgaa gagttcaatt gagaatctaa ggagagaact gctgagacta 2280
gtcttgcgca aagagggtag tgtagttcca agagcttgca aggatttgtt ttggaatatg 2340
agtaaagtgc tacatcaatt ttacaacaaa gatgatggat ttacttcaga ggagatgatt 2400
cagcttgtga agtcgatcat ttatgagcca attgcggtca atgaattttt gaatagttgc 2460
catacatga 2469

<210> SEQ ID NO 47
<211> LENGTH: 817
<212> TYPE: PRT
<213> ORGANISM: Chiococca alba

<400> SEQUENCE: 47

Met Met Ile Met Val Met Asn Thr Ala Pro Val His Ala Tyr His Ala
1 5 10 15

Leu Pro Ile Pro Thr Gln Lys Ser Ser Thr Thr Leu Phe Pro Asn Tyr
20 25 30

Asn Cys Ser Ser Arg Lys Lys Ser Ser Pro Pro Arg Ile Ser Ala Ala
35 40 45

Ser Val Ser Leu Gln Thr Gly Val Glu Arg Thr Thr Ala Ile His Ser
50 55 60

Ser Asp Leu Glu Ile Lys Glu Arg Ile Arg Lys Leu Phe His Asp Val
65 70 75 80

Asp Ile Ser Leu Ser Ser Tyr Asp Thr Ala Trp Val Ala Met Val Pro
85 90 95

Ala Pro His Ser Ser Gln Ser Pro Leu Phe Pro Gln Cys Ile Asn Trp
100 105 110

Leu Leu Asp Asn Gln Leu Pro Asp Gly Ser Trp Ser Leu Pro Pro His
115 120 125

His His His His His Pro Leu Leu Leu Lys Asp Ala Leu Ser Ser Thr
130 135 140

-continued

```
Leu Ala Cys Val Leu Ala Leu Arg Arg Trp Gly Ile Gly Gln Glu Gln
145                 150                 155                 160

Val Asp Lys Gly Ile Arg Phe Val Glu Leu Asn Phe Ala Ser Ala Ser
                165                 170                 175

Asp Gln Asn Gln His Leu Pro Val Gly Phe Asp Ile Ile Phe Pro Gly
            180                 185                 190

Met Leu Glu Tyr Ala Arg Asp Leu Asn Leu Asn Leu Gln Leu Glu Ser
        195                 200                 205

Ala Thr Val Asp Ala Leu Leu Leu Lys Arg Asp Gln Glu Leu Ile Arg
    210                 215                 220

Phe Phe Lys Ser Tyr Ser Asp Glu Ser Lys Ala Tyr Leu Ala Tyr Val
225                 230                 235                 240

Ser Glu Gly Ile Ile Lys Leu Gln Asn Trp Asp Thr Val Met Lys Phe
                245                 250                 255

Gln Arg Lys Asn Gly Ser Leu Phe Asn Ser Pro Ser Ala Thr Ala Ala
            260                 265                 270

Ala Val Met His Val His Asn Pro Gly Cys Leu Asp Tyr Leu His Ser
        275                 280                 285

Val Leu Glu Lys His Gly Asn Ala Val Pro Thr Val Tyr Pro Leu Asp
    290                 295                 300

Ile Tyr Pro Arg Leu Cys Leu Val Asp Asn Leu Glu Arg Leu Gly Ile
305                 310                 315                 320

Cys Gly His Phe Arg Lys Glu Ile Leu Ser Val Leu Asp Asp Thr Tyr
                325                 330                 335

Arg Cys Trp Met Gln Gly Asp Glu Glu Ile Phe Ala Glu Lys Ser Thr
            340                 345                 350

Cys Ala Ile Ala Phe Thr Leu Leu Arg Lys His Gly Tyr Asn Ile Ser
        355                 360                 365

Ala Asp Pro Leu Thr Pro Phe Leu Lys Glu Glu Cys Phe Ser Asn Ser
    370                 375                 380

Leu Gly Gly Cys Leu Lys Asp Thr Ser Ala Val Leu Glu Leu Tyr Arg
385                 390                 395                 400

Ala Leu Glu Met Ile Ile Ser Gln Asn Glu Ser Ala Leu Val Lys Lys
                405                 410                 415

Ser Leu Trp Ser Arg Ser Phe Leu Lys Glu His Ile Ser Gly Gly Cys
            420                 425                 430

Asp Leu Lys Gly Phe Ser Asn Gln Ile Ser Lys Gln Val Asp Asp Ile
        435                 440                 445

Leu Asn Phe Pro Ser His Ala Thr Leu Gln Arg Val Ala Asn Arg Arg
    450                 455                 460

Ser Ile Glu Gln Tyr Asn Leu Asp Ser Thr Lys Ile Leu Lys Thr Ser
465                 470                 475                 480

Tyr Cys Ser Ser Asn Phe Ser Asn Lys Asp Leu Leu Ile Leu Ala Val
                485                 490                 495

Lys Asp Phe Asn His Cys Gln Leu Ile His Arg Glu Glu Leu Lys Glu
            500                 505                 510

Leu Glu Arg Trp Val Ala Asp Asn Arg Leu Asp Lys Leu Lys Phe Ala
        515                 520                 525

Arg Gln Lys Ser Ala Tyr Cys Tyr Phe Ser Ala Ala Ala Thr Ile Phe
    530                 535                 540

Ser Pro Glu Leu Ser Asp Ala Arg Ile Ser Trp Ala Lys Asn Gly Val
545                 550                 555                 560

Leu Thr Thr Leu Val Asp Asp Phe Phe Asp Val Gly Gly Ser Leu Glu
```

```
                565                 570                 575

Glu Leu Lys Lys Leu Ile Glu Leu Val Glu Lys Trp Asp Ile Asn Val
            580                 585                 590

Ser Asp Gly Cys Cys Ser Glu Pro Val Gln Ile Leu Phe Ser Ala Leu
        595                 600                 605

His Ser Thr Ile Gln Glu Ile Gly Asp Lys Ala Phe Lys Trp Gln Ala
    610                 615                 620

Arg Ser Val Thr Asn His Ile Ile Lys Ile Trp Leu Asp Leu Leu Asn
625                 630                 635                 640

Ser Met Leu Arg Glu Ala Glu Trp Ala Arg Asn Ala Thr Val Pro Thr
                645                 650                 655

Val Glu Glu Tyr Met Thr Asn Gly Tyr Val Ser Phe Ala Leu Gly Pro
            660                 665                 670

Ile Ile Leu Pro Ala Leu Tyr Leu Val Gly Pro Lys Leu Ser Glu Glu
        675                 680                 685

Leu Val Lys Asp Ser Glu Phe His Ser Leu Phe Lys Leu Val Ser Thr
    690                 695                 700

Cys Gly Arg Leu Leu Asn Asp Val His Ser Phe Glu Arg Glu Ser Lys
705                 710                 715                 720

Ala Gly Gln Leu Asn Ala Leu Ser Leu Arg Leu Ile His Gly Gly Val
                725                 730                 735

Gly Ile Thr Glu Ala Ala Ala Val Ala Glu Met Lys Ser Ser Ile Glu
            740                 745                 750

Lys Gln Arg Arg Glu Leu Leu Arg Leu Val Leu Arg Lys Glu Gly Ser
        755                 760                 765

Val Val Pro Arg Ala Cys Lys Asp Leu Phe Trp Asn Met Ser Arg Val
    770                 775                 780

Leu His Gln Phe Tyr Val Lys Asp Asp Gly Phe Thr Ser Glu Glu Met
785                 790                 795                 800

Ile Glu Leu Val Lys Ser Ile Ile Tyr Glu Pro Ile Ala Val Asn Glu
                805                 810                 815

Phe
```

<210> SEQ ID NO 48
<211> LENGTH: 2454
<212> TYPE: DNA
<213> ORGANISM: Chiococca alba

<400> SEQUENCE: 48

```
atgatgataa tggtgatgaa cacagctccc gtccacgctt accacgcttt acccattccc     60

acccaaaaat cctcaaccac actttttccc aattataact gttccagtag gaagaaatca    120

tcgccacctc gcatctctgc cgcctcagtt tctttgcaaa ctggagttga aagaacgacg    180

gcaattcatt cttcagacct agagatcaaa gaaagaataa ggaaactatt tcatgatgtt    240

gatatctcgc tttcttcata tgacactgca tgggtggcaa tggtccctgc tccacattct    300

tcccagtctc cccttttTcc ccagtgcatt aattggttat tggacaatca gcttcctgat    360

ggctcatgga gtcttcctcc tcatcatcat catcatcatc ccctattact taaagatgca    420

ttatcctcta cgcttgcatg tgttcttgcg ctcaggagat ggggaattgg tcaagaacaa    480

gttgacaagg gtattcgttt tgttgagtta aattttgctt ctgcatctga ccagaaccag    540

catttgccag ttggatttga cattatattc cctggcatgc tcgaatatgc tagagattta    600

aatttaaatc ttcaactaga atccgcaact gtagatgcct tacttctcaa aagagatcag    660
```

```
gagcttataa gattctttaa aagctactca gacgagagta aagcatacct tgcatatgta    720

tcagaaggta tcataaagtt acagaactgg gatacagtta tgaagttcca aagaaagaac    780

gggtcactgt tcaattcacc ttcagctaca gcagctgctg ttatgcatgt ccacaatcct    840

ggctgcctcg attaccttca ctcagtgttg gagaagcatg gcaatgctgt tccaacagtt    900

taccctttgg atatatatcc acgcctctgc ttggttgaca accttgagag actgggtatt    960

tgtggtcatt ttaggaagga aattctgagt gtattggatg atacatacag atgctggatg   1020

caggggggatg aagagatatt tgcagaaaaa tcaacttgtg ccatagcatt tacattattg   1080

cgaaagcatg ggtacaacat ctctgcagat ccattgaccc cattcttaaa ggaagagtgt   1140

ttttccaatt ctttgggtgg atgtttgaaa gatactagtg ctgtacttga attataccgg   1200

gcattagaga tgattattag ccagaatgaa tcagctctgg tgaaaaaaag cttgtggtcc   1260

agaagcttcc tgaaagagca tatttctggt ggttgtgatt taaagggatt cagcaatcaa   1320

atttccaaac aggtggatga tatcctcaac tttccatcgc atgctacttt gcaacgggtt   1380

gctaacagga gaagcataga gcaatacaac ttagacagta caaaaatttt aaaaacttca   1440

tattgctcgt cgaattttag taacaaagat ttattgatcc tggcagtcaa agattttaat   1500

cattgccaac tcatacaccg tgaagaactg aaagaactag aaaggtgggt cgcagacaat   1560

agattggaca agttaaagtt tgctaggcag aagtctgcat actgttactt ttctgctgca   1620

gcaaccatat tctcacctga actttctgat gcccgcatct catgggccaa aaatggtgta   1680

cttactactt tggttgatga cttctttgac gtgggaggtt ctctagagga attaaagaaa   1740

ctgattgagt tggttgaaaa gtgggatata aatgtcagtg atggttgttg ctctgaacca   1800

gtgcaaatcc tcttctcagc actacatagt acaatccagg agattggaga taaagcattc   1860

aaatggcaag cacgcagtgt aacaaaccac ataattaaga tatggttaga tttgcttaat   1920

tctatgttga gggaagctga gtgggctaga aatgcaacag tgcctacagt tgaagaatat   1980

atgacaaatg gttatgtatc atttgccttg ggccaattta tcctccctgc tctttatctt   2040

gttggaccta agctgtcaga ggaattagtt aaggattctg aattccactc cctttttaag   2100

ctagtgagta cctgtgggcg gcttctgaat gatgtccaca gcttcgagag ggaatcaaag   2160

gccggccaac taaatgctct ttctctgcgc ctgattcatg gtggagttgg cattactgaa   2220

gcagctgctg ttgcagagat gaagagttca attgagaagc aaaggagaga actgctgaga   2280

ctagtcttgc gcaaagaggg tagtgtagtt ccaagagctt gcaaggattt gttttggaat   2340

atgagtaggg tgctacatca attttacgtc aaagatgatg gatttacttc agaggagatg   2400

attgagcttg tgaagtcgat catttatgag ccaattgcgg tcaatgaatt ttga         2454
```

<210> SEQ ID NO 49
<211> LENGTH: 796
<212> TYPE: PRT
<213> ORGANISM: Chiococca alba

<400> SEQUENCE: 49

```
Met Ile His Thr Leu Pro His Gly Gly Gln Ala His Phe Ile Ser His
1               5                   10                  15

Lys Thr Gln Pro Tyr Tyr Ser Ser Arg Pro Arg Phe Ser Ser Ala Ala
            20                  25                  30

Ser Leu Asp Thr Arg Val Arg Arg Thr Ser Pro Ser Asn Ser Ser Val
        35                  40                  45

Leu Asp Phe Asn Glu Thr Lys Glu Arg Ile Thr Lys Leu Phe His Asn
    50                  55                  60
```

-continued

```
Val Asp Tyr Ser Ile Ser Ser Tyr Asp Thr Ala Trp Val Ala Met Val
65                  70                  75                  80

Pro Asp Pro His Ser Ser Gln Ala Pro Leu Phe Pro Glu Cys Ile Asn
                85                  90                  95

Trp Leu Leu Asp Asn Gln Phe His Asp Gly Ser Trp Ser Leu Pro His
            100                 105                 110

His Asn Ser Leu Leu Leu Lys Asp Val Leu Ser Ser Thr Leu Ala Cys
        115                 120                 125

Val Leu Ala Leu Lys Arg Trp Gly Ile Gly Gly Arg Gln Ile Asp Lys
    130                 135                 140

Gly Val Arg Phe Ile Glu Met Asn Phe Gly Ser Ala Ser Asp Asn Cys
145                 150                 155                 160

Gln His Thr Pro Ile Gly Phe Asp Ile Ile Phe Pro Gly Met Leu Glu
                165                 170                 175

Asn Ala Arg Asp Leu Asp Leu Asn Leu Arg Leu Glu Pro Arg Ile Val
            180                 185                 190

Thr Asp Met Gln Arg Lys Arg Asp Met Gln Leu Thr Arg Leu His Glu
        195                 200                 205

Ser Asp Leu Lys Gly Asp Gln Ala Tyr Leu Ala Tyr Val Ser Glu Gly
    210                 215                 220

Met Gln Lys Leu Gln Asn Trp Asp Leu Ala Met Lys Phe Gln Arg Lys
225                 230                 235                 240

Asn Gly Ser Leu Phe Asn Ser Pro Ser Ala Thr Ala Ala Ala Val Met
                245                 250                 255

His Val Gln Asn Pro Ala Ser Leu Asn Tyr Leu His Ser Val Val Asp
            260                 265                 270

Lys Phe Gly His Ala Val Pro Ala Val Tyr Pro Leu Asp Leu Tyr Ala
        275                 280                 285

Arg Leu Cys Leu Val Asp Asn Leu Glu Arg Leu Gly Ile Cys Arg His
    290                 295                 300

Phe Thr Asn Glu Ile Glu Ile Val Met Glu Asp Thr Tyr Arg Cys Trp
305                 310                 315                 320

Leu Gln Asp Asp Glu Asp Ile Phe Ala Glu Ile Ser Thr Cys Ala Leu
                325                 330                 335

Ala Phe Arg Leu Leu Arg Lys His Gly Tyr Val Val Ser Pro Asp Pro
            340                 345                 350

Leu Thr Lys Ile Ile Glu Glu Glu Asp Val Ser Asn Ser Ser Gly Asn
        355                 360                 365

Gly Tyr Trp Asn Asp Ile His Ala Val Met Glu Val His Arg Ala Ser
    370                 375                 380

Glu Val Val Ile His Glu Asn Glu Ser Asp Leu Lys Asn Gln Asn Thr
385                 390                 395                 400

Ile Ser Lys His Leu Leu Arg His His Leu Phe Asn Gly Ser Asp Val
                405                 410                 415

Lys Pro Phe Pro Asn Pro Ile Tyr Lys Gln Val Asp Tyr Ala Leu Lys
            420                 425                 430

Phe Pro Thr Pro Leu Ile Leu Gln Arg Val Glu Asn Lys Thr Leu Ile
        435                 440                 445

Gln Asn Tyr Asp Val Asp Ser Thr Arg Leu Leu Lys Thr Ser Tyr Arg
    450                 455                 460

Ser Ser Asn Phe Cys Asn Glu Asp Leu Leu Arg Leu Ala Val Lys Asp
465                 470                 475                 480
```

-continued

```
Phe Asn Asp Cys Gln Leu Leu His Arg Lys Glu Leu Lys Glu Leu Glu
                485                 490                 495

Arg Trp Ser Ala Asp Asn Arg Leu His Glu Leu Lys Phe Ala Arg Gln
            500                 505                 510

Lys Ala Ile Tyr Cys Ser Phe Ser Ala Ala Ala Thr Ile Phe Ile Pro
        515                 520                 525

Glu Trp Tyr Glu Ala Arg Met Ser Leu Ala Lys Asn Ser Val Leu Ala
    530                 535                 540

Thr Val Val Asp Asp Phe Phe Asp Val Gly Gly Ser Met Glu Glu Leu
545                 550                 555                 560

Lys Lys Leu Ile Glu Phe Val Glu Lys Trp Asp Ile Asp Ile Thr Lys
                565                 570                 575

Glu Ser Cys Ser Glu Pro Leu Lys Ile Ile Phe Ser Ala Leu His Ser
            580                 585                 590

Thr Ile Ser Glu Ile Gly Glu Gln Ala Val Lys Trp Gln Gly Arg Asn
        595                 600                 605

Val Thr Ser His Ile Ile Glu Ile Trp Leu Asp Leu Leu Asn Ser Met
    610                 615                 620

Leu Arg Glu Ser Glu Trp Thr Thr Asp Val His Met Pro Thr Leu Asp
625                 630                 635                 640

Glu Tyr Met Glu Ala Ala Tyr Val Ser Phe Ala Met Gly Pro Ile Ile
                645                 650                 655

Ile Pro Ala Leu Tyr Phe Val Gly Pro Lys Leu Ser Asp Glu Ile Val
            660                 665                 670

Arg Asp Pro Glu Ile Arg Ser Leu His Lys Leu Val Ser Ile Cys Gly
        675                 680                 685

Arg Leu Leu Asn Asp Met Gln Gly Phe Glu Arg Glu Lys Lys Ala Gly
    690                 695                 700

Lys Pro Asn Ala Val Ser Ile Arg Ile Ser Gln Asn Gly Asp Gly Ile
705                 710                 715                 720

Thr Glu Ser Ala Ala Phe Glu Glu Val Lys Met Glu Leu Glu Asp Ala
                725                 730                 735

Arg Arg Glu Leu Leu Arg Leu Val Val Gln Lys Asp Gly Ser Val Val
            740                 745                 750

Pro Arg Ala Cys Lys Asp Ala Phe Trp Ser Val Ser Arg Met Leu His
        755                 760                 765

His Phe Tyr Phe Asn Asn Asp Gly Tyr Thr Ser Glu Val Glu Met Val
    770                 775                 780

Glu Leu Val Asn Ser Ile Ile His Glu Pro Leu Lys
785                 790                 795
```

<210> SEQ ID NO 50
<211> LENGTH: 2391
<212> TYPE: DNA
<213> ORGANISM: Chiococca alba

<400> SEQUENCE: 50

```
atgattcata ctctccctca tggcggccag gctcacttca tttcccacaa aacacagcct      60

tattattcca gtagacctcg cttttcttca gcagcttctt tggacacacg agtccggaga     120

acatcgccct ctaattcctc tgtcctagac ttcaacgaga ccaaagaaag aatcacaaaa     180

ttatttcata atgttgatta ttcaatttct tcatatgata cagcatgggt tgctatggtc     240

ccggacccac attcttctca ggctcccctt ttcccagagt gcataaattg gttgctagat     300

aatcaatttc atgatggctc ctggagtctt cctcatcaca attctctatt gcttaaggat     360
```

```
gttttatcct ctacgcttgc gtgtgttctt gctcttaaga gatggggaat aggaggaagg    420
cagattgaca aaggtgttcg ctttattgag atgaattttg gctcagcatc tgacaattgc    480
cagcatactc caataggatt tgacataata tttccaggaa tgcttgaaaa tgccagagat    540
ttggatctaa atcttagact agaacccaga attgtaactg acatgcaacg taaaagagac    600
atgcagctta caagactcca tgaaagcgat ctaaaggggg accaagcata cttggcatat    660
gtatccgaag ggatgcaaaa gttacagaat tgggatttgg cgatgaagtt tcaaaggaag    720
aatggatcgc tcttcaactc accatcagct acagcagccg ctgttatgca tgtccaaaat    780
cctgcttccc tcaattatct tcattcagtc gtcgacaaat tcggccatgc agttccggct    840
gtttaccctt tggatctcta tgcgcgcctt tgcttggttg acaatcttga gaggctgggt    900
atctgtcgac attttactaa tgaaattgaa attgtaatgg aggacacgta caggtgctgg    960
ctgcaggatg atgaagatat atttgccgaa atatcaactt gtgccttagc ttttcggtta   1020
ttgagaaaac atggctatgt tgtctcccca gatccactga caaaaatcat agaagaagaa   1080
gatgtttcca attcttctgg taatggatat tggaatgata tacatgctgt aatggaagtg   1140
catcgggcat cagaggtggt tatacatgaa aatgaatcag atttaaagaa tcaaaatacc   1200
atatcaaaac accttctcag acaccatctt ttcaatggtt ctgatgtgaa gccctttcct   1260
aatccaatat acaagcaggt ggactatgct ctcaagtttc caaccccctt aattctacaa   1320
cgtgttgaaa acaagaccct catacagaac tacgacgtag acagtacaag acttcttaaa   1380
acttcatatc gatcatcaaa tttctgcaat gaagatttac tgaggttagc agtgaaagat   1440
tttaatgact gtcaactcct gcaccggaaa gaactaaaag aactagaaag atggtccgca   1500
gataacagac tgcacgaact aaaatttgct cggcagaaag ctatatactg ctccttttct   1560
gctgcagcaa cgattttcat acctgaatgg tacgaagccc gcatgtcatt ggccaaaaat   1620
agtgtacttg ctactgtggt tgatgacttc tttgatgtgg gtggttcgat ggaggaatta   1680
aagaagctaa ttgaatttgt tgaaaagtgg gatattgaca tcaccaagga atcctgctct   1740
gagccactca aaatcatatt ttcagcactg cacagtacaa tctctgagat tggagagcaa   1800
gcagttaaat ggcaaggacg caatgtaaca agccacataa ttgagatctg gttggatttg   1860
ctcaattcga tgttgaggga gtctgaatgg actacagatg tgcacatgcc aacattggat   1920
gaatatatgg aagctgctta tgtatcattc gccatggggc caattatcat ccctgctctg   1980
tattttgttg ggcctaagct atctgatgaa attgttcggg atcctgaaat acgatccctc   2040
cataagcttg tgagcatttg tgggcggctt ctaaatgata tgcaagggtt cgagagggaa   2100
aagaaggctg gtaaaccaaa tgccgtgtct atacgcatta gtcaaaatgg tgatggcatt   2160
accgaatcag cagctttcga agaagtgaag atggaattag aggatgcaag gagagaattg   2220
ctaagattag ttgtgcaaaa agatggtagt gtagttccaa gagcttgcaa ggatgcgttt   2280
tggagcgtaa gcagaatgtt gcatcatttc tacttcaata atgatggata cacgtcagag   2340
gtggagatgg ttgagctcgt gaattcaatt attcatgaac cactaaaata a            2391
```

<210> SEQ ID NO 51
<211> LENGTH: 792
<212> TYPE: PRT
<213> ORGANISM: Salvia hispanica

<400> SEQUENCE: 51

```
Met Ser Ile Gln Ala Asn Met Ser Phe Ala Thr Ser Leu His Arg Ser
1               5                   10                  15
```

-continued

```
Thr Thr Pro Gly Val Gly Leu Pro Leu Lys Pro Cys Ile Ser Pro Ser
            20                  25                  30

Pro Ser Leu Ser Phe Ser Pro Asn Phe Gly Thr Phe Asn Asn Thr Ser
        35                  40                  45

Leu Arg Leu Lys Pro Glu Ala Gly Ser Lys Ser Tyr Glu Gly Ile Arg
    50                  55                  60

Arg Ser His Gln Leu Ala Ala Ser Thr Ile Leu Glu Gly Gln Thr Pro
65                  70                  75                  80

Ile Thr Pro Glu Val Glu Ser Glu Lys Thr Arg Leu Ile Glu Arg Ile
                85                  90                  95

Arg Ser Met Leu Gln Asp Met Asp Asn Asp Gly Gln Ile Ser Val Ser
            100                 105                 110

Pro Tyr Asp Thr Ala Trp Val Ala Leu Val Glu Asp Ile Gly Gly Ser
        115                 120                 125

Gly Gly Pro Gln Phe Pro Thr Ser Leu Glu Trp Ile Ser Asn His Gln
    130                 135                 140

Tyr Asp Asp Gly Ser Trp Gly Asp Arg Lys Phe Val Leu Tyr Asp Arg
145                 150                 155                 160

Ile Leu Asn Thr Leu Ala Cys Val Val Ala Leu Thr Asn Trp Lys Met
                165                 170                 175

His Pro Asn Lys Cys Glu Lys Gly Leu Arg Phe Ile His Glu Asn Ile
            180                 185                 190

Lys Lys Leu Ala Asp Glu Asp Glu Glu Leu Met Pro Val Gly Phe Glu
        195                 200                 205

Ile Ala Leu Pro Ser Val Ile Asp Leu Ala Lys Arg Leu Gly Ile Glu
    210                 215                 220

Ile Pro Glu Asn Ser Ala Ser Ile Lys Arg Ile Tyr Glu Leu Arg Asp
225                 230                 235                 240

Ser Lys Leu Lys Lys Ile Pro Met Asp Leu Val His Lys Arg Pro Thr
                245                 250                 255

Ser Leu Leu Phe Ser Leu Glu Gly Met Glu Gly Leu Asn Trp Asp Lys
            260                 265                 270

Leu Met Asn Phe Leu Ala Glu Gly Ser Phe Leu Ser Ser Pro Ser Ser
        275                 280                 285

Thr Ala Tyr Ala Leu Gln His Thr Lys Asn Glu Leu Cys Leu Glu Tyr
    290                 295                 300

Leu Leu Lys Ala Val Lys Arg Phe Asn Gly Gly Val Pro Asn Ala Tyr
305                 310                 315                 320

Pro Val Asp Met Phe Glu His Leu Trp Ser Val Asp Arg Leu Gln Arg
                325                 330                 335

Leu Gly Ile Ser Arg Tyr Phe Gln Ala Glu Ile Glu Glu Asn Met Ala
            340                 345                 350

Tyr Ala Tyr Arg Tyr Trp Thr Asn Lys Gly Ile Thr Trp Ala Arg Asn
        355                 360                 365

Met Val Val Gln Asp Ser Asp Asp Ser Ala Gln Gly Phe Arg Leu Leu
    370                 375                 380

Arg Leu Tyr Gly Tyr Asp Ile Pro Ile Asp Val Phe Lys His Phe Glu
385                 390                 395                 400

Gln Gly Gly Gln Phe Cys Ser Ile Pro Gly Gln Met Thr His Ala Ile
                405                 410                 415

Thr Gly Met Tyr Asn Leu Tyr Arg Ala Ser Glu Leu Leu Phe Pro Gly
            420                 425                 430
```

-continued

```
Glu His Ile Leu Ser Asp Ala Arg Lys Tyr Thr Gly Asn Phe Leu His
        435                 440                 445

Gln Arg Arg Ile Thr Asn Thr Val Val Asp Lys Trp Ile Ile Thr Lys
    450                 455                 460

Asp Leu His Gly Glu Val Ala Tyr Ala Leu Asp Val Pro Phe Tyr Ala
465                 470                 475                 480

Ser Leu Pro Arg Leu Glu Ala Arg Phe Phe Ile Glu Gln Tyr Gly Gly
                485                 490                 495

Asp Glu Asp Val Trp Ile Gly Lys Thr Leu Tyr Arg Met Phe Lys Val
            500                 505                 510

Asn Ser Asp Thr Tyr Leu Glu Met Ala Lys Leu Asp Tyr Lys Gln Cys
        515                 520                 525

Gln Ser Val His Gln Leu Glu Trp Asn Ser Met Gln Arg Leu Tyr Arg
    530                 535                 540

Asp Cys Asn Leu Gly Glu Phe Gly Leu Ser Glu Arg Ser Leu Leu Leu
545                 550                 555                 560

Ala Tyr Tyr Ile Ala Ala Ser Thr Thr Phe Glu Pro Glu Lys Ser Ser
                565                 570                 575

Glu Arg Leu Ala Trp Ala Ile Thr Thr Ile Leu Val Glu Ile Ile Ala
            580                 585                 590

Ser Gln Lys Leu Ser Asp Glu Gln Lys Arg Glu Phe Val Asp Glu Phe
        595                 600                 605

Val Lys Gly Ser Ile Val Asn Asn Gln Asn Gly Gly Arg His Lys Pro
    610                 615                 620

Gly Asn Arg Leu Val Glu Val Leu Ile Asn Asn Ile Thr Leu Met Ala
625                 630                 635                 640

Glu Gly Arg Gly Thr Tyr Gln Gln Leu Ser Asn Ala Trp Lys Lys Trp
                645                 650                 655

Leu Lys Thr Trp Glu Glu Gly Gly Asp Leu Gly Glu Ala Glu Ala Arg
            660                 665                 670

Leu Leu Leu His Thr Ile His Leu Ser Ser Gly Leu Asp Asp Ser Ser
        675                 680                 685

Phe Ser His Pro Lys Tyr Gln Gln Leu Leu Glu Ala Thr Ser Lys Val
    690                 695                 700

Cys His Gln Leu Arg Val Phe Gln Ser Val Lys Val Tyr Asp Asp Gln
705                 710                 715                 720

Glu Ser Thr Ser Gln Leu Val Thr Arg Thr Thr Phe Gln Ile Glu Ala
                725                 730                 735

Gly Met Gln Glu Leu Val Lys Leu Val Phe Thr Lys Thr Leu Glu Asp
            740                 745                 750

Leu Pro Ser Thr Thr Lys Gln Ser Phe Phe Ser Val Ala Arg Ser Phe
        755                 760                 765

Tyr Tyr Thr Ala Cys Ile His Ala Asp Thr Ile Asp Ser His Ile Asn
    770                 775                 780

Lys Val Leu Phe Glu Lys Ile Val
785                 790
```

<210> SEQ ID NO 52
<211> LENGTH: 2379
<212> TYPE: DNA
<213> ORGANISM: Salvia hispanica

<400> SEQUENCE: 52

```
atgagtattc aagcaaacat gtcatttgcc acctccctcc accgatcaac cacccccgga      60
```

gttggccttc cgctaaaacc atgtatctct ccctctccct ctctttcctt ttccccaaac 120
tttggcactt ttaacaacac aagtttgaga ctcaaaccag aggctgggag caaaagttat 180
gaggggattc gaagaagtca tcaattagca gcatcaacaa ttttggaggg tcaaactccg 240
attactccgg aggttgaatc ggagaaaaca cgcctgattg aaaggattcg ttcgatgtta 300
caagacatgg acaacgatgg ccagataagt gtgtcaccat acgacacagc atgggtggcg 360
ctcgtggaag atattggtgg cagcggaggg ccacagtttc caacgagcct agagtggatt 420
tctaaccacc agtacgacga tggatcgtgg ggggatcgca aatttgttct ctatgaccgg 480
atactcaata cattagcatg tgttgtcgca ctcacgaatt ggaaaatgca tcctaacaaa 540
tgcgaaaaag ggttgaggtt tattcatgag aatattaaga aactcgcgga tgaagatgaa 600
gagctcatgc ccgtaggatt cgaaatcgca ctgccatcag tcattgattt agctaaaaga 660
ctgggtatag aaatcccaga aaattctgca agcataaaaa gaatttatga attgagagat 720
tcaaaactta aaaaaatacc aatggattta gtgcacaaaa ggcccacatc actactcttc 780
agcttggaag gcatggaagg ccttaactgg gacaaactaa tgaattttct agccgagggt 840
tcgtttcttt catcgccatc gtccactgcc tacgctctcc aacacaccaa gaatgagtta 900
tgcctagagt atttactcaa ggcagtcaag agattcaatg gtggagttcc aaatgcatac 960
cctgtcgaca tgtttgagca tctgtggtcc gtggatcgct tacagagatt aggaatttct 1020
cggtattttc aagctgaaat tgaagaaaac atggcctatg cttacagata ctggacaaat 1080
aaaggaatca cctgggcaag aaatatggtt gtccaagaca gtgacgacag cgcacaggga 1140
ttcaggctct taaggttgta cggatacgat attcctatag atgttttcaa acatttcgag 1200
caaggtggac aattctgcag cataccagga cagatgacac acgctattac aggaatgtac 1260
aacttgtata gagcttctga acttctgttc cctggagaac acatactttc tgatgctaga 1320
aaatacacag gtaacttctt gcatcaaaga agaattacta acacggtagt agacaagtgg 1380
atcattacca aagaccttca cggcgaggtg gcttatgcat tggatgtgcc attctacgcc 1440
agtctgccac gactggaagc acgattcttc atagaacaat atgggggtga tgaagatgtt 1500
tggattggga aaacattgta caggatgttt aaagtaaact ccgacacata ccttgagatg 1560
gcaaaattag attacaaaca atgccagtct gtgcatcagt tagagtggaa tagcatgcaa 1620
agattgtata gagattgcaa tctaggagag tttgggttga gcgaaagaag ccttctccta 1680
gcttactaca tagcagcctc aactacattt gagccggaaa aatcaagtga aagactggct 1740
tgggctataa caacaatttt agtcgaaata atcgcatccc aaaaactctc tgatgagcaa 1800
aagagagagt ttgttgatga atttgtaaaa ggaagcatcg tcaataacca aaatggagga 1860
agacataaac cgggaaacag attggttgaa gttttgatca acaatataac actgatggca 1920
gaaggcagag gcacatatca gcagttgtct aatgcgtgga aaaaatggct aaagacatgg 1980
gaagagggag gtgacctggg ggaagcagaa gcacggcttc tcctgcacac gatacatttg 2040
agctccggat tggatgattc atcattttcc catccaaaat atcagcagct cttggaggca 2100
accagcaaag tctgccacca acttcgcgta ttccagagtg taaaggtgta tgatgaccaa 2160
gagtctacaa gccaactggt aactaggaca actttccaaa tagaagcagg catgcaagaa 2220
ctagtgaaat tagttttcac aaaaaccttg gaagatttgc cttctactac caagcaaagc 2280 tttttttagtg ttgctagaag tttctattac actgcctgta ttcatgcaga cactatagac 2340
tcccacataa acaaagtatt gtttgaaaaa attgtctag 2379

<210> SEQ ID NO 53
<211> LENGTH: 790
<212> TYPE: PRT
<213> ORGANISM: Teucrium canadense

<400> SEQUENCE: 53

Met Ser Phe Ala Ser Gln Ala Thr Ser Leu Leu Leu Ser Ser His Asn
1               5                   10                  15

Ala Thr Ala Leu Pro Pro Leu Ser Ala Ala Arg Leu Pro Pro Leu Thr
            20                  25                  30

Ala Gly Ala Ala Pro Phe Gly Arg Ile Ser Phe Thr Thr Thr Ser Leu
        35                  40                  45

Arg Gln Tyr Lys Leu Val Ser Arg Ala Gln Ser Gln Glu Val Asp Glu
    50                  55                  60

Ile Glu Lys Val Thr Gln Val Val Leu Glu Ala Glu Lys Asp Ile Asp
65                  70                  75                  80

Gln Glu Ala Lys Val Arg Glu Leu Val Glu Asn Val Arg Val Lys Leu
                85                  90                  95

Gln Asn Ile Gly Glu Gly Gly Ile Ser Ile Ser Pro Tyr Asp Thr Ala
            100                 105                 110

Trp Val Ala Leu Val Glu Asp Val Gly Gly Ser Gly Arg Pro Gln Phe
        115                 120                 125

Pro Glu Ser Leu Asp Trp Ile Ser Asn His Gln Phe Pro Asp Gly Ser
    130                 135                 140

Trp Gly Ser His Lys Phe Leu Tyr Tyr Asp Arg Val Leu Cys Thr Leu
145                 150                 155                 160

Ala Cys Ile Val Ala Leu Lys Thr Trp Asn Leu His Pro His Lys Phe
                165                 170                 175

Asp Lys Gly Leu Lys Phe Val Arg Glu Asn Ile Gly Lys Leu Ala Asp
            180                 185                 190

Glu Glu Asp Val His Met Pro Ile Gly Phe Glu Val Ala Phe Pro Ser
        195                 200                 205

Leu Ile Glu Thr Ala Lys Arg Lys Gly Ile Asp Ile Pro Glu Asp Phe
    210                 215                 220

Pro Gly Lys Lys Glu Ile Tyr Ala Lys Arg Asp Leu Lys Leu Lys Lys
225                 230                 235                 240

Ile Pro Met Asp Ile Leu His Lys Ile Pro Thr Pro Leu Leu Phe Ser
                245                 250                 255

Ile Glu Gly Ile Glu Gly Leu Asp Trp Gln Lys Leu Phe Lys Phe Arg
            260                 265                 270

Asp His Gly Ser Phe Leu Thr Ser Pro Ser Ser Thr Ala His Ala Leu
        275                 280                 285

Gln Gln Thr Lys Asp Glu Leu Cys Leu Lys Tyr Leu Thr Asn Leu Val
    290                 295                 300

Lys Lys Asn Asn Gly Gly Val Pro Asn Ala Phe Pro Val Asp Leu Phe
305                 310                 315                 320

Asp Arg Asn Tyr Thr Val Asp Arg Leu Arg Arg Leu Gly Ile Leu Arg
                325                 330                 335

Tyr Phe Gln Pro Glu Ile Glu Glu Cys Met Lys Tyr Val Tyr Arg Phe
            340                 345                 350

Trp Asp Lys Arg Gly Ile Ser Trp Ala Arg Asn Thr His Val Gln Asp
        355                 360                 365

Leu Asp Asp Thr Val Gln Gly Phe Arg Asn Leu Arg Met His Gly Tyr
    370                 375                 380

-continued

```
Asp Val Thr Leu Asp Val Phe Lys Gln Phe Glu Arg Cys Gly Glu Phe
385                 390                 395                 400

Phe Ser Phe His Gly Gln Ser Ser Asp Ala Val Leu Gly Met Phe Asn
                405                 410                 415

Leu Tyr Arg Ala Ser Gln Val Leu Phe Pro Gly Glu Asp Met Leu Ala
            420                 425                 430

Asp Ala Arg Lys Tyr Ala Ala Asn Tyr Leu His Lys Arg Arg Val Ser
        435                 440                 445

Asn Arg Val Val Asp Lys Trp Ile Ile Asn Lys Asp Leu Pro Gly Glu
    450                 455                 460

Val Ala Tyr Gly Leu Asp Val Pro Phe Tyr Ala Ser Leu Pro Arg Leu
465                 470                 475                 480

Glu Ala Arg Phe Tyr Val Glu Gln Tyr Gly Gly Asn Asp Asp Val Trp
                485                 490                 495

Ile Gly Lys Ala Leu Tyr Arg Met Leu Asn Val Ser Cys Asp Thr Tyr
            500                 505                 510

Leu Glu Leu Ala Lys Leu Asp Tyr Asn Ile Cys Gln Ala Val His Gln
        515                 520                 525

Lys Glu Trp Lys Ser Phe Gln Lys Trp His Arg Asp Gly Glu Phe Gly
    530                 535                 540

Leu Asp Glu Lys Ser Leu Leu Leu Ala Tyr Tyr Ile Ala Ala Ser Thr
545                 550                 555                 560

Val Phe Glu Pro Glu Lys Ser Leu Glu Arg Leu Ala Trp Ala Lys Thr
                565                 570                 575

Ala Val Leu Met Glu Ala Ile Leu Ser Gln Gln Leu Pro Ser Thr Lys
            580                 585                 590

Lys His Glu Leu Val Asp Glu Phe Lys His Ala Ser Ile Leu Asn Asn
        595                 600                 605

Gln Asn Gly Gly Ser Tyr Lys Thr Arg Thr Pro Leu Val Glu Thr Leu
    610                 615                 620

Val Asn Ala Ile Ser Glu Leu Ser Thr Thr Ile Leu Leu Glu Gln Asp
625                 630                 635                 640

Arg Asp Ile His Leu Gln Leu Ser Asn Ala Trp Leu Lys Trp Leu Ser
                645                 650                 655

Arg Trp Glu Ala Arg Gly Asn Leu Val Glu Ala Glu Ala Glu Leu Leu
            660                 665                 670

Leu Gln Thr Leu His Leu Ser Asn Gly Leu Glu Glu Ser Ser Phe Ser
        675                 680                 685

His Pro Lys Tyr Gln Gln Leu Leu Gln Val Thr Ser Lys Val Cys His
    690                 695                 700

Leu Leu Arg Leu Phe Gln Lys Arg Lys Val His Asp Pro Glu Gly Cys
705                 710                 715                 720

Thr Thr Asp Ile Ala Thr Gly Thr Thr Phe Gln Ile Glu Ala Cys Met
                725                 730                 735

Gln Gln Val Val Lys Leu Val Phe Thr Lys Ser Ser His Asp Leu Asp
            740                 745                 750

Ser Val Val Lys Gln Arg Phe Leu Asp Val Ala Arg Ser Phe Tyr Tyr
        755                 760                 765

Thr Ala His Cys Asp Pro Gln Val Ile Gln Ser His Ile Asn Lys Val
    770                 775                 780

Leu Phe Glu Lys Val Val
785                 790
```

-continued

<210> SEQ ID NO 54
<211> LENGTH: 2373
<212> TYPE: DNA
<213> ORGANISM: Teucrium canadense

<400> SEQUENCE: 54
atgtcatttg cttcccaagc cacctccctc ctcctttctt cccacaacgc caccgctctt 60
ccgcctctct ctgccgcccg ccttccgcct ctcactgccg gtgctgctcc attcggaaga 120
atatcattta ctactacctc tcttcggcag tataaactgg tgtcaagagc tcaaagccaa 180
gaggtggatg agattgaaaa agtgacacaa gtggtattgg aggcagaaaa agacatcgat 240
caagaggcga aggtaaggga gctggtggaa aatgtccgag tgaagctgca aaatatcggg 300
gaaggaggga taagcatatc gccgtacgac accgcatggg tggcgctggt ggaggatgtc 360
ggcggcagcg gcagaccgca gttcccggag agcctggatt ggatatcaaa ccaccagttc 420
ccggacgggt cgtggggcag ccacaaattc ttgtactatg accgggtttt gtgcacgtta 480
gcatgtatag ttgcattgaa aacttggaat ctgcatcctc acaaattcga caaagggttg 540
aaattcgtca gagagaacat tggaaagctc gcggatgaag aagacgtgca catgccgatt 600
gggttcgaag tggcattccc atcacttata gagactgcaa agagaaaagg aattgacatc 660
ccggaagatt tccctggcaa gaaagaaatc tatgcaaaaa gagacctaaa gctgaaaaag 720
atacctatgg atatactgca caaaatcccc acaccattac tgttcagcat agaagggata 780
gaaggccttg attggcagaa gctattcaaa ttccgcgatc acggctcctt cctcacgtcc 840
ccgtcctcaa cggcccacgc tctccagcaa acaaaggacg agttatgcct caaatatctg 900
accaatcttg tcaaaaagaa caatgggga gttccaaatg catttccggt ggacctattt 960
gatcgtaact atacagtaga tcgcctgagg aggctgggaa ttttgcgcta ttttcaacct 1020
gaaatcgagg aatgcatgaa atatgtatac agattctggg ataaaagagg aatcagctgg 1080
gcaagaaata cccatgttca ggaccttgat gataccgtac agggattcag gaacttaagg 1140
atgcatggtt atgatgtcac cttagatgtt ttcaaacagt tcgagagatg tggagaattc 1200
tttagcttcc acgggcaatc aagtgatgct gtcttaggaa tgttcaactt gtaccgagct 1260
tctcaggttc tgtttccagg agaagacatg cttgcagatg caaggaagta cgcggccaac 1320
tatttgcata aaagaagagt tagtaatagg gtcgtggaca aatggattat taacaaagat 1380
cttccaggcg aggtggcgta tgggctagat gttccgttct acgccagtct acctcgactg 1440
gaagcaagat tctacgtcga acaatatggg ggtaacgatg atgtctggat tggaaaagct 1500
ttatatagaa tgttgaatgt gagctgtgat acttaccttg agctagcaaa attagactac 1560
aatatttgcc aggctgtgca tcagaaagag tggaaaagct ttcaaaaatg gcacagggat 1620
ggggagtttg gattggatga aaaaagctta cttttagctt actacatagc agcctcgact 1680
gttttcgagc ctgaaaaatc tctagagcga ctggcttggg ctaaaaccgc agttctaatg 1740
gaggcaattt tgtcccaaca acttcctagc acaaaaaaac atgagcttgt tgacgaattt 1800
aaacatgcaa gcatcctcaa caaccaaaat ggaggaagct ataaaacaag aactcctttg 1860
gtagagactc tagtaaacgc cataagtgag ctctcaacta ccatactatt ggagcaagac 1920
agagacattc atctgcaatt atctaatgcg tggctgaagt ggctaagtag atgggaggca 1980
agaggcaacc tagtggaagc agaagcagag cttcttctgc aaaccttaca tctgagcaat 2040
ggattagaag aatcatcatt ttctcatcca aaatatcaac aactcttaca ggttaccagc 2100
aaagtctgtc acctacttcg gctattccag aaacgaaagg tgcatgatcc ggaagggtgt 2160
acaacagaca ttgcaacagg gacaactttc caaatagaag catgcatgca acaagtagtg 2220
aaattagtgt tcaccaaatc ctcacatgat ttagattctg ttgttaagca gagatttttg 2280
gatgttgcca gaagtttcta ttacacagcc cactgtgatc cacaagtgat ccagtcccac 2340
attaataaag tgttgtttga aaaagtagtc tag 2373

<210> SEQ ID NO 55
<211> LENGTH: 785
<212> TYPE: PRT
<213> ORGANISM: Salvia officinalis

<400> SEQUENCE: 55

Met Ser Phe Ala Ser Thr Thr Ser Leu Leu Arg Pro Ser Val Thr Gly
1 5 10 15

Phe Gly Val Ser Pro Arg Val Thr Ser Thr Ser Ile Leu Ser Arg Ser
20 25 30

Tyr Gly Gln Ile Leu Lys Gly Lys Thr Lys Tyr Ile Thr Asp Asn Arg
35 40 45

Arg Asn Arg Gln Leu Ala Val Lys Phe Glu Gly Gln Ile Ala Leu Asp
50 55 60

Leu Glu Asp Gly Val Ala Lys Gln Thr Asn Gln Glu Ala Glu Ser Glu
65 70 75 80

Lys Ile Arg Gln Leu Lys Gly Lys Ile Arg Trp Ile Leu Gln Asn Met
85 90 95

Glu Asp Gly Glu Met Ser Val Ser Pro Tyr Asp Thr Ala Trp Val Ala
100 105 110

Leu Val Glu Asp Ile Ser Gly Gly Gly Gly Pro Gln Phe Pro Thr Ser
115 120 125

Leu Glu Trp Ile Ser Lys Asn Gln Leu Ala Asp Gly Ser Trp Gly Asp
130 135 140

Pro Asn Tyr Phe Leu Leu Tyr Asp Arg Ile Leu Asn Thr Leu Ala Cys
145 150 155 160

Val Val Ala Leu Thr Thr Trp Asn Met His Pro His Lys Cys Asp Gln
165 170 175

Gly Leu Arg Phe Ile Arg Asp Asn Ile Glu Lys Leu Glu Asp Glu Asp
180 185 190

Glu Glu Leu Ile Leu Val Gly Phe Glu Ile Ala Leu Pro Ser Leu Ile
195 200 205

Asp Tyr Ala Gln Asn Leu Gly Ile Gln Ile Gln Tyr Asp Ser Pro Phe
210 215 220

Ile Lys Lys Ile Cys Ala Lys Arg Asp Leu Lys Leu Arg Lys Ile Pro
225 230 235 240

Met Asp Leu Met His Arg Lys Pro Thr Ser Leu Leu Tyr Ser Leu Glu
245 250 255

Gly Met Glu Gly Leu Glu Trp Glu Lys Leu Met Asn Leu Arg Ser Glu
260 265 270

Gly Ser Phe Leu Ser Ser Pro Ser Ser Thr Ala Tyr Ala Leu Gln His
275 280 285

Thr Lys Asp Glu Leu Cys Leu Asp Tyr Leu Val Lys Ala Val Asn Lys
290 295 300

Phe Asn Gly Gly Val Pro Asn Val Tyr Pro Val Asp Met Tyr Glu His
305 310 315 320

Leu Trp Cys Val Asp Arg Leu Gln Arg Leu Gly Ile Ser Arg Tyr Phe
325 330 335

```
Gln Leu Glu Ile Gln Gln Cys Leu Asp Tyr Val Tyr Arg Tyr Trp Thr
            340                 345                 350

Asn Glu Gly Ile Ser Trp Ala Arg Tyr Thr Asn Ile Arg Asp Ser Asp
        355                 360                 365

Asp Thr Ala Met Gly Phe Arg Leu Leu Arg Leu Tyr Gly Tyr Asp Val
    370                 375                 380

Ser Ile Asp Ala Phe Lys Pro Phe Glu Glu Ser Gly Glu Phe Tyr Ser
385                 390                 395                 400

Met Ala Gly Gln Met Asn His Ala Val Thr Gly Met Tyr Asn Leu Tyr
                405                 410                 415

Arg Ala Ser Gln Leu Met Phe Pro Gln Glu His Ile Leu Ser Asp Ala
            420                 425                 430

Arg Asn Phe Ser Ala Lys Phe Leu His Gln Lys Arg Arg Thr Asn Ala
        435                 440                 445

Leu Val Asp Lys Trp Ile Ile Thr Lys Asp Leu Pro Gly Glu Val Gly
    450                 455                 460

Tyr Ala Leu Asp Val Pro Phe Tyr Ala Ser Leu Pro Arg Leu Glu Ala
465                 470                 475                 480

Arg Phe Phe Leu Glu Gln Tyr Gly Gly Asp Asp Asp Val Trp Ile Gly
                485                 490                 495

Lys Thr Leu Tyr Arg Met Pro Tyr Val Asn Ser Asn Thr Tyr Leu Glu
            500                 505                 510

Leu Ala Lys Val Asp Tyr Lys Asn Cys Gln Ser Val His Gln Leu Glu
        515                 520                 525

Trp Lys Ser Met Gln Lys Trp Tyr Arg Glu Cys Asn Ile Gly Glu Phe
    530                 535                 540

Gly Leu Ser Glu Arg Ser Leu Leu Leu Ala Tyr Tyr Ile Ala Ala Ser
545                 550                 555                 560

Thr Thr Phe Glu Pro Glu Lys Ser Gly Glu Arg Leu Ala Trp Ala Thr
                565                 570                 575

Thr Ala Ile Leu Ile Glu Thr Ile Ala Ser Gln Gln Leu Ser Asp Glu
            580                 585                 590

Gln Lys Arg Glu Phe Val Asp Glu Phe Glu Asn Ser Ile Ile Ile Lys
        595                 600                 605

Asn Gln Asn Gly Gly Arg Tyr Lys Ala Arg Asn Arg Leu Val Lys Val
    610                 615                 620

Leu Ile Asn Thr Val Thr Leu Val Ala Glu Gly Arg Gly Ile Asn Gln
625                 630                 635                 640

Gln Leu Phe Asn Ala Trp Gln Lys Trp Leu Lys Thr Trp Glu Glu Gly
                645                 650                 655

Gly Asp Met Gly Glu Ala Glu Ala Gln Leu Leu Leu Arg Thr Leu His
            660                 665                 670

Leu Ser Ser Gly Phe Asp Gln Ser Ser Phe Ser His Pro Lys Tyr Glu
        675                 680                 685

Gln Leu Leu Glu Ala Thr Ser Lys Val Cys His Gln Leu Arg Leu Phe
    690                 695                 700

Gln Asn Arg Lys Val Asp Asp Gly Gln Gly Cys Ile Ser Arg Leu Val
705                 710                 715                 720

Ile Gly Thr Thr Ser Gln Ile Glu Ala Gly Met Gln Glu Val Val Lys
                725                 730                 735

Leu Val Phe Thr Lys Thr Ser Gln Asp Leu Thr Ser Ala Thr Lys Gln
            740                 745                 750

Ser Phe Phe Asn Ile Ala Arg Ser Phe Tyr Tyr Thr Ala Tyr Phe His
```

755 760 765

Ala Asp Thr Ile Asp Ser His Ile Tyr Lys Val Leu Phe Gln Thr Ile
770 775 780

Val
785

<210> SEQ ID NO 56
<211> LENGTH: 2358
<212> TYPE: DNA
<213> ORGANISM: Salvia officinalis

<400> SEQUENCE: 56
atgtcatttg cttccaccac ctccctcctc cgaccaagcg tcactgggtt cggtgtttct 60
ccaagggtta cttccacctc cattcttagc cgaagttatg gtcaaatatt aaaaggaaaa 120
acaaaataca taactgataa ccgtagaaat cgacaattgg cggtaaaatt tgagggccaa 180
attgctttgg atttggagga tggcgtagca aagcagacga atcaagaggc ggaatctgag 240
aagataaggc aactgaaggg aaagatccga tggattctgc aaaacatgga ggacggcgag 300
atgagcgtgt cgccgtacga caccgcatgg gtggcgctgg tggaagatat cagcggcggc 360
ggcgggccgc agttcccgac gagcctcgag tggatttcca agaatcagtt ggcggatggg 420
tcatgggggg atcctaatta tttccttctc tacgacagaa tactcaatac tttagcatgt 480
gtagtcgcac tcacgacttg gaatatgcat cctcacaaat gcgatcaagg gttgaggttt 540
ataagagaca acattgagaa acttgaggat gaagatgagg agctaattct cgtaggattc 600
gagatcgcac tgccttcact cattgattat gctcaaaacc ttgggataca aatccaatat 660
gattctccat tcattaaaaa aatttgtgca aagagagatc taaaactcag aaaaatacca 720
atggatttaa tgcacagaaa gccaacatca ttgctctaca gcttggaagg catggaaggc 780
cttgagtggg aaaagctaat gaatttgcga tcggagggtt cgtttctgtc atcgccgtcg 840
tccacggcct acgctctcca acacaccaag gatgagttat gccttgacta tctggtcaag 900
gcggtcaaca aattcaatgg tggagttccc aacgtgtacc ctgtcgacat gtatgagcat 960
ctatggtgcg tagaccgctt gcagaggttg ggaatttctc gctattttca acttgaaatt 1020
caacaatgcc tcgactatgt ttacagatac tggacaaatg aaggaatttc gtgggcaaga 1080
tatactaata tccgggatag tgacgacacc gcaatgggat tcaggcttct aaggttgtac 1140
ggctatgatg tctctataga tgcttttaaa ccattcgagg aaagcggaga attctatagc 1200
atggcagggc agatgaacca cgctgttaca ggaatgtaca acttgtacag agcttctcaa 1260
cttatgttcc ctcaagaaca catactttcc gatgccagaa acttctctgc caaattcttg 1320
catcaaaaga ggcgtactaa tgcactagta gacaagtgga tcattaccaa agaccttccc 1380
ggcgaggttg gatatgcatt ggatgtgccg ttctacgcca gtctgcctcg actggaagca 1440
cgattcttct tagaacaata tggggggtgat gatgatgttt ggattggaaa aactttgtac 1500
aggatgccat atgtgaactc caacacatac cttgagcttg caaaagtaga ctacaaaaac 1560
tgccagtccg tgcatcagtt ggagtggaag agcatgcaaa aatggtacag agaatgcaat 1620
ataggtgagt ttgggttgag cgaaagaagc cttctcctag cttactacat agcagcctca 1680
actacattcg agccagaaaa atcaggtgag cggctcgctt gggctacaac agcaatttta 1740
atcgagacaa tcgcgtccca acaactctcc gatgaacaaa agagagagtt cgttgatgaa 1800
tttgaaaaca gcatcattat caagaatcaa aatggaggga gatataaagc aagaaacaga 1860
ttggtcaagg ttttgatcaa cactgtaaca ctggtagcag aaggcagagg cataaatcag 1920

```
cagttgttta atgcgtggca aaaatggcta aagacatggg aagaaggagg tgacatgggg   1980

gaagcagaag cccagcttct tctgcgcacg ctacatttga gctccggatt cgatcaatca   2040

tcattttccc atccaaaata tgagcagctc ttggaggcga ccagcaaagt ttgccaccaa   2100

cttcgcctat tccagaatcg aaaggtggat gatggccaag ggtgtataag tcgattggta   2160

attgggacaa cttcccaaat agaagcaggc atgcaagaag tagtgaaatt agttttcacc   2220

aaaacctcac aagacttgac ttctgctacc aagcaaagct tttcaatat tgctagaagt   2280

ttctattata ctgcctactt tcatgcagac actatagact cccacatata caaagtattg   2340

tttcaaacaa tagtatag                                                 2358
```

<210> SEQ ID NO 57
<211> LENGTH: 808
<212> TYPE: PRT
<213> ORGANISM: Scutellaria baicalensis

<400> SEQUENCE: 57

```
Met Pro Phe Leu Leu Pro Ser Ser Ala Thr Ser Ser Pro Ala Phe Tyr
1               5                   10                  15

Thr Pro Ala Ala Pro Leu Ala Gly His His Val Phe Pro Ser Phe Lys
            20                  25                  30

Pro Leu Ile Ile Ser Arg Ser Ser Leu Gln Cys Asn Ala Ile Ser Arg
        35                  40                  45

Pro Arg Thr Gln Glu Tyr Ile Asp Val Ile Gln Asn Gly Leu Pro Val
    50                  55                  60

Ile Lys Trp His Glu Ala Val Glu Glu Asp Glu Thr Asp Lys Asp Ser
65                  70                  75                  80

Leu Asn Lys Glu Ala Thr Ser Asp Lys Ile Arg Glu Leu Val Asn Leu
                85                  90                  95

Ile Arg Ser Met Leu Gln Ser Met Gly Asp Gly Glu Ile Ser Ser Ser
            100                 105                 110

Pro Tyr Asp Ala Ala Trp Val Ala Leu Val Pro Asp Val Gly Gly Ser
        115                 120                 125

Gly Gly Pro Gln Phe Pro Ser Ser Leu Glu Trp Ile Ser Lys Asn Gln
    130                 135                 140

Leu Pro Asp Gly Ser Trp Gly Asp Thr Cys Thr Phe Ser Ile Tyr Asp
145                 150                 155                 160

Arg Ile Ile Asn Thr Leu Ala Cys Val Val Ala Leu Lys Ser Trp Asn
                165                 170                 175

Ile His Pro His Lys Thr Tyr Gln Gly Ile Ser Phe Ile Lys Ala Asn
            180                 185                 190

Met Asp Lys Leu Glu Asp Glu Asn Glu Glu His Met Pro Ile Gly Phe
        195                 200                 205

Glu Val Ala Leu Pro Ser Leu Ile Glu Ile Ala Lys Arg Leu Asp Ile
    210                 215                 220

Asp Ile Ser Ser Asp Ser Arg Gly Leu Gln Glu Ile Tyr Thr Arg Arg
225                 230                 235                 240

Glu Val Lys Leu Lys Arg Ile Pro Lys Glu Ile Met His Gln Val Pro
                245                 250                 255

Thr Thr Leu Leu His Ser Leu Glu Gly Met Ala Glu Leu Thr Trp His
            260                 265                 270

Lys Leu Leu Lys Leu Gln Cys Gln Asp Gly Ser Phe Leu Phe Ser Pro
        275                 280                 285
```

-continued

```
Ser Ser Thr Ala Phe Ala Leu His Gln Thr Lys Asp His Asn Cys Leu
    290                 295                 300

His Tyr Leu Thr Lys Tyr Val His Lys Phe His Gly Gly Val Pro Asn
305                 310                 315                 320

Val Tyr Pro Val Asp Leu Phe Glu His Leu Trp Ala Val Asp Arg Ile
                325                 330                 335

Gln Arg Leu Gly Ile Ser Arg His Phe Lys Pro Gln Val Asp Glu Cys
            340                 345                 350

Ile Ala Tyr Val Tyr Arg Tyr Trp Thr Asp Lys Gly Ile Cys Trp Ala
        355                 360                 365

Arg Asn Ser Val Val Gln Asp Leu Asp Asp Thr Ala Met Gly Phe Arg
    370                 375                 380

Leu Leu Arg Leu His Gly Tyr Asp Val Ser Ala Asp Val Phe Lys His
385                 390                 395                 400

Phe Glu Asn Gly Gly Glu Phe Phe Cys Phe Lys Gly Gln Ser Thr Gln
                405                 410                 415

Ala Val Thr Gly Met Tyr Asn Leu Tyr Arg Ala Ser Gln Leu Met Phe
            420                 425                 430

Pro Gly Glu Ser Ile Leu Glu Asp Ala Lys Thr Phe Ser Ser Lys Phe
        435                 440                 445

Leu Gln Arg Lys Arg Ala Asn Asn Glu Leu Leu Asp Lys Trp Ile Ile
    450                 455                 460

Thr Lys Asp Leu Pro Gly Glu Val Gly Tyr Ala Leu Asp Val Pro Trp
465                 470                 475                 480

Tyr Ala Ser Leu Pro Arg Val Glu Thr Arg Phe Tyr Leu Glu Gln Tyr
                485                 490                 495

Gly Gly Glu Asp Asp Val Trp Ile Gly Lys Thr Leu Tyr Arg Met Pro
            500                 505                 510

Tyr Val Asn Asn Asn Lys Tyr Leu Glu Leu Ala Lys Leu Asp Tyr Ser
        515                 520                 525

Asn Cys Gln Ser Leu His Gln Gln Glu Trp Lys Asn Ile Gln Lys Trp
    530                 535                 540

Tyr Glu Ser Cys Asn Leu Gly Glu Phe Gly Leu Ser Glu Arg Arg Val
545                 550                 555                 560

Leu Leu Ala Tyr Tyr Val Ala Ala Ala Cys Ile Tyr Glu Pro Glu Lys
                565                 570                 575

Ser Asn Gln Arg Leu Ala Trp Ala Lys Thr Val Ile Leu Met Glu Thr
            580                 585                 590

Ile Thr Ser Tyr Phe Glu His Gln Gln Leu Ser Ala Glu Gln Arg Arg
        595                 600                 605

Ala Phe Val Asn Glu Phe Glu His Gly Ser Ile Leu Lys Tyr Ala Asn
    610                 615                 620

Gly Gly Arg Tyr Lys Arg Arg Ser Val Leu Gly Thr Leu Leu Lys Thr
625                 630                 635                 640

Leu Asn Gln Leu Ser Leu Asp Ile Leu Leu Thr His Gly Arg Asn Val
                645                 650                 655

His Gln Pro Phe Lys Asn Ala Trp His Lys Trp Leu Lys Thr Trp Glu
            660                 665                 670

Glu Gly Gly Asp Ile Glu Glu Gly Glu Ala Glu Val Leu Val Arg Thr
        675                 680                 685

Leu Asn Leu Ser Gly Glu Gly Arg His Asp Ser Tyr Val Leu Glu Gln
    690                 695                 700

Ser Leu Leu Ser Gln Pro Ile Tyr Glu Gln Leu Leu Lys Ala Thr Met
```

-continued 705 710 715 720

Ser Val Cys Lys Lys Leu Arg Leu Phe Gln His Arg Lys Asp Glu Asn
725 730 735

Gly Cys Met Thr Lys Met Arg Gly Ile Thr Thr Leu Glu Ile Glu Ser
740 745 750

Glu Met Gln Glu Leu Val Lys Leu Val Phe Thr Lys Ser Ser Asp Asp
755 760 765

Leu Asp Cys Glu Ile Lys Gln Asn Phe Phe Thr Ile Ala Arg Ser Phe
770 775 780

Tyr Tyr Val Ala Tyr Cys Asn Gln Gly Thr Ile Asn Phe His Ile Ala
785 790 795 800

Lys Val Leu Phe Glu Arg Val Leu
805

<210> SEQ ID NO 58
<211> LENGTH: 2427
<212> TYPE: DNA
<213> ORGANISM: Scutellaria baicalensis

<400> SEQUENCE: 58
atgcctttcc tcctcccttc ctccgccacc agctccccg cgttctatac tccggccgcg 60
cctctcgccg gtcatcatgt ttttccatct ttcaagccac tcattatttc ccgttcttca 120
ctccaatgca atgcaatctc tcgacctcgt acccaagaat acatagatgt gattcagaat 180
ggattgccag taataaagtg gcacgaagct gtggaagaag atgagacaga taaagattct 240
cttaataagg aggccacgtc agacaagata agagagttgg taaatctgat ccgttcgatg 300
ctccaatcaa tgggcgacgg agagataagc tcgtcgccgt acgacgccgc atgggtggcg 360
ctggtgccgg acgtcggcgg ctccggcggg ccccagttcc cctccagcct cgaatggata 420
tccaaaaacc aactccccga cggctcctgg ggcgacacgt gtaccttttc catttatgat 480
cgaatcatca acacactggc ttgcgttgtt gctttgaaat cttggaacat acatccccac 540
aaaacttatc aagggatttc attcataaag gcaaatatgg acaaacttga agacgagaac 600
gaggagcaca tgccgatcgg atttgaagtg gcactcccgt cgctaatcga gatagcgaaa 660
aggctcgata tcgatatttc cagcgattcg agagggctgc aagagatata cacgaggagg 720
gaggtaaagc tgaaaaggat accgaaagag ataatgcacc aagtgcccac aacactgctt 780
catagcttgg agggtatggc cgagctgacg tggcacaagc ttttgaaatt acagtgccaa 840
gatggctcct ttcttttctc tccatcttca actgcctttg ctcttcacca aactaaggac 900
cataattgtc tccattattt gaccaaatat gttcacaaat ttcatggtgg agtgccaaat 960
gtgtatccgg tggacttgtt cgagcatcta tgggcagttg atcggatcca acggctgggg 1020
atttcccggc atttcaagcc ccaagttgat gaatgtattg cctatgttta tagatattgg 1080
acagataaag gaatatgctg ggcaagaaat tcagtagttc aagatcttga tgacacagcc 1140
atgggattca ggcttcttag gttgcatggc tacgatgttt cagcagatgt tttcaaacat 1200
tttgaaaatg gtggagagtt cttctgcttc aaagggcaaa gcacgcaggc agtgactgga 1260
atgtacaatc tgtacagagc ttctcagttg atgtttcctg gagaaagcat actggaagat 1320
gctaagacct tctcatctaa gtttttgcaa cgaaaacgag ccaataacga gttgttagat 1380
aagtggatta ttaccaagga tcttcctgga gaggtgggat atgctctaga tgtaccatgg 1440
tatgctagct tacctagagt tgaaactaga ttctacttgg aacaatatgg tggtgaagat 1500
gatgtttgga ttggcaaaac tttatacagg atgccatatg ttaacaataa taaatatcta 1560

-continued

```
gaactggcaa aattagacta tagtaactgc cagtcattac atcaacaaga gtggaaaaac   1620

attcaaaaat ggtatgagag ttgcaatctg ggagaatttg gtttgagtga aagaagggtt   1680

ctactagcct actacgtagc tgctgcgtgt atatatgagc ccgaaaagtc aaaccagcgc   1740

ttggcttggg ccaaaaccgt aattttaatg gagactatta cttcctattt tgagcaccaa   1800

caactctccg cagaacagag acgcgccttt gttaatgaat ttgaacatgg gagtatcctc   1860

aaatatgcaa atggaggaag atacaaaagg aggagtgttt tggggacttt gctcaaaaca   1920

ctaaatcagc tttcattgga tatattattg acacacggtc gaaacgtcca tcagcctttc   1980

aaaaatgcgt ggcacaagtg gctaaaaacg tgggaagaag gaggtgacat tgaagaaggc   2040

gaagcagagg tattggtccg aaccctaaac ctaagcggcg aagggaggca cgactcctat   2100

gtattggagc aatcattatt gtcacaacct atatatgaac aacttttgaa agccaccatg   2160

agtgtttgca agaagcttcg attgttccaa catcgaaagg atgagaatgg atgtatgacg   2220

aagatgagag gcattacaac gttagagata gaatcggaga tgcaagaatt agtgaaatta   2280

gtatttacta aatcctcaga tgatttagat tgtgaaatta aacaaaactt ttttacaatt   2340

gctaggagtt tctattatgt ggcttattgt aaccaaggaa ctatcaactt tcacattgct   2400

aaggtgctct ttgaaagagt tctttag                                       2427


<210> SEQ ID NO 59
<211> LENGTH: 802
<212> TYPE: PRT
<213> ORGANISM: Scutellaria baicalensis

<400> SEQUENCE: 59

Met Ala Ser Leu Ser Thr Leu Ser Leu Asn Phe Ser Pro Ala Ile His
1               5                   10                  15

Arg Lys Ile Gln Gln Ser Ser Ala Lys Leu Gln Phe Gln Gly His Cys
            20                  25                  30

Phe Thr Ile Ser Ser Cys Met Asn Asn Ser Lys Arg Leu Ser Leu Asn
        35                  40                  45

His Gln Ser Asn His Lys Arg Thr Ser Asn Val Ser Glu Leu Gln Val
    50                  55                  60

Ala Thr Leu Asp Ala Pro Gln Ile Arg Glu Lys Glu Asp Tyr Ser Thr
65                  70                  75                  80

Ala Gln Gly Tyr Glu Lys Val Asp Glu Val Glu Asp Pro Ile Glu Tyr
                85                  90                  95

Ile Arg Met Leu Leu Asn Thr Thr Gly Asp Gly Arg Ile Ser Val Ser
            100                 105                 110

Pro Tyr Asp Thr Ala Trp Ile Ala Leu Ile Lys Asp Val Glu Gly Arg
        115                 120                 125

Asp Ala Pro Gln Phe Pro Ser Ser Leu Glu Trp Ile Ala Asn Asn Gln
    130                 135                 140

Leu Ser Asp Gly Ser Trp Gly Asp Glu Lys Phe Phe Cys Val Tyr Asp
145                 150                 155                 160

Arg Leu Val Asn Thr Leu Ala Cys Val Val Ala Leu Arg Ser Trp Asn
                165                 170                 175

Ile Asp Ala Glu Lys Ser Glu Lys Gly Ile Arg Tyr Ile Lys Glu Asn
            180                 185                 190

Val Asp Lys Leu Lys Asp Gly Asn Pro Glu His Met Thr Cys Gly Phe
        195                 200                 205

Glu Val Val Phe Pro Ser Leu Leu Gln Arg Ala Gln Ser Met Gly Ile
```

-continued

```
    210                 215                 220

His Asp Leu Pro Tyr Asp Ala Pro Val Ile Gln Asp Ile Tyr Asn Thr
225                 230                 235                 240

Arg Glu Ser Lys Leu Lys Arg Ile Pro Met Glu Val Met His Lys Val
                245                 250                 255

Pro Thr Ser Leu Leu Phe Ser Leu Glu Gly Leu Glu Asn Leu Glu Trp
            260                 265                 270

Asp Lys Leu Leu Lys Leu Gln Ser Ser Asp Gly Ser Phe Leu Thr Ser
        275                 280                 285

Pro Ser Ser Thr Ala Tyr Ala Phe Met His Thr Lys Asp Pro Lys Cys
    290                 295                 300

Phe Glu Phe Ile Lys Asn Thr Val Glu Thr Phe Asn Gly Gly Ala Pro
305                 310                 315                 320

His Thr Tyr Pro Val Asp Val Phe Gly Arg Leu Trp Ala Ile Asp Arg
                325                 330                 335

Leu Gln Arg Leu Gly Ile Ser Arg Phe Phe Glu Ser Glu Ile Ala Asp
            340                 345                 350

Cys Leu Asp His Ile Tyr Lys Tyr Trp Thr Asp Lys Gly Val Phe Ser
        355                 360                 365

Gly Arg Glu Ser Asp Phe Val Asp Val Asp Asp Thr Ser Met Gly Val
    370                 375                 380

Arg Leu Leu Arg Met His Gly Tyr Gln Val Asp Pro Asn Val Leu Arg
385                 390                 395                 400

Asn Phe Lys Gln Gly Asp Lys Phe Ser Cys Tyr Gly Gly Gln Met Ile
                405                 410                 415

Glu Ser Ser Ser Pro Ile Tyr Asn Leu Tyr Arg Ala Ser Gln Leu Arg
            420                 425                 430

Phe Pro Gly Glu Asp Ile Leu Glu Asp Ala Asn Lys Phe Ala Tyr Glu
        435                 440                 445

Phe Leu Gln Glu Gln Leu Ser Asn Asn Gln Leu Leu Asp Lys Trp Val
    450                 455                 460

Ile Ser Lys His Leu Pro Asp Glu Ile Lys Leu Gly Leu Gln Met Pro
465                 470                 475                 480

Trp Tyr Ala Thr Leu Pro Arg Val Glu Ala Lys Tyr Tyr Leu Gln Tyr
                485                 490                 495

Tyr Ala Gly Ala Asp Asp Val Trp Ile Gly Lys Thr Leu Tyr Arg Met
            500                 505                 510

Pro Glu Ile Ser Asn Asp Thr Tyr Leu Glu Leu Ala Arg Met Asp Phe
        515                 520                 525

Lys Arg Cys Gln Ala Gln His Gln Phe Glu Trp Ile Ser Met Gln Glu
    530                 535                 540

Trp Tyr Glu Ser Cys Asn Ile Glu Glu Phe Gly Ile Ser Arg Lys Glu
545                 550                 555                 560

Leu Leu Gln Ala Tyr Phe Leu Ala Cys Ser Ser Val Phe Glu Leu Glu
                565                 570                 575

Arg Thr Thr Glu Arg Ile Gly Trp Ala Lys Ser Gln Ile Ile Ser Arg
            580                 585                 590

Met Ile Ala Ser Phe Phe Asn Asn Glu Thr Thr Thr Ala Asp Glu Lys
        595                 600                 605

Asp Ala Leu Leu Thr Arg Phe Arg Asn Ile Asn Gly Pro Asn Lys Thr
    610                 615                 620

Lys Ser Gly Gln Arg Glu Ser Glu Ala Val Asn Met Leu Val Ala Thr
625                 630                 635                 640
```

```
Leu Gln Gln Tyr Leu Ala Gly Phe Asp Arg Tyr Thr Arg His Gln Leu
                645                 650                 655

Lys Asp Ala Trp Ser Val Trp Phe Arg Lys Val Gln Glu Glu Glu Ala
            660                 665                 670

Ile Tyr Gly Ala Glu Ala Glu Leu Leu Thr Thr Thr Leu Asn Ile Cys
        675                 680                 685

Ala Gly His Ile Ala Phe Asp Glu Asn Ile Met Ala Asn Lys Asp Tyr
    690                 695                 700

Thr Thr Leu Ser Ser Leu Thr Ser Lys Ile Cys Gln Lys Leu Ser Glu
705                 710                 715                 720

Ile Arg Asn Glu Lys Val Glu Glu Met Glu Ser Gly Ile Lys Ala Lys
                725                 730                 735

Ser Ser Ile Lys Asp Lys Glu Val Glu His Asp Met Gln Ser Leu Val
            740                 745                 750

Lys Leu Val Leu Glu Arg Cys Glu Gly Ile Asn Asn Arg Lys Leu Lys
        755                 760                 765

Gln Thr Phe Leu Ser Val Ala Lys Thr Tyr Tyr Tyr Arg Ala Tyr Asn
    770                 775                 780

Ala Asp Glu Thr Met Asp Ile His Met Phe Lys Val Leu Phe Glu Pro
785                 790                 795                 800

Val Met


<210> SEQ ID NO 60
<211> LENGTH: 2409
<212> TYPE: DNA
<213> ORGANISM: Scutellaria baicalensis

<400> SEQUENCE: 60

atggcctctc tatcaactct gagcctcaac ttttccccag caattcaccg caaaatacag      60

caatcatctg caaaacttca gttccaggga cattgtttca ccataagttc atgcatgaac     120

aacagtaaaa gactgtcttt gaaccaccaa tctaatcaca aaagaacgtc aaacgtatct     180

gagctgcaag ttgccacttt ggatgcgccc caaatacgtg aaaaagaaga ctactccact     240

gctcaaggct atgagaaggt ggatgaagta gaggatccta tcgaatatat tagaatgctg     300

ttgaacacaa caggtgatgg gcgaataagt gtgtcgccat acgacacagc ctggatcgct     360

cttattaaag acgtggaagg acgtgatgct ccccagttcc catctagtct cgaatggatt     420

gccaataatc aactgagtga tgggtcgtgg ggcgatgaga agtttttctg tgtgtatgat     480

cgccttgtta atacacttgc atgtgtcgtg gcattgagat catggaatat tgatgctgaa     540

aagagcgaga aaggaataag atacataaaa gaaaacgtgg ataaactgaa agatgggaat     600

ccagagcaca tgacctgtgg ttttgaggtg gtgtttcctt cccttcttca gagagcccaa     660

agtatgggaa ttcatgatct tccctatgat gctcctgtca tccaagacat ttacaatacc     720

agggagagta aattgaaaag gattccaatg gaggttatgc acaaggtgcc aacatctcta     780

ttgttcagct tggaaggatt ggagaatttg gagtgggata agctcctcaa acttcagtct     840

tctgatggtt cattcctcac ttctccatcc tcaactgcct atgctttcat gcacactaag     900

gaccctaaat gcttcgaatt catcaaaaac accgtcgaaa catttaatgg aggagcacct     960

catacttatc cggtggatgt ttttggaaga ctgtgggcca ttgacaggct gcagcgcctc    1020

ggaatctctc gcttctttga gtccgagatt gctgattgct tagatcacat ctataaatat    1080

tggacagaca aaggagtgtt cagtggaaga gaatcagatt ttgtggatgt ggatgacaca    1140
```

```
tccatgggtg ttaggcttct aaggatgcac ggatatcaag ttgatccaaa tgtattgagg   1200

aacttcaagc agggtgacaa attttcatgc tatggtggtc aaatgataga gtcatcatct   1260

ccgatataca atctctatag ggcttctcaa ctccgatttc caggagaaga cattcttgaa   1320

gatgccaaca aattcgcata cgagttcttg caagaacagc tatccaacaa tcaacttttg   1380

gacaaatggg ttatatccaa gcacttgcct gatgagataa agcttggatt gcagatgcca   1440

tggtatgcca ccctaccccg agtggaggct aaatactacc tacagtatta tgctggtgct   1500

gatgatgtct ggatcggcaa gactctctac agaatgccag aaatcagtaa tgatacatat   1560

ctggagttag caagaatgga tttcaagaga tgccaagcac agcatcaatt tgagtggatt   1620

tccatgcaag aatggtatga aagttgcaac attgaagaat ttgggataag cagaaaagag   1680

cttcttcagg cttacttttt ggcctgctca agtgtatttg aactcgagag gacaacagag   1740

agaataggat gggccaaatc ccaaattatt tcaaggatga tagcttcttt cttcaacaat   1800

gaaactacaa cagccgatga aaaagatgca cttttaacca gattcagaaa catcaatggc   1860

ccaaacaaaa caaaaagtgg tcagagagag agtgaagctg tgaacatgtt ggtagcaacg   1920

ctccaacaat acctggcagg atttgataga tataccagac atcaattgaa agatgcttgg   1980

agtgtgtggt tcagaaaagt gcaagaagaa gaggccatct acggggcaga agcggagctt   2040

ctaacaacca ccttaaacat ctgtgctggt catattgctt tcgacgaaaa cataatggcc   2100

aacaaagatt acaccactct ttccagcctt acaagcaaaa tttgccagaa gctttctgaa   2160

attcgaaatg aaaaggttga ggaaatggag agtggaatta aagcaaaatc aagcatcaaa   2220

gacaaggaag tggaacatga tatgcagtca ctggtgaaat tagtcctgga gagatgtgaa   2280

ggcataaaca acagaaaact gaagcaaaca tttctatcgg ttgcaaaaac atattactac   2340

agagcctata atgctgatga aaccatggac atccatatgt tcaaagtact tttcgaacca   2400

gtcatgtga                                                           2409
```

<210> SEQ ID NO 61
<211> LENGTH: 575
<212> TYPE: PRT
<213> ORGANISM: Salvia sclarea

<400> SEQUENCE: 61

```
Met Ser Leu Ala Phe Asn Val Gly Val Thr Pro Phe Ser Gly Gln Arg
1               5                   10                  15

Val Gly Ser Arg Lys Glu Lys Phe Pro Val Gln Gly Phe Pro Val Thr
            20                  25                  30

Thr Pro Asn Arg Ser Arg Leu Ile Val Asn Cys Ser Leu Thr Thr Ile
        35                  40                  45

Asp Phe Met Ala Lys Met Lys Glu Asn Phe Lys Arg Glu Asp Asp Lys
    50                  55                  60

Phe Pro Thr Thr Thr Thr Leu Arg Ser Glu Asp Ile Pro Ser Asn Leu
65                  70                  75                  80

Cys Ile Ile Asp Thr Leu Gln Arg Leu Gly Val Asp Gln Phe Phe Gln
                85                  90                  95

Tyr Glu Ile Asn Thr Ile Leu Asp Asn Thr Phe Arg Leu Trp Gln Glu
            100                 105                 110

Lys His Lys Val Ile Tyr Gly Asn Val Thr Thr His Ala Met Ala Phe
        115                 120                 125

Arg Leu Leu Arg Val Lys Gly Tyr Glu Val Ser Ser Glu Glu Leu Ala
    130                 135                 140
```

-continued

```
Pro Tyr Gly Asn Gln Glu Ala Val Ser Gln Gln Thr Asn Asp Leu Pro
145                 150                 155                 160

Met Ile Ile Glu Leu Tyr Arg Ala Ala Asn Glu Arg Ile Tyr Glu Glu
                165                 170                 175

Glu Arg Ser Leu Glu Lys Ile Leu Ala Trp Thr Thr Ile Phe Leu Asn
            180                 185                 190

Lys Gln Val Gln Asp Asn Ser Ile Pro Asp Lys Lys Leu His Lys Leu
        195                 200                 205

Val Glu Phe Tyr Leu Arg Asn Tyr Lys Gly Ile Thr Ile Arg Leu Gly
    210                 215                 220

Ala Arg Arg Asn Leu Glu Leu Tyr Asp Met Thr Tyr Tyr Gln Ala Leu
225                 230                 235                 240

Lys Ser Thr Asn Arg Phe Ser Asn Leu Cys Asn Glu Asp Phe Leu Val
                245                 250                 255

Phe Ala Lys Gln Asp Phe Asp Ile His Glu Ala Gln Asn Gln Lys Gly
            260                 265                 270

Leu Gln Gln Leu Gln Arg Trp Tyr Ala Asp Cys Arg Leu Asp Thr Leu
        275                 280                 285

Asn Phe Gly Arg Asp Val Val Ile Ile Ala Asn Tyr Leu Ala Ser Leu
    290                 295                 300

Ile Ile Gly Asp His Ala Phe Asp Tyr Val Arg Leu Ala Phe Ala Lys
305                 310                 315                 320

Thr Ser Val Leu Val Thr Ile Met Asp Asp Phe Phe Asp Cys His Gly
                325                 330                 335

Ser Ser Gln Glu Cys Asp Lys Ile Ile Glu Leu Val Lys Glu Trp Lys
            340                 345                 350

Glu Asn Pro Asp Ala Glu Tyr Gly Ser Glu Glu Leu Glu Ile Leu Phe
        355                 360                 365

Met Ala Leu Tyr Asn Thr Val Asn Glu Leu Ala Glu Arg Ala Arg Val
    370                 375                 380

Glu Gln Gly Arg Ser Val Lys Glu Phe Leu Val Lys Leu Trp Val Glu
385                 390                 395                 400

Ile Leu Ser Ala Phe Lys Ile Glu Leu Asp Thr Trp Ser Asn Gly Thr
                405                 410                 415

Gln Gln Ser Phe Asp Glu Tyr Ile Ser Ser Ser Trp Leu Ser Asn Gly
            420                 425                 430

Ser Arg Leu Thr Gly Leu Leu Thr Met Gln Phe Val Gly Val Lys Leu
        435                 440                 445

Ser Asp Glu Met Leu Met Ser Glu Glu Cys Thr Asp Leu Ala Arg His
    450                 455                 460

Val Cys Met Val Gly Arg Leu Leu Asn Asp Val Cys Ser Ser Glu Arg
465                 470                 475                 480

Glu Arg Glu Glu Asn Ile Ala Gly Lys Ser Tyr Ser Ile Leu Leu Ala
                485                 490                 495

Thr Glu Lys Asp Gly Arg Lys Val Ser Glu Asp Glu Ala Ile Ala Glu
            500                 505                 510

Ile Asn Glu Met Val Glu Tyr His Trp Arg Lys Val Leu Gln Ile Val
        515                 520                 525

Tyr Lys Lys Glu Ser Ile Leu Pro Arg Arg Cys Lys Asp Val Phe Leu
    530                 535                 540

Glu Met Ala Lys Gly Thr Phe Tyr Ala Tyr Gly Ile Asn Asp Glu Leu
545                 550                 555                 560

Thr Ser Pro Gln Gln Ser Lys Glu Asp Met Lys Ser Phe Val Phe
```

-continued 565 570 575

<210> SEQ ID NO 62
<211> LENGTH: 1728
<212> TYPE: DNA
<213> ORGANISM: Salvia sclarea

<400> SEQUENCE: 62
atgtcgctcg ccttcaacgt cggagttacg cctttctccg gccaaagagt tgggagcagg 60
aaagaaaaat ttccagtcca aggatttcct gtgaccaccc ccaataggtc acgtctcatc 120
gttaactgca gccttactac aatagatttc atggcgaaaa tgaaagagaa tttcaagagg 180
gaagacgata aatttccaac gacaacgact cttcgatccg aagatatacc ctctaatttg 240
tgtataatcg acacccttca aaggttgggg gtcgatcaat tcttccaata tgaaatcaac 300
actattctag ataacacatt caggttgtgg caagaaaaac acaaagttat atatggcaat 360
gttactactc atgcaatggc atttaggctt ttgcgagtga aaggatacga agtttcatca 420
gaggagttgg ctccatatgg taaccaagag gctgttagcc agcaaacaaa tgacctgccg 480
atgattattg agctttatag agcagcaaat gagagaatat atgaagaaga gaggagtctt 540
gaaaaaattc ttgcttggac taccatcttt ctcaataagc aagtgcaaga taactcaatt 600
cccgacaaaa aactgcacaa actggtggaa ttctacttga ggaattacaa aggcataacc 660
ataagattgg gagctagacg aaacctcgag ctatatgaca tgacctacta tcaagctctg 720
aaatctacaa acaggttctc taatttatgc aacgaagatt ttctagtttt cgcaaagcaa 780
gatttcgata tacatgaagc ccagaaccag aaaggacttc aacaactgca aaggtggtat 840
gcagattgta ggttggacac cttaaacttt ggaagagatg tagttattat tgctaattat 900
ttggcttcat taattattgg tgatcatgcg tttgactatg ttcgtctcgc atttgccaaa 960
acatctgtgc ttgtaacaat tatggatgat tttttcgact gtcatggctc tagtcaagag 1020
tgtgacaaga tcattgaatt agtaaaagaa tggaaggaga atccggatgc agagtacgga 1080
tctgaggagc ttgagatcct ttttatggcg ttgtacaata cagtaaatga gttggcggag 1140
agggctcgtg ttgaacaggg gcgtagtgtc aaagagtttc tagtcaaact gtgggttgaa 1200
atactctcag ctttcaagat agaattagat acatggagca atggcacgca gcaaagcttc 1260
gatgaataca tttcttcgtc gtggttgtcg aacggttccc ggctgacagg tctcctgacg 1320
atgcaattcg tcggagtaaa attgtccgat gaaatgctta tgagtgaaga gtgcactgat 1380
ttggctaggc atgtctgtat ggtcggccgg ctgctcaacg acgtgtgcag ttctgagagg 1440
gagcgcgagg aaaatattgc aggaaaaagt tatagcattc tactagcaac tgagaaagat 1500
ggaagaaaag ttagtgaaga tgaagccatt gcagagatca atgaaatggt tgaatatcac 1560
tggagaaaag tgttgcagat tgtgtataaa aaagaaagca ttttgccaag aagatgcaaa 1620
gatgtatttt tggagatggc taagggtacg ttttatgctt atgggatcaa cgatgaattg 1680
acttctcctc agcaatccaa ggaagatatg aaatcctttg tcttttga 1728

<210> SEQ ID NO 63
<211> LENGTH: 776
<212> TYPE: PRT
<213> ORGANISM: Marrubium vulgare

<400> SEQUENCE: 63

Met Ala Ser Thr Pro Thr Leu Asn Leu Ser Ile Thr Thr Pro Phe Val
1 5 10 15

-continued

```
Arg Thr Lys Ile Pro Ala Lys Ile Ser Leu Pro Ala Cys Ser Trp Leu
            20                  25                  30

Asp Arg Ser Ser Ser Arg His Val Glu Leu Asn His Lys Phe Cys Arg
        35                  40                  45

Lys Leu Glu Leu Lys Val Ala Met Cys Arg Ala Ser Leu Asp Val Gln
    50                  55                  60

Gln Val Arg Asp Glu Val Tyr Ser Asn Ala Gln Pro His Glu Leu Val
65                  70                  75                  80

Asp Lys Lys Ile Glu Glu Arg Val Lys Tyr Val Lys Asn Leu Leu Ser
                85                  90                  95

Thr Met Asp Asp Gly Arg Ile Asn Trp Ser Ala Tyr Asp Thr Ala Trp
            100                 105                 110

Ile Ser Leu Ile Lys Asp Phe Glu Gly Arg Asp Cys Pro Gln Phe Pro
        115                 120                 125

Ser Thr Leu Glu Arg Ile Ala Glu Asn Gln Leu Pro Asp Gly Ser Trp
    130                 135                 140

Gly Asp Lys Asp Phe Asp Cys Ser Tyr Asp Arg Ile Ile Asn Thr Leu
145                 150                 155                 160

Ala Cys Val Val Ala Leu Thr Thr Trp Asn Val His Pro Glu Ile Asn
                165                 170                 175

Gln Lys Gly Ile Arg Tyr Leu Lys Glu Asn Met Arg Lys Leu Glu Glu
            180                 185                 190

Thr Pro Thr Val Leu Met Thr Cys Ala Phe Glu Val Val Phe Pro Ala
        195                 200                 205

Leu Leu Lys Lys Ala Arg Asn Leu Gly Ile His Asp Leu Pro Tyr Asp
    210                 215                 220

Met Pro Ile Val Lys Glu Ile Cys Lys Ile Gly Asp Glu Lys Leu Ala
225                 230                 235                 240

Arg Ile Pro Lys Lys Met Met Glu Lys Glu Thr Thr Ser Leu Met Tyr
                245                 250                 255

Ala Ala Glu Gly Val Glu Asn Leu Asp Trp Glu Arg Leu Leu Lys Leu
            260                 265                 270

Arg Thr Pro Glu Asn Gly Ser Phe Leu Ser Ser Pro Ala Ala Thr Val
        275                 280                 285

Val Ala Phe Met His Thr Lys Asp Glu Asp Cys Leu Arg Tyr Ile Lys
    290                 295                 300

Tyr Leu Leu Asn Lys Phe Asn Gly Gly Ala Pro Asn Val Tyr Pro Val
305                 310                 315                 320

Asp Leu Trp Ser Arg Leu Trp Ala Thr Asp Arg Leu Gln Arg Leu Gly
                325                 330                 335

Ile Ser Arg Tyr Phe Glu Ser Glu Ile Lys Asp Leu Leu Ser Tyr Val
            340                 345                 350

His Ser Tyr Trp Thr Asp Ile Gly Val Tyr Cys Thr Arg Asp Ser Lys
        355                 360                 365

Tyr Ala Asp Ile Asp Asp Thr Ser Met Gly Phe Arg Leu Leu Arg Val
    370                 375                 380

Gln Gly Tyr Asn Met Asp Ala Asn Val Phe Lys Tyr Phe Gln Lys Asp
385                 390                 395                 400

Asp Lys Phe Val Cys Leu Gly Gly Gln Met Asn Gly Ser Ala Thr Ala
                405                 410                 415

Thr Tyr Asn Leu Tyr Arg Ala Ala Gln Tyr Gln Phe Pro Gly Glu Gln
            420                 425                 430

Ile Leu Glu Asp Ala Arg Lys Phe Ser Gln Gln Phe Leu Gln Glu Ser
```

```
        435                 440                 445

Ile Asp Thr Asn Asn Leu Leu Asp Lys Trp Val Ile Ser Pro His Ile
    450                 455                 460

Pro Glu Glu Met Arg Phe Gly Met Glu Met Thr Trp Tyr Ser Cys Leu
465                 470                 475                 480

Pro Arg Ile Glu Ala Ser Tyr Tyr Leu Gln His Tyr Gly Ala Thr Glu
                485                 490                 495

Asp Val Trp Leu Gly Lys Thr Phe Phe Arg Met Glu Glu Ile Ser Asn
            500                 505                 510

Glu Asn Tyr Arg Glu Leu Ala Ile Leu Asp Phe Ser Lys Cys Gln Ala
        515                 520                 525

Gln His Gln Thr Glu Trp Ile His Met Gln Glu Trp Tyr Glu Ser Asn
    530                 535                 540

Asn Val Lys Glu Phe Gly Ile Ser Arg Lys Asp Leu Leu Phe Ala Tyr
545                 550                 555                 560

Phe Leu Ala Ala Ala Ser Ile Phe Glu Thr Glu Arg Ala Lys Glu Arg
                565                 570                 575

Ile Leu Trp Ala Arg Ser Lys Ile Ile Cys Lys Met Val Lys Ser Phe
            580                 585                 590

Leu Glu Lys Glu Thr Gly Ser Leu Glu His Lys Ile Ala Phe Leu Thr
        595                 600                 605

Gly Ser Gly Asp Lys Gly Asn Gly Pro Val Asn Asn Ala Met Ala Thr
    610                 615                 620

Leu His Gln Leu Leu Gly Glu Phe Asp Gly Tyr Ile Ser Ile Gln Leu
625                 630                 635                 640

Glu Asn Ala Trp Ala Ala Trp Leu Thr Lys Leu Glu Gln Gly Glu Ala
                645                 650                 655

Asn Asp Gly Glu Leu Leu Ala Thr Thr Ile Asn Ile Cys Gly Gly Arg
            660                 665                 670

Val Asn Gln Asp Thr Leu Ser His Asn Glu Tyr Lys Ala Leu Ser Asp
        675                 680                 685

Leu Thr Asn Lys Ile Cys His Asn Leu Ala Gln Ile Gln Asn Asp Lys
    690                 695                 700

Gly Asp Glu Ile Lys Asp Ser Lys Arg Ser Glu Arg Asp Lys Glu Val
705                 710                 715                 720

Glu Gln Asp Met Gln Ala Leu Ala Lys Leu Val Phe Glu Glu Ser Asp
                725                 730                 735

Leu Glu Arg Ser Ile Lys Gln Thr Phe Leu Ala Val Val Arg Thr Tyr
            740                 745                 750

Tyr Tyr Gly Ala Tyr Ile Ala Ala Glu Lys Ile Asp Val His Met Phe
        755                 760                 765

Lys Val Leu Phe Lys Pro Val Gly
    770                 775
```

<210> SEQ ID NO 64
<211> LENGTH: 580
<212> TYPE: PRT
<213> ORGANISM: Marrubium vulgare

<400> SEQUENCE: 64

```
Met Ser Ile Thr Phe Asn Leu Lys Ile Ala Pro Phe Ser Gly Pro Gly
1               5                   10                  15

Ile Gln Arg Ser Lys Glu Thr Phe Pro Ala Thr Glu Ile Gln Ile Thr
            20                  25                  30
```

-continued

```
Ala Ser Thr Lys Ser Thr Met Thr Thr Lys Cys Ser Phe Asn Ala Ser
        35                  40                  45

Thr Asp Phe Met Gly Lys Leu Arg Glu Lys Val Gly Gly Lys Ala Asp
    50                  55                  60

Lys Pro Pro Val Val Ile His Pro Val Asp Ile Ser Ser Asn Leu Cys
65                  70                  75                  80

Met Ile Asp Thr Leu Gln Ser Leu Gly Val Asp Arg Tyr Phe Gln Ser
                85                  90                  95

Glu Ile Asn Thr Leu Leu Glu His Thr Tyr Arg Leu Trp Lys Glu Lys
            100                 105                 110

Lys Lys Asn Ile Ile Phe Lys Asp Val Ser Cys Cys Ala Ile Ala Phe
        115                 120                 125

Arg Leu Leu Arg Glu Lys Gly Tyr Gln Val Ser Ser Asp Lys Leu Ala
    130                 135                 140

Pro Phe Ala Asp Tyr Arg Ile Arg Asp Val Ala Thr Ile Leu Glu Leu
145                 150                 155                 160

Tyr Arg Ala Ser Gln Ala Arg Leu Tyr Glu Asp Glu His Thr Leu Glu
                165                 170                 175

Lys Leu His Asp Trp Ser Ser Asn Leu Leu Lys Gln His Leu Leu Asn
            180                 185                 190

Gly Ser Ile Pro Asp His Lys Leu His Lys Gln Val Glu Tyr Phe Leu
        195                 200                 205

Lys Asn Tyr His Gly Ile Leu Asp Arg Val Ala Val Arg Arg Ser Leu
    210                 215                 220

Asp Leu Tyr Asn Ile Asn His His His Arg Ile Pro Asp Val Ala Asp
225                 230                 235                 240

Gly Phe Pro Lys Glu Asp Phe Leu Glu Tyr Ser Met Gln Asp Phe Asn
                245                 250                 255

Ile Cys Gln Ala Gln Gln Gln Glu Glu Leu His Gln Leu Gln Arg Trp
            260                 265                 270

Tyr Ala Asp Cys Arg Leu Asp Thr Leu Asn Tyr Gly Arg Asp Val Val
        275                 280                 285

Arg Ile Ala Asn Phe Leu Thr Ser Ala Ile Phe Gly Glu Pro Glu Phe
    290                 295                 300

Ser Asp Ala Arg Leu Ala Phe Ala Lys His Ile Ile Leu Val Thr Arg
305                 310                 315                 320

Ile Asp Asp Phe Phe Asp His Gly Gly Ser Arg Glu Glu Ser Tyr Lys
                325                 330                 335

Ile Leu Asp Leu Val Gln Glu Trp Lys Glu Lys Pro Ala Glu Glu Tyr
            340                 345                 350

Gly Ser Lys Glu Val Glu Ile Leu Phe Thr Ala Val Tyr Asn Thr Val
        355                 360                 365

Asn Asp Leu Ala Glu Lys Ala His Ile Glu Gln Gly Arg Cys Val Lys
    370                 375                 380

Pro Leu Leu Ile Lys Leu Trp Val Glu Ile Leu Thr Ser Phe Lys Lys
385                 390                 395                 400

Glu Leu Asp Ser Trp Thr Glu Glu Thr Ala Leu Thr Leu Asp Glu Tyr
                405                 410                 415

Leu Ser Ser Ser Trp Val Ser Ile Gly Cys Arg Ile Cys Ile Leu Asn
            420                 425                 430

Ser Leu Gln Tyr Leu Gly Ile Lys Leu Ser Glu Glu Met Leu Ser Ser
        435                 440                 445

Gln Glu Cys Thr Asp Leu Cys Arg His Val Ser Ser Val Asp Arg Leu
```

```
    450                 455                 460

Leu Asn Asp Val Gln Thr Phe Lys Lys Glu Arg Leu Glu Asn Thr Ile
465                 470                 475                 480

Asn Ser Val Gly Leu Gln Leu Ala Ala His Lys Gly Glu Arg Ala Met
                485                 490                 495

Thr Glu Glu Asp Ala Met Ser Lys Ile Lys Glu Met Ala Asp Tyr His
            500                 505                 510

Arg Arg Lys Leu Met Gln Ile Val Tyr Lys Glu Gly Thr Val Phe Pro
        515                 520                 525

Arg Glu Cys Lys Asp Val Phe Leu Arg Val Cys Arg Ile Gly Tyr Tyr
    530                 535                 540

Leu Tyr Ser Ser Gly Asp Glu Phe Thr Ser Pro Gln Gln Met Lys Glu
545                 550                 555                 560

Asp Met Lys Ser Leu Val Tyr Gln Pro Val Lys Ile His Pro Leu Glu
                565                 570                 575

Ala Ile Asn Val
            580


<210> SEQ ID NO 65
<211> LENGTH: 311
<212> TYPE: PRT
<213> ORGANISM: Kitasatospora griseola

<400> SEQUENCE: 65

Met Pro Asp Ala Ile Glu Phe Glu His Glu Gly Arg Arg Asn Pro Asn
1               5                   10                  15

Ser Ala Glu Ala Glu Ser Ala Tyr Ser Ser Ile Ile Ala Ala Leu Asp
            20                  25                  30

Leu Gln Glu Ser Asp Tyr Ala Val Ile Ser Gly His Ser Arg Ile Val
        35                  40                  45

Gly Ala Ala Ala Leu Val Tyr Pro Asp Ala Asp Ala Glu Thr Leu Leu
    50                  55                  60

Ala Ala Ser Leu Trp Thr Ala Cys Leu Ile Val Asn Asp Asp Arg Trp
65                  70                  75                  80

Asp Tyr Val Gln Glu Asp Gly Gly Arg Leu Ala Pro Gly Glu Trp Phe
                85                  90                  95

Asp Gly Val Thr Glu Val Val Asp Thr Trp Arg Thr Ala Gly Pro Arg
            100                 105                 110

Leu Pro Asp Pro Phe Phe Glu Leu Val Arg Thr Thr Met Ser Arg Leu
        115                 120                 125

Asp Ala Ala Leu Gly Ala Glu Ala Ala Asp Glu Ile Gly His Glu Ile
    130                 135                 140

Lys Arg Ala Ile Thr Ala Met Lys Trp Glu Gly Val Trp Asn Glu Tyr
145                 150                 155                 160

Thr Lys Lys Thr Ser Leu Ala Thr Tyr Leu Ser Phe Arg Arg Gly Tyr
                165                 170                 175

Cys Thr Met Asp Val Gln Val Val Leu Asp Lys Trp Ile Asn Gly Gly
            180                 185                 190

Arg Ser Phe Ala Ala Leu Arg Asp Asp Pro Val Arg Arg Ala Ile Asp
        195                 200                 205

Asp Val Val Val Arg Phe Gly Cys Leu Ser Asn Asp Tyr Tyr Ser Trp
    210                 215                 220

Gly Arg Glu Lys Lys Ala Val Asp Lys Ser Asn Ala Val Arg Ile Leu
225                 230                 235                 240
```

Met Asp His Ala Gly Tyr Asp Glu Ser Thr Ala Leu Ala His Val Arg
245 250 255

Asp Asp Cys Val Gln Ala Ile Thr Asp Leu Asp Cys Ile Glu Glu Ser
260 265 270

Ile Lys Arg Ser Gly His Leu Gly Ser His Ala Gln Glu Leu Leu Asp
275 280 285

Tyr Leu Ala Cys His Arg Pro Leu Ile Tyr Ala Ala Ala Thr Trp Pro
290 295 300

Thr Glu Thr Asn Arg Tyr Arg
305 310

<210> SEQ ID NO 66
<211> LENGTH: 796
<212> TYPE: PRT
<213> ORGANISM: Origanum majorana

<400> SEQUENCE: 66

Met Thr Asp Val Ser Ser Leu Arg Leu Ser Asn Ala Pro Ala Ala Gly
1 5 10 15

Gly Arg Leu Pro Leu Pro Gly Lys Val His Leu Pro Glu Phe Arg Thr
20 25 30

Val Cys Ala Trp Leu Asn Asn Gly Cys Lys Tyr Glu Pro Leu Thr Cys
35 40 45

Arg Ile Ser Arg Arg Lys Ile Ser Glu Cys Arg Val Ala Ser Leu Asn
50 55 60

Ser Ser Gln Leu Ile Glu Lys Val Gly Ser Pro Ala Gln Ser Leu Glu
65 70 75 80

Glu Ala Asn Lys Lys Ile Glu Asp Ser Ile Glu Tyr Ile Lys Asn Leu
85 90 95

Leu Met Thr Ser Gly Asp Gly Arg Ile Ser Val Ser Ala Tyr Asp Thr
100 105 110

Ser Leu Val Ala Leu Ile Lys Asp Val Lys Gly Arg Asp Ala Pro Gln
115 120 125

Phe Pro Ser Cys Leu Glu Trp Ile Ala Gln Asn Gln Met Ala Asp Gly
130 135 140

Ser Trp Gly Asp Glu Phe Phe Cys Ile Tyr Asp Arg Ile Val Asn Thr
145 150 155 160

Leu Ala Cys Leu Val Ala Leu Lys Ser Trp Asn Leu His Pro Asp Lys
165 170 175

Ile Glu Lys Gly Val Thr Tyr Ile Asn Glu Asn Val His Lys Leu Lys
180 185 190

Asp Gly Ser Thr Glu His Met Thr Ser Gly Phe Glu Ile Val Val Pro
195 200 205

Ala Thr Leu Glu Arg Ala Lys Val Leu Gly Ile Gln Gly Leu Pro Tyr
210 215 220

Asp His Pro Phe Ile Lys Glu Ile Ile Asn Thr Lys Glu Arg Arg Leu
225 230 235 240

Ser Lys Ile Pro Lys Asp Leu Ile Tyr Lys Leu Pro Thr Thr Leu Leu
245 250 255

Phe Ser Leu Glu Gly Gln Gly Glu Leu Asp Trp Glu Lys Ile Leu Lys
260 265 270

Leu Gln Ser Ser Asp Gly Ser Phe Leu Thr Ser Pro Ser Ser Thr Ala
275 280 285

Ser Val Phe Met Arg Thr Lys Asp Glu Lys Cys Leu Lys Phe Ile Glu
290 295 300

```
Asn Ala Val Lys Asn Cys Gly Gly Gly Ala Pro His Thr Tyr Pro Val
305                 310                 315                 320

Asp Val Phe Ala Arg Leu Trp Ala Val Asp Arg Leu Gln Arg Leu Gly
                325                 330                 335

Ile Ser Arg Phe Phe Gln His Glu Ile Lys Tyr Phe Leu Asp His Ile
            340                 345                 350

Asn Ser Val Trp Thr Glu Asn Gly Val Phe Ser Gly Arg Asp Ser Gln
        355                 360                 365

Phe Cys Asp Ile Asp Asp Thr Ser Met Gly Val Arg Leu Leu Lys Met
    370                 375                 380

His Gly Tyr Asn Val Asp Pro Asn Ala Leu Lys His Phe Lys Gln Glu
385                 390                 395                 400

Asp Gly Lys Phe Ser Cys Tyr Pro Gly Gln Met Ile Glu Ser Ala Ser
                405                 410                 415

Pro Ile Tyr Asn Leu Tyr Arg Ala Ala Gln Leu Arg Phe Pro Gly Glu
            420                 425                 430

Glu Ile Leu Glu Glu Ala Ser Arg Phe Ala Phe Asn Phe Leu Gln Glu
        435                 440                 445

Lys Ile Ala Asn His Glu Ile Gln Glu Lys Trp Val Ile Ser Glu His
    450                 455                 460

Leu Ile Asp Glu Ile Lys Leu Gly Leu Lys Met Pro Trp Tyr Ala Thr
465                 470                 475                 480

Leu Pro Arg Val Glu Ala Ala Tyr Tyr Leu Glu Tyr Tyr Ala Gly Ser
                485                 490                 495

Gly Asp Val Trp Ile Gly Lys Thr Phe Tyr Arg Met Pro Glu Ile Ser
            500                 505                 510

Asn Asp Thr Tyr Lys Glu Val Ala Ile Leu Asp Phe Asn Thr Cys Gln
        515                 520                 525

Ala Gln His Gln Phe Glu Trp Ile Tyr Met Gln Glu Trp Tyr Glu Ser
    530                 535                 540

Ser Lys Val Lys Asp Phe Gly Ile Ser Lys Lys Asp Leu Leu Val Ala
545                 550                 555                 560

Tyr Phe Leu Ala Ala Ser Thr Ile Phe Glu Pro Glu Arg Thr Gln Glu
                565                 570                 575

Arg Ile Ile Trp Ala Lys Thr Leu Ile Leu Ser Arg Met Ile Thr Ser
            580                 585                 590

Phe Leu Asn Lys Gln Ala Thr Leu Ser Ser Gln Gln Lys Asn Ala Ile
        595                 600                 605

Leu Thr Gln Leu Gly Glu Ser Val Asp Gly Leu Asp Lys Ile Tyr Ser
    610                 615                 620

Gly Glu Lys Asp Ser Gly Leu Ala Glu Thr Leu Leu Ala Thr Phe Gln
625                 630                 635                 640

Gln Leu Leu Asp Gly Phe Asp Arg Tyr Thr Arg His Gln Leu Arg Asn
                645                 650                 655

Ala Trp Gly Gln Trp Leu Met Lys Val Gln Gln Gly Glu Ala Asn Gly
            660                 665                 670

Gly Ala Asp Ala Glu Leu Ile Ala Asn Thr Leu Asn Ile Cys Ala Gly
        675                 680                 685

Leu Ile Ala Phe Asn Glu Asp Val Leu Leu His Ser Glu Tyr Thr Thr
    690                 695                 700

Leu Ser Ser Leu Thr Asn Lys Ile Cys Gln Arg Leu Ser Gln Ile Glu
705                 710                 715                 720
```

-continued

```
Asp Glu Lys Thr Leu Glu Val Ile Glu Gly Gly Ile Lys Asp Lys Glu
                725                 730                 735

Leu Glu Glu Asp Ile Gln Ala Leu Val Lys Leu Ala Leu Glu Glu Asn
            740                 745                 750

Gly Gly Cys Gly Val Asp Arg Arg Ile Lys Gln Ser Phe Leu Ser Val
        755                 760                 765

Phe Lys Thr Phe Tyr Tyr Arg Ala Tyr His Asp Ala Glu Thr Thr Asp
    770                 775                 780

Leu His Ile Phe Lys Val Leu Phe Gly Pro Val Met
785                 790                 795


<210> SEQ ID NO 67
<211> LENGTH: 563
<212> TYPE: PRT
<213> ORGANISM: Origanum majorana

<400> SEQUENCE: 67

Met Ser Leu Ala Phe Ser His Val Ser Thr Phe Phe Ser Gly Gln Arg
1               5                   10                  15

Val Val Gly Ser Arg Arg Glu Ile Ile Pro Val Asn Gly Val Pro Thr
            20                  25                  30

Thr Ala Asn Lys Pro Ser Phe Ala Val Lys Cys Asn Leu Thr Thr Lys
        35                  40                  45

Asp Leu Met Val Lys Met Lys Glu Lys Leu Lys Gly Gln Asp Gly Asn
    50                  55                  60

Leu Thr Val Gly Val Ala Asp Met Pro Ser Ser Leu Cys Val Ile Asp
65                  70                  75                  80

Thr Leu Glu Arg Leu Gly Val Asp Arg Tyr Phe Arg Ser Glu Ile His
                85                  90                  95

Val Ile Leu His Asp Thr Tyr Arg Leu Trp Gln Gln Lys Asp Lys Asp
            100                 105                 110

Ile Cys Ser Asn Val Thr Thr His Ala Met Ala Phe Arg Leu Leu Arg
        115                 120                 125

Val Asn Gly Tyr Glu Val Ser Ser Glu Glu Leu Ala Pro Tyr Ala Asn
    130                 135                 140

Leu Glu His Phe Ser Gln Gln Lys Val Asp Thr Ala Met Ala Ile Glu
145                 150                 155                 160

Leu Tyr Arg Ala Ala Gln Glu Arg Ile His Glu Asp Glu Ser Gly Leu
                165                 170                 175

Asp Lys Ile Leu Ala Trp Thr Thr Thr Phe Leu Glu Gln Gln Leu Leu
            180                 185                 190

Thr Asn Ser Ile Leu Asp Asn Lys Leu His Lys Leu Val Glu Tyr Tyr
        195                 200                 205

Leu Asn Asn Tyr His Gly Gln Thr Asn Arg Val Gly Ala Arg Arg His
    210                 215                 220

Leu Asp Leu Tyr Glu Met Ser His Tyr Gln Asn Leu Lys Pro Ser His
225                 230                 235                 240

Ser Leu Cys Asn Glu Asp Leu Leu Ala Phe Ala Lys Gln Gly Phe Arg
                245                 250                 255

Asp Phe Gln Ile Gln Gln Gln Lys Glu Phe Glu Gln Leu Gln Arg Trp
            260                 265                 270

Tyr Glu Asp Cys Arg Leu Asp Lys Leu Ser Tyr Gly Arg Asp Val Val
        275                 280                 285

Lys Ile Ser Ser Phe Met Ala Ser Ile Leu Met Asp Asp Pro Glu Leu
    290                 295                 300
```

-continued

Ala Asp Val Arg Leu Ser Ile Ala Lys Gln Met Val Leu Val Thr Arg
305 310 315 320

Ile Asp Asp Phe Phe Asp His Gly Gly Ser Arg Glu Asp Ser Tyr Lys
325 330 335

Ile Ile Glu Leu Val Lys Glu Trp Lys Glu Lys Ala Glu Tyr Asp Ser
340 345 350

Glu Glu Val Lys Ile Leu Phe Thr Ala Val Tyr Thr Thr Val Asn Glu
355 360 365

Leu Ala Glu Ala Cys Val Gln Gln Gly Arg Asn Ser Thr Thr Val Lys
370 375 380

Glu Phe Leu Val Gln Leu Trp Ile Glu Ile Leu Ser Ala Phe Lys Val
385 390 395 400

Glu Leu Asp Thr Trp Ser Asp Gly Thr Glu Val Ser Leu Asp Glu Tyr
405 410 415

Leu Ser Trp Ser Trp Ile Ser Asn Gly Cys Arg Val Ser Ile Val Thr
420 425 430

Thr Met His Leu Leu Pro Thr Lys Leu Cys Ser Asp Glu Met Leu Arg
435 440 445

Ser Glu Glu Cys Lys Asp Leu Cys Arg His Val Ser Met Val Gly Arg
450 455 460

Leu Leu Asn Asp Ile His Ser Phe Glu Lys Glu His Glu Glu Asn Thr
465 470 475 480

Gly Asn Ser Val Ser Ile Leu Val Ala Gly Glu Asp Thr Glu Glu Glu
485 490 495

Ala Ile Gly Lys Ile Lys Glu Ile Val Glu Tyr Glu Arg Arg Lys Leu
500 505 510

Met Gln Ile Val Tyr Lys Arg Gly Thr Ile Leu Pro Arg Glu Cys Lys
515 520 525

Asp Ile Phe Leu Lys Ala Cys Arg Ala Thr Phe Tyr Val Tyr Ser Ser
530 535 540

Thr Asp Glu Phe Thr Ser Pro Arg Gln Val Met Glu Asp Met Lys Thr
545 550 555 560

Leu Ser Ser

<210> SEQ ID NO 68
<211> LENGTH: 497
<212> TYPE: PRT
<213> ORGANISM: Plectranthus barbatus

<400> SEQUENCE: 68

Met Glu Phe Asp Phe Pro Ser Ala Leu Ile Phe Pro Ala Val Ser Leu
1 5 10 15

Leu Leu Leu Leu Trp Leu Thr Lys Thr Arg Lys Pro Lys Ser Asp Leu
20 25 30

Asp Arg Ile Pro Gly Pro Arg Arg Leu Pro Leu Ile Gly Asn Leu His
35 40 45

His Leu Ile Ser Leu Thr Pro Pro Pro Arg Leu Phe Arg Glu Met Ala
50 55 60

Ala Lys Tyr Gly Pro Leu Met Arg Leu Gln Leu Gly Gly Val Pro Phe
65 70 75 80

Leu Ile Val Ser Ser Val Asp Val Ala Lys His Val Val Lys Thr Asn
85 90 95

Asp Val Pro Phe Ala Asn Arg Pro Pro Met His Ala Ala Arg Ala Ile
100 105 110

Thr Tyr Asn Tyr Thr Asp Ile Gly Phe Ala Pro Tyr Gly Glu Tyr Trp
115 120 125

Arg Asn Leu Arg Lys Ile Cys Thr Leu Glu Leu Leu Ser Ala Arg Arg
130 135 140

Val Arg Ser Phe Arg His Ile Arg Glu Glu Glu Asn Ala Gly Val Ala
145 150 155 160

Lys Trp Ile Ala Ser Lys Glu Gly Ser Pro Ala Asn Leu Ser Glu Arg
165 170 175

Val Tyr Leu Ser Ser Phe Asp Ile Thr Ser Arg Ala Ser Ile Gly Lys
180 185 190

Ala Thr Glu Glu Lys Gln Thr Leu Thr Ser Ser Ile Lys Asp Ala Met
195 200 205

Lys Leu Gly Gly Phe Asn Val Ala Asp Leu Tyr Pro Ser Ser Lys Leu
210 215 220

Leu Leu Leu Ile Thr Gly Leu Asn Phe Arg Ile Gln Arg Val Phe Arg
225 230 235 240

Lys Thr Asp Arg Ile Leu Asp Asp Leu Leu Ser Gln His Arg Ser Thr
245 250 255

Ser Ala Thr Thr Glu Arg Pro Glu Asp Leu Val Asp Val Leu Leu Lys
260 265 270

Tyr Gln Lys Glu Glu Thr Glu Val His Leu Asn Asn Asp Lys Ile Lys
275 280 285

Ala Val Ile Met Asp Met Phe Leu Ala Gly Gly Glu Thr Ser Ala Thr
290 295 300

Ala Val Asp Trp Ala Met Ala Glu Met Ile Arg Asn Pro Thr Thr Leu
305 310 315 320

Lys Lys Ala Gln Glu Glu Val Arg Arg Val Phe Asp Gly Lys Gly Tyr
325 330 335

Val Asp Glu Glu Glu Phe His Glu Leu Lys Tyr Leu Lys Leu Val Ile
340 345 350

Lys Glu Met Leu Arg Met His Pro Pro Leu Pro Phe Leu Val Pro Arg
355 360 365

Met Asn Ser Glu Arg Cys Glu Ile Asn Gly Tyr Glu Ile Pro Ala Asn
370 375 380

Thr Arg Leu Leu Ile Asn Ala Trp Ala Ile Gly Arg Asp Pro Lys Tyr
385 390 395 400

Trp Asn Asp Ala Glu Lys Phe Ile Pro Glu Arg Phe Glu Asn Ser Ser
405 410 415

Ile Asp Phe Lys Gly Asn Asn Leu Glu Tyr Ile Pro Phe Gly Ala Gly
420 425 430

Arg Arg Met Cys Pro Gly Met Thr Phe Gly Leu Ala Ser Val Glu Phe
435 440 445

Thr Leu Ala Met Leu Leu Tyr His Phe Asp Trp Lys Met Pro Gln Gly
450 455 460

Ile Lys Leu Asp Met Thr Glu Ser Phe Gly Ala Ser Leu Lys Arg Lys
465 470 475 480

His Asp Leu Leu Met Ile Pro Thr Leu Lys Arg Pro Leu Arg Leu Ala
485 490 495

Pro

<210> SEQ ID NO 69
<211> LENGTH: 773
<212> TYPE: PRT

<213> ORGANISM: Coleus forskohlii

<400> SEQUENCE: 69

Met Lys Met Leu Met Ile Lys Ser Gln Phe Arg Val His Ser Ile Val
1               5                   10                  15

Ser Ala Trp Ala Asn Asn Ser Asn Lys Arg Gln Ser Leu Gly His Gln
            20                  25                  30

Ile Arg Arg Lys Gln Arg Ser Gln Val Thr Glu Cys Arg Val Ala Ser
        35                  40                  45

Leu Asp Ala Leu Asn Gly Ile Gln Lys Val Gly Pro Ala Thr Ile Gly
    50                  55                  60

Thr Pro Glu Glu Glu Asn Lys Lys Ile Glu Asp Ser Ile Glu Tyr Val
65                  70                  75                  80

Lys Glu Leu Leu Lys Thr Met Gly Asp Gly Arg Ile Ser Val Ser Pro
                85                  90                  95

Tyr Asp Thr Ala Ile Val Ala Leu Ile Lys Asp Leu Glu Gly Gly Asp
            100                 105                 110

Gly Pro Glu Phe Pro Ser Cys Leu Glu Trp Ile Ala Gln Asn Gln Leu
        115                 120                 125

Ala Asp Gly Ser Trp Gly Asp His Phe Phe Cys Ile Tyr Asp Arg Val
    130                 135                 140

Val Asn Thr Ala Ala Cys Val Val Ala Leu Lys Ser Trp Asn Val His
145                 150                 155                 160

Ala Asp Lys Ile Glu Lys Gly Ala Val Tyr Leu Lys Glu Asn Val His
                165                 170                 175

Lys Leu Lys Asp Gly Lys Ile Glu His Met Pro Ala Gly Phe Glu Phe
            180                 185                 190

Val Val Pro Ala Thr Leu Glu Arg Ala Lys Ala Leu Gly Ile Lys Gly
        195                 200                 205

Leu Pro Tyr Asp Asp Pro Phe Ile Arg Glu Ile Tyr Ser Ala Lys Gln
    210                 215                 220

Thr Arg Leu Thr Lys Ile Pro Lys Gly Met Ile Tyr Glu Ser Pro Thr
225                 230                 235                 240

Ser Leu Leu Tyr Ser Leu Asp Gly Leu Glu Gly Leu Glu Trp Asp Lys
                245                 250                 255

Ile Leu Lys Leu Gln Ser Ala Asp Gly Ser Phe Ile Thr Ser Val Ser
            260                 265                 270

Ser Thr Ala Phe Val Phe Met His Thr Asn Asp Leu Lys Cys His Ala
        275                 280                 285

Phe Ile Lys Asn Ala Leu Thr Asn Cys Asn Gly Gly Val Pro His Thr
    290                 295                 300

Tyr Pro Val Asp Ile Phe Ala Arg Leu Trp Ala Val Asp Arg Leu Gln
305                 310                 315                 320

Arg Leu Gly Ile Ser Arg Phe Phe Glu Pro Glu Ile Lys Tyr Leu Met
                325                 330                 335

Asp His Ile Asn Asn Val Trp Arg Glu Lys Gly Val Phe Ser Ser Arg
            340                 345                 350

His Ser Gln Phe Ala Asp Ile Asp Asp Thr Ser Met Gly Ile Arg Leu
        355                 360                 365

Leu Lys Met His Gly Tyr Asn Val Asn Pro Asn Ala Leu Glu His Phe
    370                 375                 380

Lys Gln Lys Asp Gly Lys Phe Thr Cys Tyr Ala Asp Gln His Ile Glu
385                 390                 395                 400

-continued

```
Ser Pro Ser Pro Met Tyr Asn Leu Tyr Arg Ala Ala Gln Leu Arg Phe
                405                 410                 415

Pro Gly Glu Glu Ile Leu Gln Gln Ala Leu Gln Phe Ala Tyr Asn Phe
            420                 425                 430

Leu His Glu Asn Leu Ala Ser Asn His Phe Gln Glu Lys Trp Val Ile
        435                 440                 445

Ser Asp His Leu Ile Asp Glu Val Arg Ile Gly Leu Lys Met Pro Trp
    450                 455                 460

Tyr Ala Thr Leu Pro Arg Val Glu Ala Ser Tyr Tyr Leu Gln His Tyr
465                 470                 475                 480

Gly Gly Ser Ser Asp Val Trp Ile Gly Lys Thr Leu Tyr Arg Met Pro
                485                 490                 495

Glu Ile Ser Asn Asp Thr Tyr Lys Ile Leu Ala Gln Leu Asp Phe Asn
            500                 505                 510

Lys Cys Gln Ala Gln His Gln Leu Glu Trp Met Ser Met Lys Glu Trp
        515                 520                 525

Tyr Gln Ser Asn Asn Val Lys Glu Phe Gly Ile Ser Lys Lys Glu Leu
    530                 535                 540

Leu Leu Ala Tyr Phe Leu Ala Ala Ala Thr Met Phe Glu Pro Glu Arg
545                 550                 555                 560

Thr Gln Glu Arg Ile Met Trp Ala Lys Thr Gln Val Val Ser Arg Met
                565                 570                 575

Ile Thr Ser Phe Leu Asn Lys Glu Asn Thr Met Ser Phe Asp Leu Lys
            580                 585                 590

Ile Ala Leu Leu Thr Gln Pro Gln His Gln Ile Asn Gly Ser Glu Met
        595                 600                 605

Lys Asn Gly Leu Ala Gln Thr Leu Pro Ala Ala Phe Arg Gln Leu Leu
    610                 615                 620

Lys Glu Phe Asp Lys Tyr Thr Arg His Gln Leu Arg Asn Thr Trp Asn
625                 630                 635                 640

Lys Trp Leu Met Lys Leu Lys Gln Gly Asp Asp Asn Gly Gly Ala Asp
                645                 650                 655

Ala Glu Leu Leu Ala Asn Thr Leu Asn Ile Cys Ala Gly His Asn Glu
            660                 665                 670

Asp Ile Leu Ser His Tyr Glu Tyr Thr Ala Leu Ser Ser Leu Thr Asn
        675                 680                 685

Lys Ile Cys Gln Arg Leu Ser Gln Ile Gln Asp Lys Lys Met Leu Glu
    690                 695                 700

Ile Glu Glu Gly Ser Ile Lys Asp Lys Glu Met Glu Leu Glu Ile Gln
705                 710                 715                 720

Thr Leu Val Lys Leu Val Leu Gln Glu Thr Ser Gly Gly Ile Asp Arg
                725                 730                 735

Asn Ile Lys Gln Thr Phe Leu Ser Val Phe Lys Thr Phe Tyr Tyr Arg
            740                 745                 750

Ala Tyr His Asp Ala Lys Thr Ile Asp Ala His Ile Phe Gln Val Leu
        755                 760                 765

Phe Glu Pro Val Val
    770
```

<210> SEQ ID NO 70
<211> LENGTH: 500
<212> TYPE: PRT
<213> ORGANISM: Euphorbia lathyris

<400> SEQUENCE: 70

```
Met Asp Leu Gln Leu Gln Ile Pro Ser Tyr Pro Ile Ile Phe Ser Phe
1               5                   10                  15

Phe Ile Phe Ile Phe Met Leu Ile Lys Ile Trp Lys Lys Gln Thr Gln
            20                  25                  30

Thr Ser Ile Phe Pro Pro Gly Pro Phe Lys Phe Pro Ile Val Gly Asn
        35                  40                  45

Ile Pro Gln Leu Ala Thr Gly Gly Thr Leu Pro His His Arg Leu Arg
    50                  55                  60

Asp Leu Ala Lys Ile Tyr Gly Pro Ile Met Thr Ile Gln Leu Gly Gln
65                  70                  75                  80

Val Lys Ser Val Val Ile Ser Ser Pro Glu Thr Ala Lys Glu Val Leu
                85                  90                  95

Lys Thr Gln Asp Ile Gln Phe Ala Asp Arg Pro Leu Leu Leu Ala Gly
            100                 105                 110

Glu Met Val Leu Tyr Asn Arg Lys Asp Ile Leu Tyr Gly Thr Tyr Gly
        115                 120                 125

Asp Gln Trp Arg Gln Met Arg Lys Ile Cys Thr Leu Glu Leu Leu Ser
    130                 135                 140

Ala Lys Arg Ile Gln Ser Phe Lys Ser Val Arg Glu Lys Glu Val Glu
145                 150                 155                 160

Ser Phe Ile Lys Thr Leu Arg Ser Lys Ser Gly Ile Pro Val Asn Leu
                165                 170                 175

Thr Asn Ala Val Phe Glu Leu Thr Asn Thr Ile Met Met Ile Thr Thr
            180                 185                 190

Ile Gly Gln Lys Cys Lys Asn Gln Glu Ala Val Met Ser Val Ile Asp
        195                 200                 205

Arg Val Ser Glu Ala Ala Ala Gly Phe Ser Val Ala Asp Val Phe Pro
    210                 215                 220

Ser Leu Lys Phe Leu His Tyr Leu Ser Gly Glu Lys Thr Lys Leu Gln
225                 230                 235                 240

Lys Leu His Lys Glu Thr Asp Gln Ile Leu Glu Glu Ile Ile Ser Glu
                245                 250                 255

His Lys Ala Asn Ala Lys Val Gly Ala Gln Ala Asp Asn Leu Leu Asp
            260                 265                 270

Val Leu Leu Asp Leu Gln Lys Asn Gly Asn Leu Gln Val Pro Leu Thr
        275                 280                 285

Asn Asp Asn Ile Lys Ala Ala Thr Leu Glu Met Phe Gly Ala Gly Ser
    290                 295                 300

Asp Thr Ser Ser Lys Thr Thr Asp Trp Ala Met Ala Gln Met Met Arg
305                 310                 315                 320

Lys Pro Thr Thr Met Lys Lys Ala Gln Glu Glu Val Arg Arg Val Phe
                325                 330                 335

Gly Glu Asn Gly Lys Val Glu Glu Ser Arg Ile Gln Glu Leu Lys Tyr
            340                 345                 350

Leu Lys Leu Val Val Lys Glu Thr Leu Arg Leu His Pro Ala Val Ala
        355                 360                 365

Leu Ile Pro Arg Glu Cys Arg Glu Lys Thr Lys Ile Asp Gly Phe Asp
    370                 375                 380

Ile Tyr Pro Lys Thr Lys Ile Leu Val Asn Pro Trp Ala Ile Gly Arg
385                 390                 395                 400

Asp Pro Lys Val Trp Asn Glu Pro Glu Ser Phe Asn Pro Glu Arg Phe
                405                 410                 415
```

-continued

```
Gln Asp Ser Pro Ile Asp Tyr Lys Gly Thr Asn Phe Glu Leu Ile Pro
            420                 425                 430

Phe Gly Ala Gly Lys Arg Ile Cys Pro Gly Met Thr Leu Gly Ile Thr
        435                 440                 445

Asn Leu Glu Leu Phe Leu Ala Asn Leu Leu Tyr His Phe Asp Trp Lys
    450                 455                 460

Phe Pro Asp Gly Ile Thr Ser Glu Asn Leu Asp Met Thr Glu Ala Ile
465                 470                 475                 480

Gly Gly Ala Ile Lys Arg Lys Leu Asp Leu Glu Leu Ile Ser Ile Pro
                485                 490                 495

Tyr Thr Ser Ser
            500
```

<210> SEQ ID NO 71
<211> LENGTH: 513
<212> TYPE: PRT
<213> ORGANISM: Euphorbia lathyris

<400> SEQUENCE: 71

```
Met Glu Leu Glu Phe Arg Ser Pro Ser Ser Pro Ser Glu Trp Ala Ile
1               5                   10                  15

Thr Ser Thr Ile Thr Leu Leu Phe Leu Ile Leu Leu Arg Lys Ile Leu
            20                  25                  30

Lys Pro Lys Thr Pro Thr Pro Asn Leu Pro Pro Gly Pro Lys Lys Leu
        35                  40                  45

Pro Leu Ile Gly Asn Ile His Gln Leu Ile Gly Gly Ile Pro His Gln
    50                  55                  60

Lys Met Arg Asp Leu Ser Gln Ile His Gly Pro Ile Met His Leu Lys
65                  70                  75                  80

Leu Gly Glu Leu Glu Asn Val Ile Ile Ser Ser Lys Glu Ala Ala Glu
                85                  90                  95

Lys Ile Leu Lys Thr His Asp Val Leu Phe Ala Gln Arg Pro Gln Met
            100                 105                 110

Ile Val Ala Lys Ser Val Thr Tyr Asp Phe His Asp Ile Thr Phe Ser
        115                 120                 125

Pro Tyr Gly Asp Tyr Trp Arg Gln Leu Arg Lys Ile Thr Met Ile Glu
    130                 135                 140

Leu Leu Ala Ala Lys Arg Val Leu Ser Phe Arg Ala Ile Arg Glu Glu
145                 150                 155                 160

Glu Thr Thr Lys Leu Val Glu Leu Ile Arg Gly Phe Gln Ser Gly Glu
                165                 170                 175

Ser Ile Asn Phe Thr Arg Met Ile Asp Ser Thr Thr Tyr Gly Ile Thr
            180                 185                 190

Ser Arg Ala Ala Cys Gly Lys Ile Trp Glu Gly Glu Asn Leu Phe Ile
        195                 200                 205

Ser Ser Leu Glu Lys Ile Met Phe Glu Val Gly Ser Gly Ile Ser Phe
    210                 215                 220

Ala Asp Ala Tyr Pro Ser Val Lys Leu Leu Lys Val Phe Ser Gly Ile
225                 230                 235                 240

Arg Ile Arg Val Asp Arg Leu Gln Lys Asn Ile Asp Lys Ile Phe Glu
                245                 250                 255

Ser Ile Ile Glu Glu His Arg Glu Glu Arg Lys Gly Arg Lys Lys Gly
            260                 265                 270

Glu Asp Asp Leu Asp Leu Val Asp Val Leu Leu Asn Leu Gln Glu Ser
        275                 280                 285
```

-continued

```
Gly Thr Leu Glu Ile Pro Leu Ser Asp Val Thr Ile Lys Ala Val Ile
    290                 295                 300

Met Asp Met Phe Val Ala Gly Val Asp Thr Ser Ala Ala Thr Thr Glu
305                 310                 315                 320

Trp Leu Met Ser Glu Leu Ile Lys Asn Pro Glu Val Met Lys Lys Ala
                325                 330                 335

Gln Ala Glu Ile Arg Glu Lys Phe Lys Gly Lys Ala Ser Ile Asp Glu
            340                 345                 350

Ala Asp Leu Gln Asp Leu His Tyr Leu Lys Leu Val Ile Lys Glu Thr
        355                 360                 365

Phe Arg Leu His Pro Ser Val Pro Leu Leu Val Pro Arg Glu Cys Arg
    370                 375                 380

Glu Ser Cys Val Ile Glu Gly Tyr Asp Ile Pro Val Lys Thr Lys Ile
385                 390                 395                 400

Met Val Asn Ala Trp Ala Met Gly Arg Asp Thr Lys Tyr Trp Gly Glu
                405                 410                 415

Asp Ala Glu Lys Phe Lys Pro Glu Arg Phe Ile Asp Ser Pro Ile Asp
            420                 425                 430

Phe Lys Gly His Asn Phe Glu Tyr Leu Pro Phe Gly Ser Gly Arg Arg
        435                 440                 445

Ser Cys Pro Gly Met Ala Phe Gly Val Ala Asn Val Glu Ile Ala Val
    450                 455                 460

Ala Lys Leu Leu Tyr His Phe Asp Trp Arg Leu Gly Asp Gly Met Val
465                 470                 475                 480

Pro Glu Asn Leu Asp Met Thr Glu Lys Ile Gly Gly Thr Thr Arg Arg
                485                 490                 495

Leu Ser Glu Leu Tyr Ile Ile Pro Thr Pro Tyr Val Pro Gln Asn Ser
            500                 505                 510

Ala
```

BIOSYNTHESIS OF CHEMICALLY DIVERSIFIED NON-NATURAL TERPENE PRODUCTS

CROSS-REFERENCE TO RELATED APPLICATIONS

This application is U.S. National Stage Filing under 35 U.S.C. 371 of International Patent Application No. PCT/US2020/059144, filed Nov. 5, 2020, and published WO 2021/092200 A1 on May 14, 2021, which claims the benefit of U.S. Provisional Patent Appl. Ser. No. 62/930,898, filed Nov. 5, 2019, which is incorporated by reference as if fully set forth herein.

Incorporation by Reference of Sequence Listing Provided as a Text File A Sequence Listing is provided herewith as a text file, "2089186.txt" created on Nov. 5, 2020 and having a size of 303,104 bytes. The contents of the text file are incorporated by reference herein in their entirety.

BACKGROUND

Plant diterpenes occupy a unique molecular space with critical pharmaceutical applications over a diverse spectrum including anti-cancer, anti-microbial and immunomodulatory properties. In addition, plant-derived terpenoids have a wide range of commercial and industrial uses. Examples of uses for terpenoids include specialty fuels, agrochemicals, fragrances, nutraceuticals and pharmaceuticals. However, currently available methods for synthesis, extraction, and purification of terpenoids from the native plant sources have limited economic sustainability. Moreover, currently available methods for do not provide the substrates and methods for biosynthesis of non-natural terpenoids.

The enzymes of terpene synthesis pathways are evolutionarily optimized to deliver bioactive molecules, novel molecular scaffolds and chemistry. Yet, cost-effective synthesis and access to analogs of plant diterpenoids and their derivatives is technologically limited on the levels of isolation, purification, detection and synthesis.

SUMMARY

While the terpene biosynthetic enzymes catalyze some of nature's most complex chemistries, the natural entry into terpenoid pathways is limited to a single precursor, geranylgeranyl diphosphate (GGPP). And although GGPP is a compound having all-trans double bonds, it has been recently shown that the cis-prenyl is also relevant in other plant species. See, e.g., https://doi.org/10.1111/tpj.14957. However, as described herein a variety of non-natural substrates can be used by terpene biosynthetic enzymes to produce structurally diverse unnatural diterpene analogs and unnatural terpene key intermediates for further functionalization. Products formed using the non-natural substrates and methods described herein are bioactive and compared to related natural compounds they have modulated specificity against their molecular targets.

For example, methods are described herein that include contacting an unnatural substrate with one or more enzymes that can synthesize a terpene to generate a primary terpene product.

DESCRIPTION OF THE FIGURES

FIG. 1A illustrates building and screening unnatural substrates for cyclization into unnatural decalin-core and irregular scaffolds. FIG. 1B illustrates combinatorial biosynthesis of unnatural decalin-core scaffolds. FIG. 1C illustrates bioprocessing of unnatural forskolin and jolkinol c compounds. The decalin-core representative, forskolin, and an irregular jolkinol C structure are shown. Enzyme families are delineated by dashed lines.

FIG. 5A illustrates the retention time of the product formed by casbene synthase with geranylgeranyl diphosphate (GGPP) as substrate, as detected by gas chromatography. FIG. 5B illustrates the retention time of the product formed by casbene synthase with an unnatural methyl derivative of geranylgeranyl diphosphate (unGGPP) as substrate, as detected by gas chromatography. FIG. 5C illustrates the mass (m/z) of fragments of the product formed by casbene synthase with geranylgeranyl diphosphate (GGPP) as substrate, as detected by GC-MS. FIG. 5D illustrates the mass (m/z) of fragments of the product formed by casbene synthase with unnatural methyl derivative of geranylgeranyl diphosphate (unGGPP) as substrate, as detected by GC-MS.

FIG. 6A shows structures of unnatural variants of GGPP (unGGPP) and lists their names. Three classes of chemistries are represented by different hatching overlays for the different unGGPP substrates. FIG. 6B shows which of fifteen heterologously expressed diTPS produce novel unnatural product analogs (indicated by cross-hatched circle), where the type of cross-hatching overlay corresponds to the substrate types listed in FIG. 6B. GC-MS analyses from in vitro assays were used to analyze which of the fifteen diTPS enzymes generate novel unnatural product analogs generated. Top nine rows were labdane-type class II diTPS assayed with *Salvia sclarea* sclareol synthase, SsSCS. Lower six rows were class I irregular diTPS that were analyzed directly (without SsSCS).

FIG. 9A shows that P450 enzymes from Salvia and Rosemary oxidize the non-native heteroatom-containing manoyl oxide as detected by GC/MS analysis of 13R-manoyl oxide and miltiradiene derived diterpenoids. FIG. 9B shows diterpene structures. FIG. 9C illustrates that CYP76AH15 from *Coleus* quantitatively converts the non-native miltiradiene to ferruginol. Ro, *Rosmarinus officinalis*; Sf, *Salvia fruticosa*; Cf, *Coleus forskohlii.*

DETAILED DESCRIPTION

Figures 1A, 1B, 1C:
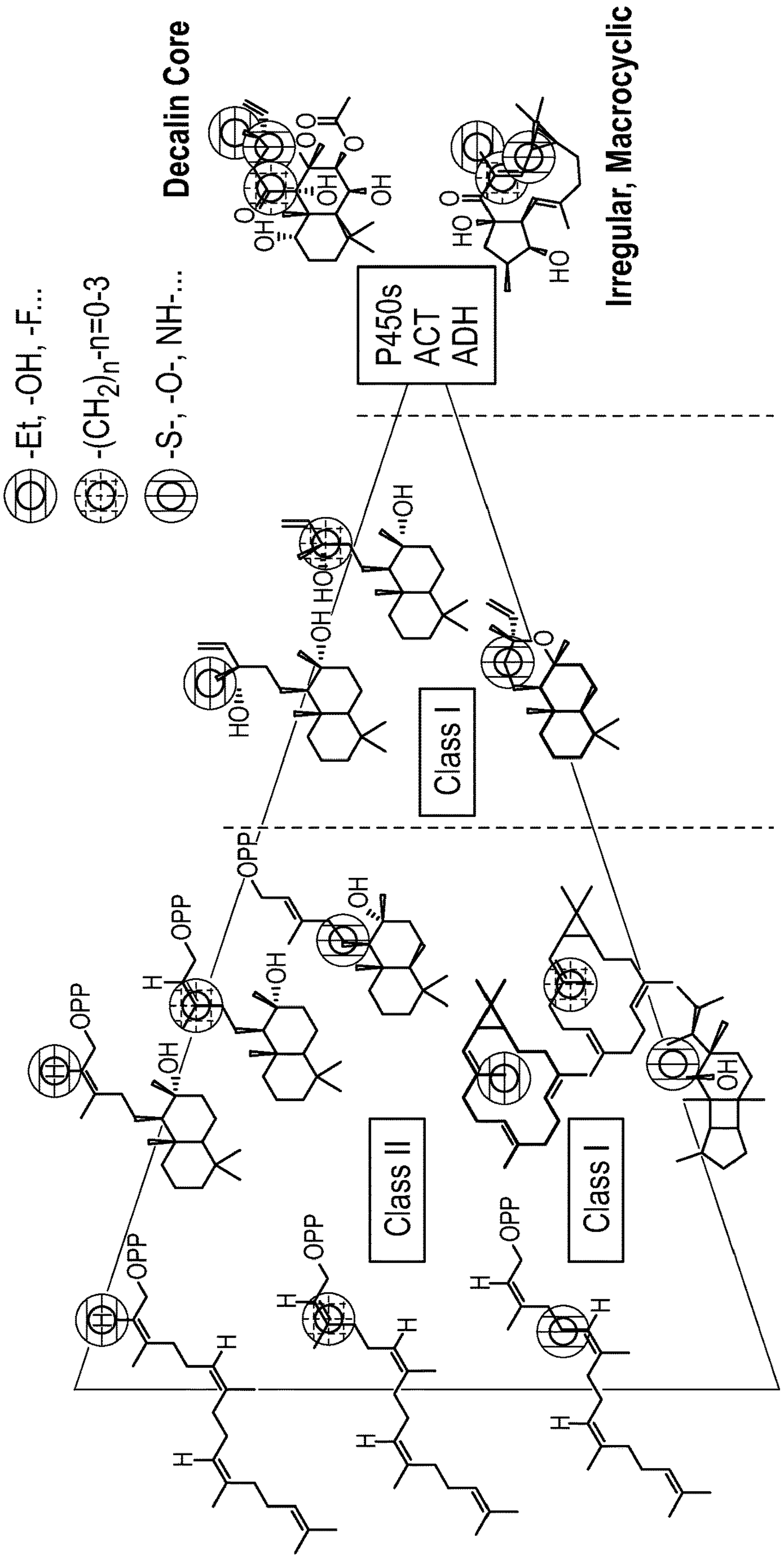
FIG. 1A-1C illustrate a process for evaluating unnatural substrates as candidates to produce novel diterpene-inspired drug candidates.

New substrates for terpene biosynthesis and methods for making new types of terpenes are described herein. Diterpenes occupy a unique molecular space with critical pharmaceutical applications over a diverse spectrum including anti-microbial, anti-cancer, immunomodulatory and psychoactive properties. Many diterpenoids are currently recognized as "drugs" (351 of over 12,500 are listed in the Dictionary of Natural Products, Taylor and Francis Group, DNP 28.1). A key challenge, however, is optimization of these compounds, and derivatization is usually not synthetically tractable.

While terpene synthase enzymes catalyze some of nature's most complex chemistries, the natural entry into the pathways is limited to a single precursor, geranylgeranyl diphosphate (GGPP), a precursor to almost all of natural diterpenes. Small molecule libraries for novel and promising leads for further manipulation are in demand as in vitro tools to investigate disease mechanisms, as in vivo probes, and to serve as starting points for the development of effective drugs. New compound libraries with high $sp^3$-character, rather than the $sp^2$-character typically observed in existing libraries, are generally missed by current technologies for library production (Karaki et al. Chem Med Chem (2019)). A unique three-dimensional space, or molecular complexity is correlated with success in the transition from discovery, to clinical testing, to approved drugs (Lovering, Medchemcomm 4: 515-519 (2013); Lovering et al. J. Med. Chem. 52, 6752-6756 (2009)). Complexity is measured by two descriptors, the fraction of tetrahedral $sp^3$ carbons ($Fsp^3$) where $Fsp^3$ equals the number of $sp^3$ hybridized carbons by total carbon count, and the chiral carbon count.

As described herein the terpene synthesis pathway is unexpectedly modular and the enzymes involved in terpene synthesis are surprisingly promiscuous. Unique, novel substrates for terpenes are described herein that are useful for making diverse types of new terpenoids.

Terpenes

Terpenes are the oldest and structurally most complex family of specialized metabolites on the planet. The class of diterpenes with their characteristic C20 scaffold is structurally diverse with over 12,500 compounds reported with a significant spectrum of pharmaceutical applications (Banerjee & Hamberger, *P450s controlling metabolic bifurcations in plant terpene specialized metabolism*. Phytochem. Rev. (2017)). Their molecular weight, extraordinary high fraction of $sp^a$ centers ($Fsp^3$ often >0.8), number of stereogenic centers, and regiospecific and stereospecific heteroatom functionalization (exceeding 95% with 2+ oxygens) makes them superior candidates for the discovery and development of novel therapeutics. The structural complexity of a representative diterpenoid is illustrated by the diterpene scaffold of stevioside shown below, which has an $Fsp^3$ of 0.9.

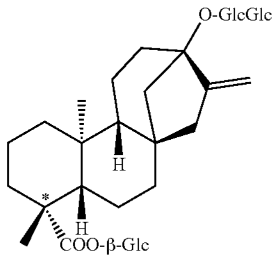

The enzymes of terpene synthesis pathways are evolutionarily optimized to deliver bioactive molecules, novel molecular scaffolds, and novel chemistries, with pharmaceutical targets and modes of action identified only for a few, due to their limited availability (e.g., Picato®, Taxol®, forskolin, and salvinorin).

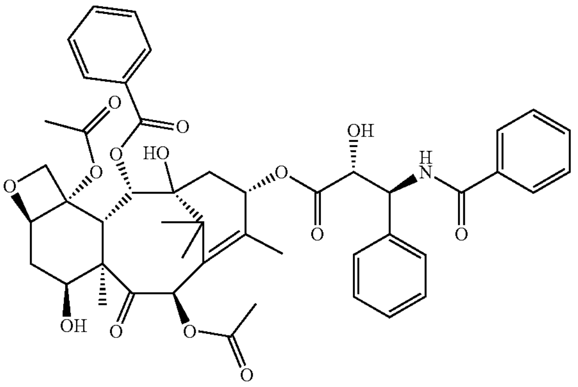

Taxol®

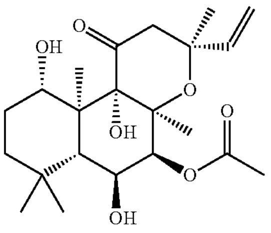

Forskolin

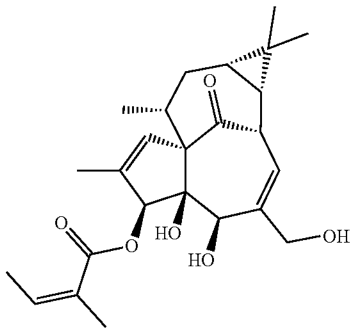

Picato®

-continued

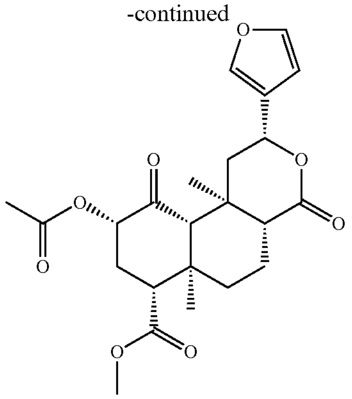

Salvinorin

Cost-effective synthesis and access to analogs of plant diterpenoids and their derivatives is technologically limited by the levels of isolation, purification, detection and synthesis. Isolation and purification for screening of their pharmaceutical properties and clinical development are severely impeded by a lack of sustainable supply through their natural sources where diterpenoids accumulate in complex mixtures of closely related, but unwanted compounds. Formal chemical synthesis is economically challenging, as targets are still deconstructed one at a time, and even the most elegant biomimetic routes can be mind-bending in their complexity (Jorgensen et al. Science 341: 878-882 (2013); Appendino et al. Angew. Chemie Int. Ed. 53, 927-929 (2014)).

Synthetic Biology can alleviate the bottleneck of access. However, despite earlier successes by others (C15 anti-malaria drug artemisinin, Paddon et al. Nature 496: 528—32 (2013)) and by the inventors (C20 drugs forskolin and phorbol-ester lead molecule jolkinol C, Luo et al. Proc. Natl. Acad. Sci. 113(34): E5082-9 (2016); Pateraki et al. Elife 6, (2017)), these approaches were limited to single targets and are incompatible with the need to generate diversified libraries that can be structurally manipulated by terpene synthases and other enzymes.

Jolkinol C represents the scaffold of the class of lathyrane-type phorbol esters with a macrocyclic, irregular structure. Compounds of this class exhibit potent antineoplastic activities against multidrug-resistant carcinoma lines. The NF-KB transcription factor provides a model system to study the posttranslational activation of a phorbol-ester-inducible transcription factor. The induction of NF-KB proceeds directly from protein kinase C upon binding of phorbol esters. The labdane-type diterpene forskolin is an important tool to raise cellular levels of cyclic AMP, a second messenger necessary for responses to hormones and cell communication. The mechanism proceeds via direct activation of all membrane bound isoforms of the adenylate cyclase. Acyl-analogs of forskolin were shown to strongly modulate the potency. The inventors have found that individual enzymes of both pathways, when probed with a small number of substrates, showed multifunctionality and promising promiscuity. In view of the utility of compounds similar to jolkinol C and forskolin the inventors have defined jolkinol C and forskolin functionalization pathways and identified diterpene scaffolds derived from GGPP, for biosynthesis using unnatural substrate scaffolds.

Described herein is a chemical strategy to bioprocess libraries of plant-inspired small molecules of the diterpene class. Novel synthetic substrate analogs are provided (i) to interrogate the intricate mechanism and substrate tolerance of terpene cyclization leading to unnatural decalin-core and irregular terpenes, (ii) to generate a panel of unnatural terpene key intermediates for functionalization through two pharmaceutically relevant pathways, and (iii) to characterize the function of such compounds with bioassays.

Figure 2:
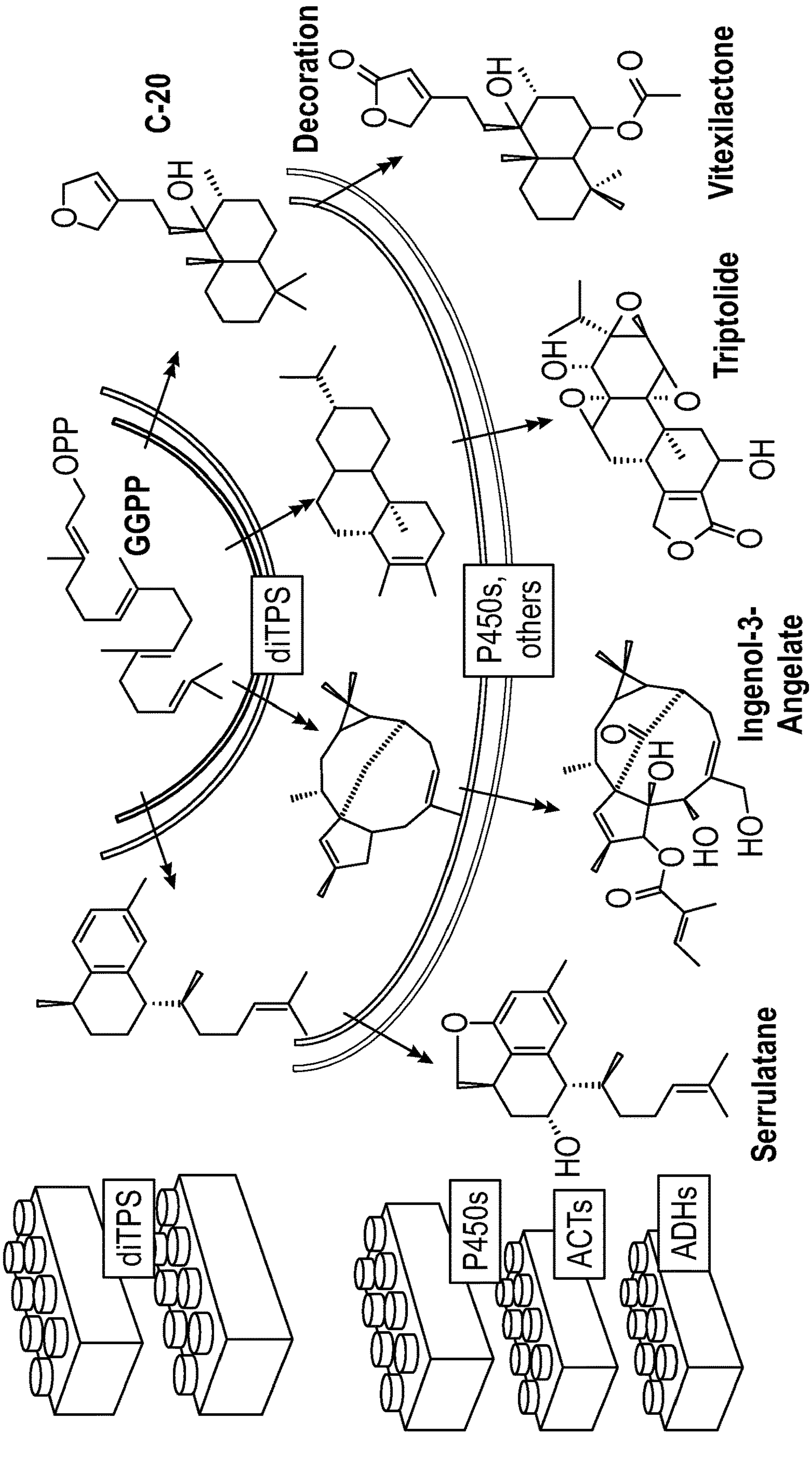
FIG. 2 illustrates the modular biosynthesis of diterpenes from the substrate geranylgeranyl diphosphate (GGPP).

Despite their structural complexity, the biosynthesis routes of diterpenes are modular. This is illustrated in FIG. 2. For example, as shown in FIG. 2, pairs of enzymes or single enzymes (diterpene synthases, diTPS), cyclize the diterpene scaffold, followed by cytochromes P450 (P450s) that functionalize the scaffold in regiospecific and stereospecific fashion, thereby creating molecular handles for further modification such as acylation or further cyclization (acyl transferases, ACTs; aldehyde dehydrogenases, ADHs). The typical natural substrate all-trans (E,E,E)-geranylgeranyl diphosphate (GGPP) for diterpenes is a shared acyclic, achiral $C_{20}$-building block. Such hierarchical organization and shared entry are not found in other pathways, including those leading to alkaloids or polyketides.

Terpene Substrates

Figure 8:
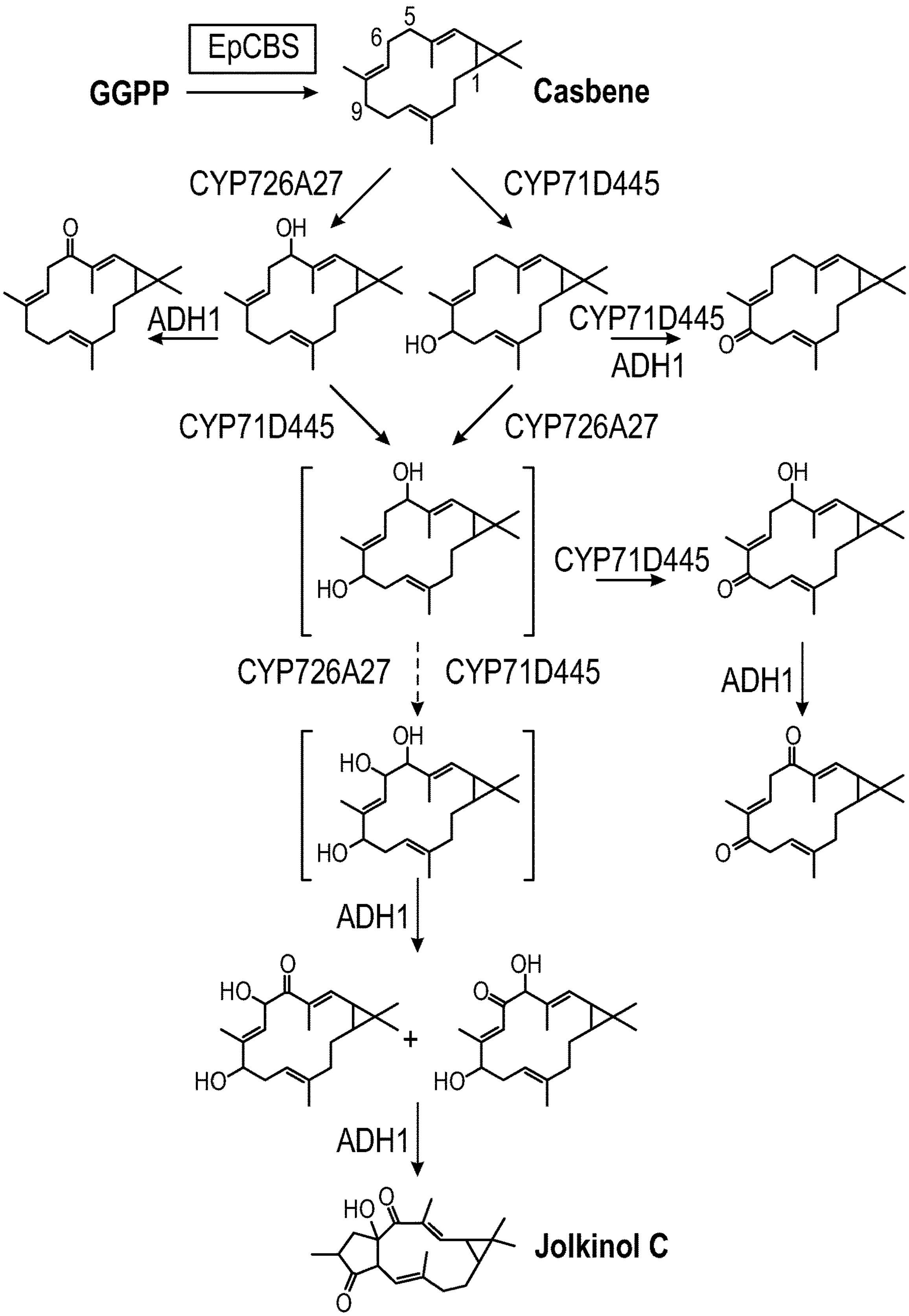
FIG. 8 illustrates the biosynthetic pathway to Jolkinol C within *Euphorbia*. GGPP was cyclized to the irregular diterpene scaffold Casbene, which was subsequently oxidized and further re-arranged by P450s and an ADH1.

Enzymatic bioprocessing of novel pharmaceutical candidates is increasingly important for securing access to relevant chemistries, scalability of production, and long-term reduction in cost for synthesis of scaffolds. Genetic information was used to reconstruct the pathways to the pharmacologically active cyclic AMP booster forskolin, and jolkinol C (shown in FIG. 8), precursors of phorbol esters drugs with unique anti-cancer, anti-HIV and analgesic activities (Luo et al. Proc. Natl. Acad. Sci. 113(34): E5082-9 (2016); Pateraki et al. Elife 6, (2017); Pateraki et al. Plant Physiol. 164, 1222-36 (2014)).

A degree of substrate promiscuity was unexpectedly observed on all three hierarchical levels of the biosynthetic route, indicating that the enzymes involved in such biosynthesis have an ability to act on substrates that they do not normally encounter and that the enzymes can convert a broader range of intermediates to diverse end products.

Taking advantage of natural substrate promiscuity, precursor-directed biosynthesis was used to generate variants of the drugs in the family of non-ribosomal peptides, polyketides and non-natural indole alkaloids. Modification of natural products can provide analogs with improved or novel medicinal properties. To that end, the disclosure relates to substrates of the formula (I) or (II):

(I)

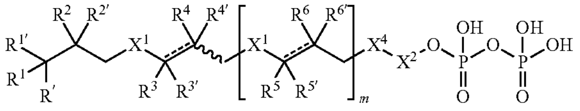

(II)

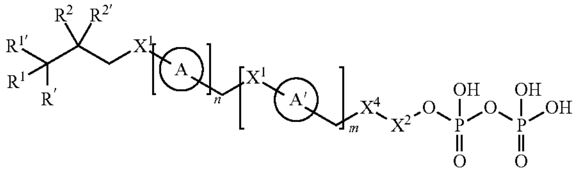

wherein: m is an integer from 0 to 3 (e.g., 1 or 2), with the understanding that if m is 2 or 3, each repeating subunit can be the same or different;

n is an integer from 0 to 1;

the dashed lines ----- represent a double bond when $R^{3'}$ and $R^{4'}$ are absent or when $R^{5'}$ and $R^{6'}$ are absent, A and A' are each independently cycloalkyl, aryl or heterocyclyl, each of which can be optionally substituted;

$X^1$ is a heteroatom, —$X^3$-alkyl, -alkyl-$X^3$— or alkyl, wherein $X^3$ is a heteroatom or alkyl or $X^1$ is:

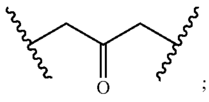 [SMILES: *CC(=O)C*]

;

$R^1$ and $R^2$ form a double bond or an epoxide;

each R', $R^{1'}$, $R^2$, $R^{2'}$, and $R^3$—$R^6$ is, independently, H, alkyl, halo, aryl, and alkylaryl;

$R^{3'}$ and $R^{4'}$ are absent or $R^{3'}$ and $R^{4'}$, together with the carbon atoms to which they are attached, form an epoxide, a cycloalkyl group, an aryl group or a heterocyclyl group;

$R^{5'}$ and $R^{6'}$ are absent or $R^{5'}$ and $R^{6'}$, together with the carbon atoms to which they are attached, form an epoxide, a cycloalkyl group, an aryl group or a heterocyclyl group;

$X^2$ is a bond, alkenyl or acyl; and $X^4$ is a absent, a heteroatom or alkyl;

with the proviso that the compound of the formula (I) is not a compound of the formula:

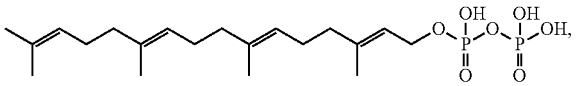

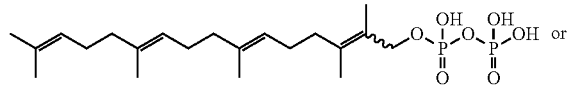

or

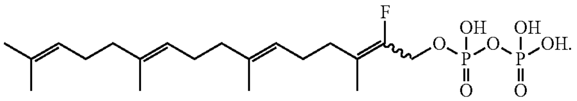

Examples of compounds of the formula (I) include compounds of the formula:

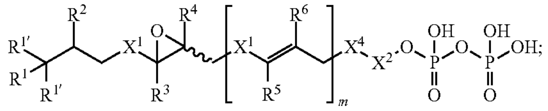

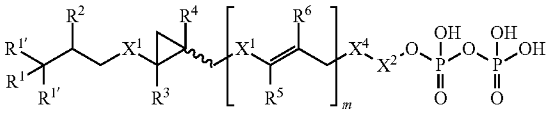

-continued

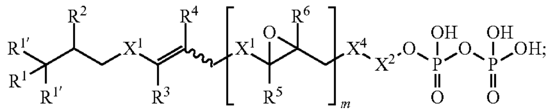

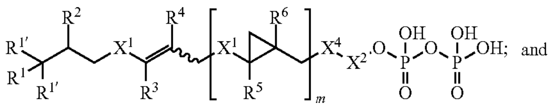

and

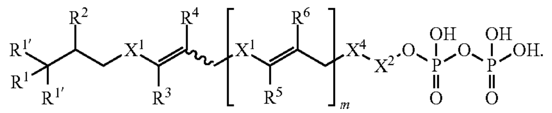

Examples of the formula (II) include compounds of the formula:

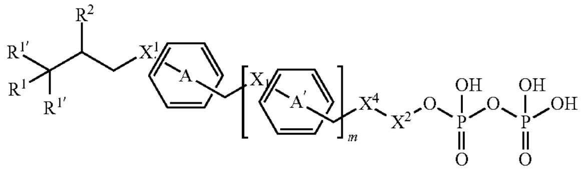

Examples of compounds of the formula (I) include compounds wherein if $X^1$ is a heteroatom, the heteroatom is oxygen. Other examples of compounds of the formula (I) include compounds wherein $X^3$ is oxygen or $C_1$-$C_5$-alkyl, such as —$CH_2$— and $C_2$-$C_3$-alkyl. Still other examples of compounds of the formula (I) include compounds wherein $R^3$-$R^6$ are each H or $C_1$-$C_5$-alkyl, such as methyl and $C_2$-$C_3$-alkyl. Still other examples of compounds of the formula (I) include compounds wherein $R^3$ and $R^5$ are each H or $C_1$-$C_5$-alkyl, such as methyl and $C_2$-$C_3$-alkyl; and $R^4$ and $R^6$ are each H. Yet other examples of compounds of the formula (I) include compounds wherein m is 1 or 2. In other examples, m is 0. Other examples of compound of the formula (I) include compounds wherein $X^2$ is an alkenyl group of the formula:

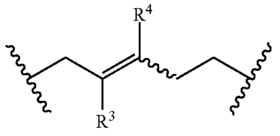

or

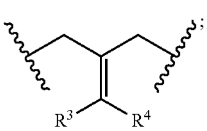

;

or an acyl group of the formula:

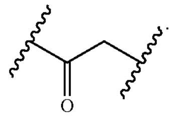 [SMILES: *CC(*)=O]

.

Examples of compounds of the formula (I) include compounds of the formulae:
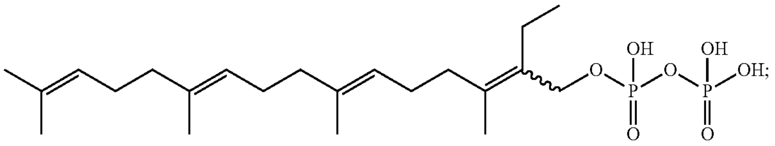
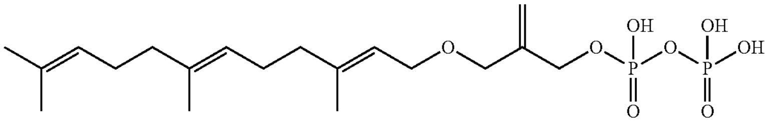
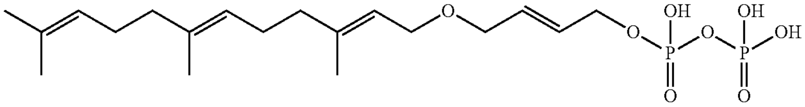
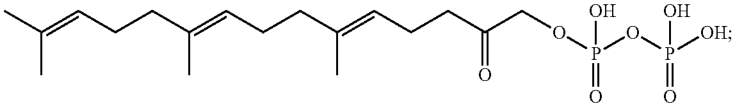
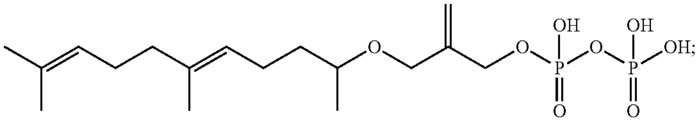
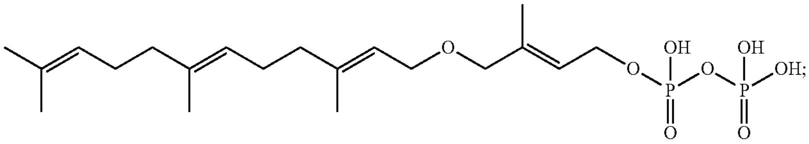
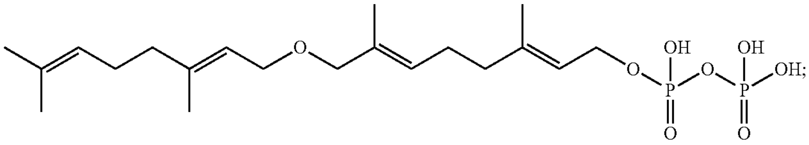
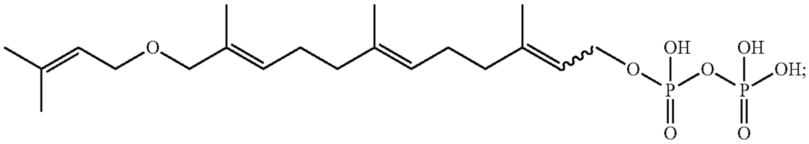
and
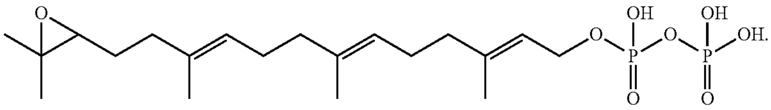
The compounds of the formula (I) or (II) can be enzymatically transformed into terpenoids having compound cores of the formula:
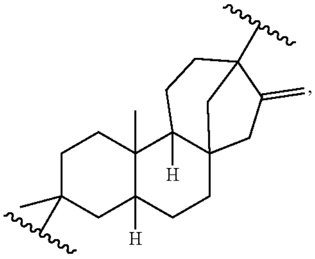
-continued
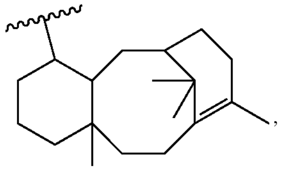
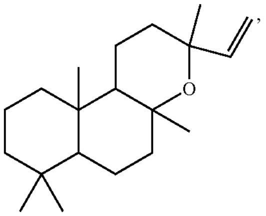

-continued

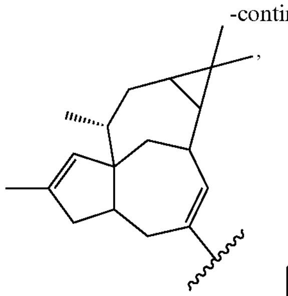

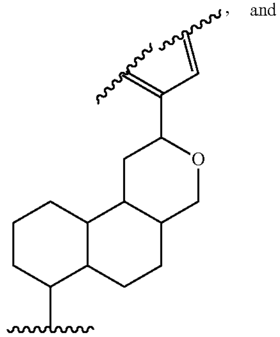

and

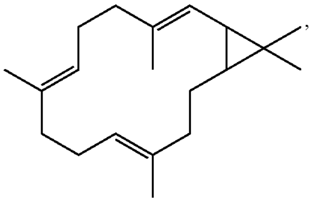

which correspond to the cores of stevioside, Taxol®, Forskolin, Picato®, and Salvinorin, Casbene, CPP respectively; or the core shared by CPP, LPP, PgPP, and KPP, namely:

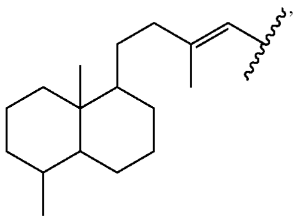 [SMILES: */C=C(\C)CCC1CCCC2C(C)CCCC12C]

and derivatives thereof, wherein derivatives can comprise additional double bonds, alkyl groups, hydroxy groups, acyl groups, and the like, dispersed about the cores.

As used herein, the term "heteroatom" refers to heteroatom such as, but not limited to, $NR^7$, O, and SO, wherein $R^7$ is H, alkyl or arylalkyl, and x is 0, 1 or 2.

The term "alkyl" as used herein refers to substituted or unsubstituted straight chain, branched and cyclic, saturated mono- or bi-valent groups having from 1 to 20 carbon atoms, 10 to 20 carbon atoms, 12 to 18 carbon atoms, 6 to about 10 carbon atoms, 1 to 10 carbons atoms, 1 to 8 carbon atoms, 2 to 8 carbon atoms, 3 to 8 carbon atoms, 4 to 8 carbon atoms, 5 to 8 carbon atoms, 1 to 6 carbon atoms, 2 to 6 carbon atoms, 3 to 6 carbon atoms, or 1 to 3 carbon atoms. Examples of straight chain mono-valent ($C_1$-$C_{20}$-alkyl groups include those with from 1 to 8 carbon atoms such as methyl (i.e., $CH_3$), ethyl, n-propyl, n-butyl, n-pentyl, n-hexyl, n-heptyl, n-octyl groups. Examples of branched mono-valent ($C_1$-$C_{20}$-alkyl groups include isopropyl, isobutyl, sec-butyl, t-butyl, neopentyl, and isopentyl. Examples of straight chain bi-valent ($C_1$-$C_{20}$)alkyl groups include those with from 1 to 6 carbon atoms such as $—CH_2—$, $—CH_2CH_2—$, $—CH_2CH_2CH_2—$, $—CH_2CH_2CH_2CH_2—$, and $—CH_2CH_2CH_2CH_2CH_2—$. Examples of branched bi-valent alkyl groups include $—CH(CH_3)CH_2—$ and $—CH_2CH(CH_3)CH_2—$. Examples of cyclic alkyl groups include cyclopropyl, cyclobutyl, cyclopentyl, cyclohexyl, cyclooctyl, bicyclo[1.1.1]pentyl, bicyclo[2.1.1]hexyl, and bicyclo[2.2.1]heptyl. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. In some embodiments, alkyl includes a combination of substituted and unsubstituted alkyl. As an example, alkyl, and also ($C_1$)alkyl, includes methyl and substituted methyl. As a particular example, ($C_1$)alkyl includes benzyl. As a further example, alkyl can include methyl and substituted ($C_2$-$C_8$)alkyl. Alkyl can also include substituted methyl and unsubstituted ($C_2$-$C_8$)alkyl. In some embodiments, alkyl can be methyl and $C_2$-$C_8$ linear alkyl. In some embodiments, alkyl can be methyl and $C_2$-$C_8$ branched alkyl. The term methyl is understood to be $—CH_3$, which is not substituted. The term methylene is understood to be $—CH_2—$, which is not substituted. For comparison, the term ($C_1$)alkyl is understood to be a substituted or an unsubstituted $—CH_3$ or a substituted or an unsubstituted $—CH_2—$. Representative substituted alkyl groups can be substituted one or more times with any of the groups listed herein, for example, cycloalkyl, heterocyclyl, aryl, amino, haloalkyl, hydroxy, cyano, carboxy, nitro, thio, alkoxy, and halogen groups. As further example, representative substituted alkyl groups can be substituted one or more fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. In some embodiments, representative substituted alkyl groups can be substituted from a set of groups including amino, hydroxy, cyano, carboxy, nitro, thio and alkoxy, but not including halogen groups.

The terms "halo," "halogen," or "halide" group, as used herein, by themselves or as part of another substituent, mean, unless otherwise stated, a fluorine, chlorine, bromine, or iodine atom.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, alkenyl, alkynyl, aryl, cycloalkyl, heterocyclyl, group or the like.

The term "alkenyl" as used herein refers to substituted or unsubstituted straight chain, branched and cyclic, saturated mono- or bi-valent groups having at least one carbon-carbon double bond and from 2 to 20 carbon atoms, 10 to 20 carbon atoms, 12 to 18 carbon atoms, 6 to about 10 carbon atoms, 2 to 10 carbons atoms, 2 to 8 carbon atoms, 3 to 8 carbon atoms, 4 to 8 carbon atoms, 5 to 8 carbon atoms, 2 to 6 carbon atoms, 3 to 6 carbon atoms, 4 to 6 carbon atoms, 2 to 4 carbon atoms, or 2 to 3 carbon atoms. The double bonds can be trans or cis orientation. The double bonds can be terminal or internal. The alkenyl group can be attached via the portion of the alkenyl group containing the double bond, e.g., vinyl, propen-1-yl and buten-1-yl, or the alkenyl group can be attached via a portion of the alkenyl group that does not contain the double bond, e.g., penten-4-yl. Examples of mono-valent ($C_2$-$C_{20}$)-alkenyl groups include those with from 1 to 8 carbon atoms such as vinyl, propenyl, propen-1-yl, propen-2-yl, butenyl, buten-1-yl, buten-2-yl, sec-buten-1-yl, sec-buten-3-yl, pentenyl, hexenyl, heptenyl and octenyl groups. Examples of branched mono-valent ($C_2$-$C_{20}$)-alkenyl groups include isopropenyl, iso-butenyl, sec-butenyl, t-butenyl, neopentenyl, and isopentenyl. Examples of straight chain bi-valent ($C_2$-$C_{2o}$)alkenyl groups include those with from 2 to 6 carbon atoms such as —CHCH—, —CHCHCH$_2$—, —CHCHCH$_2$CH$_2$—, and —CHCHCH$_2$CH$_2$CH$_2$—. Examples of branched bi-valent alkyl groups include —C(CH$_3$)CH— and —CHC(CH$_3$) CH$_2$—. Examples of cyclic alkenyl groups include cyclopentenyl, cyclohexenyl and cyclooctenyl. It is envisaged that alkenyl can also include masked alkenyl groups, precursors of alkenyl groups or other related groups. As such, where alkenyl groups are described it, compounds are also envisaged where a carbon-carbon double bond of an alkenyl is replaced by an epoxide or aziridine ring. Substituted alkenyl also includes alkenyl groups which are substantially tautomeric with a non-alkenyl group. For example, substituted alkenyl can be 2-aminoalkenyl, 2-alkylaminoalkenyl, 2-hydroxyalkenyl, 2-hydroxyvinyl, 2-hydroxypropenyl, but substituted alkenyl is also understood to include the group of substituted alkenyl groups other than alkenyl which are tautomeric with non-alkenyl containing groups. In some embodiments, alkenyl can be understood to include a combination of substituted and unsubstituted alkenyl. For example, alkenyl can be vinyl and substituted vinyl. For example, alkenyl can be vinyl and substituted ($C_3$-$C_8$) alkenyl. Alkenyl can also include substituted vinyl and unsubstituted ($C_3$-$C_8$)alkenyl. Representative substituted alkenyl groups can be substituted one or more times with any of the groups listed herein, for example, monoalkylamino, dialkylamino, cyano, acetyl, amido, carboxy, nitro, alkylthio, alkoxy, and halogen groups. As further example, representative substituted alkenyl groups can be substituted one or more fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. In some embodiments, representative substituted alkenyl groups can be substituted from a set of groups including monoalkylamino, dialkylamino, cyano, acetyl, amido, carboxy, nitro, alkylthio and alkoxy, but not including halogen groups. Thus, in some embodiments, alkenyl can be substituted with a non-halogen group. In some embodiments, representative substituted alkenyl groups can be substituted with a fluoro group, substituted with a bromo group, substituted with a halogen other than bromo, or substituted with a halogen other than fluoro. For example, alkenyl can be 1-fluorovinyl, 2-fluorovinyl, 1,2-difluorovinyl, 1,2,2-trifluorovinyl, 2,2-difluorovinyl, trifluoropropen-2-yl, 3,3,3-trifluoropropenyl, 1-fluoropropenyl, 1-chlorovinyl, 2-chlorovinyl, 1,2-dichlorovinyl, 1,2,2-trichlorovinyl or 2,2-dichlorovinyl. In some embodiments, representative substituted alkenyl groups can be substituted with one, two, three or more fluoro groups or they can be substituted with one, two, three or more non-fluoro groups.

The term "alkynyl" as used herein, refers to substituted or unsubstituted straight and branched chain alkyl groups, except that at least one triple bond exists between two carbon atoms. Thus, alkynyl groups have from 2 to 50 carbon atoms, 2 to 20 carbon atoms, 10 to 20 carbon atoms, 12 to 18 carbon atoms, 6 to about 10 carbon atoms, 2 to 10 carbons atoms, 2 to 8 carbon atoms, 3 to 8 carbon atoms, 4 to 8 carbon atoms, 5 to 8 carbon atoms, 2 to 6 carbon atoms, 3 to 6 carbon atoms, 4 to 6 carbon atoms, 2 to 4 carbon atoms, or 2 to 3 carbon atoms. Examples include, but are not limited to ethynyl, propynyl, propyn-1-yl, propyn-2-yl, butynyl, butyn-1-yl, butyn-2-yl, butyn-3-yl, butyn-4-yl, pentynyl, pentyn-1-yl, hexynyl, Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "aryl" as used herein refers to substituted or unsubstituted univalent groups that are derived by removing a hydrogen atom from an arene, which is a cyclic aromatic hydrocarbon, having from 6 to 20 carbon atoms, 10 to 20 carbon atoms, 12 to 20 carbon atoms, 6 to about 10 carbon atoms or 6 to 8 carbon atoms. Examples of ($C_6$-$C_{20}$)aryl groups include phenyl, napthalenyl, azulenyl, biphenylyl, indacenyl, fluorenyl, phenanthrenyl, triphenylenyl, pyrenyl, naphthacenyl, chrysenyl, anthracenyl groups. Examples include substituted phenyl, substituted napthalenyl, substituted azulenyl, substituted biphenylyl, substituted indacenyl, substituted fluorenyl, substituted phenanthrenyl, substituted triphenylenyl, substituted pyrenyl, substituted naphthacenyl, substituted chrysenyl, and substituted anthracenyl groups. Examples also include unsubstituted phenyl, unsubstituted napthalenyl, unsubstituted azulenyl, unsubstituted biphenylyl, unsubstituted indacenyl, unsubstituted fluorenyl, unsubstituted phenanthrenyl, unsubstituted triphenylenyl, unsubstituted pyrenyl, unsubstituted naphthacenyl, unsubstituted chrysenyl, and unsubstituted anthracenyl groups. Aryl includes phenyl groups and also non-phenyl aryl groups. From these examples, it is clear that the term ($C_6$-$C_{20}$)aryl encompasses mono- and polycyclic ($C_6$-$C_{20}$)aryl groups, including fused and non-fused polycyclic ($C_6$-$C_{20}$)aryl groups. The term "heterocyclyl" as used herein refers to substituted aromatic, unsubstituted aromatic, substituted non-aromatic, and unsubstituted non-aromatic rings containing 3 or more atoms in the ring, of which, one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms ($C_3$-$C_8$), 3 to 6 carbon atoms ($C_3$-$C_6$) or 6 to 8 carbon atoms ($C_6$-$C_8$). A heterocyclyl group designated as a $C_2$-heterocyclyl can be a 5-membered ring with two carbon atoms and three heteroatoms, a 6-membered ring with two carbon atoms and four heteroatoms and so forth. Likewise, a $C_4$-heterocyclyl can be a 5-membered ring with one heteroatom, a 6-membered ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. Representative heterocyclyl groups include, but are not limited to piperidynyl, piperazinyl, morpholinyl, furanyl, pyrrolidinyl, pyridinyl, pyrazinyl, pyrimidinyl, triazinyl, thiophenyl, tetrahydrofuranyl, pyrrolyl, oxazolyl, imidazolyl, triazyolyl, tetrazolyl, benzoxazolinyl, and benzimidazolinyl groups. For example, heterocyclyl groups include, without limitation:

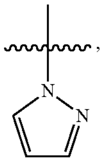,
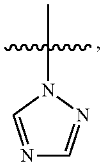,
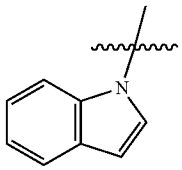,

-continued

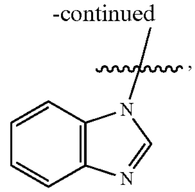,

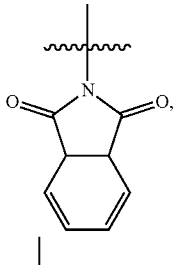, 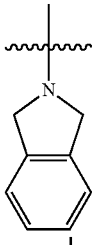, 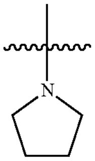, 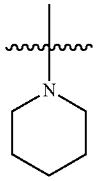,

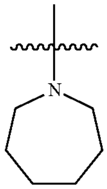, 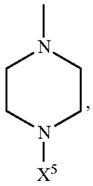, 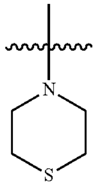; 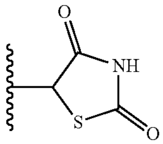, and

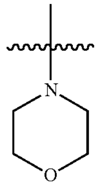, wherein $X^5$ represents H, $(C_1\text{-}C_{20})$alkyl, $(C_6\text{-}C_{20})$aryl or an amine protecting group (e.g., a t-butyloxycarbonyl group) and wherein the heterocyclyl group can be substituted or unsubstituted. A nitrogen-containing heterocyclyl group is a heterocyclyl group containing a nitrogen atom as an atom in the ring. In some embodiments, the heterocyclyl is other than thiophene or substituted thiophene. In some embodiments, the heterocyclyl is other than furan or substituted furan.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl, biphenylmethyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "substituted" as used herein refers to a group that is substituted with one or more groups including, but not limited to, the following groups: halogen (e.g., F, Cl, Br, and I), R, OR, ROH (e.g., $CH_2OH$), $OC(O)N(R)_2$, CN, NO, $NO_2$, $ONO_2$, azido, $CF_3$, $OCF_3$, methylenedioxy, ethylenedioxy, $(C_3\text{-}C_{20})$heteroaryl, $N(R)_2$, $Si(R)_3$, SR, SOR, $SO_2R$, $SO_2N(R)_2$, $SO_3R$, $P(O)(OR)_2$, $OP(O)(OR)_2$, C(O)R, C(O)C(O)R, $C(O)CH_2C(O)R$, C(S)R, C(O)OR, OC(O)R, $C(O)N(R)_2$, C(O)N(R)OH, $OC(O)N(R)_2$, $C(S)N(R)_2$, $(CH_2)_{0\text{-}2}N(R)C(O)R$, $(CH_2)_{0\text{-}2}N(R)N(R)_2$, N(R)N(R)C(O)R, N(R)N(R)C(O)OR, $N(R)N(R)CON(R)_2$, $N(R)SO_2R$, $N(R)SO_2N(R)_2$, N(R)C(O)OR, N(R)C(O)R, N(R)C(S)R, $N(R)C(O)N(R)_2$, $N(R)C(S)N(R)_2$, N(COR)COR, N(OR)R, $C({=}NH)N(R)_2$, C(O)N(OR)R, or C(=NOR)R wherein R can be hydrogen, $(C_1\text{-}C_{20})$alkyl, $(C_6\text{-}C_{20})$aryl, heterocyclyl or polyalkylene oxide groups, such as polyalkylene oxide groups of the formula $—(CH_2CH_{20})_f—R—OR$, $—(CH_2CH_2CH_{20})_g—R—OR$, $—(CH_2CH_{20})_f(CH_2CH_2CH_{20})_g—R—OR$ each of which can, in turn, be substituted or unsubstituted and wherein f and g are each independently an integer from 1 to 50 (e.g., 1 to 10, 1 to 5, 1 to 3 or 2 to 5). Substituted also includes a group that is substituted with one or more groups including, but not limited to, the following groups: fluoro, chloro, bromo, iodo, amino, amido, alkyl, hydroxy, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. Where there are two or more adjacent substituents, the substituents can be linked to form a carbocyclic or heterocyclic ring. Such adjacent groups can have a vicinal or germinal relationship, or they can be adjacent on a ring in, e.g., an ortho-arrangement. Each instance of substituted is understood to be independent. For example, a substituted aryl can be substituted with bromo and a substituted heterocycle on the same compound can be substituted with alkyl. It is envisaged that a substituted group can be substituted with one or more non-fluoro groups. As another example, a substituted group can be substituted with one or more non-cyano groups. As another example, a substituted group can be substituted with one or more groups other than haloalkyl. As yet another example, a substituted group can be substituted with one or more groups other than tert-butyl. As yet a further example, a substituted group can be substituted with one or more groups other than trifluoromethyl. As yet even further examples, a substituted group can be substituted with one or more groups other than nitro, other than methyl, other than methoxymethyl, other than dialkylaminosulfonyl, other than bromo, other than chloro, other than amido, other than halo, other than benzodioxepinyl, other than polycyclic heterocyclyl, other than polycyclic substituted aryl, other than methoxycarbonyl, other than alkoxycarbonyl, other than thiophenyl, or other than nitrophenyl, or groups meeting a combination of such descriptions. Further, substituted is also understood to include fluoro, cyano, haloalkyl, tert-butyl, trifluoromethyl, nitro, methyl, methoxymethyl, dialkylaminosulfonyl, bromo, chloro, amido, halo, benzodioxepinyl, polycyclic heterocyclyl, polycyclic substituted aryl, methoxy carbonyl, alkoxycarbonyl, thiophenyl, and nitrophenyl groups.

Enzymes

A variety of enzymes can be used to convert the substrates into useful products. Examples of enzymes that can be used include terpene synthases. For example, the enzymes employed can be those that naturally convert geranylgeranyl diphosphate (GGPP) into biosynthesis of gibberellins, carotenoids, chlorophylls, isoprenoid quinones, and geranylgeranylated proteins. However, the enzymes are also promiscuous and can accept unnatural substrates such as the unnatural GGPP analogs or derivatives described herein. Additional enzymes can also be employed that convert the products formed from the unnatural substrates (e.g., the primary products) into other products (e.g., secondary products).

For example, the enzymes can be from organisms such as *Tripterygium wilfordii* (Tw), *Euphorbia peplus* (Ep), *Coleus forskohlii* (Cf), *Ajuga reptans* (Ar), *Perovskia atriciplifolia* (Pa), *Nepeta mussini* (Nm), *Origanum majorana* (Om), *Hyptis suaveolens* (Hs), *Grindelia robusta* (Gr), *Leonotis leonurus* (Ll), *Marrubium vulgare* (Mv), *Vitex agnus-castus*

(Vac), *Euphorbia peplus* (Ep), *Ricinus communis* (Rc), *Daphne genkwa* (Dg), *Zea mays* (Zm), and other organisms.

The enzymes can in some cases, for example, be type I or type II enzymes. In general, a type II enzyme can catalyze transformation of an unnatural substrate derivative of geranylgeranyl diphosphate (GGPP) to a primary terpene product, while the type I enzymes can modify such a terpene product to generate a second terpene product.

The enzymes can be used in single step reactions, or in multi-step reactions when mixed together or when used sequentially. Multi-step reactions can occur by enzyme coupling. Enzyme coupling refers to one enzyme catalyzing a reaction to produce a product that is a substrate for a second enzyme. For example, the type II and type I enzymes can be coupled together, where a type II enzyme can accept and enzymatically convert an unnatural substrate to a first product and where a type I enzyme accepts the first product as a substrate for enzymatic conversion to generate a second product. Such enzyme coupling is demonstrated in the Examples. In some cases, an unnatural substrate can undergo efficient conversion to a first product by one enzyme without producing side products or undesirable fragments that could undermine the efficiency of a second enzyme to produce desirable yields of a second product.

Examples of enzymes that can be used include those that naturally produce ent-CPP (e.g., TwTPS3, EpTPS7, ZmAN2), shown below.

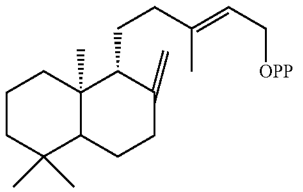

ent-CPP

Examples of enzymes that can be used include those that naturally produce (+)-CPP (e.g., CfTPS1, ArTPS1, PaTPS1, NmTPS1, OmTPS1, TwTPS9 and CfTPS16), shown below.

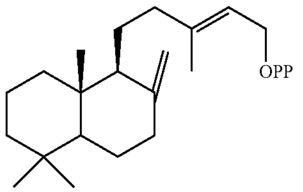

(+)-CPP

Examples of enzymes that can be used include those that naturally produce (13E)-labda-7,13-dien-15-yl diphosphate (i.e., (7,13)-LPP) (e.g., HsTPS1, GrTPS), shown below.

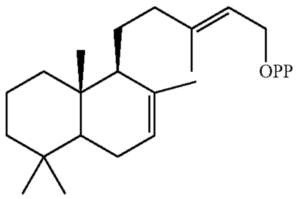

Examples of enzymes that can be used include those that naturally produce peregrinol diphosphate (PGPP) (e.g., LlTPS1, MvCPS1, VacTPS1), shown below.

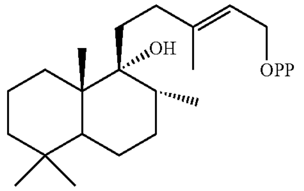

PgPP

Examples of enzymes that can be used include those that naturally produce (−)-kolavenyl diphosphate (KPP) (e.g., TwTPS10, TwTPS14, VacTPS5), shown below.

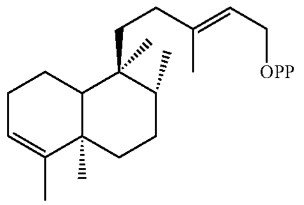

KPP

Examples of enzymes that can be used include those that naturally produce casbene (e.g., EpCBS, RcCBS, DgTPS1), shown below.

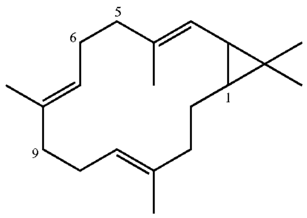

Casbene

Approximately 30 functional diTPS of the mint family have been identified and isolated by the inventors as having both labdane-type and irregular diterpene biosynthetic activities. These enzymes represent a repository of enzymes that can be used in the methods and reaction mixtures described herein.

For example, an *Ajuga reptans* miltiradiene synthase (ArTPS3), a *Leonotis leonurus* sandaracopimaradiene synthase (L1TPS4), a *Mentha spicata* class I diterpene synthase (MsTPS1), an *Origanum majorana* trans-abienol synthase (OmTPS3), an *Origanum majorana* manool synthase (OmTPS4), an *Origanum majorana* palustradiene synthase (OmTPS5), *Perovskia atriplicifolia* miltiradiene synthase (PaTPS3), *Prunella vulgaris* miltiradiene synthase (PvTPS1), *Salvia officinalis* miltiradiene synthase (SoTPS1) were identified and isolated.

Eight of these enzymes, ArTPS3, L1TPS4, MsTPS1, OmTPS4, OmTPS5, PaTPS3, PvTPS1, and SoTPS1 can convert a labda-13-en-8-ol diphosphate ((+) LPP) [compound 10]) to 13R-(+)-manoyl oxide [8].

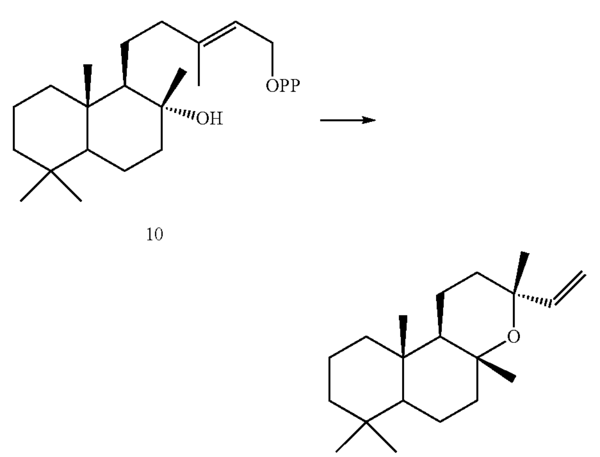

10

8

The ArTPS3, L1TPS4, OmTPS4, OmTPS5, PaTPS3, PvTPS1, and SoYPS1 enzymes can also convert peregrinol diphosphate (PgPP) [5]to a combination of compounds 1, 2, and 3, as illustrated below.

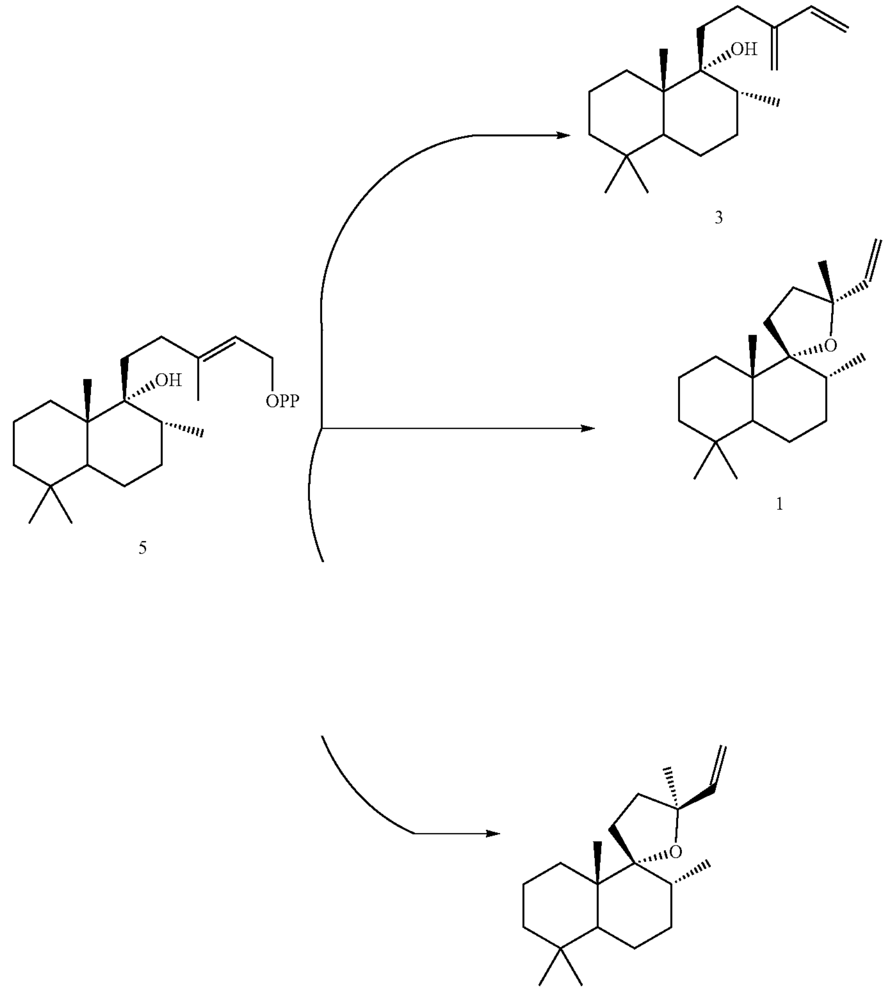

3

1

5

2

However, MsTPS1 produced only compound 3 from compound 5, while the OmTPS3 enzyme produced only 1, and 2. The OmTPS4 enzyme produced compound 4 (shown below) in addition to compounds 1, 2, and 3.

4

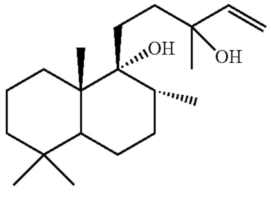

The ArTPS3, PaTPS3, PvTPS1, and SoTPS1 enzymes can also convert (+)-copalyl diphosphate ((+)-CPP) [31]) to miltiradiene [32].

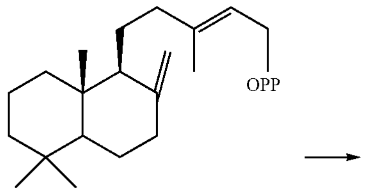

31

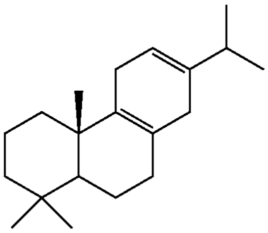

32

However, LlTPS4 and MsTPS1 converted (+)-copalyl diphosphate ((+)-CPP) [31]) to sadaracopimaradiene [27], while OmTPS3 converted (+)-copalyl diphosphate ((+)-CPP) [31]) to trans-biformene [34].

27

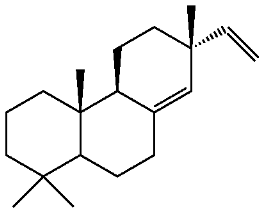

34

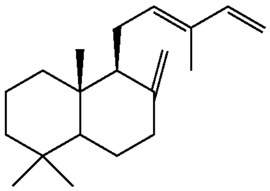

The *Ajuga reptans* miltiradiene synthase (ArTPS3) has the amino acid sequence shown below (SEQ ID NO:1).

1 MSLSETIKVT PFSGQRVHSS TESFPIQQFP TITTKSAMAV

41 KCSSLSTATV SFQDFVGKIR DTINGKVDNS PAATTIHPAD

81 IPSNLCVVDT LQRLGVDRYF QSEIDSVLND TYRFWQQKGE

121 DIFTDVACRA MAFRLLRVKG YEVSSDELAS YAEQEHVNLQ

161 PSDITTVIEL YRASQTRLYE DEGNLEKLHT WTSNFLKQQL

201 QSETISDEKL HKQVEYYLKN YHGILDRAGV RQSLDLYDIN

241 QYQNLKSTDR FPTLSNEDLL EFAKQDFNFC QAQHQKELQQ

281 LQRWYADCKL DTLTYGRDVV RVASFLTAAI FGEPEFSDAR

321 LAFAKHIILV TRIDDFFDHG GSIEESYKIL DLVKEWEDKP

361 AEEYPSKEVE ILFTAVYNTV NDLAEMAYIE QGRSIKPLLI

401 KLWVEILTSF KKELDSWTED TELTLEEYLA SSWVSIGCRI

-continued

441 CSLNSLQFLG ITLSEEMLSS EECMELCRHV SSVDRLLNDV

481 QTFEKERLEN TINSVSLQLA EAQREGRTIT EEEAMSKIKD

521 LADYHRRQLM QMVYKDGTIF PRQCKDVFLR VCRIGYYLYA

561 SGDEFTTPQQ MMGDMKSLVY EPLNTSSS

A nucleic acid encoding the *Ajuga reptans* miltiradiene synthase (ArTPS3) with SEQ ID NO:1 is shown below as SEQ ID NO:2.

1 ATGTCACTCT CGTTCACCAT CAAAGTCACC CCCTTTTCGG

41 GCCAGAGAGT TCACAGCAGC ACAGAAAGCT TTCCAATCCA

81 ACAATTTCCA ACGATCACCA CCAAATCCGC CATGGCTGTC

121 AAATGCAGCA GCCTCAGTAC CGCAACAGTA AGCTTCCAGG

161 ATTTCGTCGG AAAAATCAGA GATACGATCA ACGGGAAAGT

201 TGACAATTCT CCAGCAGCGA CCACTATTCA TCCTGCAGAT

241 ATACCCTCCA ATCTCTGCGT GGTGGATACC CTCCAAAGAT

281 TGGGAGTTGA CCGTTACTTC CAATCTGAAA TCGACAGCGT

321 TCTTAACGAC ACATACAGGT TCTGGCAGCA GAAAGGAGAA

361 GATATCTTCA CTGATGTTGC TTGTCGTGCA ATGGCATTTC

401 GACTTTTGCG AGTTAAAGGA TATGAAGTTT CATCAGATGA

521 ACTGGCTTCG TATGCTGAAC AAGAGCATGT TAACCTGCAA

561 CCAAGTGACA TAACTACGGT TATCGAGCTT TACAGAGCAT

601 CACAGACAAG ATTATATGAA GACGAGGGCA ATCTTGAGAA

641 GTTACATACT TGGACTAGCA ATTTTCTGAA GCAACAATTG

681 CAGAGTGAAA CTATTTCTGA CGAGAAATTG CACAAACAGG

721 TGGAGTATTA CTTGAAGAAC TACCACGGCA TACTAGACCG

761 TGCTGGAGTT AGACAAAGTC TCGATTTATA TGACATAAAC

801 CAATACCAGA ATCTAAAATC TACAGATAGA TTCCCTACTT

841 TAAGTAACGA AGATTTACTT GAATTCGCGA AGCAAGATTT

881 TAACTTTTGC CAAGCTCAAC ACCAGAAAGA GCTTCAGCAA

921 CTGCAAAGGT GGTATGCGGA TTGTAAATTG GATACATTGA

961 CTTACGGAAG AGATGTGGTA CGTGTTGCAA GTTTCCTGAC

1001 AGCTGCAATT TTTGGTGAGC CTGAATTCTC TGATGCTCGT

1041 CTAGCCTTCG CCAAACACAT CATCCTCGTG ACACGTATTG

1081 ATGATTTCTT CGATCATGGT GGGTCTATAG AAGAGTCATA

1121 CAAGATCCTG GATTTAGTAA AAGAATGGGA AGATAAGCCA

1161 GCTGAGGAAT ATCCTTCCAA GGAAGTTGAA ATCCTCTTTA

1201 CAGCAGTATA TAATACAGTA AATGACTTGG CAGAAATGGC

1241 TTATATTGAG CAAGGCCGTT CCATTAAACC TCTTCTAATT

1281 AAACTGTGGG TTGAAATACT GACAAGTTTC AAGAAAGAAC

1321 TGGATTCATG GACAGAAGAC ACAGAACTAA CCTTGGAGGA

1361 GTACTTGGCT TCCTCCTGGG TGTCGATCGG TTGCAGAATC

-continued

```
1401 TGCAGTCTCA ATTCGCTGCA GTTCCTTGGT ATAACATTAT
1441 CCGAAGAAAT GCTTTCAAGC GAAGAGTGCA TGGAGTTGTG
1481 TAGGCATGTT TCTTCAGTCG ACAGGCTACT CAATGACGTG
1521 CAAACTTTCG AGAAGGAACG CCTAGAAAAT ACGATAAACA
1561 GTGTGAGCCT ACAGCTAGCA GAAGCTCAGA GAGAAGGAAG
1601 AACCATTACA GAAGAGGAGG CTATGTCAAA GATTAAAGAC
1641 CTGGCTGATT ATCACAGGAG ACAACTGATG CAGATGGTTT
1681 ATAAGGATGG GACCATATTT CCGAGACAAT GCAAAGATGT
1721 CTTTTTGAGG GTATGCAGGA TTGGCTACTA CTTATACGCG
1761 AGCGGCGATG AATTCACTAC TCCACAACAA ATGATGGGGG
1801 ATATGAAATC ATTGGTTTAT GAACCCCTAA ACACTTCATC
1841 CTCTTGA
```

The *Leonotis leonurus* sandaracopimaradiene synthase (L1TPS4) has the amino acid sequence shown below (SEQ ID NO:3).

```
  1 MSVAFNLIVV RFPGHGIQSS RETFPAKIIT RTKSSMRFQS
 41 SLNTSTDFVG KIREMIRGKT DNSINPLDIP STLCVIDTLH
 81 SFGIDRYFQS EINSVLHHTY RLWNDRNNII FKDVICCAIA
121 FRLLRVKGYQ VSSDELAPFA QQQVTGLQTS DIATILELYR
161 ASQERLHEDD DTLDKLHDWS SNLLKLHLLN ENIPDHKLHK
201 RVGYFLKNYH GMLDRVAVRR NIDLHNINHY QIPEVADRFP
241 TEAFLEFSRQ DFNICQAQHQ KELQQLHRWY ADCRLDTLNH
281 GTDVVHFANF LTSAIFGEPE FSEARLAFAK QVILITRMDD
321 FFDHDGSREE SHKILHLVQQ WKEKPAEEYG SKEVEILFTA
361 VYTTVNSLAE KACMEQGRSV KQLLIKLWVE LLTSFKKELD
401 SWTEKMALTL DEYLSFSWVS IGCRLCILNS LQFLGIKLSE
441 EMLWSQECLD LCRHVSSVVR LLNDLQTFKK ERIENTINGV
481 DVQLAARKGE RAITEEEAMS KIKEMADHHR RKLMQIVYKE
521 GTIFPRECKD VFLRVCRIGY YLYSGDELTS PQQMKEDMKA
561 LVHESSS
```

A nucleic acid encoding the *Leonotis leonurus* sandaracopimaradiene synthase (L1TPS4) with SEQ ID NO:3 is shown below as SEQ ID NO:4.

```
  1 ATGTCGGTGG CGTTCAACCT CATAGTCGTC CGTTTTCCGG
 41 GCCATGGAAT TCAGAGCAGT AGAGAAACTT TTCCAGCCAA
 81 AATTATTACC AGAACTAAAT CAAGCATGAG ATTCCAAAGC
121 AGCCTCAACA CTTCAACAGA TTTCGTGGGA AAAATAAGAG
161 AGATGATCAG AGGGAAAACT GATAATTCTA TTAATCCCCT
201 GGATATTCCC TCCACTCTAT GCGTAATCGA CACCCTACAC
241 AGCTTCGGAA TTGATCGCTA CTTTCAATCC GAAATCAACT
281 CTGTTCTTCA CCACACATAC AGATTATGGA ACGACAGAAA
```

-continued

```
 321 TAATATCATC TTCAAAGATG TCATTTGCTG CGCAATTGCC
 361 TTTAGACTTT TGCGAGTGAA AGGATATCAA GTCTCATCAG
 401 ATGAACTGGC GCCATTTGCC CAACAACAGG TGACTGGACT
 441 ACAAACAAGC GACATTGCCA CGATTCTAGA GCTCTACAGA
 481 GCATCACAGG AGAGATTACA CGAAGACGAC GACACTCTTG
 521 ACAAACTACA TGATTGGAGC AGCAACCTTC TGAAGCTGCA
 561 TCTGCTGAAT GAGAACATTC CTGATCATAA ACTGCACAAA
 601 CGGGTGGGGT ATTTCTTGAA GAACTACCAT GGCATGCTAG
 641 ATCGCGTTGC GGTTAGACGA AACATCGACC TTCACAACAT
 681 AAACCATTAC CAAATCCCAG AAGTTGCAGA TAGGTTCCCT
 721 ACTGAAGCTT TTCTTGAATT TTCAAGGCAA GATTTTAATA
 761 TTTGCCAAGC TCAACACCAG AAAGAACTTC AGCAACTGCA
 801 TAGGTGGTAT GCAGATTGTA GATTGGACAC ACTGAATCAC
 841 GGAACAGACG TAGTACATTT TGCTAATTTT CTAACTTCAG
 881 CAATTTTCGG AGAGCCTGAA TTCTCCGAGG CTCGTCTAGC
 921 CTTTGCTAAA CAGGTTATCC TAATAACACG TATGGATGAT
 961 TTCTTCGATC ACGATGGGTC TAGAGAAGAA TCACACAAGA
1001 TCCTCCATCT AGTTCAACAA TGGAAAGAGA AGCCCGCCGA
1041 AGAATATGGT TCAAAGGAAG TTGAGATCCT CTTTACAGCA
1081 GTGTACACTA CAGTAAATAG CTTGGCAGAA AAGGCTTGTA
1121 TGGAGCAAGG CCGTAGTGTC AAACAACTTC TAATTAAGCT
1161 GTGGGTCGAG CTGCTAACAA GTTTCAAGAA AGAATTGGAT
1201 TCATGGACGG AGAAGATGGC GCTAACCTTG GATGAGTACT
1241 TGTCTTTCTC CTGGGTGTCA ATTGGCTGCA GACTCTGCAT
1281 TCTCAATTCC CTGCAATTTC TTGGGATAAA ATTATCTGAA
1321 GAAATGCTGT GGAGTCAAGA GTGTCTGGAT TTATGCCGGC
1361 ATGTTTCATC AGTGGTTCGC CTGCTCAACG ATTTACAAAC
1401 TTTCAAGAAG GAGCGCATAG AAAATACGAT AAACGGTGTG
1441 GACGTTCAGC TAGCTGCTCG TAAAGGCGAA AGAGCCATTA
1481 CAGAAGAGGA GGCCATGTCC AAGATTAAGG AAATGGCTGA
1521 CCATCACAGG AGAAAACTGA TGCAAATTGT GTATAAAGAA
1561 GGAACCATTT TTCCAAGAGA ATGCAAAGAT GTGTTTTTGA
1601 GAGTGTGCAG GATTGGCTAC TATCTCTACT CGGGCGATGA
1641 GTTAACTTCT CCACAACAAA TGAAGGAGGA TATGAAAGCG
1681 TTGGTACATG AATCATCCTC TTGA
```

The *Mentha spicata* class I diterpene synthase (MsTPS1) has the amino acid sequence shown below (SEQ ID NO:5).

```
  1 MSSIRNLSLH IDLPKAEKKL VEKIRERIRN GRVEMSPSAY
 41 DTAWVAMVPS RGYSGRPGFP ECVDWIIENQ NPDGSWGLDS
 81 DQPLLVKDSL SSTLACLLAL RKWKTHNQLV QRGMEFIDSR
```

-continued

```
121 GWAATDDDNQ ISPIGFNIAF PAMINYAKEL NLTLPLHPPS
161 IHSLLHIRDS EIRKRNWEYV AEGVVDDTSN WKQIIGTHQR
201 NNGSLFNSPA TTAAAVIHSH DDKCFRYLIS TLENSNGGWV
241 PTIYPYDIYA PLCMIDTLER LGIHTYFEVE LSGIFDDIYR
281 NWQEREEEIF CNVMCRALAF RLLRMRGYHV SSDELAEFVD
321 KEEFFNSVSM QESGEGTVLE LYRASLTKIN EEERILDKIH
361 AWTKPFLKHQ LLNRSIRDKR LEKQVEYDLK NFYGALVRFQ
401 NRRTIDSYDA KSIQISKTAY RCSTVYNEDF IHLSVEDFKI
441 SRAQYLKELE EMNKWYSDCR LDLLTKGRNA CRESYILTAA
481 IIVDPHESMA RISYAQSILL ITVFDDFFDH YGSKEEALNI
521 IDLVKEWKPA GSYCSKEVEI LFTALHDTIN EIAAKADAEQ
561 GFSSKQQLIN MWVELLESAV REKDSLSXNK VSTLEEYLSF
601 APITIGCKLC VLTSVHFLGI KLSEEIWTSE ELSSLCRHGN
641 WCRLLNDLK  TYEREREENT LNSVSVQTVG GGVSEEEAVT
681 KVEEVLEFHR RKVMQLACRR GGSSVPRECK ELVWKTCTIG
721 YCLYGHDGGD ELSSPKDILK DINAMMFEPL K
```

A nucleic acid encoding the *Mentha spicata* class I diterpene synthase (MsTPS1) with SEQ ID NO:5 is shown below as SEQ ID NO:6.

```
   1 ATGAGTTCCA TTCGAAATTT AAGTTTGCAT ATTGATCTGC
  41 CAAAGGCCGA GAAGAAGTTG GTTGAGAAAA TCAGAGAGAG
  81 GATAAGAAAT GGGAGGGTGG AGATGTCGCC GTCGGCTTAC
 121 GACACCGCGT GGGTGGCCAT GGTGCCGTCT CGAGGATATT
 161 CCGGCAGGCC GGGTTTCCCG GAGTGCGTGG ATTGGATAAT
 201 CGAGAACCAG AATCCGGACG GGTCGTGGGG TTTGGATTCG
 241 GATCAACCAC TTCTGGTCAA AGACTCCCTC TCGTCCACCT
 281 TGGCATGCCT ACTTGCCCTG CGTAAATGGA AAACACACAA
 321 CCAACTAGTG CAAAGGGGCA TGGAGTTCAT CGACTCCCGT
 361 GGTTGGGCTG CAACTGATGA TGACAATCAG ATTTCTCCTA
 401 TTGGATTCAA TATTGCCTTT CCTGCAATGA TTAATTACGC
 441 CAAAGAGCTT AATTTAACTC TGCCTCTACA TCCACCTTCG
 481 ATTCATTCAT TGTTACACAT TAGAGATTCA GAAATAAGAA
 521 AGCGAAACTG GGAATACGTA GCTGAAGGAG TAGTCGACGA
 561 TACAAGCAAT TGGAAGCAAA TAATCGGCAC GCATCAAAGA
 601 AATAATGGAT CCTTGTTCAA CTCACCTGCT ACCACTGCAG
 641 CTGCTGTTAT TCACTCTCAC GACGATAAAT GTTTCCGATA
 681 TTTGATCTCC ACTCTTGAGA ATTCTAACGG TGGATGGGTA
 721 CCAACTATCT ATCCATACGA TATATACGCT CCTCTCTGCA
 761 TGATCGATAC GCTAGAAAGA TTAGGAATAC ACACATATTT
 801 TGAAGTTGAA CTCAGCGGCA TTTTTGATGA CATATACAGG
 841 AATTGGCAAG AGAGAGAAGA AGAGATCTTT TGTAATGTTA
 881 TGTGTCGAGC TCTGGCATTT CGGCTTCTAC GAATGAGGGG
 921 ATATCATGTT TCATCTGATG AACTAGCAGA ATTTGTGGAC
 961 AAGGAGGAGT TTTTTAATAG CGTGAGCATG CAAGAGAGCG
1001 GCGAAGGCAC AGTGCTTGAG CTTTACAGAG CTTCACTCAC
1041 AAAAATCAAC GAAGAAGAAA GGATTCTCGA CAAAATTCAT
1081 GCATGGACCA AACCATTTCT CAAGCACCAG CTTCTCAACC
1121 GCAGCATTCG CGACAAACGA TTAGAGAAGC AGGTGGAATA
1161 CGACTTGAAG AACTTCTACG GCGCACTAGT CCGATTCCAG
1201 AACAGAAGAA CCATCGACTC ATACGATGCT AAATCAATCC
1241 AAATTTCGAA AACAGCATAT AGGTGCTCTA CAGTTTACAA
1281 TGAAGACTTC ATCCATTTAT CCGTTGAGGA CTTCAAAATC
1321 TCCCGAGCAC AATACCTAAA AGAACTTGAA GAAATGAACA
1361 AGTGGTACTC TGATTGTAGG TTGGACCTCT TAACTAAAGG
1401 AAGAAATGCA TGTCGAGAAT CTTACATTTT AACAGCTGCA
1441 ATCATTGTCG ATCCTCACGA ATCCATGGCT CGAATCTCTT
1481 ACGCTCAATC TATTCTTCTT ATAACTGTTT TCGACGACTT
1521 TTTCGATCAT TATGGGTCTA AAGAAGAGGC TCTCAATATT
1561 ATTGATCTAG TCAAGGAATG GAAGCCAGCT GGCAGTTACT
1601 GCTCCAAAGA AGTGGAGATT TTGTTTACTG CATTACACGA
1641 CACGATAAAT GAGATTGCAG CCAAGGCTGA TGCAGAGCAA
1681 GGCTTTTCTT CCAAACAACA GCTTATCAAC ATGTGGGTGG
1721 AGCTACTTGA GAGCGCCGTG AGAGAAAAGG ACTCGCTGAG
1761 TGGNAACAAA GTGTCGACTC TAGAAGAGTA CTTATCTTTC
1801 GCACCAATCA CCATCGGCTG CAAACTTTGC GTCCTGACGT
1841 CTGTCCATTT CCTCGGAATC AAACTGTCCG AGGAAATCTG
1881 GACTTCCGAG GAGTTGAGCA GTCTGTGCAG GCACGGCAAT
1921 GTTGTCTGCA GACTGCTCAA CGACCTCAAG ACTTACGAGA
1961 GAGAGCGCGA AGAGAACACG CTCAACAGCG TGAGCGTGCA
2001 GACAGTGGGA GGAGGCGTTT CGGAGGAAGA GGCGGTGACG
2041 AAGGTGGAGG AGGTGTTGGA ATTTCATAGA AGAAAAGTGA
2081 TGCAGCTCGC GTGTCGAAGA GGAGGAAGCA GTGTTCCGAG
2121 AGAATGTAAG GAGCTGGTGT GGAAGACGTG CACGATAGGT
2161 TACTGCTTGT ACGGTCACGA CGGAGGCGAT GAGTTATCGT
2201 CTCCGAAGGA TATTCTAAAG GACATTAATG CAATGATGTT
2241 TGAGCCTCTC AAGTGA
```

A *Nepeta mussinii* ent-kaurene synthase (NmTPS2) was identified and isolated. This NmTPS2 enzyme was identified as an ent-kaurene synthase, which converts ent-CPP [16] into ent-kaurene [19].

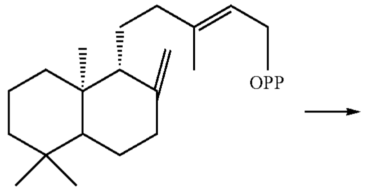

16

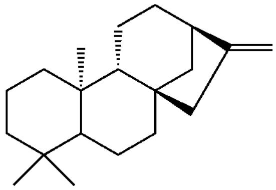

19

The *Nepeta mussinii* ent-kaurene synthase (NmTPS2) has the amino acid sequence shown below (SEQ ID NO:7).

```
  1 MSLPLSSCVL FPPNDSRFPV SRFSRASASL EVGLQGATSA
 41 KVSSQSSCFE ETKRRITKLF HKDELSVSTY DTAWVAMVPS
 81 PTSSEEPCFP GCLTWLLENQ CRDGSWARPH HHSLLKKDVL
121 SSTLACILAL KKWGVGEEQI NKGLHFIELN CASATEKCQI
161 TPVGFDIIFP AMLDYARDFS LNLRLEPTTF NDLMDKRDLE
201 LKRCYQNYTP EREAYLAYIV EGMGRLQDWE LVMKYQRKNG
241 SLFNCPSTTA AAFIALRDSA CLNYLNLSLK KFGNAVPAVY
281 PLDIYSQLCT VDNLERLGIN QYFIAEIQSV LDETYRCWIQ
321 GNEDIFLDTS TCALAFRILR MNGYDVTSDS LTKILEECFS
361 SSFRGNMTDI NTTLDLYRAS ELMLYPDEKD LEKHNLRLKL
401 LLKQKLSTVL IQSFQLGRNI NEEVKQTLEH PFYASLDRIA
441 KRKNIEHYNF DNTRILKTSY CSPNFGNKDF FFLSIEDFNW
481 CQVIHRQELA ELERWLIENR LDELKFARSK SAYCYFSAAA
521 TFFAPELSDA RMSWAKSGVL TTVVDDFFDV GGSMEELKNL
561 IQLVELWDVD ASTKCSSHNV HIIFSALRRT IYEIGNKGFK
601 LQGRNITNHI IDIWLDLLNS MMKETEWARD NFVPTIDEYM
641 SNAYTSFALG PIVLPTLYLV GPKLSEEMIN HSEYHNLFKL
681 MSTCGRLLND IRGYERELKD GKLNALSLYI INNGGKVSKE
721 AGISEMKSWI EAQRRELLRL VLESNKSVLP KSCKELFWHM
761 CSVVHLFYCK DDGFTSQDLI QVVNAVIHEP IALKDFKVHE
```

A nucleic acid encoding the *Nepeta mussinii* ent-kaurene synthase (NmTPS2) with SEQ ID NO:7 is shown below as SEQ ID NO:8.

```
   1 ATGTCTCTTC CGCTCTCCTC TTGTGTCTTA TTTCCCCCCA
  41 ATGACTCACG TTTTCCGGTC TCCCGCTTTT CTCGCGCTTC
  81 AGCTTCTTTG GAAGTCGGGC TTCAAGGAGC TACTTCAGCA
```

-continued

```
 121 AAAGTCTCCT CACAATCATC GTGTTTTGAG GAGACAAAGA
 161 GAAGGATAAC AAAGTTGTTT CATAAGGACG AACTTTCGGT
 201 TTCGACATAT GACACAGCAT GGGTTGCTAT GGTCCCTTCT
 241 CCAACTTCTT CAGAGGAACC TTGCTTCCCA GGTTGTTTGA
 281 CTTGGTTGCT TGAAAACCAG TGTCGAGATG GTTCATGGGC
 321 TCGTCCCCAC CATCACTCTT TGTTAAAAAA AGATGTCCTT
 361 TCTTCTACCT TGGCATGCAT TCTCGCACTT AAAAAATGGG
 401 GGGTTGGTGA AGAACAAATC AACAAGGGTT TGCATTTTAT
 441 AGAGCTAAAT TGTGCTTCAG CTACCGAGAA GTGTCAAATT
 481 ACTCCCGTGG GGTTTGACAT TATATTTCCT GCCATGCTTG
 521 ATTATGCAAG AGACTTCTCT TTGAACTTGC GTTTAGAGCC
 561 AACTACGTTT AATGATTTGA TGGATAAAAG GGATTTAGAG
 601 CTCAAAAGGT GTTACCAAAA TTACACACCG GAGAGGGAAG
 641 CATACTTGGC ATATATAGTT GAAGGAATGG GAAGATTGCA
 681 AGATTGGGAA TTGGTGATGA AATATCAAAG AAAGAATGGA
 721 TCTCTTTTCA ATTGTCCATC TACAACTGCA GCAGCTTTTA
 761 TTGCCCTTCG GGATTCTGCG TGCCTCAACT ATCTGAATTT
 801 GTCTTTGAAA AAGTTCGGGA ATGCAGTTCC TGCAGTTTAT
 841 CCTCTAGATA TATATTCTCA ACTTTGCACG GTTGATAATC
 881 TTGAAAGGCT GGGGATCAAC CAATATTTTA TAGCAGAAAT
 921 TCAGAGTGTG TTGGATGAAA CGTACAGATG TTGGATACAG
 961 GGAAACGAAG ACATATTTTT GGACACCTCA ACTTGTGCTT
1001 TAGCATTCCG AATATTGAGA ATGAATGGCT ATGATGTGAC
1041 TTCAGATTCA CTTACAAAAA TCCTAGAAGA GTGCTTTTCA
1081 AGTTCCTTTC GTGGAAATAT GACAGACATT AACACAACTC
1121 TTGACTTATA TAGGGCATCA GAACTTATGT TATATCCAGA
1161 TGAAAAGGAT CTGGAGAAAC ATAATTTAAG GCTTAAACTC
1201 TTACTTAAGC AAAAACTATC CACTGTTTTA ATCCAATCAT
1241 TTCAACTTGG AAGAAATATC AATGAAGAGG TGAAACAGAC
1281 TCTCGAGCAT CCCTTTTATG CAAGTTTGGA TAGGATTGCA
1321 AAGCGGAAAA ATATAGAGCA TTACAACTTT GATAACACAA
1361 GAATTCTTAA AACTTCATAT TGTTCGCCAA ATTTTGGCAA
1401 CAAGGATTTC TTTTTTCTTT CCATAGAAGA CTTCAATTGG
1441 TGTCAAGTCA TACATCGACA AGAACTCGCA GAACTTGAAA
1481 GATGGTTAAT TGAAAATAGA TTGGATGAGC TGAAGTTTGC
1521 AAGGAGTAAG TCTGCATACT GTTATTTTTC TGCGGCAGCA
1561 ACTTTTTTTG CTCCAGAATT GTCGGATGCC CGCATGTCAT
1601 GGGCTAAAAG TGGTGTTCTA ACCACAGTGG TAGATGACTT
1641 TTTTGATGTT GGAGGTTCTA TGGAGGAATT GAAGAACTTA
1681 ATTCAATTGG TTGAACTATG GGATGTGGAT GCTAGCACAA
1721 AATGCTCTTC TCATAATGTC CATATAATAT TTTCAGCACT
```

-continued

```
1761 TAGGCGCACC ATCTATGAGA TAGGGAACAA AGGATTTAAG

1801 CTACAAGGAC GTAACATTAC CAATCATATA ATTGACATTT

1841 GGCTAGATTT ACTAAACTCT ATGATGAAAG AAACCGAATG

1881 GGCCAGAGAC AACTTTGTCC CAACAATTGA TGAATACATG

1921 AGCAATGCAT ATACATCGTT TGCTCTGGGG CCAATTGTCC

1961 TTCCAACTCT CTATCTTGTC GGGCCCAAGC TCTCAGAAGA

2001 GATGATTAAC CACTCCGAAT ACCATAACCT ATTCAAATTG

2041 ATGAGTACGT GCGGACGTCT TCTAAATGAC ATCCGTGGTT

2081 ATGAGAGAGA ACTGAAAGAT GGTAAATTGA ACGCGTTATC

2121 ATTGTACATA ATTAATAATG GTGGTAAAGT AAGTAAAGAA

2161 GCTGGCATCT CGGAGATGAA AAGTTGGATC GAGGCACAAC

2201 GAAGAGAGTT ACTGAGATTA GTTTTGGAGA GCAACAAAAG

2241 CGTCCTTCCG AAGTCGTGCA AGGAATTGTT TTGGCATATG

2281 TGCTCAGTGG TGCATCTATT CTACTGCAAA GATGATGGAT

2321 TCACCTCGCA GGATTTGATT CAAGTTGTAA ATGCAGTTAT

2361 TCATGAACCT ATTGCTCTCA AGGATTTTAA GGTGCATGAA

2401 TAA
```

An *Origanum majorana* trans-abienol synthase (OmTPS3) was identified and isolated. When this OmTPS3 enzyme was expressed in *N. benthamiana* with *Hyptis suaveolens* labda-7,13E-dienyl diphosphate synthase (HsTPS1) a new compound, labda-7,12E,14-triene [24], was produced. The HsTPS1 enzyme produced labda-7,13(16),14-triene [22] when HsTPS1 was expressed in *N. benthamiana*.

24

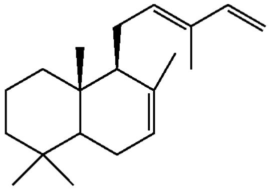

22

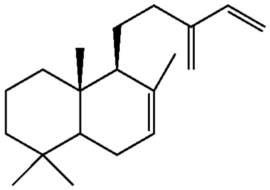

OmTPS3 also produced trans-abienol [11] from labda-13-en-8-ol diphosphate ((+)-8-LPP) [10]).

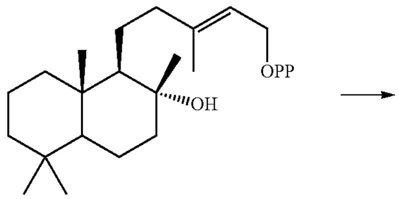

10

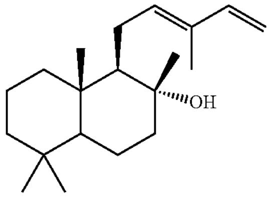

11

The *Origanum majorana* trans-abienol synthase (OmTPS3) has the amino acid sequence shown below (SEQ ID NO:9).

```
MASLAETPGA ATFSGNVVRR RKDNFPVHGF PTTIRSSVSV
TVKCYVSTTN LMVKIKEKFK GKNVNSLTVE AADDDMPSNL
CIIDTLQRLG IDRYFQPQVD SVLDHAYKLW QGKEKDTVYS
DISIHAMAFR LLRVKGYQVS SEELDPYIDV ERMKKLKTVD
VPTVIELYRA AQERMYEEEG SLERLHVWST NFLMHQLQAN
SIPDEKLHKL VEYYLKNYHG ILDRVGVRRN LDLFDISHYP
TLRARVPNLC TEDFLSFAKE DFNTCQAQHQ KEHEQLQRWF
EDCRFDTLKF GRETAVGAAH FLSSAILGES ELCNVRLALA
KHMVLVVFID DFFDHYGSRE DSFKILHLLK EWKEKPAGEY
GSEEVEILFT AVYNTVNELA EMAHVEQGRN IKGFLIELWV
EIVSIFKIEL DTWSNDTTLT LDEYLSSSWV SVGCRICILV
SMQLLGVQLT DEMLLSDECI NLCKHVSMVD RLLNDVGTFE
KERKENTGNS VSLLLAAAVK EGRPITEEEA IIKIKKMAEN
ERRKLMQIVY KRESVFPRKC KDMFLKVCRI GCYLYASGDE
FTSPQKMKED VKSLIYESL
```

A nucleic acid encoding the *Origanum majorana* trans-abienol synthase (OmTPS3) with SEQ ID NO:9 is shown below as SEQ ID NO:10.

```
ATGGCGTCGC TCGCGTTCAC ACCCGGAGCC GCCACTTTCT
CCGGCAACGT AGTTCGGAGG AGGAAAGATA ACTTTCCGGT
CCACGGATTT CCGACGACGA TCAGGTCATC GGTCTCCGTC
ACCGTCAAAT GCTACGTCAG TACAACGAAT TTGATGGTGA
AAATCAAAGA GAAGTTCAAG GGTAAAAACG TCAATTCGCT
GACAGTTGAA GCTGCTGATG ACGATATGCC CTCTAATCTG
TGCATAATTG ACACCCTCCA ACGATTGGGA ATCGACCGTT
ACTTCCAACC CCAAGTCGAC TCTGTTCTCG ACCACGCCTA
```

-continued

```
CAAACTATGG CAAGGGAAAG AGAAAGATAC GGTGTATTCG
GACATTAGTA TTCATGCGAT GGCATTTAGA CTTTTACGAG
TCAAAGGCTA TCAAGTCTCT TCGGAGGAAC TGGATCCATA
CATCGATGTG GAGCGAATGA AGAAACTGAA AACAGTTGAT
GTTCCGACGG TTATCGAACT GTACAGAGCG GCACAGGAGA
GAATGTATGA AGAAGAAGGT AGCCTTGAGA GACTCCATGT
TTGGAGCACC AACTTCCTCA TGCACCAGCT GCAGGCTAAC
TCAATTCCTG ATGAAAAGCT ACACAAACTG GTGGAATACT
ACTTGAAGAA CTACCATGGC ATACTGGATA GAGTTGGAGT
TCGACGAAAC CTCGACCTAT TCGACATAAG CCATTATCCA
ACACTCAGAG CTAGGGTTCC GAACCTATGT ACCGAAGATT
TTCTATCGTT CGCGAAGGAA GATTTCAATA CTTGCCAAGC
CCAACACCAG AAAGAACATG AGCAACTACA AAGGTGGTTC
GAAGATTGTA GGTTCGATAC GTTGAAGTTC GGAAGGGAGA
CAGCCGTAGG CGCTGCTCAT TTTCTATCTT CAGCAATACT
TGGTGAATCT GAACTATGTA ATGTTCGTCT TGCCCTTGCT
AAGCATATGG TGCTTGTGGT ATTCATCGAT GACTTCTTCG
ACCATTATGG CTCTAGAGAA GACTCCTTCA AGATCCTCCA
CCTCTTAAAA GAATGGAAAG AGAAGCCGGC CGGAGAATAC
GGTTCCGAGG AAGTCGAAAT CCTCTTCACA GCCGTATACA
ATACAGTAAA CGAGTTGGCG GAGATGGCTC ATGTCGAACA
AGGACGTAAT ATCAAAGGAT TTCTAATTGA ATTGTGGGTT
GAAATAGTGT CAATTTTCAA GATAGAACTG GATACATGGA
GCAATGACAC AACACTAACC TTGGATGAGT ACTTGTCCTC
CTCATGGGTG TCGGTCGGTT GCAGAATCTG CATCCTCGTC
TCAATGCAGC TCCTCGGTGT ACAACTAACC GACGAAATGC
TTCTGAGCGA CGAGTGCATA AACCTGTGTA AGCATGTCTC
GATGGTCGAT CGCCTCCTCA ACGACGTCGG AACATTCGAG
AAGGAACGGA AGGAGAATAC AGGAAACAGT GTGAGCCTTC
TGCTAGCAGC AGCTGTGAAA GAAGGAAGGC CTATTACCGA
AGAGGAAGCT ATTATTAAAA TTAAAAAAAT GGCGGAAAAC
GAGAGGAGGA AACTAATGCA GATTGTGTAT AAAAGAGAGA
GTGTTTTCCC CAGAAAATGC AAGGATATGT TCTTGAAGGT
GTGTAGAATT GGGTGCTATC TATACGCGAG CGGCGACGAA
TTTACGTCTC CTCAGAAAAT GAAGGAAGAT GTGAAATCCT
TAATTTATGA ATCCTTGTAG
```

The *Origanum majorana* manool synthase (OmTPS4) can also convert ent-copalyl diphosphate (ent-CPP) [16] to ent-manool [20].

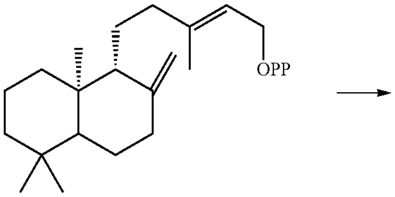

16

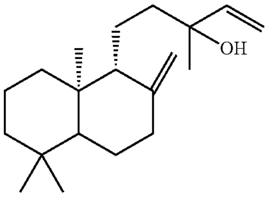

20

In addition, *Origanum majorana* manool synthase (OmTPS4) can also convert (+)-copalyl diphosphate ((+)-CPP) [31]) to manool [33].

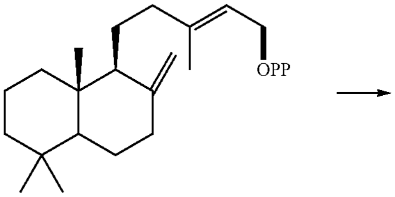

31

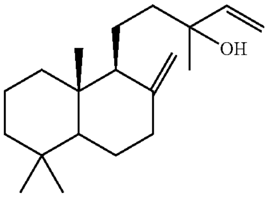

33

The *Origanum majorana* manool synthase (OmTPS4) can have the amino acid sequence shown below (SEQ ID NO:11).

```
MSLAFSHVST FFSGQRVVGS RREIIPVNGV PTTANKPSFA
VKCNLTTKDL MVKMKEKLKG QDGNLTVGVA DMPSSLCVID
TLERLGVDRY FRSEIHVILH DTYRLWQQKD KDICSNVTTH
AMAFRLLRVN GYEVSSEELA PYANLEHFSQ QKVDTAMAIE
LYRAAQERIH EDESGLDKIL AWTTTFLEQQ LLTNSILDNK
LHKLVEYYLN NYHGQTNRVG ARRHLDLYEM SHYQNLKPSH
SLCNEDLLAF AKQGFRDFQI QQQKEFEQLQ RWYEDCRLDK
LSYGRDVVKI SSFMASILMD DPELADVRLS IAKQMVLVTR
IDDFFDHGGS REDSYKIIEL VKEWKEKAEY DSEEVKILFT
AVYTTVNELA EACVQQGRNS TTVKEFLVQL WIEILSAFKV
ELDTWSDGTE VSLDEYLSWS WISNGCRVSI VTTMHLLPTK
LCSDEMLRSE ECKDLCRHVS MVGRLLNDIH SFEKEHEENT
```

-continued

GNSVSILVAG EDTEEEAIGK IKEIVEYERR KLMQIVYKRG

TILPRECKDI FLKACRATFY VYSSTDEFTS PRQVMEDMKT

LSS

A nucleic acid encoding *Origanum majorana* manool synthase (OmTPS4) with SEQ ID NO:11 is shown below as SEQ ID NO:12.

ATGTCACTCG CCTTCAGCCA TGTTAGTACC TTTTTCTCCG

GCCAAAGAGT CGTCGGAAGC AGGAGAGAGA TTATTCCAGT

TAACGGAGTT CCGACGACGG CCAATAAGCC GTCGTTCGCC

GTTAAGTGCA ACCTTACTAC AAAGGATTTG ATGGTGAAAA

TGAAGGAGAA GTTGAAGGGG CAAGACGGTA ATTTGACTGT

CGGAGTAGCC GATATGCCCT CTAGCCTGTG CGTGATCGAC

ACTCTTGAAA GGTTGGGAGT TGACCGATAC TTCCGATCTG

AAATCCACGT TATTCTACAC GACACTTACC GGTTATGGCA

ACAAAAGGAC AAAGATATAT GTTCCAACGT TACTACTCAT

GCAATGGCGT TTAGACTTCT GAGAGTGAAT GGATACGAGG

TTTCATCAGA GGAACTGGCT CCATATGCTA ACCTAGAGCA

CTTTAGCCAG CAAAAAGTTG ATACTGCAAT GGCTATAGAG

CTCTACAGAG CAGCACAGGA GAGAATACAC GAAGACGAGA

GCGGTCTCGA CAAAATACTT GCTTGGACCA CCACTTTTCT

CGAGCAACAG CTGCTCACTA ACTCCATTCT TGACAATAAA

TTGCATAAAC TGGTGGAGTA CTACTTGAAC AACTACCACG

GCCAAACGAA TAGGGTCGGA GCTAGACGAC ACCTCGACCT

ATATGAGATG AGCCATTACC AAAATCTAAA ACCTTCACAT

AGTCTATGCA ATGAAGACCT TCTAGCATTT GCAAAGCAAG

GTTTTCGAGA TTTTCAAATC CAGCAGCAGA AAGAATTCGA

GCAACTGCAA AGGTGGTATG AAGATTGCAG GTTGGACAAG

TTGAGTTATG GGAGAGATGT AGTAAAAATT TCTAGTTTCA

TGGCTTCAAT ATTGATGGAT GATCCAGAAT TAGCCGATGT

TCGTCTCTCC ATCGCCAAAC AGATGGTGCT CGTGACACGT

ATCGATGATT TCTTCGACCA CGGTGGCTCT AGAGAAGACT

CCTACAAGAT CATTGAACTA GTAAAAGAAT GGAAGGAGAA

GGCaGAATAC GATTCCGAGG AAGTAAAAAT CCTTTTTACA

GCAGTATACA CCACAGTAAA TGAGCTAGCA GAGGCTTGTG

TTCAACAAGG AAGGAATAGT ACTACTGTCA AAGAATTCCT

AGTTCAGTTG TGGATTGAAA TACTATCAGC TTTCAAGGTC

GAGCTAGATA CGTGGAGCGA TGGCACGGAA GTAAGCCTGG

ACGAGTACTT GTCGTGGTCG TGGATTTCGA ATGGCTGCAG

AGTGTCTATA GTAACGACGA TGCATTTGCT CCCTACGAAA

TTATGCAGTG ATGAAATGCT TAGGAGTGAA GAGTGCAAGG

-continued

ATTTGTGTAG GCATGTTTCT ATGGTTGGCC GCTTGCTCAA

CGACATCCAC TCTTTTGAGA AGGAGCATGA GGAGAATACG

GGAAACAGTG TGAGCATTCT AGTAGCAGGT GAGGATACCG

AAGAGGAAGC TATTGGAAAG ATCAAAGAGA TAGTTGAGTA

TGAGAGGAGA AAATTGATGC AAATTGTGTA CAAGAGAGGA

ACCATTCTCC CAAGAGAATG CAAAGACATA TTCTTGAAGG

CGTGTAGGGC TACATTTTAC GTGTACTCGA GCACGGATGA

GTTTACGTCT CCTCGACAAG TGATGGAAGA TATGAAAACC

CTAAGCTCCT AG

*Origanum majorana* palustradiene synthase (OmTPS5) can also convert (+)-copalyl diphosphate ((+)-CPP) [M]) to palustradiene [29].

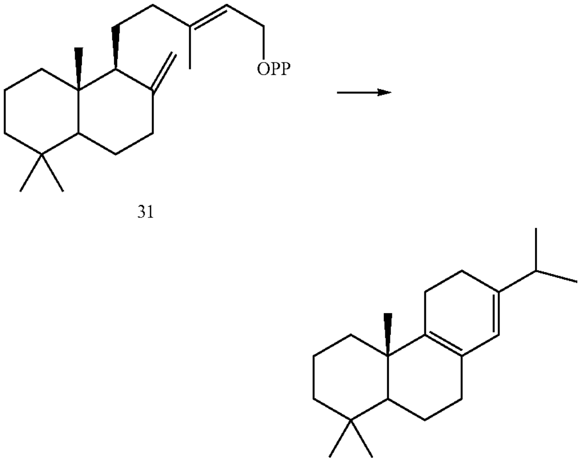

31

29

The *Origanum majorana* palustradiene synthase (OmTPS5) can have the amino acid sequence shown below (SEQ ID NO:13).

MVSACLKLKN NPFLDHRFRK SSNGFSVNFP ATMLTTVKCS

RDNSEDLIAK IKERMNEKFV TVPAREYSVI EHRNPKPAWC

GGLQSKTVIE EEVCSRLFLV EHLQDLGVDR FFQSEIQHIL

HHTFRLWQQK DEQVFKDVTC RAMAFRLLRL EGYHVSSGEL

GEYVDEEKFF RTVRLEWRST DTILELYKAS QVRLPEDDND

NSNILKNLHE WTFIFLKEQL RRKTILDKGL ERKVEFYLKN

YHGILDAVKH RRSLDHTRFW KTTAYNPAVY DEDLFRLSAQ

DFMARQAQSQ KELEMLLKWY DECRLDKMEY GRNVIHVSHF

LNANNFPDPR LSETRLSFAK TMTLVTRLDD FFDHHGSRED

SVLIIELIRQ WNEPSTITTI FPSEEVEILY SALHSTVTDI

AEKAYPIQGR CIKSLIIHLW VEILSSFMSE MDSCTAETQP

DFHEYLGFAW ISIGCRICIL IAIHFLGEKV SQQMVMGAEC

TELCRHVSTI ARLLNDLQTF KKEREERKVN SVIIQLKGDK

-continued

ISEEVAVSNI ERMVEYHRKE LLKMVVRREG SLVPKRCKDV

FWKSCNIAYY LYAFTDEFTS PQQMKEDMKL LFRDPINCVP

SIPS

A nucleic acid encoding the *Origanum majorana* palustradiene synthase (OmTPS5) with SEQ ID NO:13 is shown below as SEQ ID NO:14.

ATGGTATCTG CATGTCTAAA ACTCAAAAAT AATCCTTTCT

TGGACCATCG ATTCAGGAAA AGCAGCAATG GATTTTCAGT

TAATTTTCCG GCGACCATGC TCACCACTGT CAAGTGCAGC

CGCGATAATT CAGAAGACTT GATAGCAAAG ATAAAAGAAA

GGATGAATGA AAAATTTGTT ACGGTGCCGG CGAGGGAATA

TTCCGTCATT GAGCATCGGA ATCCGAAGCC GGCGTGGTGC

GGTGGTTTGC AATCCAAAAC AGTAATAGAA GAAGAAGTGT

GCAGCCGTCT GTTTCTGGTC GAACACCTTC AAGATTTAGG

AGTAGACCGC TTCTTTCAAT CAGAAATCCA ACATATTCTA

CATCACACAT TCAGATTATG GCAGCAAAAA GATGAACAAG

TTTTTAAAGA CGTGACATGT CGCGCCATGG CATTCAGACT

CCTGCGTCTC GAAGGTTATC ATGTCTCGTC AGGAGAATTG

GGGGAGTATG TTGATGAGGA AAAATTCTTT AGAACGGTAA

GGTTAGAATG GAGAAGTACG GATACAATTC TTGAGCTGTA

CAAAGCATCA CAGGTAAGAC TACCTGAAGA CGACAACGAC

AATTCCAATA TCCTCAAAAA CTTGCACGAA TGGACCTTCA

TATTTTTGAA GGAGCAGTTG CGGCGTAAAA CTATTCTTGA

TAAAGGTTTA GAGAGAAAGG TAGAATTTTA CTTGAAGAAT

TACCACGGCA TATTAGACGC GGTTAAGCAT AGACGAAGCC

TCGATCACAC ACGATTCTGG AAAACTACTG CGTATAACCC

TGCAGTGTAT GATGAGGATC TTTTCCGATT GTCGGCCCAA

GATTTCATGG CTCGCCAAGC TCAGAGCCAG AAGGAACTTG

AGATGTTGCT CAAGTGGTAC GATGAATGTA GACTGGACAA

GATGGAGTAT GGGCGAAACG TGATACACGT TTCCCATTTC

TTAAACGCAA ACAACTTCCC CGATCCTCGC CTGTCCGAAA

CTCGTCTATC CTTTGCGAAA ACCATGACTC TCGTCACGCG

TTTGGATGAT TTCTTCGATC ACCATGGCTC TAGAGAAGAT

TCGGTCCTCA TCATCGAATT AATAAGGCAG TGGAATGAGC

CTTCAACTAT TACAACAATA TTCCCCTCCG AAGAAGTGGA

GATTCTCTAC TCTGCACTCC ACTCCACCGT AACAGATATA

GCAGAGAAGG CTTATCCCAT CCAGGGTCGC TGCATCAAAT

CGCTCATAAT TCATCTGTGG GTCGAGATAC TGTCGAGCTT

CATGAGCGAA ATGGACTCGT GCACCGCGGA AACTCAGCCG

GACTTTCACG AGTACTTAGG GTTTGCATGG ATCTCGATCG

GCTGCAGAAT CTGCATTCTC ATAGCTATAC ATTTCTTGGG

-continued

GGAGAAGGTA TCTCAACAAA TGGTTATGGG TGCTGAGTGC

ACCGAGTTAT GTAGGCACGT TTCTACGATC GCACGCCTTC

TCAACGATCT CCAAACCTTT AAGAAGGAGA GAGAAGAGAG

GAAGGTAAAC AGCGTGATAA TCCAGCTCAA AGGGGATAAG

ATATCGGAGG AGGTGGCCGT GTCGAATATA GAGAGAATGG

TTGAATATCA CAGGAAAGAG CTGCTGAAGA TGGTGGTTCG

GAGAGAAGGA AGCTTGGTTC CTAAGAGGTG TAAGGACGTG

TTCTGGAAAT CCTGCAACAT TGCTTACTAT CTGTACGCTT

TTACAGATGA ATTCACTTCG CCTCAACAAA TGAAGGAAGA

TATGAAACTA CTCTTTCGTG ATCCAATCAA CTGCGTTCCT

TCAATTCCTT CATGA

The *Perovskia atriplicifolia* miltiradiene synthase (PaTPS3) can have the amino acid sequence shown below (SEQ ID NO:15).

MLLAFNISDV PLSQHRVILS RREHFPRHAF QEFPMIAATK

SSVNAICSLA TPTDLMGKIK EKFKAKDGDP LAAAAIQLAA

DIPSSLCIID TLQRLGVDRY FQSEIDSILE ETHKLWKVKD

RDIYSEVTTH AMAFRLLRVK GYEVSSEELA PYAEQERFDL

QTIDLATVIE LYRAAQERTC EENDNSLEKL LAWTTTFLKH

QLLTNSIPDT KLHKQVEYYL KNYHGILDRM GVRRSLDLYD

ISHYRPLRAR FPNLCNEDFL SFARQDFSMC QAQHQKELEQ

LQRWYSDCRL DALLKFGRNV VRVSSFLTSA IIGEPELSEV

RLVFAKHIIL VTLIDDLFDH GGTREESYKI LELVTEWKEK

TAAEYGSEEV EILFTAVYNT VNELVERAHV EQGRSVKEFL

IKLWVQILSI FKIELDTWSD ETALTLDEYL SSSWVSIGCR

ICILMSMQFI GIKLTDEMLL SEECTDLCRH VSMVDRLLND

VQTFEKERKE NTGNSVSLLL AANKDVTEEE AIRRAKEMAE

CNRRQLMQIV YKTGTIFPRK CKDMFLKVCR IGCYLYASGD

EFTSPQQMME DMKSLVYEPL YLPN

A nucleic acid encoding the *Perovskia atriplicifolia* miltiradiene synthase (PaTPS3) with SEQ ID NO:15 is shown below as SEQ ID NO:16.

ATGTTACTTG CGTTCAACAT AAGCGATGTC CCTCTCTCGC

AGCATAGAGT AATTCTGAGC AGGAGGGAAC ATTTTCCACG

TCATGCATTC CAGGAATTTC CGATGATCGC CGCTACTAAG

TCATCTGTTA ATGCCATTTG CAGCCTCGCT ACTCCAACTG

ATTTGATGGG AAAAATAAAA GAGAAGTTCA AGGCCAAGGA

CGGCGATCCT CTTGCCGCCG CGGCTATTCA ACTCGCGGCG

GATATACCCT CGAGTCTGTG TATAATCGAC ACCCTCCAGA

GGTTGGGAGT CGACCGATAC TTCCAATCCG AAATCGACTC

-continued

```
TATTCTAGAG GAAACACACA AGTTATGGAA AGTGAAAGAT
AGAGATATAT ACTCTGAGGT TACTACTCAT GCAATGGCGT
TTAGACTTCT GCGAGTGAAG GGATATGAAG TTTCATCAGA
GGAACTAGCT CCGTATGCTG AGCAAGAGCG CTTTGACCTG
CAAACGATTG ATCTGGCGAC GGTTATCGAG CTTTACAGAG
CAGCACAGGA GAGAACATGC GAAGAAAACG ACAACAGTCT
TGAGAAACTA CTTGCTTGGA CCACCACCTT TCTCAAGCAC
CAATTGCTCA CCAACTCCAT ACCTGACACC AAATTGCACA
AACAGGTGGA ATACTACTTG AAGAACTACC ACGGGATATT
AGATAGAATG GGAGTTAGAC GAAGCCTCGA CCTATACGAC
ATAAGCCATT ATCGACCTCT GAGAGCAAGA TTCCCTAATC
TGTGTAATGA AGATTTCCTA TCATTTGCGA GGCAAGATTT
CAGTATGTGC CAAGCCCAAC ACCAGAAGGA ACTTGAGCAA
CTGCAAAGGT GGTATTCTGA TTGTAGGTTG GACGCGTTGT
TGAAGTTTGG AAGAAATGTA GTGCGCGTTT CTAGCTTTCT
GACTTCAGCA ATTATTGGTG AACCCGAATT GTCTGAAGTT
CGACTAGTCT TTGCCAAACA TATTATTCTC GTTACACTTA
TTGATGATTT ATTCGATCAT GGTGGAACTA GAGAAGAGTC
ATACAAGATC CTTGAATTAG TAACAGAATG GAAAGAGAAG
ACCGCAGCAG AATATGGTTC CGAGGAAGTT GAAATCCTTT
TTACAGCGGT CTACAACACA GTAAATGAGT TGGTAGAGAG
GGCTCATGTC GAACAAGGGC GCAGTGTCAA AGAATTTCTT
ATTAAACTGT GGGTTCAAAT ACTATCAATT TTCAAGATAG
AATTAGATAC ATGGAGCGAT GAGACTGCGC TAACCTTGGA
TGAATACTTG TCTTCGTCGT GGGTGTCAAT TGGTTGCAGA
ATCTGCATTC TCATGTCGAT GCAATTCATC GGTATAAAAT
TAACTGATGA AATGCTTCTG AGTGAAGAGT GCACTGATTT
GTGTAGGCAT GTTTCGATGG TTGACCGGCT GCTCAACGAT
GTGCAAACCT TCGAGAAGGA ACGCAAAGAA AATACAGGAA
ACAGTGTAAG CCTTCTGCTA GCAGCTAACA AAGATGTTAC
TGAAGAGGAA GCAATTAGAA GAGCAAAAGA AATGGCGGAA
TGCAACAGGA GACAACTGAT GCAGATTGTG TATAAAACAG
GAACCATTTT CCCAAGAAAA TGCAAAGATA TGTTTCTCAA
GGTATGCAGG ATTGGCTGTT ATTTGTATGC AAGCGGCGAC
GAATTCACAT CTCCACAACA AATGATGGAA GATATGAAAT
CCTTGGTTTA TGAACCCCTC TACCTACCTA ATTAA
```

A *Perovskia atriplicifolia* miltiradiene synthase (PaTPS1) can have the amino acid sequence shown below (SEQ ID NO:17).

```
MSLTFNAGVV RFSSHRVRST KDCFTVYGFP MIANKAAFAV
KCSLTPTDLM GRVEEKFKGK NGNSLAASTT VESADIPSNL
```

-continued

```
CIIDTLQRLG VDRYFQTEIN AILEDTYRLW ERKDKDIYSD
ATTHAMAFRL LRVKGYEVSS EELAPYADQE CVNVQTADVA
TVIELYRAAQ VRISEEESSL KKLHAWTTTF LKYQLQSNSI
PEKKLHKLVE YYLKNYHGIL DRMGVRMDLD LFDISHYRTL
QASDRFSSLR NEDFLEFARQ DFNICQAKHQ KELQQLQRWY
ADCRLDTLKF GRDVVRVANF LTSAIFGEPE LSDARLIFAK
HIVLVTCIDE FFDHGGSKEE SYKILELVEE WKEKPTGEYG
CEEVEILFTA VYSTVNELAE MAHVEQGRSV KEFLVKLWVQ
ILSIFKIELD TWSDDTELTL DSYLNNSWVS IGCRICILMS
MQFAGVKLSD EMLLSEECVD LCRHVSMVDR LLNDVQTFEK
ERKENTGNSV SLLQAAAERE GRAITEEEAI TQIKELAEYH
RRKLMQIVYK TDTIFPRKCK DMFLKVCRIG CYLYASGDEF
TTPQQMMEDM KSLVYQPLTV DDMSAKELTS VRN
```

A nucleic acid encoding the *Perovskia atriplicifolia* miltiradiene synthase (PaTPS1) with SEQ ID NO:17 is shown below as SEQ ID NO:18.

```
ATGTCACTCA CTTTCAACGC TGGAGTCGTC CGTTTCTCCA
GCCACCGCGT TCGGAGCACG AAAGATTGCT TTACAGTTTA
CGGATTTCCG ATGATTGCAA ATAAGGCAGC TTTCGCAGTT
AAATGCAGCC TTACTCCAAC CGATTTGATG GGGAGAGTAG
AGGAGAAGTT CAAGGGCAAA AATGGTAATT CACTAGCAGC
CTCGACGACG GTTGAATCCG CGGATATACC CTCGAACCTG
TGTATAATCG ACACCCTCCA AAGATTGGGA GTCGACCGAT
ACTTTCAAAC TGAAATCAAT GCCATTCTAG AGGACACTTA
CAGATTATGG GAACGAAAAG ACAAAGACAT ATATTCCGAT
GCCACAACTC ACGCGATGGC GTTTAGGTTA CTACGAGTGA
AAGGATACGA AGTTTCATCA GAGGAACTGG CTCCTTACGC
TGATCAAGAG TGCGTGAACG TGCAAACGGC TGATGTGGCA
ACAGTTATCG AGCTTTACAG AGCAGCGCAG GTGAGAATAA
GCGAAGAAGA GAGCAGTCTT AAGAAGCTTC ATGCTTGGAC
CACCACCTTT CTCAAATATC AGTTGCAGAG TAACTCCATA
CCTGAAAAGA AACTGCACAA ACTGGTGGAA TATTACTTGA
AGAACTACCA TGGCATATTG GATAGAATGG GAGTTCGAAT
GGACCTCGAC TTATTCGACA TCAGCCATTA TCGAACTCTA
CAAGCTTCCG ATAGGTTCTC TAGTCTGCGT AACGAAGATT
TTCTAGAGTT TGCAAGGCAA GATTTCAATA TCTGCCAAGC
CAAGCACCAG AAAGAACTCC AACAACTGCA AAGGTGGTAT
GCAGATTGCA GGCTCGACAC CTTGAAGTTC GGGAGAGACG
TCGTACGCGT TGCTAATTTT CTGACTTCAG CAATCTTTGG
CGAACCCGAG CTATCCGATG CTCGTCTGAT CTTTGCCAAG
```

-continued

```
CATATCGTGC TCGTAACATG TATCGATGAA TTCTTCGATC
ATGGTGGGTC TAAAGAAGAG TCCTACAAGA TCCTTGAATT
AGTAGAAGAA TGGAAAGAGA AGCCAACTGG AGAATATGGG
TGTGAGGAGG TTGAGATCCT TTTCACAGCA GTGTACAGTA
CAGTGAATGA GTTGGCAGAG ATGGCTCATG TCGAACAAGG
ACGTAGTGTG AAAGAGTTTC TAGTTAAACT GTGGGTGCAG
ATACTGTCGA TTTTCAAGAT AGAACTGGAT ACATGGAGTG
ATGACACGGA ACTGACGTTG GACAGCTACT TGAACAACTC
GTGGGTGTCG ATCGGATGCA GAATCTGCAT TCTCATGTCG
ATGCAGTTCG CCGGTGTAAA ACTGTCCGAC GAAATGCTTC
TGAGTGAAGA GTGTGTTGAC TTGTGCAGGC ACGTCTCCAT
GGTCGATCGC CTCCTGAACG ATGTGCAAAC TTTCGAGAAG
GAACGCAAGG AAAATACAGG AAACAGTGTG AGCCTTCTGC
AAGCAGCAGC TGAGAGAGAA GGAAGAGCCA TTACAGAAGA
GGAAGCTATT ACACAGATCA AAGAATTGGC TGAATACCAC
AGGAGAAAAC TGATGCAGAT TGTGTACAAA ACAGACACCA
TTTTCCCAAG AAAATGCAAA GATATGTTCT TGAAGGTGTG
CAGGATTGGG TGCTATCTGT ACGCAAGTGG AGACGAATTC
ACAACTCCAC AACAAATGAT GGAAGACATG AAATCATTGG
TTTATCAACC CCTAACAGTT GATGACATGA GTGCCAAAGA
ATTGACTTCT GTGAGAAACT AG
```

The *Salvia officinalis* miltiradiene synthase (SoTPS1) can have the amino acid sequence shown below (SEQ ID NO:19).

```
MSLAFNAAVA TFSGHRIRSR REILPGQGFP MITNKSSFAV
KCNLTTTDLM GKITEKFKGR DSNFSAATAV QPAADIPSNL
CIIDTLQRLG VDRYFQSEID TILEDTYRLW QRKEREIFSD
ITIHAMAFRL LRVKGYVVSS EELAPYADQE RINLQRIDVA
TVIELYRAAQ ERISEDESSL EKLHAWTATY LKQQLLTNSI
PDKKLNKLVE CYLKNYHGIL DRMGVRQNLD LYDISHYQTL
KAADRFSNLR NEDFLAFARQ DFNICQEQHQ KELQQLQRWY
ADCRLDTLKY GRDVVRVANF LTSAIIGDPE LSEVRLVFAK
HIVLVTRIDD FFDHGGSREE SYKILELLKE WKEKPAAEYG
SKEVEILFTA VYNTVNELAE MAHIEQGRSV KEFLIKLWVQ
IISIFKIELD TWSDETALTL DEYLSSSWVS IGCRICILMS
MQFIGIKLSD EMLLSEECID LCRHVSMVDR LLNDVQTFEK
ERKENTGNSV SLLLAANKDD SAFTEEEAIT KAKEMAECNR
RQLMKIVYKT GTIFPRKCKD MFLKVCRIGC YLYASGDEFT
SPQQMMEDMK SLVYEPLTVD PLEAKNVSGK
```

A nucleic acid encoding the *Salvia officinalis* miltiradiene synthase (SoTPS1) with SEQ ID NO:19 is shown below as SEQ ID NO:20.

```
ATGTCCCTCG CCTTCAACGC AGCAGTTGCC ACTTTCTCCG
GCCACAGAAT TCGGAGCAGG AGAGAAATTC TTCCGGGGCA
AGGATTTCCG ATGATCACCA ACAAGTCGTC TTTCGCCGTG
AAATGTAACC TTACTACAAC AGATTTGATG GGCAAGATAA
CAGAGAAATT CAAGGGAAGA GACAGTAATT TTTCAGCAGC
AACGGCTGTT CAACCTGCGG CGGATATACC CTCTAACCTG
TGCATAATCG ACACCCTCCA AAGGTTGGGA GTCGACCGAT
ACTTCCAATC TGAAATCGAC ACTATTCTAG AGGACACATA
CAGGTTATGG CAAAGGAAAG AGAGAGAGAT ATTTTCGGAT
ATAACTATTC ATGCAATGGC ATTTAGACTT TTGCGAGTTA
AAGGATATGT AGTTTCATCA GAGGAACTGG CTCCGTATGC
TGACCAAGAG CGCATTAACC TGCAAAGGAT TGATGTAGCG
ACAGTTATCG AGCTTTACAG AGCAGCACAG GAGAGAATAA
GTGAAGACGA GAGCAGTCTT GAGAAACTAC ATGCTTGGAC
CGCCACCTAT CTCAAGCAGC AGCTGCTCAC TAACTCCATT
CCTGACAAGA AATTGAACAA ACTGGTGGAA TGCTACTTGA
AGAACTATCA CGGGATATTA GATAGAATGG GAGTTAGACA
AAACCTCGAC CTCTACGACA TAAGCCACTA TCAAACTCTA
AAAGCTGCAG ATAGGTTCTC TAATCTACGT AATGAAGATT
TTCTAGCATT TGCGAGGCAA GATTTTAATA TTTGCCAAGA
ACAACACCAA AAAGAACTTC AGCAACTGCA AAGGTGGTAT
GCAGATTGTA GGTTGGACAC ATTGAAGTAT GGAAGAGATG
TCGTGCGGGT TGCTAATTTT CTAACATCAG CAATTATTGG
TGATCCTGAA TTGTCTGAAG TCCGTCTAGT CTTCGCCAAA
CATATTGTGC TTGTAACACG TATTGATGAT TTTTTCGATC
ATGGTGGATC TAGAGAAGAG TCCTACAAGA TCCTTGAATT
ACTAAAAGAA TGGAAAGAGA AGCCAGCTGC AGAATATGGT
TCCAAAGAAG TTGAAATTCT TTTCACAGCA GTATACAATA
CAGTAAACGA GTTGGCAGAG ATGGCTCACA TCGAACAAGG
ACGTAGTGTT AAAGAATTTC TAATAAAGCT GTGGGTTCAA
ATCATATCGA TTTTCAAGAT AGAATTAGAT ACATGGAGCG
ATGAGACAGC GCTGACCTTG GATGAGTACT TGTCTTCGTC
GTGGGTGTCA ATTGGGTGCA GAATCTGCAT TCTCATGTCG
ATGCAATTCA TTGGTATAAA ATTATCTGAT GAAATGCTTC
TGAGTGAAGA GTGTATTGAT TTGTGTCGGC ATGTCTCCAT
GGTTGACCGG CTGCTCAACG ACGTGCAGAC TTTCGAGAAG
GAACGCAAGG AAAATACAGG AAATAGCGTG AGCCTTCTGC
TAGCAGCTAA CAAAGACGAC AGCGCCTTTA CTGAAGAGGA
AGCTATTACA AAAGCAAAAG AAATGGCGGA ATGTAACAGG
AGACAACTGA TGAAGATTGT GTATAAAACA GGAACCATTT
TCCCAAGAAA ATGCAAAGAT ATGTTTCTGA AGGTATGCAG
```

-continued

GATTGGCTGT TACTTGTATG CAAGCGGCGA TGAATTCACA

TCTCCACAAC AAATGATGGA AGATATGAAA TCCTTGGTCT

ATGAACCCCT AACAGTTGAT CCTCTCGAGG CCAAAAATGT

GAGTGGCAAA TGA

*Ajuga reptans* (+)-copalyl diphosphate synthase (ArTPS1) is a (+)-copalyl diphosphate ((+)-CPP) [31] synthase, and compound 31 is shown below.

31

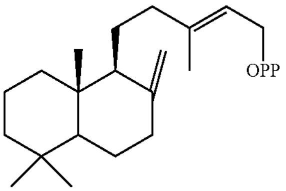

The *Ajuga reptans* (+)-copalyl diphosphate synthase (ArTPS1) can have the amino acid sequence shown below (SEQ ID NO:21).

MASLSTFHLY SSSLLHRKTL QSSPKLNLSS ECFSTRTWMN

SSKNLSLNYQ VNQKIGKLTG TRVATVDAPQ QLEHDDSTAK

GHDIVDIETQ DPIEYIRMLL NTTGDGRISV SPYDTAWIAL

IKDVEGRDFP QFPSSLEWIA NHQLADGSWG DEGFFCVYDR

LVNTIACVVA LRSWNVHHDK SQRGIQYIKE NVHQLKDGNA

EHMMCGFEVV FPALLQKAKN MGIDDLPYEA PVIQDIYHTR

EQKLKRIPLE MMHKVPTSLL FSLEGLENLD WDKLLKLQSA

DGSFLTSPSS TAFAFMQTKD EKCFQFIKNT VETFNGGAPH

TYPVDVFGRL WAVDRLQRLG ISRFFEAEIA DCLSHIHRYW

NDKGLFSGRE SDFVDIDDTS MGFRLLRMQG YDVSPNVLRN

FKNGDKFSCY GGQTIESSTP IYNLYRASQF RFPGEEILEE

ADKFAHEFLS EQLGNNQLLD KWVISDRLQE EISIGLGMPF

YATLPRVEAS YYIQHYAGAD DVWIGKTLYR MPEISNDTYL

ELARNDFKRC QAQHQFEWIY MQEWYESCNI EEFGISRKEL

LRVYFLACSS IFEVERTKER MAWAKSQIIS RMITSFFNKQ

TTSSEEKETL LTEFRNINGL HKSNNTRDGD MNIVLATLHQ

FFAGFDRYTS HQLKNAWGVW LSKLQRGAVD GGADAELITT

TINVCAGHIA LKEDILSHDE YKTLTDLTSK ICQQLSHIQN

EKVVEIDGGI TAKSRLKNEE LQRDMQSLVK LVLEKSVGLN

RNIKQTFLTV AKTYYYRAYN AEETMDAHIF KVLFEPVA

A nucleic acid encoding the *Ajuga reptans* (+)-copalyl diphosphate synthase (ArTPS1) with SEQ ID NO:21 is shown below as SEQ ID NO:22.

ATGGCCTCTT TGTCCACTTT CCACCTCTAC TCTTCCTCAC

TCCTTCACCG CAAAACACTG CAATCTTCAC CAAAGCTTAA

CCTGTCTTCA GAATGCTTCT CCACCAGAAC TTGGATGAAC

AGCAGCAAAA ACTTGTCGTT AAATTACCAA GTTAATCAGA

AAATAGGAAA GCTGACAGGG ACTCGAGTTG CCACTGTGGA

TGCGCCACAA CAACTTGAAC ACGATGATTC AACTGCTAAA

GGCCATGATA TAGTCGATAT TGAAACTCAG GATCCAATTG

AATATATTAG AATGCTGTTG AACACAACAG GCGATGGCAG

AATCAGCGTT TCGCCTTACG ACACAGCATG GATTGCTCTT

ATTAAGGACG TGGAAGGACG TGATTTTCCT CAATTTCCAT

CCAGCCTTGA GTGGATCGCG AACCATCAAC TCGCTGATGG

TTCATGGGGA GACGAAGGAT TTTTCTGTGT GTATGATCGG

CTCGTAAATA CTATAGCATG TGTCGTAGCA TTGAGATCAT

GGAATGTCCA TCACGACAAG AGCCAAAGAG GAATACAATA

TATCAAGGAA AATGTGCATC AACTTAAGGA TGGAAATGCT

GAGCACATGA TGTGTGGTTT CGAAGTAGTG TTTCCTGCAC

TTCTTCAAAA AGCCAAAAAT ATGGGCATTG ATGATCTTCC

ATATGAGGCT CCTGTCATCC AGGATATTTA CCATACAAGG

GAGCAGAAAT TGAAAAGGAT ACCATTGGAG ATGATGCACA

AAGTGCCTAC TTCTCTGCTG TTTAGTTTGG AAGGACTGGA

GAATTTAGAT TGGGATAAAC TCCTTAAGTT GCAGTCAGCT

GATGGCTCTT TCCTCACTTC TCCCTCCTCT ACTGCTTTCG

CATTCATGCA AACAAAAGAC GAAAAATGCT TCCAGTTCAT

CAAGAACACT GTTGAAACCT TTAATGGAGG AGCACCACAT

ACTTATCCGG TCGATGTTTT TGGAAGACTT TGGGCGGTTG

ATAGGCTGCA GCGCCTCGGA ATTTCTCGAT TCTTTGAGGC

TGAGATTGCT GATTGCTTAA GTCACATTCA TAGATATTGG

AATGATAAGG GGCTTTTCAG TGGACGTGAA TCGGACTTTG

TCGATATTGA CGACACATCC ATGGGTTTCA GACTTCTAAG

AATGCAAGGC TATGATGTTA GTCCAAATGT ACTGAGGAAT

TTCAAGAATG GTGACAAGTT TTCATGTTAC GGAGGTCAAA

CGATCGAGTC ATCAACTCCA ATATACAATC TGTACAGAGC

TTCTCAATTC CGGTTTCCAG GAGAAGAAAT TCTTGAAGAA

GCCGACAAGT TCGCCCATGA GTTCTTGTCC GAACAGCTTG

GCAACAACCA ATTGCTTGAT AAATGGGTTA TATCCGACCG

CTTGCAGGAA GAGATAAGTA TTGGATTGGG GATGCCATTT

TATGCCACCC TTCCCAGAGT TGAAGCAAGC TACTATATAC

AACATTACGC TGGTGCCGAC GACGTGTGGA TCGGCAAGAC

-continued

ACTCTACAGG ATGCCGGAAA TAAGTAATGA TACATACCTG

GAGCTAGCAA GAAATGATTT CAAGAGATGC CAAGCACAAC

ATCAGTTCGA GTGGATCTAC ATGCAAGAAT GGTATGAGAG

TTGCAACATT GAAGAATTCG GGATAAGCCG AAAGGAGCTC

CTTCGCGTTT ACTTTTTGGC TTGCTCTAGC ATCTTTGAGG

TCGAGAGGAC TAAAGAGAGA ATGGCATGGG CAAAATCTCA

AATTATTTCT AGAATGATCA CTTCTTTCTT TAATAAACAA

ACTACTTCAT CTGAGGAAAA AGAAACACTT TTAACCGAAT

TCAGAAACAT CAACGGTCTG CACAAATCAA ACAATACAAG

AGATGGAGAT ATGAACATTG TGCTTGCAAC CCTCCATCAA

TTCTTCGCTG GATTTGACAG ATATACTAGC CATCAACTGA

AAAATGCTTG GGGAGTATGG TTGAGCAAGC TGCAACGAGG

AGCAGTAGAC GGTGGAGCAG ACGCAGAGCT GATAACAACC

ACCATAAACG TATGCGCCGG TCATATAGCT CTTAAGGAAG

ACATATTGTC CCACGATGAG TACAAGACTC TCACCGACCT

CACCAGCAAG ATTTGTCAGC AGCTTTCTCA TATTCAAAAC

GAAAAGGTTG TGGAAATTGA CGGTGGGATT ACAGCAAAAT

CTAGGTTGAA GAATGAGGAA CTGCAACGTG ACATGCAATC

ATTGGTGAAA TTAGTACTTG AGAAATCAGT TGGGCTCAAC

CGGAATATAA AGCAAACATT TCTAACGGTT GCAAAAACAT

ACTACTACAG AGCCTACAAT GCTGAGGAAA CTATGGATGC

CCATATATTC AAAGTTCTTT TCGAACCAGT TGCGTGA

*Ajuga reptans* cleroda-4(18),13E-dienyl diphosphate synthase (ArTPS2) was identified and isolated. ArTPS2 was identified as a (5R,8R,9S,10R) neo-cleroda-4(18),13E-dienyl diphosphate [38] synthase. In addition, the combination of ArTPS2 and SsSS enzymes generated neo-cleroda-4(18),14-dien-13-ol [37]. These compounds are shown below.

37

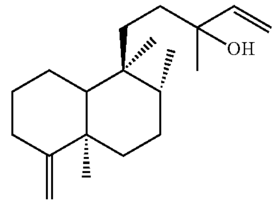

38

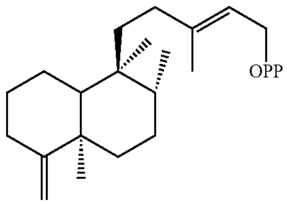

ArTPS2 is of particular interest for applications in agricultural biotechnology, for example, because it is useful for production of neo-clerodane diterpenoids. Neo-clerodane diterpenoids, particularly those with an epoxide moiety at the 4(18) position, have garnered significant attention for their ability to deter insect herbivores (Coll et al., Phytochem Rev 7(1):25 (2008); Klein Gebbinck et al. Phytochemistry 61(7):737-770 (2002); Li et al. Nat Prod Rep 33(10):1166-1226 (2016)). The 4(18)-desaturated products produced by ArTPS2 (e.g., compounds 37 and 38 with the $=CH_2$ 4(18) desaturation projecting from the A ring) the can be used in biosynthetic or semisynthetic routes to yield potent insect antifeedants.

The *Ajuga reptans* cleroda-4(18),13E-dienyl diphosphate synthase (ArTPS2) can have the amino acid sequence shown below (SEQ ID NO:23).

MSFASQATSL LSSPNRLGHV PTPSSPARFA AGGAPFWKIL

FTARSNGQYK AISRARNQGN VEYIDEIQKG PQVVLEAENS

LEDDTQKDTD QIRELVENVR VKLQNIGGGG ISISAYDTAW

VALVEDINGS GQPQFPTSLD WISNHQFPDG SWGSSKFLYY

DRILCTLACI VALKTWNVHP DKYHKGLDFI RENIHKLADE

EEVHMPIGFE VAFPSIIETA KKVGIEIPED FPGKKEIYAK

RDLKLKKIPM DILHKMPTPL LFSIEGMEGL DWQKLFKFRD

DGSFLTSPSS TAYALQQTKD ELCLKYLTDL VKKDNGGVPN

AFPVDLFDRN YTVDRLRRLG ISRYFQPEIE ECMKYVYRFW

DKRGISWARN TNVQDLDDTA QGFRNLRMHG YEVTLDVFKQ

FEKCGEFFSF HGQSSDAVLG MFNLYRASQV LFPGEHMLAD

ARKYAANYLH KRRLNNRVVD KWIINKDLEG EVAYGLDVPF

YASLPRLEAR FYIEQYGGSD DVWIGKALYR MVNVSCDTYL

ELAKLDYNKC QSVHQNEWKS FQKWYKSCSL GEFGFSEGSL

LQAYYIAAST IFEPEKSGER LAWAKTAALM ETIQQLSSQQ

KREFVDEFKH KNILKNENGE RYRSSTSLVE TLISTVNQLS

SDILLEQGRD VHQELCHVWL KWLSTWEERG NLVEAEAELL

LRTLHLNSGL DESSFSHPKY QQLLEVSTKV CHLLRLFQKR

KVYDPEGCTT DIATGTTFQI EACMQELVKL VFSRSSEDLD

SLTKLRFLDV ARSFYYTAHC DPQVVESHID KVLFEKVV

A nucleic acid encoding the *Ajuga reptans* cleroda-4(18),13E-dienyl diphosphate synthase (ArTPS2) with SEQ ID NO:23 is shown below as SEQ ID NO:24.

ATGTCATTTG CTTCCCAAGC CACCTCCCTC CTATCATCCC

CCAACCGTCT CGGCCATGTT CCGACGCCAA GCTCGCCGGC

TCGTTTCGCT GCCGGTGGTG CCCCATTTTG GAAGATATTA

TTTACAGCTA GGTCTAATGG GCAGTATAAA GCTATTTCAA

GAGCTCGTAA CCAAGGAAAT GTAGAGTACA TTGATGAGAT

TCAGAAAGGC CCGCAAGTCG TATTGGAGGC AGAAAACAGC

TTGGAAGATG ACACACAAAA AGATACTGAT CAGATAAGGG

AACTAGTGGA AAATGTCCGA GTAAAGCTGC AGAATATCGG

TGGTGGAGGG ATAAGCATAT CGGCGTACGA CACCGCATGG

GTGGCGCTGG TGGAGGACAT CAACGGCAGT GGCCAGCCAC

-continued

AGTTTCCGAC GAGCCTCGAT TGGATATCGA ACCATCAGTT

CCCTGATGGG TCATGGGGCA GCAGCAAGTT TTTGTATTAT

GATCGGATTC TATGCACATT AGCATGTATA GTTGCATTGA

AAACCTGGAA TGTGCATCCT GATAAGTACC ACAAAGGGTT

GGATTTCATC AGAGAGAACA TTCACAAGCT TGCGGACGAA

GAAGAAGTGC ACATGCCAAT TGGGTTCGAA GTGGCATTCC

CATCAATTAT TGAAACAGCT AAAAAAGTAG GAATCGAAAT

CCCTGAGGAT TTTCCTGGCA AGAAAGAAAT TTATGCAAAA

AGAGATTTAA AGCTAAAAAA AATACCAATG GATATACTGC

ATAAAATGCC CACACCATTG CTCTTCAGCA TAGAAGGAAT

GGAAGGCCTT GACTGGCAAA AGCTATTCAA ATTCCGCGAT

GATGGCTCGT TTCTTACGTC TCCGTCCTCA ACAGCCTATG

CACTCCAGCA AACAAAGGAT GAGCTATGCC TCAAGTATCT

AACAGATCTT GTCAAGAAAG ACAACGGAGG AGTTCCGAAT

GCATTTCCAG TAGACCTGTT TGATCGTAAC TATACAGTAG

ACCGCTTGCG AAGGCTAGGA ATTTCACGGT ACTTTCAACC

TGAAATTGAA GAATGCATGA AATATGTTTA CAGATTTTGG

GATAAAAGAG GAATTAGCTG GGCAAGAAAT ACCAATGTTC

AGGACCTTGA TGACACTGCA CAGGGATTCA GGAATTTAAG

GATGCATGGT TATGAAGTCA CTCTAGATGT TTTCAAACAA

TTTGAGAAAT GTGGAGAGTT TTTCAGTTTT CATGGGCAAT

CCAGCGATGC TGTTTTAGGA ATGTTCAACT TGTACCGGGC

TTCTCAGGTT TTATTTCCGG GAGAACACAT GCTTGCAGAT

GCGAGGAAGT ATGCAGCCAA CTATTTGCAT AAACGAAGAC

TTAATAATAG GGTGGTCGAC AAATGGATTA TCAACAAAGA

CCTTGAAGGC GAGGTGGCAT ATGGGCTAGA TGTTCCGTTC

TACGCCAGCC TACCTCGACT CGAAGCAAGG TTCTACATAG

AACAATATGG GGGTAGTGAT GATGTGTGGA TTGGAAAAGC

TTTATACAGA ATGGTAAATG TAAGCTGCGA CACTTACCTT

GAGCTAGCAA AATTAGACTA CAACAAATGC CAATCCGTGC

ATCAGAATGA GTGGAAAAGC TTTCAAAAAT GGTACAAAAG

TTGCAGTCTT GGGGAGTTTG GGTTCAGTGA AGGAAGCCTA

CTCCAAGCTT ACTACATAGC AGCCTCAACT ATATTCGAGC

CAGAGAAATC AGGAGAACGC CTAGCTTGGG CTAAAACAGC

AGCTCTAATG GAGACAATTC AACAACTTTC CAGCCAGCAA

AAACGTGAAT TTGTTGATGA ATTCAAACAT AAAAACATAC

TGAAGAATGA AAATGGAGAA AGGTATAGAT CAAGTACCAG

TTTGGTAGAG ACTCTGATAA GCACTGTAAA TCAGCTCTCA

TCAGACATAC TATTGGAGCA AGGCAGAGAC GTTCATCAAG

AATTATGTCA CGTGTGGCTA AAATGGCTGA GTACATGGGA

GGAAAGAGGA AACCTGGTGG AAGCGGAAGC CGAGCTTCTT

-continued

CTGCGAACCT TACATCTCAA CAGCGGATTG GATGAATCAT

CATTTTCCCA CCCTAAATAT CAACAGCTCT TGGAGGTGTC

TACCAAAGTT TGCCACCTCC TTCGCCTATT TCAGAAACGA

AAGGTGTATG ATCCCGAAGG GTGTACAACC GACATAGCAA

CAGGAACAAC GTTCCAGATA GAAGCATGCA TGCAAGAACT

AGTGAAATTA GTGTTCAGCA GATCCTCAGA AGATTTAGAT

TCTCTTACTA AGTTGAGATT TTTGGATGTT GCTAGAAGTT

TCTATTACAC TGCCCATTGT GATCCACAGG TGGTCGAGTC

CCACATCGAT AAAGTATTGT TTGAGAAGGT AGTCTAG

The *Plectranthus barbatus* (+)-Copalyl diphosphate synthase (CfTPS16) was identified and isolated using the methods described herein, and this CfTPS116 protein can have the amino acid sequence shown below (SEQ ID NO:25).

MQASMSSLNL NNAPAVCSSR SQLSAKLHPP EYSTVGAWLN

RGNKNQRLGY RIRPKQLSKL TECRVASADV SQEIGKVGQS

VRTPEEVNKK IEESIKYVKE LLMTSGDGRI SVAPYDTAIV

ALIKDLEGRD APEFPSCLEW IANNQKDDGS WGDDFFCIYD

RIVNTIASVV ALKSWNVHPD KIERGVSYIK ENAHKLKGGN

LEHMTSGEEF VVPGCFDRAK ALGIEGLPYD DPIIKEIYAT

KERRLSKVPK DMIYKVPTTL LFSLEGLGME DLDWQKILKL

QSGDGSFLTS PSSTAYAFMQ TGDEKCYKFL QNAVRNCNGG

APHTYPVDVF ARLWAVDRLQ RLGISRFFQP EIKFCLDHIK

NVWTKNGVFS GRDSEFVDID DTSMGIRLLK MHGYDVDPNA

LKHFKQEDGR FSCYGGQMIE SASPIYNLYR AAQLRFPGEE

ILEEATKFAY NFLQQKLANN QIQEKWVISE HLIDEIKMGL

KMPWYATLPR VEASYYLQYY AASGDVWIGK TFYRMPEISN

DTYKELALLD FNRCQAQHQF EWIYMQEWYQ SNNIKEFGIS

KKELLLAYFL AAATIFEPER SQERIVWAKT QVVSKMITSF

LSQENALSSX QKTALFIDFG HSINGLNQIT SVEKENGLAQ

TVLATFGQLL EEFDRYTRHQ LKNAWSQWFM KLQQGDDNGG

ADAELLANTL NICAGHIAFN EDILSHNEYT SLSSLTNKIC

QRLSQIRDNK ILEIEDGSIK DKELEQEMQA LVKLVLEETG

GIDRNIKQTF LSVFKMFYYR AYHDAEAIDX HIFKVMFEPV

V

A nucleic acid encoding the *Plectranthus barbatus* (+)-Copalyl diphosphate synthase (CfTPS16) with SEQ ID NO:25 is shown below as SEQ ID NO:26.

ATGCAGGCTT CTATGTCATC TCTGAACTTG AACAATGCAC

CGGCCGTCTG CAGCAGCAGG TCACAGCTAT CCGCTAAACT

TCACCCGCCG GAATATTCCA CCGTGGGTGC ATGGCTGAAT

CGTGGCAACA AAAACCAGCG GTTGGGCTAC CGGATTCGTC

-continued

```
CAAAGCAACT ATCAAAACTA ACTGAGTGTC GAGTAGCAAG
TGCAGATGTG TCACAAGAGA TTGGAAAAGT CGGCCAATCT
GTTCGGACTC CTGAAGAGGT AAATAAAAAG ATAGAGGAAT
CCATCAAGTA CGTGAAGGAG CTGCTGATGA CGTCGGGCGA
CGGGCGAATC AGTGTGGCGC CCTACGACAC GGCCATAGTT
GCCCTTATCA AGGACTTGGA AGGGCGCGAT GCCCCGGAGT
TTCCATCTTG CTTGGAGTGG ATTGCAAACA ATCAAAAAGA
CGATGGTTCT TGGGGGGATG ACTTCTTCTG CATCTATGAT
CGGATCGTTA ATACCATAGC ATCCGTCGTC GCCTTAAAAT
CATGGAATGT GCACCCAGAC AAGATTGAGA GAGGAGTATC
CTACATCAAG GAAAACGCGC ATAAACTAAA AGGTGGGAAT
CTCGAACACA TGACATCAGG GTTCGAGTTC GTGGTTCCCG
GCTGTTTTGA CAGAGCCAAA GCCTTGGGGA TCGAAGGCCT
TCCCTATGAT GATCCCATCA TCAAGGAGAT TTATGCTACA
AAAGAAAGGA GATTGAGCAA GGTACCGAAG GACATGATCT
ACAAAGTTCC GACAACTCTA TTGTTTAGTT TAGAGGGACT
GGGCATGGAG GATTTGGACT GGCAAAAGAT ACTGAAACTG
CAGTCGGGCG ACGGCTCATT CCTCACCTCT CCGTCGTCCA
CCGCCTACGC ATTCATGCAG ACCGGAGACG AAAAATGCTA
CAAATTCCTC CAGAACGCCG TCAGAAATTG CAACGGCGGA
GCGCCGCACA CTTATCCAGT CGACGTCTTT GCACGGCTCT
GGGCGGTCGA CCGACTTCAG CGACTCGGAA TTTCTCGCTT
CTTTCAGCCC GAGATCAAGT TTTGCCTAGA CCACATCAAA
AATGTGTGGA CTAAGAACGG AGTTTTCAGT GGACGGGATT
CAGAGTTTGT GGATATCGAC GACACATCCA TGGGCATCAG
GCTTCTGAAA ATGCACGGAT ACGATGTCGA CCCAAATGCA
CTGAAACATT TCAAGCAGGA GGATGGGAGG TTTTCATGCT
ACGGTGGTCA AATGATCGAG TCTGCATCTC CGATTTACAA
TCTCTACAGG GCTGCTCAGC TTCGTTTTCC AGGAGAAGAA
ATTCTTGAAG AAGCCACTAA ATTTGCCTAC AACTTCCTGC
AACAGAAGCT GGCCAACAAT CAAATTCAAG AAAAGTGGGT
CATATCCGAG CACCTAATTG ATGAGATAAA AATGGGATTG
AAGATGCCAT GGTACGCCAC CCTACCTAGA GTTGAGGCTT
CATACTATCT CCAATATTAT GCAGCTTCTG GCGACGTATG
GATTGGCAAG ACTTTTTACA GGATGCCAGA AATAAGTAAT
GACACGTACA AAGAGCTTGC ACTATTGGAT TTCAACCGAT
GCCAAGCACA ACATCAGTTC GAATGGATTT ACATGCAAGA
GTGGTATCAA AGCAACAACA TTAAAGAATT TGGGATAAGC
AAGAAAGAGC TTCTTCTTGC TTACTTCTTG GCTGCTGCAA
CCATTTTTGA ACCCGAACGA TCGCAAGAGC GGATCGTGTG
```

-continued

```
GGCTAAAACC CAAGTTGTTT CTAAGATGAT CACATCGTTT
CTGTCTCAAG AAAACGCTTT GTCATCGGAN CAAAAGACTG
CACTTTTCAT CGATTTTGGG CATAGTATCA ATGGCCTCAA
TCAAATAACT AGTGTTGAGA AAGAGAATGG GCTTGCTCAG
ACTGTGCTGG CAACCTTCGG ACAACTACTC GAGGAATTCG
ACAGATACAC AAGGCATCAA CTGAAAAATG CTTGGAGCCA
ATGGTTCATG AAACTGCAGC AAGGAGATGA CAATGGCGGG
GCAGACGCAG AGCTCCTAGC AAACACATTG AACATCTGCG
CTGGTCATAT TGCTTTTAAC GAAGACATAT TATCTCACAA
CGAATACACC TCTCTCTCCT CCCTCACAAA CAAAATCTGT
CAGCGGCTAA GTCAAATTCG AGATAATAAG ATACTGGAAA
TTGAGGATGG GAGCATAAAA GATAAGGAAC TAGAACAGGA
AATGCAGGCG CTGGTGAAGT TAGTCCTGGA AGAAACCGGT
GGCATCGACA GGAACATCAA GCAAACATTT TTGTCAGTTT
TCAAAATGTT TTACTACAGA GCCTACCACG ATGCTGAGGC
TATCGATGNC CATATTTTCA AAGTAATGTT TGAACCAGTC
GTATGA
```

*Hyptis suaveolens* labda-7,13E-dienyl diphosphate synthase (HsTPS1) was identified and isolated, and is a (5S, 9S, 10S) labda-7,13E-dienyl diphosphate [21] synthase. When HsTPS1 was expressed in *N. benthamiana*, labda-7,13(16),14-triene [22] was formed. The combination of HsTPS1 with OmTPS3 produced labda-7,12E,14-triene [24].

21

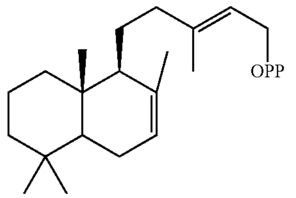

24

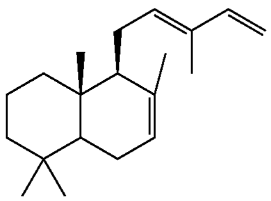

22

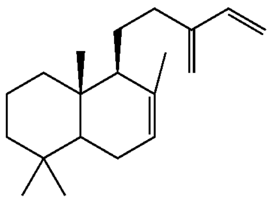

The *Hyptis suaveolens* labda-7,13E-dienyl diphosphate synthase (HsTPS1) can have the amino acid sequence shown below (SEQ ID NO:27).

MAYMISISNL NCSSLLNTNL SAKIQLHQGL KGTWLKTSKR
MCMDQQVHGK QIAKVIESRV TDKDVSTAQD FEVLKVNRVE
DLISSIKSSL KTMEDGRISV SPYSTSWIAL IPSIDGRQTP
QFPSSLEWIV KHQLSDGSWG DALFFCVYDR LVNTIACIIA
LHTWKVHADK VKKGVSFVKE NIWKLEDANE VHMTSGFEVI
FPILLRRARD MGIDGLPSDD TPVVRMISAA RDHKLKKIPR
EVMHQVTTTL LYSLEGLEDL DWSRLFKLQS ADGSFLTSPS
STAFAFMQTN NHNCLRFITS VVQTFNGGAP DNYPIDIFAR
LWAVDRLQRL GISRFFEQEI NDCLSYVYRF WNANGVFSAG
ATNFCDLDDT SMAFRLLRLH GYDVDPNVLR KFKEGDRFCC
HSGEVAMSTS PTYALYRASQ IQFPGEEILD EAFSFTRDYL
QDWLARDQVL DKWIVSKDLP DEIKVGLEVP WYASLPRVEA
AYYMQRHYGG STDAWVAKTC YRMPDVSNDD YLELARLDFK
RCQAQHQSEL SYMQRWYDSC NVEEFGISRK ELLVAYFVAA
ATIFEPERAT ERIVWAKTEI VSKMIKAFFG EDSLDQKTML
LKEFRNSINN GSHRFMKSEH RIVNILLQAL QELLHGSDDC
RIGQLKNAWY EWLMKFEGGD EASLWGEGEL LVTTLNICTA
HFLQHHDLLL NHDYITLSEL TNKICLKLSQ IQVGEMNEMR
EDMQALTKLV IGESCIVNKN IKQTFLAVAK TFYYRAYFDA
DTVDLHIFKV LFEPIV

A nucleic acid encoding the *Hyptis suaveolens* labda-7,13E-dienyl diphosphate synthase (HsTPS1) with SEQ ID NO:27 is shown below as SEQ ID NO:28.

ATGGCGTATA TGATATCTAT TTCAAATCTC AACTGTTCCT
CGCTACTAAA CACCAATCTT TCAGCAAAGA TTCAGCTGCA
CCAAGGTCTC AAAGGAACAT GGCTAAAAAC CAGCAAACGC
ATGTGCATGG ATCAACAGGT TCATGGCAAG CAGATAGCAA
AAGTGATCGA GAGCCGAGTT ACTGATAAGG ATGTTTCCAC
TGCTCAGGAC TTTGAAGTGT TAAAGGTCAA TAGAGTGGAG
GATCTGATAT CAAGCATTAA GAGTTCATTG AAGACAATGG
AAGATGGAAG AATAAGCGTG TCGCCCTACA GCACATCATG
GATCGCACTC ATTCCAAGTA TTGATGGGCG CCAGACGCCC
CAGTTTCCAT CTTCACTGGA GTGGATCGTG AAGCATCAGC
TATCAGATGG TTCATGGGGT GATGCCCTTT TTTTCTGCGT
TTATGATCGT CTCGTAAATA CGATTGCATG CATCATTGCC
CTGCACACCT GGAAGGTTCA TGCAGACAAG GTTAAAAAAG
GAGTAAGTTT TGTGAAGGAA AATATATGGA AACTTGAAGA
CGCCAACGAG GTCCACATGA CTAGTGGTTT CGAAGTTATA
TTTCCCATCC TTCTTCGAAG AGCACGAGAC ATGGGAATTG
ATGGTCTTCC TTCTGATGAT ACTCCAGTTG TTAGGATGAT
TTCTGCTGCT AGGGATCACA AATTGAAAAA GATTCCGAGG

-continued

GAGGTGATGC ACCAAGTGAC AACAACTCTA TTATATAGTT
TGGAAGGGTT GGAAGATTTA GACTGGTCAA GGCTTTTCAA
ACTTCAGTCA GCTGATGGTT CATTCTTAAC TTCTCCATCT
TCAACTGCCT TCGCATTCAT GCAAACTAAT AACCACAATT
GCTTGAGATT CATCACTAGC GTTGTCCAAA CATTCAATGG
AGGAGCTCCA GATAACTATC CAATCGACAT CTTTGCGAGA
CTGTGGGCAG TTGACAGGTT ACAGCGGTTA GGGATTTCTC
GTTTCTTCGA GCAGGAGATA AATGATTGCC TAAGCTATGT
ATATAGATTT TGGAATGCAA ATGGAGTTTT CAGTGCAGGA
GCCACTAATT TTTGTGATCT TGACGACACA TCCATGGCTT
TCCGGCTACT ACGTTTGCAT GGATATGATG TCGACCCAAA
TGTTCTGAGG AAATTCAAAG AGGGAGACAG ATTCTGTTGC
CACAGTGGTG AAGTGGCGAT GTCGACATCG CCAACGTACG
CTCTCTACAG AGCTTCCCAA ATTCAGTTTC CAGGAGAAGA
AATTCTGGAT GAAGCCTTCA GCTTCACTCG CGACTATCTA
CAGGACTGGT TAGCAAGAGA TCAAGTTCTT GATAAGTGGA
TTGTATCCAA GGACCTTCCA GATGAGATTA AGGTAGGACT
AGAGGTGCCA TGGTATGCCA GCCTGCCACG GGTAGAGGCT
GCTTATTACA TGCAACGACA TTACGGCGGG TCTACTGATG
CGTGGGTGGC CAAGACTTGT TACAGGATGC CTGATGTGAG
CAACGATGAT TACCTGGAGC TTGCAAGATT GGATTTCAAG
AGATGTCAAG CCCAACATCA GAGTGAATTG AGTTACATGC
AACGATGGTA TGACAGTTGC AATGTCGAAG AATTCGGAAT
AAGCAGAAAA GAGTTGCTTG TAGCTTATTT TGTGGCTGCT
GCAACTATTT TTGAACCTGA GAGAGCAACT GAGAGAATTG
TGTGGGCAAA AACTGAAATA GTTTCTAAGA TGATCAAAGC
ATTTTTTGGT GAAGACTCAT TAGACCAAAA AACTATGTTG
TTAAAAGAAT TCAGAAACAG CATCAATAAT GGCTCCCACA
GATTCATGAA GAGTGAGCAT AGAATCGTCA ACATTCTACT
ACAAGCCTTG CAGGAGCTAT TACATGGATC TGATGATTGT
CGTATTGGTC AACTCAAAAA TGCTTGGTAT GAGTGGCTGA
TGAAATTCGA GGGAGGAGAT GAAGCAAGTT TGTGGGGAGA
AGGAGAGCTT CTTGTCACCA CCTTAAACAT TTGCACAGCT
CATTTCCTTC AACACCATGA TTTACTGTTG AATCATGACT
ACATAACTCT TTCTGAGCTC ACAAACAAGA TCTGCCTCAA
GCTTTCTCAG ATTCAGGTAG GAGAAATGAA TGAAATGAGA
GAAGATATGC AGGCGTTGAC GAAATTAGTG ATTGGGGAAT
CATGCATCGT CAACAAAAAC ATTAAGCAAA CATTTCTTGC
AGTTGCAAAG ACTTTCTATT ACAGAGCCTA CTTCGATGCC

-continued

```
GACACCGTTG ATCTCCATAT ATTTAAAGTT CTATTTGAGC

CCATTGTCTG A
```

*Leonotis leonurus* peregrinol diphosphate synthase (L1TPS1) was identified and isolated using the methods described herein. The LlTPS1 enzyme was identified as a peregrinol diphosphate (PgPP) [5] synthase, where the peregrinol diphosphate (PgPP) [5] compound is shown below.

5

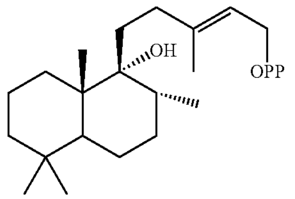

The *Leonotis leonurus* peregrinol diphosphate synthase (L1TPS1) can have the amino acid sequence shown below (SEQ ID NO:29).

```
MASTASTLNL TINSTPFVST KTQAKVSLPA CLWMQDRSSS

RHVSLKHKFC RNQQLKCRAS LDVQQVRDEV FSTAQSPESV

DKKIEERKKW VKNLLSTMDD GRINWSAYDT AWISLIKEFE

GRDAPQFPST LMRIAENQLA DGSWGDPDYD CSYDRIINTL

ACWALTTVVN AHPEHNKKGI KYIKENMYKL EETPVVLMTS

AFEVVFPALL NRAKNLGIQD LPYDMPIVKE ICKIGDEKLA

RIPKKMMEKE PTSLMYAAEG VENLDWEKLL KQRTPENGSF

LSSPAATAVA FMHTKDENCL RYIMYLLDKF NGGAPNVYPI

DLWSRLWATD RIQRLGISRF FKEEIKEILS YVYSYWTDIG

VYCTRDSKYA DIDDTSMGFR LLRMHGFKMD PNVFKYFQKD

DRFVCLGGQM NDSPTATYNL YRAAQYQFPG EKILEDARKF

SQEFLQHCID TNNLLDKWVI SPRFPEELKF GMEMTWYSCL

PRIEARYYVQ HYGATEDVWL GKTFFRMEEI SNENYKELAK

LDFSKCQAQH QTEWIHMQEW YESSNAKEFG ISRKDLLFAY

FLAAASIFET ERAKERILWA KSQIICKMVK SYLENQTASL

EHKIAFLTGF GDNNNGLHTI NKGSGPVNNV MRTLQQLLGE

FDGYISSQLE NAWAAWLTKL EQGEANDGEL LATTLNICSG

RIVYNEDTLS NKEYKAFADL TNKICQNLAQ IQNKKGDEIK

DPNEGEKDKE VEQGMQALAK LVFEESGLER SIKETFLAVV

RTYHYGAYVA DEKIDVHMFK VLFEPVE
```

A nucleic acid encoding the *Leonotis leonurus* peregrinol diphosphate synthase (L1TPS1) with SEQ ID NO:29 is shown below as SEQ ID NO:30.

```
ATGGCCTCCA CTGCATCCAC TCTAAATTTG ACCATCAATA

GTACACCATT TGTAAGCACC AAAACGCAAG CAAAGGTTTC
```

-continued

```
CTTGCCCGCA TGTTTATGGA TGCAGGATAG AAGCAGCAGT

AGACACGTGT CGTTAAAACA CAAATTCTGT CGAAATCAAC

AACTTAAGTG TCGAGCAAGT CTGGATGTTC AGCAAGTACG

TGATGAAGTT TTTTCCACTG CTCAATCCCC TGAATCGGTG

GATAAAAAAA TAGAGGAACG TAAAAAATGG GTGAAGAATT

TGTTGAGTAC AATGGACGAT GGACGAATAA ATTGGTCAGC

CTATGACACG GCATGGATTT CACTTATTAA AGAATTTGAA

GGACGAGATG CTCCCCAGTT TCCGTCGACT CTCATGCGCA

TCGCGGAGAA CCAATTGGCC GACGGGTCAT GGGGCGATCC

AGATTACGAC TGCTCCTATG ATCGGATAAT AAACACACTA

GCGTGTGTTG TAGCCTTGAC AACATGGAAT GCTCATCCTG

AACACAATAA AAAAGGAATA AAATACATCA AGGAAAATAT

GTATAAACTA GAAGAGACGC CTGTTGTACT CATGACTAGT

GCATTTGAAG TTGTGTTTCC GGCGCTTCTT AACAGAGCTA

AAAACTTGGG CATTCAAGAT CTTCCCTATG ATATGCCCAT

CGTGAAGGAG ATTTGTAAAA TAGGGGATGA GAAGTTGGCA

AGGATACCAA AGAAAATGAT GGAGAAAGAG CCAACATCGC

TGATGTATGC CGCGGAAGGA GTCGAAAACT TGGACTGGGA

AAAGCTTCTG AAACAGCGGA CACCCGAGAA TGGCTCGTTC

CTCTCTTCCC CGGCCGCAAC TGCCGTTGCA TTTATGCACA

CAAAAGATGA AAATTGCTTA AGATACATCA TGTACCTTTT

GGACAAATTT AATGGAGGAG CACCAAATGT TTATCCGATC

GACCTCTGGT CAAGACTTTG GGCAACGGAC AGGATACAAC

GTCTGGGAAT TTCCCGCTTC TTTAAGGAAG AGATTAAGGA

AATCTTAAGT TATGTCTATA GCTATTGGAC AGACATTGGA

GTCTATTGTA CACGAGATTC CAAATATGCT GACATTGACG

ACACATCCAT GGGATTCAGG CTTCTGAGGA TGCACGGATT

TAAAATGGAC CCAAATGTAT TTAAATACTT CCAGAAAGAC

GACAGATTTG TTTGTCTAGG TGGTCAAATG AATGATTCTC

CAACTGCAAC ATACAATCTT TACAGGGCTG CTCAATACCA

ATTTCCAGGT GAAAAAATTC TAGAAGATGC TAGAAAGTTC

TCTCAAGAGT TTCTACAACA TTGTATAGAC ACCAATAACC

TTCTAGATAA ATGGGTGATA TCCCCGCGCT TTCCGGAAGA

GTTGAAATTT GGAATGGAGA TGACATGGTA TTCCTGCCTA

CCACGAATTG AGGCTAGATA CTACGTACAA CATTATGGTG

CTACAGAGGA CGTCTGGCTT GGAAAGACTT TTTTCAGGAT

GGAAGAAATC AGTAATGAGA ACTATAAGGA GCTTGCAAAA

CTTGATTTCA GTAAATGCCA AGCACAACAT CAGACAGAGT

GGATTCATAT GCAAGAGTGG TATGAAAGTA GCAATGCTAA

GGAATTTGGG ATAAGCAGAA AAGACCTACT TTTTGCTTAC
```

-continued

```
TTTTTGGCTG CAGCTTCCAT ATTTGAAACC GAAAGGGCAA
AAGAGAGAAT TCTGTGGGCA AAATCTCAAA TTATTTGCAA
GATGGTTAAG TCATATCTGG AAAACCAAAC GGCGTCGTTG
GAGCACAAAA TCGCCTTTTT AACTGGATTC GGAGATAACA
ACAATGGCCT GCACACAATT AATAAGGGGT CTGGACCTGT
TAACAATGTC ATGAGAACCC TCCAACAGCT CCTTGGAGAA
TTCGACGGAT ATATTAGTAG TCAATTGGAA AATGCTTGGG
CAGCATGGTT GACGAAACTC GAGCAAGGCG AGGCCAACGA
TGGCGAGCTC CTCGCAACCA CACTAAACAT TTGTTCTGGG
CGTATTGTGT ATAACGAGGA TACATTATCG AACAAGGAGT
ACAAGGCTTT CGCAGACCTC ACAAATAAAA TTTGTCAAAA
TCTTGCTCAA ATCCAAAATA AAAAGGGTGA CGAAATTAAG
GATCCGAATG AAGGCGAAAA GGACAAGGAA GTCGAGCAAG
GCATGCAGGC ATTGGCTAAG TTAGTTTTTG AGGAATCTGG
GCTTGAGAGG AGTATCAAAG AAACATTCTT AGCAGTGGTG
AGAACTTATC ACTATGGGGC CTATGTTGCT GATGAGAAGA
TTGATGTCCA CATGTTCAAG GTTTTGTTCG AACCAGTTGA
ATGA
```

*Nepeta mussinii* (+)-copalyl diphosphate synthase (NmTPS1) was identified and isolated. The NmTPS1 enzyme can synthesize compound 31, shown below.

31

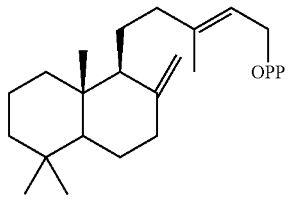

The *Nepeta mussinii* (+)-copalyl diphosphate synthase (NmTPS1) can have the amino acid sequence shown below (SEQ ID NO:31).

```
MTSISSLNLS NAAAARRRLQ LPANVHLPEF HSVCAWLNSS
SKHDPFSCRI HRKQKSKVTE CRVASVDASP VSDHKMSSPV
QTQEEANKNM EESIEYIKNL LMTSGDGRIS VSAYDTSIVA
LIKDIEGRDA PQFPSCLEWI GQNQKADGSW GDDFFCIYDR
FVNTLACIVA LKSWNLHPHK IQKGVTYIKK NVHKLKDGRP
ELMTSGFEIC VPAILQRAKD LGIQDLPYDD PMIKQITDTK
ERRLKKIPKD FIYQLPTTLL FSLEGQENLD WEKILKLQSA
DGSFLTSPSS TAAVFMHTKD EKCLKFIENA VKNCDGGVPH
TYPVDVFARL WAVDRLQRLG ISRFFQPEIK YFLDHIQSVW
TENGVFSGRD SQFCDIDDTS MGIRLLKMHG YKIDPNALEH
FKQEDGKFSC YGGQMIESAS PIYNLYRAAQ LRFPGEEILE
```

-continued

```
EAIKFSYNFL QEKLAKDEIQ EKWVISEHLI DEIKIGLKMP
WYATLPRVEA AYYLDYYAGS GDVWIGKTFY RMPEISNDTY
KEMAILDFNR CQAQHQFEWI YMQEWYESSN VKEFGISKKE
LLVAYFLAAS TIFEPERAQE RIMWAKTKIV SKMIASSLNK
QTTLSLDQKT ALFTQLEHSL NGLDSDEKDN GVAETKNLVA
TFQQLLDGFD KYTRHQLKNA WSQWLKQVQQ GEATGGADAE
LEANTLNICA GHIAFNEQVL SHNEYTTLST LTNKICHRLT
QIQDKKTLEI IDGGIRYKEL EQEMQALVKL VVEENDGGGI
DRNIKQTFLS VFKNYYYSAY HDAHTTDVHI FKVLFGPVV
```

A nucleic acid encoding the *Nepeta mussinii* (+)-copalyl diphosphate synthase (NmTPS1) with SEQ ID NO:31 is shown below as SEQ ID NO:32.

```
ATGACTTCAA TATCCTCTCT AAATTTGAGC AATGCAGCAG
CTGCTCGCCG CAGGTTACAA CTACCAGCAA ACGTTCACCT
GCCGGAATTT CACTCCGTCT GTGCATGGCT GAATAGCAGC
AGCAAACACG ATCCCTTTAG TTGCCGAATT CATCGAAAGC
AAAAATCGAA AGTAACCGAG TGTCGAGTAG CAAGCGTGGA
TGCATCACCA GTGAGTGATC ATAAAATGAG TTCTCCTGTT
CAAACTCAAG AAGAGGCAAA TAAAAATATG GAGGAGTCAA
TCGAGTACAT AAAGAATTTG TTGATGACAT CTGGAGACGG
GCGAATAAGC GTGTCGGCAT ACGACACGTC AATAGTCGCC
CTAATTAAGG ACATAGAAGG ACGGGACGCC CCGCAATTTC
CATCATGCCT GGAGTGGATC GGGCAAAACC AAAAGGCCGA
TGGCTCGTGG GGGGACGACT TCTTCTGTAT TTACGACCGC
TTCGTAAATA CACTAGCATG TATCGTGGCC TTGAAATCAT
GGAACCTTCA CCCTCACAAG ATTCAAAAAG GAGTGACATA
CATCAAGAAA AACGTGCATA AGCTTAAAGA TGGGAGGCCT
GAGCTGATGA CGTCAGGGTT CGAAATTTGT GTTCCCGCCA
TTCTTCAAAG AGCCAAAGAC TTGGGCATCC AAGATCTTCC
CTATGATGAT CCCATGATTA AACAGATCAC TGATACGAAA
GAGCGACGAC TCAAAAAGAT ACCGAAGGAT TTTATATACC
AATTGCCGAC GACTTTACTC TTCAGTTTGG AAGGGCAGGA
GAATTTGGAC TGGGAAAAGA TACTCAAACT GCAGTCAGCT
GACGGCTCCT TCCTTACTTC GCCGTCCTCC ACCGCCGCCG
TCTTCATGCA TACCAAAGAT GAAAAATGCT TGAAGTTCAT
AGAGAACGCC GTCAAAAATT GCGACGGCGG AGTGCCCCAT
ACCTACCCAG TAGACGTGTT TGCAAGACTT TGGGCAGTTG
ACAGACTACA ACGCCTAGGG ATTTCTCGCT TTTTTCAGCC
TGAGATTAAA TATTTCTTAG ATCACATACA AAGCGTTTGG
ACTGAGAACG GAGTTTTCAG TGGACGAGAT TCACAATTTT
```

-continued

```
GCGACATTGA TGATACGTCC ATGGGGATAA GGCTTCTGAA
AATGCATGGA TACAAAATCG ACCCAAATGC ACTTGAGCAT
TTCAAGCAGG AGGATGGTAA ATTTTCGTGC TACGGTGGTC
AAATGATCGA GTCTGCATCA CCGATATACA ATCTGTACCG
AGCTGCTCAA CTCCGATTTC CAGGAGAAGA AATTCTTGAA
GAGGCCATTA AATTTTCCTA TAACTTTTTG CAAGAAAAGC
TAGCCAAGGA TGAAATTCAA GAAAAATGGG TCATATCGGA
GCACTTAATT GATGAGATTA AGATCGGGCT AAAGATGCCA
TGGTACGCCA CTCTACCCCG AGTTGAAGCT GCATATTACC
TGGACTATTA TGCAGGATCC GGCGATGTGT GGATTGGCAA
GACTTTCTAC AGGATGCCAG AAATCAGTAA TGATACATAC
AAAGAAATGG CCATTTTGGA TTTCAACCGA TGCCAAGCAC
AACATCAGTT TGAATGGATT TACATGCAAG AGTGGTATGA
AAGTAGCAAC GTAAAGGAAT TTGGGATAAG CAAAAAAGAG
CTACTTGTTG CTTATTTCTT GGCTGCATCA ACCATATTTG
AACCGGAAAG AGCACAAGAG AGGATTATGT GGGCAAAAAC
AAAAATTGTT TCCAAAATGA TCGCATCATC TCTTAACAAA
CAAACCACTC TATCGTTAGA CCAAAAGACT GCACTTTTTA
CCCAACTCGA ACATAGTCTC AATGGCCTCG ACAGTGATGA
GAAAGATAAT GGAGTAGCTG AGACGAAAAA TCTAGTGGCA
ACCTTCCAGC AGCTGCTAGA TGGATTCGAC AAATACACTC
GCCATCAATT GAAAAATGCT TGGAGCCAGT GGTTGAAGCA
AGTGCAGCAA GGAGAGGCGA CCGGGGGCGC AGACGCGGAG
CTGGAAGCAA ACACGTTGAA CATCTGTGCC GGTCATATCG
CATTCAACGA ACAAGTATTA TCGCACAACG AATACACAAC
TCTCTCCACA CTCACAAACA AGATCTGCCA CCGGCTTACC
CAAATTCAAG ACAAAAAGAC GCTTGAGATA ATCGACGGCG
GCATAAGATA TAAGGAGCTG GAGCAGGAGA TGCAGGCGTT
GGTGAAATTA GTTGTTGAAG AAAACGACGG CGGCGGCATA
GACAGGAATA TTAAACAAAC ATTTTTATCA GTTTTCAAGA
ATTATTACTA CAGTGCCTAC CACGATGCTC ACACAACCGA
TGTTCATATT TTCAAAGTAT TATTTGGACC GGTCGTCTGA
```

*Origanum majorana* (+)-copalyl diphosphate synthase (OmTPS1) was identified and isolated as describe herein. The OmTPS1 enzyme can synthesize compound 31. OmTPS1 can also synthesize palustradiene [29] (shown below), when combined with OmTPS5.

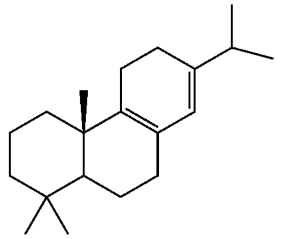

29

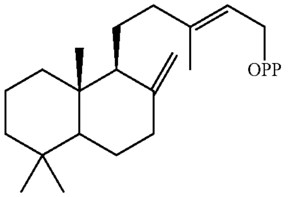

31

The *Origanum majorana* (+)-copalyl diphosphate synthase (OmTPS1) can have the amino acid sequence shown below (SEQ ID NO:33).

```
MTDVSSLRLS NAPAAGGRLP LPGKVHLPEF RTVCAWLNNG
CKYEPLTCRI SRRKISECRV ASLNSSQLIE KVGSPAQSLE
EANKKIEDSI EYIKNLLMTS GDGRISVSAY DTSLVALIKD
VKGRDAPQFP SCLEWIAQNQ MADGSWGDEF FCIYDRIVNT
LACLVALKSW NLHPDKIEKG VTYINENVHK LKDGSTEHMT
SGFEIVVPAT LERAKVLGIQ GLPYDHPFIK EIINTKERRL
SKIPKDLIYK LPTTLLFSLE GQGELDWEKI LKLQSSDGSF
LTSPSSTASV FMRTKDEKCL KFIENAVKNC GGGAPHTYPV
DVFARLWAVD RLQRLGISRF FQHEIKYFLD HINSVWTENG
VFSGRDSQFC DIDDTSMGVR LLKMHGYNVD PNALKHFKQE
DGKFSCYPGQ MIESASPIYN LYRAAQLRFP GEEILEEASR
FAFNFLQEKI ANHEIQEKWV ISEHLIDEIK LGLKMPWYAT
LPRVEAAYYL EYYAGSGDVW IGKTFYRMPE ISNDTYKEVA
ILDFNTCQAQ HQFEWIYMQE WYESSKVKDF GISKKDLLVA
YFLAASTIFE PERTQERIIW AKTLILSRMI TSFLNKQATL
SSQQKNAILT QLGESVDGLD KIYSGEKDSG LAETLLATFQ
QLLDGFDRYT RHQLRNAWGQ WLMKVQQGEA NGGADAELIA
NTLNICAGLI AFNEDVLLHS EYTTLSSLTN KICQRLSQIE
DEKTLEVIEG GIKDKELEED IQALVKLALE ENGGCGVDRR
IKQSFLSVFK TFYYRAYHDA ETTDLHIFKV LFGPVM
```

A nucleic acid encoding the *Origanum majorana* (+)-copalyl diphosphate synthase (OmTPS1) with SEQ ID NO:33 is shown below as SEQ ID NO:34.

```
ATGACCGATG TATCCTCTCT TCGTTTGAGC AATGCACCAG
CTGCCGGCGG CAGGTTGCCG CTGCCGGGAA AGGTTCACCT
GCCTGAATTT CGCACCGTTT GTGCATGGTT GAACAATGGC
```

-continued

```
TGCAAATACG AGCCCTTGAC TTGTCGAATT AGTCGACGGA
AGATATCTGA ATGTCGAGTA GCAAGTCTGA ATTCGTCGCA
ACTAATTGAA AAGGTCGGTT CTCCTGCTCA ATCTCTAGAA
GAGGCAAACA AAAAGATCGA GGACTCCATC GAGTACATTA
AGAATCTATT GATGACATCT GGCGACGGGC GGATAAGTGT
GTCGGCTTAC GACACGTCGC TAGTCGCCCT AATAAAGGAC
GTGAAAGGAC GAGATGCCCC TCAGTTCCCG TCGTGCCTGG
AGTGGATAGC GCAAAACCAA ATGGCCGACG GGTCGTGGGG
GGATGAGTTC TTCTGTATTT ACGACCGGAT CGTGAATACA
TTAGCATGCC TCGTTGCCTT GAAATCATGG AACCTTCACC
CCGACAAGAT CGAAAAAGGA GTGACGTACA TCAACGAAAA
TGTGCACAAA CTGAAAGACG GGAGCACCGA GCACATGACG
TCAGGGTTCG AAATCGTGGT CCCCGCCACT CTAGAAAGAG
CCAAAGTCTT GGGCATCCAA GGCCTCCCTT ATGATCATCC
CTTCATTAAG GAGATTATTA ATACTAAGGA GCGAAGATTA
AGCAAAATAC CCAAGGATTT GATATACAAA CTGCCAACGA
CGCTGCTGTT CAGTTTAGAA GGGCAGGGAG AATTAGATTG
GGAAAAGATA CTGAAACTGC AGTCAAGCGA TGGCTCCTTC
CTTACTTCGC CCTCGTCGAC CGCCTCCGTC TTCATGCGGA
CGAAAGACGA GAAATGCCTC AAGTTCATTG AGAACGCCGT
TAAGAATTGC GGCGGGGGAG CGCCGCATAC TTACCCAGTG
GATGTGTTTG CAAGACTTTG GGCAGTTGAC AGACTACAGC
GATTAGGGAT TTCTCGATTC TTCCAACACG AGATTAAATA
CTTCTTAGAT CACATTAACA GTGTATGGAC CGAGAATGGA
GTTTTCAGTG GACGAGATTC ACAATTTTGT GATATCGACG
ACACTTCTAT GGGAGTTAGG CTTCTAAAAA TGCATGGATA
CAATGTTGAT CCAAATGCGC TCAAGCATTT CAAGCAGGAG
GATGGCAAAT TCTCTTGCTA CCCTGGCCAA ATGATCGAGT
CTGCATCTCC GATATACAAT CTCTACCGAG CCGCTCAACT
CCGGTTCCCC GGAGAAGAAA TTCTCGAAGA AGCAAGTCGA
TTCGCCTTCA ACTTTCTGCA GGAAAAGATA GCCAACCATG
AAATTCAAGA AAAATGGGTC ATATCTGAGC ACTTAATTGA
TGAGATAAAG TTGGGACTGA AGATGCCATG GTACGCGACT
CTGCCCCGAG TTGAGGCCGC TTATTATCTA GAGTATTATG
CTGGCTCAGG CGACGTATGG ATTGGAAAGA CTTTCTACCG
GATGCCGGAA ATCAGTAACG ATACGTATAA AGAGGTGGCC
ATTTTGGATT TCAACACATG CCAAGCTCAA CACCAGTTTG
AATGGATTTA CATGCAAGAG TGGTACGAAA GTAGCAAGGT
TAAAGATTTC GGGATAAGCA AAAAGGACCT ACTTGTTGCT
TACTTTCTGG CGGCATCGAC TATATTTGAA CCCGAAAGAA
```

-continued

```
CACAAGAGAG GATTATTTGG GCAAAAACCC TAATTCTTTC
TAGGATGATC ACATCATTTC TCAACAAACA AGCTACACTT
TCATCCCAAC AAAAGAATGC CATCTTAACA CAACTTGGAG
AGAGTGTCGA TGGCCTCGAT AAAATATATA GTGGTGAGAA
AGATTCTGGG CTGGCTGAGA CTCTGCTGGC TACCTTCCAG
CAACTGCTCG ACGGATTCGA TAGATACACT CGCCATCAAC
TGAGAAATGC TTGGGGGCAA TGGTTGATGA AAGTGCAGCA
AGGAGAGGCC AACGGTGGCG CCGACGCTGA GCTCATAGCA
AACACACTCA ATATCTGCGC CGGCCTTATC GCCTTCAACG
AAGACGTATT GTTGCACAGC GAATACACGA CTCTCTCCTC
CCTCACCAAC AAAATATGCC AGCGCCTTAG CCAGATTGAA
GATGAAAAGA CGCTTGAAGT GATTGAAGGG GGCATAAAAG
ATAAGGAACT GGAGGAGGAT ATTCAGGCGT TGGTGAAGCT
AGCCCTCGAA GAAAACGGCG GCTGCGGCGT CGACAGAAGA
ATCAAGCAGT CATTCTTATC AGTATTCAAG ACTTTTTACT
ACAGAGCCTA CCATGATGCT GAGACCACCG ATCTTCATAT
TTTCAAAGTA CTGTTTGGGC CGGTTATGTG A
```

A *Perovskia atriplicifolia* (+)-Copalyl diphosphate synthase (PaTPS1) enzyme was identified and isolated. This *Perovskia atriplicifolia* (+)-Copalyl diphosphate synthase (PaTPS1) enzyme was identified to be a (+)-copalyl diphosphate ((+)-CPP) synthase that can synthesize compound 31. The *Perovskia atriplicifolia* (+)-Copalyl diphosphate synthase (PaTPS1) can have the amino acid sequence shown below (SEQ ID NO:35).

```
MTSMSSLNLS RAPATTHRLQ LQAKVHVPEF YAVCAWLNSS
SKQAPLSCQI RCKQLSRVTE CRVASLDASQ VSEKDTSHVQ
TPDEVNKKIE DYIEYVKNLL MTSGDGRISV SPYDTSIVAL
IKDSKGRNIP QFPSCLEWIA QHQMADGSWG DQFFCIYDRI
LNTLACVVAL KSWNVHGDMI EKGVTYVKEN VHKLKDGNIE
HMTSGFEIVV PALVQRAKDL GIQGLPYDDP LIKEIADTKE
RRLKKIPKDM IYQTPTTLLF SLEGQGDLEW EKILKLQSGD
GSFLTSPSST AHVFVQTKDE KCLKFIENAV KNCSGGAPHT
YPVDVFARLW AIDRLQRLGI SRFFQPEIKY FIDHINSVWT
ENGVFSGRDS EFCDIDDTSM GIRLLKMHGY KVDPNALNHF
KQQDGKFSCY GGQMIESASP IYNLYRAAQL RFPGEEILEE
ASKFAFNFLQ EKIANDQFQE KWVISDHLID EVKLGLKMPW
YATLPRVEAA YYLQYYAGSG DVWIGKVFYR MPEISNDTYK
ELAILDFNRC QAQHQFEWIY MQEWYHRSSV SEFGISKKEL
LRTYFLAAAT IFEPERTQER LVWAKTQIVS RMITSFVNNG
TTLSLDQMTA LATQIGHNFD GLDQIISAMK DHGLAGTLLT
TFQQLLDGFD RYTRHQLKNA WSQWFMKLQQ GEANGGEDAE
LLANTLNICA GFIAFNEDVL SHDEYTTLST LTNKICKRLS
```

-continued

QIQDKKALEV VDGSIKDKEL EQDMQALVKL VLEENGGGVD
RNIKQTFLSV FKTFYYTAYH DDETTDVHIF KVLFGPVV

A nucleic acid encoding the *Perovskia atriplicifolia* (+)-Copalyl diphosphate synthase (PaTPS1) enzyme with SEQ ID NO:35 is shown below as SEQ ID NO:36.

ATGACCTCTA TGTCCTCTCT AAATTTGAGC AGAGCACCAG
CTACCACCCA CCGGTTACAG CTACAGGCAA AGGTTCACGT
GCCGGAATTT TATGCCGTGT GTGCATGGCT GAATAGCAGC
AGCAAACAGG CACCCTTGAG TTGCCAAATT CGCTGCAAGC
AACTATCAAG AGTAACTGAA TGTCGGGTAG CAAGTCTGGA
TGCGTCGCAA GTGAGTGAAA AAGACACTTC TCATGTCCAA
ACTCCCGATG AGGTGAACAA AAAGATCGAG GACTATATCG
AGTACGTCAA GAATCTGTTG ATGACGTCGG GCGACGGGCG
AATAAGCGTG TCGCCCTACG ACACGTCAAT AGTCGCCCTT
ATTAAGGACT CGAAAGGGCG CAACATCCCG CAGTTTCCGT
CGTGCCTCGA GTGGATAGCG CAGCACCAAA TGGCGGATGG
CTCATGGGGG GATCAATTCT TCTGCATTTA CGACCGGATT
CTAAATACAT TAGCATGTGT CGTAGCTTTG AAATCCTGGA
ACGTTCACGG TGACATGATC GAAAAAGGAG TGACGTACGT
CAAGGAAAAT GTGCATAAGC TTAAAGATGG GAATATTGAG
CACATGACGT CGGGGTTCGA AATTGTGGTT CCCGCCCTTG
TTCAAAGAGC CAAAGACTTG GGCATCCAAG GCCTGCCCTA
TGATGATCCC CTCATCAAGG AGATTGCTGA TACAAAAGAA
AGAAGATTGA AAAAGATACC CAAGGATATG ATTTACCAAA
CGCCAACGAC ATTACTATTC AGTTTAGAAG GGCAGGGAGA
TTTGGAGTGG GAAAAGATAC TGAAACTGCA GTCAGGCGAT
GGCTCCTTCC TCACTTCGCC GTCATCCACC GCCCACGTGT
TCGTGCAGAC CAAAGATGAA AAATGCTTGA AATTCATCGA
GAACGCCGTC AAGAATTGCA GTGGAGGAGC GCCGCATACT
TATCCAGTCG ATGTCTTCGC AAGACTTTGG GCAATTGACA
GACTACAACG CCTAGGAATT TCTCGTTTCT TCCAGCCGGA
AATTAAGTAT TTCATAGACC ACATCAACAG CGTTTGGACA
GAGAACGGAG TTTTCAGTGG GCGAGATTCG GAATTTTGCG
ATATTGATGA CACGTCCATG GGCATCAGGC TTCTCAAAAT
GCACGGATAC AAAGTCGACC CAAATGCACT CAATCATTTC
AAGCAGCAAG ATGGTAAATT TTCTTGCTAC GGTGGTCAAA
TGATCGAGTC TGCATCTCCA ATATACAATC TCTACAGGGC
TGCTCAGCTA CGATTTCCAG GAGAAGAAAT TCTTGAAGAA
GCCAGTAAAT TTGCCTTTAA CTTTTTGCAA GAAAAAATAG
CCAACGATCA ATTTCAAGAA AAATGGGTGA TATCCGACCA

-continued

CTTAATCGAT GAGGTGAAGC TCGGGCTGAA GATGCCATGG
TACGCCACTC TACCCCGGGT TGAGGCTGCA TATTATCTAC
AATACTATGC TGGTTCTGGC GACGTATGGA TTGGCAAGGT
TTTCTACAGG ATGCCGGAAA TCAGCAATGA TACATACAAA
GAGCTGGCCA TATTGGATTT CAACAGATGC CAAGCACAGC
ATCAGTTCGA ATGGATTTAT ATGCAAGAGT GGTATCACAG
AAGCAGCGTT AGTGAATTCG GGATAAGCAA AAAAGAGCTG
CTTCGTACTT ACTTTCTGGC TGCAGCAACC ATATTCGAAC
CCGAGAGAAC ACAAGAGAGG CTTGTGTGGG CAAAAACCCA
AATTGTCTCT AGGATGATCA CATCATTTGT TAACAATGGA
ACTACACTAT CTTTGGACCA AATGACTGCA CTTGCAACAC
AAATCGGCCA TAATTTCGAT GGCCTCGATC AAATAATTAG
TGCTATGAAA GATCATGGAC TGGCTGGGAC TCTGCTGACA
ACCTTCCAGC AACTTCTAGA TGGATTCGAC AGATACACTC
GCCATCAACT CAAAAATGCT TGGAGCCAAT GGTTCATGAA
ACTCCAGCAA GGGGAGGCGA ACGGCGGGGA AGACGCGGAG
CTCCTAGCAA ACACGCTCAA CATCTGCGCG GGTTTCATTG
CTTTCAACGA AGACGTATTG TCGCACGATG AATACACGAC
TCTCTCCACC CTTACAAACA AAATCTGCAA GCGCCTTAGC
CAAATTCAAG ATAAAAAGGC GCTGGAAGTT GTCGACGGGA
GCATAAAGGA TAAGGAGCTC GAACAGGATA TGCAGGCGTT
GGTGAAGTTG GTCCTTGAAG AAAATGGCGG CGGCGTCGAC
AGGAACATCA AACAGACATT TTTGTCCGTT TTCAAGACTT
TTTACTACAC CGCCTACCAC GATGATGAGA CCACTGATGT
TCATATTTTC AAAGTACTGT TTGGACCGGT CGTATGA

*Pogostemon cablin* (10R)-labda-8,13E-dienyl diphosphate synthase (PcTPS1) was identified and isolated. This *Pogostemon cablin* (10R)-labda-8,13E-dienyl diphosphate synthase (PcTPS1) enzyme was identified to be a (10R)-labda-8,13E-dienyl diphosphate synthase, which can synthesize compound 25.

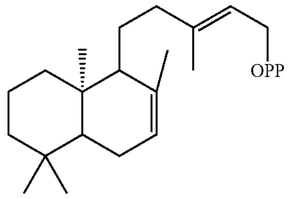

25

The combination of PcTPS1 and SsSS, both in-vitro, and in *N. benthamiana* expression produced (10R)-labda-8,14-en-13-ol [26], shown below.

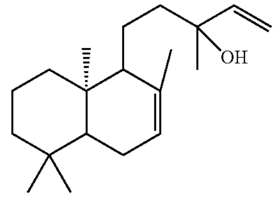

26

This *Pogostemon cablin* (10R)-labda-8,13E-dienyl diphosphate synthase (PcTPS1) can have the amino acid sequence shown below (SEQ ID NO:37).

```
MSFASQSHVA FVLRRPSAVA PPPPTRIPTT AALSPLKPGD
FSHGRSSFMP TSIKCNAIST SRVEEYKYTD DHNQSGLLEH
DGLISDKINE LVTKIQLMLQ NMDDGEISIS PYDTAWVSLV
EDVGGNDRPQ FPTSLEWISN NQLPDGSWGD PNAFLVHDRI
LNTLACVVAL KSWKMHPHKC NRGVSFVREN IYRMDDEKEE
HMPNGFEVVF PALLQKAKTL NIDIPYEFPG IQKFYAKRDL
KFARIPMDIL HSVPTTLLFS LEGVRCGLDL DWGKLLELQA
ADGSFLYSPS STAFALEQTK DQNCLKYLSK LVRKFDGGVP
NVYPVDLFEH NWAVDRLQRL GISRYFTPEI NQCLDYSYRY
WSNSKGMYSA SNSQIQDVDD TAMGFRLLRL NGYDVSTQGF
RQFEAGGDFF CFAGQSSQAV TGMYNLYRAS QVMFPGEKLL
EDAKKFSTNF LQQKRANNQL TDKWVIAKDV PAEVGYALDI
PWYASLPRLE ARFFIQQYGG DDDVWIGKTL YRMGYVNNNT
YLELAKLDYN TCQRLHQHEW ITIQRWYEIN LKITSVGLSK
RGVLLSYYLA AANLFEPQNS THRIAWAKTS ILVSAIQLSP
LQKRDFINQF HRSTANNGYE TSNVLVKSVI KGVHELSMDA
MLTHNKDIHR QLFNAWRKWM SVWEEGGDGE AELLLSTLNT
CDGVDESTFS DPKYEHLLEI TVRVTHQLHL IQNAETKRVG
DREEIDLSMQ QLVKLVFTKS SSDLDSCIKQ RFFAIARSFY
YVAHCDPEMV DSHIAKVLFE RVM
```

A nucleic acid encoding the *Pogostemon cablin* (10R)-labda-8,13E-dienyl diphosphate synthase (PcTPS1) enzyme with SEQ ID NO:37 is shown below as SEQ ID NO:38.

```
ATGTCATTTG CTTCTCAATC ACATGTCGCC TTTGTACTCC
GACGGCCATC TGCCGTTGCT CCGCCACCAC CGACTAGAAT
TCCGACAACA GCCGCTCTTT CTCCTCTCAA ACCAGGTGAT
TTTTCCCATG GCAGATCATC ATTTATGCCC ACTTCCATTA
AATGTAATGC AATTTCCACA TCTCGCGTCG AAGAATACAA
GTACACGGAT GATCATAATC AGAGTGGTTT ATTGGAGCAT
GATGGTTTGA TATCAGACAA GATAAATGAA TTGGTGACCA
AGATACAATT GATGCTACAA AACATGGATG ACGGAGAGAT
AAGCATCTCC CCATATGACA CCGCATGGGT GTCGTTGGTG
```

-continued

```
GAGGATGTGG GCGGCAACGA CCGCCCACAG TTTCCTACGA
GCCTGGAGTG GATATCGAAT AACCAGCTCC CCGACGGCTC
GTGGGGCGAC CCGAATGCCT TTTTGGTGCA CGACCGTATC
CTCAACACAT TGGCATGCGT CGTTGCACTC AAATCCTGGA
AAATGCACCC CCACAAATGC AATAGAGGAG TTAGTTTCGT
GAGAGAAAAT ATATACAGAA TGGATGATGA AAAAGAGGAA
CACATGCCAA ATGGATTCGA AGTGGTATTT CCAGCACTCC
TTCAAAAAGC GAAAACCCTA AACATTGATA TCCCGTACGA
GTTTCCAGGA ATACAAAAAT TTTATGCCAA AAGAGATTTA
AAATTCGCCA GGATTCCAAT GGATATATTG CATAGCGTTC
CGACAACATT ACTGTTCAGC TTAGAAGGTG TAAGATGTGG
TCTTGATCTG GATTGGGGGA AGCTTCTAGA ATTGCAAGCT
GCTGATGGCT CATTTCTCTA CTCTCCATCC TCTACTGCCT
TTGCACTAGA ACAAACCAAG GATCAAAACT GCCTCAAATA
TCTATCTAAA CTTGTTCGAA AATTCGATGG CGGAGTACCC
AACGTGTACC CGGTGGACTT GTTCGAACAT AATTGGGCAG
TTGATCGTCT CCAAAGGCTC GGAATTTCTC GTTATTTTAC
GCCTGAAATC AACCAATGTC TTGATTATTC TTACAGATAT
TGGTCAAATA GTAAAGGGAT GTACTCGGCA AGCAATTCCC
AGATTCAGGA CGTTGATGAC ACCGCCATGG GATTCAGGCT
TTTGAGACTC AACGGCTACG ATGTCTCTAC ACAAGGGTTT
AGGCAATTCG AGGCAGGGGG GGACTTCTTC TGCTTCGCGG
GGCAGTCGAG CCAAGCTGTA ACCGGAATGT ACAACCTCTA
CAGAGCTTCC CAAGTGATGT TCCCTGGAGA GAAGCTACTG
GAAGATGCCA AGAAATTCTC CACCAACTTC TTGCAACAAA
AACGAGCCAA TAACCAGCTC ACTGACAAGT GGGTTATTGC
CAAAGATGTT CCAGCTGAGG TGGGATATGC CTTGGATATT
CCCTGGTATG CCAGTCTGCC CCGACTGGAA GCAAGATTTT
TCATACAACA ATACGGTGGA GACGACGACG TTTGGATCGG
CAAAACCTTG TATAGAATGG GATATGTGAA CAACAACACT
TATCTGGAAC TCGCAAAGCT AGACTACAAC ACCTGCCAAA
GGTTGCATCA GCATGAGTGG ATAACCATTC AACGATGGTA
CGAAATTAAT TTAAAAATTA CTAGTGTTGG GTTGAGCAAA
AGAGGGGTCC TGTTGAGTTA TTACTTAGCC GCAGCCAATC
TGTTTGAGCC TCAAAACTCA ACACACCGCA TCGCTTGGGC
CAAAACTTCG ATTTTAGTAA GCGCTATTCA ACTTTCTCCC
CTCCAAAAGC GCGACTTTAT TAACCAATTC CACCGCTCCA
CCGCAAATAA TGGGTATGAA ACAAGTAATG TGTTGGTGAA
GAGTGTAATC AAGGGTGTGC ATGAGCTCTC CATGGACGCT
ATGTTGACGC ACAATAAAGA CATACATCGC CAACTTTTTA
```

-continued

```
ATGCTTGGCG AAAGTGGATG TCAGTGTGGG AAGAGGGAGG

TGATGGAGAA GCGGAGCTGT TATTGTCGAC GCTTAACACG

TGCGACGGAG TAGATGAATC CACATTCAGC GATCCCAAAT

ACGAGCACCT CTTAGAGATC ACCGTCAGAG TCACCCACCA

GCTTCATCTC ATTCAGAATG CAGAGACGAA GCGTGTGGGT

GACCGTGAGG AAATAGATTT GAGCATGCAA CAACTTGTTA

AGTTGGTGTT CACTAAATCA TCATCGGATC TGGATTCTTG

TATCAAGCAA AGATTTTTTG CGATTGCCAG AAGTTTCTAT

TACGTGGCTC ATTGTGATCC GGAGATGGTG GACTCCCACA

TAGCCAAAGT ATTGTTTGAG AGGGTGATGT AG
```

*Prunella vulgaris* 11-hydroxy vulgarisane synthase (PvHVS) was identified and isolated. The *Prunella vulgaris* 11-hydroxy vulgarisane synthase (PvHVS) enzyme catalyzes the first committed step and forms the scaffold found in all Vulgarisins, a class of diterpenes with pharmaceutical applications (e.g., gout, cancer). For example, PvHVS can synthesize 11-hydroxy vulgarisane (shown below).

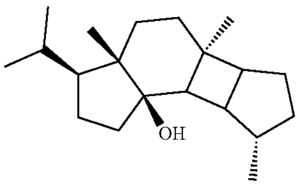

11-hydroxy vulgarisane

An example of a formula for several Vulgarisin diterpenes is shown below.

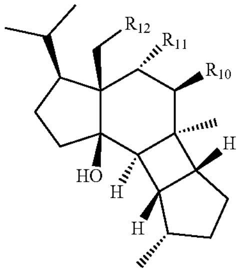

Vulgarisin B (1) $R_{10}$ =

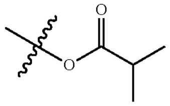

$R_{11}$ = OH $R_{12}$ =

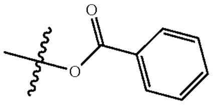

Vulgarisin C (2) $R_{10}$ = OH $R_{11}$ =

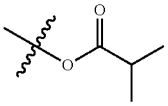

$R_{12}$ =

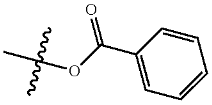

-continued

Vulgarisin D (3) $R_{10}$ = OH $R_{11}$ =

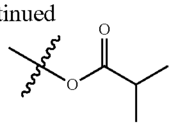

$R_{12}$ =

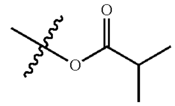

Vulgarisins B (1) and C (2) exhibit modest cytotoxicity activity against human lung carcinoma A549 cell line (Lou et al. Tetrahedron Letters 58: 401-404 (2017)).

The *Prunella vulgaris* 11-hydroxy vulgarisane synthase (PvHVS) can have the amino acid sequence shown below (SEQ ID NO:39).

```
MSSLSIPFSS AICTSSIPKI STGHHRRTAR MPAHDTSRLV

FRPSAVMVEG SPMTTSSNGK EVQRLITTFK PSMWKDIFST

FSFDNQVQEK YLKEIEELKK EVRSTLMSAT HRKLFDLIDN

LERMGIAYHF ETEIEDKLKQ AHASLEEEDD YDLFTTALRF

RLLRQHRYHV SCDPFAKFVD QDNKLKESLS SDVEGLLSLF

EASHLRIHNE DVLDEAIVFT THHLNRMMPQ LESPLKEEVK

HALRYPLHKC LGILSLRFHI DRYENDKSRD EVVLRLGQVN

FNYMQNIYMN ELYEITTWWN KLQMTSKVPY FRDRLVECYM

WGLAYHFEPE YAPVRVLITK YYMTATTVDD TYDNYATLEE

IELFTQAIDR WSEDEIDQLP DEYLKIVYKG LMNFTEEFRR

DAEERGKGYV IPYFIEETKR ATQGYANEQR WIMKREMPSF

EEYMVNSRVT SLMYVTYVAV VAVIESATKE TVDWALSDSD

IFVYTNDIGR LIDDLATHRR ERKDGTMLTS MDYYMKEYGG

TMEEGEAAFR KLMEEKWKLL NAAWVDTING KESKEIVVQV

LDLARICGTL YGDEEDGFTY PEKNFAPLVA ALLMNPIHI
```

A nucleic acid encoding the i *Prunella vulgaris* 11-hydroxy vulgarisane synthase (PvHVS) enzyme with SEQ ID NO:39 is shown below as SEQ ID NO:40.

```
ATGAGCTCTC TCTCAATTCC CTTTTCTTCC GCCATTTGCA

CTTCATCAAT CCCAAAGATC AGTACTGGGC ATCATCGCCG

CACCGCGAGG ATGCCCGCGC ACGACACATC GCGTCTCGTC

TTTCGCCCTT CAGCTGTGAT GGTGGAAGGA AGTCCGATGA

CTACTTCAAG CAACGGGAAG GAAGTCCAAC GACTTATAAC

CACTTTCAAG CCTAGCATGT GGAAAGATAT TTTTTCTACC

TTCTCTTTCG ATAATCAGGT GCAAGAAAAG TATTTGAAAG

AAATTGAGGA ATTGAAGAAA GAAGTAAGAA GCACACTAAT

GAGTGCTACG CATAGGAAAT TGTTTGACTT GATCGACAAT

CTCGAGCGTA TGGGAATCGC CTATCATTTC GAGACAGAAA

TCGAAGACAA GCTCAAACAA GCTCATGCTT CTCTAGAGGA

GGAAGATGAC TACGACTTGT TCACTACTGC ACTTCGCTTT
```

-continued

CGTCTGCTCA GACAACATCG CTATCATGTT TCTTGCGATC

CCTTTGCGAA ATTTGTTGAC CAAGACAACA AATTGAAAGA

GAGTCTTAGT AGCGACGTCG AGGGGCTATT AAGCTTGTTC

GAGGCATCCC ATCTTCGGAT CCACAACGAG GATGTTCTAG

ATGAAGCTAT AGTGTTCACA ACCCATCACT TGAATCGAAT

GATGCCACAA TTGGAATCGC CCCTTAAAGA AGAAGTGAAG

CATGCTCTTC GATACCCCCT TCACAAGTGT CTTGGAATCC

TTAGCCTTCG TTTTCATATC GACAGATATG AGAATGATAA

GTCGAGGGAT GAAGTTGTTC TCAGACTAGG CCAAGTTAAT

TTCAATTACA TGCAGAACAT TTACATGAAC GAGCTCTATG

AAATCACCAC GTGGTGGAAC AAGTTGCAGA TGACTTCAAA

AGTACCTTAC TTTAGAGATA GATTGGTAGA GTGCTATATG

TGGGGTTTGG CATATCATTT CGAACCAGAA TACGCTCCCG

TTCGAGTCCT CATTACCAAG TACTATATGA CCGCCACAAC

TGTCGACGAT ACCTATGATA ATTATGCTAC ACTCGAAGAA

ATCGAACTCT TCACTCAGGC CATTGACAGG TGGAGCGAGG

ATGAGATTGA TCAGCTACCT GATGAATACC TAAAAATAGT

GTACAAAGGT CTAATGAACT TCACTGAAGA GTTTAGACGT

GACGCAGAAG AGCGAGGGAA AGGCTATGTG ATTCCTTACT

TTATTGAAGA AACGAAGAGA GCAACACAGG GTTATGCAAA

CGAGCAGAGG TGGATAATGA AGAGAGAAAT GCCGAGTTTT

GAAGAGTATA TGGTGAACTC AAGGGTAACA TCACTTATGT

ATGTGACCTA CGTTGCTGTT GTGGCAGTCA TAGAATCAGC

TACCAAAGAA ACCGTAGATT GGGCGCTAAG TGACTCCGAT

ATCTTTGTCT ACACTAACGA TATCGGCCGA CTTATCGACG

ACCTTGCCAC TCATCGACGC GAGAGGAAAG ACGGGACAAT

GCTTACATCG ATGGATTATT ACATGAAGGA ATATGGCGGT

ACGATGGAAG AGGGGGAAGC TGCATTTAGG AAATTGATGG

AGGAGAAATG GAAACTTTTG AATGCAGCAT GGGTAGATAC

TATTAATGGA AAAGAGTCGA AGGAAATAGT TGTGCAAGTT

CTCGACCTCG CCAGGATATG CGGAACGCTC TATGGGGACG

AAGAAGATGG CTTCACCTAC CCAGAGAAGA ATTTTGCACC

ACTCGTTGCT GCTCTATTGA TGAATCCTAT ACATATTTGA

A *Chiococca alba* ent-CPP synthase (CaTPS1) was identified and isolated. This CaTPS1 enzyme was identified that converts GGPP to ent-CPP [16].

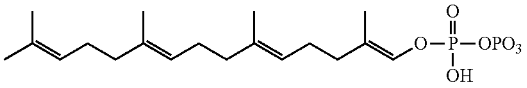

Geranylgeranyl diphosphate (GGPP)

-continued

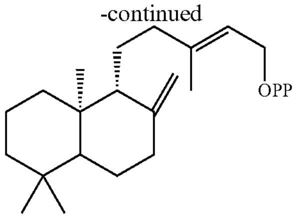

16

The *Chiococca alba* ent-CPP synthase (CaTPS1) has the amino acid sequence shown below (SEQ ID NO:41).

1 MSSSTSAAAT LLGLSPASRR FVSFPPANGP IETITGIWSP

41 GKALHHFNFR LRCSTVSSPR TQELGQVSQN GMSGIKWHDI

81 VEEGVTEKGT LEANTSSWIK ESIEAIRWML RTMDDGDISI

121 SAYDTAWVAL VEDINGSGGP QFPSSLEWIA NNQLPDGSWG

161 DSDIFSAHDR ILNTLGCVVA LKSWNMHPEK SEKGLLYLRD

201 NIHKLEDENV EHMPIGFEVA FPSLIEIAKK LSIDIPDDSA

241 ILQEIYARRN LKLTRIPKDI MHTVPTTLLH SLEGMPELDW

281 KRLISLKCED GSFLFSPSST AFALTQTKDA DCLRYLTKTV

321 QKFNGGVPNV YPVDLFEHIW AVDRLQRLGI SRYFQSEIRE

361 CIDYVHRYWT DKGICWARNT HVYDIDDTAM GFRLLRLHGY

401 DVSADVFRYY EKDGEFVCFA GQSNQAVTGM YNLYRASQVM

441 FPGENILSDA RKFSSEFLHD KRANNELLDK WIITKDLPGE

481 VAYALDVPWY ASLPRLETRL YLEQYGGEDD VWIGKTLYRM

521 QKVNNNIYLE LGKLDYNNCQ ALHQLEWRSI QKWYNECGLG

561 EYGLSERSLL LSYYLAAASI FEPERSKERL AWAKTTMLIR

601 TIESYLSSEQ MVEDHNGAFV SEFQYYCSNL DYVNGGRHKP

641 TQRLVRTLLG TLNQISLDAV LVHGRDIHQY LRQAWEKWLI

681 ALQEGDDSDM GQEEAELLVR TLNLCAGRYA SEELLLSHPK

721 YQQLLHITTR VCNQIRHFQH KKVQDGENGR ANMGDGITSI

761 SSIESDMQEL TKLVVGNTQN DLDADTKQTF LTVAKSFYYT

801 AHCNPGTINC HIAKVLFERV L

A nucleic acid encoding the *Chiococca alba* ent-CPP synthase (CaTPS1) with SEQ ID NO:41 is shown below as SEQ ID NO:42.

1 ATGTCTTCTT CTACCTCAGC AGCAGCAACC CTTCTCGGAT

41 TATCGCCGGC AAGCCGCCGG TTTGTATCAT TTCCTCCGGC

81 AAATGGACCT ATAGAAACTA TTACCGGTAT TTGGTCGCCC

121 GGCAAAGCTC TTCATCACTT TAATTTCCGT CTGCGTTGTA

161 GCACGGTGTC CAGTCCTCGC ACCCAAGAAT TGGGCCAGGT

201 GTCACAAAAT GGCATGTCTG GTATAAAGTG GCATGACATA

241 GTGGAAGAAG GAGTCACAGA AAAAGGAACT CTTGAGGCGA

281 ACACATCAAG CTGGATAAAA GAAAGCATAG AAGCCATTCG

-continued

```
 321 TTGGATGCTG CGTACCATGG ATGACGGGGA TATCAGCATA
 361 TCTGCTTATG ATACTGCATG GGTTGCCCTT GTGGAAGATA
 401 TCAACGGAAG TGGCGGTCCT CAATTTCCTT CAAGCCTCGA
 441 GTGGATTGCC AACAATCAGC TTCCTGATGG TTCATGGGGC
 481 GACAGCGACA TCTTTTCAGC TCACGATCGG ATTCTCAACA
 521 CTTTGGGATG CGTTGTTGCA TTAAAATCTT GGAACATGCA
 561 CCCTGAAAAG AGTGAAAAAG GATTATTATA TTTAAGGGAT
 601 AACATTCACA AGCTTGAGGA TGAAAATGTC GAGCACATGC
 641 CTATCGGTTT TGAAGTGGCA TTTCCTTCAC TAATTGAGAT
 681 AGCCAAAAAG TTGAGCATTG ATATTCCGGA TGATTCTGCA
 721 ATCTTGCAGG AGATATATGC CAGAAGAAAT CTAAAGCTAA
 761 CAAGGATACC GAAGGACATT ATGCACACAG TGCCCACAAC
 801 ATTGCTCCAC AGCTTGGAAG GCATGCCAGA ACTAGACTGG
 841 AAAAGGCTAA TATCTCTAAA GTGTGAGGAT GGTTCCTTTC
 881 TGTTTTCTCC ATCCTCCACT GCTTTTGCCC TCACGCAAAC
 921 TAAAGATGCT GATTGCCTCA GATATTTAAC TAAAACCGTA
 961 CAAAAATTCA ATGGAGGAGT TCCCAATGTT TACCCCGTGG
1001 ACTTATTCGA ACACATCTGG GCTGTTGATC GACTTCAAAG
1041 ACTAGGAATT TCTCGATACT TCCAGTCAGA AATCCGCGAG
1081 TGCATCGATT ATGTTCACCG ATATTGGACG GATAAAGGTA
1121 TCTGTTGGGC TAGAAATACC CACGTTTATG ACATTGATGA
1161 TACAGCTATG GGTTTTAGAC TTCTAAGGTT GCATGGCTAC
1201 GATGTTTCTG CAGATGTTTT CAGATACTAT GAGAAGGATG
1241 GCGAATTCGT TTGCTTTGCC GGACAGTCAA ACCAGGCGGT
1281 GACCGGAATG TATAACCTGT ATAGAGCTTC TCAAGTGATG
1321 TTTCCAGGGG AGAATATACT TTCGGATGCT AGGAAATTCT
1361 CGTCCGAATT CTTGCATGAT AAGCGAGCCA ACAATGAGCT
1401 CCTAGATAAA TGGATCATAA CCAAAGATTT GCCTGGGGAG
1441 GTAGCATATG CTTTAGATGT TCCATGGTAT GCCAGTTTAC
1481 CTCGTTTAGA AACCAGATTG TATTTGGAAC AATATGGCGG
1521 CGAAGATGAT GTCTGGATTG GCAAGACATT GTACAGGATG
1561 CAAAAAGTTA ACAACAACAT CTATCTTGAA CTTGGCAAAT
1601 TAGATTACAA CAACTGTCAG GCATTGCATC AGCTTGAGTG
1641 GAGAAGCATC CAAAAATGGT ACAATGAATG CGGTCTTGGA
1681 GAGTACGGAT TAAGCGAGAG AAGCCTCCTT CTTTCGTATT
1721 ATTTGGCCGC AGCCAGTATA TTTGAACCGG AGAGGTCAAA
1761 GGAACGGCTT GCCTGGGCCA AAACTACTAT GCTAATCCGC
1801 ACAATTGAAT CTTATTTGAG TAGTGAACAA ATGGTTGAGG
1841 ATCACAATGG AGCCTTTGTT AGCGAGTTCC AATACTATTG
1881 CAGTAACCTT GACTACGTAA ATGGTGGAAG GCATAAGCCA
1921 ACACAAAGGC TAGTGAGGAC TCTACTCGGA ACTTTAAATC
```

-continued

```
1961 AGATTTCTTT GGACGCAGTG TTAGTCCACG GCAGAGATAT
2001 CCATCAATAT TTGCGTCAAG CCTGGGAAAA GTGGTTGATA
2041 GCTTTGCAAG AGGGAGATGA TAGTGACATG GGTCAAGAGG
2081 AAGCAGAACT TTTAGTGCGC ACACTAAACC TATGCGCCGG
2121 TCGCTACGCA TCGGAGGAGC TATTGTTGTC CCATCCCAAG
2161 TATCAACAAC TTTTGCACAT CACTACTAGA GTCTGTAACC
2201 AAATTCGTCA TTTCCAACAC AAAAAGGTGC AAGATGGGGA
2241 AAATGGAAGA GCAAACATGG GTGATGGCAT CACAAGCATC
2281 AGCTCAATAG AGTCGGACAT GCAAGAACTA ACGAAATTAG
2321 TTGTCGGCAA TACCCAAAAC GATCTAGATG CTGATACGAA
2361 GCAAACATTT CTCACGGTGG CAAAAAGCTT CTACTACACC
2401 GCCCACTGCA ATCCCGGAAC AATCAATTGC CATATTGCTA
2441 AAGTATTATT TGAGAGAGTA CTTTGA
```

A *Chiococca alba* (5R,8S,9S,10S)-labda-13-en-8-ol diphosphate (ent-8-LPP) synthase (CaTPS2) was identified and isolated. This CaTPS2 enzyme was identified as an 5R,8S,9S,10S)-labda-13-en-8-ol diphosphate (ent-8-LPP) synthase, which converts GGPP to 5R,8S,9S,10S)-labda-13-en-8-ol diphosphate (ent-8-LPP, [7]).

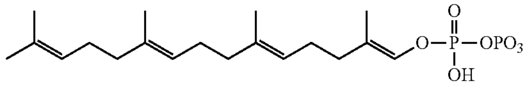

Geranylgeranyl diphosphate (GGPP)

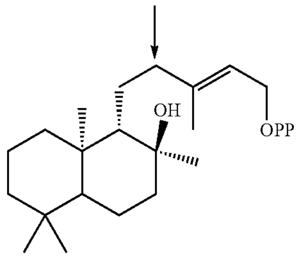

17

The *Chiococca alba* (5R,8S,9S,10S)-labda-13-en-8-ol diphosphate (ent-8-LPP) synthase (CaTPS2) has the amino acid sequence shown below (SEQ ID NO:43).

```
  1 MPVIKSHEFI EEVGPEKGTL KLSRSSRINE LVESIQTMLQ
 41 SMDDGEISMS AYDTAWVALV EDINGSSYPQ FPMSLEWIAN
 81 NQLPDGSWGD GSIFSVHDRI ISTLGCVLAL KSWNMHPDKS
121 EKGLLFIRDN IHKVGDESAE HMPIGFEVVF PSLIERAKNL
161 DIDIPDISAI LQEIYARRNL KLARIPKDIL YTVPTTLLHS
201 LEGMPELDWQ KLLPLKCEDG SFLFSPSCTA FALMQTKDGD
241 CLRYLTNTIE KFNGGVPGVY PVDLFEHIWA VDRLQRLGIS
281 RYFQTEIEEC MSYVYRYWTD KGICWARNSK VEDIDDTAMG
321 FRLLRLHGYM VSADVFAQFE KGGEFVCFAG QSNQALTGMF
```

-continued

361 NLYRASQVMF PGEKILADAK KFSSNFLHEK RANNELLDKW

401 IITKDLPGEV TYALDVPWYA SLPRVETRLY LEQYGGEDDV

441 WIAKTLYRMR KVNNKIYLEL GILDYNNCQA LHQLEWRSIQ

481 KWYKDSGLEE YGLSERNLLL AYYLATACIF EPERLVERLS

521 WAKTTALIYT TKSYFRTECN SGEQRKAFLH EFQQYCNDLD

561 YVSGARHKPT IRLIEALLGT LEQVSLDAIL DHGRYIHQDL

601 RNAWEKWLIA LQEGVDMDQE EAELTVLTLH LCAGSYTSEE

641 LLLSHPKYQQ LLNITSRVCH QIRQFQREKA QDTDNGRENL

681 VAITSIKAIE SDMQELAKLV LTKSTGDLAA KIKQTFLIVA

721 KSFYYTAHCL PGIISTHIAK VLFEKVF

A nucleic acid encoding the *Chiococca alba* (5R,8S,9S,10S)-labda-13-en-8-ol diphosphate (ent-8-LPP) synthase (CaTPS2) with SEQ ID NO:43 is shown below as SEQ ID NO:44.

1 ATGCCAGTAA TAAAGTCGCA TGAGTTTATT GAAGAGGTCG

41 GCCCGGAAAA AGGAACTCTG AAGCTGAGCA GATCAAGTAG

81 GATAAACGAA CTTGTAGAAT CAATTCAAAC GATGCTTCAA

121 TCGATGGATG ATGGGGAAAT AAGCATGTCT GCTTATGACA

161 CCGCGTGGGT TGCCCTTGTG GAAGATATTA ATGGAAGCAG

201 CTACCCTCAA TTCCCTATGA GCCTCGAGTG GATTGCCAAC

241 AATCAGCTTC CTGATGGTTC ATGGGGTGAC GGCAGTATCT

281 TTTCGGTTCA TGATCGGATA ATCAGCACAT TAGGATGTGT

321 TCTTGCATTA AAATCATGGA ACATGCACCC GGACAAAAGC

361 GAAAAAGGAC TGTTATTTAT AAGGGACAAT ATTCACAAGG

401 TTGGAGATGA GAGCGCTGAG CACATGCCTA TTGGTTTTGA

441 GGTGGTATTT CCTTCGCTTA TTGAGAGAGC CAAAAACTTG

481 GACATTGATA TTCCAGATAT TTCTGCTATC TTGCAAGAGA

521 TTTATGCACG AAGAAATCTA AAGCTCGCAA GGATTCCAAA

561 GGATATACTG TATACCGTGC CCACGACATT ACTTCATAGC

601 TTAGAAGGAA TGCCAGAACT GGACTGGCAA AAGCTACTGC

641 CATTAAAATG TGAGGATGGT TCATTTCTAT TTTCTCCATC

681 GTGCACTGCT TTTGCCCTCA TGCAGACTAA GGATGGTGAT

721 TGCCTCAGAT ATCTAACTAA TACCATAGAA AAATTCAATG

761 GGGGAGTTCC CGGTGTATAC CCTGTGGACT TGTTCGAACA

801 CATTTGGGCT GTTGATCGCT TGCAAAGACT AGGAATTTCC

841 CGGTATTTTC AGACAGAAAT TGAAGAATGT ATGAGTTATG

881 TTTACCGATA TTGGACGGAT AAAGGTATCT GTTGGGCTAG

921 AAACTCCAAA GTTGAAGACA TCGATGACAC AGCCATGGGT

961 TTTAGACTTC TAAGGTTGCA TGGTTACATG GTTTCTGCAG

1001 ATGTGTTTGC ACAGTTTGAG AAAGGGGGTG AATTCGTTTG

1041 CTTTGCTGGA CAGTCGAACC AGGCGCTGAC TGGAATGTTT

-continued

1081 AACCTGTATA GAGCTTCTCA AGTAATGTTT CCAGGGGAGA

1121 AGATACTTGC TGATGCCAAG AAATTCTCAT CGAACTTCTT

1161 ACATGAAAAG CGTGCAAACA ACGAGCTTCT AGATAAATGG

1201 ATCATAACTA AAGATTTGCC TGGAGAGGTG ACGTATGCGC

1241 TAGATGTTCC ATGGTACGCC AGTTTACCTC GTGTAGAAAC

1281 GAGATTATAT CTGGAACAAT ATGGAGGAGA GGATGATGTC

1321 TGGATTGCCA AGACATTGTA CAGGATGAGA AAAGTTAACA

1361 ACAAAATTTA CCTTGAACTT GGCATATTAG ATTACAATAA

1401 CTGTCAAGCA TTGCATCAGC TGGAGTGGAG AAGCATCCAA

1441 AAATGGTATA AGGATTCTGG CCTTGAAGAG TACGGGTTGA

1481 GCGAGAGGAA CCTTCTCCTG GCATATTATC TGGCCACAGC

1521 TTGTATATTT GAACCCGAAA GGTTGGTGGA GCGCCTTTCC

1561 TGGGCGAAAA CAACCGCCTT AATCTACACA ACAAAATCTT

1601 ATTTCAGAAC TGAATGCAAC TCTGGGGAAC AGAGAAAAGC

1641 TTTTCTTCAT GAGTTCCAAC AGTACTGCAA TGACCTGGAC

1681 TACGTTAGTG GCGCAAGGCA CAAGCCAACA ATAAGATTGA

1721 TCGAAGCTCT ACTTGGAACC CTAGAGCAGG TCTCTTTGGA

1761 TGCAATATTA GATCATGGCC GATATATCCA TCAAGATTTG

1801 CGTAATGCTT GGGAGAAATG GTTGATAGCT TTGCAAGAGG

1841 GAGTTGACAT GGACCAAGAA GAAGCAGAAC TTACAGTGCT

1881 CACACTACAC CTGTGTGCCG GCAGCTACAC ATCGGAGGAG

1921 TTACTGTTAT CTCATCCCAA GTATCAACAA CTTTTAAATA

1961 TCACTAGTAG AGTCTGCCAC CAAATTCGTC AATTCCAGCG

2001 CGAAAAGGCA CAGGATACGG ATAATGGAAG AGAAAACTTG

2041 GTTGCCATCA CAAGCATCAA GGCGATAGAA TCAGACATGC

2081 AAGAACTTGC GAAATTAGTT CTGACCAAAT CCACTGGCGA

2121 TTTAGCTGCT AAAATCAAGC AAACATTTCT TATAGTGGCA

2161 AAGAGCTTCT ACTACACCGC ACATTGCCTT CCTGGAATTA

2201 TCAGTACCCA CATTGCCAAA GTACTATTTG AGAAAGTTTT

2241 CTGA

A *Chiococca alba* CaTPS3 and CaTPS4 were identified and isolated. CaTPS3 and CaTPS4 were identified as an ent-kaurene synthase, converting ent-CPP [16] into ent-kaurene [19].

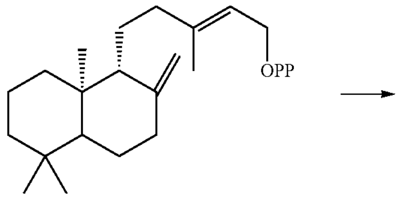

16

-continued

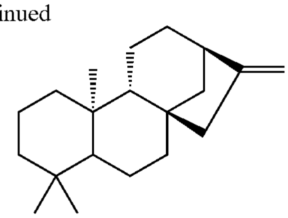

19

The *Chiococca alba* ent-kaurene synthase (CaTPS3) has the amino acid sequence shown below (SEQ ID NO:45).

```
  1 MMMMMVVMNT APAHSYHPFP FAGPKSSATL FSNYYCSSRK
 41 KSSPPRISAS VSLLTGVEST TAINSSDPEI KERIRKLFHD
 81 VDISLSSYDT AWVAMVPAPH SSQSPLFPQC INWLLDNQLP
121 DGSWSLPPPH HHPLLLKDAL SSTLACVLAL RRWGIGQEQV
161 DKGIRFVELN FASASDQNQH LPVGFDIIFP GMLEYARDLN
201 LNLQLESATV NALLLKRDQE LTRFFKSYSD ESKAYLAYVS
241 EGIVKLQNWD TVMKFQRKNG SLFNSPSATA AAVMHVHNPG
281 CLDYLHSVLE KHGNAVPTVY PLDIYPRLCL VDNLERLGIC
321 GHFRKEILSV LDDTYRCWMQ GDEEIFAEKS TCAIAFTLLR
361 KHGYNISADP LTPFLKEECF SNSLGGCLKD TSAVLELYRA
401 LEMIISQNES ALVKKSLWSR SFLKEHISGG CDLKGFSNQI
441 SILVDDILNF PSHATLQRVA NRRSIEQYNL DSTKILKTSY
481 CSSNFSNKDL LILAVKDFNH CQLIHREELK ELERWVTDNR
521 LDKLKFARQK SAYCYFSAAA TIFSPELSDA RMSWAKNGVL
561 ATLVDDFFDV GGSLEELKKL IELVEKWDIN VSDGCCSEPV
601 QILFSALHST IQEIGDKAFK WQARSVTNHI FKIWLDLLNS
641 MLREAEWARN ATVPTVEEYM TNGYVSFALG PIILPALYLV
681 GPKLSEEVVK DSEFHSLFKL VSTCGRLLND VHSFERESKS
721 GQLNALSLRL IHGGVGITEA AAVAEMKSSI ENLRRELLRL
761 VLRKEGSVVP RACKDLFWNM SKVLHQFYNK DDGFTSEEMI
801 QLVKSIIYEP IAVNEFLNSC HT
```

A nucleic acid encoding the *Chiococca alba* ent-kaurene synthase (CaTPS3) with SEQ ID NO:45 is shown below as SEQ ID NO:46.

```
   1 ATGATGATGA TGATGGTGGT GATGAACACA GCTCCCGCCC
  41 ACTCTTACCA TCCTTTCCCC TTTGCCGGCC CAAAATCCTC
  81 AGCCACACTT TTTTCCAATT ATTATTGTTC CAGTAGGAAG
 121 AAATCATCGC CACCTCGCAT CTCTGCCTCA GTTTCTTTGC
 241 TAACTGGAGT TGAAAGCACA ACTGCAATTA ATTCTTCAGA
 281 CCCGGAGATC AAAGAAAGAA TAAGGAAACT ATTTCATGAT
 321 GTTGATATCT CGCTTTCTTC ATATGACACT GCATGGGTGG
 361 CAATGGTCCC TGCTCCACAT TCTTCCCAGT CTCCCCTTTT
```

-continued

```
 401 TCCCCAGTGC ATTAATTGGT TATTGGACAA TCAGCTTCCT
 441 GATGGCTCAT GGAGTCTTCC TCCTCCTCAT CATCATCCTC
 481 TATTACTTAA AGATGCATTA TCCTCTACCC TTGCATGTGT
 521 TCTTGCGCTC AGGAGATGGG GAATTGGTCA AGAACAAGTT
 561 GACAAGGGTA TTCGTTTTGT TGAGTTAAAT TTTGCTTCAG
 601 CATCTGACCA GAACCAGCAT TTGCCAGTTG GATTTGACAT
 641 TATATTCCCT GGCATGCTCG AATATGCTAG AGATTTAAAT
 681 TTAAATCTTC AACTAGAATC TGCAACAGTA AATGCCTTAC
 721 TTCTTAAAAG AGATCAGGAG CTTACAAGAT TCTTTAAAAG
 761 CTACTCAGAC GAGAGTAAAG CATACCTTGC ATATGTATCA
 801 GAAGGTATAG TAAAGTTACA GAACTGGGAT ACAGTTATGA
 841 AGTTCCAAAG AAAGAACGGG TCACTATTCA ATTCACCTTC
 881 AGCTACAGCA GCTGCTGTTA TGCATGTCCA CAATCCTGGT
 921 TGCCTCGATT ACCTTCACTC AGTGTTGGAG AAGCATGGAA
 961 ATGCTGTTCC AACAGTTTAC CCTTTGGATA TATATCCACG
1001 CCTCTGCTTG GTTGACAACC TTGAGAGACT GGGTATTTGT
1041 GGTCATTTTA GGAAGGAAAT TCTGAGTGTA TTGGATGATA
1081 CATACAGATG CTGGATGCAG GGGGATGAAG AGATATTTGC
1121 AGAAAAATCA ACTTGTGCCA TAGCATTTAC ATTATTGCGA
1161 AAGCATGGGT ACAACATCTC TGCAGATCCA TTGACCCCAT
1201 TCTTAAAGGA AGAGTGTTTT TCCAATTCTT TGGGTGGATG
1241 TTTGAAAGAT ACTAGTGCTG TACTTGAATT ATACCGGGCA
1281 TTAGAGATGA TTATTAGCCA GAATGAATCA GCTCTGGTGA
1321 AAAAAAGCTT GTGGTCCAGA AGCTTCCTGA AAGAGCATAT
1361 TTCTGGTGGT TGTGATTTAA AGGGATTCAG CAATCAAATT
1401 TCCATACTGG TGGATGATAT CCTCAACTTT CCATCGCATG
1481 CTACTTTGCA ACGGGTTGCT AACAGGAGAA GCATAGAGCA
1521 ATACAACTTA GACAGTACAA AAATTTTAAA AACTTCATAT
1561 TGCTCGTCGA ATTTTAGCAA CAAAGATTTA TTGATCCTGG
1601 CAGTCAAAGA TTTTAATCAT TGCCAACTCA TACACCGTGA
1641 AGAACTGAAA GAACTAGAAA GGTGGGTCAC AGACAATAGA
1681 TTGGACAAGT TAAAGTTTGC TAGGCAGAAG TCTGCATACT
1721 GTTACTTTTC TGCTGCAGCA ACCATATTCT CACCTGAACT
1761 TTCTGATGCC CGCATGTCAT GGGCCAAGAA TGGTGTACTT
1801 GCTACTTTGG TTGATGACTT CTTTGACGTG GGAGGTTCTC
1841 TAGAGGAATT AAAGAAACTG ATTGAGTTGG TTGAAAAGTG
1881 GGATATAAAT GTCAGTGATG GTTGTTGCTC TGAACCAGTG
1921 CAAATCCTCT TCTCAGCACT ACATAGTACA ATCCAGGAGA
1961 TTGGAGATAA AGCATTCAAA TGGCAAGCAC GCAGTGTAAC
2001 AAACCACATA TTTAAGATAT GGTTAGATTT GCTTAATTCT
2041 ATGTTGAGGG AAGCTGAGTG GGCTAGAAAT GCAACAGTGC
```

-continued

```
2081 CTACAGTTGA AGAATATATG ACAAATGGTT ATGTATCATT

2121 TGCTTTGGGG CCAATTATCC TCCCTGCTCT TTATCTTGTT

2161 GGACCTAAGC TGTCAGAGGA AGTAGTTAAG GATTCTGAAT

2201 TCCACTCCCT TTTTAAGCTA GTGAGTACCT GTGGGCGGCT

2241 TCTGAATGAT GTCCACAGCT TCGAGAGGGA ATCAAAGTCC

2281 GGCCAACTAA ATGCTCTGTC TCTGCGCCTG ATTCATGGTG

2321 GTGTTGGCAT TACTGAAGCA GCTGCTGTTG CAGAGATGAA

2361 GAGTTCAATT GAGAATCTAA GGAGAGAACT GCTGAGACTA

2401 GTCTTGCGCA AAGAGGGTAG TGTAGTTCCA AGAGCTTGCA

2441 AGGATTTGTT TTGGAATATG AGTAAAGTGC TACATCAATT

2481 TTACAACAAA GATGATGGAT TTACTTCAGA GGAGATGATT

2521 CAGCTTGTGA AGTCGATCAT TTATGAGCCA ATTGCGGTCA

2561 ATGAATTTTT GAATAGTTGC CATACATGA
```

The *Chiococca alba* ent-kaurene synthase (CaTPS4) has the amino acid sequence shown below (SEQ ID NO:47).

```
  1 MMIMVMNTAP VHAYHALPIP TQKSSTTLFP NYNCSSRKKS

 41 SPPRISAASV SLQTGVERTT AIHSSDLEIK ERIRKLFHDV

 81 DISLSSYDTA WVAMVPAPHS SQSPLFPQCI NWLLDNQLPD

121 GSWSLPPHHH HHHPLLLKDA LSSTLACVLA LRRWGIGQEQ

161 VDKGIRFVEL NFASASDQNQ HLPVGFDIIF PGMLEYARDL

201 NLNLQLESAT VDALLLKRDQ ELIRFFKSYS DESKAYLAYV

241 SEGIIKLQNW DTVMKFQRKN GSLFNSPSAT AAAVMHVHNP

281 GCLDYLHSVL EKHGNAVPTV YPLDIYPRLC LVDNLERLGI

321 CGHFRKEILS VLDDTYRCWM QGDEEIFAEK STCAIAFTLL

361 RKHGYNISAD PLTPFLKEEC FSNSLGGCLK DTSAVLELYR

401 ALEMIISQNE SALVKKSLWS RSFLKEHISG GCDLKGFSNQ

441 ISKQVDDILN FPSHATLQRV ANRRSIEQYN LDSTKILKTS

481 YCSSNFSNKD LLILAVKDFN HCQLIHREEL KELERWVADN

521 RLDKLKFARQ KSAYCYFSAA ATIFSPELSD ARISWARNGV

561 LTTLVDDFFD VGGSLEELKK LIELVEKWDI NVSDGCCSEP

601 VQILFSALHS TIQEIGDKAF KWQARSVTNH IIKIWLDLLN

641 SMLREAEWAR NATVPTVEEY MTNGYVSFAL GPIILPALYL

681 VGPKLSEELV KDSEFHSLFK LVSTCGRLLN DVHSFERESK

721 AGQLNALSLR LIHGGVGITE AAAVAEMKSS IEKQRRELLR

761 LVLRKEGSVV PRACKDLFWN MSRVLHQFYV KDDGFTSEEM

801 IELVKSIIYE PIAVNEF
```

A nucleic acid encoding the *Chiococca alba* ent-kaurene synthase (CaTPS4) with SEQ ID NO:47 is shown below as SEQ ID NO:48.

```
   1 ATGATGATAA TGGTGATGAA CACAGCTCCC GTCCACGCTT

  41 ACCACGCTTT ACCCATTCCC ACCCAAAAAT CCTCAACCAC

  81 ACTTTTTCCC AATTATAACT GTTCCAGTAG GAAGAAATCA

 121 TCGCCACCTC GCATCTCTGC CGCCTCAGTT TCTTTGCAAA

 161 CTGGAGTTGA AAGAACGACG GCAATTCATT CTTCAGACCT

 201 AGAGATCAAA GAAAGAATAA GGAAACTATT TCATGATGTT

 241 GATATCTCGC TTTCTTCATA TGACACTGCA TGGGTGGCAA

 281 TGGTCCCTGC TCCACATTCT TCCCAGTCTC CCCTTTTTCC

 321 CCAGTGCATT AATTGGTTAT TGGACAATCA GCTTCCTGAT

 361 GGCTCATGGA GTCTTCCTCC TCATCATCAT CATCATCATC

 401 CCCTATTACT TAAAGATGCA TTATCCTCTA CGCTTGCATG

 441 TGTTCTTGCG CTCAGGAGAT GGGGAATTGG TCAAGAACAA

 481 GTTGACAAGG GTATTCGTTT TGTTGAGTTA AATTTTGCTT

 521 CTGCATCTGA CCAGAACCAG CATTTGCCAG TTGGATTTGA

 561 CATTATATTC CCTGGCATGC TCGAATATGC TAGAGATTTA

 601 AATTTAAATC TTCAACTAGA ATCCGCAACT GTAGATGCCT

 641 TACTTCTCAA AAGAGATCAG GAGCTTATAA GATTCTTTAA

 681 AAGCTACTCA GACGAGAGTA AAGCATACCT TGCATATGTA

 721 TCAGAAGGTA TCATAAAGTT ACAGAACTGG GATACAGTTA

 761 TGAAGTTCCA AAGAAAGAAC GGGTCACTGT TCAATTCACC

 801 TTCAGCTACA GCAGCTGCTG TTATGCATGT CCACAATCCT

 841 GGCTGCCTCG ATTACCTTCA CTCAGTGTTG GAGAAGCATG

 881 GCAATGCTGT TCCAACAGTT TACCCTTTGG ATATATATCC

 921 ACGCCTCTGC TTGGTTGACA ACCTTGAGAG ACTGGGTATT

 961 TGTGGTCATT TTAGGAAGGA AATTCTGAGT GTATTGGATG

1001 ATACATACAG ATGCTGGATG CAGGGGGATG AAGAGATATT

1041 TGCAGAAAAA TCAACTTGTG CCATAGCATT TACATTATTG

1081 CGAAAGCATG GGTACAACAT CTCTGCAGAT CCATTGACCC

1121 CATTCTTAAA GGAAGAGTGT TTTTCCAATT CTTTGGGTGG

1161 ATGTTTGAAA GATACTAGTG CTGTACTTGA ATTATACCGG

1201 GCATTAGAGA TGATTATTAG CCAGAATGAA TCAGCTCTGG

1241 TGAAAAAAAG CTTGTGGTCC AGAAGCTTCC TGAAAGAGCA

1281 TATTTCTGGT GGTTGTGATT TAAAGGGATT CAGCAATCAA

1321 ATTTCCAAAC AGGTGGATGA TATCCTCAAC TTTCCATCGC

1361 ATGCTACTTT GCAACGGGTT GCTAACAGGA GAAGCATAGA

1401 GCAATACAAC TTAGACAGTA CAAAAATTTT AAAAACTTCA

1441 TATTGCTCGT CGAATTTTAG TAACAAAGAT TTATTGATCC

1481 TGGCAGTCAA AGATTTTAAT CATTGCCAAC TCATACACCG
```

-continued

```
1521 TGAAGAACTG AAAGAACTAG AAAGGTGGGT CGCAGACAAT
1561 AGATTGGACA AGTTAAAGTT TGCTAGGCAG AAGTCTGCAT
1601 ACTGTTACTT TTCTGCTGCA GCAACCATAT TCTCACCTGA
1641 ACTTTCTGAT GCCCGCATCT CATGGGCCAA AAATGGTGTA
1681 CTTACTACTT TGGTTGATGA CTTCTTTGAC GTGGGAGGTT
1721 CTCTAGAGGA ATTAAAGAAA CTGATTGAGT TGGTTGAAAA
1761 GTGGGATATA AATGTCAGTG ATGGTTGTTG CTCTGAACCA
1801 GTGCAAATCC TCTTCTCAGC ACTACATAGT ACAATCCAGG
1841 AGATTGGAGA TAAAGCATTC AAATGGCAAG CACGCAGTGT
1881 AACAAACCAC ATAATTAAGA TATGGTTAGA TTTGCTTAAT
1921 TCTATGTTGA GGGAAGCTGA GTGGGCTAGA AATGCAACAG
1961 TGCCTACAGT TGAAGAATAT ATGACAAATG GTTATGTATC
2001 ATTTGCCTTG GGGCCAATTA TCCTCCCTGC TCTTTATCTT
2041 GTTGGACCTA AGCTGTCAGA GGAATTAGTT AAGGATTCTG
2081 AATTCCACTC CCTTTTTAAG CTAGTGAGTA CCTGTGGGCG
2121 GCTTCTGAAT GATGTCCACA GCTTCGAGAG GGAATCAAAG
2161 GCCGGCCAAC TAAATGCTCT TTCTCTGCGC CTGATTCATG
2201 GTGGAGTTGG CATTACTGAA GCAGCTGCTG TTGCAGAGAT
2241 GAAGAGTTCA ATTGAGAAGC AAAGGAGAGA ACTGCTGAGA
2281 CTAGTCTTGC GCAAAGAGGG TAGTGTAGTT CCAAGAGCTT
2321 GCAAGGATTT GTTTTGGAAT ATGAGTAGGG TGCTACATCA
2361 ATTTTACGTC AAAGATGATG GATTTACTTC AGAGGAGATG
2401 ATTGAGCTTG TGAAGTCGAT CATTTATGAG CCAATTGCGG
2441 TCAATGAATT TTGA
```

A *Chiococca alba* 13(R)-epi-dolabradiene synthase (CaTPS5) was identified and isolated. This CaTPS5 enzyme was identified as an 13(R)-epi-dolabradiene synthase, which converts ent-CPP [16] to 13(R)-epi-dolabradiene.

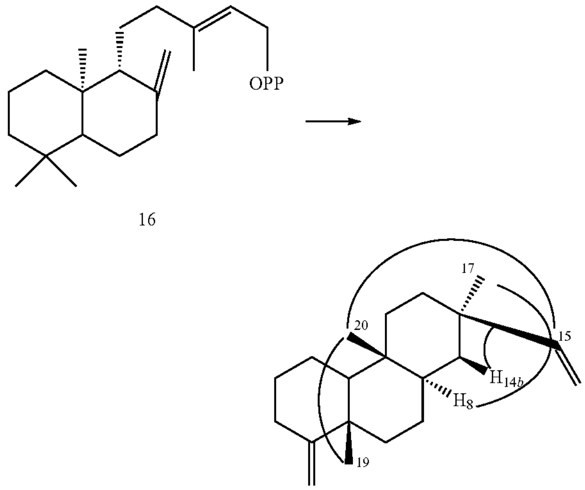

16

The *Chiococca alba* 13(R)-epi-dolabradiene synthase (CaTPS5) has the amino acid sequence shown below (SEQ ID NO:49).

```
  1 MIHTLPHGGQ AHFISHKTQP YYSSRPRFSS AASLDTRVRR
 41 TSPSNSSVLD FNETKERITK LFHNVDYSIS SYDTAWVAMV
 81 PDPHSSQAPL FPECINWLLD NQFHDGSWSL PHHNSLLLKD
121 VLSSTLACVL ALKRWGIGGR QIDKGVRFIE MNFGSASDNC
161 QHTPIGFDII FPGMLENARD LDLNLRLEPR IVTDMQRKRD
201 MQLTRLHESD LKGDQAYLAY VSEGMQKLQN WDLAMKFQRK
241 NGSLFNSPSA TAAAVMHVQN PASLNYLHSV VDKFGHAVPA
281 VYPLDLYARL CLVDNLERLG ICRHFTNEIE IVMEDTYRCW
321 LQDDEDIFAE ISTCALAFRL LRKHGYVVSP DPLTKIIEEE
361 DVSNSSGNGY WNDIHAVMEV HRASEVVIHE NESDLKNQNT
401 ISKHLLRHHL FNGSDVKPFP NPIYKQVDYA LKFPTPLILQ
441 RVENKTLIQN YDVDSTRLLK TSYRSSNFCN EDLLRLAVKD
481 FNDCQLLHRK ELKELERWSA DNRLHELKFA RQKAIYCSFS
521 AAATIFIPEW YEARMSLAKN SVLATVVDDF FDVGGSMEEL
561 KKLIEFVEKW DIDITKESCS EPLKIIFSAL HSTISEIGEQ
601 AVKWQGRNVT SHIIEIWLDL LNSMLRESEW TTDVHMPTLD
641 EYMEAAYVSF AMGPIIIPAL YFVGPKLSDE IVRDPEIRSL
681 HKLVSICGRL LNDMQGFERE KKAGKPNAVS IRISQNGDGI
721 TESAAFEEVK MELEDARREL LRLVVQKDGS VVPRACKDAF
761 WSVSRMLHHF YFNNDGYTSE VEMVELVNSI IHEPLK
```

A nucleic acid encoding the *Chiococca alba* 13(R)-epi-dolabradiene synthase (CaTPS5) with SEQ ID NO:49 is shown below as SEQ ID NO:50.

```
  1 ATGATTCATA CTCTCCCTCA TGGCGGCCAG GCTCACTTCA
 41 TTTCCCACAA AACACAGCCT TATTATTCCA GTAGACCTCG
 81 CTTTTCTTCA GCAGCTTCTT TGGACACACG AGTCCGGAGA
121 ACATCGCCCT CTAATTCCTC TGTCCTAGAC TTCAACGAGA
161 CCAAAGAAAG AATCACAAAA TTATTTCATA ATGTTGATTA
201 TTCAATTTCT TCATATGATA CAGCATGGGT TGCTATGGTC
241 CCGGACCCAC ATTCTTCTCA GGCTCCCCTT TTCCCAGAGT
281 GCATAAATTG GTTGCTAGAT AATCAATTTC ATGATGGCTC
321 CTGGAGTCTT CCTCATCACA ATTCTCTATT GCTTAAGGAT
361 GTTTTATCCT CTACGCTTGC GTGTGTTCTT GCTCTTAAGA
401 GATGGGGAAT AGGAGGAAGG CAGATTGACA AAGGTGTTCG
441 CTTTATTGAG ATGAATTTTG GCTCAGCATC TGACAATTGC
481 CAGCATACTC CAATAGGATT TGACATAATA TTTCCAGGAA
521 TGCTTGAAAA TGCCAGAGAT TTGGATCTAA ATCTTAGACT
561 AGAACCCAGA ATTGTAACTG ACATGCAACG TAAAAGAGAC
```

-continued

```
 601 ATGCAGCTTA CAAGACTCCA TGAAAGCGAT CTAAAGGGGG

 641 ACCAAGCATA CTTGGCATAT GTATCCGAAG GGATGCAAAA

 681 GTTACAGAAT TGGGATTTGG CGATGAAGTT TCAAAGGAAG

 721 AATGGATCGC TCTTCAACTC ACCATCAGCT ACAGCAGCCG

 801 CTGTTATGCA TGTCCAAAAT CCTGCTTCCC TCAATTATCT

 841 TCATTCAGTC GTCGACAAAT TCGGCCATGC AGTTCCGGCT

 881 GTTTACCCTT TGGATCTCTA TGCGCGCCTT TGCTTGGTTG

 921 ACAATCTTGA GAGGCTGGGT ATCTGTCGAC ATTTTACTAA

 961 TGAAATTGAA ATTGTAATGG AGGACACGTA CAGGTGCTGG

1001 CTGCAGGATG ATGAAGATAT ATTTGCCGAA ATATCAACTT

1041 GTGCCTTAGC TTTTCGGTTA TTGAGAAAAC ATGGCTATGT

1081 TGTCTCCCCA GATCCACTGA CAAAAATCAT AGAAGAAGAA

1121 GATGTTTCCA ATTCTTCTGG TAATGGATAT TGGAATGATA

1161 TACATGCTGT AATGGAAGTG CATCGGGCAT CAGAGGTGGT

1201 TATACATGAA AATGAATCAG ATTTAAAGAA TCAAAATACC

1241 ATATCAAAAC ACCTTCTCAG ACACCATCTT TTCAATGGTT

1281 CTGATGTGAA GCCCTTTCCT AATCCAATAT ACAAGCAGGT

1321 GGACTATGCT CTCAAGTTTC CAACCCCCTT AATTCTACAA

1361 CGTGTTGAAA ACAAGACCCT CATACAGAAC TACGACGTAG

1401 ACAGTACAAG ACTTCTTAAA ACTTCATATC GATCATCAAA

1441 TTTCTGCAAT GAAGATTTAC TGAGGTTAGC AGTGAAAGAT

1481 TTTAATGACT GTCAACTCCT GCACCGGAAA GAACTAAAAG

1521 AACTAGAAAG ATGGTCCGCA GATAACAGAC TGCACGAACT

1601 AAAATTTGCT CGGCAGAAAG CTATATACTG CTCCTTTTCT

1641 GCTGCAGCAA CGATTTTCAT ACCTGAATGG TACGAAGCCC

1681 GCATGTCATT GGCCAAAAAT AGTGTACTTG CTACTGTGGT

1721 TGATGACTTC TTTGATGTGG GTGGTTCGAT GGAGGAATTA

1761 AAGAAGCTAA TTGAATTTGT TGAAAAGTGG GATATTGACA

1801 TCACCAAGGA ATCCTGCTCT GAGCCACTCA AAATCATATT

1841 TTCAGCACTG CACAGTACAA TCTCTGAGAT TGGAGAGCAA

1881 GCAGTTAAAT GGCAAGGACG CAATGTAACA AGCCACATAA

1921 TTGAGATCTG GTTGGATTTG CTCAATTCGA TGTTGAGGGA

1961 GTCTGAATGG ACTACAGATG TGCACATGCC AACATTGGAT

2001 GAATATATGG AAGCTGCTTA TGTATCATTC GCCATGGGGC

2041 CAATTATCAT CCCTGCTCTG TATTTTGTTG GGCCTAAGCT

2081 ATCTGATGAA ATTGTTCGGG ATCCTGAAAT ACGATCCCTC

2121 CATAAGCTTG TGAGCATTTG TGGGCGGCTT CTAAATGATA

2161 TGCAAGGGTT CGAGAGGGAA AAGAAGGCTG GTAAACCAAA

2201 TGCCGTGTCT ATACGCATTA GTCAAAATGG TGATGGCATT

2241 ACCGAATCAG CAGCTTTCGA AGAAGTGAAG ATGGAATTAG

2281 AGGATGCAAG GAGAGAATTG CTAAGATTAG TTGTGCAAAA
```

-continued

```
2321 AGATGGTAGT GTAGTTCCAA GAGCTTGCAA GGATGCGTTT

2361 TGGAGCGTAA GCAGAATGTT GCATCATTTC TACTTCAATA

2401 ATGATGGATA CACGTCAGAG GTGGAGATGG TTGAGCTCGT

2441 GAATTCAATT ATTCATGAAC CACTAAAATA A
```

A *Salvia hispanica* (−)-kolavenyl diphosphate synthase (ShTPS1) was identified and isolated. This ShTPS1 enzyme was identified as an (−)-kolavenyl 35 diphosphate synthase, which converts GGPP to (−)-kolavenyl diphosphate [36].

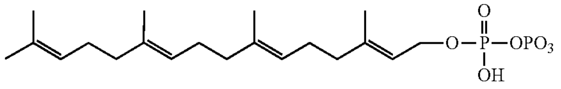

Geranylgeranyl diphosphate (GGPP)

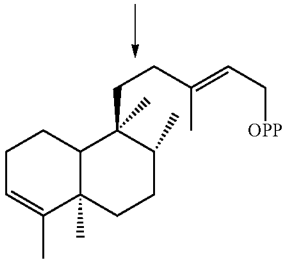

36

The *Salvia hispanica* (−)-kolavenyl diphosphate synthase (ShTPS1) has, for example, an amino acid sequence shown below (SEQ ID NO:51).

```
  1 MSIQANMSFA TSLHRSTTPG VGLPLKPCIS PSPSLSFSPN

 41 FGTFNNTSLR LKPEAGSKSY EGIRRSHQLA ASTILEGQTP

 81 ITPEVESEKT RLIERIRSML QDMDNDGQIS VSPYDTAWVA

121 LVEDIGGSGG PQFPTSLEWI SNHQYDDGSW GDRKFVLYDR

161 ILNTLACVVA LTNWKMHPNK CEKGLRFIHE NIKKLADEDE

201 ELMPVGFEIA LPSVIDLAKR LGIEIPENSA SIKRIYELRD

241 SKLKKIPMDL VHKRPTSLLF SLEGMEGLNW DKLMNFLAEG

281 SFLSSPSSTA YALQHTKNEL CLEYLLKAVK RFNGGVPNAY

321 PVDMFEHLWS VDRLQRLGIS RYFQAEIEEN MAYAYRYWTN

361 KGITWARNMV VQDSDDSAQG FRLLRLYGYD IPIDVFKHFE

401 QGGQFCSIPG QMTHAITGMY NLYRASELLF PGEHILSDAR

441 KYTGNFLHQR RITNTWDKVV IITKDLHGEV AYALDVPFYA

481 SLPRLEARFF IEQYGGDEDV WIGKTLYRMF KVNSDTYLEM

521 AKLDYKQCQS VHQLEWNSMQ RLYRDCNLGE FGLSERSLLL

561 AYYIAASTTF EPEKSSERLA WAITTILVEI IASQKLSDEQ

601 KREFVDEFVK GSIVNNQNGG RHKPGNRLVE VLINNITLMA

641 EGRGTYQQLS NAWKKWLKTW EEGGDLGEAE ARLLLHTIHL

681 SSGLDDSSFS HPKYQQLLEA TSKVCHQLRV FQSVKVYDDQ
```

-continued

721 ESTSQLVTRT TFQIEAGMQE LVKLVFTKTL EDLPSTTKQS

761 FFSVARSFYY TACIHADTID SHINKVLFEK IV

A nucleic acid encoding the *Salvia hispanica* (−)-kolavenyl diphosphate synthase (ShTPS1) with SEQ ID NO:51 is shown below as SEQ ID NO:52.

1 ATGAGTATTC AAGCAAACAT GTCATTTGCC ACCTCCCTCC

41 ACCGATCAAC CACCCCCGGA GTTGGCCTTC CGCTAAAACC

81 ATGTATCTCT CCCTCTCCCT CTCTTTCCTT TTCCCCAAAC

121 TTTGGCACTT TTAACAACAC AAGTTTGAGA CTCAAACCAG

161 AGGCTGGGAG CAAAAGTTAT GAGGGGATTC GAAGAAGTCA

201 TCAATTAGCA GCATCAACAA TTTTGGAGGG TCAAACTCCG

241 ATTACTCCGG AGGTTGAATC GGAGAAAACA CGCCTGATTG

281 AAAGGATTCG TTCGATGTTA CAAGACATGG ACAACGATGG

321 CCAGATAAGT GTGTCACCAT ACGACACAGC ATGGGTGGCG

361 CTCGTGGAAG ATATTGGTGG CAGCGGAGGG CCACAGTTTC

401 CAACGAGCCT AGAGTGGATT TCTAACCACC AGTACGACGA

441 TGGATCGTGG GGGGATCGCA AATTTGTTCT CTATGACCGG

481 ATACTCAATA CATTAGCATG TGTTGTCGCA CTCACGAATT

521 GGAAAATGCA TCCTAACAAA TGCGAAAAAG GGTTGAGGTT

561 TATTCATGAG AATATTAAGA AACTCGCGGA TGAAGATGAA

601 GAGCTCATGC CCGTAGGATT CGAAATCGCA CTGCCATCAG

641 TCATTGATTT AGCTAAAAGA CTGGGTATAG AAATCCCAGA

681 AAATTCTGCA AGCATAAAAA GAATTTATGA ATTGAGAGAT

721 TCAAAACTTA AAAAAATACC AATGGATTTA GTGCACAAAA

761 GGCCCACATC ACTACTCTTC AGCTTGGAAG GCATGGAAGG

801 CCTTAACTGG GACAAACTAA TGAATTTTCT AGCCGAGGGT

841 TCGTTTCTTT CATCGCCATC GTCCACTGCC TACGCTCTCC

881 AACACACCAA GAATGAGTTA TGCCTAGAGT ATTTACTCAA

921 GGCAGTCAAG AGATTCAATG GTGGAGTTCC AAATGCATAC

961 CCTGTCGACA TGTTTGAGCA TCTGTGGTCC GTGGATCGCT

1001 TACAGAGATT AGGAATTTCT CGGTATTTTC AAGCTGAAAT

1041 TGAAGAAAAC ATGGCCTATG CTTACAGATA CTGGACAAAT

1081 AAAGGAATCA CCTGGGCAAG AAATATGGTT GTCCAAGACA

1121 GTGACGACAG CGCACAGGGA TTCAGGCTCT TAAGGTTGTA

1161 CGGATACGAT ATTCCTATAG ATGTTTTCAA ACATTTCGAG

1201 CAAGGTGGAC AATTCTGCAG CATACCAGGA CAGATGACAC

1241 ACGCTATTAC AGGAATGTAC AACTTGTATA GAGCTTCTGA

1281 ACTTCTGTTC CCTGGAGAAC ACATACTTTC TGATGCTAGA

1321 AAATACACAG GTAACTTCTT GCATCAAAGA AGAATTACTA

1361 ACACGGTAGT AGACAAGTGG ATCATTACCA AAGACCTTCA

-continued

1401 CGGCGAGGTG GCTTATGCAT TGGATGTGCC ATTCTACGCC

1441 AGTCTGCCAC GACTGGAAGC ACGATTCTTC ATAGAACAAT

1481 ATGGGGGTGA TGAAGATGTT TGGATTGGGA AAACATTGTA

1521 CAGGATGTTT AAAGTAAACT CCGACACATA CCTTGAGATG

1561 GCAAAATTAG ATTACAAACA ATGCCAGTCT GTGCATCAGT

1601 TAGAGTGGAA TAGCATGCAA AGATTGTATA GAGATTGCAA

1641 TCTAGGAGAG TTTGGGTTGA GCGAAAGAAG CCTTCTCCTA

1681 GCTTACTACA TAGCAGCCTC AACTACATTT GAGCCGGAAA

1721 AATCAAGTGA AAGACTGGCT TGGGCTATAA CAACAATTTT

1761 AGTCGAAATA ATCGCATCCC AAAAACTCTC TGATGAGCAA

1801 AAGAGAGAGT TTGTTGATGA ATTTGTAAAA GGAAGCATCG

1841 TCAATAACCA AAATGGAGGA AGACATAAAC CGGGAAACAG

1881 ATTGGTTGAA GTTTTGATCA ACAATATAAC ACTGATGGCA

1921 GAAGGCAGAG GCACATATCA GCAGTTGTCT AATGCGTGGA

1961 AAAAATGGCT AAAGACATGG GAAGAGGGAG GTGACCTGGG

2001 GGAAGCAGAA GCACGGCTTC TCCTGCACAC GATACATTTG

2041 AGCTCCGGAT TGGATGATTC ATCATTTTCC CATCCAAAAT

2081 ATCAGCAGCT CTTGGAGGCA ACCAGCAAAG TCTGCCACCA

2121 ACTTCGCGTA TTCCAGAGTG TAAAGGTGTA TGATGACCAA

2161 GAGTCTACAA GCCAACTGGT AACTAGGACA ACTTTCCAAA

2201 TAGAAGCAGG CATGCAAGAA CTAGTGAAAT TAGTTTTCAC

2241 AAAAACCTTG GAAGATTTGC CTTCTACTAC CAAGCAAAGC

2281 TTTTTTAGTG TTGCTAGAAG TTTCTATTAC ACTGCCTGTA

2321 TTCATGCAGA CACTATAGAC TCCCACATAA ACAAAGTATT

2361 GTTTGAAAAA ATTGTCTAG

A *Teucrium canadense* cleroda-4(18),13E-dienyl diphosphate synthase (TcTPS1) was identified and isolated. This TcTPS1 enzyme was identified as a cleroda-4(18),13E-dienyl diphosphate synthase, which converts GGPP to cleroda-4(18),13E-dienyl diphosphate [38]. In addition, the combination of TcTPS1 and SsSS enzymes generated neo-cleroda-4(18),14-dien-13-ol [37]. These compounds are shown below.

37

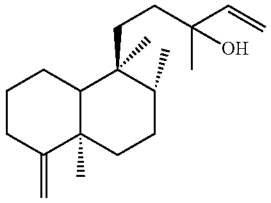

-continued

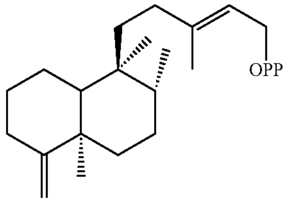

38

5 The *Teucrium canadense* cleroda-4(18),13E-dienyl diphosphate synthase (TcTPS1) amino acid sequence is shown below as SEQ ID NO:53.

```
  1 MSFASQATSL LLSSHNATAL PPLSAARLPP LTAGAAPFGR
 41 ISFTTTSLRQ YKLVSRAQSQ EVDEIEKVTQ WLEAEKDID
 81 QEAKVRELVE NVRVKLQNIG EGGISISPYD TAWVALVEDV
121 GGSGRPQFPE SLDWISNHQF PDGSWGSHKF LYYDRVLCTL
161 ACIVALKTWN LHPHKFDKGL KFVRENIGKL ADEEDVHMPI
201 GFEVAFPSLI ETAKRKGIDI PEDFPGKKEI YAKRDLKLKK
241 IPMDILHKIP TPLLFSIEGI EGLDWQKLFK FRDHGSFLTS
281 PSSTAHALQQ TKDELCLKYL TNLVKKNNGG VPNAFPVDLF
321 DRNYTVDRLR RLGILRYFQP EIEECMKYVY RFWDKRGISW
361 ARNTHVQDLD DTVQGFRNLR MHGYDVTLDV FKQFERCGEF
401 FSFHGQSSDA VLGMFNLYRA SQVLFPGEDM LADARKYAAN
441 YLHKRRVSNR VVDKWIINKD LPGEVAYGLD VPFYASLPRL
481 EARFYVEQYG GNDDVWIGKA LYRMLNVSCD TYLELAKLDY
521 NICQAVHQKE WKSFQKWHRD GEFGLDEKSL LLAYYIAAST
561 VFEPEKSLER LAWAKTAVLM EAILSQQLPS TKKHELVDEF
601 KHASILNNQN GGSYKTRTPL VETLVNAISE LSTTILLEQD
641 RDIHLQLSNA WLKWLSRWEA RGNLVEAEAE LLLQTLHLSN
681 GLEESSFSHP KYQQLLQVTS KVCHLLRLFQ KRKVHDPEGC
721 TTDIATGTTF QIEACMQQVV KLVFTKSSHD LDSWKQRFL
761 DVARSFYYTA HCDPQVIQSH INKVLFEKW
```

A nucleic acid encoding the *Teucrium canadense* Cleroda-4(18),13E-dienyl diphosphate synthase (TcTPS1) has with SEQ ID NO:53 is shown below as SEQ ID NO:54.

```
   1 ATGTCATTTG CTTCCCAAGC CACCTCCCTC CTCCTTTCTT
  41 CCCACAACGC CACCGCTCTT CCGCCTCTCT CTGCCGCCCG
  81 CCTTCCGCCT CTCACTGCCG GTGCTGCTCC ATTCGGAAGA
 121 ATATCATTTA CTACTACCTC TCTTCGGCAG TATAAACTGG
 161 TGTCAAGAGC TCAAAGCCAA GAGGTGGATG AGATTGAAAA
 201 AGTGACACAA GTGGTATTGG AGGCAGAAAA AGACATCGAT
 241 CAAGAGGCGA AGGTAAGGGA GCTGGTGGAA AATGTCCGAG
 281 TGAAGCTGCA AAATATCGGG GAAGGAGGGA TAAGCATATC
 321 GCCGTACGAC ACCGCATGGG TGGCGCTGGT GGAGGATGTC
```

-continued

```
 361 GGCGGCAGCG GCAGACCGCA GTTCCCGGAG AGCCTGGATT
 401 GGATATCAAA CCACCAGTTC CCGGACGGGT CGTGGGGCAG
 441 CCACAAATTC TTGTACTATG ACCGGGTTTT GTGCACGTTA
 481 GCATGTATAG TTGCATTGAA AACTTGGAAT CTGCATCCTC
 521 ACAAATTCGA CAAAGGGTTG AAATTCGTCA GAGAGAACAT
 561 TGGAAAGCTC GCGGATGAAG AAGACGTGCA CATGCCGATT
 601 GGGTTCGAAG TGGCATTCCC ATCACTTATA GAGACTGCAA
 641 AGAGAAAAGG AATTGACATC CCGGAAGATT TCCCTGGCAA
 681 GAAAGAAATC TATGCAAAAA GAGACCTAAA GCTGAAAAAG
 721 ATACCTATGG ATATACTGCA CAAAATCCCC ACACCATTAC
 761 TGTTCAGCAT AGAAGGGATA GAAGGCCTTG ATTGGCAGAA
 801 GCTATTCAAA TTCCGCGATC ACGGCTCCTT CCTCACGTCC
 841 CCGTCCTCAA CGGCCCACGC TCTCCAGCAA ACAAAGGACG
 881 AGTTATGCCT CAAATATCTG ACCAATCTTG TCAAAAAGAA
 921 CAATGGGGGA GTTCCAAATG CATTTCCGGT GGACCTATTT
 961 GATCGTAACT ATACAGTAGA TCGCCTGAGG AGGCTGGGAA
1001 TTTTGCGCTA TTTTCAACCT GAAATCGAGG AATGCATGAA
1041 ATATGTATAC AGATTCTGGG ATAAAAGAGG AATCAGCTGG
1081 GCAAGAAATA CCCATGTTCA GGACCTTGAT GATACCGTAC
1121 AGGGATTCAG GAACTTAAGG ATGCATGGTT ATGATGTCAC
1161 CTTAGATGTT TTCAAACAGT TCGAGAGATG TGGAGAATTC
1201 TTTAGCTTCC ACGGGCAATC AAGTGATGCT GTCTTAGGAA
1241 TGTTCAACTT GTACCGAGCT TCTCAGGTTC TGTTTCCAGG
1281 AGAAGACATG CTTGCAGATG CAAGGAAGTA CGCGGCCAAC
1321 TATTTGCATA AAAGAAGAGT TAGTAATAGG GTCGTGGACA
1401 AATGGATTAT TAACAAAGAT CTTCCAGGCG AGGTGGCGTA
1441 TGGGCTAGAT GTTCCGTTCT ACGCCAGTCT ACCTCGACTG
1481 GAAGCAAGAT TCTACGTCGA ACAATATGGG GGTAACGATG
1521 ATGTCTGGAT TGGAAAAGCT TTATATAGAA TGTTGAATGT
1601 GAGCTGTGAT ACTTACCTTG AGCTAGCAAA ATTAGACTAC
1641 AATATTTGCC AGGCTGTGCA TCAGAAAGAG TGGAAAAGCT
1681 TTCAAAAATG GCACAGGGAT GGGGAGTTTG GATTGGATGA
1721 AAAAAGCTTA CTTTTAGCTT ACTACATAGC AGCCTCGACT
1761 GTTTTCGAGC CTGAAAAATC TCTAGAGCGA CTGGCTTGGG
1801 CTAAAACCGC AGTTCTAATG GAGGCAATTT TGTCCCAACA
1841 ACTTCCTAGC ACAAAAAAAC ATGAGCTTGT TGACGAATTT
1881 AAACATGCAA GCATCCTCAA CAACCAAAAT GGAGGAAGCT
1921 ATAAAACAAG AACTCCTTTG GTAGAGACTC TAGTAAACGC
1961 CATAAGTGAG CTCTCAACTA CCATACTATT GGAGCAAGAC
2001 AGAGACATTC ATCTGCAATT ATCTAATGCG TGGCTGAAGT
```

-continued

```
2041 GGCTAAGTAG ATGGGAGGCA AGAGGCAACC TAGTGGAAGC
2081 AGAAGCAGAG CTTCTTCTGC AAACCTTACA TCTGAGCAAT
2121 GGATTAGAAG AATCATCATT TTCTCATCCA AAATATCAAC
2161 AACTCTTACA GGTTACCAGC AAAGTCTGTC ACCTACTTCG
2201 GCTATTCCAG AAACGAAAGG TGCATGATCC GGAAGGGTGT
2241 ACAACAGACA TTGCAACAGG GACAACTTTC CAAATAGAAG
2281 CATGCATGCA ACAAGTAGTG AAATTAGTGT TCACCAAATC
2321 CTCACATGAT TTAGATTCTG TTGTTAAGCA GAGATTTTTG
2361 GATGTTGCCA GAAGTTTCTA TTACACAGCC CACTGTGATC
2401 CACAAGTGAT CCAGTCCCAC ATTAATAAAG TGTTGTTTGA
2441 AAAAGTAGTC TAG
```

*Salvia officinalis* (SoTPS2), *Scutellaria baicalensis* SbTPS1, and SbTPS2 enzymes were identified and isolated. These SoTPS2, SbTPS1, SbTPS2, CfTPS18a and CfTPS18b enzymes were all identified as ent-CPP synthases, which convert GGPP to ent-CPP.

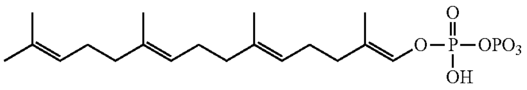

Geranylgeranyl diphosphate (GGPP)

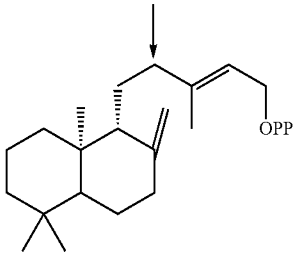

16

The *Salvia officinalis* (SoTPS2) enzyme can have the amino acid sequence shown below (SEQ ID NO:55).

```
  1 MSFASTTSLL RPSVTGFGVS PRVTSTSILS RSYGQILKGK
 41 TKYITDNRRN RQLAVKFEGQ IALDLEDGVA KQTNQEAESE
 81 KIRQLKGKIR WILQNMEDGE MSVSPYDTAW VALVEDISGG
121 GGPQFPTSLE WISKNQLADG SWGDPNYFLL YDRILNTLAC
161 VVALTTWNMH PHKCDQGLRF IRDNIEKLED EDEELILVGF
201 EIALPSLIDY AQNLGIQIQY DSPFIKKICA KRDLKLRKIP
241 MDLMHRKPTS LLYSLEGMEG LEWEKLMNLR SEGSFLSSPS
281 STAYALQHTK DELCLDYLVK AVNKFNGGVP NVYPVDMYEH
321 LWCVDRLQRL GISRYFQLEI QQCLDYVYRY WTNEGISWAR
361 YTNIRDSDDT AMGFRLLRLY GYDVSIDAFK PFEESGEFYS
401 MAGQMNHAVT GMYNLYRASQ LMFPQEHILS DARNFSAKFL
441 HQKRRTNALV DKWIITKDLP GEVGYALDVP FYASLPRLEA
```

-continued

```
481 RFFLEQYGGD DDVWIGKTLY RMPYVNSNTY LELAKVDYKN
521 CQSVHQLEWK SMQKWYRECN IGEFGLSERS LLLAYYIAAS
561 TTFEPEKSGE RLAWATTAIL IETIASQQLS DEQKREFVDE
601 FENSIIIKNQ NGGRYKARNR LVKVLINTVT LVAEGRGINQ
641 QLFNAWQKWL KTWEEGGDMG EAEAQLLLRT LHLSSGFDQS
681 SFSHPKYEQL LEATSKVCHQ LRLFQNRKVD DGQGCISRLV
721 IGTTSQIEAG MQEVVKLVFT KTSQDLTSAT KQSFFNIARS
761 FYYTAYFHAD TIDSHIYKVL FQTIV
```

A nucleic acid encoding the *Salvia officinalis* (SoTPS2) has with SEQ ID NO:55 is shown below as SEQ ID NO:56.

```
   1 ATGTCATTTG CTTCCACCAC CTCCCTCCTC CGACCAAGCG
  41 TCACTGGGTT CGGTGTTTCT CCAAGGGTTA CTTCCACCTC
  81 CATTCTTAGC CGAAGTTATG GTCAAATATT AAAAGGAAAA
 121 ACAAAATACA TAACTGATAA CCGTAGAAAT CGACAATTGG
 161 CGGTAAAATT TGAGGGCCAA ATTGCTTTGG ATTTGGAGGA
 201 TGGCGTAGCA AAGCAGACGA ATCAAGAGGC GGAATCTGAG
 241 AAGATAAGGC AACTGAAGGG AAAGATCCGA TGGATTCTGC
 281 AAAACATGGA GGACGGCGAG ATGAGCGTGT CGCCGTACGA
 321 CACCGCATGG GTGGCGCTGG TGGAAGATAT CAGCGGCGGC
 361 GGCGGGCCGC AGTTCCCGAC GAGCCTCGAG TGGATTTCCA
 401 AGAATCAGTT GGCGGATGGG TCATGGGGGG ATCCTAATTA
 441 TTTCCTTCTC TACGACAGAA TACTCAATAC TTTAGCATGT
 481 GTAGTCGCAC TCACGACTTG GAATATGCAT CCTCACAAAT
 521 GCGATCAAGG GTTGAGGTTT ATAAGAGACA ACATTGAGAA
 561 ACTTGAGGAT GAAGATGAGG AGCTAATTCT CGTAGGATTC
 601 GAGATCGCAC TGCCTTCACT CATTGATTAT GCTCAAAACC
 641 TTGGGATACA AATCCAATAT GATTCTCCAT TCATTAAAAA
 681 AATTTGTGCA AAGAGAGATC TAAAACTCAG AAAAATACCA
 721 ATGGATTTAA TGCACAGAAA GCCAACATCA TTGCTCTACA
 761 GCTTGGAAGG CATGGAAGGC CTTGAGTGGG AAAAGCTAAT
 801 GAATTTGCGA TCGGAGGGTT CGTTTCTGTC ATCGCCGTCG
 841 TCCACGGCCT ACGCTCTCCA ACACACCAAG GATGAGTTAT
 881 GCCTTGACTA TCTGGTCAAG GCGGTCAACA AATTCAATGG
 921 TGGAGTTCCC AACGTGTACC CTGTCGACAT GTATGAGCAT
 961 CTATGGTGCG TAGACCGCTT GCAGAGGTTG GGAATTTCTC
1001 GCTATTTTCA ACTTGAAATT CAACAATGCC TCGACTATGT
1041 TTACAGATAC TGGACAAATG AAGGAATTTC GTGGGCAAGA
1081 TATACTAATA TCCGGGATAG TGACGACACC GCAATGGGAT
1121 TCAGGCTTCT AAGGTTGTAC GGCTATGATG TCTCTATAGA
1161 TGCTTTTAAA CCATTCGAGG AAAGCGGAGA ATTCTATAGC
```

-continued

```
1201 ATGGCAGGGC AGATGAACCA CGCTGTTACA GGAATGTACA
1241 ACTTGTACAG AGCTTCTCAA CTTATGTTCC CTCAAGAACA
1281 CATACTTTCC GATGCCAGAA ACTTCTCTGC CAAATTCTTG
1321 CATCAAAAGA GGCGTACTAA TGCACTAGTA GACAAGTGGA
1361 TCATTACCAA AGACCTTCCC GGCGAGGTTG GATATGCATT
1401 GGATGTGCCG TTCTACGCCA GTCTGCCTCG ACTGGAAGCA
1441 CGATTCTTCT TAGAACAATA TGGGGGTGAT GATGATGTTT
1481 GGATTGGAAA AACTTTGTAC AGGATGCCAT ATGTGAACTC
1521 CAACACATAC CTTGAGCTTG CAAAAGTAGA CTACAAAAAC
1561 TGCCAGTCCG TGCATCAGTT GGAGTGGAAG AGCATGCAAA
1601 AATGGTACAG AGAATGCAAT ATAGGTGAGT TTGGGTTGAG
1641 CGAAAGAAGC CTTCTCCTAG CTTACTACAT AGCAGCCTCA
1681 ACTACATTCG AGCCAGAAAA ATCAGGTGAG CGGCTCGCTT
1721 GGGCTACAAC AGCAATTTTA ATCGAGACAA TCGCGTCCCA
1761 ACAACTCTCC GATGAACAAA AGAGAGAGTT CGTTGATGAA
1801 TTTGAAAACA GCATCATTAT CAAGAATCAA AATGGAGGGA
1841 GATATAAAGC AAGAAACAGA TTGGTCAAGG TTTTGATCAA
1881 CACTGTAACA CTGGTAGCAG AAGGCAGAGG CATAAATCAG
1921 CAGTTGTTTA ATGCGTGGCA AAAATGGCTA AAGACATGGG
1961 AAGAAGGAGG TGACATGGGG GAAGCAGAAG CCCAGCTTCT
2001 TCTGCGCACG CTACATTTGA GCTCCGGATT CGATCAATCA
2041 TCATTTTCCC ATCCAAAATA TGAGCAGCTC TTGGAGGCGA
2081 CCAGCAAAGT TTGCCACCAA CTTCGCCTAT TCCAGAATCG
2121 AAAGGTGGAT GATGGCCAAG GGTGTATAAG TCGATTGGTA
2161 ATTGGGACAA CTTCCCAAAT AGAAGCAGGC ATGCAAGAAG
2201 TAGTGAAATT AGTTTTCACC AAAACCTCAC AAGACTTGAC
2241 TTCTGCTACC AAGCAAAGCT TTTTCAATAT TGCTAGAAGT
2281 TTCTATTATA CTGCCTACTT TCATGCAGAC ACTATAGACT
2321 CCCACATATA CAAAGTATTG TTTCAAACAA TAGTATAG
```

A *Scutellaria baicalensis* SbTPS1 amino acid sequence shown below (SEQ ID NO:57).

```
  1 MPFLLPSSAT SSPAFYTPAA PLAGHHVFPS FKPLIISRSS
 41 LQCNAISRPR TQEYIDVIQN GLPVIKWHEA VEEDETDKDS
 81 LNKEATSDKI RELVNLIRSM LQSMGDGEIS SSPYDAAWVA
121 LVPDVGGSGG PQFPSSLEWI SKNQLPDGSW GDTCTFSIYD
161 RIINTLACVV ALKSWNIHPH KTYQGISFIK ANMDKLEDEN
201 EEHMPIGFEV ALPSLIEIAK RLDIDISSDS RGLQEIYTRR
241 EVKLKRIPKE IMHQVPTTLL HSLEGMAELT WHKLLKLQCQ
281 DGSFLFSPSS TAFALHQTKD HNCLHYLTKY VHKFHGGVPN
321 VYPVDLFEHL WAVDRIQRLG ISRHFKPQVD ECIAYVYRYW
361 TDKGICWARN SVVQDLDDTA MGFRLLRLHG YDVSADVFKH
401 FENGGEFFCF KGQSTQAVTG MYNLYRASQL MFPGESILED
441 AKTFSSKFLQ RKRANNELLD KWIITKDLPG EVGYALDVPW
481 YASLPRVETR FYLEQYGGED DVWIGKTLYR MPYVNNNKYL
521 ELAKLDYSNC QSLHQQEWKN IQKWYESCNL GEFGLSERRV
561 LLAYYVAAAC IYEPEKSNQR LAWAKTVILM ETITSYFEHQ
601 QLSAEQRRAF VNEFEHGSIL KYANGGRYKR RSVLGTLLKT
641 LNQLSLDILL THGRNVHQPF KNAWHKWLKT WEEGGDIEEG
681 EAEVLVRTLN LSGEGRHDSY VLEQSLLSQP IYEQLLKATM
721 SVCKKLRLFQ HRKDENGCMT KMRGITTLEI ESEMQELVKL
761 VFTKSSDDLD CEIKQNFFTI ARSFYYVAYC NQGTINFHIA
801 KVLFERVL
```

A nucleic acid encoding the *Scutellaria baicalensis* SbTPS1 with SEQ ID NO:57 is shown below as SEQ ID NO:58.

```
   1 ATGCCTTTCC TCCTCCCTTC CTCCGCCACC AGCTCCCCCG
  41 CGTTCTATAC TCCGGCCGCG CCTCTCGCCG GTCATCATGT
  81 TTTTCCATCT TTCAAGCCAC TCATTATTTC CCGTTCTTCA
 121 CTCCAATGCA ATGCAATCTC TCGACCTCGT ACCCAAGAAT
 161 ACATAGATGT GATTCAGAAT GGATTGCCAG TAATAAAGTG
 201 GCACGAAGCT GTGGAAGAAG ATGAGACAGA TAAAGATTCT
 241 CTTAATAAGG AGGCCACGTC AGACAAGATA AGAGAGTTGG
 281 TAAATCTGAT CCGTTCGATG CTCCAATCAA TGGGCGACGG
 521 AGAGATAAGC TCGTCGCCGT ACGACGCCGC ATGGGTGGCG
 561 CTGGTGCCGG ACGTCGGCGG CTCCGGCGGG CCCCAGTTCC
 601 CCTCCAGCCT CGAATGGATA TCCAAAAACC AACTCCCCGA
 641 CGGCTCCTGG GGCGACACGT GTACCTTTTC CATTTATGAT
 681 CGAATCATCA ACACACTGGC TTGCGTTGTT GCTTTGAAAT
 721 CTTGGAACAT ACATCCCCAC AAAACTTATC AAGGGATTTC
 761 ATTCATAAAG GCAAATATGG ACAAACTTGA AGACGAGAAC
 801 GAGGAGCACA TGCCGATCGG ATTTGAAGTG GCACTCCCGT
 841 CGCTAATCGA GATAGCGAAA AGGCTCGATA TCGATATTTC
 881 CAGCGATTCG AGAGGGCTGC AAGAGATATA CACGAGGAGG
 921 GAGGTAAAGC TGAAAAGGAT ACCGAAAGAG ATAATGCACC
 961 AAGTGCCCAC AACACTGCTT CATAGCTTGG AGGGTATGGC
1041 CGAGCTGACG TGGCACAAGC TTTTGAAATT ACAGTGCCAA
1081 GATGGCTCCT TTCTTTTCTC TCCATCTTCA ACTGCCTTTG
1121 CTCTTCACCA AACTAAGGAC CATAATTGTC TCCATTATTT
1161 GACCAAATAT GTTCACAAAT TTCATGGTGG AGTGCCAAAT
1201 GTGTATCCGG TGGACTTGTT CGAGCATCTA TGGGCAGTTG
1241 ATCGGATCCA ACGGCTGGGG ATTTCCCGGC ATTTCAAGCC
```

-continued

```
1281 CCAAGTTGAT GAATGTATTG CCTATGTTTA TAGATATTGG
1321 ACAGATAAAG GAATATGCTG GGCAAGAAAT TCAGTAGTTC
1361 AAGATCTTGA TGACACAGCC ATGGGATTCA GGCTTCTTAG
1401 GTTGCATGGC TACGATGTTT CAGCAGATGT TTTCAAACAT
1441 TTTGAAAATG GTGGAGAGTT CTTCTGCTTC AAAGGGCAAA
1481 GCACGCAGGC AGTGACTGGA ATGTACAATC TGTACAGAGC
1521 TTCTCAGTTG ATGTTTCCTG GAGAAAGCAT ACTGGAAGAT
1601 GCTAAGACCT TCTCATCTAA GTTTTTGCAA CGAAAACGAG
1641 CCAATAACGA GTTGTTAGAT AAGTGGATTA TTACCAAGGA
1681 TCTTCCTGGA GAGGTGGGAT ATGCTCTAGA TGTACCATGG
1721 TATGCTAGCT TACCTAGAGT TGAAACTAGA TTCTACTTGG
1801 AACAATATGG TGGTGAAGAT GATGTTTGGA TTGGCAAAAC
1841 TTTATACAGG ATGCCATATG TTAACAATAA TAAATATCTA
1881 GAACTGGCAA AATTAGACTA TAGTAACTGC CAGTCATTAC
1921 ATCAACAAGA GTGGAAAAAC ATTCAAAAAT GGTATGAGAG
1961 TTGCAATCTG GGAGAATTTG GTTTGAGTGA AAGAAGGGTT
2001 CTACTAGCCT ACTACGTAGC TGCTGCGTGT ATATATGAGC
2041 CCGAAAAGTC AAACCAGCGC TTGGCTTGGG CCAAAACCGT
2081 AATTTTAATG GAGACTATTA CTTCCTATTT TGAGCACCAA
2121 CAACTCTCCG CAGAACAGAG ACGCGCCTTT GTTAATGAAT
2161 TTGAACATGG GAGTATCCTC AAATATGCAA ATGGAGGAAG
2201 ATACAAAAGG AGGAGTGTTT TGGGGACTTT GCTCAAAACA
2241 CTAAATCAGC TTTCATTGGA TATATTATTG ACACACGGTC
2281 GAAACGTCCA TCAGCCTTTC AAAAATGCGT GGCACAAGTG
2321 GCTAAAAACG TGGGAAGAAG GAGGTGACAT TGAAGAAGGC
2361 GAAGCAGAGG TATTGGTCCG AACCCTAAAC CTAAGCGGCG
2401 AAGGGAGGCA CGACTCCTAT GTATTGGAGC AATCATTATT
2441 GTCACAACCT ATATATGAAC AACTTTTGAA AGCCACCATG
2481 AGTGTTTGCA AGAAGCTTCG ATTGTTCCAA CATCGAAAGG
2521 ATGAGAATGG ATGTATGACG AAGATGAGAG GCATTACAAC
2561 GTTAGAGATA GAATCGGAGA TGCAAGAATT AGTGAAATTA
2601 GTATTTACTA AATCCTCAGA TGATTTAGAT TGTGAAATTA
2641 AACAAAACTT TTTTACAATT GCTAGGAGTT TCTATTATGT
2681 GGCTTATTGT AACCAAGGAA CTATCAACTT TCACATTGCT
2721 AAGGTGCTCT TTGAAAGAGT TCTTTAG
```

A *Scutellaria baicalensis* SbTPS2 amino acid sequence is shown below (SEQ ID NO:59)

```
1   MASLSTLSLN FSPAIHRKIQ QSSAKLQFQG HCFTISSCMN
41  NSKRLSLNHQ SNHKRTSNVS ELQVATLDAP QIREKEDYST
81  AQGYEKVDEV EDPIEYIRML LNTTGDGRIS VSPYDTAWIA
121 LIKDVEGRDA PQFPSSLEWI ANNQLSDGSW GDEKFFCVYD
161 RLVNTLACVV ALRSWNIDAE KSEKGIRYIK ENVDKLKDGN
201 PEHMTCGFEV VFPSLLQRAQ SMGIHDLPYD APVIQDIYNT
241 RESKLKRIPM EVMHKVPTSL LFSLEGLENL EWDKLLKLQS
281 SDGSFLTSPS STAYAFMHTK DPKCFEFIKN TVETFNGGAP
321 HTYPVDVFGR LWAIDRLQRL GISRFFESEI ADCLDHIYKY
361 WTDKGVFSGR ESDFVDVDDT SMGVRLLRMH GYQVDPNVLR
401 NFKQGDKFSC YGGQMIESSS PIYNLYRASQ LRFPGEDILE
441 DANKFAYEFL QEQLSNNQLL DKWVISKHLP DEIKLGLQMP
481 WYATLPRVEA KYYLQYYAGA DDVWIGKTLY RMPEISNDTY
521 LELARMDFKR CQAQHQFEWI SMQEWYESCN IEEFGISRKE
561 LLQAYFLAGS SVFELERTTE RIGWAKSQII SRMIASFFNN
601 ETTTADEKDA LLTRFRNING PNKTKSGQRE SEAVNMLVAT
641 LQQYLAGFDR YTRHQLKDAW SVWFRKVQEE EAIYGAEAEL
681 LTTTLNICAG HIAFDENIMA NKDYTTLSSL TSKICQKLSE
721 IRNEKVEEME SGIKAKSSIK DKEVEHDMQS LVKLVLERCE
761 GINNRKLKQT FLSVAKTYYY RAYNADETMD IHMFKVLFEP
801 VM
```

A nucleic acid encoding the *Scutellaria baicalensis* SbTPS2 with SEQ ID NO:59 is shown below as SEQ ID NO:60.

```
  1 ATGGCCTCTC TATCAACTCT GAGCCTCAAC TTTTCCCCAG
 41 CAATTCACCG CAAAATACAG CAATCATCTG CAAAACTTCA
 81 GTTCCAGGGA CATTGTTTCA CCATAAGTTC ATGCATGAAC
121 AACAGTAAAA GACTGTCTTT GAACCACCAA TCTAATCACA
161 AAAGAACGTC AAACGTATCT GAGCTGCAAG TTGCCACTTT
201 GGATGCGCCC CAAATACGTG AAAAAGAAGA CTACTCCACT
241 GCTCAAGGCT ATGAGAAGGT GGATGAAGTA GAGGATCCTA
281 TCGAATATAT TAGAATGCTG TTGAACACAA CAGGTGATGG
321 GCGAATAAGT GTGTCGCCAT ACGACACAGC CTGGATCGCT
361 CTTATTAAAG ACGTGGAAGG ACGTGATGCT CCCCAGTTCC
401 CATCTAGTCT CGAATGGATT GCCAATAATC AACTGAGTGA
441 TGGGTCGTGG GGCGATGAGA AGTTTTTCTG TGTGTATGAT
481 CGCCTTGTTA ATACACTTGC ATGTGTCGTG GCATTGAGAT
521 CATGGAATAT TGATGCTGAA AAGAGCGAGA AAGGAATAAG
561 ATACATAAAA GAAAACGTGG ATAAACTGAA AGATGGGAAT
601 CCAGAGCACA TGACCTGTGG TTTTGAGGTG GTGTTTCCTT
641 CCCTTCTTCA GAGAGCCCAA AGTATGGGAA TTCATGATCT
681 TCCCTATGAT GCTCCTGTCA TCCAAGACAT TTACAATACC
721 AGGGAGAGTA AATTGAAAAG GATTCCAATG GAGGTTATGC
761 ACAAGGTGCC AACATCTCTA TTGTTCAGCT TGGAAGGATT
```

-continued

```
 801 GGAGAATTTG GAGTGGGATA AGCTCCTCAA ACTTCAGTCT

 841 TCTGATGGTT CATTCCTCAC TTCTCCATCC TCAACTGCCT

 881 ATGCTTTCAT GCACACTAAG GACCCTAAAT GCTTCGAATT

 921 CATCAAAAAC ACCGTCGAAA CATTTAATGG AGGAGCACCT

 961 CATACTTATC CGGTGGATGT TTTTGGAAGA CTGTGGGCCA

1001 TTGACAGGCT GCAGCGCCTC GGAATCTCTC GCTTCTTTGA

1041 GTCCGAGATT GCTGATTGCT TAGATCACAT CTATAAATAT

1081 TGGACAGACA AAGGAGTGTT CAGTGGAAGA GAATCAGATT

1121 TTGTGGATGT GGATGACACA TCCATGGGTG TTAGGCTTCT

1161 AAGGATGCAC GGATATCAAG TTGATCCAAA TGTATTGAGG

1201 AACTTCAAGC AGGGTGACAA ATTTTCATGC TATGGTGGTC

1241 AAATGATAGA GTCATCATCT CCGATATACA ATCTCTATAG

1281 GGCTTCTCAA CTCCGATTTC CAGGAGAAGA CATTCTTGAA

1321 GATGCCAACA AATTCGCATA CGAGTTCTTG CAAGAACAGC

1361 TATCCAACAA TCAACTTTTG GACAAATGGG TTATATCCAA

1401 GCACTTGCCT GATGAGATAA AGCTTGGATT GCAGATGCCA

1441 TGGTATGCCA CCCTACCCCG AGTGGAGGCT AAATACTACC

1481 TACAGTATTA TGCTGGTGCT GATGATGTCT GGATCGGCAA

1521 GACTCTCTAC AGAATGCCAG AAATCAGTAA TGATACATAT

1561 CTGGAGTTAG CAAGAATGGA TTTCAAGAGA TGCCAAGCAC

1601 AGCATCAATT TGAGTGGATT TCCATGCAAG AATGGTATGA

1641 AAGTTGCAAC ATTGAAGAAT TTGGGATAAG CAGAAAAGAG

1681 CTTCTTCAGG CTTACTTTTT GGCCTGCTCA AGTGTATTTG

1721 AACTCGAGAG GACAACAGAG AGAATAGGAT GGGCCAAATC

1761 CCAAATTATT TCAAGGATGA TAGCTTCTTT CTTCAACAAT

1801 GAAACTACAA CAGCCGATGA AAAAGATGCA CTTTTAACCA

1841 GATTCAGAAA CATCAATGGC CCAAACAAAA CAAAAAGTGG

1881 TCAGAGAGAG AGTGAAGCTG TGAACATGTT GGTAGCAACG

1921 CTCCAACAAT ACCTGGCAGG ATTTGATAGA TATACCAGAC

1961 ATCAATTGAA AGATGCTTGG AGTGTGTGGT TCAGAAAAGT

2001 GCAAGAAGAA GAGGCCATCT ACGGGGCAGA AGCGGAGCTT

2041 CTAACAACCA CCTTAAACAT CTGTGCTGGT CATATTGCTT

2081 TCGACGAAAA CATAATGGCC AACAAAGATT ACACCACTCT

2121 TTCCAGCCTT ACAAGCAAAA TTTGCCAGAA GCTTTCTGAA

2161 ATTCGAAATG AAAAGGTTGA GGAAATGGAG AGTGGAATTA

2201 AAGCAAAATC AAGCATCAAA GACAAGGAAG TGGAACATGA

2241 TATGCAGTCA CTGGTGAAAT TAGTCCTGGA GAGATGTGAA

2281 GGCATAAACA ACAGAAAACT GAAGCAAACA TTTCTATCGG

2321 TTGCAAAAAC ATATTACTAC AGAGCCTATA ATGCTGATGA
```

-continued

```
2361 AACCATGGAC ATCCATATGT TCAAAGTACT TTTCGAACCA

2401 GTCATGTGA
```

An example of a *Salvia sclarea* sclareol synthase amino acid sequence is shown below (SEQ ID NO:61; NCBI accession no. AET21246.1).

```
  1 MSLAFNVGVT PFSGQRVGSR KEKFPVQGFP VTTPNRSRLI

 41 VNCSLTTIDF MAKMKENFKR EDDKFPTTTT LRSEDIPSNL

 81 CIIDTLQRLG VDQFFQYEIN TILDNTFRLW QEKHKVIYGN

121 VTTHAMAFRL LRVKGYEVSS EELAPYGNQE AVSQQTNDLP

161 MIIELYRAAN ERIYEEERSL EKILAWTTIF LNKQVQDNSI

201 PDKKLHKLVE FYLRNYKGIT IRLGARRNLE LYDMTYYQAL

241 KSTNRFSNLC NEDFLVFAKQ DFDIHEAQNQ KGLQQLQRWY

281 ADCRLDTLNF GRDVVIIANY LASLIIGDHA FDYVRLAFAK

321 TSVLVTIMDD FFDCHGSSQE CDKIIELVKE WKENPDAEYG

361 SEELEILFMA LYNTVNELAE RARVEQGRSV KEFLVKLWVE

401 ILSAFKIELD TWSNGTQQSF DEYISSSWLS NGSRLTGLLT

441 MQFVGVKLSD EMLMSEECTD LARHVCMVGR LLNDVCSSER

481 EREENIAGKS YSILLATEKD GRKVSEDEAI AEINEMVEYH

521 WRKVLQIVYK KESILPRRCK DVFLEMAKGT FYAYGINDEL

561 TSPQQSKEDM KSFVF
```

A nucleic acid encoding the *Salvia sclarea* sclareol synthase with SEQ ID NO:61 is shown below as SEQ ID NO:62.

```
  1 ATGTCGCTCG CCTTCAACGT CGGAGTTACG CCTTTCTCCG

 41 GCCAAAGAGT TGGGAGCAGG AAAGAAAAAT TTCCAGTCCA

 81 AGGATTTCCT GTGACCACCC CCAATAGGTC ACGTCTCATC

121 GTTAACTGCA GCCTTACTAC AATAGATTTC ATGGCGAAAA

161 TGAAAGAGAA TTTCAAGAGG GAAGACGATA AATTTCCAAC

201 GACAACGACT CTTCGATCCG AAGATATACC CTCTAATTTG

241 TGTATAATCG ACACCCTTCA AAGGTTGGGG GTCGATCAAT

281 TCTTCCAATA TGAAATCAAC ACTATTCTAG ATAACACATT

321 CAGGTTGTGG CAAGAAAAAC ACAAAGTTAT ATATGGCAAT

361 GTTACTACTC ATGCAATGGC ATTTAGGCTT TTGCGAGTGA

401 AAGGATACGA AGTTTCATCA GAGGAGTTGG CTCCATATGG

441 TAACCAAGAG GCTGTTAGCC AGCAAACAAA TGACCTGCCG

481 ATGATTATTG AGCTTTATAG AGCAGCAAAT GAGAGAATAT

521 ATGAAGAAGA GAGGAGTCTT GAAAAAATTC TTGCTTGGAC

561 TACCATCTTT CTCAATAAGC AAGTGCAAGA TAACTCAATT

601 CCCGACAAAA AACTGCACAA ACTGGTGGAA TTCTACTTGA

641 GGAATTACAA AGGCATAACC ATAAGATTGG GAGCTAGACG

681 AAACCTCGAG CTATATGACA TGACCTACTA TCAAGCTCTG
```

-continued

```
 721 AAATCTACAA ACAGGTTCTC TAATTTATGC AACGAAGATT
 761 TTCTAGTTTT CGCAAAGCAA GATTTCGATA TACATGAAGC
 801 CCAGAACCAG AAAGGACTTC AACAACTGCA AAGGTGGTAT
 841 GCAGATTGTA GGTTGGACAC CTTAAACTTT GGAAGAGATG
 881 TAGTTATTAT TGCTAATTAT TTGGCTTCAT TAATTATTGG
 921 TGATCATGCG TTTGACTATG TTCGTCTCGC ATTTGCCAAA
 961 ACATCTGTGC TTGTAACAAT TATGGATGAT TTTTTCGACT
1001 GTCATGGCTC TAGTCAAGAG TGTGACAAGA TCATTGAATT
1041 AGTAAAAGAA TGGAAGGAGA ATCCGGATGC AGAGTACGGA
1081 TCTGAGGAGC TTGAGATCCT TTTTATGGCG TTGTACAATA
1121 CAGTAAATGA GTTGGCGGAG AGGGCTCGTG TTGAACAGGG
1161 GCGTAGTGTC AAAGAGTTTC TAGTCAAACT GTGGGTTGAA
1201 ATACTCTCAG CTTTCAAGAT AGAATTAGAT ACATGGAGCA
1241 ATGGCACGCA GCAAAGCTTC GATGAATACA TTTCTTCGTC
1281 GTGGTTGTCG AACGGTTCCC GGCTGACAGG TCTCCTGACG
1321 ATGCAATTCG TCGGAGTAAA ATTGTCCGAT GAAATGCTTA
1361 TGAGTGAAGA GTGCACTGAT TTGGCTAGGC ATGTCTGTAT
1401 GGTCGGCCGG CTGCTCAACG ACGTGTGCAG TTCTGAGAGG
1441 GAGCGCGAGG AAAATATTGC AGGAAAAAGT TATAGCATTC
1481 TACTAGCAAC TGAGAAAGAT GGAAGAAAAG TTAGTGAAGA
1521 TGAAGCCATT GCAGAGATCA ATGAAATGGT TGAATATCAC
1561 TGGAGAAAAG TGTTGCAGAT TGTGTATAAA AAAGAAAGCA
1601 TTTTGCCAAG AAGATGCAAA GATGTATTTT TGGAGATGGC
1641 TAAGGGTACG TTTTATGCTT ATGGGATCAA CGATGAATTG
1681 ACTTCTCCTC AGCAATCCAA GGAAGATATG AAATCCTTTG
1721 TCTTTTGA
```

An example of a *Marrubium vulgare* (Mv) CPS1 amino acid sequence is shown below (SEQ ID NO:63).

```
  1 MASTPTLNLS ITTPFVRTKI PAKISLPACS WLDRSSSRHV
 41 ELNHKFCRKL ELKVAMCRAS LDVQQVRDEV YSNAQPHELV
 81 DKKIEERVKY VKNLLSTMDD GRINWSAYDT AWISLIKDFE
121 GRDCPQFPST LERIAENQLP DGSWGDKDFD CSYDRIINTL
161 ACVVALTTWN VHPEINQKGI RYLKENMRKL EETPTVLMTC
201 AFEVVFPALL KKARNLGIHD LPYDMPIVKE ICKIGDEKLA
241 RIPKKMMEKE TTSLMYAAEG VENLDWERLL KLRTPENGSF
281 LSSPAATVVA FMHTKDEDCL RYIKYLLNKF NGGAPNVYPV
321 DLWSRLWATD RLQRLGISRY FESEIKDLLS YVHSYWTDIG
361 VYCTRDSKYA DIDDTSMGFR LLRVQGYNMD ANVFKYFQKD
401 DKFVCLGGQM NGSATATYNL YRAAQYQFPG EQILEDARKF
441 SQQFLQESID TNNLLDKWVI SPHIPEEMRF GMEMTWYSCL
```

-continued

```
481 PRIEASYYLQ HYGATEDVWL GKTFFRMEEI SNENYRELAI
521 LDFSKCQAQH QTEWIHMQEW YESNNVKEFG ISRKDLLFAY
561 FLAAASIFET ERAKERILWA RSKIICKMVK SFLEKETGSL
601 EHKIAFLTGS GDKGNGPVNN AMATLHQLLG EFDGYISIQL
641 ENAWAAWLTK LEQGEANDGE LLATTINICG GRVNQDTLSH
681 NEYKALSDLT NKICHNLAQI QNDKGDEIKD SKRSERDKEV
721 EQDMQALAKL VFEESDLERS IKQTFLAVVR TYYYGAYIAA
761 EKIDVHMFKV LFKPVG
```

An example of a *Marrubium vulgare* (Mv) TPS5 (syn. MvELS) amino acid sequence is shown below (SEQ ID NO:64).

```
  1 MSITFNLKIA PFSGPGIQRS KETFPATEIQ ITASTKSTMT
 41 TKCSFNASTD FMGKLREKVG GKADKPPVVI HPVDISSNLC
 81 MIDTLQSLGV DRYFQSEINT LLEHTYRLWK EKKKNIIFKD
121 VSCCAIAFRL LREKGYQVSS DKLAPFADYR IRDVATILEL
161 YRASQARLYE DEHTLEKLHD WSSNLLKQHL LNGSIPDHKL
201 HKQVEYFLKN YHGILDRVAV RRSLDLYNIN HHHRIPDVAD
241 GFPKEDFLEY SMQDFNICQA QQQEELHQLQ RWYADCRLDT
281 LNYGRDVVRI ANFLTSAIFG EPEFSDARLA FAKHIILVTR
321 IDDFFDHGGS REESYKILDL VQEWKEKPAE EYGSKEVEIL
361 FTAVYNTVND LAEKAHIEQG RCVKPLLIKL WVEILTSFKK
401 ELDSWTEETA LTLDEYLSSS WVSIGCRICI LNSLQYLGIK
441 LSEEMLSSQE CTDLCRHVSS VDRLLNDVQT FKKERLENTI
481 NSVGLQLAAH KGERAMTEED AMSKIKEMAD YHRRKLMQIV
521 YKEGTVFPRE CKDVFLRVCR IGYYLYSSGD EFTSPQQMKE
561 DMKSLVYQPV KIHPLEAINV
```

An example of a *Kitasatospora griseola* TPS2 (KgTPS2) amino acid sequence is shown below (SEQ ID NO:65).

```
  1 MPDAIEFEHE GRRNPNSAEA ESAYSSIIAA LDLQESDYAV
 41 ISGHSRIVGA AALVYPDADA ETLLAASLWT ACLIVNDDRW
 81 DYVQEDGGRL APGEWFDGVT EVVDTWRTAG PRLPDPFFEL
121 VRTTMSRLDA ALGAEAADEI GHEIKRAITA MKWEGVWNEY
161 TKKTSLATYL SFRRGYCTMD VQVVLDKWIN GGRSFAALRD
201 DPVRRAIDDV VVRFGCLSND YYSWGREKKA VDKSNAVRIL
241 MDHAGYDEST ALAHVRDDCV QAITDLDCIE ESIKRSGHLG
281 SHAQELLDYL ACHRPLIYAA ATWPTETNRY R
```

An example of an *Origanum majorana* TPS1 (0mTPS1) amino acid sequence is shown below (SEQ ID NO:66).

```
  1 MTDVSSLRLS NAPAAGGRLP LPGKVHLPEF RTVCAWLNNG
 41 CKYEPLTCRI SRRKISECRV ASLNSSQLIE KVGSPAQSLE
```

-continued

```
 81 EANKKIEDSI EYIKNLLMTS GDGRISVSAY DTSLVALIKD
121 VKGRDAPQFP SCLEWIAQNQ MADGSWGDEF FCIYDRIVNT
161 LACLVALKSW NLHPDKIEKG VTYINENVHK LKDGSTEHMT
201 SGFEIVVPAT LERAKVLGIQ GLPYDHPFIK EIINTKERRL
241 SKIPKDLIYK LPTTLLFSLE GQGELDWEKI LKLQSSDGSF
281 LTSPSSTASV FMRTKDEKCL KFIENAVKNC GGGAPHTYPV
321 DVFARLWAVD RLQRLGISRF FQHEIKYFLD HINSVWTENG
361 VFSGRDSQFC DIDDTSMGVR LLKMHGYNVD PNALKHFKQE
401 DGKFSCYPGQ MIESASPIYN LYRAAQLRFP GEEILEEASR
441 FAFNFLQEKI ANHEIQEKWV ISEHLIDEIK LGLKMPWYAT
481 LPRVEAAYYL EYYAGSGDVW IGKTFYRMPE ISNDTYKEVA
521 ILDFNTCQAQ HQFEWIYMQE WYESSKVKDF GISKKDLLVA
561 YFLAASTIFE PERTQERIIW AKTLILSRMI TSFLNKQATL
601 SSQQKNAILT QLGESVDGLD KIYSGEKDSG LAETLLATFQ
641 QLLDGFDRYT RHQLRNAWGQ WLMKVQQGEA NGGADAELIA
681 NTLNICAGLI AFNEDVLLHS EYTTLSSLTN KICQRLSQIE
721 DEKTLEVIEG GIKDKELEED IQALVKLALE ENGGCGVDRR
741 IKQSFLSVFK TFYYRAYHDA ETTDLHIFKV LFGPVM
```

An example of an *Origanum majorana* TPS4 (OmTPS4) amino acid sequence is shown below (SEQ ID NO:67).

```
  1 MSLAFSHVST FFSGQRVVGS RREIIPVNGV PTTANKPSFA
 41 VKCNLTTKDL MVKMKEKLKG QDGNLTVGVA DMPSSLCVID
 81 TLERLGVDRY FRSEIHVILH DTYRLWQQKD KDICSNVTTH
121 AMAFRLLRVN GYEVSSEELA PYANLEHFSQ QKVDTAMAIE
161 LYRAAQERIH EDESGLDKIL AWTTTFLEQQ LLTNSILDNK
201 LHKLVEYYLN NYHGQTNRVG ARRHLDLYEM SHYQNLKPSH
241 SLCNEDLLAF AKQGFRDFQI QQQKEFEQLQ RWYEDCRLDK
281 LSYGRDVVKI SSFMASILMD DPELADVRLS IAKQMVLVTR
321 IDDFFDHGGS REDSYKIIEL VKEWKEKAEY DSEEVKILFT
361 AVYTTVNELA EACVQQGRNS TTVKEFLVQL WIEILSAFKV
401 ELDTWSDGTE VSLDEYLSWS WISNGCRVSI VTTMHLLPTK
441 LCSDEMLRSE ECKDLCRHVS MVGRLLNDIH SFEKEHEENT
481 GNSVSILVAG EDTEEEAIGK IKEIVEYERR KLMQIVYKRG
521 TILPRECKDI FLKACRATFY VYSSTDEFTS PRQVMEDMKT
561 LSS
```

The inventors have described a CYP71D381 from *C. forskohlii*, which resulted in oxidized derivatives at alternative positions outside the known forskolin chemistry (Pateraki et al. Elife 6 (2017)). The sequence for the CYP71D381 from *Plectranthus barbatus* is shown below (SEQ ID NO:68).

```
  1 MEFDFPSALI FPAVSLLLLL WLTKTRKPKS DLDRIPGPRR
 41 LPLIGNLHHL ISLTPPPRLF REMAAKYGPL MRLQLGGVPF
 81 LIVSSVDVAK HVVKTNDVPF ANRPPMHAAR AITYNYTDIG
121 FAPYGEYWRN LRKICTLELL SARRVRSFRH IREEENAGVA
161 KWIASKEGSP ANLSERVYLS SFDITSRASI GKATEEKQTL
201 TSSIKDAMKL GGFNVADLYP SSKLLLLITG LNFRIQRVFR
241 KTDRILDDLL SQHRSTSATT ERPEDLVDVL LKYQKEETEV
281 HLNNDKIKAV IMDMFLAGGE TSATAVDWAM AEMIRNPTTL
321 KKAQEEVRRV FDGKGYVDEE EFHELKYLKL VIKEMLRMHP
361 PLPFLVPRMN SERCEINGYE IPANTRLLIN AWAIGRDPKY
401 WNDAEKFIPE RFENSSIDFK GNNLEYIPFG AGRRMCPGMT
441 FGLASVEFTL AMLLYHFDWK MPQGIKLDMT ESFGASLKRK
481 HDLLMIPTLK RPLRLAP
```

Mining of nearly 50 transcriptomes of related members of the mint family (Lamiaceae; Johnson et al., *J. Biol. Chem.* 294: 1349-1362 (2019)) indicates that the mint family provides rich repository of members of the CYP71D and CYP76AH enzymes (over 200 candidates, functional characterization, preliminary results by the inventors). Any of these enzymes can be used for additional/alternative oxidation chemistries to produce useful products.

The cyclization of diterpenes is among the most complex reactions found in nature. Typically, more than half of the carbons of GGPP undergo changes in connection, hybridization (sp-status), and stereochemistry during the carbocationic cascade. Stabilized in the active site of diterpene synthases, those carbocation intermediates undergo electron delocalization, hydride and alkyl-shifts, and can be quenched by access to water. For example, predicted cyclization reactions for conversion of GGPP to hydroxy-vulgarisane are shown below.

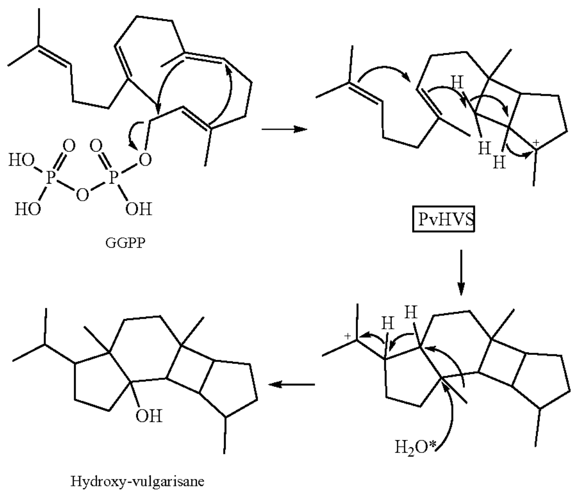

The inventors have recently discovered the PvHVS enzyme (SEQ ID NO:40), which can generate the irregular diterpene founding the class of bioactive vulgarisane compounds in *Prunella vulgaris* (see Pelot et al. Plant Physiol. 178: 54 LP-71 (2018)).

Mutated variants of diTPS can be deployed for diversification of the enzymes to increase the range of products produced, for example, by controlling the stereochemistry of the product outcome. Previously, generation of individual compounds from GGPP remained limited to the natural C20 chemical space of diterpenes (Schulte et al. Biochemistry 57: 3473-3479 (2018)). Terpene cyclization has been investigated through crystallography, structural modelling and mutagenesis studies including unreactive fluorinated, azaisoprenyl or thioloisoprenyl diphosphate analogs, by quantum-chemical calculations of intermediates, and by isotopically labelled natural precursors. With exceptions, the majority of approaches are static (non-dynamic) and have not yet been applied to terpenoid synthases, where reports are limited to single-enzyme-analog tests. Crystal structures for plant diTPS are similarly restricted to three enzymes only, the grand fir bifunctional class II/I abietadiene synthase, the class II Arabidopsis thaliana ent-CPS30, and the class I Taxus taxadiene synthase. Cyclization of rationally designed substrates with both altered spatial and electronic properties will provide a unique and dynamic facet by evaluation of the previously unrecognized substrate tolerance: steric constraints, stabilization of transition states and kinetics of the enzymes. With that, the proposed technology complements current tools exploring the mechanism of the cationic cascade of terpene cyclization. Structure-guided mutational studies for identified optimal modules, combined with the substrate tolerance described herein can broaden the accessible range of enzymes and products produced.

Enzymes that exhibit the following characteristics are generally preferred for use in methods of producing desirable products: (i) terpenoid synthases with high natural substrate tolerance, (ii) those generating a set of intermediates with maximized chemical diversity, and (iii) enzymes that provide intermediates in the pathways to forskolin and jolkinol C (P450s, ADHs, ACTs). In some cases, the enzymes can be active as recombinant enzymes in *E. coli* and/or the enzymes have demonstrated functionally in yeast.

As one example of an enzyme that can accept multiple unnatural substrates is CfTps2, which the inventors have demonstrated has such useful activity. The CfTps2 enzyme can provide the first step in synthesis of the cardiac stimulant and cognition enhancer forskolin which is derived from *Coleus forskohiii*. The CfTps2 enzyme can also serve as the first step in production of sclareol, which is an industrial precursor for ambroxoid fragrance substances. The ability to modify, in a targeted manner, these biological active or industrially significant natural products would facilitate the design, testing, and production of novel materials and biologically active agents.

Enzymes described herein can therefore have one or more deletions, insertions, replacements, or substitutions in a part of the enzyme. The enzyme(s) described herein can have, for example, at least 60%, or at least 70%, or at least 80%, or at least 90%, or at least 93%, or at least 95%, or at least 96%, or at least 97%, or at least 98%, or at least 99% sequence identity to a sequence described herein.

In some cases, enzymes can have conservative changes such as one or more deletions, insertions, replacements, or substitutions that have no significant effect on the activities of the enzymes. Examples of conservative substitutions are provided below in Table IA.

TABLE 1A

| Conservative Substitutions | |
|---|---|
| Type of Amino Acid | Substitutable Amino Acids |
| Hydrophilic | Ala, Pro, Gly, Glu, Asp, Gln, Asn, Ser, Thr |
| Sulfhydryl | Cys |
| Aliphatic | Val, Ile, Leu, Met |
| Basic | Lys, Arg, His |
| Aromatic | Phe, Tyr, Trp |

The enzymes can also include a tag, for example, as a label or to facilitate purification of the enzyme. Examples of such tags include histidine tags, streptavidin tags, biotin tags, antibody fragments, and the like.

Hosts

Terpenes, including diterpenes and terpenoids, can be made in a variety of host organisms in vivo. In some cases, the enzymes described herein can be made in host cells, and those enzymes can be extracted from the host cells for use in vitro. As used herein, a "host" means a cell, tissue or organism capable of replication. The host can have an expression cassette or expression vector that can include a nucleic acid segment encoding an enzyme that is involved in the biosynthesis of terpenes.

The term "host cell", as used herein, refers to any prokaryotic or eukaryotic cell that can be transformed with an expression cassettes or vector carrying the nucleic acid segment encoding an enzyme that is involved in the biosynthesis of one or more terpenes or terpenoids. The host cells can, for example, be a plant, bacterial, insect, or yeast cell. Expression cassettes encoding biosynthetic enzymes can be incorporated or transferred into a host cell to facilitate manufacture of the enzymes described herein or the terpene, diterpene, or terpenoid products of those enzymes. The host cells can be present in an organism. For example, the host cells can be present in a host such as a microorganism, fungus, or plant.

Expression of Enzymes

Also described herein are expression systems that include at least one expression cassette (e.g., expression vectors or transgenes) that encode one or more of the enzyme(s) described herein. For example, the expression systems can also include one or more expression cassettes any of the monoterpene synthase, diterpene synthase, sesquiterpene synthase, sesterterpene synthase, triterpene synthase, tetraterpene synthase, polyterpene synthase, transcription factor, cytochrome P450, cytochrome P450 reductase, 1-deoxy-D-xylulose 5-phosphate synthase (DXS), 1-deoxy-D-xylulose 5-phosphate-reducto-isomerase, cytidine 5'-diphosphate-methylerythritol (CDP-ME) synthetase (IspD), 2-C-methyl-d-erythritol 2,4-cyclodiphosphate synthase (IspF), HMG-CoA synthase, HMG-CoA reductase (HMGR), mevalonic acid kinase (MVK), phosphomevalonate kinase (PMK), mevalonate-5-diphosphate decarboxylase (MPD), isopentenyl diphosphate isomerase, abietadiene synthase (ABS), farnesylpyrophosphate synthase (FPPS), or squalene synthase (SQS), LDSP-protein fusions, or enzymes that facilitate production of terpenoids, terpene precursors, terpene building blocks, or products derived from terpenoids.

Nucleic acids encoding the enzymes can have sequence modifications. For example, nucleic acid sequences described herein can be modified to more optimally express the enzymes. Hence, the nucleic acid segment encoding the enzymes can be optimized to improve expression in different host cells. Most amino acids can be encoded by more than one codon, but when an amino acid is encoded by more than one codon, the codons are referred to as degenerate codons. A listing of degenerate codons is provided in Table 1B below.

TABLE 1B

Degenerate Amino Acid Codons

| Amino Acid | Three Nucleotide Codon |
|---|---|
| Ala/A | GCT, GCC, GCA, GCG |
| Arg/R | CGT, CGC, CGA, CGG, AGA, AGG |
| Asn/N | AAT, AAC |
| Asp/D | GAT, GAC |
| Cys/C | TGT, TGC |
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Leu/L | TTA, TTG, CTT, CTC, CTA, CTG |
| Lys/K | AAA, AAG |
| Met/M | ATG |
| Phe/F | TTT, TTC |
| Pro/P | CCT, CCC, CCA, CCG |
| Ser/S | TCT, TCC, TCA, TCG, AGT, AGC |
| Thr/T | ACT, ACC, ACA, ACG |
| Trp/W | TGG |
| Tyr/Y | TAT, TAC |
| Val/V | GTT, GTC, GTA, GTG |
| START | ATG |
| STOP | TAG, TGA, TAA |

Different organisms may translate different codons more or less efficiently (e.g., because they have different ratios of tRNAs) than other organisms. Hence, when some amino acids can be encoded by several codons, a nucleic acid segment can be designed to optimize the efficiency of expression of an enzyme by using codons that are preferred by an organism of interest. For example, the nucleotide coding regions of the enzymes described herein can be codon optimized for expression in various microorganisms, fungi, or plant species.

An optimized nucleic acid can have less than 100%, less than 99%, less than 98%, less than 97%, less than 95%, or less than 94%, or less than 93%, or less than 92%, or less than 91%, or less than 90%, or less than 89%, or less than 88%, or less than 85%, or less than 83%, or less than 80%, or less than 75% nucleic acid sequence identity to a corresponding non-optimized (e.g., a non-optimized parental or wild type enzyme nucleic acid) sequence. Nucleic acid segment(s) encoding one or more enzyme(s) can therefore have one or more nucleotide deletions, insertions, replacements, or substitutions.

The nucleic acid segments encoding one or more enzyme can be operably linked to a promoter, which provides for expression of mRNA from the nucleic acid segments. The promoter is typically a promoter functional in a microorganism, fungus or plant. A nucleic acid segment encoding one or more enzyme is operably linked to the promoter, for example, when it is located downstream from the promoter. The combination of a coding region for an enzyme operably linked to a promoter forms an expression cassette, which can include other elements and regulatory sequences as well.

Promoter regions are typically found in the flanking DNA upstream from the coding sequence in both the prokaryotic and eukaryotic cells. A promoter sequence provides for regulation of transcription of the downstream gene sequence and typically includes from about 50 to about 2,000 nucleotide base pairs. Promoter sequences can also contain regulatory sequences such as enhancer sequences that can influence the level of gene expression. Some isolated promoter sequences can provide for gene expression of heterologous DNAs, that is a DNA different from the native or homologous DNA.

Promoter sequences are also known to be strong or weak, or inducible. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. For example, a bacterial promoter such as the $P_{tac}$ promoter can be induced to varying levels of gene expression depending on the level of isopropyl-beta-D-thiogalactoside added to the transformed cells. Promoters can also provide for tissue specific or developmental regulation. An isolated promoter sequence that is a strong promoter for heterologous DNAs is often advantageous because it provides for a sufficient level of gene expression for easy detection and selection of transformed cells and provides for a high level of gene expression when desired.

Examples of prokaryotic promoters that can be used include, but are not limited to, SP6, T7, T5, tac, bla, trp, gal, lac, or maltose promoters. Examples of eukaryotic promoters that can be used include, but are not limited to, constitutive promoters, e.g., viral promoters such as CMV, SV40 and RSV promoters, as well as regulatable promoters, e.g., an inducible or repressible promoter such as the tet promoter, the hsp70 promoter and a synthetic promoter regulated by CRE.

Examples of plant promoters include the CaMV 35S promoter (Odell et al., *Nature.* 313:810-812 (1985)), or others such as CaMV 19S (Lawton et al., *Plant Molecular Biology.* 9:315-324 (1987)), nos (Ebert et al., *Proc. Natl. Acad. Sci. USA.* 84:5745-5749 (1987)), *Adhl* (Walker et al., *Proc. Natl. Acad. Sci. USA.* 84:6624-6628 (1987)), sucrose synthase (Yang et al., *Proc. Natl. Acad. Sci. USA.* 87:4144-4148 (1990)), α-tubulin, ubiquitin, actin (Wang et al., *Mol. Cell. Biol.* 12:3399 (1992)), cab (Sullivan et al., *Mol. Gen. Genet.* 215:431 (1989)), PEPCase (Hudspeth et al., *Plant Molecular Biology.* 12:579-589 (1989)) or those associated with the R gene complex (Chandler et al., *The Plant Cell.* 1:1175-1183 (1989)). Further suitable promoters include a CYP71D16 trichome-specific promoter and the CBTS (cembratrienol synthase) promotor, cauliflower mosaic virus promoter, the Z10 promoter from a gene encoding a 10 kD zein protein, a Z27 promoter from a gene encoding a 27 kD zein protein, the plastid rRNA-operon (rrn) promoter, inducible promoters, such as the light inducible promoter derived from the pea rbcS gene (Coruzzi et al., *EMBO J.* 3:1671 (1971)), RUBISCO-SSU light inducible promoter (SSU) from tobacco and the actin promoter from rice (McElroy et al., *The Plant Cell.* 2:163-171 (1990)). Other promoters that are useful can also be employed.

Examples of leaf-specific promoters include the promoter from the *Populus* ribulose-1,5-bisphosphate carboxylase small subunit gene (Wang et al. *Plant Molec Biol Reporter* 31 (1): 120-127 (2013)), the promoter from the *Brachypodium distachyon* sedoheptulose-1,7-bisphosphatase (SBPase-p) gene (Alotaibi et al. *Plants* 7(2): 27 (2018)), the fructose-1,6-bisphosphate aldolase (FBPA-p) gene from *Brachypodium distachyon* (Alotaibi et al. *Plants* 7(2): 27 (2018)), and the photosystem-II promoter (CAB2-p) of the rice (*Oryza sativa* L.) light-harvest chlorophyll a/b binding protein (CAB) (Song et al. *J Am Soc Hort Sci* 132(4): 551-556 (2007)). Additional promoters that can be used include those available in expression databases, see for example, website bar.utoronto.ca/eplant/ which includes poplar or heterologous promoters from Arabidopsis (for example from AT2G26020/PDF1.2b or AT5G44420/LCR77).

Alternatively, novel tissue specific promoter sequences may be employed. cDNA clones from a particular tissue can be isolated and those clones which are expressed specifically in that tissue can be identified, for example, using Northern blotting. Preferably, the gene isolated is not present in a high copy number but is relatively abundant in specific tissues. The promoter and control elements of corresponding genomic clones can then be localized using techniques well known to those of skill in the art.

Plant plastid originated promoters can also be used, for example, to improve expression in plastids, for example, a rice clp promoter, or tobacco rrn promoter. Chloroplast-specific promoters can also be utilized for targeting the foreign protein expression into chloroplasts. For example, the 16S ribosomal RNA promoter (Prrn) like psbA and atpA gene promoters can be used for chloroplast transformation.

A nucleic acid encoding one or more enzyme can be combined with the promoter by standard methods to yield an expression cassette, for example, as described in Sambrook et al. (MOLECULAR CLONING: A LABORATORY MANUAL. Second Edition (Cold Spring Harbor, NY: Cold Spring Harbor Press (1989); MOLECULAR CLONING: A LABORATORY MANUAL. Third Edition (Cold Spring Harbor, NY: Cold Spring Harbor Press (2000)). Briefly, a plasmid containing a promoter such as the 35S CaMV promoter or the CYP71D16 trichome-specific promoter can be constructed as described in Jefferson (*Plant Molecular Biology Reporter* 5:387-405 (1987)) or obtained from Clontech Lab in Palo Alto, California (e.g., pBI121 or pBI221). Typically, these plasmids are constructed to have multiple cloning sites having specificity for different restriction enzymes downstream from the promoter.

The expression cassette or vector can include nucleic acid sequence encoding a marker product. This marker product is used to determine if the gene has been delivered to the cell and once delivered is being expressed. Marker genes can include the *E. coli* lacZ gene which encodes β-galactosidase, and green fluorescent protein. In some embodiments the marker can be a selectable marker. When such selectable markers are successfully transferred into a host cell, the transformed host cell can survive if placed under selective pressure. There are two widely used distinct categories of selective regimes. The first category is based on a cell's metabolism and the use of a mutant cell line which lacks the ability to grow independent of a supplemented media. The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)).

The expression cassettes can be within vectors such as plasmids, viral vectors, viral nucleic acids, phage nucleic acids, phages, cosmids, or artificial chromosomes.

Transfer of the expression cassettes or vectors into host cells can be by methods available in the art and readily adaptable for use in the method described herein. Expression cassettes and vectors can be incorporated into host cells, for example, calcium-mediated transformation, electroporation, microinjection, lipofection, particle bombardment, chemical transfectants, physico-mechanical methods such as electroporation, or direct diffusion of DNA.

In some cases, one or more enzyme cassettes can be introduced into a single host cell. Such transformed host cells can then be used either for producing one or more enzymes or for chemical conversion of an unnatural substrate into a useful terpene product.

After expression in a suitable host, in some cases the enzymes can be purified or semi-purified for use within in vitro enzyme catalyzed reactions to generate terpenes. For example, the host cells can be lysed, and the enzymes purified or semi-purified to the extent needed to reduce side reactions. Purification of the enzymes also removes cellular debris that can complicate purification of the terpene products of enzymatic reactions. Purification of the enzymes can include lysis of host cells, removal of cellular debris by centrifugation or precipitation, solubilization of proteins, column chromatography (e.g., size selection chromatography, ion exchange chromatography), retrieval of tagged enzymes using affinity chromatography, and combinations thereof. For example, in some cases the enzymes can be histidine-tagged and purified or semi-purified by Ni-NTA agarose or Ni-NTA columns.

Methods

Methods are described herein that are useful for synthesizing terpenoids and products made from terpenoids. The methods can involve contacting one or more of the substrates described herein with one or more enzymes capable of synthesizing at least one terpene to produce a terpenoid product. In some cases, the methods can involve incubating one or more of the substrates described herein with a population of host cells having a at least one heterologous expression cassette or expression vector that can express one or more enzymes capable of synthesizing at least one terpenoid product. The enzymes capable of synthesizing at least one terpenoid product can be referred to as a primary enzyme. The methods can also involve contacting the terpenoid product with a secondary enzyme that can modify the terpenoid product into another useful product.

For example, one method can involve contacting one or more of the substrates described herein with one or more enzymes capable of synthesizing at least one terpene to produce a terpenoid product.

For example, another method can involve (a) incubating a population of host cells or host tissue that includes one or more expression cassettes (or vectors) that have a promoter operably linked to a nucleic acid segment encoding an enzyme capable of synthesizing at least one terpene; and (b) isolating at least one terpenoid product from the population of host cells or the host tissue.

The enzymes can be any of the enzymes described herein. For example, the enzymes can be a monoterpene synthase, diterpene synthase, sesquiterpene synthase, sesterterpene synthase, triterpene synthase, tetraterpene synthase, or polyterpene synthase. Enzymes used for modifying a terpenoid product (e.g., secondary enzymes) can include one or more transcription factor, cytochrome P450, cytochrome P450 reductase, 1-deoxy-D-xylulose 5-phosphate synthase (DXS), 1-deoxy-D-xylulose 5-phosphate-reducto-isomerase, cytidine 5'-diphosphate-methylerythritol (CDP-ME) synthetase (IspD), 2-C-methyl-d-erythritol 2,4-cyclo-diphosphate synthase (IspF), geranylgeranyl diphosphate synthase (GGDPS), HMG-CoA synthase, HMG-CoA reductase (HMGR), mevalonic acid kinase (MVK), phosphomevalonate kinase (PMK), mevalonate-5-diphosphate decarboxylase (MPD), isopentenyl diphosphate isomerase (IDI), abietadiene synthase (ABS), farnesylpyrophosphate synthase (FPPS), ribulose bisphosphate carboxylase, squalene synthase (SQS), patchoulol synthase, or WRI1 protein; and (b) isolating lipids from the population of host cells, the host plant's cells, or the host tissue. In some cases, a combination of enzymes, transcription factors, and lipid droplet proteins can be expressed in host cells, host plant, or host tissues.

Definitions

As used herein, the singular forms "a," "an," and "the" are intended to include the plural forms as well, unless the context clearly indicates otherwise. Also, as used herein, "and/or" refers to, and encompasses, any and all possible combinations of one or more of the associated listed items. Unless otherwise defined, all terms, including technical and scientific terms used in the description, have the same meaning as commonly understood by one of ordinary skill in the art to which this invention pertains.

The term "about", as used herein, can allow for a degree of variability in a value or range, for example, within 10%, within 5%, or within 1% of a stated value or of a stated limit of a range.

The term "enzyme" or "enzymes", as used herein, refers to a protein catalyst capable of catalyzing a reaction. Herein, the term does not mean only an isolated enzyme, but also includes a host cell expressing that enzyme. Accordingly, the conversion of A to B by enzyme C should also be construed to encompass the conversion of A to B by a host cell expressing enzyme C. However, in some cases, purified or semi-purified enzymes are used to catalyze formation of terpenes within in vitro reactions.

The term "heterologous" when used in reference to a nucleic acid refers to a nucleic acid that has been manipulated in some way. For example, a heterologous nucleic acid includes a nucleic acid from one species introduced into another species. A heterologous nucleic acid also includes a nucleic acid native to an organism that has been altered in some way (e.g., mutated, added in multiple copies, linked to a non-native promoter or enhancer sequence, etc.). Heterologous nucleic acids can include cDNA forms of a nucleic acid; the cDNA may be expressed in either a sense (to produce mRNA) or anti-sense orientation (to produce an anti-sense RNA transcript that is complementary to the mRNA transcript). For example, heterologous nucleic acids can be distinguished from endogenous plant nucleic acids in that the heterologous nucleic acids are typically joined to nucleic acids comprising regulatory elements such as promoters that are not found naturally associated with the natural gene for the protein encoded by the heterologous gene. Heterologous nucleic acids can also be distinguished from endogenous plant nucleic acids in that the heterologous nucleic acids are in an unnatural chromosomal location or are associated with portions of the chromosome not found in nature (e.g., the heterologous nucleic acids are expressed in tissues where the gene is not normally expressed).

The terms "identical" or percent "identity", as used herein, in the context of two or more nucleic acids or polypeptide sequences, refer to two or more sequences or subsequences that are the same or have a specified percentage of amino acid residues or nucleotides that are the same (e.g., 75% identity, 80% identity, 85% identity, 90% identity, 95% identity, 97% identity, 98% identity, 99% identity, or 100% identity in pairwise comparison). Sequence identity can be determined by comparison and/or alignment of sequences for maximum correspondence over a comparison window, or over a designated region as measured using a sequence comparison algorithm, or by manual alignment and visual inspection. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. A "reference sequence" is a defined sequence used as a basis for a sequence comparison; a reference sequence may be a subset of a larger sequence.

As used herein, a "native" nucleic acid or polypeptide means a DNA, RNA, or amino acid sequence or segment thereof that has not been manipulated in vitro, i.e., has not been isolated, purified, amplified and/or modified.

The terms "in operable combination," "in operable order," and "operably linked" refer to the linkage of nucleic acid sequences in such a manner that a nucleic acid molecule capable of directing the transcription of a coding region (e.g., gene) and/or the synthesis of a desired protein molecule is produced. The term also refers to the linkage of amino acid sequences in such a manner so that a functional protein is produced.

As used herein the term "terpene" includes any type of terpene or terpenoid, including for example any monoterpene, diterpene, sesquiterpene, sesterterpene, triterpene, tetraterpene, polyterpene, and any mixture thereof.

As used herein, the term "wild-type" when made in reference to a gene refers to a functional gene common throughout an outbred population. As used herein, the term "wild-type" when made in reference to a gene product refers to a functional gene product common throughout an outbred population. A functional wild-type gene is that which is most frequently observed in a population and is thus arbitrarily designated the "normal" or "wild-type" form of the gene.

The following Examples illustrate some of the experimental work involved in development of the invention.

EXAMPLE 1

Method Overview

This Example summarizes methods that include synthesizing and screening an inventory of unnatural substrates producing novel decalin-core diphosphate intermediates and irregular terpene-like products. Preliminary results indicate that novel, structurally diverse unnatural diterpene substrates, mimicking the natural precursor, are accessible and can be processed to produce unnatural terpenes.

Initially, a panel of substrates with altered carbon number, inserted heteroatoms and rearranged linear and branched structures will be prepared. Class II diterpene synthases (diTPS) produce a characteristic decalin core intermediate. Screens are performed of functionally distinct class II diTPS enzymes with a panel of substrates (FIG. 1A) to identify enzymes with substrate tolerance and capacity. As illustrated in FIG. 1B, class I diTPS directly produce irregular scaffolds, such as polycyclic diterpenes. Various enzymes can be used for bioprocessing of unnatural forskolin and jolkinol c compounds. Hence, sets of diTPS enzymes selected for functional diversity will be probed for their substrate tolerance to generate unnatural diterpene scaffolds.

Many class I diTPS of the decalin-core diterpene biosynthesis accept a range of class II intermediates, producing diverse products. The inventors have selected promiscuous class I diTPS and will examine their substrate tolerance against the unnatural class II intermediates. Products formed, for example as illustrated in FIG. 1B-1C, constitute a pilot library of diverse unnatural diterpene scaffolds.

EXAMPLE 2

Methods for Development of Substrates for Making Terpenoids

Modular pairs of diterpene synthases forming decalin core scaffolds were assembled through combinatorial biochemistry into new-to-nature pathways, yielding regioselective and stereoselective access to a panel of over 50 diterpene scaffolds, including novel compounds and those previously inaccessible. P450 enzymes were found to catalyze oxygenations of multiple substrates not native to the pathways and could also be substituted by enzymes from other species. Hence, our current repertoire of diTPS gives access to an estimated 75 scaffolds, while P450s, ACTs and ADHs can further modify each scaffold leading to an at least ten-fold diversification of possible diterpene pathways (see FIG. 3).

Figure 3:
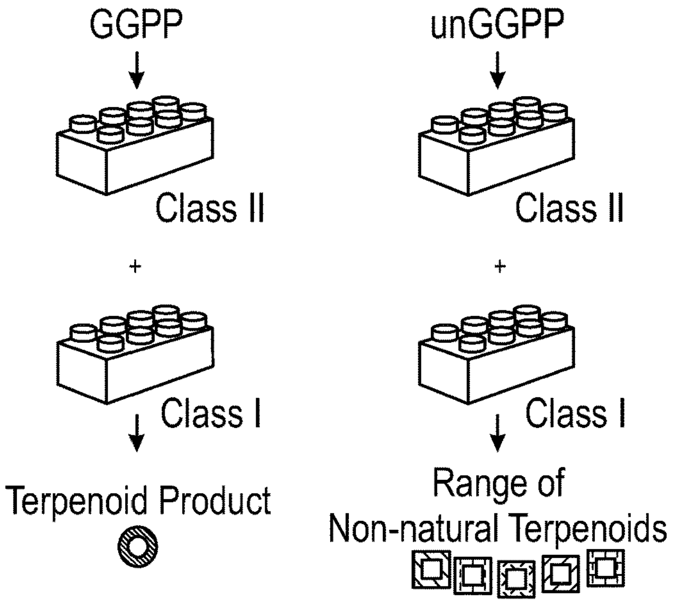
FIG. 3 schematically illustrates development of unnatural terpene scaffolds where the diversity of diterpenes that can be formed from geranylgeranyl diphosphate (GGPP) using a variety of different enzymes (represented as building blocks) and unnatural substrates. Such unnatural substrates can be converted into novel diterpenes through combinatorial biochemistry.
Figure 4:
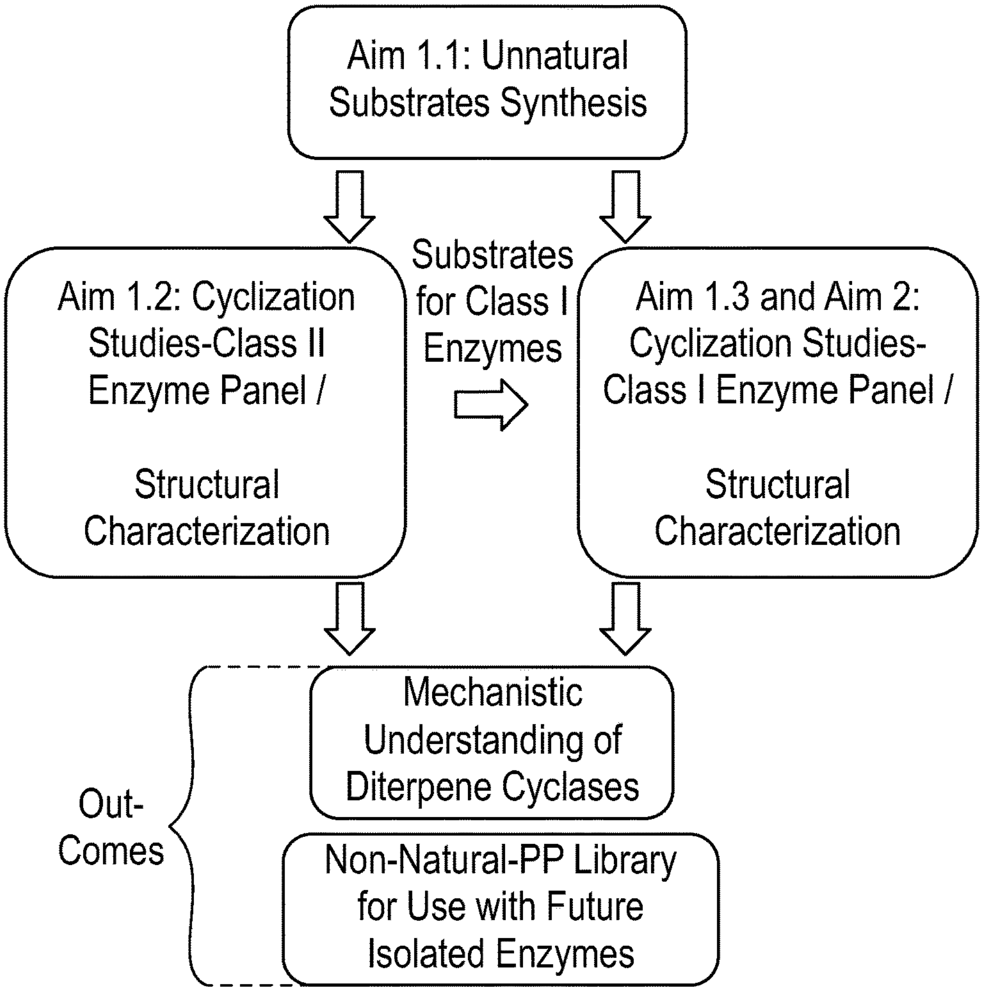
FIG. 4 is a schematic diagram of the strategy and process for making a library of unnatural substrates for terpenoid synthesis.

A prototype pipeline was developed to generate chemically diversified and naturally inspired small molecules of the diterpene class at unprecedented chemical diversity (see FIG. 3). Specifically, this required (i) establishment of a routine scheme for chemical synthesis of novel unnatural substrate derivatives of GGPP; (ii) combinatorial bioprocessing through a set of enzymes selected for their promiscuity; and (iii) iterative refinement of identified combinations of enzymes with their respective substrates. This process therefore involves test-learn-design cycles.

Over a dozen unnatural GGPP substrates were developed. The test-learn-design cycle informs further structural refinement of substrates, bringing the anticipated number to approximately 100 compounds. With its inherent building block principle, this strategy will be invaluable for high-throughput development of similar substrates for other classes of terpenoids and the resulting library of substrates will serve as a screening tool for future studies against an ever-expanding number of isolated enzymes.

EXAMPLE 3

Library of Unnatural Isoprenyl-Diphosphate Derivatized Substrates

This Example describes preparation of a library of unnatural isoprenyl-diphosphate derivatized substrates and screening a panel of class II labdane-type and class I macrocyclic, irregular-type diterpene synthases to advance mechanistic and structural understanding of the cationic cyclization cascades of these enzymes and to produce a collection of novel unnatural small molecules.

The diversity of substrates is synthetically explored that can be tolerated by the inventors' expansive toolbox of class II and I diterpene synthases (diTPS). Initial findings will provide key data guiding more extensive investigation of features that influence the cationic cyclization cascade and an understanding of substrate features that are tolerated, to generate a wide diversity of previously unknown products. The goal is to prepare unnatural products using a diversity of structural motifs that would, upon cyclization generate novel structures. These cyclization precursors will then be tested/fed to both class I and class II enzymes and the products isolated and characterized.

A broad spectrum of GGPP unnatural substrates are initially be prepared, exploring both spatial and electronic considerations. Altered backbones manipulating carbon numbers, insertion of heteroatoms and shifting double bonds are of interest. These substrates will also be functionalized with halogens, oxygen, nitrogen, and sulfur. More than a dozen compounds have been synthesized. The test-learn-design cycle is used to identify subgroups of acceptable substrates for further subtle structural refinement will be applied. Substrates are prepared according to Scheme 1, shown below.

Scheme 1

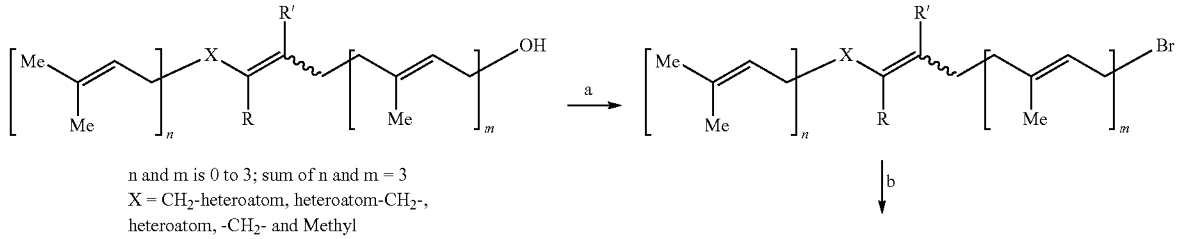

n and m is 0 to 3; sum of n and m = 3
X = $CH_2$-heteroatom, heteroatom-$CH_2$-, heteroatom, -$CH_2$- and Methyl
R and R′ are independently H, alkyl, halo, etc.

-continued

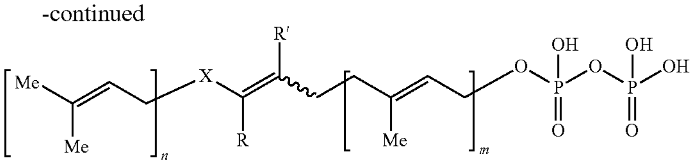

a. $PBr_3$, ether, 0° C.; b. Tris(tetrabutylammonium)-H-$P_2O_7$. $CH_3CN$

Recognizing that Scheme 1 generally shows activation of an allylic center and formation of the pyrophosphate, those of skill in the art should recognize that compounds such as those of the Formulae (III) and (IV) described herein can be accessed via the general methodology described in Scheme 1.

The substrate with a terminal allylic alcohol, substituted as described above, is prepared using methods described by Oberhauser et al. Angew. Chemie Int. Ed. 57, 11802-11806 (2018); Hoshino et al. Chem.—A Eur. J. 18: 13108-13116 (2012); Isaka et al. Biosci. Biotechnol. Biochem. 75: 2213-2222 (2011). The substrate with a terminal allylic alcohol is then converted via a simple two-step process (Davisson et al. *J. Org. Chem.* 51, 4768-4779 (1986)) to generate the non-natural substrates.

EXAMPLE 4

Analysis of an Unnatural Methyl-Derivative of GGPP

A methyl-derivative of GGPP ('unGGPP') was synthesized as described in the previous Example. A comparison of the structures of GGPP and this methyl-derivative of GGPP ('unGGPP') is shown below.

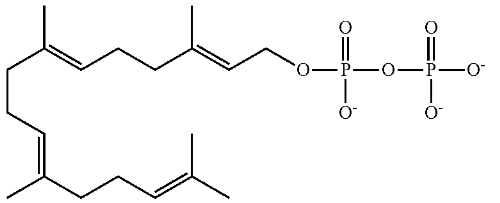

GGPP

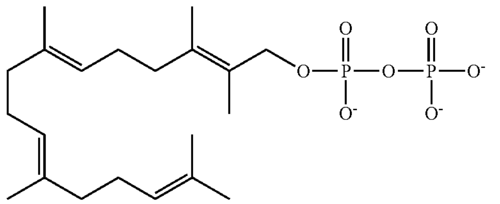

unGGPP

Figure 5A:
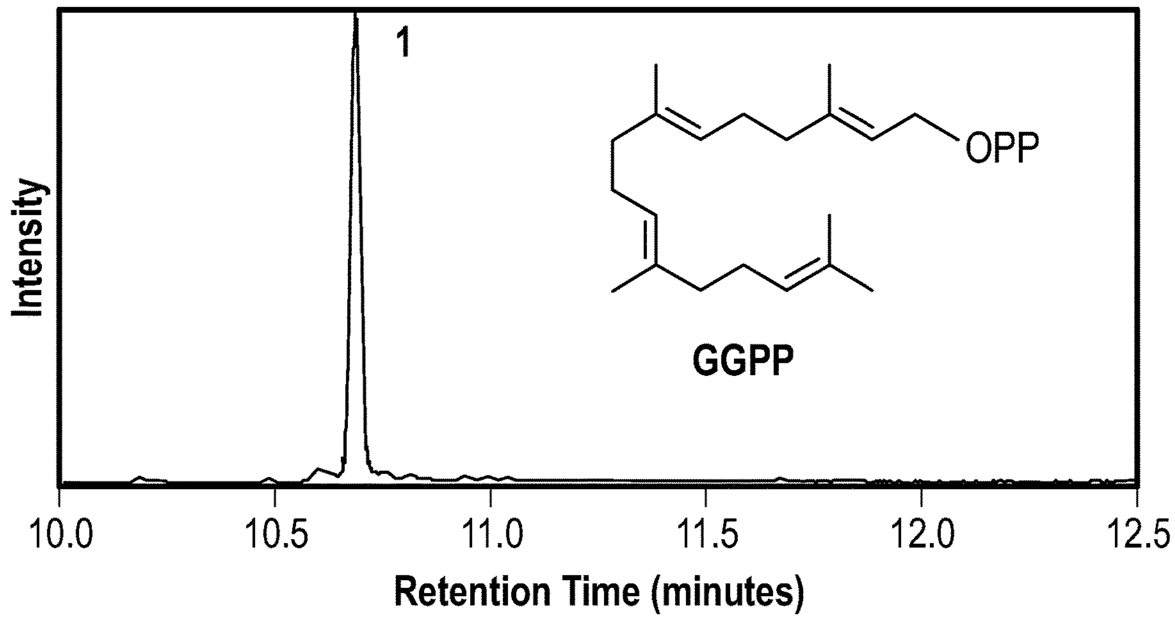
FIG. 5A-5D illustrate in vitro conversion of unGGPP by a casbene synthase to a macrocyclic product with a fragmentation pattern and an increase in m/z that was predicted by the inventors.
Figure 5B:
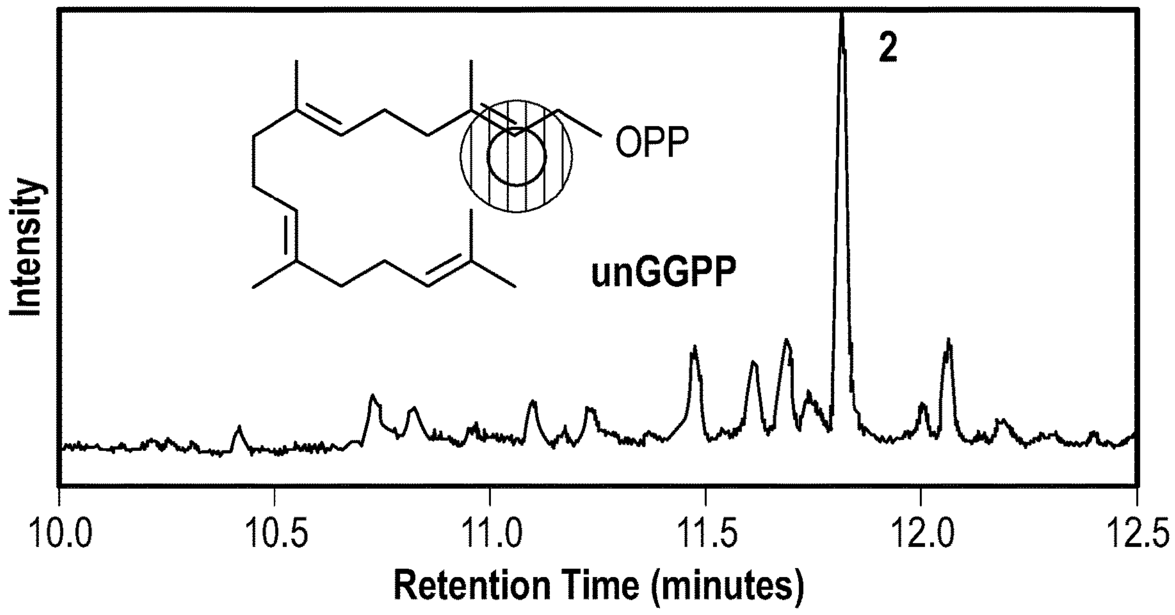
Figure 5C:
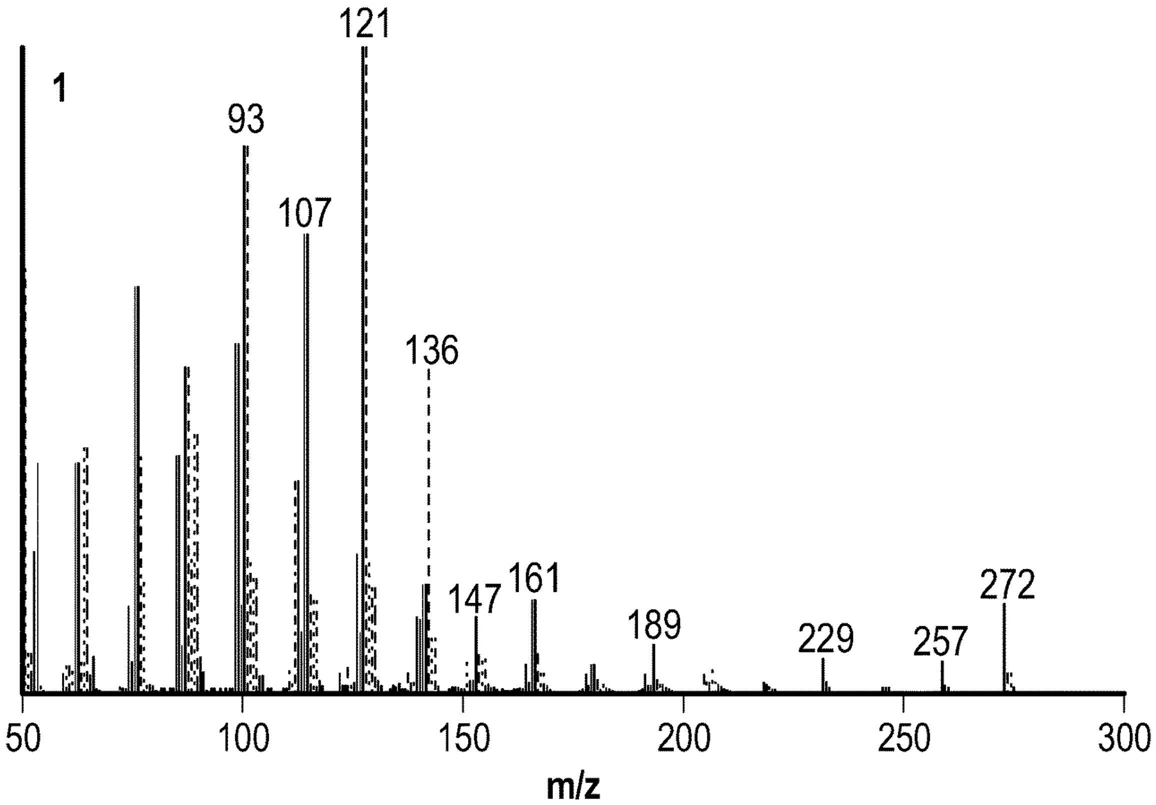
Figure 5D:
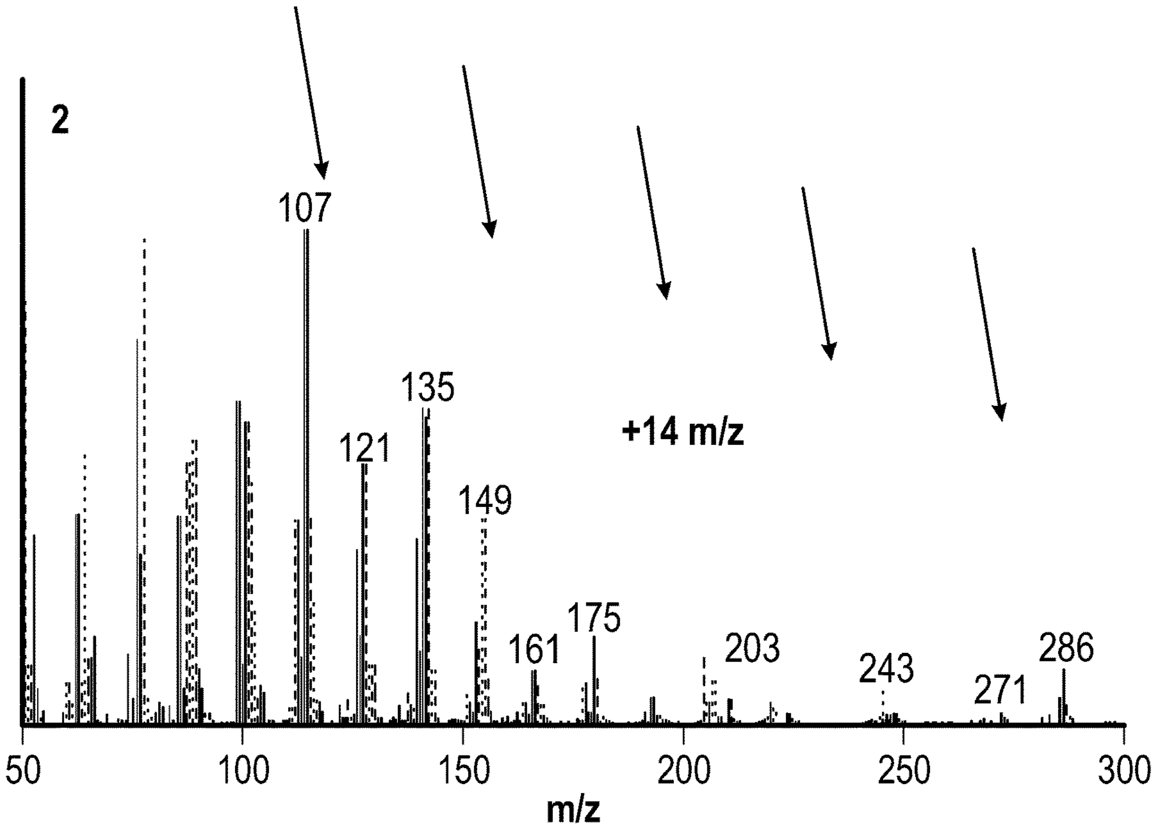

DgTPS1 (casbene synthase) was reacted with the unGGPP substrate to yield a novel product with a shifted retention time as detected by gas chromatography (see FIG. 5A-5B). The product had a mass consistent with a methyl-derivative of casbene (FIG. 5C-5D). A conserved irregular, macrocyclic structure is consistent with the fragmentation pattern of the major fragments of casbene (FIG. 5C-5D).

Systematic testing against five additional irregular-type diTPS indicated successful bioprocessing of this first substrate by three enzymes. The molecular mass and the fragmentation pattern of the products were consistent with unnatural diterpene-analogs.

Figure 6A:
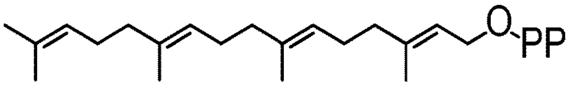
FIG. 6A-6B illustrate which enzymes can produce a product after enzymatic action on unnatural variants of GGPP (unGGPP).
Figure 6A:
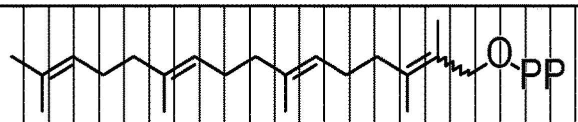
Figure 6A:
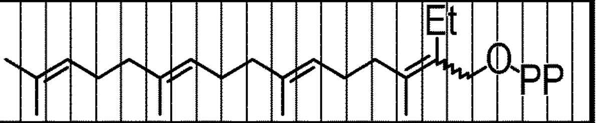
Figure 6A:
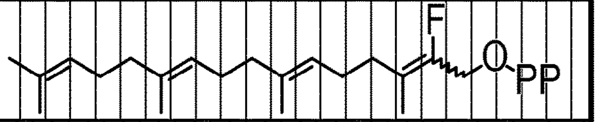
Figure 6A:
Figure 6A:
Figure 6A:
Figure 6A:
Figure 6A:
Figure 6A:
Figure 6A:
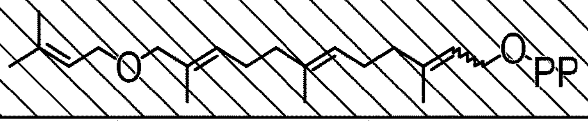
Figure 6A:
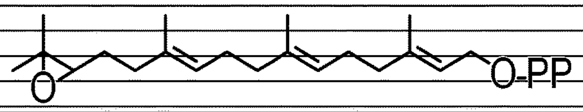
Figure 6B:
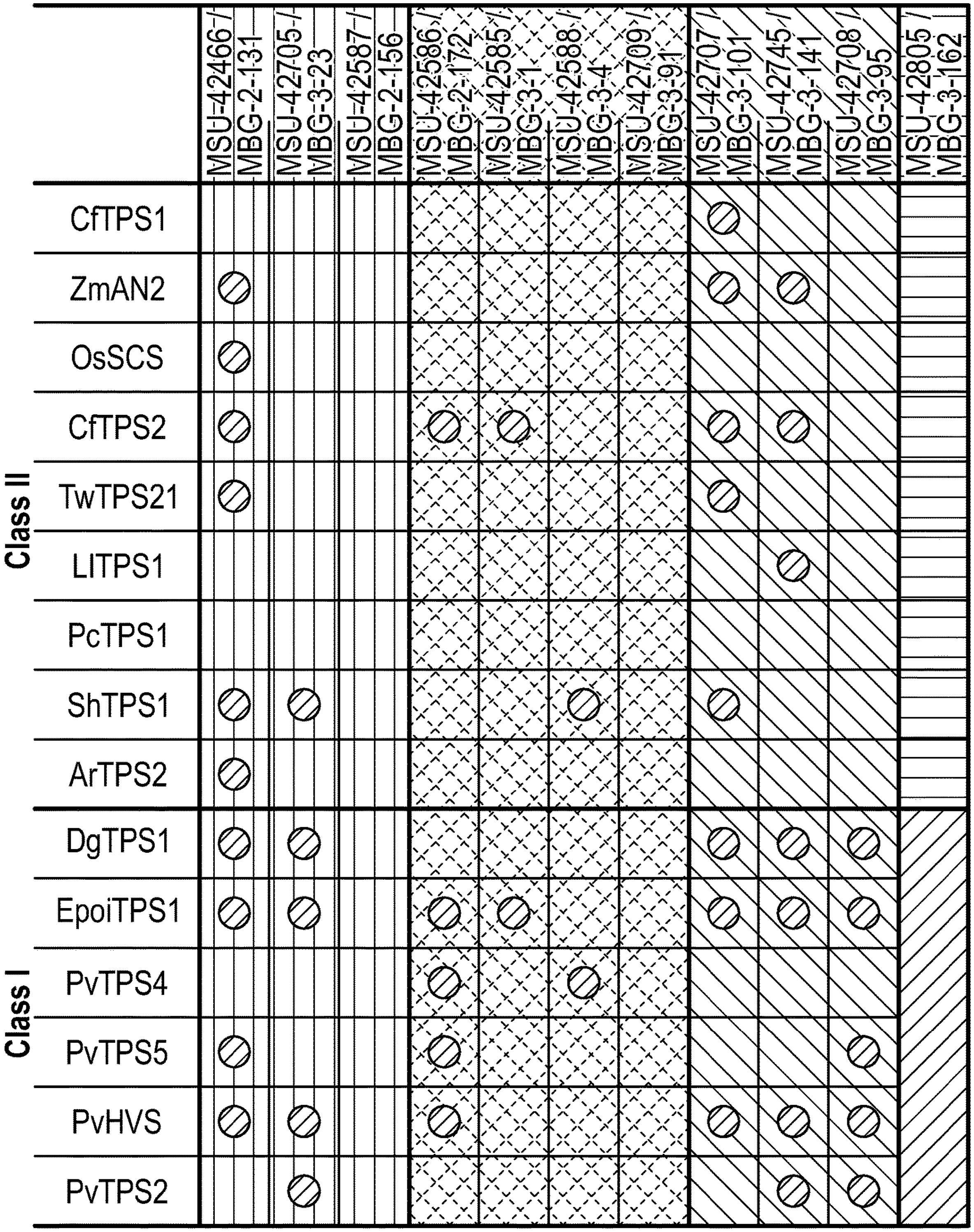

A dozen modified unnatural substrates were synthesized and tested for conversion to unnatural products. The results indicated that the enzymes employed had broad substrate tolerance. With only two exceptions, chain and sidechain substituted derivatives were readily accepted and converted by select enzymes of both the class I irregular type and class II labdane-type diTPS. The conversion pattern across all enzymes indicated astounding levels of activity. A total of fifty-six products (possibly with some structural redundancy) were identified in 159 assays (FIG. 6A-6B).

EXAMPLE 5

Screen of Unnatural Substrates Against 25 Class II Diterpene Synthases

Class II diTPS forming the decalin core labdanoid-type products catalyze cyclizations initiated by cation formation at carbon $C_{15}$ of the linear achiral isoprenyl diphosphate, retaining the diphosphate moiety, for example as shown below.

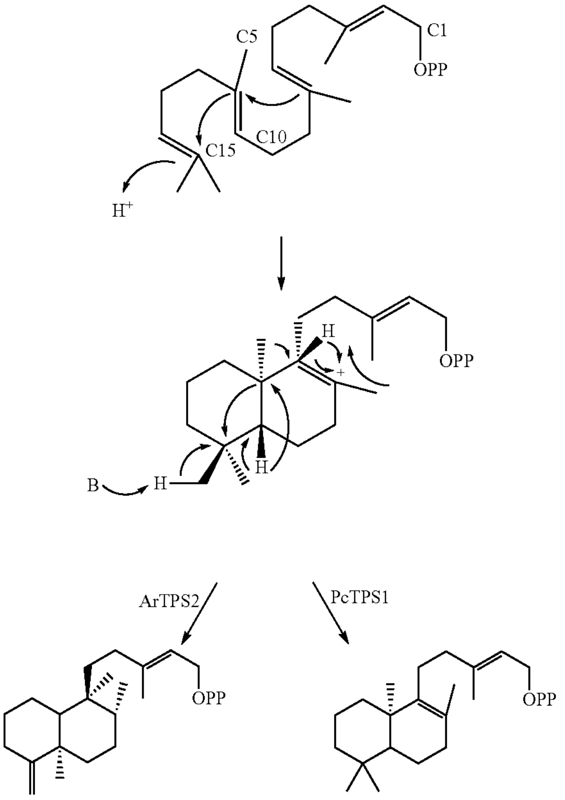

Shown is a typical cyclo-isomerization of GGPP into (4,13)-CLPP and ent-(8,13)-LPP by class II diTPS, where Ar refers to *Ajuga reptans*, and Pc refers to *Pogostemon cablin.*

To assess substrate tolerance of class II diTPS, substrates are screened against a panel of twenty-five enzymes. Recombinant diTPS were expressed heterologously in *E. coli*, purified, and reconstituted in in vitro assays with the substrate to be tested. The products from the enzymatic action on the substrate were analyzed structural elucidation and downstream functionalization.

In particular, pET28b+plasmids containing N-terminally truncated diTPS variants (having the plastidial targeting signal removed to generate pseudomature enzymes) are transformed into *E. coli* BL-21DE3-C41 OverExpress cells. Cultures are grown at 37° C. and 180 rpm until the optical density at 600 nm reached 0.3 to 0.4. Cultures are cooled to 16° C., and expression is induced at an optical density at 600 nm of approximately 0.6 with 0.2 mM isopropylthiogalactoside. Cells are collected and lysed before purification of the His6-tagged enzymes with Ni-NTA columns.

A typical high-throughput in vitro diTPS assay in lml contained 5 μg substrate, 200 μg purified enzyme (class II plus class I for labdanoid-type diterpenes, or class I for irregular diterpenes), and 10 mM buffer with magnesium. Reactions are carried out for 1 hour at 16° C., followed by vortexing with an equal volume of hexane to extract the products into the organic phase, prior to removal for GC/MS analysis.

Active enzyme/substrate combinations are validated by GC/MS analysis of the extract and products compared against references and authentic standards. Structural elucidation of novel products can be by NMR in some cases. The diphosphate intermediate can be converted by lysis to an alcohol for analysis, and the universally acting class I diTPS sclareol synthase from *Salvia sclarea* can be used for this purpose.

Reactions leading to novel compounds can be scaled up for structural elucidation. The scale-up procedure involved the same composition. However, in coupled assays of pairs of diTPS, the class II enzyme may be pre-incubated with substrate for two hours, before adding the class I diTPS. The diTPS enzymes exhibit excellent stability. Hence, the assays can be extended to overnight reactions to increase product yields, before extraction with hexane.

Results

Thirteen labdane-type diphosphate intermediates (partially redundant with intermediates made from substrate GGPP) were made by the twenty-five plant class II enzymes (see FIG. 6A-6B):

ent-8,13-copalyl diphosphate (ent-CPP)
normal-(+)-copalyl diphosphate ((+)-CPP)
syn-copalyl diphosphate (syn-CPP)
(+)-8,13-copalyl diphosphate ((8,13)-CPP)
(5S,9S,10S)-labda-7,13Edienyl diphosphate((7,13)-LPP)
ent-(10R)-labda-8,13E-dienyl diphosphate (ent-(8,13)-LPP)
normal-H-labda-13-en-8-ol diphosphate ((+)-8-LPP)
peregrinol (labda-13-en-9-ol diphosphate (PGPP)
(−)-kolavenyl diphosphate (KPP)
(5R,8S,9S,10S)-labda-13-en-8-ol diphosphate (ent-8-LPP)
ent-neo-cis-transclerodienyl diphosphate (CT-CLPP)
(5R,8R,9S,10R)-neo-cleroda-4(18),13E-dienyl diphosphate ((4,13)-CLPP)
(+)-labden-9-ol diphosphate ((+)-9-LPP).

Approximately 100 substrate analogs will be generated. Based on preliminary results (FIGS. 5 and 6), a significant number of these substrates will, upon testing provide diversified chemistries, novel structures and structural motifs not previously seen with known diTPS (products in the range of 100-200 compounds). Insights associated with the mechanistic details of how these enzymes operate in relation to the unnatural steric and electronic properties of the substrate, and structural information of which substrates are tolerated will guide the test-learn-design cycle. Specifically, after identification of well-accepted substrates, individual unnatural chemical features will be combined, and further subtle modifications will permit refining the substrates for iterative testing against a subset of diTPS identified as active and highly tolerant.

EXAMPLE 6

Screening of Unnatural Substrates Against 15 class I Irregular-Type Diterpene Synthases, Including 5 Macrocyclase- and Vulgarisane-Type Enzymes Class I diTPS use a different chemical strategy for the initial carbocation formation. The diTPS initiate the cascade of cyclization into irregular, macrocyclic or polycyclic compounds by lysis of the isoprenoid diphosphate to yield an allylic cation at the opposite end of the substrate, carbon $C_1$ and inorganic pyrophosphate, for example, as shown below.

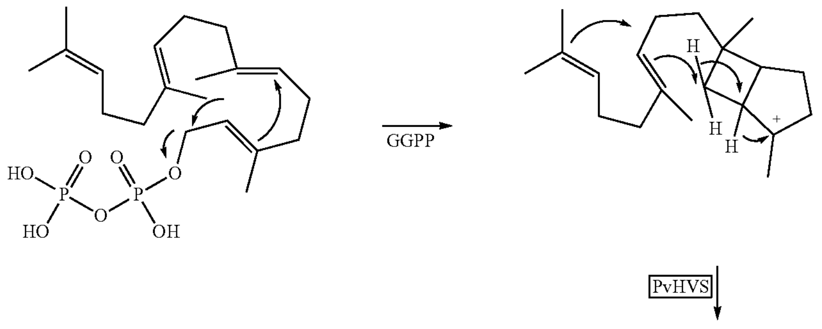

-continued

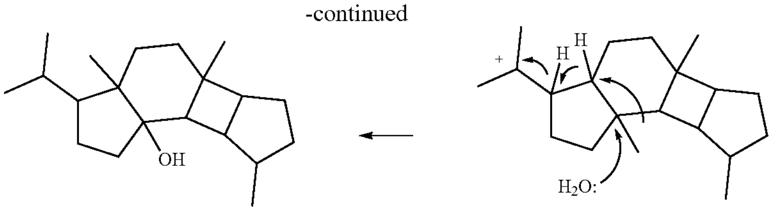

hydroxy-vulgarisane

Analogously to class II diTPS, the resulting carbocation intermediate further undergoes cyclo-isomerizations including hydride shifts, alkyl migrations and double bond rearrangements before termination of the reaction by proton abstraction or addition of a water molecule. In contrast to the paired modules of class II and I diTPS involved in formation of the labdanoid-type chemistry, irregular diterpenes are formed by the class I diTPS directly (Mau et al. Proc. Natl. Acad. Sci. 91: 8497 LP-8501 (1994)).

To explore unnatural substrate tolerance of the irregular diterpene formation, the inventors are screening all substrates produced in the library against a panel of six plant diTPS, including four macrocyclase-type and two polycyclic—type enzymes, followed by analysis of the products.

The products include the entry-step into the formation of jolkinol C, casbene and the closely related neo-cembrene, next to the structurally more complex taxadiene and hydroxyvulgarisane.

EXAMPLE 7

Screen of Class I Enzymes Against Substrates

The general function of class I enzymes of labdane-type diterpene metabolism is shared with those yielding irregular polycyclic diterpenes, i.e., generation of the initial carbocation at carbon $C_1$ by metal-dependent ionization.

Instead of accepting the acyclic GGPP, class I enzymes can use structurally diverse decalin-core diphosphate intermediates generated by class II enzymes. At this stage, additional cyclizations, double-bond-, hydride and alkyl shifts can occur, followed by either proton abstraction or quenching of the final carbocation through a water molecule. A panel of eight (seven plant and one microbial) class I labdane-type diTPS was selected for their demonstrated substrate promiscuity (Table 2).

TABLE 2

Class I labdane-type diTPS and tested substrates converted

| Class I diTPS | Substrate |
|---|---|
| SsSCS | ent-, syn-, (+)-CPP, (+)-8-LPP, ent-8-LPP, KPP, 9-LPP |
| CfTPS3 | syn-, (+)-CPP, (+)-8-LPP, ent-8-LPP, KPP, 9-LPP |
| EpTPS8 | ent-, (+)-CPP, 9-LPP, KPP |
| ArTPS3 | PgPP, (+)-CPP, (+)-8-LPP, ent-CPP |
| OmTPS4 | PgPP, (+)-CPP, (+)-8-LPP, ent-CPP |
| MvTPS5 | syn-, (+)-CPP, (+)-8-LPP, KPP, 9-LPP |
| EpTPS1 | ent-CPP, ent-8-LPP |
| KgTPS2 | ent-, syn-, (+)-CPP, (+)-8-LPP, ent-8-LPP, KPP, 9-LPP |

Ss *Salvia sclarea*;
Cf *Coleus forskohlii*;
Ep *Euphorbia peplus*;
Ar *Ajuga reptans;*
Om *Origanum majoranum*;
Mv *Marrubium vulgare*;
Kg *Kitasatospora griseola.*

Figure 7:
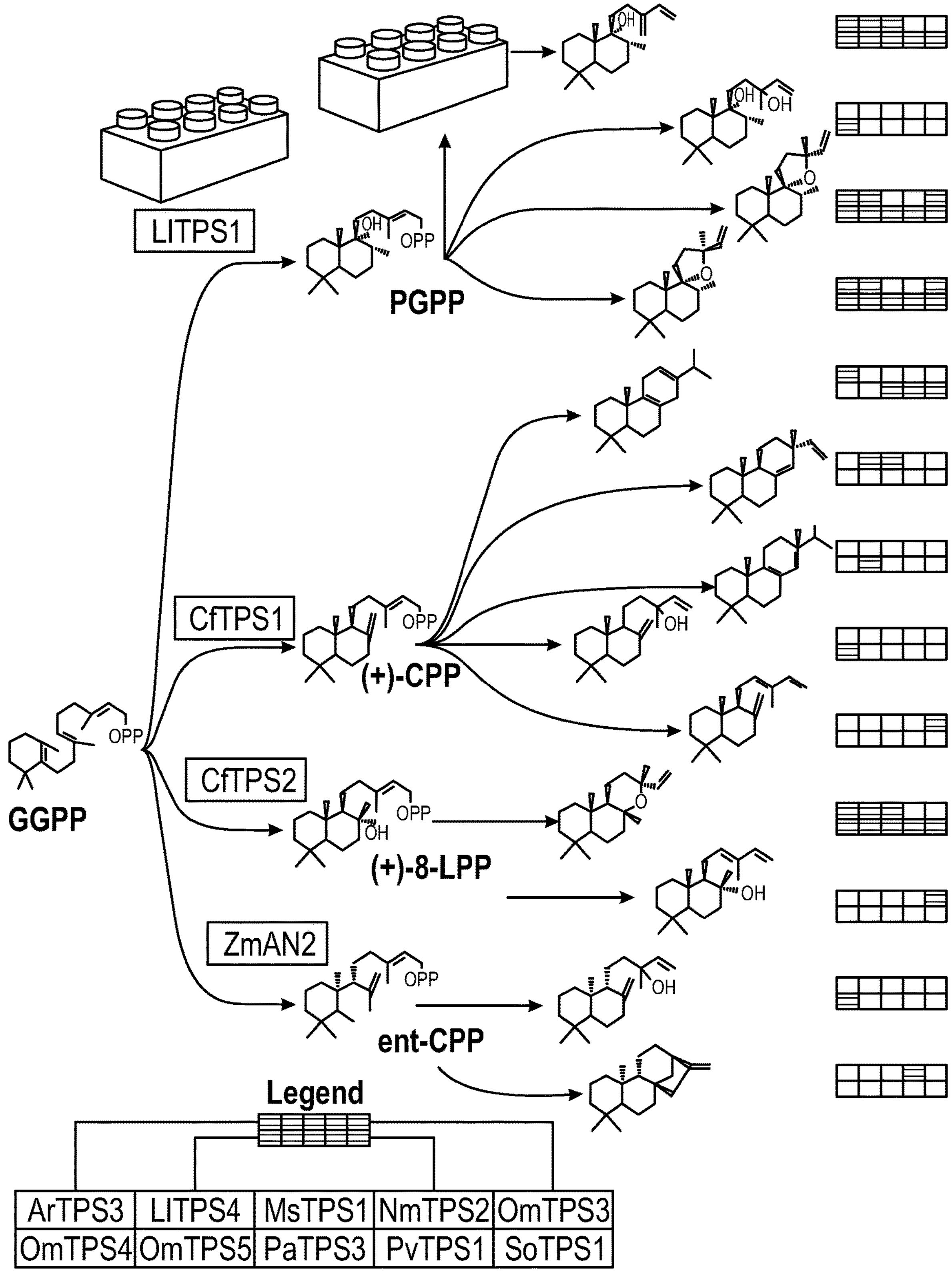
FIG. 7 illustrates typical cyclo-isomerization of diphosphate intermediates by class I diTPS. Ar, *Ajuga reptans*; Ll, *Leonotis leonorus*; Ms, *Mentha* spicata; Nm, *Nepeta mussini*; Om, *Origanum majorana*; Pa, *Perovskia atriplicifolia*; Pv, *Prunella vulgare*; So, *Salvia officinalis.*

All enzymes in Table 2 were functionally expressed. Microbial sequences were expressed as synthetic variants, expression optimized for *E. coli*. See also FIG. 7.

One example of an enzyme that can accept multiple unnatural substrates is CfTps2, which the inventors have demonstrated can provide the first step in synthesis of the cardiac stimulant and cognition enhancer forskolin. CfTps2 derived from *Coleus forskohiii* (also referred to as *Plectranthus barbatus*), an is shown below as SEQ ID NO:69.

```
  1 MKMLMIKSQE RVHSIVSAWA NNSNKRQSLG HQIRRKQRSQ
 41 VTECRVASLD ALNGIQKVGP ATIGTPEEEN KKIEDSIEYV
 81 KELLKTMGDG RISVSPYDTA IVALIKDLEG GDGPEFPSCL
121 EWIAQNQLAD GSWGDHFFCI YDRVVNTAAC VVALKSWNVH
161 ADKIEKGAVY LKENVHKLKD GKIEHMPAGF EFVVPATLER
201 AKALGIKGLP YDDPFIREIY SAKQTRLTKI PKGMIYESPT
241 SLLYSLDGLE GLEWDKILKL QSADGSFITS VSSTAFVFMH
281 TNDLKCHAFI KNALTNCNGG VPHTYPVDIF ARLWAVDRLQ
321 RLGISRFFEP EIKYLMDHIN NVWREKGVFS SRHSQFADID
361 DTSMGIRLLK MHGYNVNPNA LEHFKQKDGK FTCYADQHIE
401 SPSPMYNLYR AAQLRFPGEE ILQQALQFAY NFLHENLASN
441 HFQEKWVISD HLIDEVRIGL KMPWYATLPR VEASYYLQHY
481 GGSSDVWIGK TLYRMPEISN DTYKILAQLD FNKCQAQHQL
521 EWMSMKEWYQ SNNVKEFGIS KKELLLAYFL AAATMFEPER
561 TQERIMWAKT QVVSRMITSF LNKENTMSFD LKIALLTQPQ
601 HQINGSEMKN GLAQTLPAAF RQLLKEFDKY TRHQLRNTWN
641 KWLMKLKQGD DNGGADAELL ANTLNICAGH NEDILSHYEY
681 TALSSLTNKI CQRLSQIQDK KMLEIEEGSI KDKEMELEIQ
721 TLVKLVLQET SGGIDRNIKQ TFLSVFKTFY YRAYHDAKTI
761 DAHIFQVLFE PW
```

The CfTps2 enzyme can also serve as the first step in production of sclareol, manoyl oxide and structurally related compounds which are industrial precursors for ambroxoid fragrance substances.

Similarly, the neo-cleroda-4(18),13E-dienyl diphosphate synthase, which affords entry into a class of insect-antifeedants ArTPS2 is of particular interest for applications in agricultural biotechnology. Neo-clerodane diterpenoids, particularly those with an epoxide moiety at the 4(18) position, such as clerodin, the ajugarins, and the jodrellins have garnered significant attention for their ability to deter insect herbivores. The 4(18) desaturated product of ArTPS2 could be used in biosynthetic or semisynthetic routes to these potent insect antifeedants (BRH: compound 38, below).

38

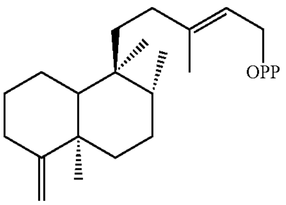

The ability to modify, in a targeted manner, these biological active or industrially significant natural products would facilitate the design, testing, and production of novel materials and biologically active agents.

EXAMPLE 8

Enzymatic Pathway to Jolkinol C

Genetic information was used to reconstruct the pathways to the pharmacologically active cyclic AMP booster forskolin, and jolkinol C (FIG. 8), which are precursors of phorbol esters drugs with unique anti-cancer, anti-HIV and analgesic activities.

For example, the inventors have described a CYP726A27 from *Euphorbia lathyris*, which has the following sequence (SEQ ID NO:70).

```
  1 MDLQLQIPSY PIIFSFFIFI FMLIKIWKKQ TQTSIFPPGP
 41 FKFPIVGNIP QLATGGTLPH HRLRDLAKIY GPIMTIQLGQ
 81 VKSVVISSPE TAKEVLKTQD IQFADRPLLL AGEMVLYNRK
121 DILYGTYGDQ WRQMRKICTL ELLSAKRIQS FKSVREKEVE
161 SFIKTLRSKS GIPVNLTNAV FELTNTIMMI TTIGQKCKNQ
```

-continued

```
201 EAVMSVIDRV SEAAAGFSVA DVFPSLKFLH YLSGEKTKLQ
241 KLHKETDQIL EEIISEHKAN AKVGAQADNL LDVLLDLQKN
281 GNLQVPLTND NIKAATLEMF GAGSDTSSKT TDWAMAOMMR
321 KPTTMKKAQE EVRRVFGENG KVEESRIQEL KYLKLVVKET
361 LRLHPAVALI PRECREKTKI DGFDIYPKTK ILVNPWAIGR
401 DPKVWNEPES FNPERFQDSP IDYKGTNFEL IPFGAGKRIC
441 PGMTLGITNL ELFLANLLYH FDWKFPDGIT SENLDMTEAI
481 GGAIKRKLDL ELISIPYTSS
```

The inventors have also described a CYP71D445 from *Euphorbia lathyris*, which has the following sequence (SEQ ID NO:71).

```
  1 MELEFRSPSS PSEWAITSTI TLLFLILLRK ILKPKTPTPN
 41 LPPGPKKLPL IGNIHQLIGG IPHQKMRDLS QIHGPIMHLK
 81 LGELENVIIS SKEAAEKILK THDVLFAQRP QMIVAKSVTY
121 DEHDITFSPY GDYWRQLRKI TMIELLAAKR VLSFRAIREE
161 ETTKLVELIR GFQSGESINF TRMIDSTTYG ITSRAACGKI
201 WEGENLFISS LEKIMFEVGS GISFADAYPS VKLLKVFSGI
241 RIRVDRLQKN IDKIFESIIE EHREERKGRK KGEDDLDLVD
281 VLLNLQESGT LEIPLSDVTI KAVIMDMFVA GVDTSAATTE
321 WLMSELIKNP EVMKKAQAEI REKFKGKASI DEADLQDLHY
361 LKLVIKETFR LHPSVPLLVP RECRESCVIE GYDIPVKTKI
401 MVNAWAMGRD TKYWGEDAEK FKPERFIDSP IDFKGHNFEY
441 LPFGSGRRSC PGMAFGVANV EIAVAKLLYH FDWRLGDGMV
481 PENLDMTEKI GGTTRRLSEL YIIPTPYVPQ NSA
```

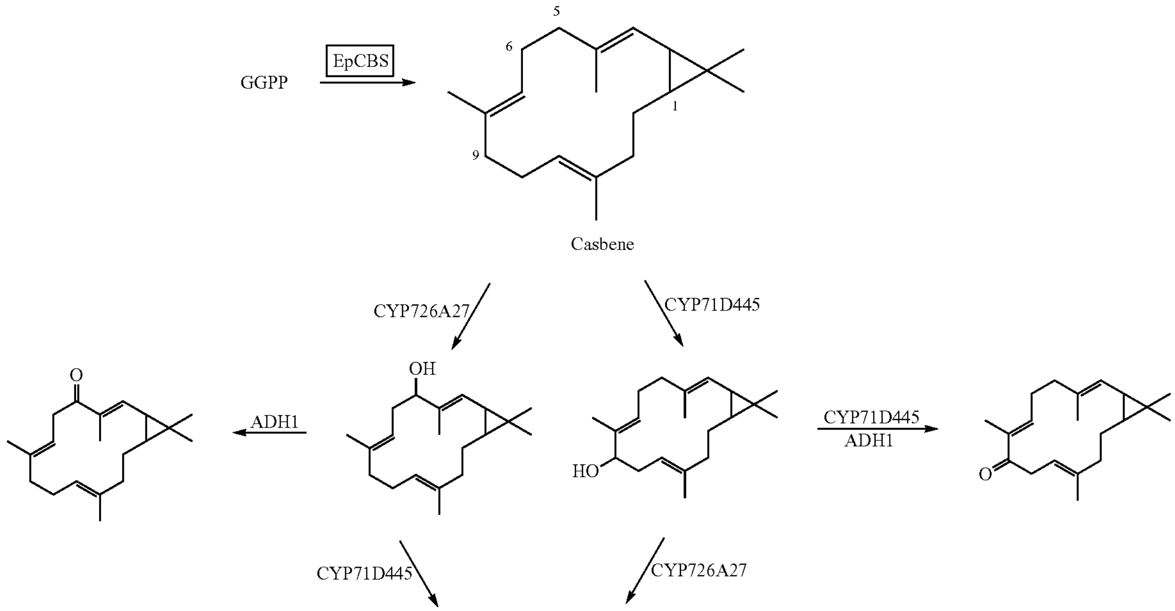

-continued
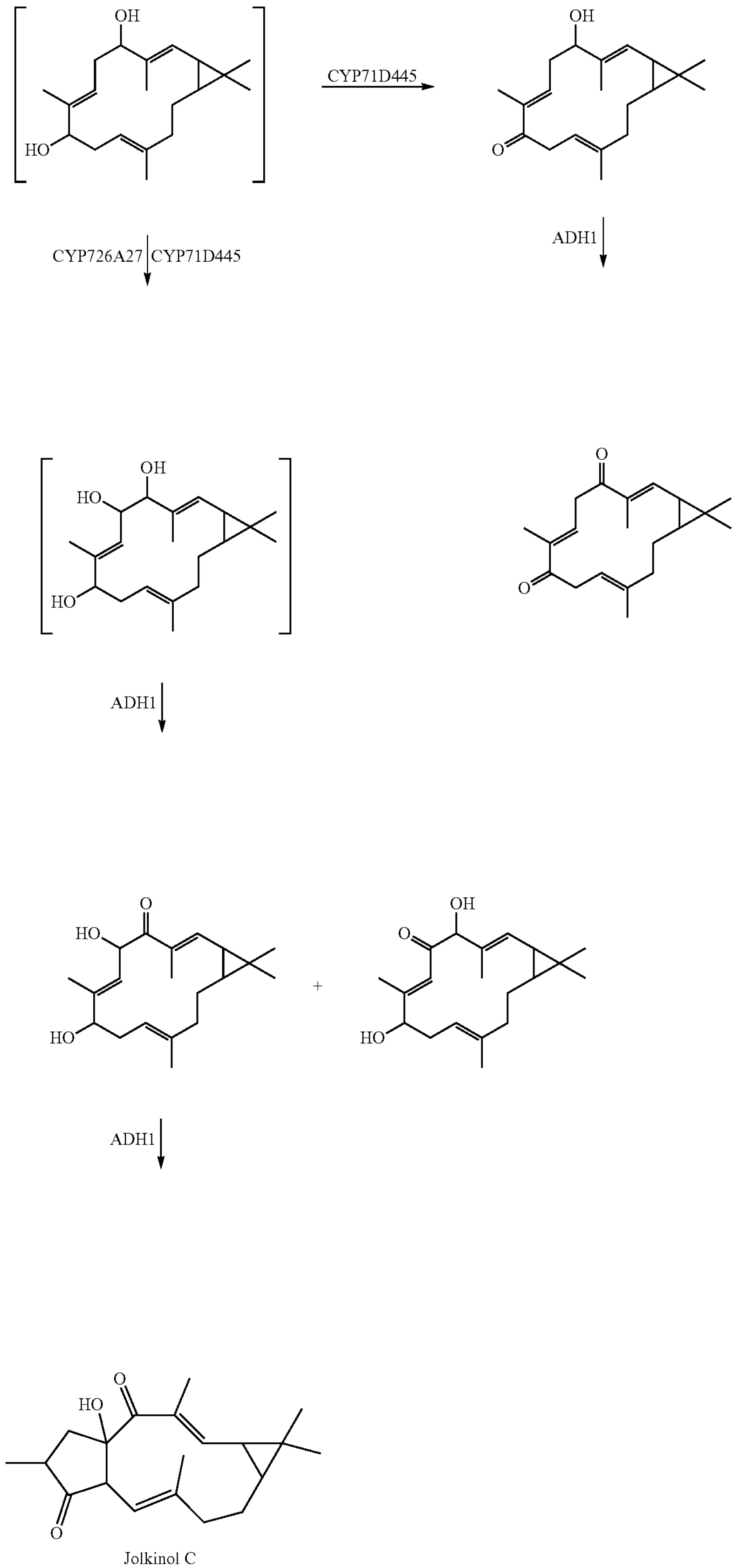
Jolkinol C

As illustrated, GGPP is cyclized to the irregular diterpene scaffold Casbene, which is subsequently oxidized and further re-arranged by P450 enzymes and an ADH1. All the functionalization enzymes involved are inherently promiscuous.

EXAMPLE 9

Selective Exploration of Substrate Tolerance of Two Model Pathways Functionalizing Bioactive Labdane-Type and Irregular, Macrocyclic Diterpenes The inventors have earlier established the metabolic pathway for oxidative functionalization of casbene to jolkinol C within *Euphorbia* (FIG. 8) and they have established functional yeast (*S. cerevisiae*) lines expressing the complete pathways from sugar to the labdane-type diterpene forskolin (40 mg/L), as illustrated below.

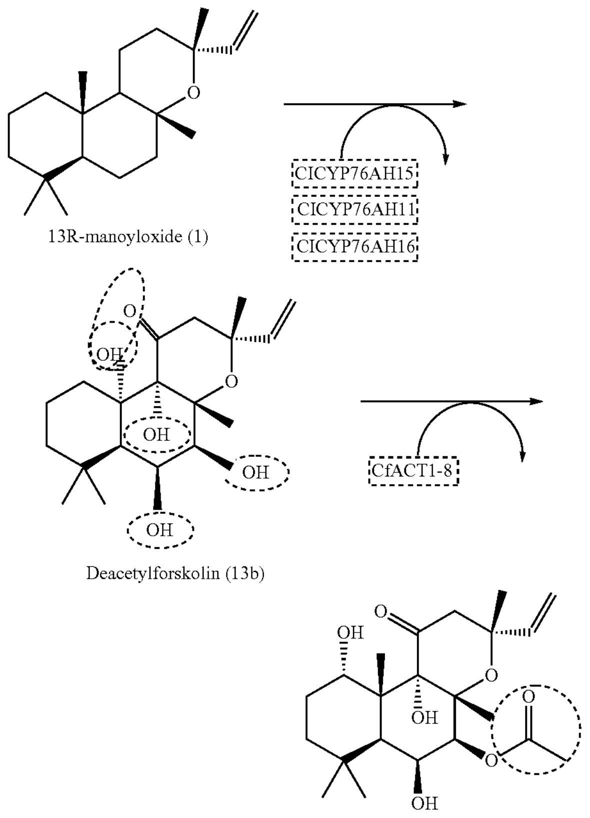

13R-manoyloxide (1)

Deacetylforskolin (13b)

Forskolin (16c)

Yeast lines expressing the corresponding characterized functionalization pathways only, i.e., P450s, ACTs and ADHs, can be supplemented with natural untested, and unnatural diterpenes synthetic analogs. Products and intermediates can be purified through the procedures described herein. The structurally elucidated products so generated can include rationally designed derivatives that are not accessible through formal synthesis. Analogs of forskolin are of high interest for their specificity to interact with the specific subgroups of adenylate cyclase, while jolkinol C analogs, not being an immediate pharmaceutical candidate, based on current knowledge, can serve as lead compounds for further chemical diversification.

EXAMPLE 10

Figure 9A:
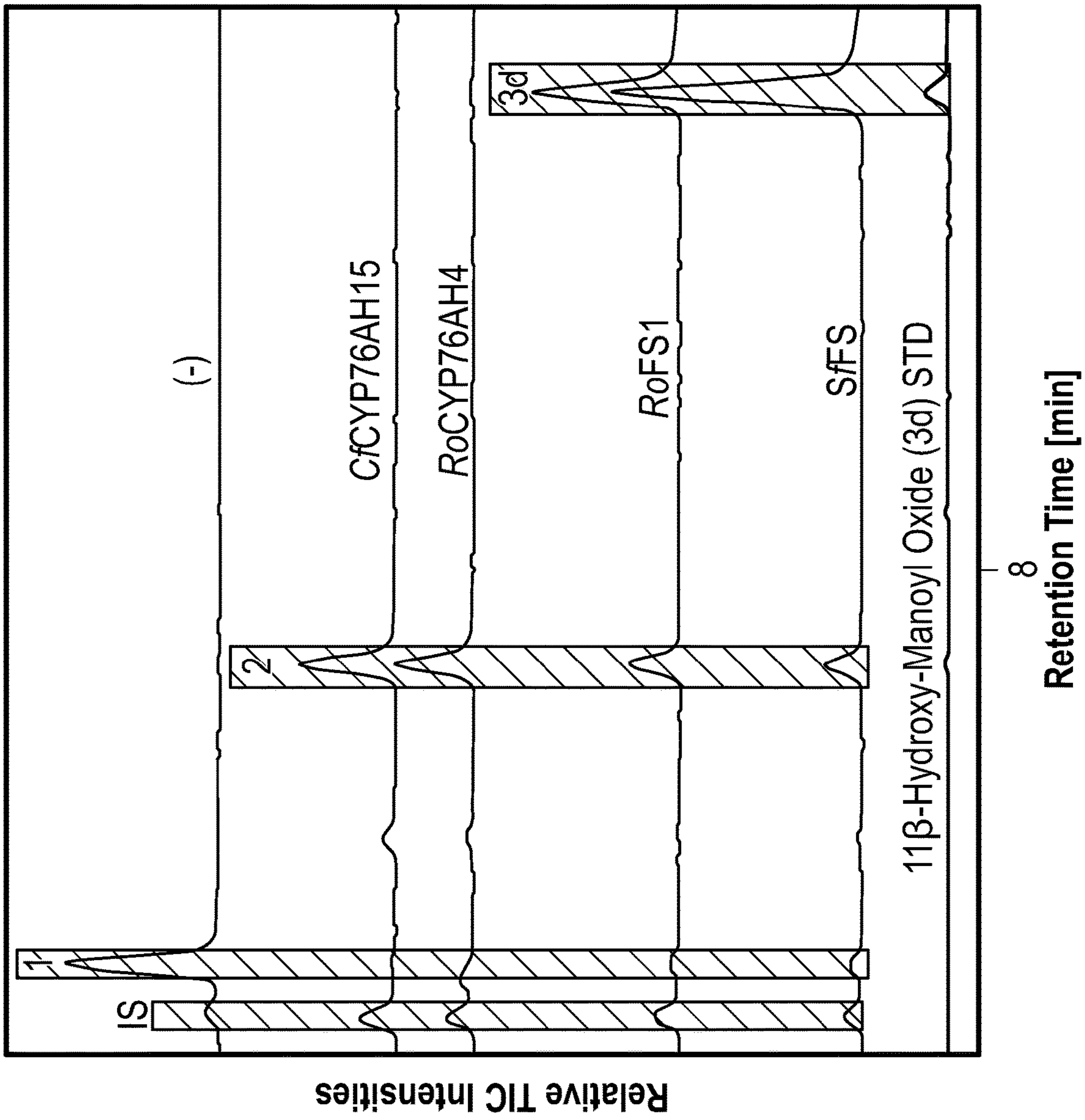
FIG. 9A-9C illustrate the substrate promiscuity of P450s of the CYP76 family.
Figure 9B:
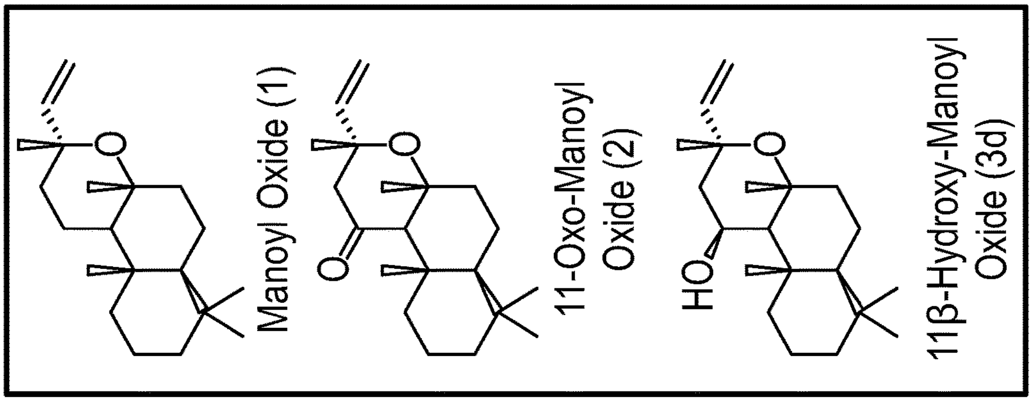
Figure 9C:
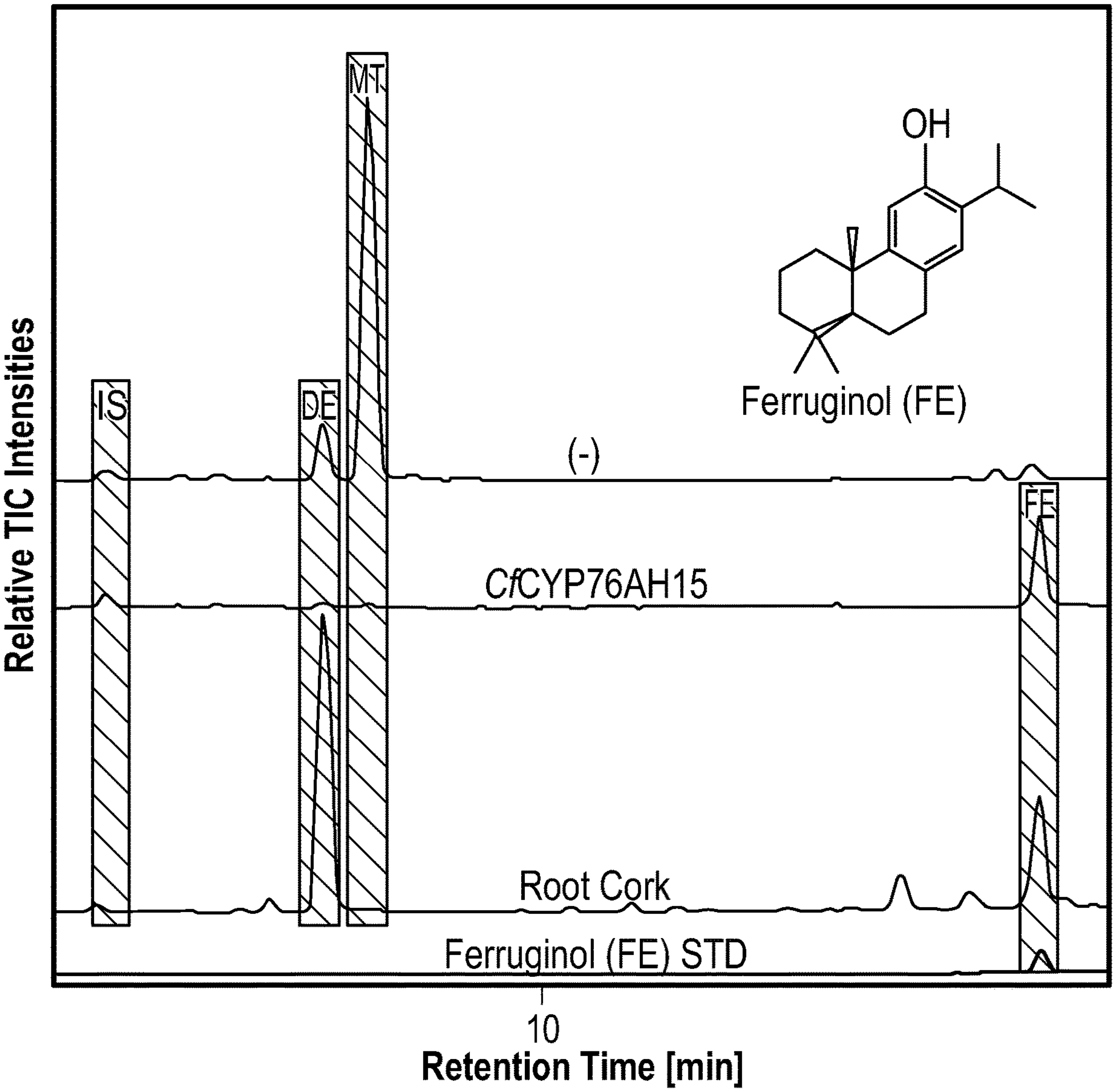

Use of Natural and Unnatural Diterpene Scaffolds in Biosynthetic Routes for the Labdane-Type Forskolin and Non-Labdane Type Ingenol Therapeutics The inventors have shown highly efficient conversion of labdane-type, synthetic diterpenes, by yeast cell lines expressing P450 enzymes (Hamberger et al. Plant Physiol. 157: 1677-1695 (2011)). See FIG. 9A-9C. The enzymes also showed conversion of non-native (yet natural) diterpenes into the corresponding oxidized forms, in the limited range where tested. Analogously, an acyl transferase was identified, which indiscriminately converted accessible alcohols into the corresponding acetyl-esters of forskolin (Pateraki et al. Elife 6 (2017).

Yeast cell lines are generated in the industrial strain CEN.PK (CEN.PK2-1C, MATa; his3D1; leu2-3_112; ura3-52; trpl-289; MAL2-8c, SUC2; Entian et al. Methods in Microbiology 36: 629-666 (2007)) that exhibited several advantages, including improved transformability and high tolerance for functionalized terpenoids. Also, the EasyClone 2.0 set of integrative vectors can be used as appropriate for over-expression of heterologous genes in industrial yeast strains. The vectors allow for selection in auxotrophic yeast strains (four different selection markers) and can carry two genes each, which allows for generation of multigene pathways. As the compounds are supplemented to the cultures, this project will not require engineering of the diterpene scaffold biosynthesis, significantly simplifying the generation of yeast strains. P450s, the corresponding cytochrome P450 reductase and enzymes encoding downstream functionalization steps can be stably, chromosomally integrated and driven by various promoters, including constitutive promoters. Isolation of products and analysis can be adapted to the physicochemical properties of the molecules. LC/MS can be used for analysis to offset problems with increasing oxygenation and the increased polarity of products.

EXAMPLE 11

Bioactivity of Unnatural Forskolin and Related Intermediate Labdane-Type Products with Adenylyl Cyclase Forskolin derivatives are tested for their activity at a representative of each of the three families of membrane adenylyl cyclase (AC1, AC2, and AC5; Dessauer et al. *Pharmacol. Rev.* 69: 93 LP-139 (2017)). Activation of AC1 could be a potential cognition enhancing target while inhibition may be beneficial in Fragile X syndrome—a genetic autism syndrome. Counter-screens can be done to assess selectivity against AC2 and AC5. Activation of AC5 would be expected to mediate cardiovascular side effects and inhibition may be beneficial. Forskolin itself activates all subtypes of AC so identifying novel derivatives that show selective activation of AC1 without stimulating AC2 or AC5 would be of significant interest. A full exploration of AC drug discovery is beyond the scope of this technology development grant application, but this section will provide initial proof-of-concept results to show potential value of our synthetic biology compound library approach in rationally designing specificity into a known terpenoid AC modulator, forskolin.

AC activity can be tested, as described by Feng et al. Neurology 89: 762 LP-770 (2017) with enhancements made possible by a novel ACA3/6 HEK cell line (Doyle et al. Biochem. Pharmacol. 163: 169-177 (2019)). The inventors can perform subtype-enriched cell-based assays using HEK293 cells transfected with AC1, AC2, and AC5. Cells with vector control plasmid or with plasmids for AC1, 2, or 5 can be stimulated with various concentrations of forskolin analogs (100 nM-30 μM) in the presence of the general PDE inhibitor IBMX. cAMP production can be assessed using the LANCE Ultra cAMP kit (Perkin Elmer; Waltham, MA) which is based on a TR-FRET detection method as described by Feng et al. (Neurology 89: 762 LP-770 (2017), see supplement). ACD73/6 HEK-293 cells transfected as indicated above are dissociated from dishes using Versene on the day of experiment. Two thousand cells cells/well in 5 μlin white 384-well microplate (Perkin Elmer) are incubated with various concentrations of forskolin or analogs for 30 min at room temperature. DMSO (0.1%) will be included in all samples for control and forskolin analogs. A cAMP standard curve was generated in triplicate according to the manual. Finally, europium (Eu)-cAMP tracer (54) and ULight™-anti-cAMP (54) were added to each well and incubated for 1 h at room temperature. Plates will be read on a TR-FRET microplate reader (Synergy NEO; Biotek, Winooski, VT) in the MSU Assay Development and Drug Repurposing Core.

Data analysis for forskolin-analog concentration-response curves can include background subtraction of activity in mock-transfected cells to estimate AC1, 2, or 5 specific activity. The resulting curves will be analyzed by non-linear least squares regression analysis to a 4-parameter logistic equation ($R_{min}$, $R_{max}$, —log$EC_{50}$ e.g. pEC50, and $n_H$) using GraphPad Prism, as described by Feng et al. (Neurology 89: 762 LP-770 (2017). Where curves are well-defined, the $pEC_{50}$ values for AC1, AC2, and AC5 as well as $R_{max}$ values are compared. Where curves may not provide a clear pEC50 value, major differences in $R_{max}$ can be noted. Significant selectivity can be defined as a 5-fold or greater differential potency (based on pEC50 values) or 5-fold or greater $R_{max}$ value for the chosen AC subtype. In addition to testing for AC activation, the inventors can also test for AC inhibition. Cells will be activated by a forskolin concentration that produces approximately 30% activation (ca. 1 μM) in the presence of increasing concentrations of the forskolin analogs. Any identified selective activators or any derivatives that significantly inhibit AC subtype activity can be tagged for future follow-up studies in receptor-regulated AC activity in HEK or native cells and in WT and AC-subtype KO animals (beyond the scope of the present application).

The catalytic capacities can be determined through gas chromatography and LC-MS analysis of products, i.e., substrate tolerance of entire assembled pathways, which will provide unique mechanistic insights (flux through the pathway, intermediates will indicate the order of conversion, potential steric/electronic hindrance). Hence, novel bioactive labdane and non-labdane type diterpenes can be identified. Structural elucidation of the products of biological interest can be performed using the procedures detailed herein. Analysis of their biological activity against a representative of adenylyl cyclases, either activation, or inhibition is expected to provide valuable data for structural refinement and is of pharmacological relevance.

EXAMPLE 12

{[(2E,6E,10E)-2,3,7,11,15-pentamethylhexadeca-2,6,10,14-tetraen-1-yl phosphonato]oxy}phosphonate and {[(2Z,6E, 10E)-2,3,7,11,15-pentamethylhexadeca-2,6,10,14-tetraen-1-yl phosphonato]oxy}phosphonate

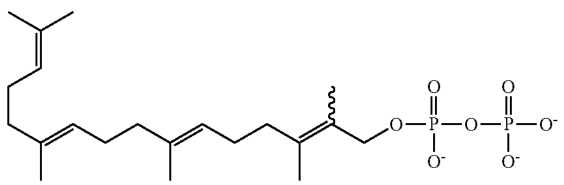

Ethyl (2E,6E,10E)-2,3,7,11,15-pentamethylhexadeca-2,6,10,14-tetraenoate and ethyl (2Z,6E,10E)-2,3,7,11,15-pentamethylhexadeca-2,6,10,14-tetraenoate. A 25.0 mL 14/20 round bottom flask was charged with sodium hydride (0.344 g, 8.60 mmol), tetrahydrofuran (4.00 mL) was, under an argon atmosphere at 0° C., was treated with triethyl-2-phosphonopropionate (2.05 g, 8.60 mmol) dissolved in tetrahydrofuran (1.00 mL). Once gas evolution ceased, farnesyl acetone (2.25 g, 8.60 mmol) was added, dissolved in tetrahydrofuran (1.00 mL), and the mixture heated to 45° C. for 24 hours. The mixture was cooled to 0° C., quenched with water, and partitioned into ethyl acetate. The organic layer was then washed with brine, dried over sodium sulfate, filtered, and concentrated to dryness. The crude product was dissolved in ethanol (20.0 mL) and cooled to 0° C. Sodium borohydride, to reduce any remaining ketone to ease purification, was added (0.312 g, 8.30 mmol) and the mixture was stirred for 1 hour at room temperature, cooled to 0° C. and quenched with 1.00 N hydrochloric acid. The reaction mixture was concentrated in vacuo and partitioned between ethyl acetate and water. The organic layer was washed with brine, dried over sodium sulfate, filtered, and concentrated in vacuo. The product was purified by silica gel chromatography (1:9 ethyl acetate: hexanes) to yield a mixture of ethyl (2E,6E,10E)-2,3,7,11,15-pentamethylhexadeca-2,6,10,14-tetraenoate and ethyl (2Z,6E,10E)-2,3,7,11,15-pentamethylhexadeca-2,6,10,14-tetraenoate (1.50 g, 50%). $^1$H NMR (500 MHz, $CDCl_3$) δ 5.18-5.04 (m, 3H), 4.22-4.13 (m, 2H), 2.35 (dd, J=9.6, 6.4 Hz, 1H), 2.20-2.02 (m, 9H), 2.02-1.94 (m, 5H), 1.89-1.82 (m, 3H), 1.78 (d, J=3.3 Hz, 1H), 1.68 (s, 5H), 1.60 (d, J=6.5 Hz, 7H), 1.29 (td, J=7.2, 4.0 Hz, 3H).

(2E,6E,10E)-2,3,7,11,15-pentamethylhexadeca-2,6,10,14-tetraen-1-ol and (2Z,6E,10E)-2,3,7,11,15-pentamethylhexadeca-2,6,10,14-tetraen-1-ol. A 50.0 mL 24/40 round bottom flask was charged with a mixture of ethyl (2E,6E,10E)-2,3,7,11,15-pentamethylhexadeca-2,6,10,14-tetraenoate and ethyl (2Z,6E,10E)-2,3,7,11,15-pentamethylhexadeca- 2,6,10,14-tetraenoate (1.10 g, 3.17 mmol), dichloromethane (15.0 mL) and on cooling to 0° C. (argon atmosphere) was treated with a 1.00 M solution of diisobutylaluminum hydride (12.7 mL, 12.7 mmol) in heptanes. The reaction was stirred for 24 hours, the mixture allowed to warm to room temperature then quenched with ethanol (2.00 mL). A solution of sodium potassium tartrate was added (4.50 g, 15.9 mmol in 20.0 mL water) and the biphasic mixture stirred vigorously for 24 hours. The product was then extracted with dichloromethane, the organic layers combined, dried over sodium sulfate, filtered, and concentrated in vacuo to an oil used without further purification (0.722 g, 75%). $^1$H NMR (500 MHz, $CDCl_3$) δ 5.18-5.06 (m, 3H), 4.15-4.05 (m, 2H), 2.20-1.91 (m, 12H), 1.76 (ddd, J=11.4, 3.0, 1.5 Hz, 4H), 1.71-1.66 (m, 6H), 1.64-1.58 (m, 8H). HRMS ESI (+) calc'd for [M+Na]=327.2664, found=327.2662.

{[(2E,6E,10E)-2,3,7,11,15-pentamethylhexadeca-2,6,10,14-tetraen-1-yl phosphonato]oxy}phosphonate and {[(2Z,6E,10E)-2,3,7,11,15-pentamethylhexadeca-2,6,10,14-tetraen-1-yl phosphonato]oxy}phosphonate. A 100 mL 24/40 round bottom flask was charged with a mixture of (2E,6E,10E)-2,3,7,11,15-pentamethylhexadeca-2,6,10,14-tetraen-1-ol and (2Z,6E,10E)-2,3,7,11,15-pentamethylhexadeca-2,6,10,14-tetraen-1-ol (0.300 g, 1.00 mmol), diethyl ether (5.00 mL) and, under an argon atmosphere, at 0° C. phosphorus tribromide (0.0500 mL, 0.500 mmol) added as a solution in diethyl ether (1.00 mL). After 15 minutes the mixture was diluted with hexanes, washed with brine, sodium bicarbonate and brine, dried over sodium sulfate, filtered, and concentrated in vacuo to dryness as an oil. The residue was redissolved in acetonitrile (5.00 mL), under an argon atmosphere, and treated with tetrabutylammonium pyrophosphate (2.10 g, 2.30 mmol). After 2 hours the reaction mixture was concentrated in vacuo to a viscous liquid and purified on a DOWEX50 column prepared by first stirring the resin (8.70 g) in concentrated ammonium hydroxide (30.0 mL) for 20 minutes. The resin was filtered and washed four times with water (100 mL), suspended in a buffer (20.0 mL of 1:49 2-propanol: 25.0 mmolar aqueous ammonium bicarbonate mixture) and poured into a column. The excess 1:49 2-propanol: 25.0 mmolar aqueous ammonium bicarbonate buffer was drained from the column and the crude product applied to the column (dissolved in 3.00 mL of 1:49 2-propanol: 25.0 mmolar aqueous ammonium bicarbonate buffer). The material was eluted with 30.0 mL of 1:49 2-propanol: 25.0 mmolar aqueous ammonium bicarbonate buffer and lyophilized to a waxy solid (0.550 g, 100%). $^{31}$P NMR (202 MHz, Deuterium Oxide) δ −8.57, −10.48 (d, J=20.2 Hz). HRMS ESI [M—H] calcd=463.2020, observed=463.2038.

EXAMPLE 13

{[(2Z,6E,10E)-2-fluoro-3,7,11,15-tetramethylhexadeca-2,6,10,14-tetraen-1-yl phosphonato]oxy}phosphonate and {[(2E,6E,10E)-2-fluoro-3,7,11,15-tetramethylhexadeca-2,6,10,14-tetraen-1-yl phosphonato]oxy}phosphonate

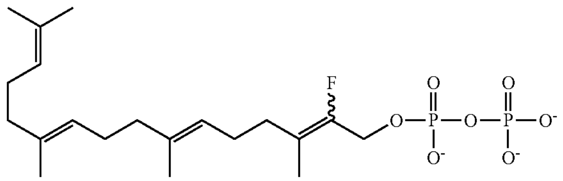 [SMILES: CC(C)=CCC/C(C)=C/CC/C(C)=C/CCC(C)=C(F)COP(=O)([O-])OP(=O)([O-])[O-]]

Ethyl (2Z,6E,10E)-2-fluoro-3,7,11,15-tetramethylhexadeca-2,6,10,14-tetraenoate and ethyl (2E,6E,10E)-2-fluoro-3,7,11,15-tetramethylhexadeca-2,6,10,14-tetraenoate. A 50.0 mL 14/20 round bottom flask was charged with sodium hydride (0.705 g, 21.0 mmol), tetrahydrofuran (20.0 mL) and at 0° C. (argon atmosphere) was added triethyl-2-fluoro-phosphonoacetate (4.84 g, 20.0 mmol) dissolved in tetrahydrofuran (5.00 mL) via syringe. Once gas evolution ceased, farnesyl acetone (2.62 g, 10 0 mmol) was added as a solution in tetrahydrofuran (1.00 mL). The mixture was heated to 45° C. for 22 hours, then concentrated and partitioned between ethyl acetate and 1.00 N hydrochloric acid. The organic layer was washed with brine, dried over sodium sulfate, filtered, and concentrated in vacuo. The crude material was purified by silica gel chromatography (1:9 ethyl acetate: hexanes) to yield the pure product as a mixture of cis and trans isomers ethyl (2Z,6E,10E)-2-fluoro-3,7,11,15-tetramethylhexadeca-2,6,10,14-tetraenoate and ethyl (2E,6E,10E)-2-fluoro-3,7,11,15-tetramethylhexadeca-2,6,10,14-tetraenoate (3.43 g, 98%). $^1$H NMR (500 MHz, $CDCl_3$) δ 5.18-5.04 (m, 3H), 4.38-4.21 (m, 3H), 4.11 (p, J=7.2 Hz, 1H), 2.58-2.48 (m, 1H), 2.25 (tt, J=8.8, 4.6 Hz, 1H), 2.16 (dq, J=14.1, 7.0 Hz, 2H), 2.11-2.00 (m, 7H), 1.97 (q, J=7.9 Hz, 3H), 1.86 (d, J=4.3 Hz, 2H), 1.68 (d, J=3.7 Hz, 5H), 1.60 (t, J=4.6 Hz, 7H). $^{19}$F NMR (470 MHz, $CDCl_3$) δ −126.96 (dd, J=14.3, 4.8 Hz), −128.66-−128.97 (m).

(2Z,6E,10E)-2-fluoro-3,7,11,15-tetramethylhexadeca-2,6,10,14-tetraen-1-ol and (2E,6E,10E)-2-fluoro-3,7,11,15-tetramethylhexadeca-2,6,10,14-tetraen-1-ol. A 50.0 mL 24/40 round bottom flask was charged with a mixture of ethyl (2Z,6E,10E)-2-fluoro-3,7,11,15-tetramethylhexadeca-2,6,10,14-tetraenoate and ethyl (2E,6E,10E)-2-fluoro-3,7,11,15-tetramethylhexadeca-2,6,10,14-tetraenoate (2.31 g, 6.50 mmol), dichloromethane (20.0 mL) and under an argon atmosphere at 0° C. was added diisobutylaluminum hydride (27.0 mL, 27.0 mmol, 1.00 M in heptanes). The reaction was stirred for 18 hours, warming to room temperature, then quenched with ethanol (5.00 mL) and a solution of sodium potassium tartrate was added (7.00 g, 24.8 mmol in 50.0 mL water). The biphasic mixture was stirred vigorously for 24 hours. The mixture was partitioned in a separatory funnel and the aqueous layer washed with dichloromethane. The organic layers were combined, dried over sodium sulfate, filtered, and concentrated in vacuo to an oil. The crude material was purified by silica gel chromatography (1:9 ethyl acetate: hexanes) to yield the products (2Z,6E,10E)-2-fluoro-3,7,11,15-tetramethylhexadeca-2,6,10,14-tetraen-1-ol and (2E,6E,10E)-2-fluoro-3,7,11,15-tetramethylhexadeca-2,6,10,14-tetraen-1-ol as a mixture of cis and trans isomers (0.859 g, 43%). $^1$H NMR (500 MHz, $CDCl_3$) δ 5.11 (dt, J=14.5, 7.5 Hz, 3H), 4.22 (dd, J=22.4, 16.6 Hz, 2H), 4.11 (p, J=7.2 Hz, 1H), 2.05 (tdd, J=33.1, 30.9, 10.8, 4.5 Hz, 12H), 1.69 (q, J=3.6, 3.1 Hz, 7H), 1.60 (t, J=3.2 Hz, 8H). $^{19}$F NMR (470 MHz, $CDCl_3$) δ −119.15-−120.01 (m), −121.10-−121.57 (m). HRMS ESI (+) calc'd for [M+Na] =331.2412, found=331.2442.

{[(2Z,6E,10E)-2-fluoro-3,7,11,15-tetramethylhexadeca-2,6,10,14-tetraen-1-yl phosphonato]oxy}phosphonate and {[(2E,6E,10E)-2-fluoro-3,7,11,15-tetramethylhexadeca-2,6,10,14-tetraen-1-yl phosphonato]oxy}phosphonate. A 25.0 mL 14/20 round bottom flask was charged with a mixture of (2Z,6E,10E)-2-fluoro-3,7,11,15-tetramethylhexadeca-2,6,10,14-tetraen-1-ol and (2E,6E,10E)-2-fluoro-3,7,11,15-tetramethylhexadeca-2,6,10,14-tetraen-1-ol (0.200 g, 0.640 mmol), diethyl ether (5.00 mL) and at 0° C., under an argon atmosphere, was added phosphorus tribromide (0.270 g, 1.00 mmol) dissolved in diethyl ether (1.00 mL). After 15 minutes, the reaction was partitioned between hexanes and brine. The organic layer was washed with sodium bicarbonate, brine, dried over sodium sulfate, filtered, and concentrated in vacuo to an oil. This crude mixture of isomers was dissolved in acetonitrile (2.00 mL), under an argon atmosphere, and treated with tetrabutylammonium pyrophosphate (0.904 g, 1.00 mmol). The reaction mixture was stirred for 2 hours, concentrated in vacuo to a viscous liquid and purified over DOWEX50 (9.40 g) resin. The resin was prepared by first stirring the DOWEX50 in concentrated ammonium hydroxide (30.0 mL) for 20 minutes. The resin was then filtered and washed four times with water (100 mL), then suspended in a buffer (20.0 mL of 1:49 2-propanol: 25.0 mmolar aqueous ammonium bicarbonate) and poured into a column. The excess 1:49 2-propanol: 25.0 mmolar aqueous ammonium bicarbonate buffer was drained from the column and the crude product material applied to the top of the column (dissolved in 3.00 mL of 1:49 2-propanol: 25.0 mmolar aqueous ammonium bicarbonate buffer). The material was eluted with 30.0 mL 1:49 2-propanol: 25.0 mmolar aqueous ammonium bicarbonate buffer and lyophilized to a waxy solid (0.250 g, 84%). $^{31}$P NMR (202 MHz, Deuterium Oxide) δ −9.34, −11.34. $^{19}$F NMR (470 MHz, $D_2O$) δ −117.52 (d, J=133.4 Hz), −118.74 (d, J=144.3 Hz). HRMS ESI [M−H] calcd=467.1769, observed=467.1786.

EXAMPLE 14

{[(2E,6E,10E)-2-ethyl-3,7,11,15-tetramethylhexadeca-2,6,10,14-tetraen-1-yl phosphonato]oxy}phosphonate and {[(2Z,6E,10E)-2-ethyl-3,7,11,15-tetramethylhexadeca-2,6,10,14-tetraen-1-yl phosphonato]oxy}phosphonate

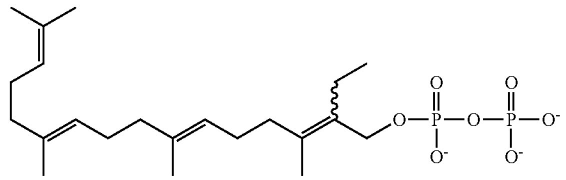 [SMILES: CCC(COP(=O)([O-])OP(=O)([O-])[O-])=C(C)CC/C=C(\C)CC/C=C(\C)CCC=C(C)C]

Ethyl (2E,6E,10E)-2-ethyl-3,7,11,15-tetramethylhexadeca-2,6,10,14-tetraenoate and ethyl (2Z,6E,10E)-2-ethyl-3,7,11,15-tetramethylhexadeca-2,6,10,14-tetraenoate. A 25.0 mL 14/20 round bottom flask was charged with sodium hydride (0.839 g, 34.9 mmol), tetrahydrofuran (20.0 mL) was, under argon atmosphere at 0° C., charged with triethyl phosphonobutyrate (4.89 g, 19.4 mmol) dissolved in tetrahydrofuran (2.00 mL). Once gas evolution ceased farnesyl acetone (1.05 g, 4.00 mmol) was added as a solution in tetrahydrofuran (2.00 mL). The reaction mixture was heated to 45° C. for 170 hours, cooled to 0° C., quenched with water and partitioned between ethyl acetate and water. The organic layer was washed with brine, dried over sodium sulfate, filtered and concentrated in vacuo to provide a mixture of ethyl (2E,6E,10E)-2-ethyl-3,7,11,15-tetramethylhexadeca-2,6,10,14-tetraenoate and ethyl (2Z,6E,10E)-2-ethyl-3,7,11,15-tetramethylhexadeca-2,6,10,14-tetraenoate, in a 1 to 1 mixture, and unreacted farnesyl acetone. The crude mixture was dissolved in ethanol (20.0 mL), cooled to 0° C. and unreacted farnesyl acetone was reduced with sodium borohydride (0.230 g, 6.20 mmol) to ease purification. The reaction mixture was stirred for 1 hour, allowed to warm to room temperature, cooled to 0° C. and quenched with 1.00 N hydrochloric acid. The reaction mixture was concentrated in vacuo, partitioned between ethyl acetate and water, the organic layer was washed with brine, dried over sodium sulfate, filtered, and concentrated in vacuo. The mixture was purified by silica gel chromatography (0-10% ethyl acetate in hexanes) to yield a mixture of cis and trans isomers, ethyl (2E,6E,10E)-2-ethyl-3,7,11,15-tetramethylhexadeca-2,6,10,14-tetraenoate and ethyl (2Z,6E,10E)-2-ethyl-3,7,11,15-tetramethylhexadeca-2,6,10,14-tetraenoate (0.770 g, 31%). $^{1}$H NMR (500 MHz, $CDCl_3$) δ 5.12 (dt, J=13.8, 6.0 Hz, 3H), 4.24-4.07 (m, 2H), 2.35-2.21 (m, 3H), 2.19-1.88 (m, 12H), 1.78 (s, 1H), 1.68 (s, 5H), 1.60 (d, J=5.0 Hz, 8H), 1.29 (td, J=7.1, 5.4 Hz, 3H), 1.04-0.80 (m, 3H).

(2E,6E,10E)-2-ethyl-3,7,11,15-tetramethylhexadeca-2,6,10,14-tetraen-1-ol and (2Z,6E,10E)-2-ethyl-3,7,11,15-tetramethylhexadeca-2,6,10,14-tetraen-1-ol. A 50.0 mL 24/40 round bottom flask was charged with a mixture ethyl (2E,6E,10E)-2-ethyl-3,7,11,15-tetramethylhexadeca-2,6,10,14-tetraenoate and ethyl (2Z,6E,10E)-2-ethyl-3,7,11,15-tetramethylhexadeca-2,6,10,14-tetraenoate (0.720 g, 2.00 mmol), dichloromethane (20.0 mL) and at 0° C., under an argon atmosphere, treated with diisobutylaluminum hydride (10.0 mL, 10.0 mmol, 1.00 M in heptanes). The mixture was stirred for 18 hours, warming to room temperature. The mixture was again cooled to 0° C., quenched with ethanol (2.00 mL), and a solution of sodium potassium tartrate added (7.10 g, 24.8 mmol in 50.0 mL water) and the biphasic mixture vigorously stirred for 24 hours. The reaction mixture was partitioned, and the aqueous layer washed with dichloromethane. The organic layers were combined, dried over sodium sulfate, filtered, and concentrated in vacuo to an oil. The crude material was purified by silica gel chromatography (1:9 ethyl acetate: hexanes) to yield an oil (mixture of cis and trans isomers, 0.622 g, 98%). $^{1}$H NMR (500 MHz, $CDCl_3$) δ 5.12 (dttd, J=12.5, 5.5, 2.8, 1.4 Hz, 3H), 4.17-4.06 (m, 2H), 2.22-2.12 (m, 3H), 2.08 (tq, J=10.7, 6.2, 5.1 Hz, 8H), 2.02-1.94 (m, 3H), 1.77 (s, 1H), 1.73-1.67 (m, 6H), 1.65-1.57 (m, 8H), 1.01 (qd, J= 7.9, 5.5 Hz, 3H), 0.94-0.80 (m, 2H). HRMS ESI (+) calc'd for [M+Na]=341.2820, found=341.2816.

{[(2E,6E,10E)-2-ethyl-3,7,11,15-tetramethylhexadeca-2,6,10,14-tetraen-1-yl phosphonato]oxy}phosphonate and {[(2Z,6E,10E)-2-ethyl-3,7,11,15-tetramethylhexadeca-2,6,10,14-tetraen-1-yl phosphonato]oxy}phosphonate. A 25.0 mL 14/20 round bottom flask was charged with a mixture of (2E,6E,10E)-2-ethyl-3,7,11,15-tetramethylhexadeca-2,6,10,14-tetraen-1-ol and (2Z,6E,10E)-2-ethyl-3,7,11,15-tetramethylhexadeca-2,6,10,14-tetraen-1-ol (0.311 g, 1.00 mmol) and anhydrous diethyl ether (5.00 mL). The reaction vessel was sealed, flushed with argon, cooled to 0° C. and phosphorus tribromide (0.405 g, 1.50 mmol) was added dissolved in diethyl ether (1.00 mL). After 15 minutes, the reaction was partitioned between hexanes and brine. The organic layer was then washed with sodium bicarbonate, brine, dried over sodium sulfate, and concentrated in vacuo to dryness as an oil. To this material was added acetonitrile (2.00 mL) and tetrabutylammonium pyrophosphate (0.585 g, 0.645 mmol). The reaction vessel was sealed and stirred, under an argon atmosphere, for 2 hours, then concentrated to a viscous liquid and purified over DOWEX50 resin column. The column was prepared by stirring DOWEX50 resin (8.50 g) in concentrated ammonium hydroxide (30.0 mL) for 20 minutes. The resin was filtered and washed four times with water (100 mL). The resin was suspended in a buffer (20.0 mL of 1:49 2-propanol: 25.0 mmolar aqueous ammonium bicarbonate) and poured into a column The excess 1:49 2-propanol: 25.0 mmolar aqueous ammonium bicarbonate buffer was drained from the column and the crude material was applied to the column (dissolved in 3.00 mL of the 1:49 2-propanol: 25.0 mmolar aqueous ammonium bicarbonate buffer). The material was eluted with 30.0 mL 1:49 2-propanol: 25.0 mmolar aqueous ammonium bicarbonate buffer and lyophilized to a waxy solid (0.230 g, 48%). $^{31}$P NMR (202 MHz, Methanol-$d_4$) δ −5.96, −9.82 (d, J=19.2 Hz). HRMS ESI [M−H] calcd.=477.2177, observed=477.2190.

EXAMPLE 15

{[(5E,9E)-6,10,14-trimethyl-2-oxopentadeca-5,9,13-trien-1-yl phosphonato]oxy}phosphonate

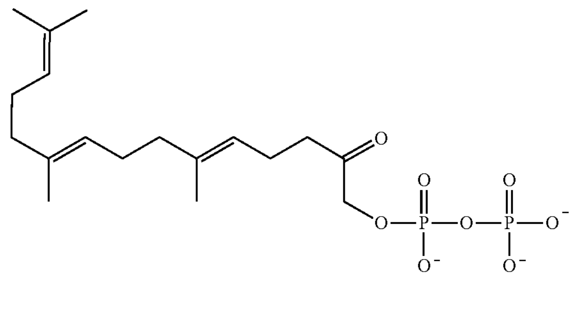 [SMILES: CC(C)=CCC/C(C)=C/CC/C(C)=C/CCC(=O)COP(=O)([O-])OP(=O)([O-])[O-]]

{[(5E,9E)-6,10,14-trimethyl-2-oxopentadeca-5,9,13-trien-1-yl phosphonato]oxy} phosphonate. Using a reported procedure (Hu, T.; Corey, E. J.; *Org. Lett.,* 2002, 4, 2441) a 25.0 mL 14/20 round bottom flask was charged with farnesyl acetone (0.524 g, 2.00 mmol), dichloromethane (32.0 mL), and cooled to 0 ° C. (argon atmosphere). Diisopropylethylamine (1.55 g, 12.0 mmol) was added, followed by trimethylsilyl triflate (1.77 g, 6.00 mmol) and the mixture stirred at 0° C. for 1.5 hours and then quenched by the addition of sodium bicarbonate. The mixture was extracted with hexanes, the organic layers combined, dried over sodium sulfate, filtered, and concentrated to yield an oil (0.720 g). The crude material was dissolved in tetrahydrofuran (40.0 mL) and solid sodium bicarbonate (0.189 g, 2.25 mmol) was added. The mixture was cooled to −78° C. and, under an argon atmosphere, n-bromosuccinimide (0.371 g, 2.10 mmol) added. The reaction mixture was stirred for 2 hours at −78° C., warmed to room temperature, filtered, and concentrated to yield the crude as a 1:4 mixture of starting material and bromide product (0.572 g, 55%). The crude product was dissolved in acetonitrile (3.00 mL) and tetrabutylammonium pyrophosphate (1.23 g, 1.30 mmol) added. The reaction was stirred at room temperature, under an argon atmosphere for 2 hours, concentrated and purified over DOWEX50 resin according to the following method. DOWEX50 resin (11.8 g) was stirred in concentrated ammonium hydroxide (40.0 mL) for 20 minutes. The resin was filtered and washed four times with water (100 mL). The resin was suspended in a buffer (20.0 mL of 1:49 2-propanol: 25.0 millimolar aqueous ammonium bicarbonate) and poured into a column. The excess 1:49 2-propanol: 25.0 millimolar aqueous ammonium bicarbonate buffer was drained from the column and the crude material was applied to the column (dissolved in 3.00 mL of the 1:49 2-propanol: 25.0 millimolar aqueous ammonium bicarbonate buffer). The material was eluted with 30.0 mL of the 1:49 2-propanol: 25.0 millimolar aqueous ammonium bicarbonate buffer and lyophilized to a waxy solid (0.692 g, 68%). $^{31}$P NMR (202 MHz, Deuterium Oxide) δ −5.91, −10.60. HRMS ESI [M−H] calcd=437.1500, observed=437.1511.

EXAMPLE 16

{[2-({[(2E,6E)-3,7,11-trimethyldodeca-2,6,10-trien-1-yl]oxy}methyl)prop-2-en-1-yl phosphonato]oxy}phosphonate

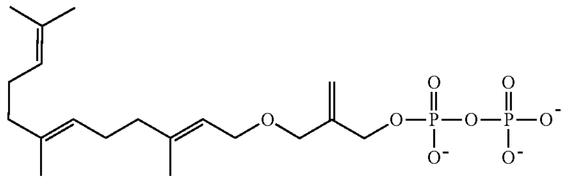 [SMILES: C=C(COC/C=C(\C)CC/C=C(\C)CCC=C(C)C)COP(=O)([O-])OP(=O)([O-])[O-]]

2-({ [(2E,6E)-3,7,11-trimethyldodeca-2,6,10-trien-1-yl]oxy}methyl)prop en-1-ol. A 25.0 mL 14/20 round bottom flask was charged with trans, trans-farnesol (0.889 g, 4.00 mmol), diethyl ether (8.00 mL) and at 0° C. was, under an argon atmosphere, added phosphorus tribromide (1.35 g, 5.00 mmol) dissolved in diethyl ether (1.00 mL). After 1 hour the reaction mixture was diluted with hexanes, washed with brine, sodium bicarbonate, and brine. The organic layer was dried over sodium sulfate, filtered, and concentrated in vacuo to yield trans, trans-farnesyl bromide. A separate 25.0 mL 14/20 round bottom flask was charged with sodium hydride (0.336 g, 10.0 mmol), tetrahydrofuran (8.00 mL) and at to 0° C., under an argon atmosphere, 2-methylidenepropane-1,3-diol (0.704 g, 8.00 mmol) was added in a dropwise fashion. Once gas evolution had ceased, the trans, trans-farnesyl bromide was added (dissolved in 3.00 mL tetrahydrofuran). The reaction was heated to 45° C. for 19 hours, quenched with saturated aqueous ammonium chloride (10.0 mL) and partitioned with ethyl acetate. The crude material was purified by silica gel chromatography (10-100% ethyl acetate in hexanes) to yield the pure product as an oil (0.900 g, 77%). $^{1}$H NMR (500 MHz, $CDCl_3$) δ 5.82 (dddd, J=12.6, 7.7, 4.6, 1.4 Hz, 1H), 5.72 (dtd, J=11.1, 6.1, 1.3 Hz, 1H), 5.35 (ddt, J=6.9, 5.5, 1.3 Hz, 1H), 5.14-5.05 (m, 2H), 4.20 (d, J=6.3 Hz, 2H), 4.06-4.03 (m, 2H), 4.01 (d, J=6.9 Hz, 2H), 2.10 (dd, J=14.5, 6.9 Hz, 3H), 2.07-2.01 (m, 5H), 1.97 (dd, J=9.1, 6.2 Hz, 3H), 1.67 (s, 6H), 1.59 (s, 6H). HRMS ESI (+) calc'd for [M+Na]=315.2300, found=315.2314.

{[2-({[(2E,6E)-3,7,11-trimethyldodeca-2,6,10-trien-1-yl]oxy}methyl)prop-2-en-1-yl phosphonato]oxy}phosphonate. A 25.0 mL 14/20 round bottom flask was charged with 2-({[(2E,6E)-3,7,11-trimethyldodeca-2,6,10-trien-1-yl]oxy}methyl)prop-2-en-1-ol (0.200 g, 0.680 mmol), ether (3.00 mL) and treated, under an argon atmosphere at 0° C., with phosphorus tribromide (0.270, 1.00 mmol) dissolved in diethyl ether (1.00 mL). The reaction mixture was stirred for 30 minutes at 0° C. The organic layer was dried over sodium sulfate, filtered, and concentrated to yield crude (6E,10E)-12-{[2-(bromomethyl)prop-2-en-1-yl]oxy}-2,6,10-trimethyldodeca-2,6,10-triene (0.182 g, 72%). The crude material was dissolved in acetonitrile (2.00 mL), tetrabutylammonium pyrophosphate (0.634 g, 0.7 mmol) was added, the reaction mixture was stirred under argon for 3 hours, at which time it was concentrated and purified over DOWEX50 resin according to the following method. DOWEX50 resin (11.8 g) was stirred in concentrated ammonium hydroxide (40.0 mL) for 20 minutes. The resin was filtered and washed four times with water (100 mL). The resin was suspended in a buffer (20.0 mL of 1:49 2-propanol: 25.0 mmolar aqueous ammonium bicarbonate) and poured into a column. The excess 1:49 2-propanol: 25.0 mmolar aqueous ammonium bicarbonate buffer was drained from the column and the crude material was applied to the column (dissolved in 3.0 mL of the 1:49 2-propanol: 25.0 mmolar aqueous ammonium bicarbonate buffer). The material was eluted with 30.0 mL of the 1:49 2-propanol: 25.0 mmolar aqueous ammonium bicarbonate buffer and lyophilized to a waxy solid (0.259 g, 90%). $^{31}$P NMR (202 MHz, Deuterium Oxide) δ −5.98 (t, J=21.2 Hz), −9.92 (d, J=20.2 Hz). HRMS ESI [M−H] calc'd=451.1656, observed=451.1666.

EXAMPLE 17

{[(2E)-4-{[(2E,6E)-3,7,11-trimethyldodeca-2,6,10-trien-1-yl]oxy}but-2-en-1-yl phosphonato]oxy}phosphonate

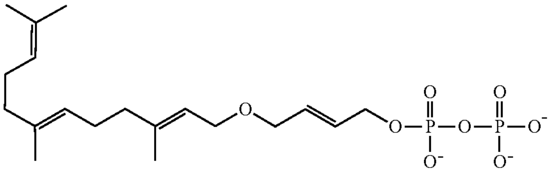 [SMILES: CC(C)=CCC/C(C)=C/CC/C(C)=C/COC/C=C/COP(=O)([O-])OP(=O)([O-])[O-]]

(2E)-4-{[(2E,6E)-3,7,11-trimethyldodeca-2,6,10-trien-1-yl]oxy}but-2-en-1-ol. A 25.0 mL 14/20 round bottom flask was charged with trans, trans-farnesol (0.222 g, 1.00 mmol), diethyl ether (5.00 mL) and at 0° C., under an argon atmosphere, phosphorus tribromide (0.475 mL, 5.00 mmol) dissolved in diethyl ether (1.00 mL) was added. The mixture was stirred for 30 minutes, diluted with hexanes, washed with brine, sodium bicarbonate, and brine. The organic layer was dried over sodium sulfate, filtered, and concentrated in vacuo to yield trans, trans-farnesyl bromide. A separate 25.0 mL 14/20 round bottom flask was charged with sodium hydride (0.134 g, 4.00 mmol), tetrahydrofuran (6.00 mL) and, under an argon atmosphere at 0° C., but-2-ene-1,4-diol (purchased commercially) was added (0.178 g, 2.00 mmol) in a dropwise fashion. Once gas evolution had ceased, the trans, trans-farnesyl bromide previously prepared was added as a solution in tetrahydrofuran (3.00 mL). The reaction was heated to 45° C. for 19 hours, quenched with saturated ammonium chloride (10.0 mL) and partitioned with ethyl acetate. The crude material was purified by silica gel chromatography (10-100% ethyl acetate in hexanes) to yield the pure product as a clear oil (0.252 g, 86%). $^{1}$H NMR (500 MHz, $CDCl_3$) δ 5.89-5.58 (m, 3H), 5.38-5.30 (m, 1H), 5.13-5.04 (m, 2H), 4.70-4.62 (m, 2H), 4.25 (dd, J=6.8, 1.4 Hz, 1H), 4.20 (d, J=6.4 Hz, 2H), 4.04 (d, J=6.2 Hz, 2H), 4.00 (d, J=7.0 Hz, 2H), 2.17-1.90 (m, 8H), 1.67 (s, 6H), 1.59 (s, 6H). HRMS ESI (+) calc'd for [M+Na]=315.2300, found=315.2300.

{[(2E)-4-{[(2E,6E)-3,7,11-trimethyldodeca-2,6,10-trien-1-yl]oxy}but-2-en-1-yl phosphonato]oxy}phosphonate. A 25.0 mL 14/20 round bottom flask was charged with (2E)-4-{[(2E,6E)-3,7,11-trimethyldodeca-2,6,10-trien-1-yl]oxy}but-2-en-1-ol (0.314 g, 1.10 mmol), diethyl ether (3.00 mL) and at 0° C., under an argon atmosphere, was added phosphorus tribromide (0.324 g, 1.20 mmol). The mixture was stirred for 20 minutes, diluted with hexanes, washed with brine, sodium bicarbonate, and brine. The organic layer was dried over sodium sulfate, filtered, and concentrated in vacuo to yield crude (6E,10E)-12-{[(2E)-4-bromobut-2-en-1-yl]oxy}-2,6,10-trimethyldodeca-2,6,10-triene (0.262 g, 62%). The crude material was dissolved in acetonitrile (2.00 mL), stirred and treated with tetrabutylammonium pyrophosphate (0.604 g, 0.660 mmol). The reaction mixture was stirred, under an argon atmosphere, for 2 hours, at which time it was concentrated in vacuo and purified over DOWEX50 resin column. The column was prepared by stirring DOWEX50 resin (8.50 g) in concentrated ammonium hydroxide (25.0 mL) for 20 minutes. The resin was filtered and washed four times with water (100 mL). The resin was suspended in a buffer (20.0 mL of 1:49 2-propanol: 25.0 mmolar aqueous ammonium bicarbonate) and poured into a column. The excess 1:49 2-propanol: 25.0 aqueous mmolar ammonium bicarbonate buffer was drained from the column and the crude material was applied to the column (dissolved in 3.00 mL of 1:49 2-propanol: 25 mmolar aqueous ammonium bicarbonate buffer). The material was eluted with 30.0 mL 1:49 2-propanol: 25.0 mmolar aqueous ammonium bicarbonate buffer and lyophilized to a waxy solid (0.196 g, 44%). $^{31}$P NMR (202 MHz, Deuterium Oxide) δ −5.70--6.25 (m), −9.92 (dd, J=66.8, 21.3 Hz). HRMS ESI [M−H] calcd=451.1656, observed=451.1662.

EXAMPLE 18

{[(2E)-3-methyl-4-{[(2E,6E)-3,7,11-trimethyldodeca-2,6,10-trien-1-yl]oxy}but-2-en-1-yl phosphonato]oxy}phosphonate

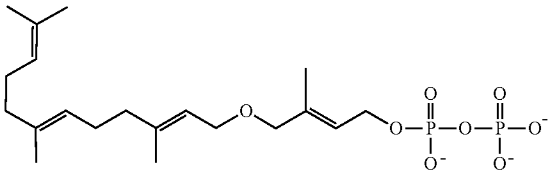 [SMILES: CC(C)=CCC/C(C)=C/CC/C(C)=C/COC/C(C)=C/COP(=O)([O-])OP(=O)([O-])[O-]]

tert-butyl({[2E)-3-methyl-4-{[(2E,6E)-3,7,11-trimethyldodeca-2,6,10-trien-1-yl]oxy}but-2-en-1-yl]oxy})diphenylsilane. A 25.0 mL 14/20 round bottom flask was charged with a stir bar, trans, trans-farnesol (0.444 g, 2.00 mmol), diethyl ether (10.0 mL) and phosphorus tribromide (0.812 g, 3.00 mmol dissolved in 1.00 mL diethyl ether) at 0° C. under an argon atmosphere. After 30 minutes the mixture was diluted with hexanes, washed with brine, sodium bicarbonate, and brine. The organic layer was dried over sodium sulfate, filtered, and concentrated in vacuo to yield trans, trans-farnesyl bromide. A separate 25.0 mL 14/20 round bottom flask was charged with sodium hydride (0.087 g, 2.60 mmol), tetrahydrofuran (5.00 mL), and under argon at 0° C. (2E)-4-[(tert-butyldiphenylsilyl)oxy]-2-methylbut-2-en-1-ol (0.749 g, 2.20 mmol, prepared according to the method described in Oberhauser, C.; Harms, V.; Seidel, K.; Schrçder, B.; Ekramzadeh, K.; Beutel, S,; Winkler, S.; Lauterbach, L.; Dickschat, J. S.; and Kirschning, A.; *Angew. Chemie. Int. Ed.,* 2018, 57, 11802.) was added. Once gas evolution ceased, the trans, trans-farnesyl bromide previously prepared was added as a solution dissolved in tetrahydrofuran (2.00 mL). The reaction was heated to 45° C. for 21 hours, quenched with saturated ammonium chloride (10.0 mL) and partitioned with ethyl acetate. The crude material was purified by silica gel chromatography (hexanes) to yield the pure product as an oil (0.390 g, 37%). $^{1}$H NMR (500

MHz, $CDCl_3$) δ 7.75-7.67 (m, 4H), 7.47-7.36 (m, 6H), 5.66 (ddt, J=7.5, 4.9, 1.4 Hz, 1H), 5.37 (dddd, J=8.1, 5.5, 2.6, 1.3 Hz, 1H), 5.16-5.07 (m, 2H), 4.28 (dq, J=6.0, 0.9 Hz, 2H), 3.93 (d, J=6.6 Hz, 2H), 3.84 (d, J=1.2 Hz, 2H), 2.17-2.03 (m, 7H), 1.99 (dd, J=9.2, 5.9 Hz, 3H), 1.69 (q, J=1.3 Hz, 3H), 1.67 (d, J=1.4 Hz, 3H), 1.61 (dd, J=2.2, 1.2 Hz, 6H), 1.50 (t, J=1.1 Hz, 3H), 1.06 (d, J=2.8 Hz, 9H).

(2E)-3-methyl-4-{[(2E,6E)-3,7,11-trimethyldodeca-2,6,10-trien-1-yl]oxy}but-2-en-1-ol. A 50.0 mL 24/40 round bottom flask was charged with tert-butyl({[(2E)-3-methyl-4-{[(2E,6E)-3,7,11-trimethyldodeca-2,6,10-trien-1-yl]oxy}but-2-en-1-yl]oxy})diphenylsilane (1.01 g, 1.90 mmol) and a stir bar. Under an argon atmosphere, tetrabutylammonium fluoride was added (15.0 mL, 15.0 mmol). The reaction mixture was heated to 45° C. for 16 hours, diluted with ethyl acetate, washed with 1.00 N HCl (20.0 mL), brine, and concentrated to an oil. The crude material was purified by silica gel chromatography (0-100% ethyl acetate in hexanes) to yield the product as an oil (0.263 g, 45%,). $^{1}H$ NMR (500 MHz, $CDCl_3$) δ 5.67 (tq, J=6.8, 1.3 Hz, 1H), 5.37 (tq, J=6.8, 1.3 Hz, 1H), 5.11 (ddddd, J=11.4, 7.0, 5.6, 2.8, 1.4 Hz, 2H), 4.22 (d, J=6.7 Hz, 2H), 3.97 (d, J=6.8 Hz, 2H), 3.87 (d, J=1.3 Hz, 2H), 2.16-2.03 (m, 7H), 1.98 (dd, J=9.1, 6.1 Hz, 2H), 1.72 (d, J=1.4 Hz, 3H), 1.69 (q, J=1.3 Hz, 3H), 1.67 (d, J=1.3 Hz, 3H), 1.61 (s, 6H). HRMS ESI (+) calc'd for [M+Na]=329.2457, found=329.2475.

{[(2E)-3-methyl-4-{[(2E,6E)-3,7,11-trimethyldodeca-2,6,10-trien yl]oxy}but-2-en-1-yl phosphonato]oxy}phosphonate. A 25.0 mL 14/20 round bottom flask was charged with (2E)-3-methyl-4-{[(2E,6E)-3,7,11-trimethyldodeca-2,6,10-trien-1-yl]oxy}but-2-en-1-ol (0.263 g, 0.850 mmol), diethyl ether (4.00 mL) and at 0° C., under an argon atmosphere, phosphorus tribromide (0.270 g, 1.00 mmol) was added. The mixture stirred for 30 minutes, diluted with hexanes, washed with brine, sodium bicarbonate, and brine. The organic layer was dried over sodium sulfate, filtered and concentrated in vacuo to yield the crude (6E,10E)-12-{[(2E)-4-bromo-2-methylbut-2-en-1-yl]oxy}-2,6,10-trimethyldodeca-2,6,10-triene (0.0720 g). The crude material was then dissolved in acetonitrile (1.00 mL), stirred and tetrabutylammonium pyrophosphate (0.497 g, 0.540 mmol) added and stirred under an argon atmosphere for 3 hours. The mixture was then concentrated in vacuo and purified over DOWEX50 resin column. The resin (6.80 g) was prepared by stirring in concentrated ammonium hydroxide (25.0 mL) for 20 minutes, then filtered and washed four times with water (100 mL). The resin was suspended in a buffer (20.0 mL of 1:49 2-propanol: 25.0 mmolar aqueous ammonium bicarbonate) and poured into a column. The excess 1:49 2-propanol: 25.0 mmolar aqueous ammonium bicarbonate buffer was drained from the column and the crude material was applied to the column (dissolved in 3.00 mL of 1:49 2-propanol: 25.0 mmolar aqueous ammonium bicarbonate buffer). The material was eluted with 30.0 mL 1:49 2-propanol: 25.0 mmolar aqueous ammonium bicarbonate buffer and lyophilized to a waxy solid (0.156 g, 40%). $^{31}P$ NMR (202 MHz, Deuterium Oxide) δ −6.01 (d, J=21.2 Hz), −9.88 (t, J=25.2 Hz). HRMS ESI [M−H] calcd=465.1813, observed=465.1814.

EXAMPLE 19

{[(2E,6E,10E)-3,7,11-trimethyl-12-[(3-methylbut-2-en-1-yl)oxy]dodeca-2,6,10-trien-1-yl phosphonato]oxy}phosphonate

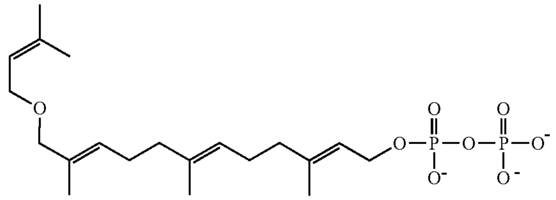 [SMILES: CC(C)=CCOC/C(C)=C/CC/C(C)=C/CC/C(C)=C/COP(=O)([O-])OP(=O)([O-])[O-]]

(2E,6E,10E)-12-[(tert-butyldiphenylsilyl)oxy]-2,6,10-trimethyldodeca-2,6,10-trien-1-ol. A 100 mL 24/40 round bottom flask was charged with trans,trans-farnesol (4.50 g, 20.2 mmol), imidazole (2.99 g, 44.4 mmol) and dimethylformamide (25.0 mL). The reaction mixture was stirred, under an argon atmosphere, and tert-butyldiphenylsilyl chloride added (5.70 mL, 22.0 mmol) dropwise. The mixture was stirred for 19 hours at room temperature, then partitioned between 1.00 N HCl (30.0 mL) and ethyl acetate. The organic layer was washed with sodium bicarbonate, twice with brine, dried over sodium sulfate, filtered, and concentrated in vacuo to provide crude tert-butyldiphenyl {[(2E,6E)-3,7,11-trimethyldodeca-2,6,10-trien-1-yl]oxy}silane (8.71 g, 95%).

In a separate 100 mL 24/40 round bottom flask was added selenium(IV) dioxide (0.103 g, 0.94 mmol), salicylic acid (0.259 g, 1.88 mmol) and dichloromethane (40.0 mL). The mixture was stirred at room temperature and tent-butylhydroperoxide added (9.00 mL, 65.8 mmol, 70% solution in water), followed by tert-butyldiphenyl {[(2E,6E)-3,7,11-trimethyldodeca-2,6,10-trien-1-yl]oxy}silane (8.71 g, 18.8 mmol, dissolved in 5.00 mL dichloromethane). The mixture was stirred at room temperature for 50 hours, washed with saturated sodium thiosulfate and concentrated in vacuo. The material was then dissolved in ethanol, cooled to 0° C., and treated with sodium borohydride (0.720 g, 19.0 mmol). After gas evolution ceased the reaction was warmed to room temperature and stirred for 30 minutes. The reaction was quenched with 1.00 N HCl (10.0 mL), partitioned between ethyl acetate and sodium bicarbonate, washed with brine, dried over sodium sulfate, filtered, and concentrated in vacuo to yield the crude product as a red oil. The crude material was purified by silica gel chromatography (1:9 ethyl acetate: hexanes) to yield the product as a clear oil (1.2 g, 13% yield). $^{1}H$ NMR (500 MHz,$CDCl_3$) δ 7.74-7.66 (m, 4H), 7.46-7.34 (m, 6H), 5.40 (dddt, J=6.3, 5.0, 2.6, 1.3 Hz, 2H), 5.14 (tq, J=6.9, 1.4 Hz, 1H), 4.29-4.19 (m, 2H), 4.02 (d, J=19.9 Hz, 2H), 2.20-1.95 (m, 8H), 1.69 (dd, J=14.6, 1.4 Hz, 3H), 1.62 (s, 3H), 1.45 (d, J=1.2 Hz, 3H), 1.05 (s, 9H).

(2E,6E,10E)-3,7,11-trimethyl-12-[(3-methylbut-2-en-1-yl)oxy]dodeca-2,6,10-trien-1-ol. A 25.0 mL 14/20 round bottom flask was charged with (2E,6E,10E)-12-[(tert-butyldiphenylsilyl) oxy]-2,6,10-trimethyldodeca-2,6,10-trien-1-ol (0.478 g, 1.00 mmol) and tetrahydrofuran (5.00 mL). The mixture was cooled to 0° C. and sodium hydride added (0.170 g, 7.00 mmol) under an argon atmosphere, followed by the addition of prenyl bromide (1.00 g, 6.20 mmol). The mixture was stirred at 40° C. for 22 hours and quenched with saturated ammonium chloride, partitioned into ethyl acetate and the organic layer washed with brine, dried over sodium sulfate, filtered, and concentrated in vacuo. The crude material was purified by silica gel chromatography (100% hexanes) to yield the product as an oil. This material was dissolved in tetrabutylammonium fluoride (10.0 mL, 10.0 mmol) and heated to 40° C. for 19 hours under argon. The crude material was purified by silica gel chromatography (1:9 ethyl acetate: hexanes) to yield the product (0.171 g, 58%). $^1$H NMR (500 MHz, $CDCl_3$) δ 5.43-5.31 (m, 3H), 5.10 (tq, J=6.9, 1.4 Hz, 1H), 4.12 (dd, J=13.9, 7.1 Hz, 2H), 3.90-3.84 (m, 2H), 3.82 (d, J=1.1 Hz, 2H), 2.17-1.97 (m, 8H), 1.73 (d, J=1.4 Hz, 3H), 1.66 (d, J=1.4 Hz, 3H), 1.65 (d, J=1.4 Hz, 3H), 1.64 (d, J=1.4 Hz, 3H), 1.59 (d, J=1.4 Hz, 3H).

{[(2E,6E,10E)-3,7,11-trimethyl-12-[(3-methylbut-2-en-1-yl)oxy]dodeca-2,6,10-trien-1-yl phosphonato] oxy}phosphonate. A 25.0 mL 14/20 round bottom flask was charged with (2E,6E,10E)-3,7,11-trimethyl-12-[(3-methylbut-2-en-1-yl)oxy]dodeca-2,6,10-trien-1-ol (0.171 g, 0.580 mmol), diethyl ether (4.00 mL) and at 0° C. under an argon atmosphere, treated phosphorus tribromide (0.094 mL, 1.00 mmol). The reaction mixture was stirred for 30 minutes, diluted with hexanes, the organic layer was then washed with brine, sodium bicarbonate, and brine. The organic layer was dried over sodium sulfate, filtered, and concentrated in vacuo to yield crude (2E,6E,10E)-12-bromo-2,6,10-trimethyl-1-[(3-methylbut-2-en-1-yl)oxy]dodeca-2,6,10-triene (0.122 g). The crude material was then dissolved in acetonitrile (1.00 mL), stirred and treated with tetrabutylammonium pyrophosphate (0.500 g, 0.540 mmol). The reaction mixture was stirred, under an argon atmosphere, for 2 hours, then concentrated in vacuo and purified over DOWEX50 resin (6.89 g) column prepared by stirring in concentrated ammonium hydroxide (30.0 mL) for 20 minutes, then filtered and washed four times with water (100 mL). The resin was suspended in a buffer (20.0 mL of 1:49 2-propanol: 25 mmolar aqueous ammonium bicarbonate) and poured into a column. The excess 1:49 2-propanol: 25 mmolar aqueous ammonium bicarbonate buffer was drained from the column and the crude material was applied to the column (dissolved in 3.00 mL of the 1:49 2-propanol: 25 mmolar aqueous ammonium bicarbonate buffer). The material was eluted with 30.0 mL of the 1:49 2-propanol: 25 mmolar aqueous ammonium bicarbonate buffer and lyophilized to a waxy solid (0.138 g, 60%). $^{31}$P NMR (202 MHz, Deuterium Oxide) δ −6.03 (d, J=21.2 Hz), -9.99 (d, J=20.6 Hz). HRMS ESI [M−H] calcd=465.1813, observed=465.1810.

EXAMPLE 20

{[2-({[(5E)-6,10-dimethylundeca-5,9-dien-2-yl] oxy}methyl)prop-2-en-1-yl phosphonato] oxy}phosphonate

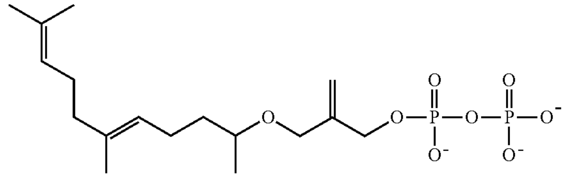 [SMILES: C=C(COC(C)CC/C=C(\C)CCC=C(C)C)COP(=O)([O-])OP(=O)([O-])[O-]]

Tert-butyl({[2-({[(5E)-6,10-dimethylundeca-5,9-dien-2-yl]oxy}methyl)prop-2-en-1-yl]oxy})diphenylsilane. A 100 mL 24/40 round bottom flask was charged with geranyl acetone (1.94 g, 10.0 mmol) and ethanol (30.0 mL). The reaction mixture was cooled to 0° C. and sodium borohydride added (0.529 g, 14.0 mmol) and stirred for 1.0 hour, quenched with 1.00 N HCl (10.0 mL) and partitioned with ethyl acetate. The organic layer was filtered through a plug of silica gel (eluted with 100% ethyl acetate) and concentrated to yield crude (5E)-6,10-dimethylundeca-5,9-dien-2-ol (1.80 g, 91%), which was used without further purification.

Using the method of Vita and coworkers (Vita, M. V.; Caramenti. P.; Waser, J. *Org. Lett.,* 2015, 17, 5832.), a separate 250 mL 24/40 round bottom flask was charged prop-2-ene-1,3-diol (8.40 mL, 102 mmol) and tetrahydrofuran (50.0 mL) under an argon atmosphere. The flask was cooled to 0° C. and sodium hydride added (3.69 g, 110 mmol), followed by tent-butyldiphenylsilyl chloride (25.9 mL, 100 mmol). The reaction was stirred for 20 hours, partitioned into ethyl acetate, which was washed with a saturated ammonium chloride solution, concentrated in vacuo and purified by silica gel chromatography (1:9 ethyl acetate: hexanes) to yield 2-{[(tert-butyldiphenylsilyl)oxy] methyl}prop-2-en-1-ol (8.00 g, 23%). $^1$H NMR (500 MHz, Chloroform-d) δ 7.71-7.68 (m, 4H), 7.48-7.38 (m, 6H), 5.72 (dtt, J=11.5, 5.7, 1.3 Hz, 1H), 5.65 (dtt, J=11.2, 6.4, 1.4 Hz, 1H), 4.31-4.25 (m, 2H), 4.02 (d, J=6.2 Hz, 2H), 1.06 (s, 9H).

2-{[(tert-butyldiphenylsilyl)oxy]methyl}prop-2-en-1-ol (1.31 g, 4.00 mmol, Heidelbrecht, R. W. Jr.; Gulledge, B.; Martin, S., *Org. Lett.,* 2010, 12, 2492.) was dissolved in dichloromethane (15.0 mL), cooled to 0° C. and triphenylphosphine added (1.25 g, 4.80 mmol), followed by n-bromosuccinimide (0.782 g, 4.80 mmol). The mixture was stirred under an argon atmosphere for 2 hours at 0° C. and treated with hexanes (200 mL). The solid was filtered and the filtrate concentrated to yield {[2-(bromomethyl)prop-2-en-1-yl]oxy}(tert-butyl)diphenylsilane (1.10 g, 71%). The product was used without further purification. 1H NMR (500 MHz, Chloroform-d) δ 7.71-7.67 (m, 4H), 7.46-7.39 (m, 6H), 5.78-5.72 (m, 2H), 4.34-4.32 (m, 2H), 3.87-3.84 (m, 2H), 1.06 (s, 9H).

A 14/20 25.0 mL round bottom flask was charged with crude {[2-(bromomethyl)prop-2-en-1-yl]oxy}(tert-butyl)diphenylsilane (0.960 g, 2.30 mmol), crude (5E)-6,10-dimethylundeca-5,9-dien-2-ol (0.976 g, 5.00 mmol), tetrahydrofuran (5.00 mL), cooled to 0° C., and treated with sodium hydride (0.235 g, 7.00 mmol). After gas evolution was complete, the mixture was heated to 45° C. for 19 hours under an argon atmosphere. The reaction was partitioned between ethyl acetate and ammonium chloride, washed with brine, dried over sodium sulfate, filtered, and concentrated in vacuo. The crude material was purified by silica gel chromatography (1:9 ethyl acetate: hexanes) to yield an oil (0.500 g, 1.00 mmol). $^1$H NMR (500 MHz, Chloroform-d) δ 7.72-7.67 (m, 4H), 7.48-7.36 (m, 6H), 5.79-5.71 (m, 2H), 5.64-5.55 (m, 1H), 5.10 (ttq, J=7.2, 4.4, 1.3 Hz, 1H), 4.33 (dd, J=3.3, 2.2 Hz, 1H), 4.29-4.25 (m, 1H), 3.97-3.76 (m, 4H), 2.10-1.95 (m, 4H), 1.69 (t, J=1.3 Hz, 3H), 1.61 (t, J=1.7 Hz, 3H), 1.59-1.54 (m, 3H), 1.09-1.03 (m, 9H), 1.00 (s, 3H).

A 25.0 mL 14/20 round bottom flask was charged with tert-butyl({[2-({[(5E)-6,10-dimethylundeca-5,9-dien-2-yl] oxy}methyl)prop-2-en-1-yl]oxy})diphenylsilane (0.500 g, 1.00 mmol) and, under an argon atmosphere, tetrabutylammonium fluoride (5.00 mL, 5.00 mmol) added. The reaction mixture was stirred at 45° C. for 15 hours then partitioned between ethyl acetate and 1.00 N HCl (15.0 mL). The organic layer was washed with brine and purified by silica gel chromatography (1:9 ethyl acetate: hexanes) to yield 2-({[(5E)-6,10-dimethylundeca-5,9-dien-2-yl]oxy}methyl) prop-2-en-1-ol (0.100 g, 38%). $^1$H NMR (500 MHz, Chloroform-d) δ 5.83-5.75 (m, 1H), 5.75-5.66 (m, 1H), 5.09 (dddddd, J=12.7, 7.0, 5.7, 4.3, 2.8, 1.4 Hz, 2H), 4.18 (dt, J=6.4, 1.2 Hz, 2H), 4.14-4.06 (m, 1H), 3.97 (dddd, J=12.4, 6.2, 2.3, 1.4 Hz, 1H), 3.44 (hept, J=6.4 Hz, 1H), 2.09-1.94 (m, 7H), 1.68 (dq, J=4.2, 1.3 Hz, 3H), 1.64-1.50 (m, 6H), 1.47-1.36 (m, 1H), 1.15 (dd, J=6.2, 2.3 Hz, 3H).

{[2-({[(5E)-6,10-dimethylundeca-5,9-dien-2-yl]oxy}methyl)prop-2-en-1-yl phosphonato]oxy}phosphonate. A 25.0 mL 14/20 round bottom flask was charged with 2-({[(5E)-6,10-dimethylundeca-5,9-dien-2-yl]oxy}methyl)prop-2-en-1-ol (0.100 g, 0.380 mmol), diethyl ether (4.00 mL), cooled to 0° C., and phosphorus tribromide was added (0.270 g, 1.00 mmol). He reaction mixture was stirred for 30 minutes at 0° C., diluted with hexanes, washed with brine, sodium bicarbonate, and brine. The organic layer was dried over sodium sulfate, filtered, and concentrated in vacuo to yield the crude (6E)-10-{[2-(bromomethyl)prop-2-en-1-yl]oxy}-2,6-dimethylundeca-2,6-diene (0.0400 g, 32%). The crude material was dissolved in acetonitrile (2.00 mL), stirred, and tetrabutylammonium pyrophosphate (0.604 g, 0.670 mmol) was added. The reaction mixture was stirred under an argon atmosphere for 2 hours, at which time it was concentrated in vacuo and purified over DOWEX50 resin column. The column was prepared by stirring DOWEX50 resin (7.00 g) in concentrated ammonium hydroxide (30.0 mL) for 20 minutes. The resin was filtered and washed four times with water (100 mL). The resin was suspended in a buffer (20.0 mL of 1:49 2-propanol: 25.0 mmolar aqueous ammonium bicarbonate) and poured into a column. The excess 1:49 2-propanol: 25.0 mmolar aqueous ammonium bicarbonate buffer was drained from the column and the crude material was applied to the column (dissolved in 3.00 mL of the 1:49 2-propanol: 25.0 mmolar aqueous ammonium bicarbonate buffer). The material was eluted with 30.0 mL of the 1:49 2-propanol: 25.0 mmolar aqueous ammonium bicarbonate buffer and lyophilized to a waxy solid (0.128 g, 82%). $^{31}$P NMR (202 MHz, Deuterium Oxide) δ −6.03 (d, J=22.8 Hz), −10.05 (d, J=22.0 Hz). HRMS ESI [M−H] calcd=425.1500, observed=425.1502.

EXAMPLE 21

{[(2E,6E)-8-{[(2Z)-3,7-dimethylocta-2,6-dien-lyl]oxy}-3,7-dimethylocta-2,6-dien-1-yl phosphonato]oxy}phosphonate

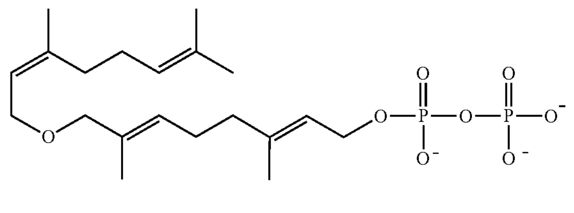 [SMILES: CC(C)=CCC/C(C)=C\COC/C(C)=C/CC/C(C)=C/COP(=O)([O-])OP(=O)([O-])[O-]]

Tert-butyl({[(2E)-3,7-dimethylocta-2,6-dien-1-yl]oxy})diphenylsilane. A 250 mL 24/40 round bottom flask was charged with trans,trans-geraniol (4.62 g, 30.0 mmol), imidazole (2.72 g, 40.0 mmol) and dimethylformamide (90.0 mL). The reaction mixture was stirred under an argon atmosphere and tert-butyldiphenylsilyl chloride added (8.55 g, 31.0 mmol) in a dropwise fashion. The reaction was stirred for 19 hours at room temperature, portioned between 1.00 N HCl (30.0 mL) and ethyl acetate. The organic layer was washed with a saturated sodium bicarbonate solution, twice with brine, dried over sodium sulfate, filtered, and concentrated in vacuo to a clear oil (8.41 g, 70%). 1H NMR (500 MHz, Chloroform-d) δ 7.74-7.69 (m, 4H), 7.47-7.35 (m, 6H), 5.40 (dddt, J=7.6, 6.2, 3.3, 1.4 Hz, 2H), 4.23 (dq, J=6.3, 0.9 Hz, 2H), 4.00 (d, J=1.3 Hz, 2H), 2.21-2.10 (m, 2H), 2.03 (dd, J=9.1, 6.3 Hz, 2H), 1.68 (d, J=1.3 Hz, 3H), 1.46 (d, J=1.3 Hz, 4H), 1.05 (s, 9H).

(2E,6E)-8-[(tert-butyldiphenylsilyl)oxy]-2,6-dimethylocta-2,6-dien-1-ol. In a 100 mL 24/40 round bottom flask was added selenium(IV) dioxide (0.118 g, 1.07 mmol), salicylic acid (0.295 g, 2.14 mmol) and dichloromethane (40.0 mL). The reaction mixture was stirred at room temperature and tent-butylhydroperoxide was added (10.0 mL, 73.1 mmol, 70% solution in water), followed by tert-butyl({[(2E)-3,7-dimethylocta-2,6-dien-1-yl]oxy})diphenylsilane (8.71 g, 18.8 mmol dissolved in 5.00 mL dichloromethane). The reaction mixture was stirred at room temperature for 75 hours, washed with a saturated sodium thiosulfate solution and concentrated in vacuo. This material was dissolved in ethanol, cooled to 0° C., and treated with sodium borohydride (0.832 g, 22.0 mmol). After gas evolution ceased, the reaction was warmed to room temperature and stirred for 1 hour, quenched with 1.00 N hydrochloric acid (20.0 mL), partitioned between ethyl acetate and sodium bicarbonate, the organic layer washed with brine, dried over sodium sulfate, filtered, and concentrated in vacuo to yield the crude product as an oil. The crude material was purified by silica gel chromatography (0-100% ethyl acetate in hexanes) to yield the product as an oil (1.20 g, 13% yield). $^1$H NMR (500 MHz, $CDCl_3$) δ 7.74-7.66 (m, 4H), 7.47-7.34 (m, 6H), 5.40 (dddt, J=7.6, 6.3, 3.3, 1.4 Hz, 2H), 4.23 (dq, J=6.3, 0.9 Hz, 2H), 4.00 (d, J=1.1 Hz, 2H), 2.19-2.09 (m, 2H), 2.03 (dd, J=9.1, 6.3 Hz, 2H), 1.68 (d, J=1.4 Hz, 3H), 1.46 (d, J=1.3 Hz, 3H), 1.05 (s, 9H). HRMS ESI (+) calc'd for [M+Na]=329.2457, found=329.2448.

Tert-butyl({[(2E,6E)-8-{[(2E)-3,7-dimethylocta-2,6-dien-1-yl]oxy}-3,7-dimethylocta-2,6-dien-1-yl]oxy})diphenylsilane. A 25.0 mL 14/20 round bottom flask was charged with (2E,6E)-8-[(tert-butyldiphenylsilyl)oxy]-2,6-dimethylocta-2,6-dien-1-ol (0.752 g, 2.0 mmol) and tetrahydrofuran (5.00 mL). The reaction mixture was cooled to 0° C. and sodium hydride was added (0.134 g, 4.00 mmol). Under an argon atmosphere, geranyl bromide (0.650 g, 3.00 mmol, Brundel, B., J., J., M.; Steen, H.; Heeres, A.; Seerden, J. P. G., WO2013157926) was added and the mixture stirred at 40° C. for 20 hours. The reaction was quenched with ammonium chloride, partitioned with ethyl acetate, washed with brine, dried over sodium sulfate, filtered and the solvent removed in vacuo. The crude material was purified by silica gel chromatography (100% hexanes) to yield the product as an oil (0.470 g, 43%). $^1$H NMR (500 MHz, $CDCl_3$) δ 7.73-7.67 (m, 4H), 7.46-7.34 (m, 6H), 5.44-5.33 (m, 3H), 5.15-5.02 (m, 1H), 4.23 (d, J=6.0 Hz, 2H), 3.95-3.90 (m, 2H), 3.87-3.80 (m, 2H), 2.16-1.99 (m, 8H), 1.72-1.65 (m, 6H), 1.59 (s, 6H), 1.45 (d, J=1.2 Hz, 3H), 1.05 (s, 9H).

(2E,6E)-8-{[(2E)-3,7-dimethylocta-2,6-dien-1-yl]oxy}-3,7-dimethylocta-2,6-dien-1-ol. Tert-butyl({[(2E,6E)-8-{[(2E)-3,7-dimethylocta-2,6-dien-1-yl]oxy}-3,7-dimethyl-octa-2,6-dien-1-yl]oxy})diphenylsilane was dissolved in tetrahydrofuran (2.00 mL), treated with a 1.00 M tetrabutylammonium fluoride (10.0 mL, 10.0 mmol) solution (in tetrahydrofuran) and heated to 40° C. for 19 hours under an argon atmosphere. The mixture was treated with water then extracted with ethyl acetate. The organic layers were combined, dried with sodium sulfate, filtered, and concentrated in vacuo. The crude material was purified by silica gel chromatography (1:9 ethyl acetate: hexanes) to yield the product (0.100 g, 42% yield). $^1$H NMR (500 MHz, $CDCl_3$)

δ 5.46-5.30 (m, 3H), 5.10 (ddp, J=7.1, 5.8, 1.5 Hz, 1H), 4.15 (d, J=6.9 Hz, 2H), 3.93 (d, J=6.8 Hz, 2H), 3.83 (d, J=1.2 Hz, 2H), 2.24-1.97 (m, 8H), 1.69 (d, J=1.3 Hz, 6H), 1.66 (d, J=1.3 Hz, 5H), 1.62-1.59 (m, 3H). {[(2E,6E)-8-{[(2Z)-3,7-dimethylocta-2,6-dien-1yl]oxy}-3,7-dimethylocta-2,6-dien-1-yl phosphonato]oxy}phosphonate. The alcohol (2E,6E)-8-{[(2Z)-3,7-dimethylocta-2,6-dien-1-yl]oxy}-3,7-dimethylocta-2,6-dien-1-ol (0.100 g, 0.340 mmol) was dissolved in diethyl ether (2.00 mL) and at 0° C., under an argon atmosphere, was added phosphorus tribromide (0.270 mL, 1.00 mmol). The reaction mixture was stirred for 30 minutes, diluted with hexanes, washed with brine, sodium bicarbonate, and brine. The organic layer was dried over sodium sulfate, filtered, and concentrated in vacuo to yield (2E,6E)-8-bromo-1-{[(2Z)-3,7-dimethylocta-2,6-dien-1-yl]oxy}-2,6-dimethylocta-2,6-diene (0.121 g, 96%). The crude material was dissolved in acetonitrile (2.00 mL) and tetrabutylammonium pyrophosphate (0.255 g, 0.280 mmol) added. The reaction mixture was stirred under an argon atmosphere for 2 hours, at which time it was concentrated in vacuo and purified over a DOWEX50 resin column. The column was prepared by treating DOWEX50 resin (7.20 g) with concentrated ammonium hydroxide (30.0 mL) for 20 minutes. The resin was filtered and washed four times with water (100 mL). The resin was suspended in a buffer (20.0 mL of 1:49 2-propanol: 25.0 mmolar aqueous ammonium bicarbonate) and poured into a column. The excess 1:49 2-propanol: 25.0 mmolar aqueous ammonium bicarbonate buffer was drained from the column and the crude material was applied to the column (dissolved in 3.00 mL of the 1:49 2-propanol: 25.0 mmolar aqueous ammonium bicarbonate buffer). The material was eluted with 30.0 mL of the 1:49 2-propanol: 25.0 mmolar aqueous ammonium bicarbonate buffer and lyophilized to a waxy solid (0.066 g, 60% yield by mass, 95% yield by $^{31}$P NMR integration). $^{31}$P NMR (202 MHz, Deuterium Oxide) δ −6.43 (d, J=97.1 Hz), −9.83-−11.41 (m). HRMS ESI [M−H] calcd=465.1813, observed=465.1814.

EXAMPLE 22

{[(2E,6E,10E)-13-(3,3-dimethyloxiran-2-yl)-3,7,11-trimethyltrideca-2,6,10-trien-1-yl phosphonato]oxy}phosphonate

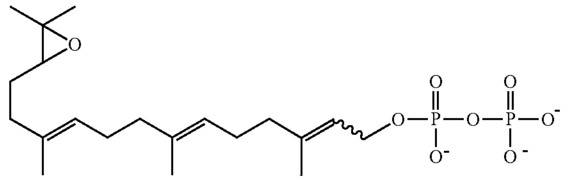 [SMILES: CC(=CCOP(=O)([O-])OP(=O)([O-])[O-])CC/C=C(\C)CC/C=C(\C)CCC1OC1(C)C]

(2E,6E,10E)-13-(3,3-dimethyloxiran-2-yl)-3,7,11-trimethyltrideca-2,6,10-trien-1-ol and (2Z,6E,10E)-13-(3,3-dimethyloxiran-2-yl)-3,7,11-trimethyltrideca-2,6,10-trien-1-ol. A 50.0 mL 24/40 round bottom flask was charged with geranyl geraniol (1.00 g, 3.50 mmol, Look, G. C., WO2015006614) as a mixture of (2E,6E,10E)-3,7,11,15-tetramethylhexadeca-2,6,10,14-tetraen-1-ol and (2Z,6E,10E)-3,7,11,15-tetramethylhexadeca-2,6,10,14-tetraen-1-ol), dichloromethane (10.0 mL), triethylamine (0.696 mL, 5.00 mmol), stirred and cooled to 0° C. To the mixture was added acetic anhydride (0.378 mL, 4.00 mmol) and dimethylaminopyridine (0.0240 g, 0.200 mmol). The reaction was stirred for 1 hour at 0° C. and quenched with brine, dried over sodium sulfate, and concentrated to yield the product as a mixture of (2E,6E,10E)-13-(3,3-dimethyloxiran-2-yl)-3,7,11-trimethyltrideca-2,6,10-trien-1-yl acetate and (2Z,6E,10E)-13-(3,3-dimethyloxiran-2-yl)-3,7,11-trimethyltrideca-2,6,10-trien-1-yl acetate (0.980 g, 84%). The oil was dissolved in a mixture of tetrahydrofuran (25.0 mL) and water (10.0 mL), cooled to 0° C., and n-bromosuccinimide (0.623 g, 3.50 mmol). The reaction was stirred at 0° C. for 2 hours, concentrated and extracted with hexanes. The organic layer was washed with brine, dried over sodium sulfate, filtered, and concentrated in vacuo to yield the intermediate as an oil (1.21 g). This material was dissolved in methanol (15.0 mL), potassium carbonate was added (0.720 g, 5.20 mmol) and the mixture was stirred for 17 hours. The reaction mixture was partitioned with ethyl acetate, filtered through a plug of silica (100% ethyl acetate) and concentrated to yield the product 3-[(3E,7E,11E)-13-bromo-3,7,11-trimethyltrideca-3,7,11-trien-1-yl]-2,2-dimethyloxirane and 3-[(3E,7E,11Z)-13-bromo-3,7,11-trimethyltrideca-3,7,11-trien-1-yl]-2,2-dimethyloxirane (0.823 g, 96%). 1H NMR (500 MHz, Chloroform-d) δ 5.39-5.31 (m, 1H), 5.10 (dddqd, J=8.4, 6.9, 4.1, 2.7, 1.9, 1.4 Hz, 3H), 4.62-4.54 (m, 2H), 2.16- 2.01 (m, 14H), 1.97 (dd, J=9.1, 6.3 Hz, 2H), 1.74-1.66 (m, 8H), 1.63-1.57 (m, 6H). HRMS ESI (+) calc'd for [M+Na]=329.2457, found=329.2455.

{[(2E,6E,10E)-13-(3,3-dimethyloxiran-2-yl)-3,7,11-trimethyltrideca-2,6,10-trien-1-yl phosphonato]oxy}phosphonate. A 25.0 mL 14/20 round bottom flask was charged with dichloromethane (10.0 mL) and n-chlorosuccinimide (0.267 g, 2.00 mmol). The mixture was stirred under argon, cooled to −30° C., and dimethyl sulfide was added (0.146 mL, 2.00 mmol). The reaction was warmed to 0° C. for 5 minutes, again cooled to −30° C. and (2E,6E,10E)-13-(3,3-dimethyloxiran-2-yl)-3,7,11-trimethyltrideca-2,6,10-trien-1-ol added (0.306 g, 1.00 mmol, dissolved in 1.0 mL dichloromethane). The mixture was stirred for 5 minutes at −30° C. then warmed to 0° C. for 2 hours. The mixture was then washed with brine and concentrated to dryness to yield the crude 3-[(3E,7E,11E)-13-chloro-3,7,11-trimethyltrideca-3,7,11-trien-1-yl]-2,2-dimethyloxirane (0.301 g, 0.920 mmol). This material was dissolved in acetonitrile (2.00 mL), stirred (argon atmosphere), then treated with tetrabutylammonium pyrophosphate (0.525 g, 0.570 mmol). The reaction mixture was stirred for 2 hours, then concentrated in vacuo and purified on a DOWEX50 resin column. The column was prepared by treating the resin (7.20 g) with concentrated ammonium hydroxide (30 mL) for 20 minutes then filtered and washed four times with water (100 mL). The resin was suspended in a buffer (20 mL of 1:49 2-propanol: 25.0 mmolar ammonium bicarbonate) and poured into a column. The excess buffer was drained from the column and the crude product was applied to the column (dissolved in 3.00 mL of the same buffer). The material was eluted with 30 mL buffer and lyophilized to a waxy solid (0.083 g, 18%). $^{31}$P NMR (202 MHz, Deuterium Oxide) δ −6.24 (d, J=21.8 Hz), −10.09 (d, J=22.4 Hz). HRMS ESI [M−H] calc'd=465.1813, observed=465.1816.

EXAMPLE 23

{[(3-{[(2E,6E)-3,6,11-trimethyldodeca-2,6,10-trien-1-yl]oxy}phenyl)methyl phosphonato]oxy}phosphonate

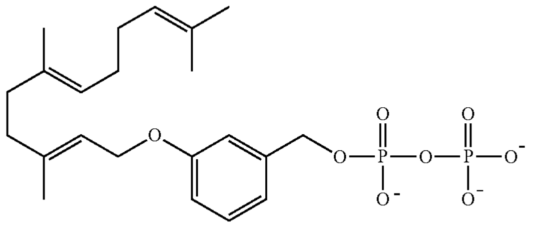 [SMILES: CC(C)=CCC/C=C(\C)CC/C(C)=C/COc1cccc(COP(=O)([O-])OP(=O)([O-])[O-])c1]

3-{[(2E,6E)-3,7,11-trimethyldodeca-2,6,10-trien-1-yl]oxy}benzaldehyde. A 25.0 mL 14/20 round bottom flask was charged with trans,trans-farnesol (0.889 g, 4.00 mmol), diethyl ether, (10.0 mL), and at 0° C. under argon was added phosphorus tribromide (1.35 g, 5.00 mmol). The reaction mixture was stirred for 30 minutes, diluted with hexanes, washed with brine, a saturated sodium bicarbonate solution, and brine. The organic layer was dried over sodium sulfate, filtered and concentrated in vacuo to yield crude trans, trans-farnesyl bromide (0.937 g, 83%). This material was diluted with tetrahydrofuran (10.0 mL) and 3-hydroxybenzaldehyde (0.463 g, 3.80 mmol) was added. The reaction mixture was cooled to 0° C. and sodium hydride added (0.151 g, 4.50 mmol). Once gas evolution ceased, the reaction mixture was heated to 45° C. for 23 hours under an argon atmosphere. The mixture was then partitioned between ethyl acetate and saturated ammonium chloride. The organic layer washed with brine, dried over sodium sulfate, filtered and concentrated in vacuo. The crude material was purified by silica gel chromatography (1:9:0.1 ethyl acetate: hexanes: triethylamine) to yield the product as an oil (0.490 g, 46%). $^1$H NMR (500 MHz, $CDCl_3$) δ 9.97 (s, 1H), 7.49-7.37 (m, 3H), 7.19 (dt, J=6.7, 2.5 Hz, 1H), 5.50 (tq, J=6.6, 1.3 Hz, 1H), 5.09 (ddddt, J=11.3, 5.7, 4.3, 2.9, 1.4 Hz, 2H), 4.60 (dd, J=6.6, 1.0 Hz, 2H), 2.18-2.02 (m, 6H), 2.01-1.94 (m, 2H), 1.76 (d, J=1.3 Hz, 3H), 1.68 (q, J=1.3 Hz, 3H), 1.60 (dd, J=2.3, 1.3 Hz, 6H).

(3-{[(2E,6E)-3,7,11-trimethyldodeca-2,6,10-trien-1-yl]oxy}phenyl)methanol. A 50.0 mL 14/20 round bottom flask was charged with 3-{[(2E,6E)-3,7,11-trimethyldodeca-2,6,10-trien-1-yl]oxy}benzaldehyde (0.470 g 1.50 mmol), ethanol (6.00 mL), cooled to 0° C., and sodium borohydride (0.0750 g, 2.00 mmol). After 10 minutes, the reaction mixture was partitioned between ethyl acetate and ammonium chloride, the organic layer washed with brine, dried over sodium sulfate, filtered, and concentrated to an oil. The crude material was purified by silica gel chromatography (0-50% ethyl acetate in hexanes) to yield the product as an oil (0.251 g, 51%). $^1$H NMR (500 MHz, $CDCl_3$) δ 7.27 (t, J=7.8 Hz, 1H), 6.98-6.90 (m, 2H), 6.86 (ddd, J=8.2, 2.7, 1.0 Hz, 1H), 5.51 (tq, J=6.6, 1.3 Hz, 1H), 5.17-5.06 (m, 2H), 4.68 (s, 2H), 4.56 (d, J=6.6 Hz, 2H), 2.21-2.03 (m, 6H), 1.98 (dd, J=9.1, 6.2 Hz, 2H), 1.75 (d, J=1.3 Hz, 3H), 1.69 (d, J=1.4 Hz, 3H), 1.62 (d, J=1.4 Hz, 6H). HRMS ESI (+) calc'd for [M+Na]=351.2300, found=351.2315.

{[(3-{[(2E,6E)-3,6,11-trimethyldodeca-2,6,10-trien-1-yl]oxy}phenyl)methyl phosphonato]oxy}phosphonate. A 25.0 mL 14/20 round bottom flask was charged with the alcohol from the prior step, (3-{[(2E,6E)-3,7,11-trimethyldodeca-2,6,10-trien-1-yl]oxy}phenyl)methanol (0.212 g, 0.640 mmol), diethyl ether (3.00 mL), cooled to 0° C., and under argon was added phosphorus tribromide (0.270 g, 1.00 mmol). The reaction was stirred at 0° C. for 1 hour, diluted with hexanes, washed with brine, sodium bicarbonate, and brine. The organic layer was dried over sodium sulfate, filtered, and concentrated in vacuo to yield the crude bromide as an oil (0.135 g). This material was dissolved in acetonitrile (2.00 mL) and tetrabutylammonium pyrophosphate added (0.409 g, 0.450 mmol) and stirred under an argon atmosphere for 2 hours, at which time it was concentrated in vacuo and purified over DOWEX50 resin column. The column was prepared by stirring DOWEX50 resin (7.20 g) in concentrated ammonium hydroxide (30.0 mL) for 20 minutes. The resin was filtered and washed four times with water (100 mL). The resin was suspended in a buffer (20.0 mL of 1:49 2-propanol:25.0 mmolar aqueous ammonium bicarbonate) and poured into a column. The excess 1:49 2-propanol:25.0 mmolar aqueous ammonium bicarbonate buffer was drained from the column and the crude material was applied to the column (dissolved in 3.00 mL of the 1:49 2-propanol:25.0 mmolar aqueous ammonium bicarbonate buffer). The material was eluted with 30.0 mL 1:49 2-propanol:25.0 mmolar aqueous ammonium bicarbonate buffer and lyophilized to a waxy solid (0.163 g, 53%). $^{31}$P NMR (202 MHz, Deuterium Oxide) δ −6.45 (d, J=21.9 Hz), −10.37 (d, J=22.6 Hz). HRMS ESI [M−H] calc'd=487.1656, observed=487.1653.

EXAMPLE 24

{[(2-{[(2E,6E)-3,6,11-trimethyldodeca-2,6,10-trien-1-yl]oxy}phenyl)methyl phosphonato]oxy}phosphonate

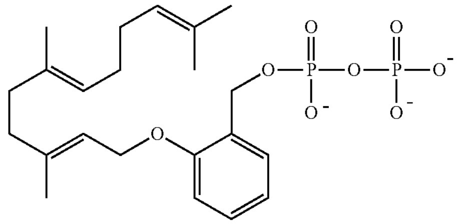 [SMILES: CC(C)=CCC/C=C(\C)CC/C(C)=C/COc1ccccc1COP(=O)([O-])OP(=O)([O-])[O-]]

(2-{[(2E,6E)-3,7,11-trimethyldodeca-2,6,10-trien-1-yl]oxy}phenyl)methanol. A 25.0 mL 14/20 round bottom flask was charged with trans, trans-farnesol (0.889 g, 4.00 mmol), diethyl ether, (10.0 mL), and at 0° C., under an argon atmosphere, was added phosphorus tribromide (1.35 g, 5.00 mmol) and the mixture stirred for 1 hour. The mixture was then diluted with hexanes and the organic layer washed with brine, a saturated sodium bicarbonate solution, and brine. The organic layer was dried over sodium sulfate, filtered, and concentrated in vacuo to yield crude trans, trans-farnesyl bromide (0.769 g, 2.70 mmol). This material was diluted with tetrahydrofuran (10.0 mL) and treated with 2-hydroxybenzyl alcohol (0.369 g, 3.00 mmol). The mixture was cooled to 0° C. and sodium hydride added (0.100 g, 3.00 mmol). After gas evolution ceased the reaction mixture was heated to 45° C. for 19 hours under an argon atmosphere, partitioned between ethyl acetate and a saturated ammonium chloride solution, washed with brine and concentrated in vacuo as an oil. The crude material was purified by silica gel chromatography (1:9:0.1 ethyl acetate: hexanes: triethylamine) to yield the product as an oil (0.258 g, 29%). $^1$H NMR (500 MHz, $CDCl_3$) δ 7.26 (ddd, J=7.8, 6.5, 2.0 Hz, 2H), 6.97-6.86 (m, 2H), 5.49 (tq, J=6.4, 1.3 Hz, 1H), 5.10 (dtp, J=8.4, 4.3, 1.4 Hz, 2H), 4.69 (s, 2H), 4.60 (d, J=6.5 Hz, 2H), 2.47 (s, 1H), 2.22-2.03 (m, 6H), 1.98 (dd, J=9.1, 6.0 Hz, 2H), 1.74 (d, J=1.3 Hz, 3H), 1.68 (p, J=1.6 Hz, 3H), 1.61 (dd, J=2.9, 1.4 Hz, 6H). HRMS ESI (+) calc'd for [M+Na]=351.2300, found=351.2340.

{[(2-{[(2E,6E)-3,6,11-trimethyldodeca-2,6,10-trien-1-yl]oxy}phenyl)methyl phosphonato]oxy}phosphonate. A 25.0 mL 14/20 round bottom flask was charged with (2-{[(2E,6E)-3,7,11-trimethyldodeca-2,6,10-trien-1-yl]oxy}phenyl)methanol (0.218 g, 0.660 mmol), diethyl ether (3.00 mL), cooled to 0° C., and under argon atmosphere, treated with phosphorus tribromide (0.270 g, 1.00 mmol). The mixture was stirred at 0° C. for 1 hour, diluted with hexanes, washed with brine, aqueous saturated sodium bicarbonate solution and brine. The organic layer was dried over sodium sulfate, filtered, and concentrated in vacuo to yield crude 1-(bromomethyl)-2-{[(2E,6E)-3,7,11-trimethyldodeca-2,6,10-trien-1-yl]oxy}benzene as an oil (0.132 g). This material was dissolved in acetonitrile (2.00 mL) and tetrabutylammonium pyrophosphate (0.292 g, 0.450 mmol) added. The reaction mixture was stirred under an argon atmosphere for 2 hours, then concentrated in vacuo and purified over a DOWEX50 resin column. The DOWEX50 column was prepared by first stirring the DOWEX50 (7.55 g) in concentrated ammonium hydroxide (30.0 mL) for 20 minutes and then filtered and washed four times with water (100 mL). The resin was suspended in a buffer (20.0 mL of 1:49 2-propanol:25.0 mmolar aqueous ammonium bicarbonate) and poured into a column. The excess 1:49 2-propanol:25.0 mmolar aqueous ammonium bicarbonate buffer was drained from the column and the crude material was applied to the column (dissolved in 3.0 mL of the same buffer). The material was eluted with 30.0 mL 1:49 2-propanol:25.0 mmolar aqueous ammonium bicarbonate and lyophilized to a waxy solid (0.075 g, 46%). $^{31}$P NMR (202 MHz, Deuterium Oxide) δ −6.22 (d, J=21.9 Hz), −10.05 (d, J=21.9 Hz). HRMS ESI [M−H] calc'd=487.1656, observed=487.1644.

EXAMPLE 25

{[(2Z,6E,10E)-2-ethoxy-3,7,11,15-tetramethylhexadeca-2,6,10,14-tetraen-1-yl phosphonato]oxy}phosphonate and {[(2E,6E,10E) ethoxy-3,7,11,15-tetramethylhexadeca-2,6,10,14-tetraen-1-yl phosphonato]oxy}phosphonate

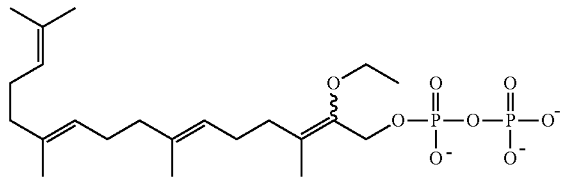 [SMILES: CCOC(COP(=O)([O-])OP(=O)([O-])[O-])=C(C)CC/C=C(\C)CC/C=C(\C)CCC=C(C)C]

Ethyl (2Z,6E,10E)-2-ethoxy-3,7,11,15-tetramethylhexadeca-2,6,10,14-tetraenoate and ethyl (2E,6E,10E)-2-ethoxy-3,7,11,15-tetramethylhexadeca-2,6,10,14-tetraenoate. A 100 mL 14/20 round bottom flask was charged with ethyl 2-(diethoxyphosphoryl)-2-ethoxyacetate (2.36 g, 8.80 mmol. Prepared according to the method described in Bach, K.; Hesham, R., E.-S.; Jensen, H. M.; Nielsen, H. B.; Thomson, I.; Torssell, K. B. G; *Tetrahedron,* 1994, 50, 7543), tetrahydrofuran (15.0 mL), cooled to 0° C., and sodium hydride (0.336 g, 10.0 mmol) added under an argon atmosphere. Farnesyl acetone (1.57 g, 6.00 mmol) dissolved in tetrahydrofuran (5.00 mL) was added in dropwise fashion. The stirring mixture was heated to 45° C. for 26 hours. The reaction was partitioned between ethyl acetate and a saturated ammonium chloride solution, the organic layer washed with brine, dried over sodium sulfate, filtered, and concentrated in vacuo. The crude material was dissolved in ethanol (30.0 mL), cooled to 0° C., and treated with sodium borohydride (0.226 g, 6.00 mmol). After 1 hour, the reaction was partitioned between ethyl acetate and a saturated ammonium chloride solution, washed with brine, dried over sodium sulfate, filtered, and concentrated in vacuo. The crude material was purified by silica gel chromatography (0-10% ethyl acetate in hexanes) to yield the product as a clear oil (0.953 g, 41%). $^1$H NMR (500 MHz, $CDCl_3$) δ 5.18-5.04 (m, 3H), 4.23 (ttd, J=7.1, 5.1, 2.6 Hz, 2H), 3.74-3.64 (m, 2H), 2.48-2.40 (m, 1H), 2.25 (ddd, J=8.7, 6.0, 1.5 Hz, 1H), 2.21-2.09 (m, 2H), 2.10-2.00 (m, 8H), 1.97 (dd, J=8.8, 5.5 Hz, 2H), 1.88-1.81 (m, 2H), 1.68 (dt, J=4.2, 1.4 Hz, 6H), 1.60 (dd, J=4.8, 2.6 Hz, 6H), 1.32 (td, J=7.1, 5.3 Hz, 3H), 1.28 (tdd, J=7.1, 2.7, 2.1 Hz, 3H).

(2Z,6E,10E)-2-ethoxy-3,7,11,15-tetramethylhexadeca-2,6,10,14-tetraen-1-ol and (2E,6E,10E)-2-ethoxy-3,7,11,15-tetramethylhexadeca-2,6,10,14-tetraen-1-ol. A mixture of ethyl (2Z,6E,10E)-2-ethoxy-3,7,11,15-tetramethylhexadeca-2,6,10,14-tetraenoate and ethyl (2E,6E,10E)-2-ethoxy-3,7,11,15-tetramethylhexadeca-2,6,10,14-tetraenoate was dissolved in dichloromethane (5.00 mL), cooled to 0° C., and treated, under an argon atmosphere, with diisobutylaluminum hydride (8.00 mL, 8.00 mmol, 1.00 M in heptanes). The reaction was warmed to room temperature and stirred for 22 hours. The reaction was cooled to 0° C., quenched with ethanol (2.00 mL) and stirred vigorously for 24 hours with a solution of sodium potassium tartrate (10.0 g, 35.0 mmol in 50.0 mL water). The mixture was partitioned, and the aqueous layer washed with dichloromethane. The organic layers were combined, dried over sodium sulfate, filtered and concentrated in vacuo to yield the crude product, which was purified by silica gel (1:4 ethyl acetate: hexanes) chromatography to yield (2Z,6E,10E)-2-ethoxy-3,7,11,15-tetramethylhexadeca-2,6,10,14-tetraen-1-ol and (2E,6E,10E)-2-ethoxy-3,7,11,15-tetramethylhexadeca-2,6,10,14-tetraen-1-ol as a mixture of isomers (0.665 g, 80%). $^1$H NMR (500 MHz, $CDCl_3$) δ 5.17-5.04 (m, 3H), 4.34-4.07 (m, 2H), 3.81-3.69 (m, 2H), 2.19-2.12 (m, 1H), 2.12-2.00 (m, 9H), 1.98 (q, J=7.5, 7.0 Hz, 3H), 1.72-1.65 (m, 9H), 1.63-1.55 (m, 6H), 1.29-1.21 (m, 3H).

{[(2Z,6E,10E)-2-ethoxy-3,7,11,15-tetramethylhexadeca-2,6,10,14-tetraen-1-yl phosphonato]oxy}phosphonate and {[(2E,6E,10E)-2-ethoxy-3,7,11,15-tetramethylhexadeca-2,6,10,14-tetraen-1-yl phosphonato]oxy}phosphonate. A 25.0 mL 14/20 round bottom flask was charged with a mixture of (2Z,6E,10E)-2-ethoxy-3,7,11,15-tetramethylhexadeca-2,6,10,14-tetraen-1-ol and (2E,6E,10E)-2-ethoxy-3,7,11,15-tetramethylhexadeca-2,6,10,14-tetraen-1-ol (0.270 g, 0.830 mmol), dichloromethane (4.00 mL), triethylamine (0.223 mL, 1.60 mmol), cooled to 0° C., and treated with methane sulfonyl chloride (0.0770 mL, 1.00 mmol). The mixture was stirred for 1 hour then quenched with brine and partitioned. The organic layer was washed with brine, dried over sodium sulfate, filtered and concentrated in vacuo to provide crude mixture of (2Z,6E,10E)-2-ethoxy-3,7,11,15-tetramethylhexadeca-2,6,10,14-tetraen-1-yl methanesulfonate and of (2E,6E,10E)-2-ethoxy-3,7,11,15-tetramethylhexadeca-2,6,10,14-tetraen-1-yl methanesulfonate (0.374 g). This material was dissolved in acetonitrile (2.00 mL), stirred, and tetrabutylammonium pyrophosphate was added (0.454 g, 0.500 mmol). The reaction mixture was stirred under argon for 2 hours, concentrated and purified over DOWEX50 resin column. The column was prepared with DOWEX50 resin (7.55 g) stirred in concentrated ammonium hydroxide (30.0 mL) for 20 minutes. The resin was filtered and washed four times with water (100 mL). The resin was suspended in a buffer (20.0 mL of 1:49 2-propanol: 25.0 mmolar aqueous ammonium bicarbonate) and poured into a column. The excess buffer 1:49 2-propanol: 25.0 mmolar aqueous ammonium bicarbonate was drained from the column and the crude product material applied to the column (dissolved in 3.00 mL of the 1:49 2-propanol: 25.0 mmolar aqueous ammonium bicarbonate buffer). The material was eluted with 30.0 mL 1:49 2-propanol: 25.0 mmolar aqueous ammonium bicarbonate buffer and lyophilized to a waxy solid (0.141 g, 35%). $^{31}$P NMR (202 MHz, Deuterium Oxide) δ −6.52, −10.38 (d, J=22.0 Hz). HRMS ESI [M−H] calc'd=493.2126, observed=493.2130.

EXAMPLE 26

{[(2Z,6E,10E)-2-chloro-3,7,11,15-tetramethylhexadeca-2,6,10,14-tetraen-1-yl phosphonato]oxy}phosphonate and {[(2E,6E,10E)-2-chloro-3,7,11,15-tetramethylhexadeca-2,6,10,14-tetraen-1-yl phosphonato]oxy}phosphonate

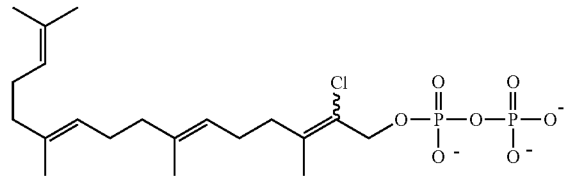 [SMILES: CC(C)=CCC/C(C)=C/CC/C(C)=C/CCC(C)=C(Cl)COP(=O)([O-])OP(=O)([O-])[O-]]

Ethyl (2Z,6E,10E)-2-chloro-3,7,11,15-tetramethylhexadeca-2,6,10,14-tetraenoate and ethyl (2E,6E,10E)-2-chloro-3,7,11,15-tetramethylhexadeca-2,6,10,14-tetraenoate. A 50.0 mL 14/20 round bottom flask was charged with sodium hydride (0.151 g, 4.50 mmol). Under an argon atmosphere at 0° C. was added anhydrous tetrahydrofuran (10.0 mL), followed by triethyl-2-chloro-phosphonoacetate (1.00 g, 3.86 mmol) dissolved in tetrahydrofuran (2.00 mL). Once gas evolution ceased, farnesyl acetone (1.04 g, 4.00 mmol) was added dissolved in tetrahydrofuran (1.00 mL). The mixture was heated to 45° C. for 19 hours, concentrated in vacuo and partitioned between ethyl acetate and a saturated ammonium chloride solution. The organic layer was washed with brine, dried over sodium sulfate, filtered, and concentrated in vacuo to provide an oil. The crude material was purified by silica gel chromatography (1:9 ethyl acetate: hexanes) to yield a mixture of ethyl (2Z,6E,10E)-2-chloro-3,7,11,15-tetramethylhexadeca-2,6,10,14-tetraenoate and ethyl (2E,6E,10E)-2-chloro-3,7,11,15-tetramethylhexadeca-2,6,10,14-tetraenoate (0.880 g, 62%). NMR (500 MHz, $CDCl_3$) δ 5.19-5.05 (m, 3H), 4.33-4.09 (m, 2H), 2.59-2.51 (m, 1H), 2.49-2.43 (m, 1H), 2.40 (dt, J=8.7, 7.2 Hz, 1H), 2.32-2.24 (m, 1H), 2.22-2.12 (m, 3H), 2.12-1.94 (m, 8H), 1.69 (dt, J=2.7, 1.3 Hz, 6H), 1.66-1.60 (m, 6H), 1.34-1.23 (td, J=7.1, 4.1 Hz, 3H).

(2Z,6E,10E)-2-chloro-3,7,11,15-tetramethylhexadeca-2,6,10,14-tetraen-1-ol and (2E,6E,10E)-2-chloro-3,7,11,15-tetramethylhexadeca-2,6,10,14-tetraen-1-ol. A 50.0 mL 24/40 round bottom flask was charged with a mixture of ethyl (2Z,6E,10E)-2-chloro-3,7,11,15-tetramethylhexadeca-2,6,10,14-tetraenoate and ethyl (2E,6E,10E)-2-chloro-3,7,11,15-tetramethylhexadeca-2,6,10,14-tetraenoate (0.840 g, 2.30 mmol). The material was dissolved in dichloromethane (5.00 mL) and, under an argon atmosphere at 0° C., treated with diisobutylaluminum hydride (7.00 mL, 7.00 mmol, 1.00 M in heptanes). The mixture was warmed to room temperature and stirred for 18 hours, then quenched with ethanol (5.00 mL). A solution of sodium potassium tartrate (7.00 g, 24.8 mmol in 50.0 mL water) was added and the biphasic mixture vigorously stirred for 24 hours. The reaction mixture partitioned, and the aqueous layer twice washed with dichloromethane (20.0 mL per wash). The organic layers were combined, dried over sodium sulfate, filtered, and concentrated in vacuo. The crude material was purified by silica gel chromatography (1:9 ethyl acetate: hexanes) to yield a mixture of (2Z,6E,10E)-2-chloro-3,7,11,15-tetramethylhexadeca-2,6,10,14-tetraen-1-ol and (2E,6E,10E)-2-chloro-3,7,11,15-tetramethylhexadeca-2,6,10,14-tetraen-1-ol (0.220 g, 30%). $^1$H NMR (500 MHz, $CDCl_3$) δ 5.18-5.06 (m, 3H), 4.29 (d, J=14.7 Hz, 1H), 4.19-3.76 (m, 1H), 2.31-2.19 (m, 1H), 2.17-2.01 (m, 9H), 1.98 (dd, J=9.5, 6.1 Hz, 2H), 1.69 (ddd, J=5.5, 2.6, 1.3 Hz, 9H), 1.64-1.58 (m, 6H). HRMS ESI (+) calc'd for [M+Na]=347.2118, found=347.2159.

{[(2Z,6E,10E)-2-chloro-3,7,11,15-tetramethylhexadeca-2,6,10,14-tetraen-1-yl phosphonato]oxy}phosphonate and {[(2Z,6E,10E)-2-chloro-3,7,11,15-tetramethylhexadeca-2,6,10,14-tetraen-1-yl phosphonato]oxy}phosphonate. A 25.0 mL 14/20 round bottom flask was charged with a mixture of (2Z,6E,10E)-2-chloro-3,7,11,15-tetramethylhexadeca-2,6,10,14-tetraen-1-ol and (2E,6E,10E)-2-chloro-3,7,11,15-tetramethylhexadeca-2,6,10,14-tetraen-1-ol. (0.227 g, 0.670 mmol) and anhydrous ether (3.00 mL). At 0° C., under an argon atmosphere, phosphorus tribromide (0.270 g, 1.00 mmol) dissolved in ether (1.00 mL) was added. The mixture was stirred for 2 hours, diluted with hexanes, washed with brine, a saturated sodium bicarbonate solution and brine, then dried over sodium sulfate, filtered, and concentrated in vacuo. To this material dissolved in acetonitrile (1.50 mL) and treated with tetrabutylammonium pyrophosphate (0.504 g, 0.550 mmol). The reaction vessel was sealed and stirred under an argon atmosphere for 2 hours, then concentrated in vacuo to a viscous liquid and purified on DOWEX50 resin column. The resin column was prepared by stirring DOWEX50 resin (7.70 g) in concentrated ammonium hydroxide (30.0 mL) for 20 minutes. The resin was then filtered and washed four times with water (100 mL) and subsequently suspended in a buffer (20.0 mL of 1:49 2-propanol: 25.0 mmolar aqueous ammonium bicarbonate), then poured into a column. The excess 1:49 2-propanol: 25.0 mmolar aqueous ammonium bicarbonate buffer was drained from the column and the crude product material applied to the column (dissolved in 3.00 mL of the 1:49 2-propanol: 25.0 mmolar aqueous ammonium bicarbonate buffer). The material was eluted with 30.0 mL of the 1:49 2-propanol: 25.0 mmolar aqueous ammonium bicarbonate buffer and lyophilized to a waxy solid (0.177 g, 55%). $^{31}$P NMR (202 MHz, Deuterium Oxide) δ −6.17, −10.51. HRMS ESI [M−H] calc'd=483.1474, observed=483.1471.

EXAMPLE 27

[(4-{[(2E,6E)-3,7,11-trimethyldodeca-2,6,10-trien-1-yl]oxy}but-2-yn-1-yl phosphonato)oxy]phosphonate

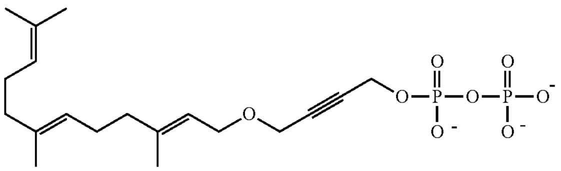 [SMILES: CC(C)=CCC/C(C)=C/CC/C(C)=C/COCC#CCOP(=O)([O-])OP(=O)([O-])[O-]]

4-{[dimethyl(phenyl)silyl]oxy}but-2-yn-1-ol. A 250 mL 24/40 round bottom flask was charged with 2-butyne-1,4-diol (2.15 g, 25.0 mmol), tetrahydrofuran (75.0 mL), cooled to 0° C., and treated with sodium hydride (0.840 g, 25.0 mmol). Under an argon atmosphere, phenyldimethylchlorosilane (1.65 mL, 10.0 mmol) was added and the mixture stirred at room temperature for 19 hours, concentrated to a solid, partitioned between ethyl acetate and a saturated ammonium chloride solution, then washed with brine, dried over sodium sulfate, filtered and concentrated to dryness. The crude material was purified by silica gel chromatography (1:9 ethyl acetate: hexanes) to yield the product (0.320 g, 14%). $^1H$ NMR (500 MHz, $CDCl_3$) δ 7.65-7.57 (m, 2H), 7.46-7.36 (m, 3H), 4.32 (t, J=1.8 Hz, 2H), 4.24 (t, J=2.0 Hz, 2H), 0.46 (s, 6H).

4-{[(2E,6E)-3,7,11-trimethyldodeca-2,6,10-trien-1-yl]oxy}but-2-yn-1-ol. A 50 mL 14/20 round bottom flask was charged with trans, trans-farnesol (0.889 g, 4.00 mmol), diethyl ether, (10.0 mL), and at 0° C. (argon atmosphere), treated with phosphorus tribromide (1.35 g, 5.00 mmol) and stirred for 30 minutes. The mixture was then diluted with hexanes, washed with brine, a saturated solution of sodium bicarbonate, and brine. The organic layer was then dried over sodium sulfate, filtered, and concentrated in vacuo to provide crude (6E,10E)-12-bromo-2,6,10-trimethyldodeca-2,6,10-triene (0.523 g, 1.80 mmol). The crude was diluted with tetrahydrofuran (10.0 mL) and charged with 4-{[dimethyl(phenyl)silyl]oxy}but-2-yn-1-ol (0.320 g, 1.30 mmol) and the mixture cooled to 0° C. and treated with sodium hydride (0.122 g, 5.00 mmol). After gas evolution ceased, the mixture (argon atmosphere) was heated to 45° C. for 19 hours. The reaction mixture was partitioned between ethyl acetate and a saturated ammonium chloride solution, the organic layer washed with brine, dried with sodium sulfate, filtered, and concentrated in vacuo. The crude material was purified by silica gel chromatography (1:9 ethyl acetate: hexanes) to provide crude dimethyl(phenyl)[(4-{[(2E,6E)-3,7,11-trimethyldodeca-2,6,10-trien-1-yl]oxy}but-2-yn-1-yl)oxy]silane (0.394 g, 71%). A 25.0 mL 14/20 round bottom flask was charged with this material and, under an argon atmosphere, tetrabutylammonium fluoride (5.00 mL, 5.00 mmol, 1.00 M solution in tetrahydrofuran) was added and the mixture stirred at 45° C. for 20 hours. The mixture was partitioned between ethyl acetate and 1.00 N HCl (10.0 mL), the organic layer was washed with brine, dried over sodium sulfate, filtered, and concentrated in vacuo. The crude material was purified by silica gel chromatography (1:9 ethyl acetate: hexanes) to yield the product (0.050 g, 18%). $^1H$ NMR (500 MHz, $CDCl_3$) δ 5.45-5.28 (m, 1H), 5.09 (dddt, J=8.4, 7.0, 5.6, 1.4 Hz, 2H), 4.30 (t, J=1.8 Hz, 2H), 4.19-4.11 (m, 2H), 4.06 (d, J=6.9 Hz, 2H), 2.15-2.00 (m, 6H), 2.00-1.91 (m, 2H), 1.73-1.65 (m, 6H), 1.63-1.56 (m, 6H).

[(4-{[(2E,6E)-3,7,11-trimethyldodeca-2,6,10-trien-1-yl]oxy}but-2-yn-1-yl phosphonato)oxy]phosphonate. A 10.0 mL 14/20 round bottom flask was charged with 4-{[(2E,6E)-3,7,11-trimethyldodeca-2,6,10-trien-1-yl]oxy}but-2-yn-1-ol (0.050, 0.170 mmol), diethyl ether (1.00 mL), cooled to 0° C., and treated with phosphorus tribromide (0.0280 mL, 0.300 mmol). The mixture was stirred at 0° C. for 15 minutes, diluted with hexanes, washed with brine, a saturated sodium bicarbonate solution, and brine. The organic layer was dried over sodium sulfate and concentrated to provide crude (6E,10E)-12-[(4-bromobut-2-yn-1-yl)oxy]-2,6,10-trimethyldodeca-2,6,10-triene (0.0600 g, 100%). This material was dissolved in acetonitrile (2.00 mL) and, under an argon atmosphere, treated with tetrabutylammonium pyrophosphate (0.251 g, 0.270 mmol), then stirred for 2 hours. The mixture was concentrated to a viscous liquid and purified over DOWEX50 resin column, the column prepared by dissolving DOWEX50 resin (5.98 g) in concentrated ammonium hydroxide (30.0 mL) for 20 minutes, then filtered and washed four times with water (100 mL). The resin was suspended in a buffer (20 mL of 1:49 2-propanol: 25 mmolar ammonium bicarbonate) and poured into the column. The excess buffer was drained from the column and the crude material applied to the column (dissolved in 3.00 mL of the same buffer). The material was eluted with 30.0 mL buffer and lyophilized to a waxy solid (0.076 g, 100 %). $^{31}P$ NMR (202 MHz, Deuterium Oxide) δ −6.46 (d, J=21.5 Hz), -10.18--11.03 (m). HRMS ESI [M−H] calc'd=449.1497, observed=449.1494.

EXAMPLE 28

{[(6E,10E)-3,7,11,15-tetramethyl-2-oxohexadeca-6,10,14-trien-1-yl phosphonato]oxy}phosphonate

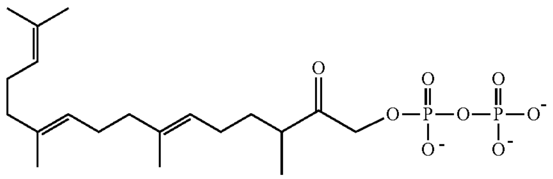 [SMILES: CC(C)=CCC/C(C)=C/CC/C(C)=C/CCC(C)C(=O)COP(=O)([O-])OP(=O)([O-])[O-]]

(2Z,6E,10E)-2-ethoxy-3,7,11,15-tetramethylhexadeca-2,6,10,14-tetraen-1-ol and (2E,6E,10E)-2-ethoxy-3,7,11,15-tetramethylhexadeca-2,6,10,14-tetraen-1-ol. A 100 mL 14/20 round bottom flask was charged with ethyl 2-(diethoxyphosphoryl)-2-ethoxyacetate (2.36 g, 8.80 mmol. Prepared according to the method described in Bach, K.; Hesham, R., E.-S.; Jensen, H. M.; Nielsen, H. B.; Thomson, I.; Torssell, K. B. G., *Tetrahedron,* 1994, 50, 7543), tetrahydrofuran (15.0 mL) then cooled to 0° C., and treated with sodium hydride (0.336 g, 10.0 mmol) under an argon atmosphere. Farnesyl acetone (1.57 g, 6.00 mmol), dissolved in tetrahydrofuran (5.00 mL), was added in dropwise fashion. The mixture was then heated to 45° C. for 26 hours and quenched with a saturated ammonium chloride solution. The reaction was partitioned with ethyl acetate, washed with brine, dried over sodium sulfate, filtered, and concentrated in vacuo. The crude material was dissolved in ethanol (30.0 mL) then cooled to 0° C. and treated with sodium borohydride (0.226 g, 6.00 mmol) and the mixture stirred for 1 hour. The mixture was partitioned between ethyl acetate and saturated ammonium chloride solution, washed with brine, dried over sodium sulfate, and concentrated in vacuo to dryness. The crude material was purified by silica gel chromatography (0-10% ethyl acetate in hexanes) to yield an oil (0.953 g, 41%). The crude was dissolved in dichloromethane (5.00 mL), cooled to 0° C., under an argon atmosphere, and treated with diisobutylaluminum hydride (8.00 mL, 8.00 mmol, 1.00 M in heptanes). The reaction was warmed to room temperature, stirred for 22 hours, then cooled to 0° C. and quenched with ethanol. The mixture was then treated with a solution of sodium potassium tartrate (10.0 g, 35.0 mmol in 50.0 mL water) and vigorously stirred for 24 hours. The mixture was partitioned, and the aqueous layer washed with dichloromethane. The organic layers were combined, dried over sodium sulfate, filtered, concentrated in vacuo and purified by silica gel chromatography to yield the product (0.665 g, 80%). $^1$H NMR (500 MHz, $CDCl_3$) δ 5.17-5.04 (m, 3H), 4.34-4.07 (m, 2H), 3.81-3.69 (m, 2H), 2.19-2.12 (m, 1H), 2.12-2.00 (m, 9H), 1.98 (q, J=7.5, 7.0 Hz, 3H), 1.72-1.65 (m, 9H), 1.63-1.55 (m, 6H), 1.29-1.21 (m, 3H).

{[(6E,10E)-3,7,11,15-tetramethyl-2-oxohexadeca-6,10,14-trien-1-yl phosphonato]oxy} phosphonate. A 25.0 mL 14/20 round bottom flask was charged with (2Z,6E,10E)-2-ethoxy-3,7,11,15-tetramethylhexadeca-2,6,10,14-tetraen-1-ol and (2E,6E,10E)-2-ethoxy-3,7,11,15-tetramethylhexadeca-2,6,10,14-tetraen-1-ol (0.385 g, 1.15 mmol), dichloromethane (5.00 mL) and triphenylphosphine (0.314 mL, 1.20 mmol). The mixture was cooled to 0° C. and treated with carbon tetrabromide (0.379 mL, 1.20 mmol dissolved in 1.00 mL dichloromethane). The mixture was stirred for 10 minutes at 0° C. and 20 minutes at room temperature. The mixture was concentrated to ~1.00 mL in vacuo and diluted with hexanes (15.0 mL). A solid precipitated and the mixture filtered through Celite, this process was repeated twice to yield crude (6E,10E)-1-bromo-3,7,11,15-tetramethylhexadeca-6,10,14-trien-2-one (0.397 g) as an oil. This material was dissolved in acetonitrile (2.00 mL) and treated with tetrabutylammonium pyrophosphate (0.775 g, 0.850 mmol). The reaction mixture was stirred under an argon atmosphere for 2 hours, concentrated in vacuo and purified on a DOWEX50 resin column, the column prepared by first suspending the DOWEX50 resin (11.7 g) in concentrated ammonium hydroxide (45.0 mL) for 20 minutes. The resin was filtered and washed four times with water (100 mL). The resin was suspended in a buffer (20.0 mL of 1:49 2-propanol: 25.0 mmolar aqueous ammonium bicarbonate) and loaded into the DOWEX50 column. The excess 1:49 2-propanol: 25.0 mmolar aqueous ammonium bicarbonate buffer was drained from the column and the crude material on the column (dissolved in 3.00 mL of the 1:49 2-propanol: 25.0 mmolar aqueous ammonium bicarbonate buffer). The material was eluted with 30.0 mL 1:49 2-propanol: 25.0 mmolar aqueous ammonium bicarbonate buffer and lyophilized to a waxy solid (0.291 g, 55%). $^{31}$P NMR (202 MHz, Deuterium Oxide) δ −6.10, −10.74. HRMS ESI [M−H] calc'd=465.1813, observed=465.1812.

EXAMPLE 29

{[(2E)-3-(4-{[(2E)-3,7-dimethylocta-2,6-dien-1-yl]oxy}phenyl)-2-methylprop-2-en-1-yl phosphonato]oxy}phosphonate

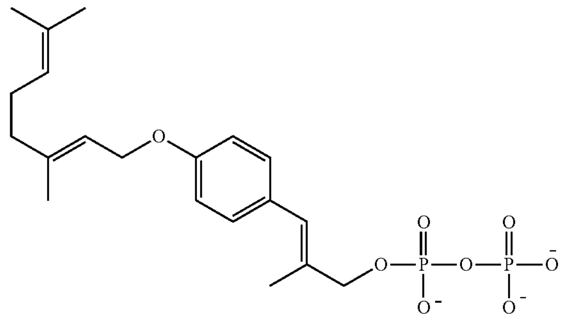 [SMILES: CC(C)=CCC/C(C)=C/COc1ccc(/C=C(\C)COP(=O)([O-])OP(=O)([O-])[O-])cc1]

4-{[(2E)-3,7-dimethylocta-2,6-dien-1-yl]oxy}benzaldehyde. A 25.0 mL 14/20 round bottom flask was charged with geranyl bromide (0.975 g, 4.50 mmol, Brundel, B., J., J., M.; Steen, H.; Heeres, A.; Seerden, J. P. G., WO2013157926), acetone (15.0 mL), 4-hydroxybenzaldehyde (0.732 g, 6.00 mmol) and potassium carbonate (1.10 g, 8.00 mmol). The mixture was stirred overnight, then partitioned between ethyl acetate and a saturated aqueous ammonium chloride solution. The organic layer was then washed with brine, dried over sodium sulfate, filtered, and concentrated in vacuo. The crude material was purified by filtration through a triethylamine-deactivated silica (100% ethyl acetate) to yield the pure product (0.980 g, 84%). $^1$H NMR (500 MHz, $CDCl_3$) δ 9.95-9.82 (m, 1H), 7.90-7.72 (m, 2H), 7.05-6.94 (my, 2H), 5.55-5.42 (m, 1H), 5.13-5.03 (m, 1H), 4.70-4.52 (m, 2H), 2.24-1.99 (m, 4H), 1.79-1.75 (m, 3H), 1.68 (d, J=1.4 Hz, 3H), 1.61 (d, J=1.3 Hz, 3H).

Ethyl (2E)-3-(4-{[(2E)-3,7-dimethylocta-2,6-dien-1-yl]oxy}phenyl)-2-methylprop-2-enoate and ethyl (2Z)-3-(4-{[(2E)-3,7-dimethylocta-2,6-dien-1-yl]oxy}phenyl)-2-methylprop-2-enoate. A 50.0 mL 14/20 round bottom flask was charged with 4-{[(2E)-3,7-dimethylocta-2,6-dien-1-yl]oxy}benzaldehyde (0.800 g, 3.10 mmol), tetrahydrofuran (15.0 mL), cooled to 0° C., and treated with sodium hydride (0.201 g, 6.00 mmol) under an argon atmosphere. Triethyl-2-phosphonopropionate (0.952 g, 4.00 mmol), dissolved in tetrahydrofuran (2.00 mL), was added dropwise. After gas evolution ceased, the mixture was heated to 45° C. for 70 hours and quenched with methanol. The mixture was partitioned between ethyl acetate and a saturated ammonium chloride solution, the organic layer washed with brine, dried over sodium sulfate, filtered, and concentrated in vacuo. The crude material was dissolved in ethanol (20.0 mL), cooled to 0° C., and sodium borohydride added (0.082 g, 2.10 mmol). After 10 minutes, the reaction was quenched with a saturated ammonium chloride solution (30.0 mL) and partitioned with ethyl acetate. The organic layer was washed with brine, dried over sodium sulfate, filtered and concentrated to dryness. The crude material was purified by silica gel chromatography (0-10% ethyl acetate in hexanes) to yield an oil (0.43 g, 41%). $^1$H NMR (500 MHz, $CDCl_3$) δ 7.65 (d, J=1.8 Hz, 1H), 7.44-7.34 (m, 2H), 7.00-6.86 (m, 2H), 5.50 (tp, J=6.6, 1.4 Hz, 1H), 5.10 (ddp, J=6.8, 5.4, 1.4 Hz, 1H), 4.62-4.54 (m, 2H), 4.27 (q, J=7.1 Hz, 2H), 2.20-2.01 (m, 7H), 1.76 (t, J=1.3 Hz, 3H), 1.69 (q, J=1.3 Hz, 3H), 1.62 (d, J=1.3 Hz, 3H), 1.36 (t, J=7.1 Hz, 3H).

(2E)-3-(4-{[(2E)-3,7-dimethylocta-2,6-dien-1-yl]oxy}phenyl)-2-methylprop-2-en-1-ol and (2Z)-3-(4-{[(2E)-3,7-dimethylocta-2,6-dien-1-yl]oxy}phenyl)-2-methylprop-2-en-1-ol. A mixture of ethyl (2E)-3-(4-{[(2E)-3,7-dimethylocta-2,6-dien-1-yl]oxy}phenyl)-2-methylprop-2-enoate and ethyl (2Z)-3-(4-{[(2E)-3,7-dimethylocta-2,6-dien-1-yl]oxy}phenyl)-2-methylprop-2-enoate (0.430, 1.20 mmol) was dissolved in dichloromethane (5.00 mL), cooled to 0° C. under an argon atmosphere, and treated with diisobutylaluminum hydride (3.00 mL, 3.00 mmol, 1.00 M in heptanes). The reaction was allowed to warm to room temperature and stirred for 22 hours, cooled to 0° C., quenched with ethanol (2.00 mL) and stirred vigorously for 24 hours with a solution of sodium potassium tartrate (10.0 g, 35.0 mmol in 40.0 mL water). The mixture was partitioned, the aqueous layer washed with dichloromethane and the organic layers combined, dried over sodium sulfate, filtered, and concentrated in vacuo. The crude was purified by silica gel chromatography to yield an oil (0.240 g, 80%). $^1$H NMR (500 MHz, $CDCl_3$) δ 7.25-7.19 (m, 2H), 6.93-6.85 (m, 2H), 6.49-6.41 (m, 1H), 5.50 (tq, J=6.6, 1.3 Hz, 1H), 5.10 (ddp, J=7.0, 5.8, 1.4 Hz, 1H), 4.55 (d, J=6.5 Hz, 2H), 4.17 (d, J=1.3 Hz, 2H), 2.20-2.02 (m, 4H), 1.91 (d, J=1.4 Hz, 3H), 1.74 (d, J=1.4 Hz, 3H), 1.69 (d, J=1.4 Hz, 3H), 1.61 (d, J=1.4 Hz, 3H).

{[(2E)-3-(4-{[(2E)-3,7-dimethylocta-2,6-dien-1-yl]oxy}phenyl)-2-methylprop-2-en-1-yl phosphonato]oxy}phosphonate and {[(2Z)-3-(4-{[(2E)-3,7-dimethylocta-2,6-dien-1-yl]oxy}phenyl)-2-methylprop-2-en-1-yl phosphonato]oxy}phosphonate. A 25.0 mL 14/20 round bottom flask was charged with a mixture of (2E)-3-(4-{[(2E)-3,7-dimethylocta-2,6-dien-1-yl]oxy}phenyl)-2-methylprop-2-en-1-ol and (2Z)-3-(4-{[(2E)-3,7-dimethylocta-2,6-dien-1-yl]oxy}phenyl)-2-methylprop-2-en-1-ol (0.212 g, 0.570 mmol), diluted in dichloromethane (3.00 mL), cooled to 0° C., and, under an argon atmosphere, treated with phosphorus tribromide (0.0940 mL, 1.00 mmol). The reaction was stirred at 0° C. for 1 hour then diluted with hexanes, quenched with brine, washed with sodium bicarbonate, and brine. The organic layer was dried over sodium sulfate, filtered, and concentrated in vacuo to provide crude mixture of 1-[{(1E)-3-bromo-2-methylprop-1-en- 1-yl]-4-[(2E)-3,7-dimethylocta-2,6-dien-1-yl]oxy}benzene and 1-[(1Z)-3-bromo-2-methylprop-1-en-1-yl]-4-{[(2E)-3,7-dimethylocta-2,6-dien-1-yl]oxy}benzene (0.216 g, 100%). This material was dissolved in acetonitrile (2.00 mL), then treated with tetrabutylammonium pyrophosphate (0.394 g, 0.430 mmol). The mixture was stirred under an argon atmosphere for 2 hours, at which time it was concentrated in vacuo and purified over DOWEX50 resin column, which was prepared according to the following method. DOWEX50 resin (6.70 g) was stirred in concentrated ammonium hydroxide (30.0 mL) for 20 minutes. The resin was filtered and washed four times with water (100 mL). The resin was suspended in a buffer (20.0 mL of 1:49 2-propanol: 25.0 mmolar aqueous ammonium bicarbonate) and poured into a column. The excess 1:49 2-propanol: 25.0 mmolar aqueous ammonium bicarbonate buffer was drained from the column and the crude material was applied to the column (dissolved in 3.00 mL of the 1:49 2-propanol: 25.0 mmolar aqueous ammonium bicarbonate buffer). The material was eluted with 30.0 mL 1:49 2-propanol: 25.0 mmolar aqueous ammonium bicarbonate buffer and lyophilized to a waxy solid (0.170 g, 65%). $^{31}$P NMR (202 MHz, Deuterium Oxide) δ −6.49 (d, J=21.8 Hz), −10.26 (d, J=21.4 Hz). HRMS ESI [M−H] calc'd=459.1343, observed=459.1305.

EXAMPLE 30

{[(2E,4E,6E,10E)-7,11,15-trimethylhexadeca-2,4,6,10,14-pentaen-1-yl phosphonato]oxy}phosphonate, {[(2Z,4E,6E,10E)-7,11,15-trimethylhexadeca-2,4,6,10,14-pentaen-1-yl phosphonato]oxy}phosphonate, {[(2E,4E,6Z,10E)-7,11,15-trimethylhexadeca-2,4,6,10,14-pentaen-1-yl phosphonato]oxy}phosphonate, {[(2Z,4E,6Z,10E)-7,11,15-trimethylhexadeca-2,4,6,10,14-pentaen-1-yl phosphonato]oxy}phosphonate

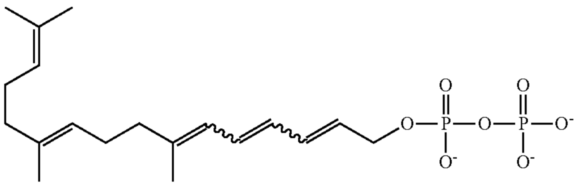 [SMILES: CC(C)=CCC/C(C)=C/CCC(C)=CC=CC=CCOP(=O)([O-])OP(=O)([O-])[O-]]

Ethyl (2E,4E,6E,10E)-7,11,15-trimethylhexadeca-2,4,6,10,14-pentaenoate, ethyl (2Z,4E,6E,10E)-7,11,15-trimethylhexadeca-2,4,6,10,14-pentaenoate, ethyl (2E,4E,6Z,10E)-7,11,15-trimethylhexadeca-2,4,6,10,14-pentaenoate, and ethyl (2Z,4E,6Z,10E)-7,11,15-trimethylhexadeca-2,4,6,10,14-pentaenoate. A 100 mL 14/20 round bottom flask was charged with triethyl-4-phosphonocrotonate (3.00 g, 12.0 mmol), tetrahydrofuran (30.0 mL), cooled to 0° C., and sodium hydride (0.504 g, 15.0 mmol). After gas evolution ceased, a mixture of (2E,6E)-3,7,11-trimethyldodeca-2,6,10-trienal and (2Z,6E)-3,7,11-trimethyldodeca-2,6,10-trienal (2.04 g, 9.20 mmol, Hu, H.; Harrison, T. J.; Wilson, P. D., *J. Org. Chem.*, 2004, 69, 3782.) was added as a solution in tetrahydrofuran (2.00 mL). After 2 hours the mixture was quenched with a saturated ammonium chloride solution and partitioned into ethyl acetate. The organic layer was washed with brine, dried over sodium sulfate, filtered, concentrated in vacuo, and purified by silica gel chromatography (1:9 ethyl acetate: hexanes) to provide an oil (1.64 g, 56%). $^1$H NMR (500 MHz, Chloroform-d) δ 7.35 (dddd, J=15.2, 11.3, 6.9, 0.8 Hz, 1H), 6.85-6.76 (m, 1H), 6.21 (dt, J=14.7, 10.7 Hz, 1H), 5.96 (dd, J=11.3, 2.0 Hz, 1H), 5.82 (dd, J=15.2, 2.0 Hz, 1H), 5.18-5.04 (m, 2H), 4.20 (q, J=7.1 Hz, 2H), 2.28-2.10 (m, 4H), 2.09-2.03 (m, 2H), 2.01-1.93 (m, 2H), 1.85 (dd, J=9.4, 1.3 Hz, 3H), 1.68 (d, J=1.6 Hz, 3H), 1.60 (dd, J=4.4, 2.8 Hz, 6H), 1.30 (t, J=7.1 Hz, 3H).

(2E,4E,6E,10E)-7,11,15-trimethylhexadeca-2,4,6,10,14-pentaen-1-ol, (2Z,4E,6E,10E)-7,11,15-trimethylhexadeca-2,4,6,10,14-pentaen-1-ol, (2E,4E,6Z,10E)-7,11,15-trimethylhexadeca-2,4,6,10,14-pentaen-1-ol, and (2Z,4E,6Z,10E)-7,11,15-trimethylhexadeca-2,4,6,10,14-pentaen-1-ol. A mixture of ethyl (2E,4E,6E,10E)-7,11,15-trimethylhexadeca-2,4,6,10,14-pentaenoate, ethyl (2Z,4E,6E,10E)-7,11,15-trimethylhexadeca-2,4,6,10,14-pentaenoate, ethyl (2E,4E,6Z,10E)-7,11,15-trimethylhexadeca-2,4,6,10,14-pentaenoate, and ethyl (2Z,4E,6Z,10E)-7,11,15-trimethylhexadeca-2,4,6,10,14-pentaenoate (1.64 g, 5.1 mmol) was dissolved in dichloromethane (10.0 mL), cooled to 0° C. under an argon atmosphere, and diisobutylaluminum hydride added (15.0 mL, 15.0 mmol, 1.00 M in heptanes). The mixture was warmed to room temperature and stirred for 22 hours. The reaction was cooled to 0° C., quenched with ethanol (2.00 mL) and stirred vigorously for 24 hours with a solution of sodium potassium tartrate (10.0 g, 35.0 mmol in 40.0 mL water). The reaction mixture was partitioned, and the aqueous layer washed with dichloromethane. The organic layers were combined, dried over sodium sulfate and concentrated in vacuo to provide the crude product mixture, which was purified by silica gel chromatography (1:9 ethyl acetate: hexanes) to yield a mixture of the products (0.610 g, 44%). $^1$H NMR (500 MHz, $CDCl_3$) δ 6.50-6.40 (m, 1H), 6.36-6.26 (m, 1H), 6.13 (dt, J=14.8, 10.7 Hz, 1H), 5.91-5.85 (m, 1H), 5.80 (ddd, J=15.2, 7.3, 5.0 Hz, 1H), 5.10 (dtdq, J=9.9, 7.0, 2.9, 1.4 Hz, 2H), 4.20 (dd, J=6.0, 1.4 Hz, 2H), 2.20-2.09 (m, 6H), 1.98 (dd, J=9.2, 6.1 Hz, 2H), 1.80 (dd, J=14.2, 1.3 Hz, 3H), 1.68 (t, J=1.4 Hz, 3H), 1.60 (d, J=1.3 Hz, 6H). HRMS ESI (+) calc'd for [M+Na]=297.2195, found=297.2242.

{[(2E,4E,6E,10E)-7,11,15-trimethylhexadeca-2,4,6,10,14-pentaen-1-yl phosphonato]oxy}phosphonate, {[(2Z,4E,6E,10E)-7,11,15-trimethylhexadeca-2,4,6,10,14-pentaen-1-yl phosphonato]oxy}phosphonate, {[(2E,4E,6Z,10E)-7,11,15-trimethylhexadeca-2,4,6,10,14-pentaen-1-yl phosphonato]oxy}phosphonate, {[(2Z,4E,6Z,10E)-7,11,15-trimethylhexadeca-2,4,6,10,14-pentaen-1-yl phosphonato]oxy}phosphonate. A 25.0 mL 14/20 round bottom flask was charged with a mixture of (2E,4E,6E,10E)-7,11,15-trimethylhexadeca-2,4,6,10,14-pentaen-1-ol, (2Z,4E,6E,10E)-7,11,15-trimethylhexadeca-2,4,6,10,14-pentaen-1-ol, (2E,4E,6Z,10E)-7,11,15-trimethylhexadeca-2,4,6,10,14-pentaen-1-ol, and (2Z,4E,6Z,10E)-7,11,15-trimethylhexadeca-2,4,6,10,14-pentaen-1-ol (0.164 g, 0.590 mmol) was dissolved in diethyl ether (3.00 mL) and under an argon atmosphere at 0° C., treated with triethylamine (0.208 mL, 1.50 mmol) followed by methanesulfonyl chloride (0.0770 mL, 1.00 mmol). A precipitate formed upon the addition and after 30 minutes at 0° C., the reaction was diluted with hexanes and washed with brine (three times), the organic layer dried over sodium sulfate, and concentrated in vacuo to yield the crude (2E,4E,6E,10E)-7,11,15-trimethylhexadeca-2,4,6,10,14-pentaen-1-yl methanesulfonate, (2Z,4E,6E,10E)-7,11,15-trimethylhexadeca-2,4,6,10,14-pentaen-1-yl methanesulfonate, (2E,4E,6Z,10E)-7,11,15-trimethylhexadeca-2,4,6,10,14-pentaen-1-yl methanesulfonate, and (2Z,4E,6Z,10E)-7,11,15-trimethylhexadeca-2,4,6,10,14-pentaen-1-yl methanesulfonate (0.211 g, 100%). This mixture was dissolved in acetonitrile (2.00 mL) and treated with tetrabutylammonium pyrophosphate (0.332 g, 0.360 mmol). The reaction mixture was stirred under argon for 2 hours, at which time it was concentrated in vacuo and purified over DOWEX50 resin column. The column was prepared via the following method. DOWEX50 resin (6.7 g) was stirred in concentrated ammonium hydroxide (30.0 mL) for 20 minutes. The resin was filtered and washed four times with water (100 mL). The resin was suspended in a buffer (20.0 mL of 1:49 2-propanol: 25.0 mmolar ammonium bicarbonate) and poured into a column. The excess buffer was drained from the column and the crude material was applied to the column (dissolved in 3.0 mL of the 1:49 2-propanol: 25.0 mmolar aqueous ammonium bicarbonate buffer). The material was eluted with 30.0 mL 1:49 2-propanol: 25.0 mmolar aqueous ammonium bicarbonate buffer and lyophilized to a solid (0.127 g, 50%). $^{31}$P NMR (202 MHz, Deuterium Oxide) δ −5.88-−6.54 (m), −21.17-−21.93 (m). HRMS ESI [M−H] calc'd=433.1550, observed=433.1552.

EXAMPLE 31

({[2-({[(2E,6E)-3,7,11-trimethyldodeca-2,6,10-trien-1 yl]oxy}methyl) cyclopropyl]methyl phosphonato}oxy)phosphonate

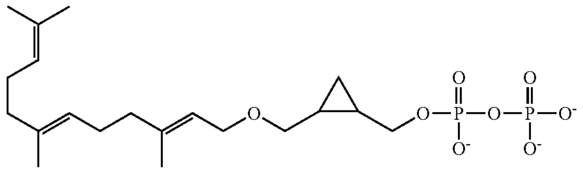 [SMILES: CC(C)=CCC/C(C)=C/CC/C(C)=C/COCC1CC1COP(=O)([O-])OP(=O)([O-])[O-]]

[2-({[(2E,6E)-3,7,11-trimethyldodeca-2,6,10-trien-1-yl]oxy}methyl)cyclopropyl]methanol. A 50.0 mL 14/20 round bottom flask was charged with trans, trans-farnesol (0.889 g, 4.00 mmol), diethyl ether (10.0 mL), and cooled to 0° C. (argon atmosphere). Phosphorus tribromide (1.35 g, 5.00 mmol) was added and the mixture allowed to stir for 1 hour, then diluted with hexanes, washed with brine, a saturated sodium bicarbonate solution, and then a second time with brine. The organic layer was dried over sodium sulfate and concentrated in vacuo to yield crude trans, trans-farnesyl bromide (1.06 g, 3.7 mmol). $^1$H NMR (500 MHz, Chloroform-d) δ 4.13-4.04 (m, 2H), 3.40 (s, 2H), 3.29-3.19 (m, 2H), 1.37-1.25 (m, 2H), 0.79 (td, J=8.2, 5.1 Hz, 1H), 0.20 (q, J=5.3 Hz, 1H). A separate flask was charged with [2-(hydroxymethyl)cyclopropyl]methanol (0.612 g, 6.0 mmol, (Ito, M.; Osaku, A.; Shiibashi, A.; Ikariya, T., Org. Lett, 2007, 9, 1821. and tetrahydrofuran (15.0 mL). The mixture was cooled to 0° C. and sodium hydride added (0.268 g, 8.0 mmol). After gas evolution ceased, a solution of crude trans, trans-farnesyl bromide dissolved in tetrahydrofuran (5.0 mL) was added and the mixture heated to 45° C. for 19 hours under an argon atmosphere. The mixture was partitioned between ethyl acetate and a saturated ammonium chloride solution and the organic layer washed with brine and concentrated to dryness to provide an oil. The crude material was purified by silica gel chromatography (1:4 ethyl acetate: hexanes) to yield the product as an oil (0.610 g, 33%). HRMS ESI [M+Na] calc'd=329.2457, observed=329.2474.

[2-([{(2E,6E)-3,7,11-trimethyldodeca-2,6,10-trien-1-yl]oxy}methyl)cyclopropyl]methanol (0.200 g, 0.650 mmol) was dissolved in diethyl ether (3.00 mL), cooled to 0° C. and under an argon atmosphere, charged phosphorus tribromide (0.270 g, 1.00 mmol) and stirred for 15 minutes. The reaction was diluted with hexanes, washed with brine, a saturated sodium bicarbonate solution, and brine. The organic layer was dried over sodium sulfate and concentrated in vacuo to yield crude 1-(bromomethyl)-2-({[(2E,6E)-3,7,11-trimethyldodeca-2,6,10-trien-1-yl]oxy}methyl) cyclopropane (0.110 g, 45%). This material was dissolved in acetonitrile (2.00 mL) and tetrabutylammonium pyrophosphate was added (0.221 g, 0.240 mmol), the reaction under an argon atmosphere for two hours. The mixture was then concentrated in vacuo and purified on a DOWEX50 resin column. The DOWEX50 resin (7.30 g) was stirred in concentrated ammonium hydroxide (30.0 mL) for 20 minutes, then filtered and washed four times with water (100 mL). The resin was suspended in a buffer (20.0 mL of 1:49 2-propanol:25.0 mmolar aqueous ammonium bicarbonate) and poured into a column. The excess 1:49 2-propanol:25.0 mmolar aqueous ammonium bicarbonate buffer was drained from the column and the crude material was applied to the column (dissolved in 3.00 mL of the 1:49 2-propanol:25.0 mmolar aqueous ammonium bicarbonate buffer). The material was eluted with 30.0 mL of the 1:49 2-propanol: 25.0 mmolar aqueous ammonium bicarbonate buffer and lyophilized to a solid (0.113 g, 38%). $^{31}P$ NMR (202 MHz, Deuterium Oxide) δ −6.32 (d, J=20.7 Hz), −10.20 (d, J=20.6 Hz). HRMS ESI [M=H] calc'd=465.1813, observed=465.1808.

EXAMPLE 32

Coupling Class II and Class I Enzymes

Enzymes *Coleus forskohlii* CfTPS2 (SEQ ID NO:69) and *Salvia sclarea* SsSCS (SEQ ID NO:61) were coupled in an in vitro assay to ascertain whether the synthetic unnatural methyl-GGDP (C21) substrate can efficiently yield the corresponding C21 methyl-diterpene. The C21 substrate does not exist in nature and has the following structure.

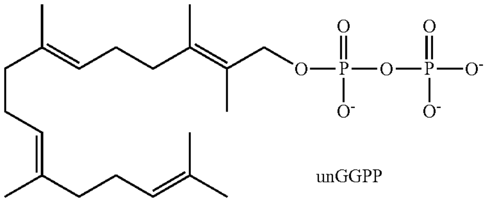 [SMILES: CC(C)=CCC/C(C)=C/CC/C(C)=C/CC/C(C)=C(\C)COP(=O)([O-])OP(=O)([O-])[O-]]

unGGPP

Figure 10:
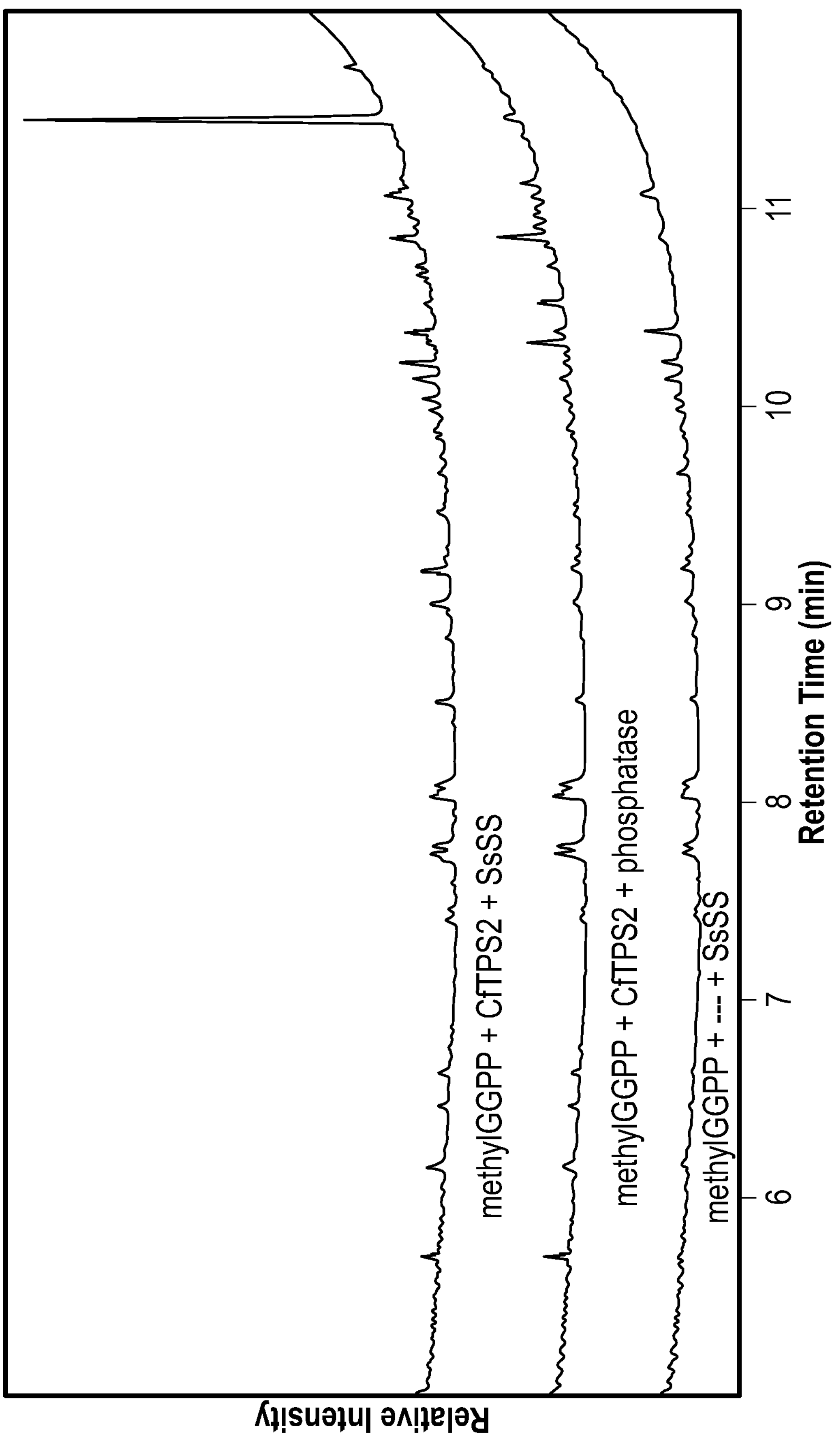
FIG. 10 illustrates detection of new methyl-diterpene product, with a structure similar to sclareol, when the *Coleus forskohlii* CfTPS2 and *Salvia sclarea* SsSCS enzymes are coupled together in an in vitro assay where the starting substrate is the unnatural methyl-GGDP (C21) substrate.

As illustrated in FIG. 10, a new methyl-diterpene product, with a structure similar to sclareol, is detected when the *Coleus forskohlii* CfTPS2 and *Salvia sclarea* SsSCS enzymes are used together in an assay with the unnatural methyl-GGDP (C21) substrate. The *Coleus forskohlii* CfTps2 enzyme catalyzed the first step to provide a substrate for the *Salvia sclarea* SsSCS enzyme, which then produced the final product that has a structure similar to sclareol.

Many of the foregoing Examples illustrate that single step class I enzymes or single step class II labdane-type enzymes can synthesize irregular type diterpenes and unnatural derivatives thereof. However, this Example demonstrates that modules consisting of coupled class II and class I enzymes can be used in function sequential conversion reaction to prepare new types of diterpenes.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements are intended to describe and summarize various features of the invention according to the foregoing description provided in the specification and figures.

Statements:

1. A compound of the formula (I) or (II):

(I)

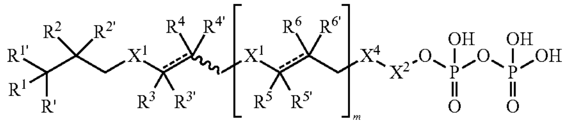

(II)

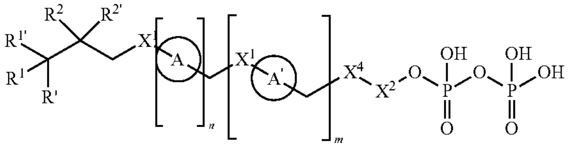

wherein:

m is an integer from 0 to 3 (e.g., 1 or 2), with the understanding that if m is 2 or 3, each repeating subunit can be the same or different;

n is an integer from 0 to 1;

the dashed lines (----- ) represent a double bond when $R^{3'}$ and $R^{4'}$ are absent or when $R^{5'}$ and $R^{6'}$ are absent, A and A' are each independently cycloalkyl, aryl or heterocyclyl, each of which can be optionally substituted;

$X^1$ is a heteroatom, $-X^3$-alkyl, -alkyl-$X^3$– or alkyl, wherein $X^3$ is a heteroatom or alkyl or $X^1$ is:

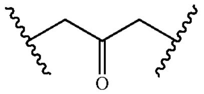

;

$R^1$ and $R^2$ form a double bond or an epoxide;

each R', $R^{1'}$, $R^2$, $R^{2'}$, and $R^3$—$R^6$ is, independently, H, alkyl, halo, aryl, and alkylaryl;

$R^{3'}$ and $R^{4'}$ are absent or $R^{3'}$ and $R^{4'}$, together with the carbon atoms to which they are attached, form an epoxide, a cycloalkyl group, an aryl group or a heterocyclyl group;

$R^{5'}$ and $R^{6'}$ are absent or $R^{5'}$ and $R^{6'}$, together with the carbon atoms to which they are attached, form an epoxide, a cycloalkyl group, an aryl group or a heterocyclyl group;

$X^2$ is a bond, alkenyl or acyl; and $X^4$ is a absent, a heteroatom or alkyl;

with the proviso that the compound of the formula (I) is not a compound of the formula:

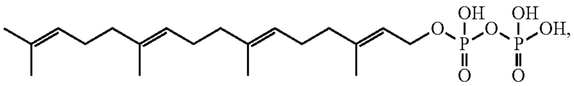

,

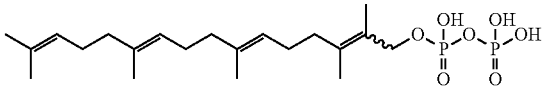

or

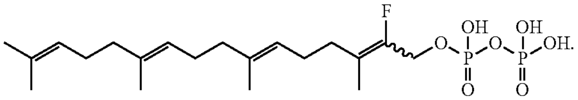

.

2. A compound of Statement 1, wherein the compound of the formula (I) is a compound of the formula:

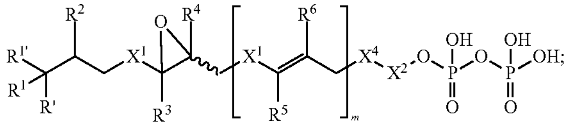

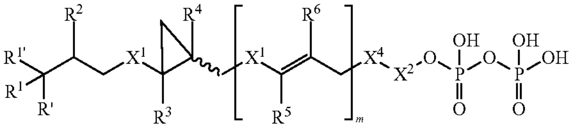

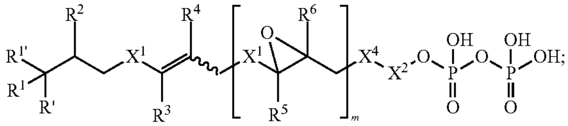

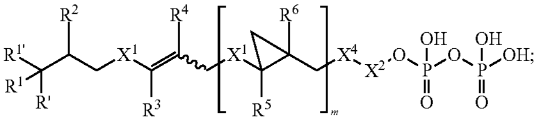

and

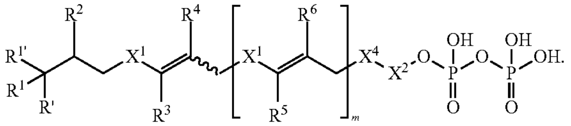

3. A compound of Statement 1, wherein the compound of the formula (II) is a compound of the formula:

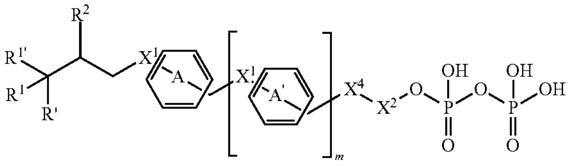

4. The compound of any preceding Statement, wherein if $X^1$ is a heteroatom, the heteroatom is oxygen.

5. The compound of any preceding Statement, wherein $X^3$ is oxygen or $C_1$-$C_5$ alkyl, such as —$CH_2$— and $C_2$-$C_3$-alkyl.

6. The compound of any preceding Statement, wherein $R^3$—$R^6$ are each H or $C_1$-$C_5$-alkyl, such as methyl and $C_2$-$C_3$-alkyl.

7. The compound of any preceding Statement, wherein $R^3$ and $R^5$ are each H or $C_1$-$C_5$-alkyl, such as methyl and $C_2$-$C_3$-alkyl; and $R^4$ and $R^6$ are each H.

8. The compound of any preceding Statement, wherein m is 1 or 2.

9. The compound of any preceding Statement, wherein, m is 0.

10. The compound of any preceding Statement, wherein $X^2$ is an alkenyl group of the formula:

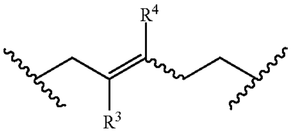

or

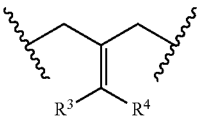

;

or an acyl group of the formula:

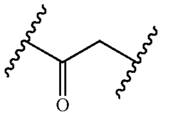

.

11. The compound of any preceding Statement, wherein the compound is a compound of the formula:

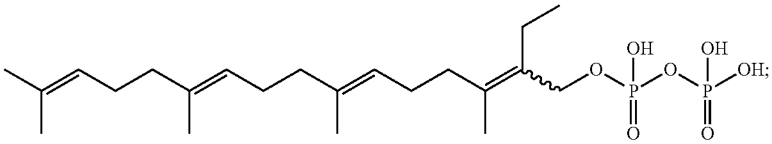

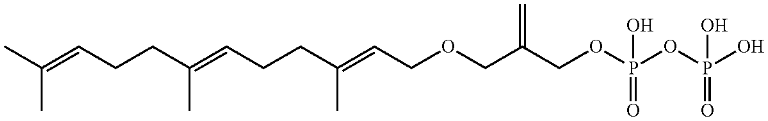

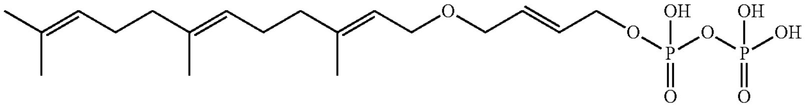

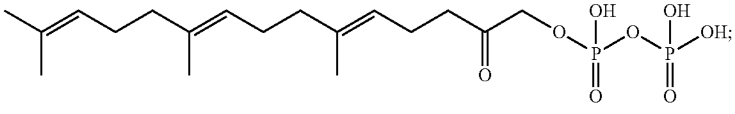

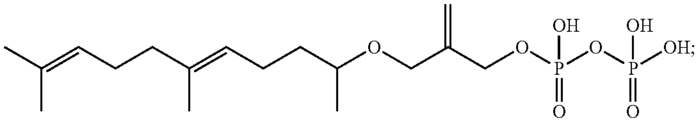

-continued

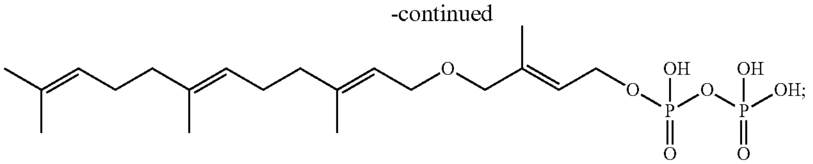

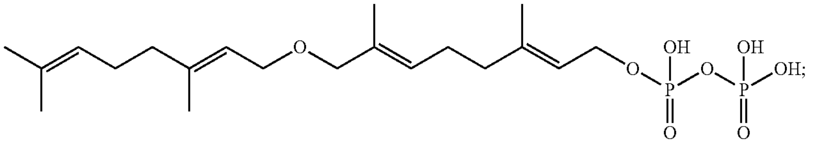

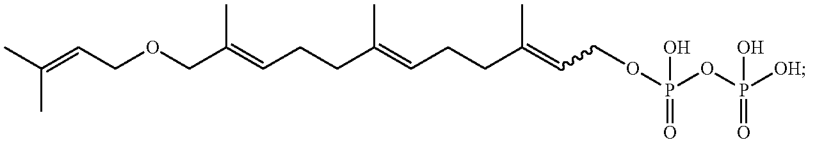

and

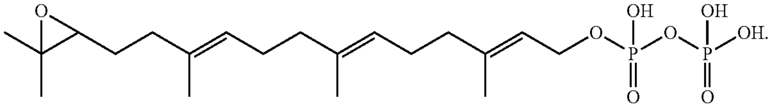

12. The compound of any preceding Statement, wherein the compounds can be enzymatically transformed into a terpenoid.

13. The compound of any preceding Statement, wherein the terpenoid comprises a compound core of the formula:

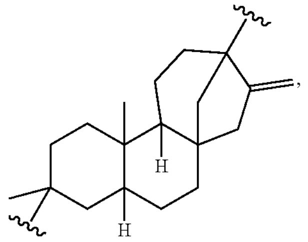

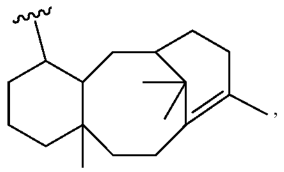

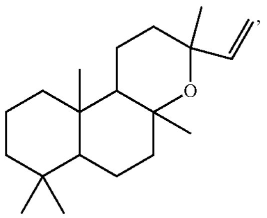

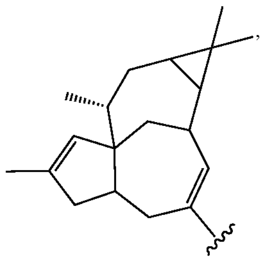

-continued

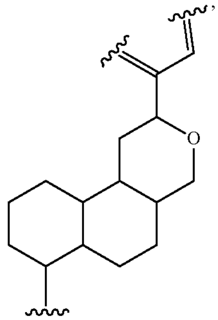

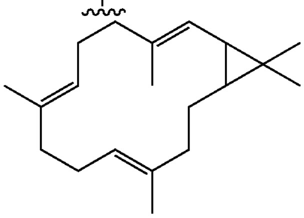

or

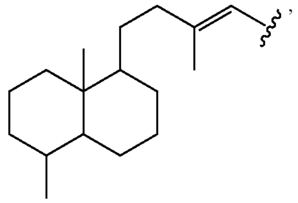

and derivatives thereof, wherein derivatives can comprise additional double bonds, alkyl groups, hydroxy groups, acyl groups, and the like, dispersed about the cores.

14. A method comprising contacting an unnatural substrate with one or more enzymes capable of synthesizing a terpene to generate a primary product.

15. The method of Statement 14, wherein the unnatural substrate is a compound of Statements 1-14.

16. The method of Statement 14, wherein the one or more enzymes are from species *Tripterygium wilfordii* (Tw), *Euphorbia peplus* (Ep), *Coleus forskohlii* (Cf), *Ajuga reptans* (Ar), *Perovskia atriciplifolia* (Pa), *Nepeta mussini* (Nm), *Origanum majorana* (Om), *Hyptis suaveolens* (Hs),

*Grindelia robusta* (Gr), *Leonotis leonurus* (Ll), *Marrubium vulgare* (Mv), *Vitex agnus-castus* (Vac), *Euphorbia peplus* (Ep), *Ricinus communis* (Rc), *Daphne genkwa* (Dg), or *Zea mays* (Zm).

17. The method of Statement 14, wherein the enzyme is from species *Salvia sclarea, Coleus forskohlii, Euphorbia peplus, Ajuga reptans, Origanum majoranum, Marrubium vulgare*, or *Kitasatospora griseola.*

18. The method of Statement 14-17, wherein the primary product is a terpenoid.

19. The method of Statement 14-18, wherein one or more of the enzymes has at least 90% sequence identity to SEQ ID NO: 1, 3, 5, 7, 9, 11, 13, 15, 17, 19, 21, 23, 25, 27, 29, 31, 33, 35, 37, 41, 43, 45, 47, 49, 51, 53, 57, 59, 61, 63, 64, 65, 66, 67, or 69.

20. The method of Statement 14-18 or 19, further comprising contacting the primary product with one or more second enzymes.

21. The method of Statement 14-20, further comprising generating a second product by one or more second enzymes, where the one or more second enzymes catalyze the formation of the second product by using the primary product as a substrate.

22. The method of Statement 20 or 21, wherein the one or more second enzymes at least one of oxidizes, reduces, acylates, and glycosylates the primary product.

23. The method of Statement 20, 21 or 22, wherein the one or more second enzymes is an enzyme listed in Table 2.

24. The method of Statement 20-22 or 23, wherein one or more of the second enzymes has at least 90% sequence identity to SEQ ID NO: 39, 68, 70, or 71.

25. The method of Statement 22-23 or 24, wherein the one or more second enzymes is Cytochrome P450 or a sclareol synthase.

26. The method of Statement 14-23 or 24, which is performed in vitro in a cell-free mixture.

27. The method of Statement 14-23 or 24, which is performed within a cell that expresses the enzyme.

28. A compound of the formula (I)-(IV):

(I)

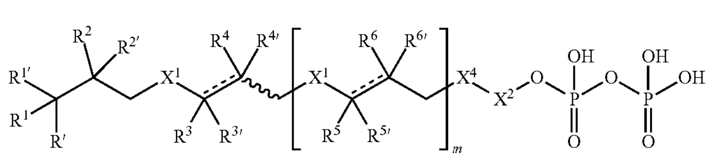

(II)

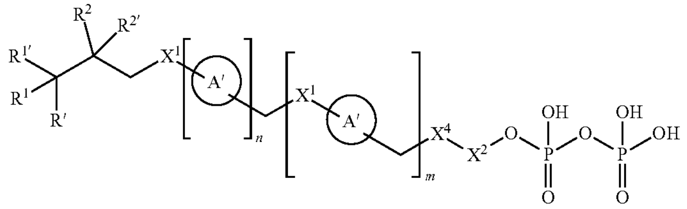

(III)

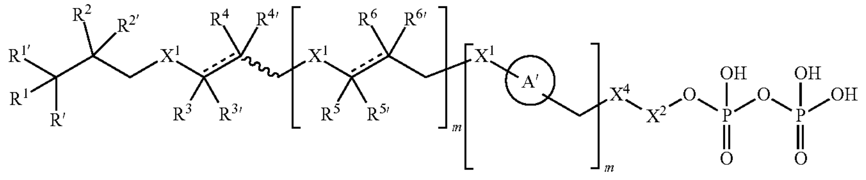

(IV)

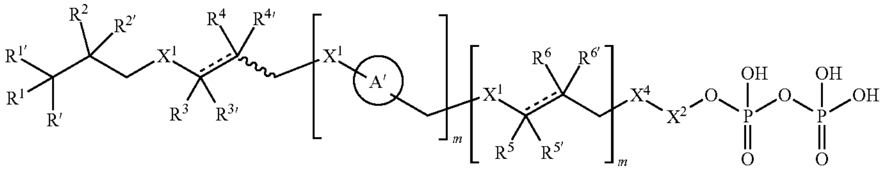

wherein:

each m is independently an integer from 0 to 3, with the understanding that if m is 2 or 3, each repeating subunit can be the same or different;

n is an integer from 0 to 1;

the dashed lines (-----) represent a double bond when $R^{3'}$ and $R^{4'}$ are absent or when $R^{5'}$ and $R^{6'}$ are absent, A and A' are each independently cycloalkyl, aryl or heterocyclyl, each of which can be optionally substituted;

$X^1$ is a heteroatom, —$X^3$-alkyl, -alkyl-$X^3$— or alkyl, wherein $X^3$ is a heteroatom or alkyl or $X^1$ is:

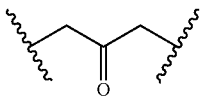

;

$R^1$ and $R^2$ form a double bond or an epoxide;

each R', $R^{1'}$, $R^2$, $R^{2'}$, and $R^3$—$R^6$ is, independently, H, alkyl, alkoxy, halo, aryl, and alkylaryl;

$R^{3'}$ and $R^{4'}$ are absent or $R^{3'}$ and $R^{4'}$, together with the carbon atoms to which they are attached, form an epoxide, a cycloalkyl group, an aryl group or a heterocyclyl group;

$R^{5'}$ and $R^{6'}$ are absent or $R^{5'}$ and $R^{6'}$, together with the carbon atoms to which they are attached, form an epoxide, a cycloalkyl group, an aryl group or a heterocyclyl group;

$X^2$ is a bond, alkenyl, alkynyl or acyl; and $X^4$ is a absent, a heteroatom or alkyl; with the proviso that the compound of the formula (I) is not a compound of the formula:

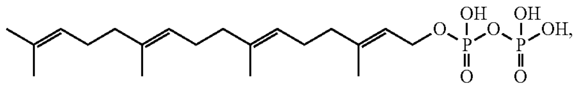

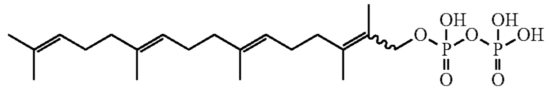

or

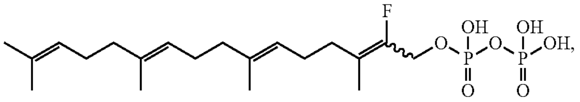

29. The compound of Statement 28, wherein $X^2$ is an alkenyl group of the formula:

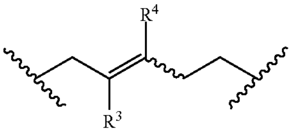

,

-continued

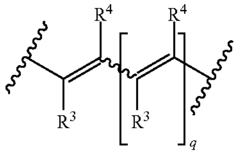

wherein q is an integer from 1 to 3; or

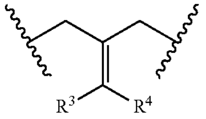

;

or an acyl group of the formula:

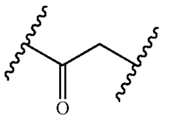

.

30. The compound of Statement 28 or 29, wherein the compound is a compound of the formula:

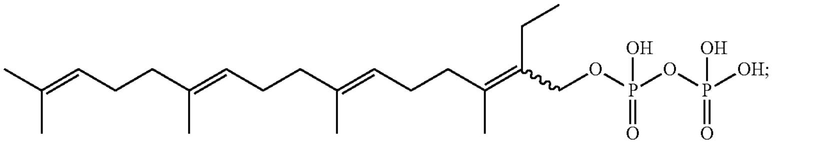

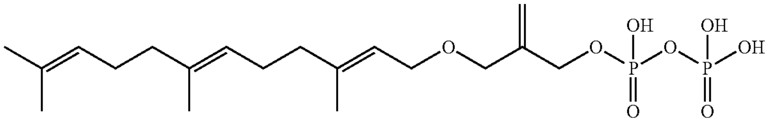

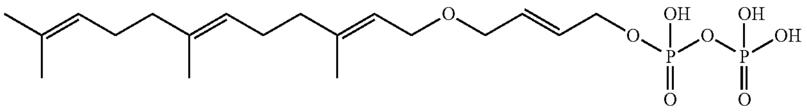

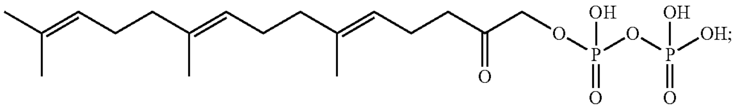

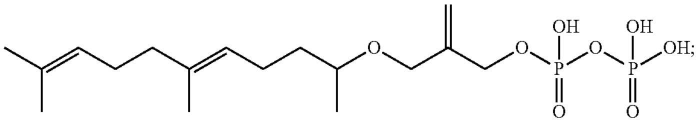

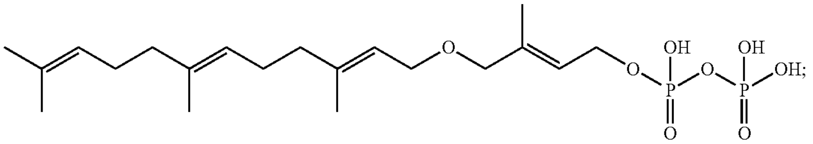

-continued
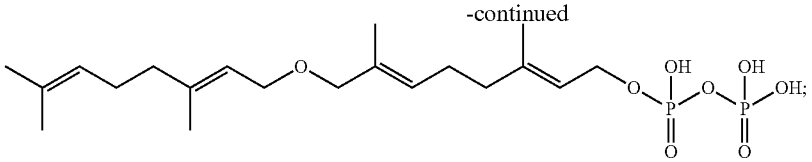
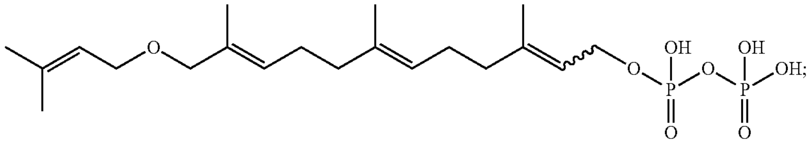
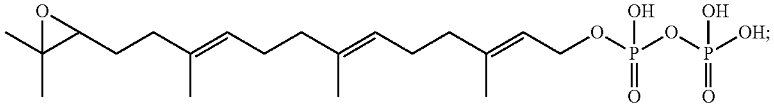
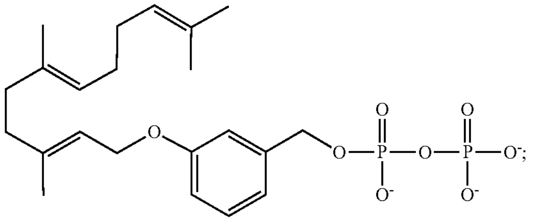
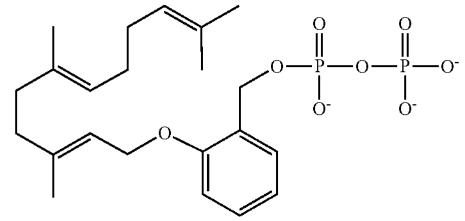
;
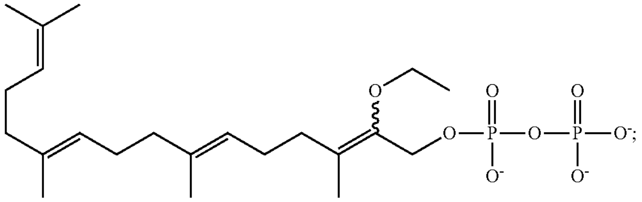
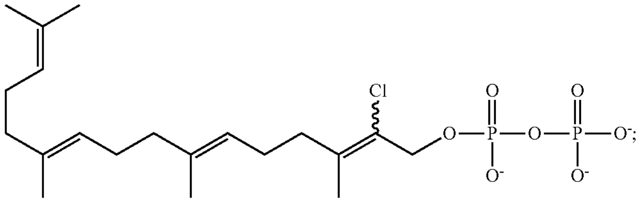
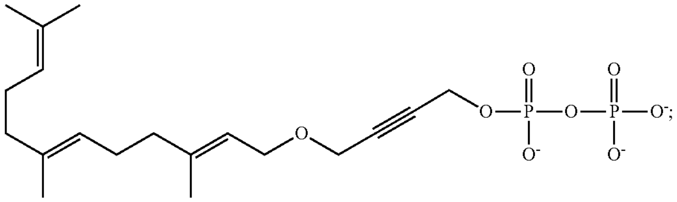
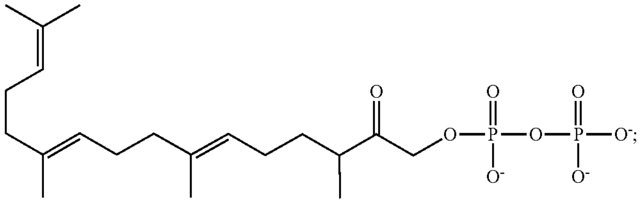
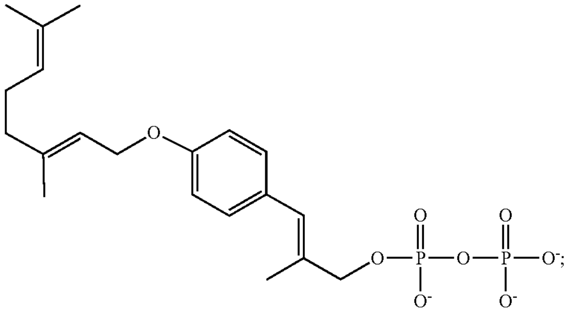
or -continued

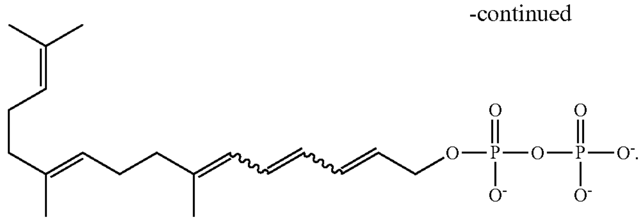

The specific methods, devices and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention.

The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

What is claimed:

1. A compound of the formula (I)-(IV):

(I)

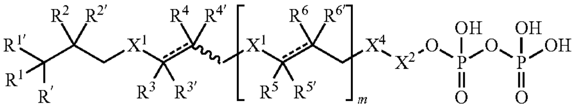

(II)

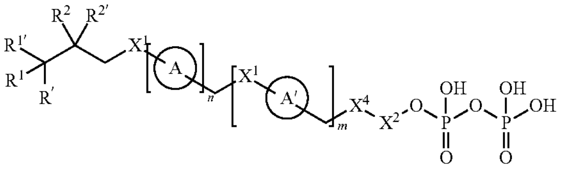

(III)

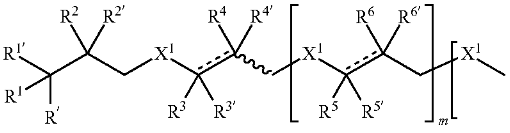

-continued

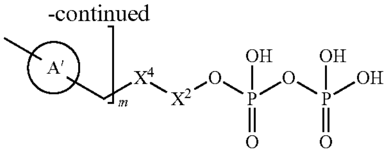

(IV)

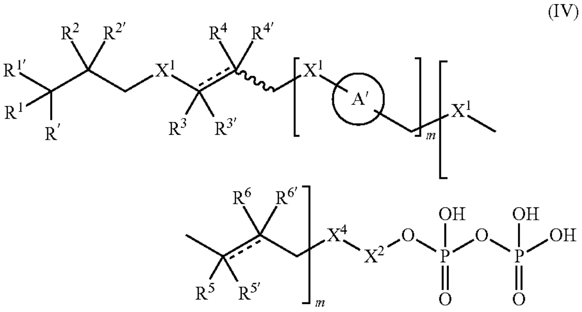

wherein:

each m is independently an integer from 0 to 3, with the understanding that if m is 2 or 3, each repeating subunit can be the same or different;

n is an integer from 0 to 1;

the dashed lines ----- represent a double bond when $R^{3'}$ and $R^{4'}$ are absent or when $R^{5'}$ and $R^{6'}$ are absent, A and A' are each independently cycloalkyl, aryl or heterocyclyl, each of which can be optionally substituted;

$X^1$ is a heteroatom, $-X^3$-alkyl, -alkyl-$X^3$- or alkyl, wherein $X^3$ is a heteroatom or alkyl or $X^1$ is:

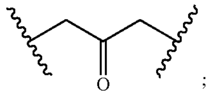 [SMILES: *CC(=O)C*]

;

$R^1$ and $R^2$ form a double bond or an epoxide;

each R', $R^{1'}$, $R^2$, $R^{2'}$, and $R^3$-$R^6$ is, independently, H, alkyl, alkoxy, halo, aryl, and alkylaryl;

$R^{3'}$ and $R^{4'}$ are absent or $R^{3'}$ and $R^{4'}$, together with the carbon atoms to which they are attached, form an epoxide, a cycloalkyl group, an aryl group or a heterocyclyl group;

$R^{5'}$ and $R^{6'}$ are absent or $R^{5'}$ and $R^{6'}$, together with the carbon atoms to which they are attached, form an epoxide, a cycloalkyl group, an aryl group or a heterocyclyl group;

$X^2$ is a bond, alkenyl, alkynyl or acyl; and $X^4$ is absent, a heteroatom or alkyl;

with the proviso that the compound of the formula (I) is not a compound of the formula:

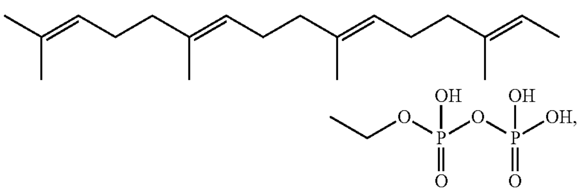

,

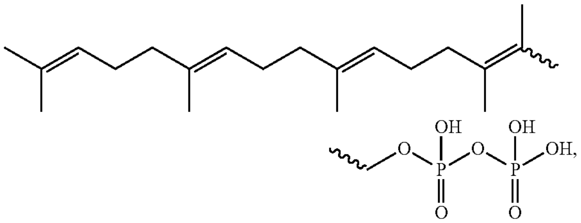

,

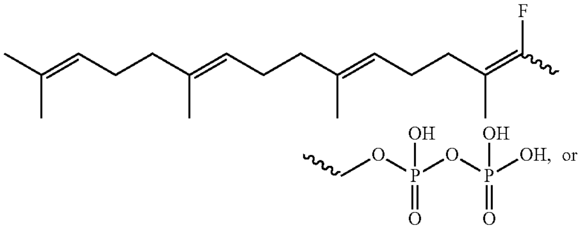

, or

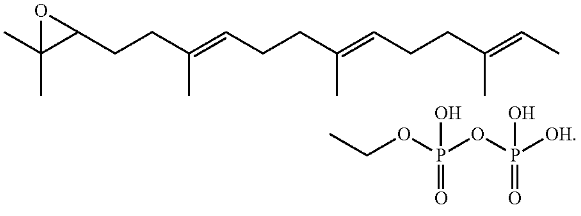

.

2. The compound of claim 1, wherein the compound of the formula (I) is a compound of the formula:

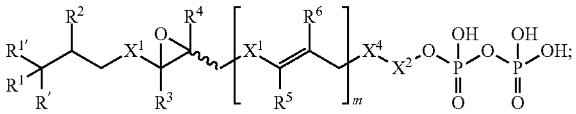

;

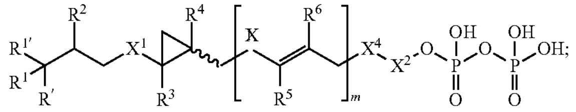

;

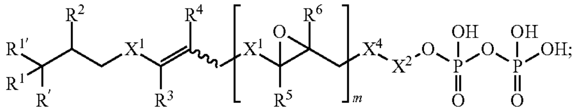

;

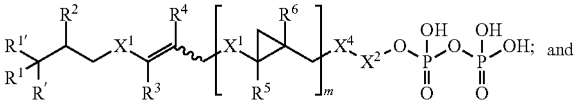

; and

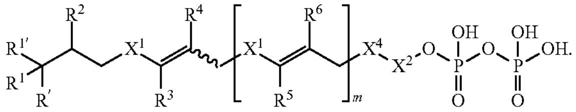

.

3. The compound of claim 1, wherein the compound of the formula (II) is a compound of the formula:

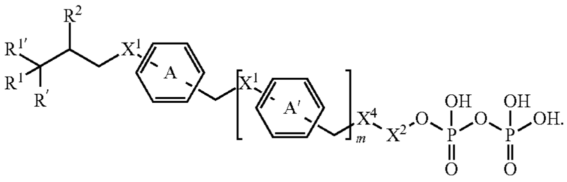

.

4. The compound of claim 1, wherein if $X^1$ is a heteroatom, the heteroatom is oxygen.

5. The compound of claim 1, wherein $X^3$ is oxygen or $C_1$-$C_6$-alkyl.

6. The compound of claim 1, wherein $R^3$-$R^6$ are each H or $C_1$-$C_5$-alkyl.

7. The compound of claim 1, wherein $R^3$ and $R^5$ are each H or $C_1$-$C_5$-alkyl; and $R^4$ and $R^6$ are each H.

8. The compound of claim 1, wherein m is 1 or 2.

9. The compound of claim 1, wherein, m is 0.

10. The compound of claim 1, wherein $X^2$ is an alkenyl group of the formula:

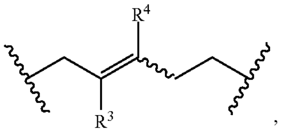

,

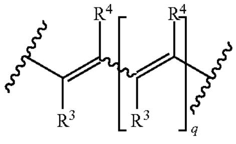

wherein q is an integer from 1 to 3; or

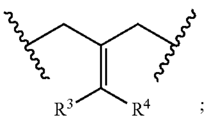

;

or an acyl group of the formula:
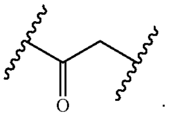 [SMILES: *CC(*)=O]
11. The compound of claim 1, wherein the compound is a compound of the formula:
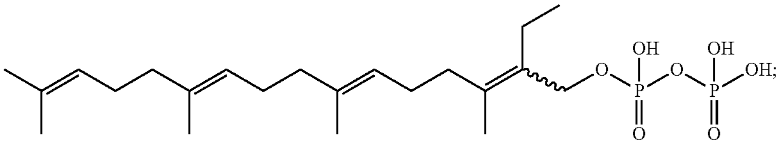
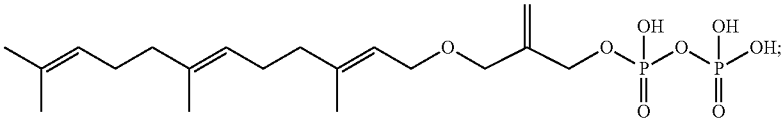
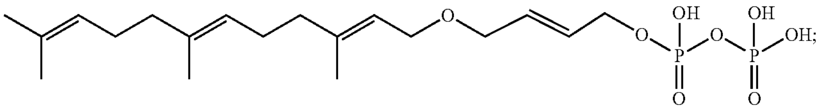
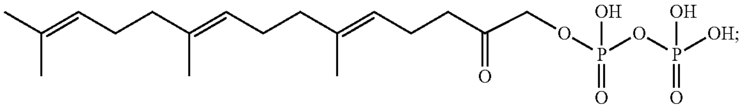
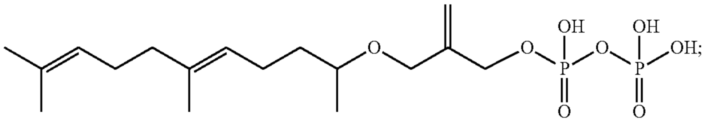
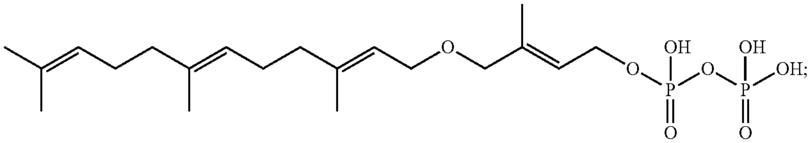
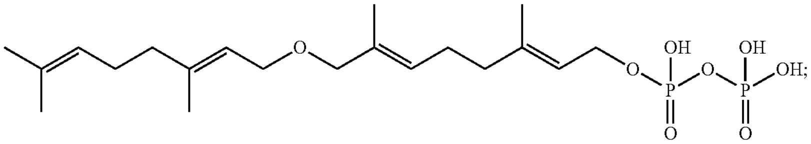
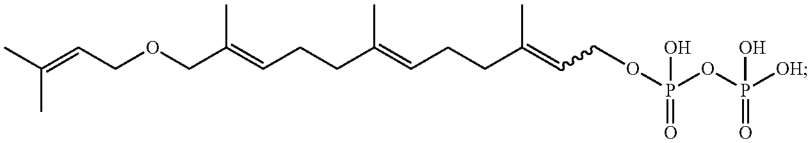
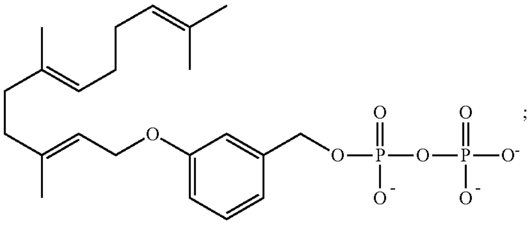
;
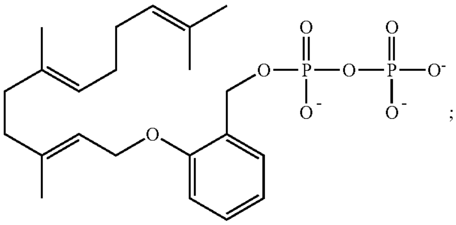
;

-continued
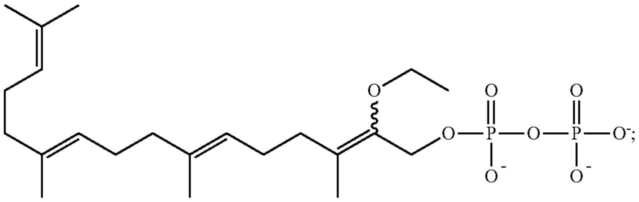
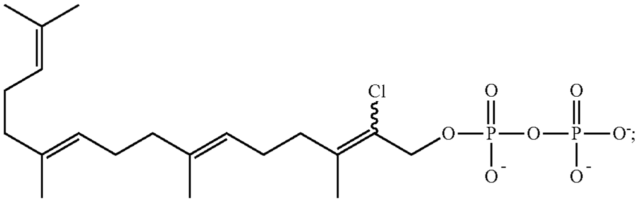
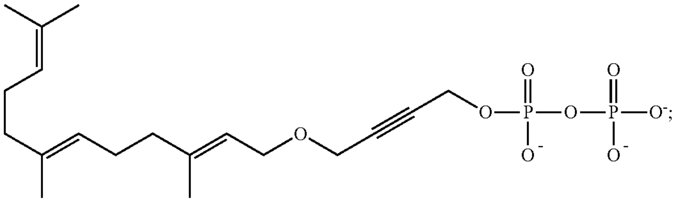
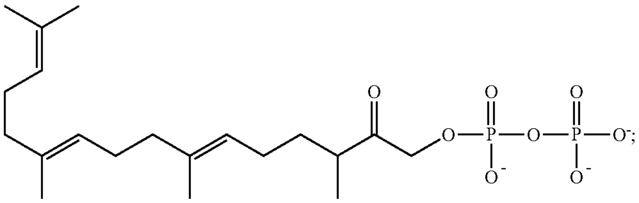
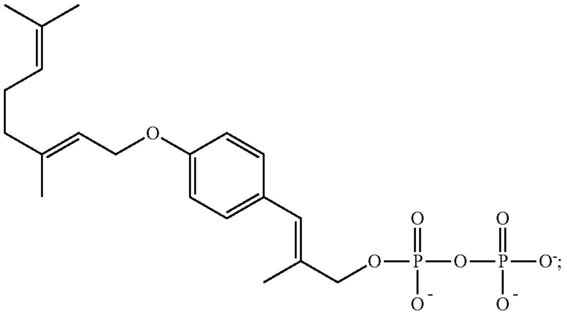
or
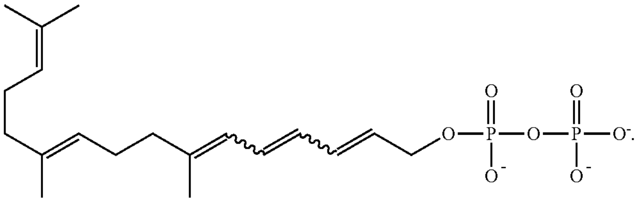

12. The compound of claim 1, wherein the compounds can be enzymatically transformed into a terpenoid.
13. The compound of claim 12, wherein the terpenoid comprises a compound core of the formula:
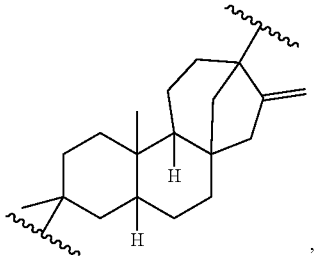
,
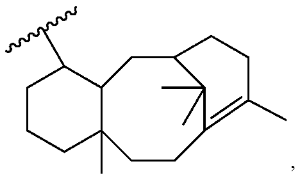
,
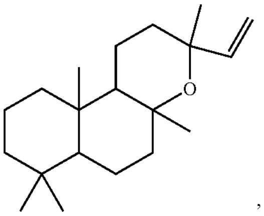
,
-continued
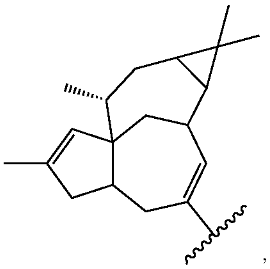
,
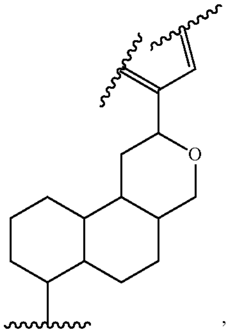
,
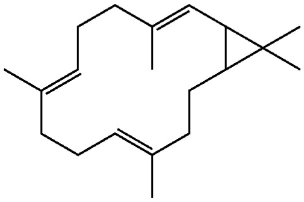
or
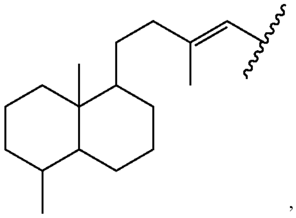
,
and derivatives thereof, wherein derivatives can comprise additional double bonds, alkyl groups, hydroxy groups, and acyl groups dispersed about the cores.
* * * * *